(12) United States Patent
Chiosis et al.

(10) Patent No.: US 10,160,729 B2
(45) Date of Patent: *Dec. 25, 2018

(54) HSP70 MODULATORS AND METHODS FOR MAKING AND USING THE SAME

(71) Applicant: Memorial Sloan Kettering Cancer Center, New York, NY (US)

(72) Inventors: Gabriela Chiosis, New York, NY (US); Yanlong Kang, Plainsboro, NJ (US); Hardik J. Patel, Kew Gardens, NY (US); Maulik Patel, New York, NY (US); Stefan Ochiana, Chevy Chase, MD (US); Anna Rodina, New York, NY (US); Tony Taldone, Forest Hills, NY (US); Liza Shrestha, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/842,755

(22) Filed: Dec. 14, 2017

(65) Prior Publication Data

US 2018/0170883 A1  Jun. 21, 2018

Related U.S. Application Data

(63) Continuation of application No. 15/310,142, filed as application No. PCT/US2015/030641 on May 13, 2015, now Pat. No. 9,878,987.

(60) Provisional application No. 61/992,838, filed on May 13, 2014.

(51) Int. Cl.

| | | |
|---|---|---|
| *A61K 31/506* | (2006.01) | |
| *C07D 239/46* | (2006.01) | |
| *C07D 401/12* | (2006.01) | |
| *C07D 239/42* | (2006.01) | |
| *C07D 413/12* | (2006.01) | |
| *A61K 31/5377* | (2006.01) | |
| *A61K 45/06* | (2006.01) | |
| *C07D 403/04* | (2006.01) | |
| *C07D 405/12* | (2006.01) | |
| *C07D 407/12* | (2006.01) | |
| *C07D 417/12* | (2006.01) | |

(52) U.S. Cl.
CPC .......... *C07D 239/46* (2013.01); *A61K 31/506* (2013.01); *A61K 31/5377* (2013.01); *A61K 45/06* (2013.01); *C07D 239/42* (2013.01); *C07D 401/12* (2013.01); *C07D 403/04* (2013.01); *C07D 405/12* (2013.01); *C07D 407/12* (2013.01); *C07D 413/12* (2013.01); *C07D 417/12* (2013.01)

(58) Field of Classification Search
CPC .. C07D 239/46; C07D 401/12; C07D 403/04; C07D 405/12; C07D 407/12; C07D 413/12; C07D 417/12; A61K 31/506; A61K 31/5377; A61K 45/06

See application file for complete search history.

(56) References Cited

U.S. PATENT DOCUMENTS

| | | |
|---|---|---|
| 3,154,551 A | 10/1964 | Hitchings et al. |
| 3,248,393 A | 4/1966 | Roth et al. |
| 4,096,264 A | 6/1978 | Bochis et al. |
| 4,251,454 A | 2/1981 | Kompis et al. |
| 4,552,900 A | 11/1985 | Sirrenberg et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,707,930 A | 1/1998 | Felix et al. |
| 5,848,551 A | 12/1998 | Ohmi et al. |
| 5,948,551 A | 9/1999 | Gompper et al. |
| 6,107,301 A | 8/2000 | Aldrich et al. |
| 7,517,886 B2 | 4/2009 | Singh et al. |
| 9,567,318 B2 | 2/2017 | Chiosis et al. |
| 9,878,987 B2 * | 1/2018 | Chiosis ............... C07D 239/46 |

(Continued)

FOREIGN PATENT DOCUMENTS

| | | |
|---|---|---|
| CN | 1930135 A | 3/2007 |
| EP | 2343282 A1 | 7/2011 |

(Continued)

OTHER PUBLICATIONS

Caldwell, W.T. and Sayin, A.N., The Preparation of a Pyrimidine Analog (Isostere) of Promizole and Other Substituted Pyrimidines, J. Am. Chem. Soc., 74(17):4314-4317 (1952).

(Continued)

*Primary Examiner* — Alexander R Pagano

(74) *Attorney, Agent, or Firm* — Choate, Hall & Stewart LLP; Brenda Herschbach Jarrell; John P. Rearick

(57) ABSTRACT

The present invention, among other things, provides compounds and compositions thereof for use in the modulation of Hsp70. In some embodiments, the present invention provides a method for inhibiting Hsp70 activity. In some embodiments, the present invention provides a method of treating a subject suffering from or susceptible to a disease, disorder, or condition responsive to Hsp70 inhibition comprising administering to the subject a therapeutically effective amount of a provided compound. In some embodiments, the present invention provides a method for treating or preventing cancer in a subject suffering therefrom, comprising administering to a patient in need thereof a therapeutically effective amount of a provided compound.

19 Claims, 3 Drawing Sheets

(56) References Cited

U.S. PATENT DOCUMENTS

| | | | |
|---|---|---|---|
| 2003/0153584 | A1 | 8/2003 | Weaver et al. |
| 2005/0070712 | A1 | 3/2005 | Kosogof et al. |
| 2005/0277654 | A1 | 12/2005 | Maynard et al. |
| 2008/0124407 | A1 | 5/2008 | Eaton et al. |
| 2012/0252818 | A1 | 10/2012 | Chiosis et al. |
| 2013/0085156 | A1 | 4/2013 | Mitsuya et al. |
| 2017/0165265 | A1 | 6/2017 | Chiosis et al. |
| 2017/0233352 | A1 | 8/2017 | Chiosis et al. |

FOREIGN PATENT DOCUMENTS

| | | |
|---|---|---|
| GB | 1014881 A | 12/1965 |
| GB | 1015784 A | 1/1966 |
| JP | 51-091273 A | 8/1976 |
| JP | 52-73896 A | 6/1977 |
| JP | 59-184167 | 10/1984 |
| JP | 2004-523474 A | 8/2004 |
| JP | 2004-528293 A | 9/2004 |
| JP | 2005-517675 A | 6/2005 |
| JP | 2007-526268 A | 9/2007 |
| JP | 2008-533166 A | 8/2008 |
| WO | WO-96/05309 A2 | 2/1996 |
| WO | WO-02/024681 A2 | 3/2002 |
| WO | WO-02/053557 A1 | 7/2002 |
| WO | WO-02/060450 A1 | 8/2002 |
| WO | WO-2004/081001 A1 | 9/2004 |
| WO | WO-2005/021552 A1 | 3/2005 |
| WO | WO-2005/095359 A1 | 10/2005 |
| WO | WO-2006/101977 A2 | 9/2006 |
| WO | WO-2007/131034 A1 | 11/2007 |
| WO | WO-2008/026768 A1 | 3/2008 |
| WO | WO-2008/073687 A2 | 6/2008 |
| WO | WO-2008/092199 A1 | 8/2008 |
| WO | WO-2008/153042 A1 | 12/2008 |
| WO | WO-2009/023846 A2 | 2/2009 |
| WO | WO-2009/061345 A2 | 5/2009 |
| WO | WO-2009/067081 A1 | 5/2009 |
| WO | WO-2010/144345 A1 | 12/2010 |
| WO | WO-2011/022440 A2 | 2/2011 |

OTHER PUBLICATIONS

Cerchietti, L.C. et al, A purine scaffold Hsp90 inhibitor destabilizes BCL-6 and has specific antitumor activity in BCL-6-dependent B cell lymphomas. Nat Med., 15(12):1369-76 (2009).

Cerchietti, L.C. et al, BCL6 repression of EP300 in human diffuse large B cell lymphoma cells provides a basis for rational combinatorial therapy, J. Clin Invest., 120(12): 4569-4582 (2010).

Chothia, C. and Lesk, A.M., The relation between the divergence of sequence and structure in proteins, The EMBO Journal, 5(4):823-6 (1986).

Database Registry [Online]: Chemical Abstracts Service, Columbus, Ohio, USA. Retrieved from STN, Registry No. 412341-81-2 (Entered STN: May 8, 2002).

Extended European Search Report for EP 10810519.8, 2 pages (dated Feb. 5, 2013).

Gompper, R. et al, Reactions of α, β-unsaturated β-amino-and β-hydroxycarbonyl compounds with sulfur monochloride and related compounds, Justus Liebigs Annalen der Chemie, 675: 151-174 (1964).

Halgren, T.A., Identifying and characterizing binding sites and assessing; druggability, Journal of Chemical Information and Modeling, 49(2):377-89 (2009).

Hanahan, D. and Weinberg, R.A., Hallmarks of cancer: the next generation, Cell, 144(5):646-74 (2011).

Hanahan, D. and Weinberg, R.A., The hallmarks of cancer, Cell, 100(1):57-70 (2000).

Håvik, B. and Bramham, C.R., Additive viability-loss following hsp70/hsc70 double interference and Hsp90 inhibition in two breast cancer cell lines, Oncology Reports, 17(6):1501-10 (2007).

International Search Report for PCT/US2010/045817, 5 pages (dated Jun. 21, 2011).

International Search Report of PCT/US2015/030641, 5 pages (dated Jul. 29, 2015).

Kang, Y. et al., Heat shock protein 70 inhibitors. 1. 2,5'-thiodipyrimidine and 5-(phenylthio)pyrimidine acrylamides as irreversible binders to an allosteric site on heat shock protein 70, Journal of Medicinal Chemistry, 57(4):1188-1207 (2014).

Koos, M. et al., Synthesis of some sulfur bridged pyrimidines, pyrazoles and imidazoles Proceedings of ECSOC-1: The First International Electronic Conference on Synthetic Organic Chemistry, and Proceedings of ECSOC-2: The Second International Electronic Conference on Synthetic Organic Chemistry, Sep. 1-30, 1997, 315-318 (1997).

Kundu, N. G. and Nandi, B., Depropargylation under palladium-copper catalysis: synthesis of diaryl sulfides, Tetrahedron, 57(27): 5885-5895 (2001).

Liebscher, M. and Roujeinikova, A., Allosteric coupling between the lid and interdomain linker in DnaK revealed by inhibitor binding studies, Journal of Bacteriology, 191(5):1456-62 (2009).

Nylandsted, J. et al., Eradication of glioblastoma, and breast and colon carcinoma xenografts by Hsp70 depletion, Cancer Research, 62(24):7139-42 (2002).

Rodina, A. et al., Affinity Purification Probes of Potential Use to Investigate the Endogenous Hsp70 Interactome in Cancer, ACS Chemical Biology, 8 pages (2014).

Rodina, A. et al., Identification of an allosteric pocket on human hsp70 reveals a mode of inhibition of this therapeutically important protein, Chemistry & Biology, 20(12):1469-80 (2013).

Roth, B. and Bunnett, J.F., 5-Arylthiopyrimidines. IV. Spectrophotometric Determination of Successive Acid Dissociation Constants Differing by Less Than Two pK Units, J. Am. Chem. Soc., 87(2):334-339 (1965).

Roth, B. and Schloemer, L.A., 5-Arylthiopyrimidines. III. Cyclization of 4-Hydroxy Derivatives to 10H-Pyrimido[5,4-b][1,4]benzothiazines (1,3-Diazaphenothiazines), J. Org. Chem., 28(10):2659-2672 (1963).

Roth, H. and Bunnett, J.F., 5-Arylthiopyrimidines. V. Kinetics of the Cyclization of 4-Oxo Derivatives to 10H- and 10-Alkylpyrimido[5,4-b][1,4]benzothiazines (1,3-Diazaphenothiazines), J. Am. Chem. Soc. 87(2):340-349 (1965).

Sugiyama, K. et al., Studies on 1,4-Benzothiazines. IV. Reactions of 2-Acyl-4H-1,4-benzothiazines with Hydroxylamine, Hydrazine, Guanidine and Acetamidine, Chem. Pharm. Bull., 32(4):1593-1596 (1984).

Taldone, T. et al., Heat shock protein 70 inhibitors. 2. 2,5'-thiodipyrimidines, 5-(phenylthio)pyrimidines, 2-(pyridin-3-ylthio)pyrimidines, and 3-(phenylthio)pyridines as reversible binders to an allosteric site on heat shock protein 70, Journal of Medicinal Chemistry, 57(4):1208-1224 (2014).

Taldone, T. et al., Protein chaperones: a composition of matter review (2008-2013), Expert Opin. Ther. Pat., 24(5):501-18 (2014).

Thomas, A.A. et al., Non-charged thiamine analogs as inhibitors of enzyme transketolase, Bioorg. Med. Chem. Lett., 18(2):509-12 (2008).

Wallner, B. and Elofsson, A., All are not equal: a benchmark of different homology modeling programs, Protein Science, 14(5):1315-27 (2005).

Weinstein, I.B., Cancer. Addiction to oncogenes—the Achilles heal of cancer, Science, 297(5578):63-4 (2002).

Written Opinion for PCT/US2010/045817, 7 pages (dated Jun. 21, 2011).

Written Opinion of PCT/US2015/030641, 7 pages (dated Jul. 29, 2015).

Yanagita, M. and Futaki, R., Pyrimidine Derivatives. II. Synthesis of p-Aminophenyl 2-amino-5-pyrimidyl Sulfone, Yakugaku Zasshi, 72(2): 236-238 (1952).

Yoshikawa, T. and Zasshi, Y., Syntheses of pyrimidine derivatives, II. Syntheses of dipyrimidyl sulfone derivatives and diazotization of 6-(5-amino-2-pyrimidylamino acid, Kumamoto University, 76:776-8 (1956).

\* cited by examiner

HSP70 MODULATORS AND METHODS FOR MAKING AND USING THE SAME

CROSS REFERENCE TO RELATED APPLICATIONS

The present application is a continuation of U.S. application Ser. No. 15/310,142, filed on Nov. 10, 2016, now U.S. Pat. No. 9,878,987, which is a U.S. National Phase Application under 35 U.S.C. § 371 of International Patent Application No. PCT/US2015/030641, filed on May 13, 2015, which claims priority to U.S. provisional Patent Application No. 61/992,838, filed May 13, 2014, the entire contents of each of which are hereby incorporated by reference.

BACKGROUND

The heat shock protein 70 (Hsp70) family members are powerful proteins with major roles in malignancy, such as inhibition of apoptosis, induction of resistance to chemotherapy and regulation of the stability of onco-proteins. Specifically, Hsp70 expression blocks apoptosis at several levels, and in this respect the chaperone inhibits key effectors of the apoptotic machinery, and also facilitates proteasome-mediated degradation of apoptosis-regulatory proteins. The contribution of Hsp70 isoforms to tumorigenesis is mainly through their role as co-chaperones of heat shock protein 90 (Hsp90), a heat shock protein known to regulate the transforming activities of several kinases and transcription factors. In this process, Hsp70 initiates the association of the client protein with Hsp90 through a bridging protein called HSP-organizing protein (HOP). These biological functions propose Hsp70 as an important target whose inhibition or downregulation may result in significant apoptosis in a wide-range of cancer cells, and also in inhibition of signaling pathways involved in tumorigenesis and metastasis. Due to these functions it is not surprising that Hsp70 is frequently overexpressed in cancer, where the elevated expression is furthermore believed to be a cause of resistance to chemotherapy and other treatments. These dual roles of Hsp70 in cancer, i.e. co-chaperone of Hsp90 and antiapoptotic molecule, suggest that inhibition of Hsp70 may offer a valuable anticancer strategy, as supported by Hsp70 knockdown studies.

Much effort has recently been dedicated towards the discovery of Hsp70 inhibitors and, unsurprisingly, molecules from a number of chemical classes have been reported to interact with Hsp70 through a variety of modes. These previous efforts have focused on either directly competing with ATP, which achieves potency but limited cellular activity, or by allosteric mechanisms. While these molecules are reported to elicit their effects through an Hsp70 mechanism, it is possible that they also act on multiple other unrelated and as yet unspecified mechanisms. Furthermore, these molecules tend to be hindered by a non-tractable SAR with subtle changes resulting in drastic changes in activity.

Hsp70 has proven to be a more difficult target to drug than Hsp90, which can be attributed to a number of reasons. Unlike Hsp90, there are no drug-like natural products for which Hsp70-bound crystal structures are available to guide drug design. In addition, the nucleotide binding pocket of Hsp70 is considerably more hydrophilic compared to that of Hsp90, requiring ATP to bind in a more extended conformation with polar contacts deep within the binding pocket. Reversible competitive inhibitors are particularly challenging to develop because of Hsp70's high affinity for ADP and high intracellular concentrations of ATP. While Hsp90 has proven highly amenable with numerous small-molecule ATP-competitive inhibitors entering into the clinic, to date no Hsp70 inhibitors have entered clinical trials.

SUMMARY OF THE INVENTION

The present invention provides, among other things, novel compounds for use in the modulation of Hsp70. In some embodiments, the present invention provides a compound of formula I:

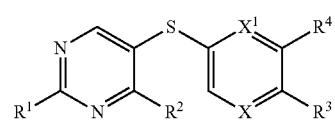

or a pharmaceutically acceptable salt thereof, wherein each variable is independently as described in classes and subclasses herein, both singly and in combination.

In some embodiments, the present invention provides a compound of formula II:

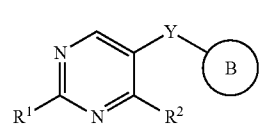

or a pharmaceutically acceptable salt thereof, wherein each variable is independently as described in classes and subclasses herein, both singly and in combination.

In certain embodiments, the present invention provides a pharmaceutical composition comprising a compound of formula I and a pharmaceutically acceptable carrier. In some embodiments, the present invention provides a pharmaceutical composition, comprising of a compound of formula II and a pharmaceutically acceptable carrier.

In some embodiments, the present invention provides a method for inhibiting Hsp70 activity. In some embodiments, the present invention provides a method for inhibiting Hsp70 activity, comprising contacting Hsp70 with a compound of formula I or a composition thereof. In some embodiments, the present invention provides a method for inhibiting Hsp70 activity, comprising contacting Hsp70 with a compound of formula II or a composition thereof. In some embodiments, the present invention provides a method for activating a caspase in cells. In some embodiments, the present invention provides a method for activating a caspase in cells, comprising administering to the cells a compound of formula I or a composition thereof. In some embodiments, the present invention provides a method for activating a caspase in cells, comprising administering to the cells a compound of formula II or a composition thereof. In some embodiments, the present invention provides a method for inducing cell death. In some embodiments, the present invention provides a method for inducing cell death, comprising administering to the cells a compound of formula I or a composition thereof. In some embodiments, the present invention provides a method for inducing cell death, comprising administering to the cells a compound of formula II or a composition thereof. In some embodiments, the present invention provides a method for inducing apoptosis. In some embodiments, the present invention provides a method for inducing apoptosis, comprising administering to the cells a compound of formula I or a composition thereof. In some embodiments, the present invention provides a method for inducing apoptosis, comprising administering to the cells a compound of formula II or a composition thereof. In some embodiments, the present invention provides a method for inhibiting cell growth. In some embodiments, the present invention provides a method for inhibiting cell growth, comprising administering to the cells a compound of formula I or a composition thereof. In some embodiments, the present invention provides a method for inhibiting cell growth, comprising administering to the cells a compound of formula II or a composition thereof. In some embodiments, the cells in a provided method are resistant to Hsp90 inhibitors.

In some embodiments, the present invention provides a method of treating a subject suffering from or susceptible to a disease, disorder, or condition responsive to Hsp70 inhibition comprising administering to the subject a therapeutically effective amount of a compound of formula I or a composition thereof. In some embodiments, the present invention provides a method of treating a subject suffering from or susceptible to a disease, disorder, or condition responsive to Hsp70 inhibition, comprising administering to the subject a therapeutically effective amount of a compound of formula II or a composition thereof.

In some embodiments, the present invention provides a method for treating or preventing cancer in a subject suffering therefrom. In some embodiments, the present invention provides a method for treating or preventing cancer in a subject suffering therefrom, comprising administering to a patient in need thereof a therapeutically effective amount of a compound of formula I or a composition thereof. In some embodiments, the present invention provides a method for treating or preventing cancer in a subject suffering therefrom, comprising administering to a patient in need thereof a therapeutically effective amount of a compound of formula II or a composition thereof. In some embodiments, a cancer in a provided method is refractory to treatment with Hsp90 inhibitors.

DEFINITIONS

Figure 1:
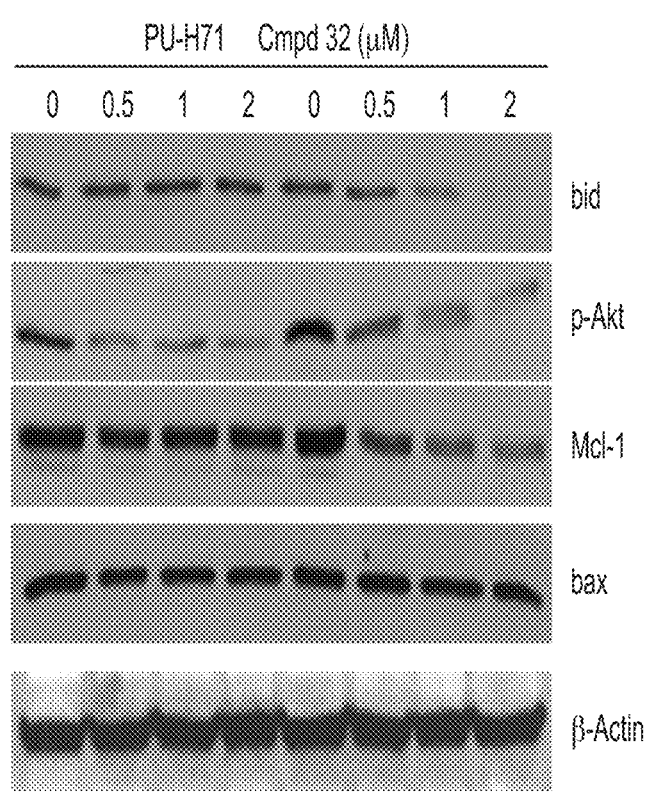
FIG. 1. A: Hsp70 regulates several anti-apoptotic protein complexes; effects reverted by compound 32 treatment. MDA-MB-468 triple negative breast cancer cells were treated with the Hsp70 inhibitor compound 32 or the Hsp90 inhibitor PU-H71 and proteins were analyzed by Western blot. B: Compound 32 retains activity in diffuse large B-cell lymphoma (DLBCL) cells with induced resistance to PU-H71. C: The spectrum of PU-H71 and compound 32—sensitive DLBCLs does not overlap.
Figure 1:
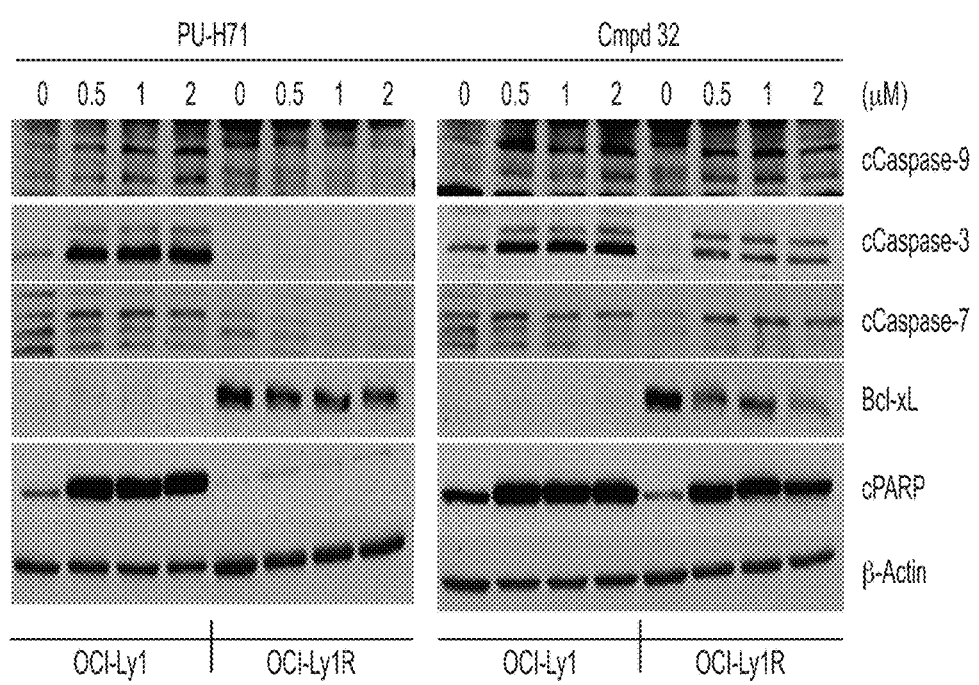
Figure 1:
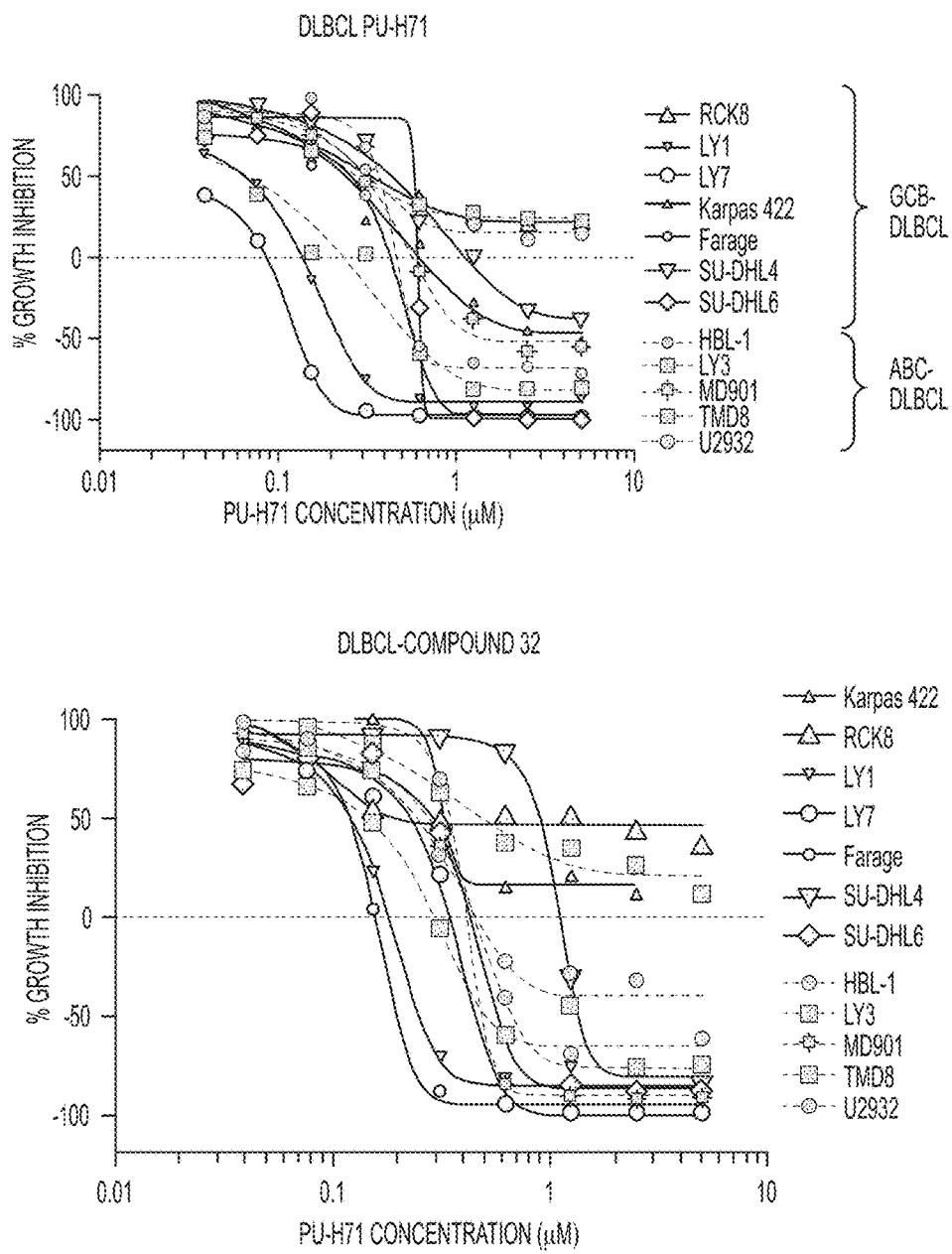

Certain compounds of the present disclosure, and definitions of specific functional groups are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic, bicyclic or polycyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "haloalkyl" refers to an alkyl group substituted with one or more halogen.

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

The term "halogen" means F, Cl, Br, or I.

The term "aryl" used alone or as part of a larger moiety as in "aralkyl," "aralkoxy," or "aryloxyalkyl," refers to monocyclic, bicyclic or polycyclic ring systems having a total of five to fourteen ring members, wherein at least one ring in the system is aromatic and wherein each ring in the system contains 3 to 7 ring members. The term "aryl" may be used interchangeably with the term "aryl ring."

In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted.

As used herein, the terms "heterocycle," "heterocyclyl," "heterocyclic radical," and "heterocyclic ring" are used interchangeably and refer to a stable 3- to 14-membered monocyclic or 7-14-membered bicyclic or polycyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

In another aspect, the present disclosure provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure.

If, for instance, a particular enantiomer of a compound of the present disclosure is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this disclosure. Such compounds are useful, for example, as analytical tools, as probes in biological assays, or as therapeutic agents in accordance with the present disclosure.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fern), N-2-picolylamino N'-oxide, N-1,1-dimethylthiomethyleneamine, N-benzylideneamine, N-p-methoxybenzylideneamine, N-diphenylmethyleneamine, N-[(2-pyridyl) mesityl]methyleneamine, N—(N',N'-dimethylaminomethylene)amine,N,N'-isopropylidenediamine, N-p-nitrobenzylideneamine, N-salicylideneamine, N-5-chlorosalicylideneamine, N-(5- chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzyl sulfonamide, trifluoromethylsulfonamide, and phenacylsulfonamide. Exemplary protecting groups are detailed herein, however, it will be appreciated that the present disclosure is not intended to be limited to these protecting groups; rather, a variety of additional equivalent protecting groups can be readily identified using the above criteria and utilized in the method of the present disclosure. Additionally, a variety of protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Unless otherwise indicated, suitable monovalent substituents on a substitutable carbon atom of an "optionally substituted" group are independently halogen, $C_{1-4}$ alkyl or $C_{1-4}$ haloalkyl.

When used as a chemical bond, " ⌇ " shall be understood to depict a single carbon-carbon bond with undefined stereochemistry at a carbon center. Thus, a substituent attached to a carbon atom with a " ⌇ " bond refers to embodiments where the substituent is coming out of the plane of the paper, embodiments where the substituent is going behind the plane of the paper, and combinations (i.e., stereochemical mixtures) thereof.

As used herein and in the claims, the singular forms "a", "an", and "the" include the plural reference unless the context clearly indicates otherwise. Thus, for example, a reference to "a compound" includes a plurality of such compounds.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

The expression "unit dose" as used herein refers to a physically discrete unit of a formulation appropriate for a subject to be treated. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. A particular unit dose may or may not contain a therapeutically effective amount of a therapeutic agent.

An individual who is "suffering from" a disease, disorder, and/or condition has been diagnosed with and/or displays one or more symptoms of the disease, disorder, and/or condition.

An individual who is "susceptible to" a disease, disorder, and/or condition has not been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

DETAILED DESCRIPTION OF CERTAIN EMBODIMENTS

The present invention encompasses the recognition that the design of potent and effective modulators of Hsp70 is a challenging endeavor given the lack of natural products known to bind Hsp70, and the general competitive and binding pocket difficulties faced by candidate modulators, particularly in the case of reversible Hsp70 modulators.

The present invention provides, among other things, novel compounds for use in the modulation of Hsp70. In some embodiments, the present invention provides unexpectedly effective reversible inhibitors of Hsp70. Certain irreversible pyrimidine-based derivatives have been previously shown to selectively bind Hsp70 present in cancer cells, induce degradation of Hsp90/Hsp70 complex oncoclient proteins without feedback induction of Hsp70, and induce apoptosis (see, for example, WO 2011/022440). However, prior to the present invention, pyrimidine-based compounds have not been demonstrated to show activity in certain Hsp70 model systems below a concentration of about 1.0 uM. The present invention surprisingly provides compounds that show activity in such model systems at concentrations below about 1.0 uM. In some embodiments, provided compounds show activity in such model systems at concentrations below about 0.5 uM. In some embodiments, provided compounds show activity in such model systems at concentrations below about 0.4 uM. In some embodiments, provided compounds show activity in such model systems at concentrations below about 0.2 uM. In some embodiments, provided compounds show activity in such model systems at concentrations below about 0.1 uM. In some embodiments, provided compounds show activity in such model systems at concentrations below about 0.01 uM. In some embodiments, a model system in which provided compounds show these activities is a caspase cleavage assay.

In some embodiments, a provided compound of the present invention selectivily inhibits Hsp70 in tumor cells. In some embodiments, a provided compound selectively inhibits tumor-specific Hsp70 and/or Hsp70 complexes. Assays for testing selective inhibition of tumor-specific Hsp70 and/or Hsp70 complexes are widely known in the art, including but not limited to those described in WO 2011/022440.

In certain embodiments, the present invention provides compounds of formula I:

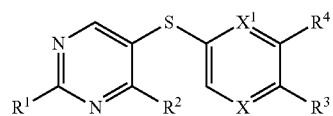

or a pharmaceutically acceptable salt thereof, wherein:

X is —N= or —CH=;

$X^1$ is —N= or —C($R^5$)=;

$R^1$ is

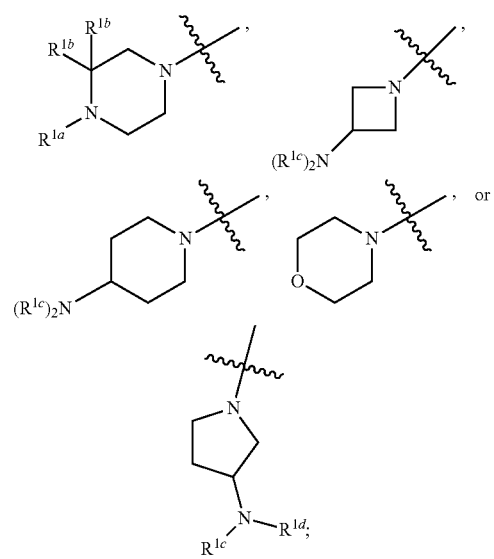

$R^{1a}$ is

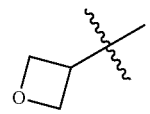 [SMILES: *C1COC1]

or $C_{1-6}$ aliphatic optionally substituted with one or more groups independently selected from —OH, cyclopropyl, or 5-membered heteroaryl having 1-2 heteroatoms independently selected from nitrogen, oxygen or sulfur;

each $R^{1b}$ is independently hydrogen, $C_{1-4}$ alkyl, or two $R^{1b}$ groups are optionally taken together to form an oxo group;

each of $R^{1c}$ and $R^{1d}$ is independently hydrogen or $C_{1-4}$ alkyl;

$R^2$ is —O—$CH_2$-Ring A, —NH—$CH_2$-Ring A, or —O—$CH_2CH_2$-Ring A;

Ring A is unsubstituted phenyl, unsubstituted furanyl,

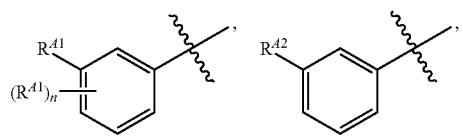

-continued

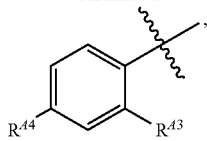

or pyridinyl optionally substituted with $R^{45}$;

each of $R^{41}$ is independently halogen, —CN, —C(O)N(R)$_2$, —N(R)$_2$, —OR, —C(O)R, —N$_3$, an optionally substituted 5- or 6-membered heterocyclyl or heteroaryl having one or two heteroatoms independently selected from nitrogen, oxygen, or sulfur, or $C_{1-4}$ alkyl optionally substituted with one or more halogen;

each R is independently hydrogen or $C_{1-4}$ alkyl optionally substituted with one or more halogen;

$R^{42}$ is —Cl, —Br, —I, —CN, —C(O)N(R)$_2$, —N(R)$_2$, —OR, —C(O)R, —N$_3$, an optionally substituted 5- or 6-membered heterocyclyl or heteroaryl having one or two heteroatoms independently selected from nitrogen, oxygen or sulfur, or $C_{1-4}$ alkyl optionally substituted with one or more halogen;

n is 1 to 4;

$R^{43}$ is —H or —F;

$R^{44}$ is —F or —OR;

$R^{45}$ is —OR or —N(R)$_2$;

$R^3$ is —C(O)N($R^{3a}$)$_2$, —OR$^{3b}$, —C(O)H, —C(O)OR, or —N($R^{3c}$)$_2$;

each $R^{3a}$ is independently hydrogen or $C_{1-4}$ alkyl optionally substituted with one or more groups independently selected from halogen or 1-pyrrolidinyl;

$R^{3b}$ is hydrogen or $C_{1-4}$ alkyl optionally substituted with one or more groups independently selected from halogen, $C_{1-4}$ alkyl, $C_{1-4}$ haloalkyl, oxo, or —N(R)$_2$;

each $R^{3c}$ is independently hydrogen or $C_{1-4}$ alkyl optionally substituted with one or more groups independently selected from halogen, $C_{1-4}$ alkyl, $C_{1-4}$ haloalkyl, oxo, or —N(R)$_2$;

$R^4$ is R, halogen, or —N(R)$_2$; and $R^5$ is hydrogen, methyl or —N(R)$_2$.

In certain embodiments, provided compounds of formula I have an activity in a caspase cleaving assay (e.g., measured as the concentration of a compound required to achieve 50% of maximum caspase cleavage) below about 1.0 µM. In certain embodiments, provided compounds of formula I have an activity in a caspase cleaving assay below about 0.5 µM. In certain embodiments, provided compounds of formula I have an activity in a caspase cleaving assay below about 0.4 µM. In certain embodiments, provided compounds of formula I have an activity in a caspase cleaving assay below about 0.2 µM. In certain embodiments, provided compounds of formula I have an activity in a caspase cleaving assay below about 0.1 µM. In certain embodiments, provided compounds of formula I have an activity in a caspase cleaving assay below about 0.01 µM.

In certain embodiments, the present invention provides compounds of formula II:

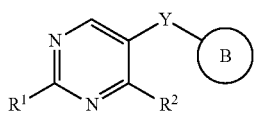

or a pharmaceutically acceptable salt thereof, wherein:
Y is —S—, —O—, or —CR$_2$—;
$R^1$ is

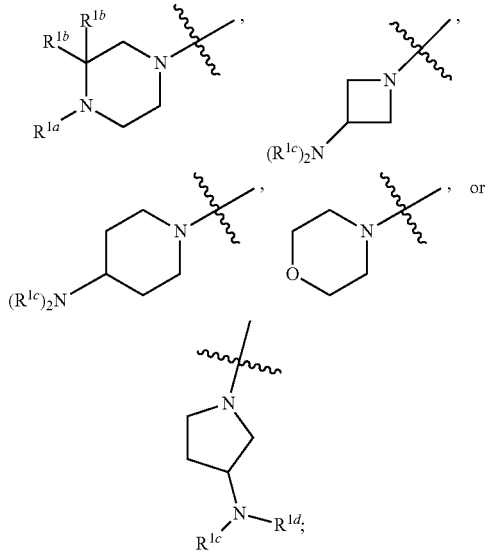

$R^{1a}$ is

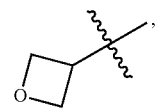

or $C_{1-6}$ aliphatic optionally substituted with one or more groups independently selected from —OH, cyclopropyl, or 5-membered heteroaryl having 1-2 heteroatoms independently selected from nitrogen, oxygen, or sulfur;

each $R^{1b}$ is independently hydrogen, $C_{1-4}$ alkyl, or two $R^{1b}$ groups are optionally taken together to form an oxo group;

each of $R^{1c}$ and $R^{1d}$ is independently hydrogen or $C_{1-4}$ alkyl;

$R^2$ is —O—CH$_2$-Ring A, —NH—CH$_2$-Ring A, or —O—CH$_2$CH$_2$-Ring A;

Ring A is unsubstituted phenyl, unsubstituted furanyl,

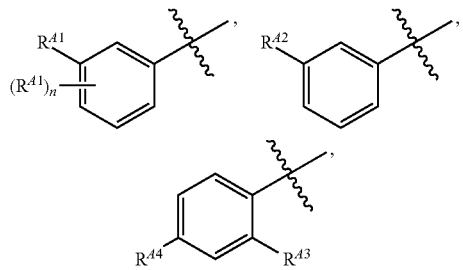

or pyridinyl optionally substituted with $R^{45}$;

each of $R^{41}$ is independently halogen, —CN, —C(O)N(R)$_2$, —N(R)$_2$, —OR, —C(O)R, —N$_3$, an optionally substituted 5- or 6-membered heterocyclyl or heteroaryl having one or two heteroatoms independently selected from nitrogen, oxygen, or sulfur, or $C_{1-4}$ alkyl optionally substituted with one or more halogen;

each R is independently hydrogen or $C_{1-4}$ alkyl optionally substituted with one or more halogen;

$R^{42}$ is —Cl, —Br, —I, —CN, —C(O)N(R)$_2$, —N(R)$_2$, —OR, —C(O)R, —N$_3$, an optionally substituted 5- or 6-membered heterocyclyl or heteroaryl having one or two heteroatoms independently selected from nitrogen, oxygen or sulfur, or $C_{1-4}$ alkyl optionally substituted with one or more halogen;

n is 1 to 4;

$R^{43}$ is —H or —F;

$R^{44}$ is —F or —OR;

$R^{45}$ is —OR or —N(R)$_2$; and

Ring B is

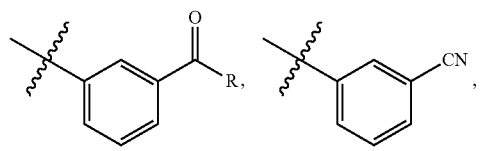

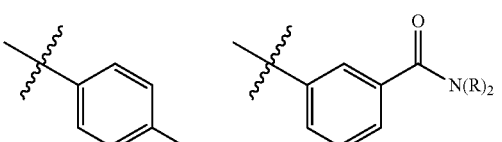

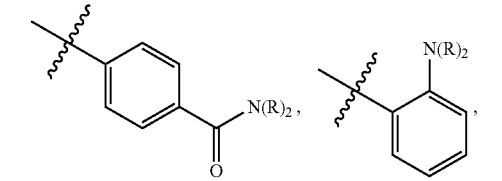

thienyl optionally substituted with —C(O)R, or furanyl optionally substituted with —C(O)R.

In certain embodiments, provided compounds of formula II have an activity in a caspase cleaving assay below about 1.0 μM. In certain embodiments, provided compounds of formula II have an activity in a caspase cleaving assay below about 0.5 μM. In certain embodiments, provided compounds of formula II have an activity in a caspase cleaving assay below about 0.4 μM. In certain embodiments, provided compounds of formula II have an activity in a caspase cleaving assay below about 0.2 μM. In certain embodiments, provided compounds of formula II have an activity in a caspase cleaving assay below about 0.1 μM. In certain embodiments, provided compounds of formula II have an activity in a caspase cleaving assay below about 0.01 μM.

In some embodiments, X is —N═. In some embodiments, X is —CH═.

In some embodiments, $X^1$ is —N═. In some embodiments, X is —C(R$^5$)═. In some embodiments, X is —C(R$^5$)═, wherein R$^5$ is hydrogen. In some embodiments, X is —C(R$^5$)═, wherein R$^5$ is methyl. In some embodiments, X is —C(R$^5$)═, wherein R$^5$ is —N(R)$_2$. In some embodiments, X is —C(R$^5$)═, wherein R$^5$ is —NH$_2$.

In some embodiments, $R^1$ is

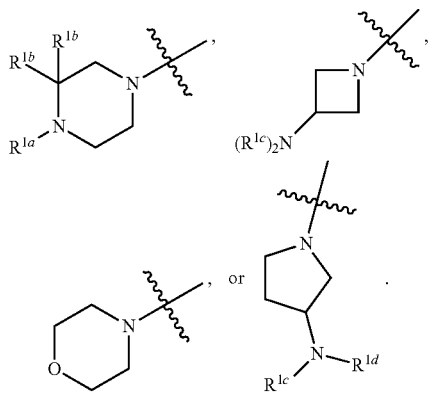

In some embodiments, $R^1$ is

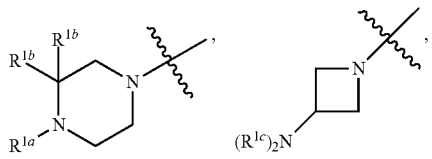

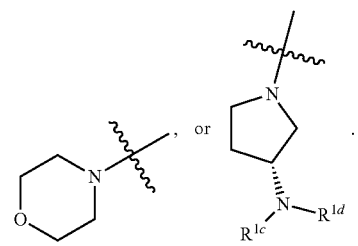

In some embodiments, $R^1$ is

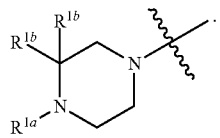

In some embodiments, $R^1$ is

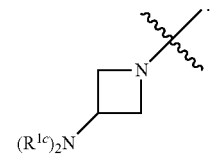

In some embodiments, $R^1$ is

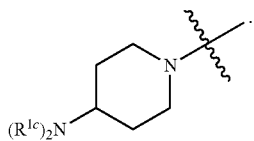

In some embodiments, $R^1$ is

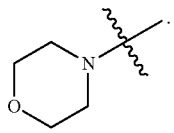 [SMILES: *N1CCOCC1]

In some embodiments, $R^1$ is

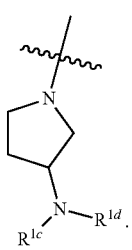

In some embodiments, $R^1$ is

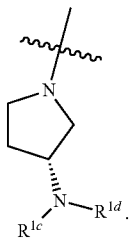

In some embodiments, $R^1$ is

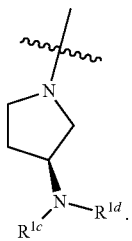

In some embodiments, $R^1$ is

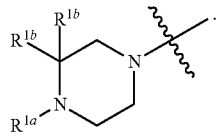

In some embodiments, each $R^{1b}$ is hydrogen. In some embodiments, $R^1$ is

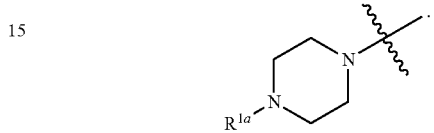

In some embodiments, $R^1$ is

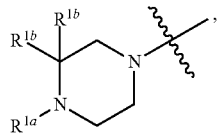

wherein each $R^{1b}$ is independently $C_{1-4}$ alkyl. In some embodiments, two $R^{1b}$ are taken together to form an oxo group. In some embodiments, $R^1$ is

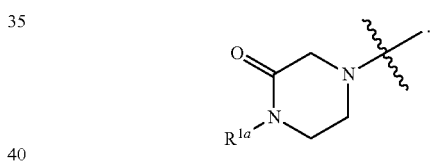

In some embodiments, $R^1$ is

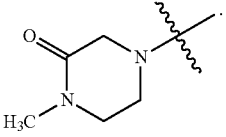

In some embodiments, $R^{1a}$ is

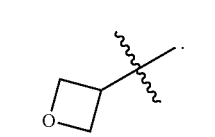

In some embodiments, $R^{1a}$ is $C_{1-6}$ aliphatic optionally substituted with one or more groups independently selected from —OH, cyclopropyl, or 5-membered heteroaryl having 1-2 heteroatoms independently selected from nitrogen, oxygen or sulfur. In some embodiments, $R^{1a}$ is $C_{1-6}$ straight chain aliphatic optionally substituted with one or more groups independently selected from —OH, cyclopropyl, or 5-membered heteroaryl having 1-2 heteroatoms independently selected from nitrogen, oxygen or sulfur. In some embodiments, $R^{1a}$ is $C_{1-6}$ straight chain aliphatic optionally substituted with one group independently selected from —OH, cyclopropyl, or 5-membered heteroaryl having 1-2 heteroatoms independently selected from nitrogen, oxygen or sulfur.

In some embodiments, $R^{1a}$ is $C_{1-6}$ aliphatic. In some embodiments, $R^{1a}$ is straight-chain $C_{1-6}$ aliphatic. In some embodiments, $R^{1a}$ is straight-chain $C_{1-6}$ alkyl. In some embodiments, $R^{1a}$ is methyl. In some embodiments, $R^{1a}$ is straight-chain alkenyl. In some embodiments, $R^{1a}$ is —CH$_2$CH=CH$_2$. In some embodiments, $R^{1a}$ is straight-chain $C_{1-6}$ alkynyl. In some embodiments, $R^{1a}$ is —(CH$_2$)$_n$C≡CH, wherein n is 1-4. In some embodiments, $R^{1a}$ is —CH$_2$C≡CH. In some embodiments, $R^{1a}$ is —(CH$_2$)$_3$C≡CH. In some embodiments, $R^{1a}$ is —(CH$_2$)$_4$C≡CH. In some embodiments, $R^{1a}$ is —CH$_2$C≡CCH$_2$OH.

In some embodiments, $R^{1a}$ is branched chain $C_{1-6}$ aliphatic. In some embodiments, $R^{1a}$ is branched chain alkynyl. In some embodiments, $R^{1a}$ is branched chain alkynyl with a terminal —C≡CH group. In some embodiments, $R^{1a}$ is —CH(CH$_3$)C≡CH. In some embodiments, $R^{1a}$ is isopropyl.

In some embodiments, $R^{1a}$ is $C_{1-6}$ straight chain aliphatic substituted with one group independently selected from —OH, cyclopropyl, or 5-membered heteroaryl having 1-2 heteroatoms independently selected from nitrogen, oxygen or sulfur. In some embodiments, $R^{1a}$ is methyl substituted with a cyclopropyl group, or a 5-membered heteroaryl having 1-2 heteroatoms independently selected nitrogen, oxygen or sulfur. In some embodiments, $R^{1a}$ is methyl substituted with cyclopropyl. In some embodiments, $R^{1a}$ is methyl substituted with a 5-membered heteroaryl having 1-2 heteroatoms independently selected nitrogen, oxygen or sulfur. In some embodiments, $R^{1a}$ is methyl substituted with

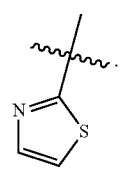

In some embodiments, $R^{1a}$ is methyl substituted with

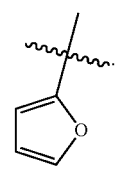 [SMILES: *c1ccco1]

In some embodiments, $R^{1a}$ is methyl substituted with

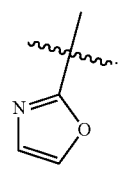 [SMILES: *c1ncco1]

In some embodiments, $R^{1a}$ is 2-hydroxyethyl.

In some embodiments, $R^{1a}$ is $C_{1-6}$ cycloaliphatic. In some embodiments, $R^{1a}$ is cyclopropyl.

In some embodiments, $R^{1a}$ is selected from methyl, 2-hydroxyethyl, —CH$_2$C≡CH, —(CH$_2$)$_3$C≡CH, —(CH$_2$)$_4$C≡CH, —CH(CH$_3$)C≡CH, isopropyl, —CH$_2$CH=CH$_2$,

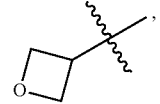 [SMILES: *C1COC1]

cyclopropyl,

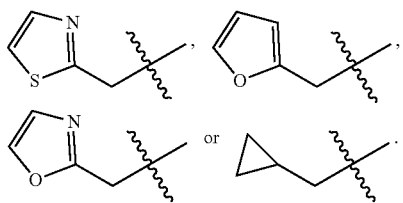

In some embodiments, $R^{1a}$ is selected from methyl, 2-hydroxyethyl, —CH$_2$C≡CH, —(CH$_2$)$_3$C≡CH, —(CH$_2$)$_4$C≡CH, —CH(CH$_3$)C≡CH, isopropyl, —CH$_2$CH=CH$_2$,

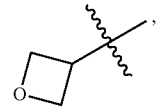 [SMILES: *C1COC1]

cyclopropyl,

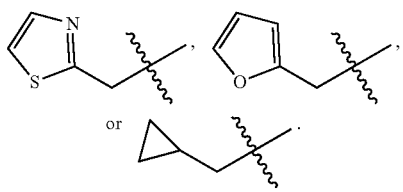

In some embodiments, $R^{1a}$ is selected from methyl, 2-hydroxyethyl, —CH$_2$C≡CH, —(CH$_2$)$_3$C≡CH, —(CH$_2$)$_4$C≡CH, —CH(CH$_3$)C≡CH, —CH$_2$CH=CH$_2$,

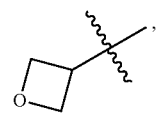 [SMILES: *C1COC1]

cyclopropyl,

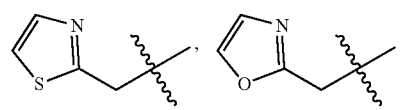

or 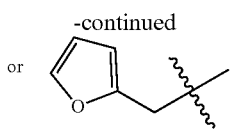

In some embodiments, $R^{1a}$ is selected from methyl, 2-hydroxyethyl, —$CH_2C\equiv CH$, —$(CH_2)_3C\equiv CH$, —$(CH_2)_4C\equiv CH$, —$CH(CH_3)C\equiv CH$, —$CH_2CH=CH_2$,

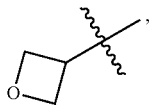 [SMILES: *C1COC1]

cyclopropyl,

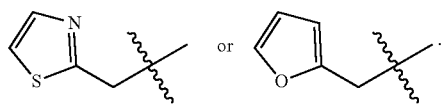 [SMILES: *Cc1nccs1 ; *Cc1ccco1] or .

In some embodiments, $R^{1a}$ does not place a quaternary carbon adjacent to the piperazine nitrogen attachment point.

In some embodiments, each $R^{1b}$ is independently hydrogen, or two $R^{1b}$ groups are optionally taken together to form an oxo group. In some embodiments, each $R^{1b}$ is hydrogen.

In some embodiments, $R^{1b}$ is $C_{1-4}$ alkyl. In some embodiments, each $R^{1b}$ is $C_{1-4}$ alkyl. In some embodiments, each $R^{1b}$ is methyl. In some embodiments, $R^1$ is

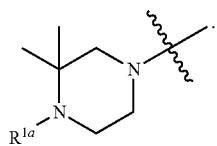

In some embodiments, $R^1$ is

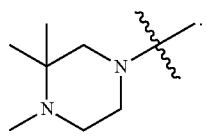 [SMILES: *N1CCN(C)C(C)(C)C1]

In some embodiments, two $R^{1b}$ groups are optionally taken together to form an oxo group.

In some embodiments, $R^1$ is

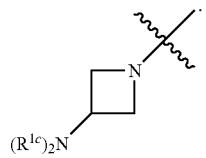

In some embodiments, $R^1$ is

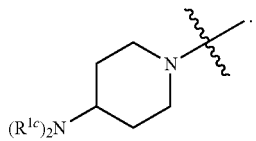

In some embodiments, each $R^{1c}$ is independently hydrogen or $C_{1-4}$ alkyl. In some embodiments, $R^{1c}$ is hydrogen. In some embodiments, $R^{1c}$ is $C_{1-4}$ alkyl. In some embodiments, $R^{1c}$ is methyl. In some embodiments, each $R^{1c}$ is hydrogen. In some embodiments, one $R^{1c}$ is hydrogen, and the other $R^{1c}$ is $C_{1-4}$ alkyl. In some embodiments, each $R^{1c}$ is independently $C_{1-4}$ alkyl. In some embodiments, each $R^{1c}$ is methyl. In some embodiments, $R^1$ is

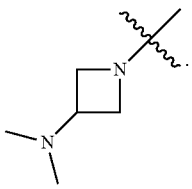 [SMILES: *N1CC(N(C)C)C1]

In some embodiments, $R^1$ is

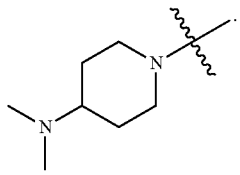 [SMILES: *N1CCC(N(C)C)CC1]

In some embodiments, $R^1$ is

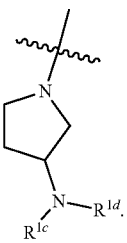

In some embodiments, $R^{1d}$ is hydrogen or $C_{1-4}$ alkyl. In some embodiments, $R^{1d}$ is hydrogen. In some embodiments, $R^{1d}$ is $C_{1-4}$ alkyl. In some embodiments, $R^{1d}$ is methyl. In some embodiments, each $R^{1c}$ is independently hydrogen or $C_{1-4}$ alkyl, and each $R^{1d}$ is independently $C_{1-4}$ alkyl.

In some embodiments, $R^1$ is

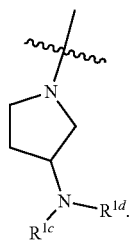

In some embodiments, $R^1$ is

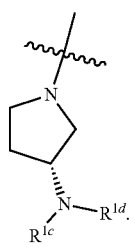

In some embodiments, $R^1$ is

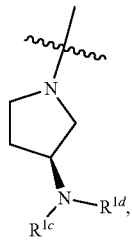

wherein each of $R^{1c}$ and $R^{1d}$ is independently hydrogen or $C_{1-4}$ alkyl.

In some embodiments, each of $R^{1c}$ and $R^{1d}$ is hydrogen. In some embodiments, $R^1$ is

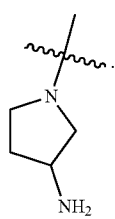

In some embodiments, $R^1$ is

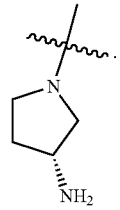

In some embodiments, $R^1$ is

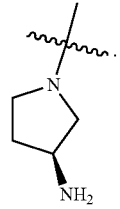

In some embodiments, $R^{1c}$ is hydrogen or $C_{1-4}$ alkyl, and $R^{1d}$ is $C_{1-4}$ alkyl. In some embodiments, $R^1$ is

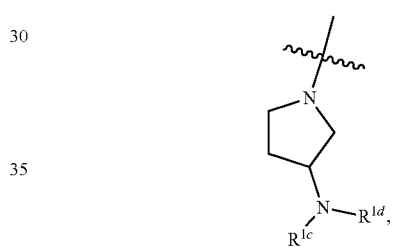

wherein $R^{1c}$ is hydrogen or $C_{1-4}$ alkyl, and $R^{1d}$ is $C_{1-4}$ alkyl. In some embodiments, $R^1$ is

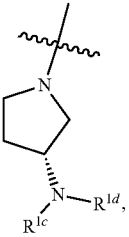

wherein $R^{1c}$ is hydrogen or $C_{1-4}$ alkyl, and $R^{1d}$ is $C_{1-4}$ alkyl. In some embodiments, $R^1$ is

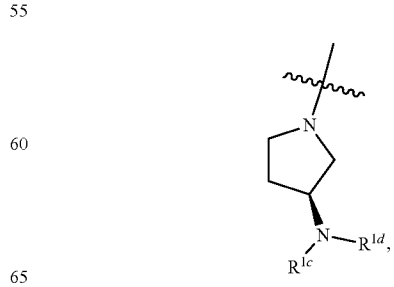

wherein $R^{1c}$ is hydrogen or $C_{1-4}$ alkyl, and $R^{1d}$ is $C_{1-4}$ alkyl.

In some embodiments, $R^{1c}$ is hydrogen, and $R^{1d}$ is $C_{1-4}$ alkyl. In some embodiments, $R^1$ is

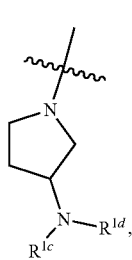

wherein $R^{1c}$ is hydrogen, and $R^{1d}$ is $C_{1-4}$ alkyl. In some embodiments, $R^1$ is

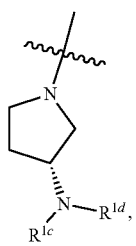

wherein $R^{1c}$ is hydrogen, and $R^{1d}$ is $C_{1-4}$ alkyl. In some embodiments, $R^1$ is

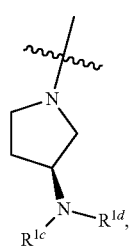

wherein $R^{1c}$ is hydrogen, and $R^{1d}$ is $C_{1-4}$ alkyl. In some embodiments, $R^{1c}$ is hydrogen, and $R^{1d}$ is methyl. In some embodiments, $R^1$ is

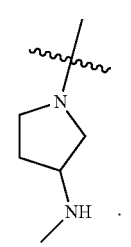

In some embodiments, $R^1$ is

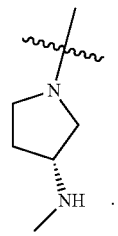

In some embodiments, $R^1$ is

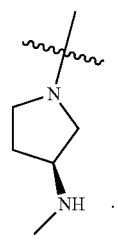

In some embodiments, each of $R^{1c}$ and $R^{1d}$ is independently $C_{1-4}$ alkyl. In some embodiments, $R^1$ is

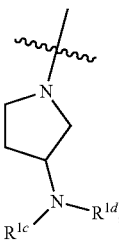

wherein each of $R^{1c}$ and $R^{1d}$ is independently $C_{1-4}$ alkyl. In some embodiments, $R^1$ is

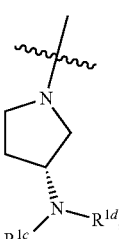

wherein each of $R^{1c}$ and $R^{1d}$ is independently $C_{1-4}$ alkyl. In some embodiments, $R^1$ is

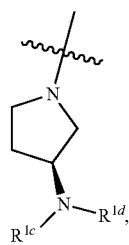
wherein each of $R^{1c}$ and $R^{1d}$ is independently $C_{1-4}$ alkyl. In some embodiments, $R^{1c}$ and $R^{1d}$ are methyl. In some embodiments, $R^1$ is
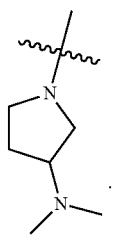 [SMILES: *N1CCC(N(C)C)C1]
In some embodiments, $R^1$ is
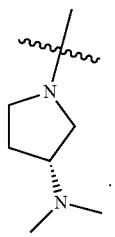 [SMILES: *N1CC[C@@H](N(C)C)C1]
In some embodiments, $R^1$ is
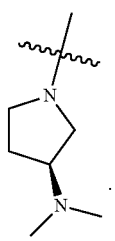 [SMILES: *N1CC[C@H](N(C)C)C1]
Exemplary $R^1$ groups are depicted below:
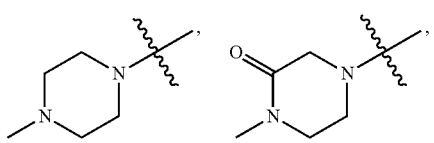
-continued
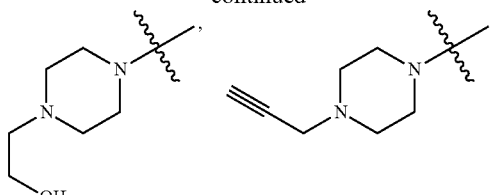
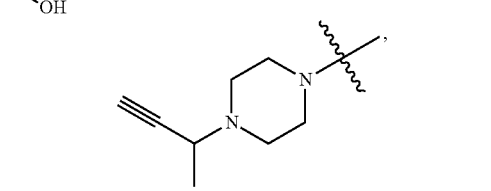
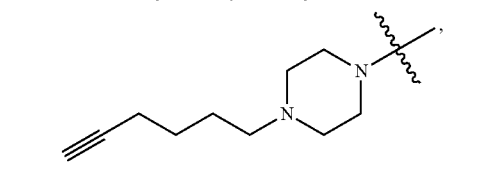 [SMILES: *N1CCN(CCCCC#C)CC1]
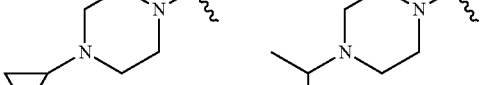
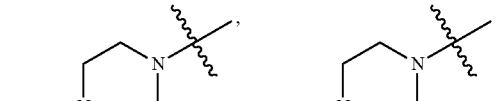
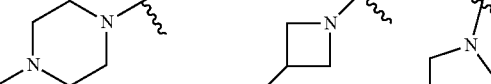
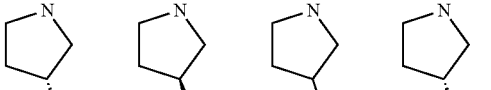

-continued

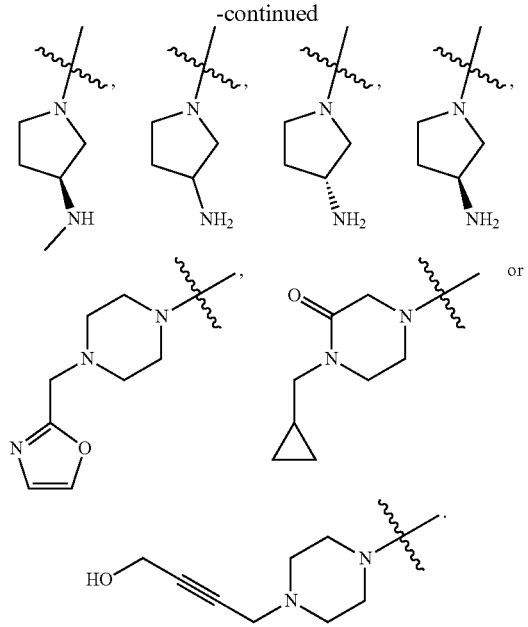

In some embodiments, $R^1$ is selected from a group in Table 1, below.

TABLE 1

Exemplary $R^1$ groups.

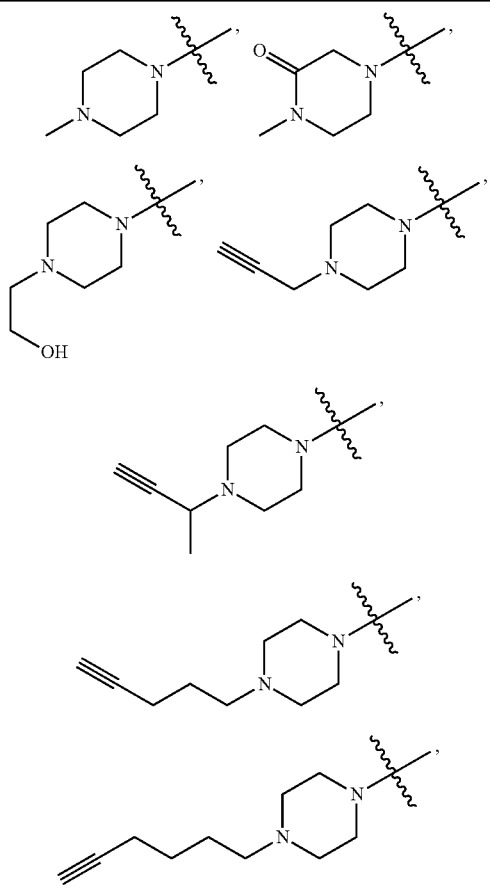

TABLE 1-continued

Exemplary $R^1$ groups.

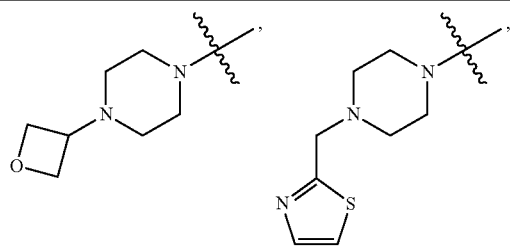

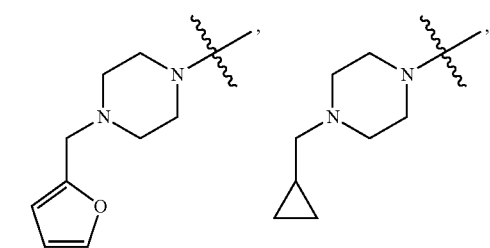 [SMILES: *N1CCN(Cc2ccco2)CC1 ; *N1CCN(CC2CC2)CC1]

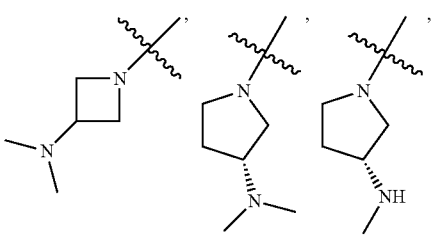

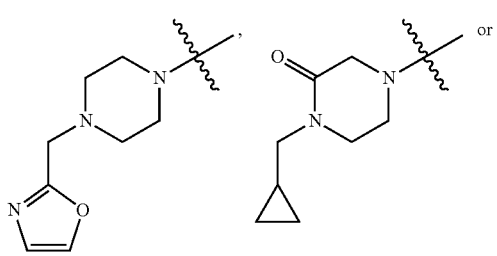 [SMILES: *N1CCN(Cc2ncco2)CC1 ; *N1CCN(CC2CC2)C(=O)C1]

In some embodiments, $R^2$ is —O—CH$_2$-Ring A, —NH—CH$_2$-Ring A, or —O—CH$_2$CH$_2$-Ring A. In some embodiments, $R^2$ is —O—CH$_2$-Ring A. In some embodiments, $R^2$ is —NH—CH$_2$-Ring A. In some embodiments, $R^2$ is —O—CH$_2$CH$_2$-Ring A.

In some embodiments, Ring A is unsubstituted phenyl. In some embodiments, Ring A is unsubstituted furanyl. In some embodiments, Ring A is

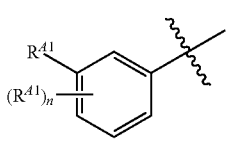

In some embodiments, Ring A is

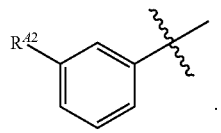

In some embodiments, Ring A is

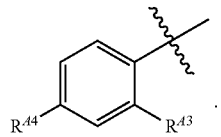

In some embodiments, Ring A is pyridinyl optionally substituted with $R^{A5}$.

In some embodiments, Ring A is phenyl. In some embodiments, Ring A is $-C_6D_5$. In some embodiments, $R^2$ is

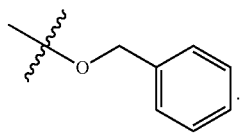 [SMILES: *OCc1ccccc1]

In some embodiments, $R^2$ is

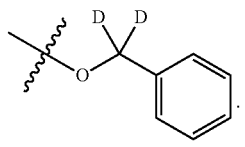 [SMILES: *OC([2H])([2H])c1ccccc1]

In some embodiments, $R^2$ is

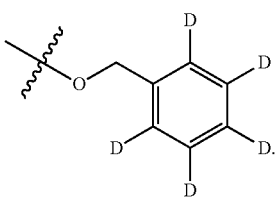

In some embodiments, Ring A is furanyl. In some embodiments, Ring A is 1-furanyl. In some embodiments, Ring A is 2-furanyl. In some embodiments, $R^2$ is

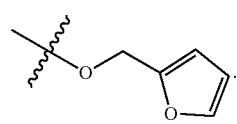 [SMILES: *OCc1ccco1]

In some embodiments, $R^2$ is

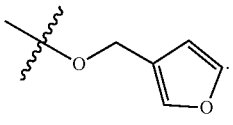 [SMILES: *OCc1ccoc1]

In some embodiments, Ring A is

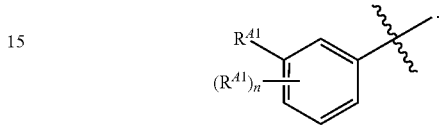

In some embodiments, each of $R^{A1}$ is independently halogen, —CN, —C(O)N(R)$_2$, —N(R)$_2$, —OR, —C(O)R, —N$_3$, an optionally substituted 5- or 6-membered heterocyclyl or heteroaryl having one or two heteroatoms independently selected from nitrogen, oxygen, or sulfur, or $C_{1-4}$ alkyl optionally substituted with one or more halogen. In some embodiments, each of $R^{A1}$ is independently halogen, —CN, —C(O)N(R)$_2$, —N(R)$_2$, —OR, —C(O)R, —N$_3$, a 5- or 6-membered heterocyclyl or heteroaryl having one or two heteroatoms independently selected from nitrogen, oxygen, or sulfur, or $C_{1-4}$ alkyl optionally substituted with one or more halogen. In some embodiments, each of $R^{A1}$ is independently halogen, —CN, —C(O)N(R)$_2$, —N(R)$_2$, —OR, —C(O)R, —N$_3$, or $C_{1-4}$ alkyl optionally substituted with one or more halogen. In some embodiments, each of $R^{A1}$ is independently halogen, —N(R)$_2$, —OR, or $C_{1-4}$ alkyl optionally substituted with one or more halogen.

In certain embodiments, one $R^{A1}$ is —F, and the other $R^{A1}$ is independently halogen, —CN, —C(O)N(R)$_2$, —N(R)$_2$, —OR, —C(O)R, —N$_3$, an optionally substituted 5- or 6-membered heterocyclyl or heteroaryl having one or two heteroatoms independently selected from nitrogen, oxygen, or sulfur, or $C_{1-4}$ alkyl optionally substituted with one or more halogen. In certain embodiments, one $R^{A1}$ is —F, and the other $R^{A1}$ is independently halogen, —CN, —C(O)N(R)$_2$, —N(R)$_2$, —OR, —C(O)R, —N$_3$, a 5- or 6-membered heterocyclyl or heteroaryl having one or two heteroatoms independently selected from nitrogen, oxygen, or sulfur, or $C_{1-4}$ alkyl optionally substituted with one or more halogen. In certain embodiments, one $R^{A1}$ is —F, and the other $R^{A1}$ is independently halogen, —CN, —C(O)N(R)$_2$, —N(R)$_2$, —OR, —C(O)R, —N$_3$, or $C_{1-4}$ alkyl optionally substituted with one or more halogen. In certain embodiments, one $R^{A1}$ is —F, and the other $R^{A1}$ is independently halogen, —N(R)$_2$, —OR, or $C_{1-4}$ alkyl optionally substituted with one or more halogen. In some embodiments, Ring A is

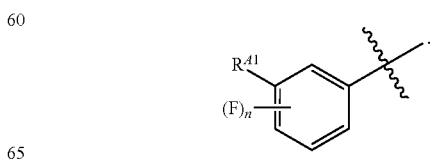

In some embodiments, Ring A is

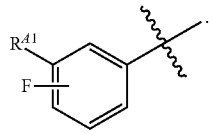

In certain embodiments, one $R^{A1}$ is $R^{A2}$, and the other $R^{A1}$ is independently halogen, —CN, —C(O)N(R)$_2$, —N(R)$_2$, —OR, —C(O)R, —N$_3$, an optionally substituted 5- or 6-membered heterocyclyl or heteroaryl having one or two heteroatoms independently selected from nitrogen, oxygen, or sulfur, or C$_{1-4}$ alkyl optionally substituted with one or more halogen. In certain embodiments, one $R^{A1}$ is $R^{A2}$, and the other $R^{A1}$ is halogen, —CN, —C(O)N(R)$_2$, —N(R)$_2$, —OR, —C(O)R, —N$_3$, a 5- or 6-membered heterocyclyl or heteroaryl having one or two heteroatoms independently selected from nitrogen, oxygen, or sulfur, or independently C$_{1-4}$ alkyl optionally substituted with one or more halogen. In certain embodiments, one $R^{A1}$ is $R^{A2}$, and the other $R^{A1}$ is independently halogen, —CN, —C(O)N(R)$_2$, —N(R)$_2$, —OR, —C(O)R, —N$_3$, or C$_{1-4}$ alkyl optionally substituted with one or more halogen. In certain embodiments, one $R^{A1}$ is $R^{A2}$, and the other $R^{A1}$ is independently halogen, —N(R)$_2$, —OR, or C$_{1-4}$ alkyl optionally substituted with one or more halogen. In some embodiments, Ring A is

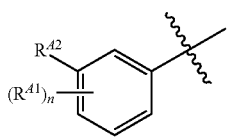

In some embodiments, Ring A is

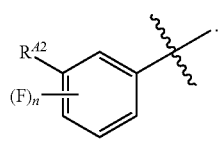

In some embodiments, Ring A is

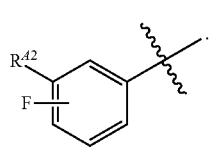

In some embodiments, $R^{A1}$ is C$_{1-4}$ alkyl optionally substituted with one or more halogen. In some embodiments, Ring A is

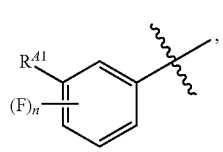

wherein $R^{A1}$ is C$_{1-4}$ alkyl optionally substituted with one or more halogen. In some embodiments, Ring A is

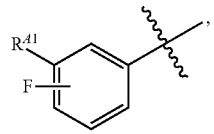

wherein $R^{A1}$ is C$_{1-4}$ alkyl optionally substituted with one or more halogen. In some embodiments, Ring A is

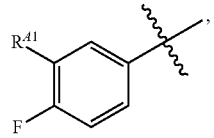

wherein $R^{A1}$ is C$_{1-4}$ alkyl optionally substituted with one or more halogen. In some embodiments, $R^{A1}$ is C$_{1-4}$ alkyl. In some embodiments, $R^{A1}$ is C$_{1-4}$ alkyl substituted with one or more halogen. In some embodiments, $R^{A1}$ is C$_{1-4}$ alkyl substituted with one or more —F. In some embodiments, $R^{A1}$ is —CF$_3$. In some embodiments, Ring A is

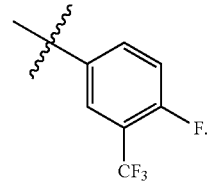

In some embodiments, $R^2$ is

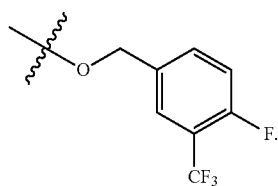 [SMILES: *OCc1ccc(F)c(C(F)(F)F)c1]

In some embodiments, $R^{A1}$ is halogen. In some embodiments, Ring A is

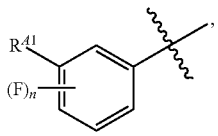

wherein $R^{A1}$ is halogen. In some embodiments, Ring A is

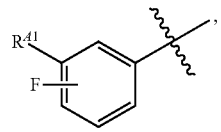

wherein $R^{A1}$ is halogen. In some embodiments, Ring A is

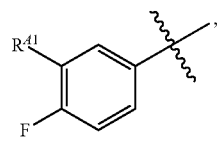

wherein $R^{A1}$ is halogen. In some embodiments, Ring A is

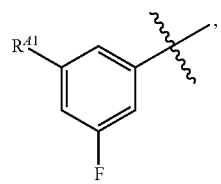

wherein $R^{A1}$ is halogen. In some embodiments, Ring A is

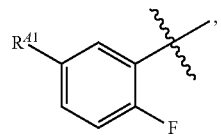

wherein $R^{A1}$ is halogen. In some embodiments, $R^{A1}$ is —F. In some embodiments, $R^{A1}$ is —Cl. In some embodiments, $R^{A1}$ is —Br. In some embodiments, $R^{A1}$ is —I. In some embodiments, one $R^{A1}$ is —F, and each of the other $R^{A1}$ groups is independently selected from —F, —Cl, —Br or —I. In some embodiments, Ring A is

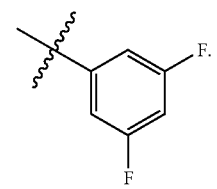 [SMILES: *c1cc(F)cc(F)c1]

In some embodiments, $R^2$ is

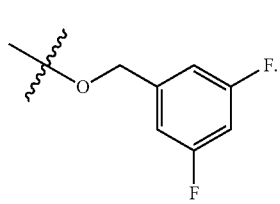

In some embodiments, Ring A is

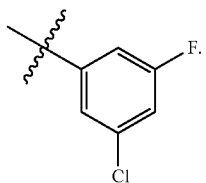 [SMILES: *c1cc(F)cc(Cl)c1]

In some embodiments, $R^2$ is

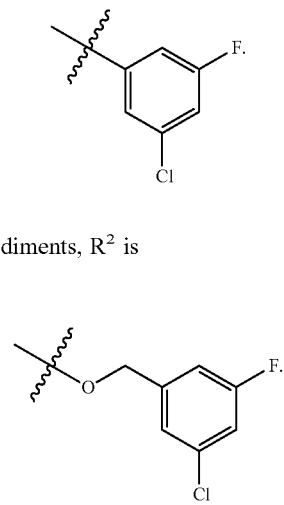

In some embodiments, Ring A is

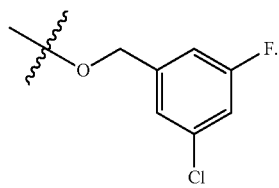 [SMILES: *OCc1cc(F)cc(Cl)c1]

In some embodiments, $R^2$ is

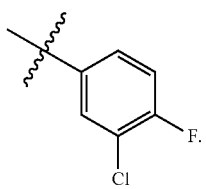

In some embodiments, Ring A is

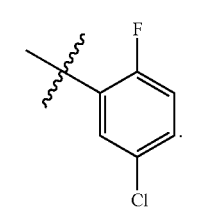 [SMILES: *c1cc(Cl)ccc1F]

In some embodiments, R² is

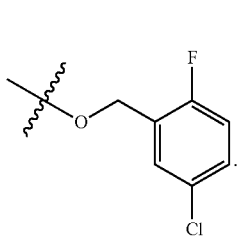 [SMILES: *OCc1cc(Cl)ccc1F]

In some embodiments, Ring A is

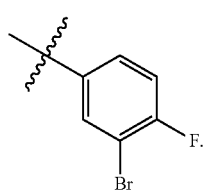 [SMILES: *c1ccc(F)c(Br)c1]

In some embodiments, R² is

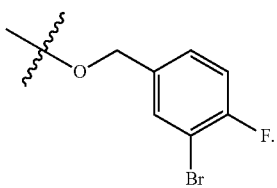 [SMILES: *OCc1ccc(F)c(Br)c1]

In some embodiments, $R^{A1}$ is —CN. In some embodiments, $R^{A1}$ is —C(O)N(R)₂.

In some embodiments, $R^{A1}$ is —N(R)₂. In some embodiments, $R^{A1}$ is —N(R)₂, wherein each R is independently C$_{1-4}$ alkyl optionally substituted with one or more halogen. In some embodiments, $R^{A1}$ is —N(R)₂, wherein each R is independently C$_{1-4}$ alkyl. In some embodiments, Ring A is

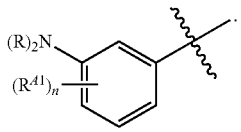

In some embodiments, Ring A is

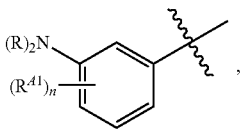

wherein each R is independently C$_{1-4}$ alkyl optionally substituted with one or more halogen. In some embodiments, Ring A is

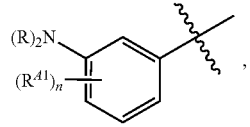

wherein each R is independently C$_{1-4}$ alkyl. In some embodiments, Ring A is

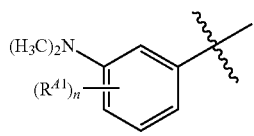

In some embodiments, Ring A is

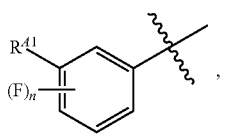

wherein $R^{A1}$ is —N(R)₂. In some embodiments, Ring A is

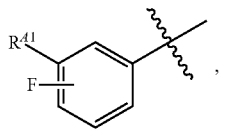

wherein $R^{A1}$ is —N(R)₂. In some embodiments, Ring A is

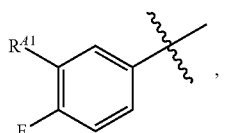

wherein $R^{A1}$ is —N(R)₂. In some embodiments, $R^{A1}$ is —NH₂. In some embodiments, Ring A is

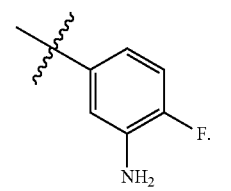 [SMILES: *c1ccc(F)c(N)c1]

In some embodiments, R² is

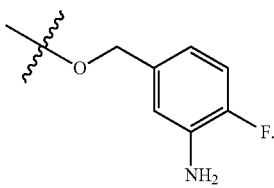 [SMILES: *OCc1ccc(F)c(N)c1]

In some embodiments, R$^{A1}$ is —N(CH$_3$)$_2$. In some embodiments, Ring A is

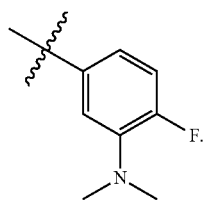 [SMILES: *c1ccc(F)c(N(C)C)c1]

In some embodiments, R² is

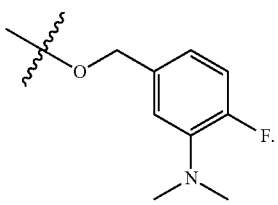 [SMILES: *OCc1ccc(F)c(N(C)C)c1]

In some embodiments, R$^{A1}$ is —OR. In some embodiments, Ring A is

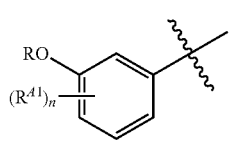

In some embodiments, Ring A is

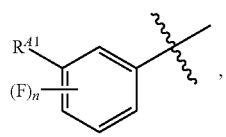

wherein R$^{A1}$ is —OR. In some embodiments, Ring A is

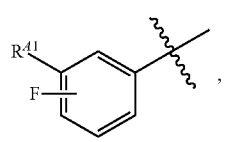

wherein R$^{A1}$ is —OR. In some embodiments, Ring A is

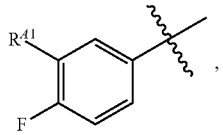

wherein R$^{A1}$ is —OR. In some embodiments, Ring A is

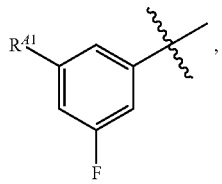

wherein R$^{A1}$ is —OR. In some embodiments, Ring A is

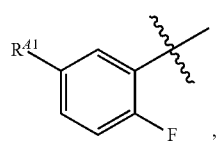

wherein R$^{A1}$ is —OR. In some embodiments, Ring A is

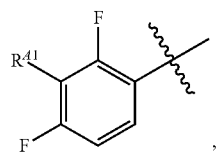

wherein R$^{A1}$ is —OR. In some embodiments, R$^{A1}$ is —OH. In some embodiments, Ring A is

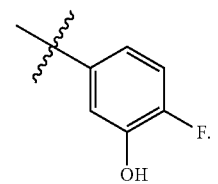 [SMILES: *c1ccc(F)c(O)c1]

In some embodiments, R² is

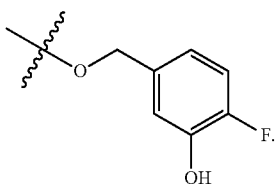 [SMILES: *OCc1ccc(F)c(O)c1]

In some embodiments, R$^{A1}$ is —OR, wherein R is C$_{1-4}$ alkyl optionally substituted with one or more halogen. In some embodiments, R$^{A1}$ is —OR, wherein R is C$_{1-4}$ alkyl. In some embodiments, $R^{A1}$ is —OR, wherein R is methyl. In some embodiments, $R^{A1}$ is —OMe. In some embodiments, Ring A is

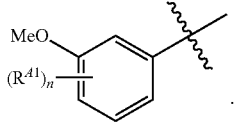

In some embodiments, Ring A is

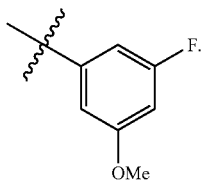 [SMILES: *c1cc(F)cc(OC)c1]

In some embodiments, $R^2$ is

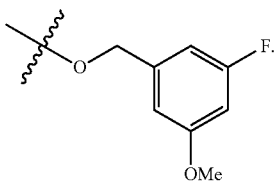 [SMILES: *OCc1cc(F)cc(OC)c1]

In some embodiments, Ring A is

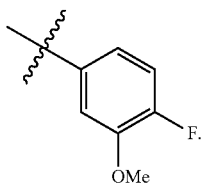 [SMILES: *c1ccc(F)c(OC)c1]

In some embodiments, $R^2$ is

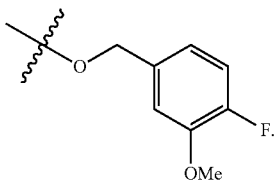 [SMILES: *OCc1ccc(F)c(OC)c1]

In some embodiments, Ring A is

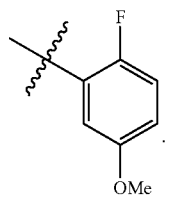

In some embodiments, $R^2$ is

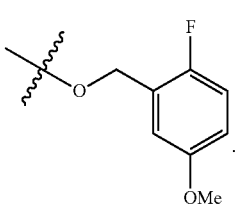 [SMILES: *OCc1cc(OC)ccc1F]

In some embodiments, Ring A is

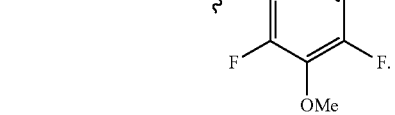

In some embodiments, $R^2$ is

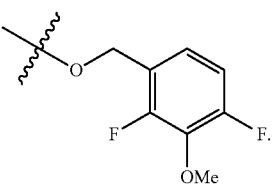 [SMILES: *OCc1ccc(F)c(OC)c1F]

In some embodiments, n is 1-4. In some embodiments, n is 1-2. In some embodiments, n is 1-3. In some embodiments, n is 2-3. In some embodiments, n is 2-4. In some embodiments, n is 1. In some embodiments, n is 2. In some embodiments, n is 3. In some embodiments, n is 4.

In some embodiments, Ring A is

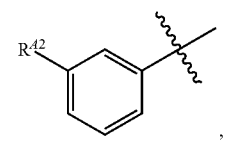

wherein $R^{A2}$ is —F, —Cl, —Br, —I, —CN, —C(O)N(R)$_2$, —N(R)$_2$, —OR, —C(O)R, —N$_3$, an optionally substituted 5- or 6-membered heterocyclyl or heteroaryl having one or two heteroatoms independently selected from nitrogen, oxygen or sulfur, or $C_{1-4}$ alkyl optionally substituted with one or more halogen. In some embodiments, Ring A is

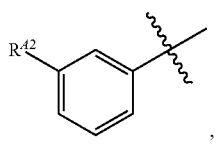

wherein $R^{A2}$ is —Cl, —Br, —I, —CN, —C(O)N(R)$_2$, —N(R)$_2$, —OR, —C(O)R, —N$_3$, a 5- or 6-membered heterocyclyl or heteroaryl having one or two heteroatoms independently selected from nitrogen, oxygen or sulfur, or C$_{1-4}$ alkyl optionally substituted with one or more halogen. In some embodiments, $R^{A2}$ is —Cl, —I, —CN, —C(O)N(R)$_2$, —N(R)$_2$, —OR, —C(O)R, —N$_3$, an optionally substituted 5- or 6-membered heterocyclyl or heteroaryl having one or two heteroatoms independently selected from nitrogen, oxygen or sulfur, or C$_{1-4}$ alkyl optionally substituted with one or more halogen. In some embodiments, $R^{A2}$ is, —I, —CN, —C(O)N(R)$_2$, —N(R)$_2$, —OR, —C(O)R, —N$_3$, a 5- or 6-membered heterocyclyl or heteroaryl having one or two heteroatoms independently selected from nitrogen, oxygen or sulfur, or C$_{1-4}$ alkyl optionally substituted with one or more halogen.

In some embodiments, $R^{A2}$ is —Cl. In some embodiments, Ring A is

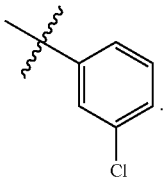 [SMILES: *c1cccc(Cl)c1]

In some embodiments, $R^2$ is

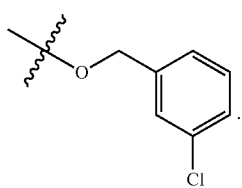 [SMILES: *OCc1cccc(Cl)c1]

In some embodiments, $R^{A2}$ is —I. In some embodiments, Ring A is

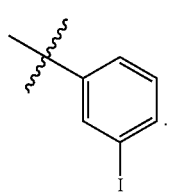 [SMILES: *c1cccc(I)c1]

In some embodiments, $R^2$ is

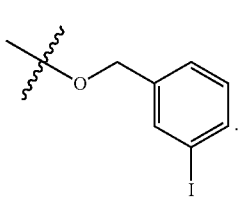

In some embodiments, $R^{A2}$ is —F. In some embodiments, $R^2$ is

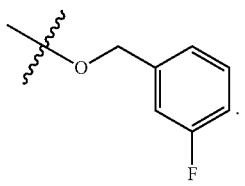 [SMILES: *OCc1cccc(I)c1]

In some embodiments, $R^{A2}$ is —Br. In some embodiments, $R^2$ is

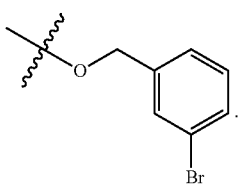 [SMILES: *OCc1cccc(F)c1]

In some embodiments, $R^{A2}$ is —CN. In some embodiments, Ring A is

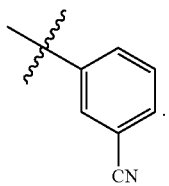 [SMILES: *c1cccc(C#N)c1]

In some embodiments, $R^2$ is

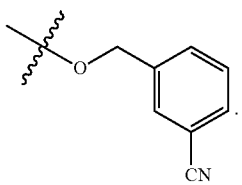

In some embodiments, $R^{A2}$ is —N(R)$_2$. In some embodiments, $R^{A2}$ is —N(R)$_2$, wherein each R is hydrogen. In some embodiments, Ring A is

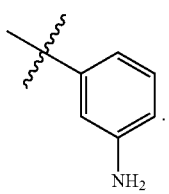

In some embodiments, $R^2$ is

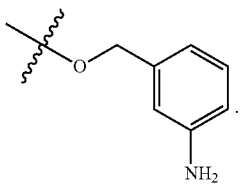

In some embodiments, $R^{A2}$ is —N(R)$_2$, wherein each R is independently C$_{1-4}$ alkyl. In some embodiments, Ring A is

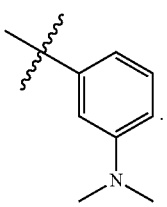 [SMILES: *c1cccc(N(C)C)c1]

In some embodiments, $R^2$ is

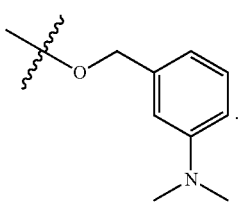 [SMILES: *OCc1cccc(N(C)C)c1]

In some embodiments, $R^{A2}$ is —N(R)$_2$, wherein one R is hydrogen, and the other R is C$_{1-4}$ alkyl. In some embodiments, $R^{A2}$ is —N(R)$_2$, wherein one R is hydrogen, and the other R is C$_{1-4}$ cycloalkyl. In some embodiments, Ring A is

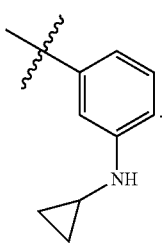 [SMILES: *c1cccc(NC2CC2)c1]

In some embodiments, $R^2$ is

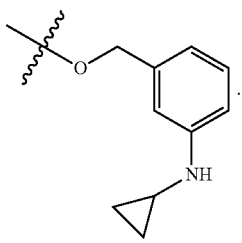 [SMILES: *OCc1cccc(NC2CC2)c1]

In some embodiments, $R^{A2}$ is —C(O)N(R)$_2$. In some embodiments, $R^{A2}$ is —C(O)N(R)$_2$, wherein each R is hydrogen. In some embodiments, Ring A is

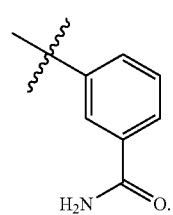 [SMILES: *c1cccc(C(N)=O)c1]

In some embodiments, $R^2$ is

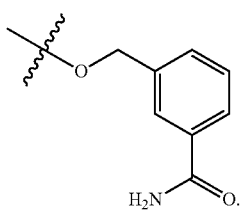 [SMILES: *OCc1cccc(C(N)=O)c1]

In some embodiments, $R^{A2}$ is —OR. In some embodiments, $R^{A2}$ is —OR, wherein each R is hydrogen. In some embodiments, Ring A is

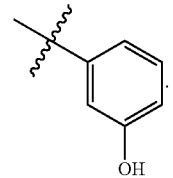 [SMILES: *c1cccc(O)c1]

In some embodiments, $R^2$ is

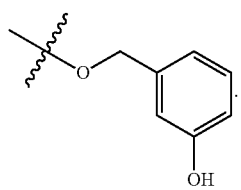 [SMILES: *OCc1cccc(O)c1]

In some embodiments, $R^{A2}$ is —OR, wherein R is $C_{1-4}$ alkyl optionally substituted with one or more halogen. In some embodiments, $R^{A2}$ is —OR, wherein R $C_{1-4}$ alkyl. In some embodiments, Ring A is

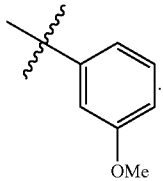 [SMILES: *c1cccc(OC)c1]

In some embodiments, $R^2$ is

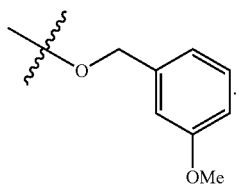 [SMILES: *OCc1cccc(OC)c1]

In some embodiments, $R^{A2}$ is —OR, wherein R $C_{1-4}$ alkyl substituted with one or more halogen. In some embodiments, $R^{A2}$ is —OR, wherein R $C_{1-4}$ alkyl substituted with one or more —F. In some embodiments, R is —CF$_3$. In some embodiments, Ring A is

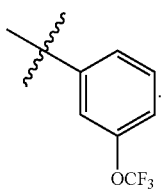 [SMILES: *c1cccc(OC(F)(F)F)c1]

In some embodiments, $R^2$ is

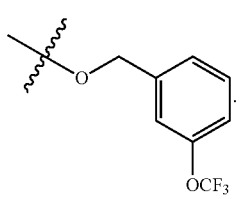 [SMILES: *OCc1cccc(OC(F)(F)F)c1]

In some embodiments, R is —CHF$_2$. In some embodiments, Ring A is

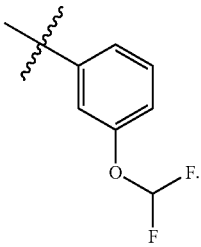 [SMILES: *c1cccc(OC(F)F)c1]

In some embodiments, $R^2$ is

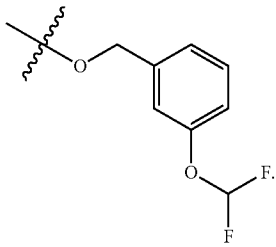 [SMILES: *OCc1cccc(OC(F)F)c1]

In some embodiments, $R^{A2}$ is —C(O)R. In some embodiments, $R^{A2}$ is —C(O)R, wherein each R is $C_{1-4}$ alkyl. In some embodiments, R is methyl. In some embodiments, Ring A is

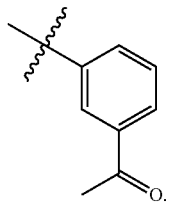 [SMILES: *c1cccc(C(C)=O)c1]

In some embodiments, $R^2$ is

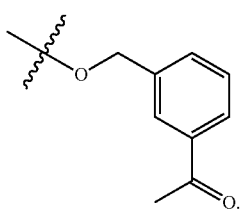 [SMILES: *OCc1cccc(C(C)=O)c1]

In some embodiments, $R^{A2}$ is —N$_3$. In some embodiments, Ring A is

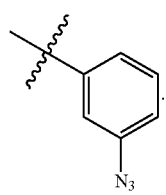 [SMILES: *c1cccc(N=[N+]=[N-])c1]

In some embodiments, $R^2$ is

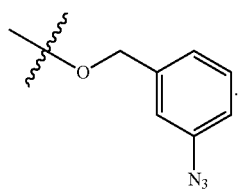 [SMILES: *OCc1cccc(N=[N+]=[N-])c1]

In some embodiments, $R^{A2}$ is $C_{1-4}$ alkyl optionally substituted with one or more halogen. In some embodiments, $R^{A2}$ is $C_{1-4}$ alkyl. In some embodiments, $R^{A2}$ is $C_{1-4}$ alkyl substituted with one or more halogen. In some embodiments, $R^{A2}$ is $C_{1-4}$ alkyl substituted with one or more —F. In some embodiments, $R^{A2}$ is —$CF_3$. In some embodiments, Ring A is

[Structure: 3-(trifluoromethyl)phenyl with attachment point]

In some embodiments, $R^2$ is

[Structure: —O—CH$_2$— linked to 3-(trifluoromethyl)phenyl]

In some embodiments, $R^{A2}$ is $C_{1-4}$ alkyl with no branching at the benzylic position.

In some embodiments, $R^{A2}$ is an optionally substituted 5- or 6-membered heterocyclyl or heteroaryl having one or two heteroatoms independently selected from nitrogen, oxygen or sulfur. In some embodiments, $R^{A2}$ is 5- or 6-membered heterocyclyl or heteroaryl having one or two heteroatoms independently selected from nitrogen, oxygen or sulfur. In some embodiments, $R^{A2}$ is an optionally substituted 5- or 6-membered heterocyclyl or heteroaryl having one or two nitrogen atoms. In some embodiments, $R^{A2}$ is 5- or 6-membered heterocyclyl or heteroaryl having one or two nitrogen atoms. In some embodiments, $R^{A2}$ is an optionally substituted 5-membered heterocyclyl or heteroaryl having one or two heteroatoms independently selected from nitrogen, oxygen or sulfur. In some embodiments, $R^{A2}$ is 5-membered heterocyclyl or heteroaryl having one or two heteroatoms independently selected from nitrogen, oxygen or sulfur. In some embodiments, $R^{A2}$ is an optionally substituted 5-membered heterocyclyl or heteroaryl having one or two nitrogen atoms. In some embodiments, $R^{A2}$ is 5-membered heterocyclyl or heteroaryl having one or two nitrogen atoms. In some embodiments, $R^{A2}$ is an optionally substituted 5-membered heterocyclyl having one or two nitrogen atoms. In some embodiments, $R^{A2}$ is 5-membered heterocyclyl having one or two nitrogen atoms. In some embodiments, $R^{A2}$ is an optionally substituted 5-membered heterocyclyl having one nitrogen atom. In some embodiments, $R^{A2}$ is 5-membered heterocyclyl having one nitrogen atom. In some embodiments, $R^{A2}$ is optionally substituted 5-membered heterocyclyl having two nitrogen atoms. In some embodiments, $R^{A2}$ is 5-membered heterocyclyl having two nitrogen atoms. In some embodiments, $R^{A2}$ is optionally substituted 5-membered heteroaryl having one or two nitrogen atoms. In some embodiments, $R^{A2}$ is 5-membered heteroaryl having one or two nitrogen atoms. In some embodiments, $R^{A2}$ is optionally substituted 5-membered heteroaryl having one nitrogen atom. In some embodiments, $R^{A2}$ is 5-membered heteroaryl having one nitrogen atom. In some embodiments, $R^{A2}$ is optionally substituted 5-membered heteroaryl having two nitrogen atoms. In some embodiments, $R^{A2}$ is 5-membered heteroaryl having two nitrogen atoms. In some embodiments, $R^{A2}$ is

[Structure: pyrrolidin-1-yl with attachment point]

In some embodiments, Ring A is

[Structure: 3-(pyrrolidin-1-yl)phenyl with attachment point]

In some embodiments, $R^2$ is

[Structure: —O—CH$_2$— linked to 3-(pyrrolidin-1-yl)phenyl]

In some embodiments, $R^{A2}$ is

[Structure: pyrazol-1-yl with attachment point]

In some embodiments, Ring A is

[Structure: 3-(pyrazol-1-yl)phenyl with attachment point]

In some embodiments, R² is

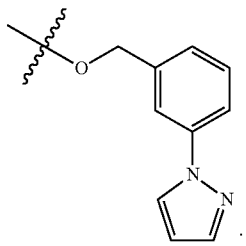 [SMILES: *OCc1cccc(-n2cccn2)c1]

In some embodiments, R^{42} is —I, —CN, —NH₂, —N(CH₃)₂, —NH(cyclopropyl), —C(O)NH₂, —OH, —OMe, —OCF₃, —OCHF₂, —C(O)Me, —N₃, —CF₃,

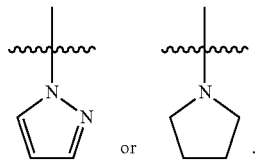 [SMILES: *n1cccn1 ; *N1CCCC1]

In some embodiments, Ring A is

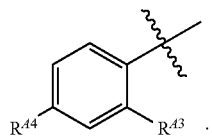

In some embodiments, R^{43} is —H or —F. In some embodiments, R^{43} is —H. In some embodiments, Ring A is

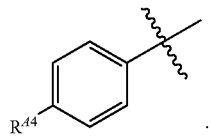

In some embodiments, R^{43} is —F. In some embodiments, Ring A is

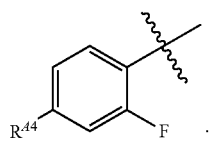

In some embodiments, R^{44} is —F or —OR. In some embodiments, R^{44} is —F. In some embodiments, Ring A is

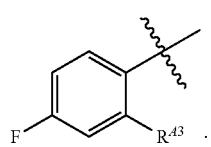

In some embodiments, Ring A is

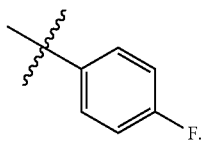

In some embodiments, R² is

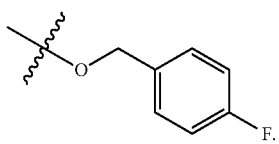 [SMILES: *OCc1ccc(F)cc1]

In some embodiments, Ring A is

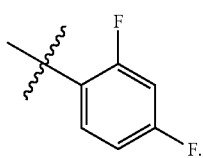

In some embodiments, R² is

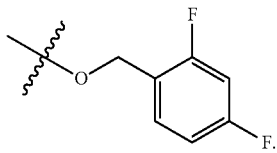 [SMILES: *OCc1ccc(F)cc1F]

In some embodiments, R^{44} is —OR. In some embodiments, Ring A is

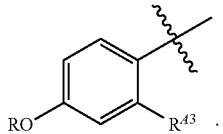

In some embodiments, R^{44} is —OR, wherein R is C_{1-4} alkyl. In some embodiments, R^{44} is —OMe. In some embodiments, Ring A is

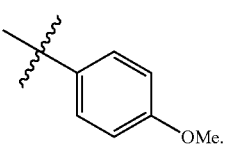 [SMILES: *c1ccc(OC)cc1]

In some embodiments, $R^2$ is

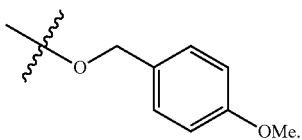 [SMILES: *OCc1ccc(OC)cc1]

In some embodiments, Ring A is pyridinyl optionally substituted with $R^{A5}$. In some embodiments, Ring A is pyridinyl. In some embodiments, Ring A is pyridinyl substituted with $R^{A5}$.

In some embodiments, $R^{A5}$ is —OR or —N(R)$_2$. In some embodiments, $R^{A5}$ is —OR. In some embodiments, Ring A is pyridinyl substituted with $R^{A5}$, wherein $R^{A5}$ is —OR. In some embodiments, $R^{A5}$ is —OR, wherein R is $C_{1-4}$ alkyl. In some embodiments, Ring A is pyridinyl substituted with $R^{A5}$, wherein $R^{A5}$ is —OR, wherein R is $C_{1-4}$ alkyl. In some embodiments, $R^{A5}$ is —OMe. In some embodiments, Ring A is pyridinyl substituted with —OMe. In some embodiments, Ring A is

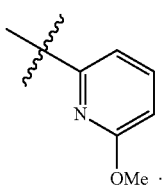 [SMILES: *c1cccc(OC)n1]

In some embodiments, $R^2$ is

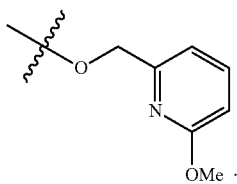 [SMILES: *OCc1cccc(OC)n1]

In some embodiments, Ring A is

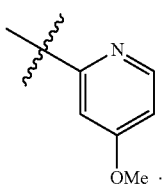 [SMILES: *c1cc(OC)ccn1]

In some embodiments, $R^2$ is

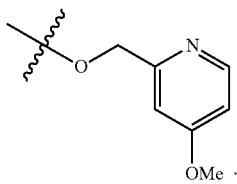 [SMILES: *OCc1cc(OC)ccn1]

In some embodiments, Ring A is

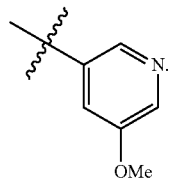 [SMILES: *c1cncc(OC)c1]

In some embodiments, $R^2$ is

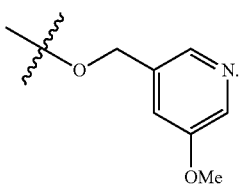 [SMILES: *OCc1cncc(OC)c1]

In some embodiments, Ring A is

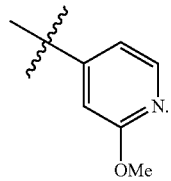 [SMILES: *c1ccnc(OC)c1]

In some embodiments, $R^2$ is

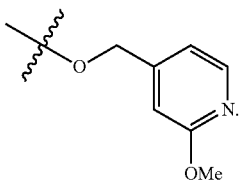 [SMILES: *OCc1ccnc(OC)c1]

In some embodiments, $R^{A5}$ is —N(R)$_2$. In some embodiments, Ring A is pyridinyl substituted with $R^{A5}$, wherein $R^{A5}$ is —N(R)$_2$. In some embodiments, $R^{A5}$ is —N(R)$_2$, wherein each R is hydrogen. In some embodiments, Ring A is pyridinyl substituted with $R^{A5}$, wherein $R^{A5}$ is —NH$_2$. In some embodiments, Ring A is

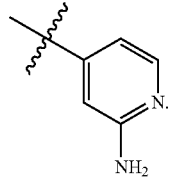

In some embodiments, $R^2$ is
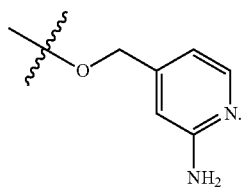
Exemplary Ring A groups are depicted in Table 2, below.
TABLE 2
Exemplary Ring A groups.
TABLE 2-continued
Exemplary Ring A groups.
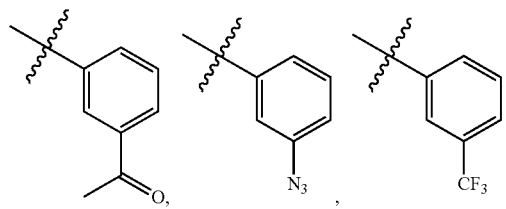

TABLE 2-continued
Exemplary Ring A groups.
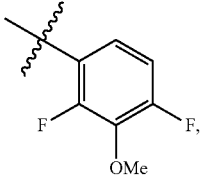
In some embodiments, R² is —NH—CH₂-Ring A. In some embodiments, R² is
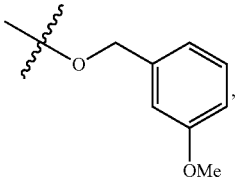
In some embodiments, R² is
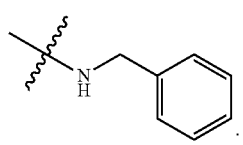 [SMILES: *NCc1ccccc1]
In some embodiments, R² is —O—CH₂CH₂-Ring A.
Exemplary R² groups are depicted in Table 3, below.
TABLE 3
Exemplary R² groups.
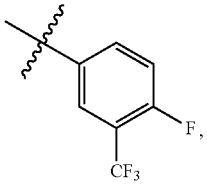

TABLE 3-continued
Exemplary R² groups.
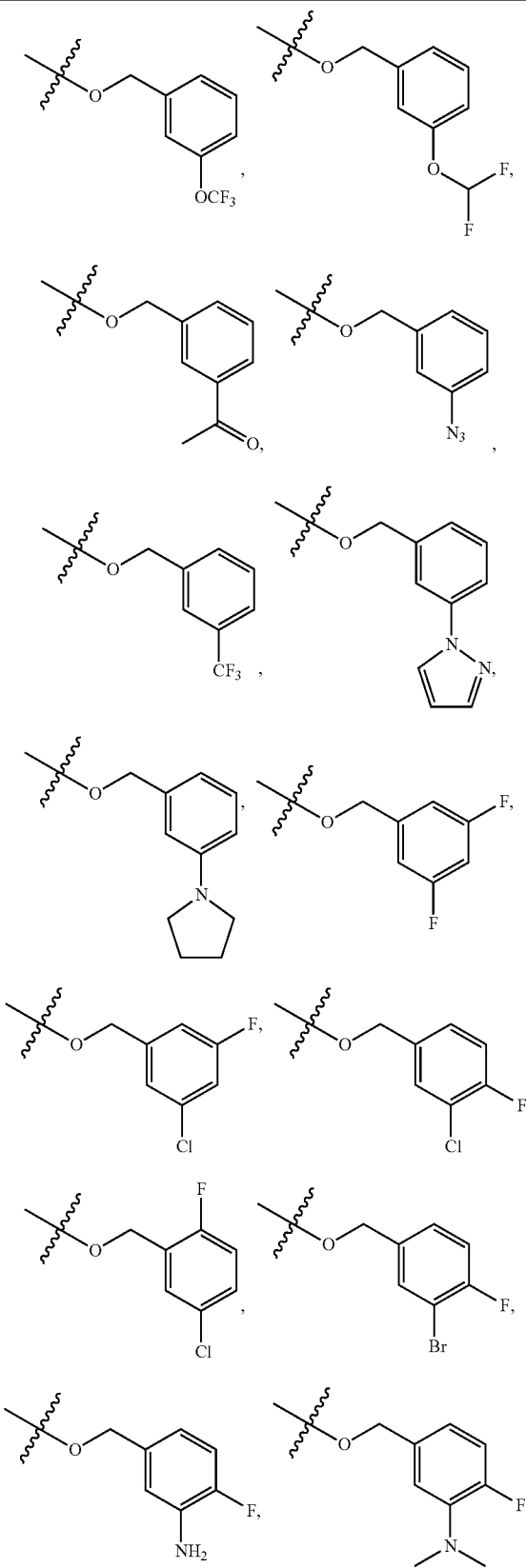
TABLE 3-continued
Exemplary R² groups.
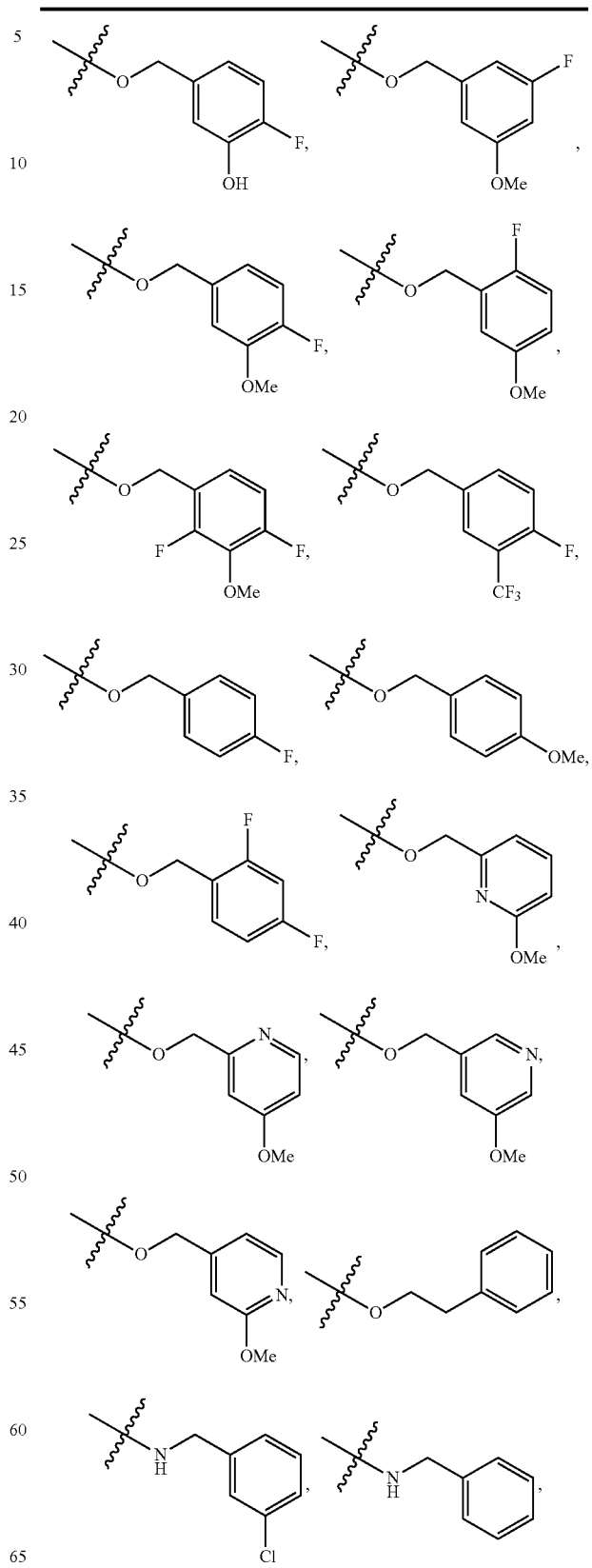

TABLE 3-continued

Exemplary R² groups.

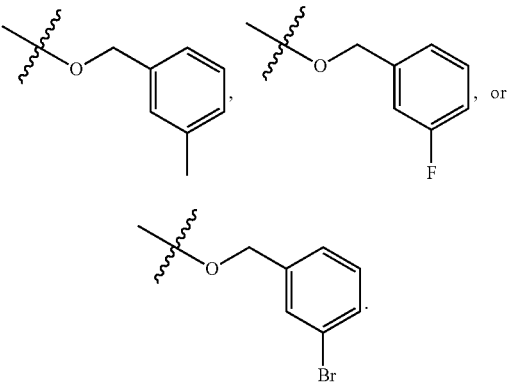

In some embodiments, R³ is —C(O)N(R³ᵃ)₂, —OR³ᵇ, —C(O)H, —C(O)OR, or —N(R³ᶜ)₂. In some embodiments, R³ is —C(O)N(R³ᵃ)₂. In some embodiments, R³ is —OR³ᵇ. In some embodiments, R³ is —C(O)H. In some embodiments, R³ is —C(O)OR. In some embodiments, R³ is —N(R³ᶜ)₂.

In some embodiments, each R³ᵃ is independently hydrogen or C₁ alkyl optionally substituted with one or more groups independently selected from halogen or 1-pyrrolidinyl.

In some embodiments, R³ᵃ is hydrogen. In some embodiments, each R³ᵃ is hydrogen. In some embodiments, R³ is —C(O)NH₂.

In some embodiments, R³ᵃ is C₁ alkyl optionally substituted with one or more groups independently selected from halogen or 1-pyrrolidinyl. In some embodiments, R³ᵃ is C₁ alkyl optionally substituted with 1-pyrrolidinyl. In some embodiments, R³ᵃ is methyl. In some embodiments, R³ᵃ is

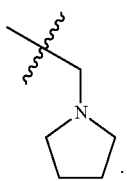 [SMILES: *CN1CCCC1]

In some embodiments, one R³ᵃ is hydrogen, and the other R³ᵃ is C₁ alkyl optionally substituted with one or more groups independently selected from halogen or 1-pyrrolidinyl. In some embodiments, one R³ᵃ is hydrogen, and the other R³ᵃ is C₁ alkyl optionally substituted with 1-pyrrolidinyl. In some embodiments, one R³ᵃ is hydrogen, and the other R³ᵃ is methyl. In some embodiments, R³ is —CONH(CH₃). In some embodiments, one R³ᵃ is hydrogen, and the other R³ᵃ is

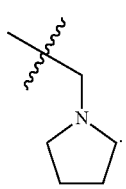 [SMILES: *CN1CCCC1]

In some embodiments, R³ is

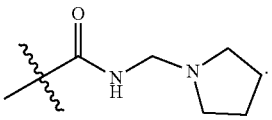 [SMILES: *C(=O)NCN1CCCC1]

In some embodiments, R³ᵇ is hydrogen or C₁₋₄ alkyl optionally substituted with one or more groups independently selected from halogen, C₁₋₄ alkyl, C₁₋₄ haloalkyl, oxo, or —N(R)₂. In some embodiments, R³ᵇ is hydrogen or C₁₋₄ alkyl.

In some embodiments, R³ᵇ is hydrogen. In some embodiments, R³ is —OH.

In some embodiments, R³ᵇ is C₁₋₄ alkyl optionally substituted with one or more groups independently selected from halogen, C₁₋₄ alkyl, C₁₋₄ haloalkyl, oxo, or —N(R)₂. In some embodiments, R³ᵇ is C₁₋₄ alkyl. In some embodiments, R³ᵇ is methyl. In some embodiments, R³ is —OMe. In some embodiments, R³ᵇ is —CH(CH₃)C(O)NH₂. In some embodiments, R³ is —OCH(CH₃)C(O)NH₂.

In some embodiments, R³ is —C(O)H.

In some embodiments, R³ is —C(O)OR, wherein R is C₁₋₄ alkyl. R is methyl. In some embodiments, R³ is —C(O)OMe.

In some embodiments, each R³ᶜ is independently hydrogen or C₁₋₄ alkyl optionally substituted with one or more groups independently selected from halogen, C₁₋₄ alkyl, C₁₋₄ haloalkyl, oxo, or —N(R)₂.

In some embodiments, R³ᶜ is hydrogen. In some embodiments, each R³ᶜ is hydrogen. In some embodiments, R³ is —NH₂.

In some embodiments, R³ᶜ is C₁₋₄ alkyl optionally substituted with one or more groups independently selected from halogen, C₁₋₄ alkyl, C₁₋₄ haloalkyl, oxo, or —N(R)₂. In some embodiments, one R³ᶜ is hydrogen, and the other R³ᶜ is C₁₋₄ alkyl optionally substituted with one or more groups independently selected from halogen, C₁₋₄ alkyl, C₁₋₄ haloalkyl, oxo, or —N(R)₂. In some embodiments, one R³ᶜ is hydrogen, and the other R³ᶜ is C₁₋₄ alkyl optionally substituted with one or more groups independently selected from oxo or —N(R)₂. In some embodiments, R³ is —NHC(O)CH₂NH₂.

In some embodiments, R⁴ is R or halogen. In some embodiments, R⁴ is R. In some embodiments, R⁴ is hydrogen. In some embodiments, R⁴ is C₁₋₄ alkyl optionally substituted with one or more halogen. In some embodiments, R⁴ is C₁₋₄ alkyl. In some embodiments, R⁴ is methyl. In some embodiments, R⁴ is C₁₋₄ alkyl substituted with one or more halogen. In some embodiments, R⁴ is —CF₃.

In some embodiments, R⁴ is halogen. In some embodiments, R⁴ is —F. In some embodiments, R⁴ is —Cl. In some embodiments, R⁴ is —Br. In some embodiments, R⁴ is —I.

In some embodiments, R⁴ is —N(R)₂. In some embodiments, R⁴ is —N(R)₂, wherein each R is hydrogen. In some embodiments, R⁴ is —NH₂.

In some embodiments, R⁵ is hydrogen, methyl or —N(R)₂. In some embodiments, R⁵ is hydrogen. In some embodiments, R⁵ is methyl. In some embodiments, R⁵ is —N(R)₂. In some embodiments, R⁵ is —N(R)₂, wherein each R is hydrogen. In some embodiments, R⁵ is —NH₂.

In some embodiments, each R is independently hydrogen or C₁₋₄ alkyl optionally substituted with one or more halogen. In some embodiments, each R is independently hydrogen or unsubstituted C₁₋₄ alkyl. In some embodiments, each R is independently hydrogen or $C_{1-4}$ alkyl optionally substituted with one or more —F.

In some embodiments, R is hydrogen. In some embodiments, R is $C_{1-4}$ alkyl optionally substituted with one or more halogen. In some embodiments, R is hydrogen or $C_{1-4}$ alkyl optionally substituted with one or more —F. In some embodiments, R is hydrogen or $C_{1-4}$ alkyl. In some embodiments, R is $C_{1-4}$ alkyl. In some embodiments, R is methyl. In some embodiments, R is hydrogen or $C_{1-4}$ alkyl substituted with one or more halogen. In some embodiments, R is hydrogen or $C_{1-4}$ alkyl substituted with one or more —F. In some embodiments, R is —$CF_3$. In some embodiments, R is —$CHF_2$.

In some embodiments, the right hand side of formula I,

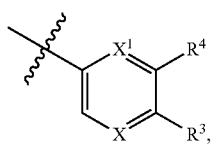

is

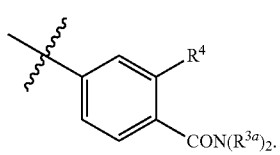

In some embodiments,

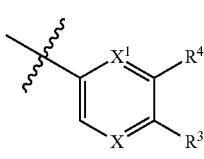 is 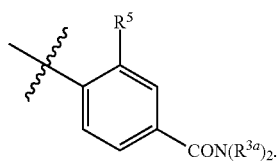

In some embodiments,

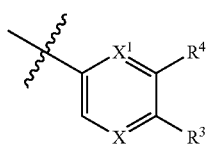 is 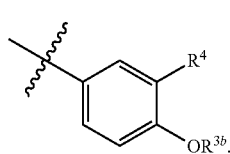

In some embodiments,

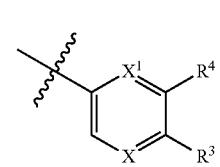 is 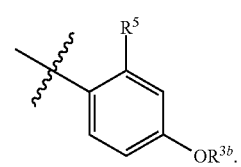

In some embodiments,

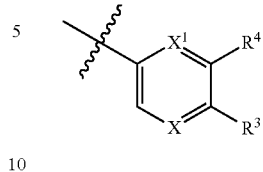 is 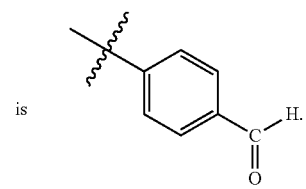

In some embodiments,

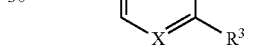 is 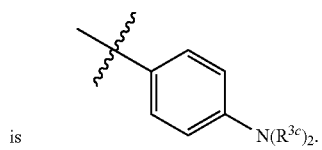

In some embodiments,

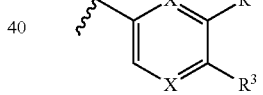 is 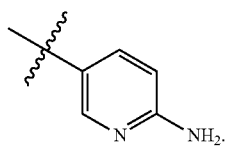

In some embodiments,

 is 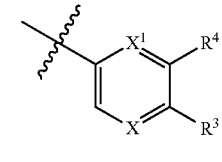

In some embodiments,

 is not 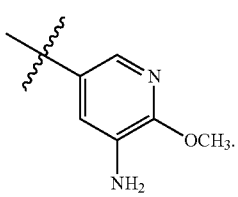

Exemplary
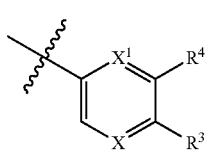
moieties are depicted in Table 4, below.
TABLE 4
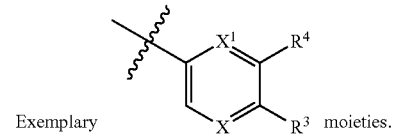
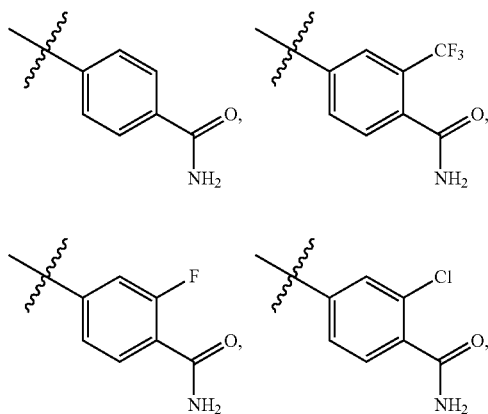
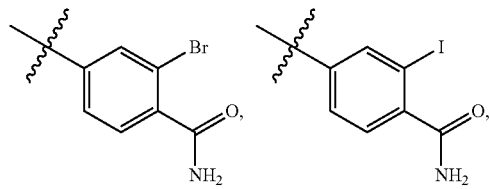 [SMILES: *c1ccc(C(N)=O)c(Br)c1 ; *c1ccc(C(N)=O)c(I)c1]
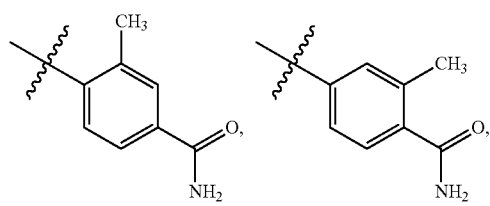 [SMILES: *c1ccc(C(N)=O)cc1C ; *c1ccc(C(N)=O)c(C)c1]
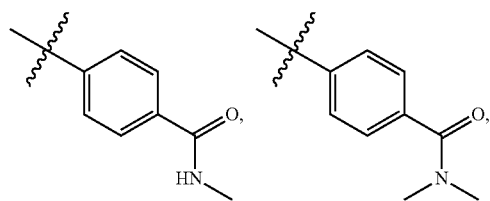 [SMILES: *c1ccc(C(=O)NC)cc1 ; *c1ccc(C(=O)N(C)C)cc1]
TABLE 4-continued
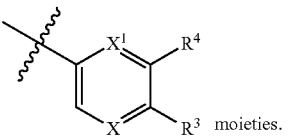
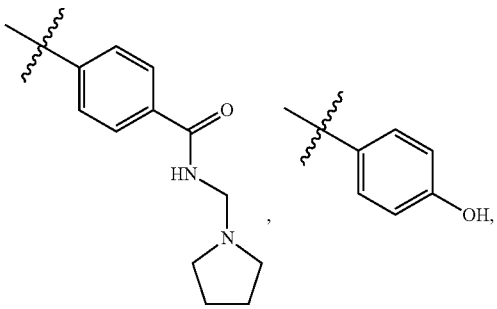 [SMILES: *c1ccc(C(=O)NCN2CCCC2)cc1 ; *c1ccc(O)cc1]
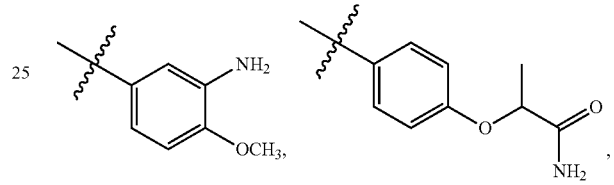
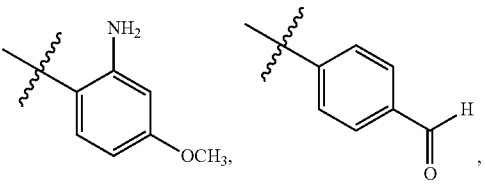 [SMILES: *c1ccc(OC)cc1N ; *c1ccc(C=O)cc1]
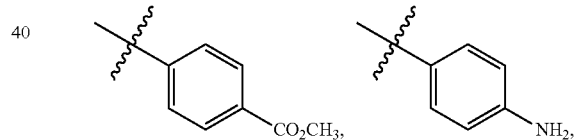
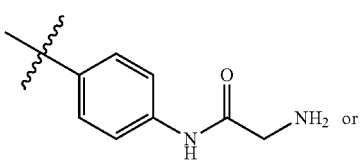 [SMILES: *c1ccc(NC(=O)CN)cc1 ; "or"]
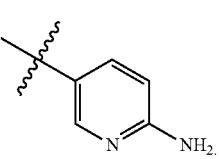

In some embodiments, a compound of formula I has the structure of formula I-a:

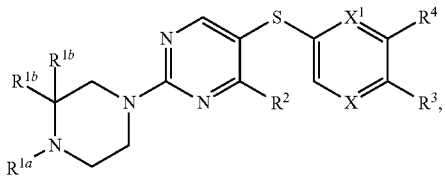

I-a or a pharmaceutically acceptable salt thereof, wherein each variable is independently as described in classes and subclasses herein, both singly and in combination. In some embodiments, $R^{1a}$ is

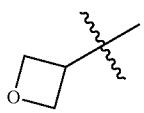 [SMILES: *C1COC1]

or straight chain $C_{1-6}$ aliphatic optionally substituted with one or more groups independently selected from —OH, cyclopropyl, —C≡CH or 5-membered heteroaryl having 1-2 heteroatoms independently selected from nitrogen, oxygen or sulfur.

In some embodiments, a compound of formula I has the structure of formula I-a-1:

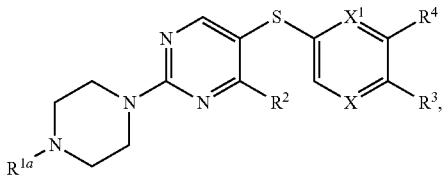

I-a-1 or a pharmaceutically acceptable salt thereof, wherein each variable is independently as described in classes and subclasses herein, both singly and in combination. In some embodiments, $R^{1a}$ is

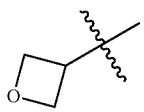 [SMILES: *C1COC1]

or straight chain $C_{1-6}$ aliphatic optionally substituted with one or more groups independently selected from —OH, cyclopropyl, —C≡CH, or 5-membered heteroaryl having 1-2 heteroatoms independently selected from nitrogen, oxygen or sulfur.

In some embodiments, a compound of formula I has the structure of formula I-a-2:

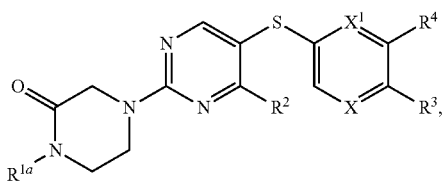

I-a-2 or a pharmaceutically acceptable salt thereof, wherein each variable is independently as described in classes and subclasses herein, both singly and in combination. In some embodiments, $R^{1a}$ is

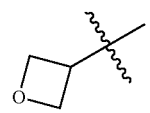 [SMILES: *C1COC1]

or straight chain $C_{1-6}$ aliphatic optionally substituted with one or more groups independently selected from —OH, cyclopropyl, —C≡CH, or 5-membered heteroaryl having 1-2 heteroatoms independently selected from nitrogen, oxygen or sulfur.

In some embodiments, a compound of formula I has the structure of formula I-b:

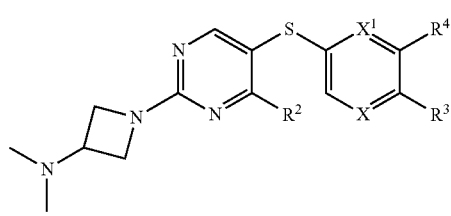

I-b or a pharmaceutically acceptable salt thereof, wherein each variable is independently as described in classes and subclasses herein, both singly and in combination.

In some embodiments, a compound of formula I has the structure of formula I-c:

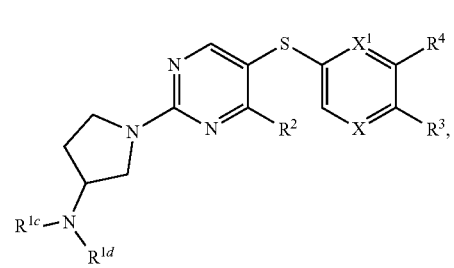

I-c or a pharmaceutically acceptable salt thereof, wherein each variable is independently as described in classes and subclasses herein, both singly and in combination. In some embodiments, each of $R^{1c}$ and $R^{1d}$ is methyl. In some embodiments, $R^{1c}$ is hydrogen and $R^{1d}$ is methyl.

In some embodiments, a compound of formula I has the structure of formula I-c-1:

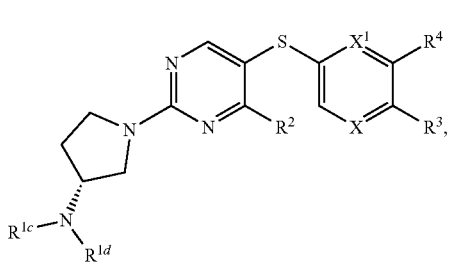

I-c-1 or a pharmaceutically acceptable salt thereof, wherein each variable is independently as described in classes and subclasses herein, both singly and in combination. In some embodiments, each of $R^{1c}$ and $R^{1d}$ is methyl. In some embodiments, $R^{1c}$ is hydrogen and $R^{1d}$ is methyl.

In some embodiments, a compound of formula I has the structure of formula I-d:

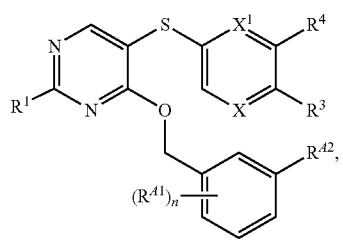

I-d or a pharmaceutically acceptable salt thereof, wherein each variable is independently as described in classes and subclasses herein, both singly and in combination. In some embodiments, $R^{A2}$ is —OMe. In some embodiments, $R^{A2}$ is —N(R)$_2$, wherein each R is independently $C_{1-4}$ alkyl. In some embodiments, $R^{A2}$ is —N(CH$_3$)$_2$. In some embodiments, $R^{A2}$ is —Cl, $R^{A1}$ is —F, and n is 1.

In some embodiments, a compound of formula I has the structure of formula I-e:

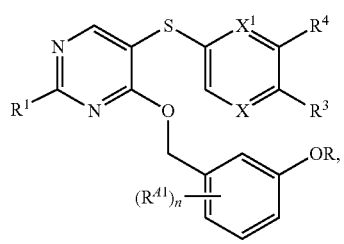

I-e or a pharmaceutically acceptable salt thereof, wherein each variable is independently as described in classes and subclasses herein, both singly and in combination.

In some embodiments, a compound of formula I has the structure of formula I-e-1.

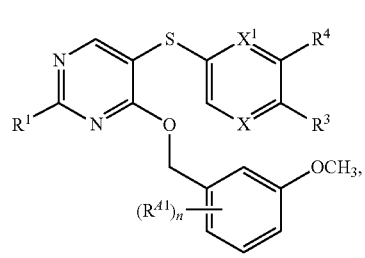

I-e-1 or a pharmaceutically acceptable salt thereof, wherein each variable is independently as described in classes and subclasses herein, both singly and in combination.

In some embodiments, a compound of formula I has the structure of formula I-f:

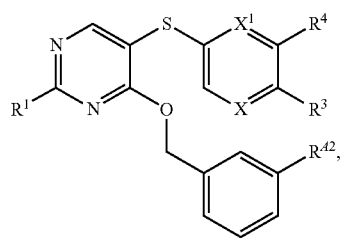

I-f or a pharmaceutically acceptable salt thereof, wherein each variable is independently as described in classes and subclasses herein, both singly and in combination. In some embodiments, $R^{A2}$ is —OMe. In some embodiments, $R^{A2}$ is —N(R)$_2$, wherein each R is independently $C_{1-4}$ alkyl. In some embodiments, $R^{A2}$ is —N(CH$_3$)$_2$. In some embodiments, $R^{A2}$ is —Cl.

In some embodiments, a compound of formula I has the structure of formula I-g:

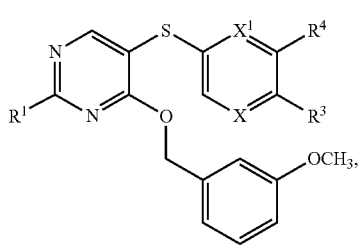

I-g or a pharmaceutically acceptable salt thereof, wherein each variable is independently as described in classes and subclasses herein, both singly and in combination.

Exemplary compounds of formula I are depicted in Table 5, below.

TABLE 5

Exemplary compounds of formula I.

TABLE 5-continued
Exemplary compounds of formula I.
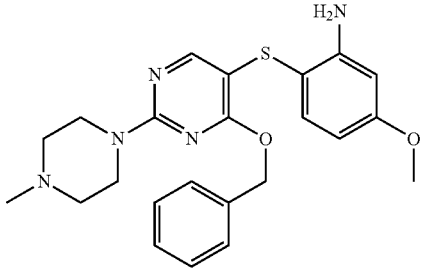
62
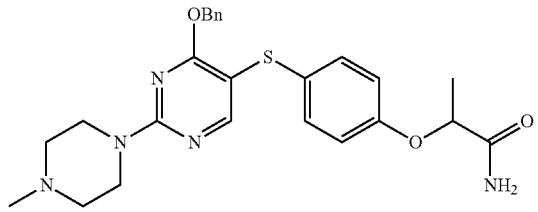 [SMILES: CC(Oc1ccc(Sc2cnc(N3CCN(C)CC3)nc2OCc2ccccc2)cc1)C(N)=O]
65
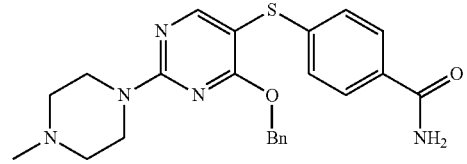 [SMILES: CN1CCN(c2ncc(Sc3ccc(C(N)=O)cc3)c(OCc3ccccc3)n2)CC1]
66
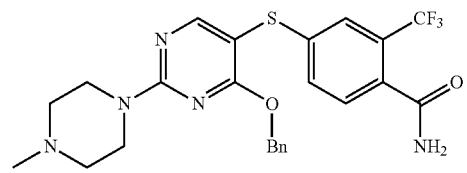 [SMILES: CN1CCN(c2ncc(Sc3ccc(C(N)=O)c(C(F)(F)F)c3)c(OCc3ccccc3)n2)CC1]
70
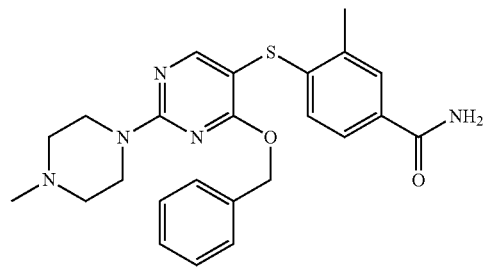 [SMILES: Cc1cc(C(N)=O)ccc1Sc1cnc(N2CCN(C)CC2)nc1OCc1ccccc1]
73
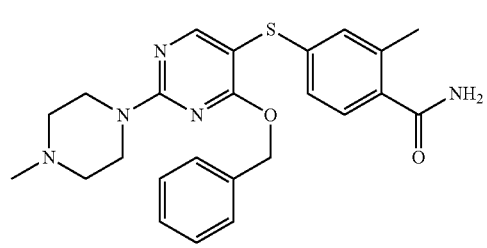
74
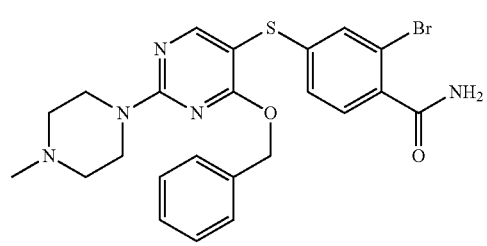
77

TABLE 5-continued
Exemplary compounds of formula I.
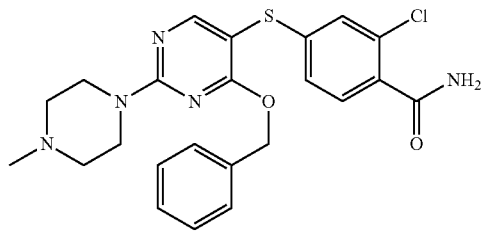
78
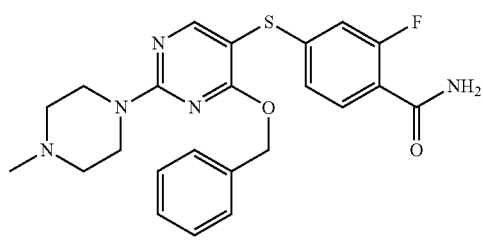
79
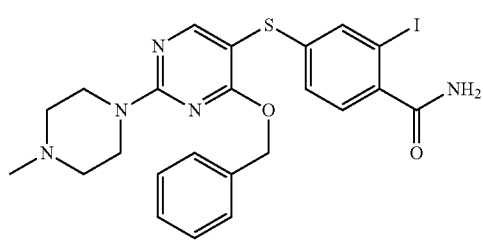 [SMILES: CN1CCN(c2ncc(Sc3ccc(C(N)=O)c(I)c3)c(OCc3ccccc3)n2)CC1]
80
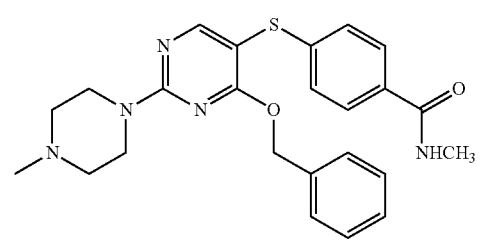 [SMILES: CNC(=O)c1ccc(Sc2cnc(N3CCN(C)CC3)nc2OCc2ccccc2)cc1]
83
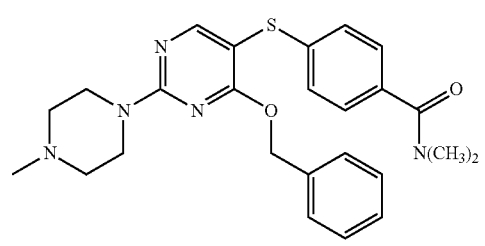 [SMILES: CN1CCN(c2ncc(Sc3ccc(C(=O)N(C)C)cc3)c(OCc3ccccc3)n2)CC1]
84
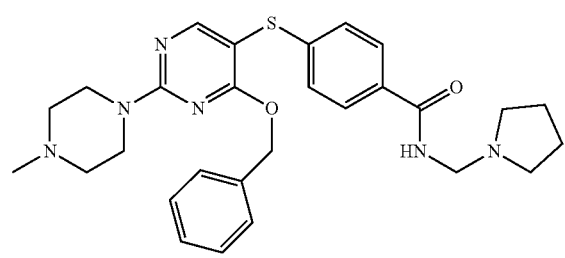 [SMILES: CN1CCN(c2ncc(Sc3ccc(C(=O)NCN4CCCC4)cc3)c(OCc3ccccc3)n2)CC1]
92

TABLE 5-continued
Exemplary componds of formula I.
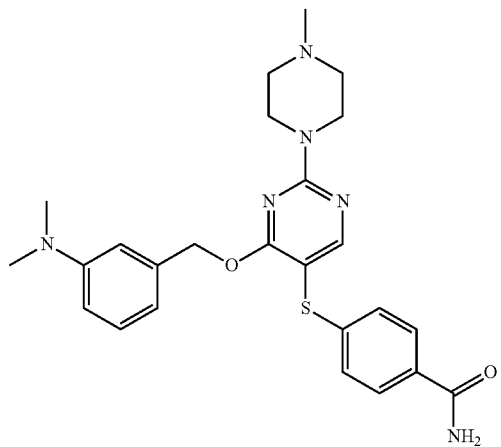 [SMILES: CN1CCN(c2ncc(Sc3ccc(C(N)=O)cc3)c(OCc3cccc(N(C)C)c3)n2)CC1]
100a
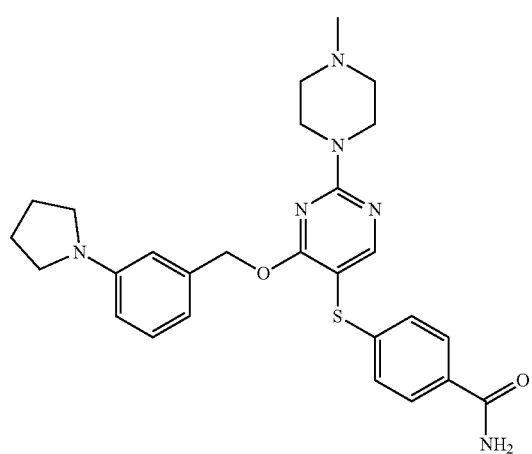 [SMILES: CN1CCN(c2ncc(Sc3ccc(C(N)=O)cc3)c(OCc3cccc(N4CCCC4)c3)n2)CC1]
100b
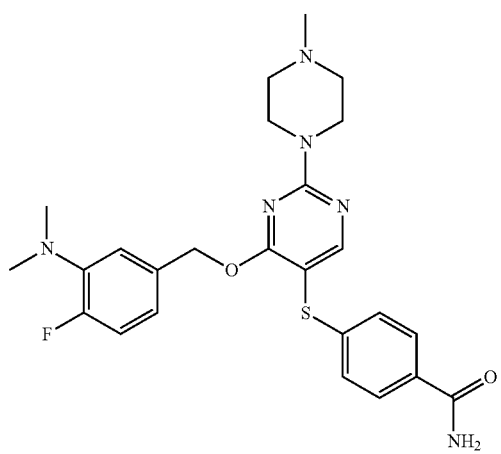 [SMILES: CN1CCN(c2ncc(Sc3ccc(C(N)=O)cc3)c(OCc3ccc(F)c(N(C)C)c3)n2)CC1]
100c

TABLE 5-continued
Exemplary compounds of formula I.
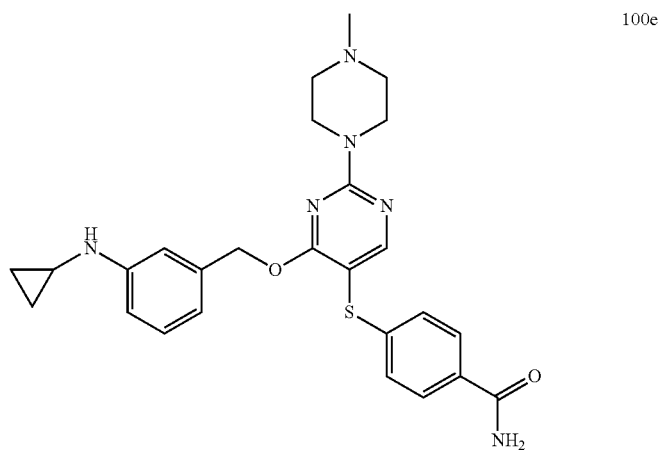
100e
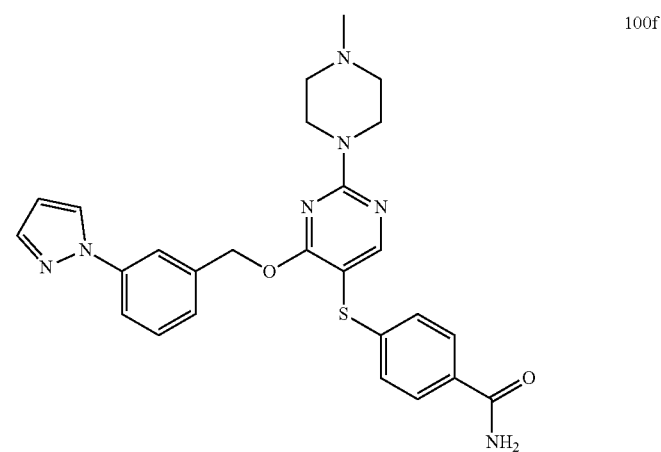
100f
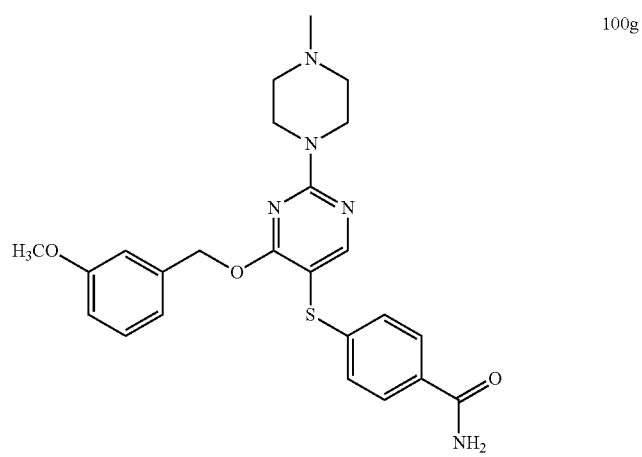
100g TABLE 5-continued
Exemplary componds of formula I.
100h
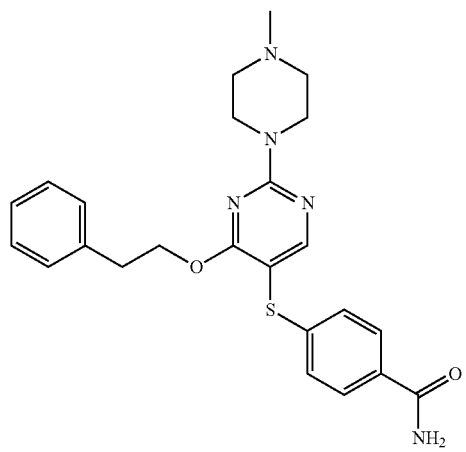 [SMILES: CN1CCN(c2ncc(Sc3ccc(C(N)=O)cc3)c(OCCc3ccccc3)n2)CC1]
100i
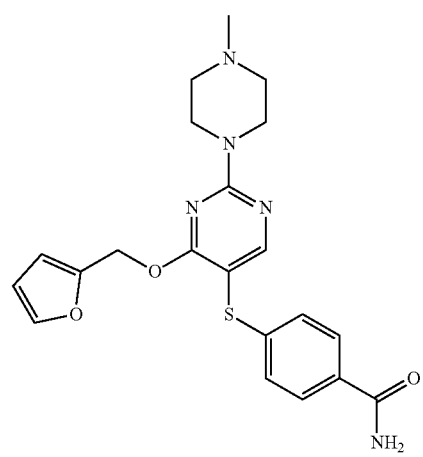 [SMILES: CN1CCN(c2ncc(Sc3ccc(C(N)=O)cc3)c(OCc3ccco3)n2)CC1]
100j
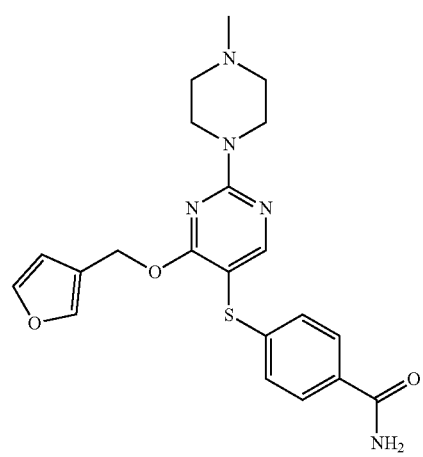 [SMILES: CN1CCN(c2ncc(Sc3ccc(C(N)=O)cc3)c(OCc3ccoc3)n2)CC1]

TABLE 5-continued
Exemplary compounds of formula I.
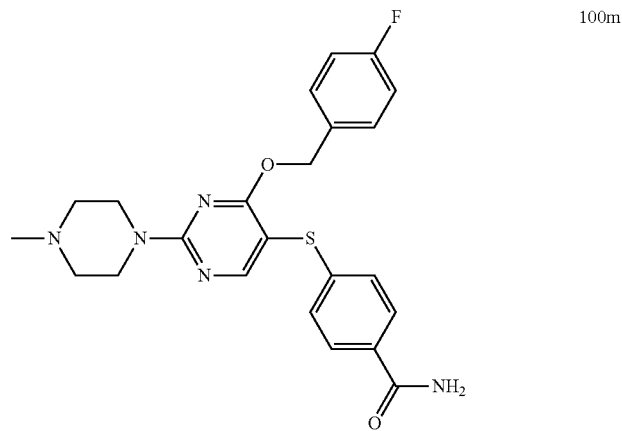
100m
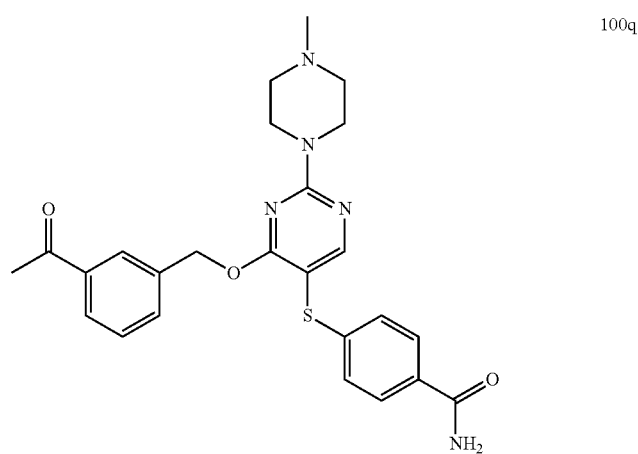
100q
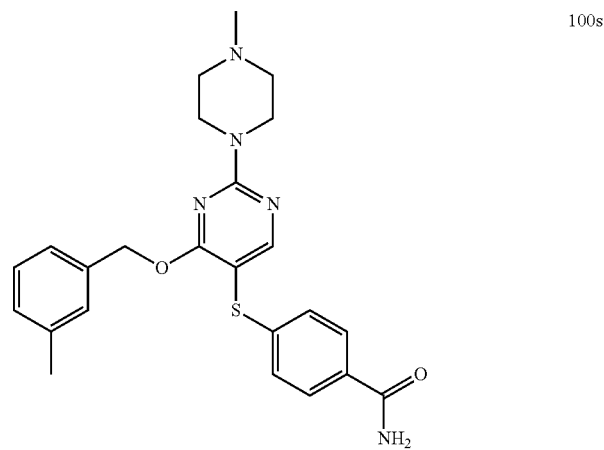
100s TABLE 5-continued
Exemplary compounds of formula I.
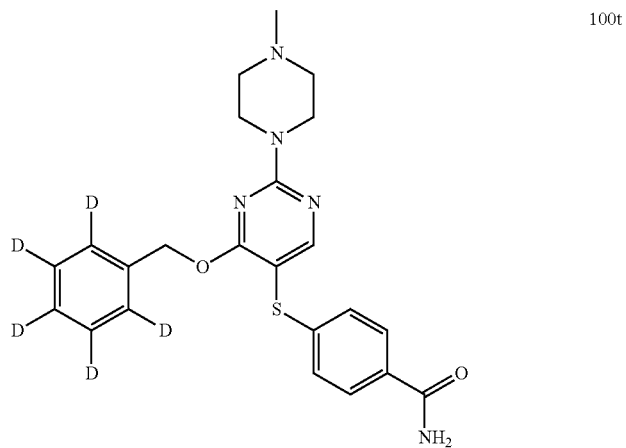
100t
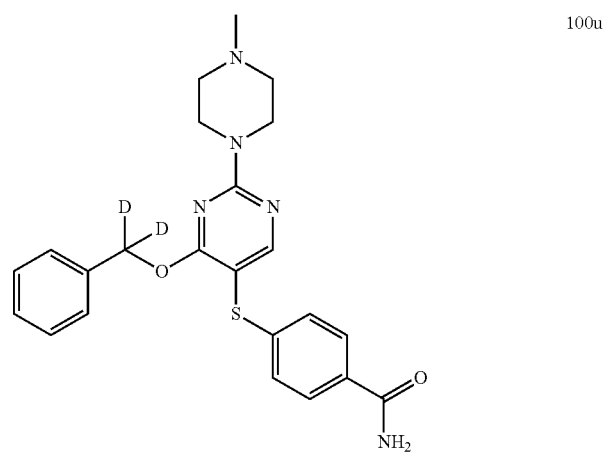
100u
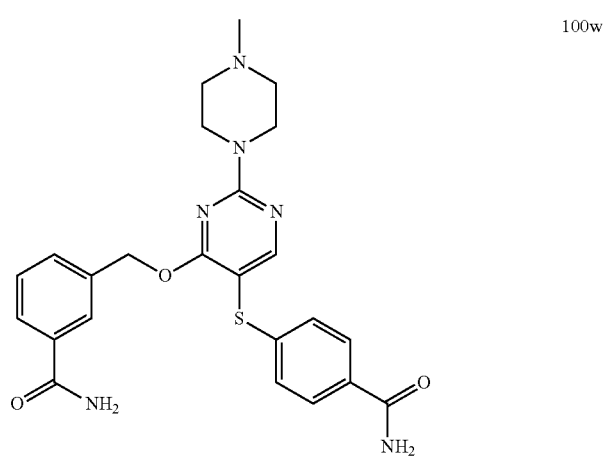
100w TABLE 5-continued
Exemplary componds of formula I.
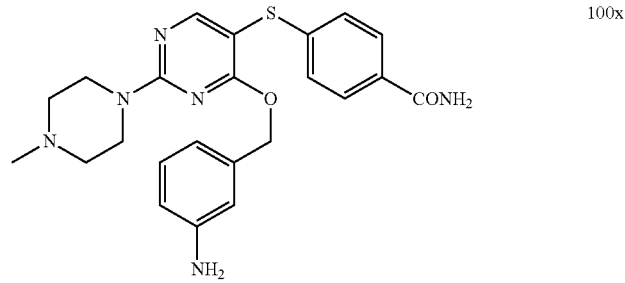
100x
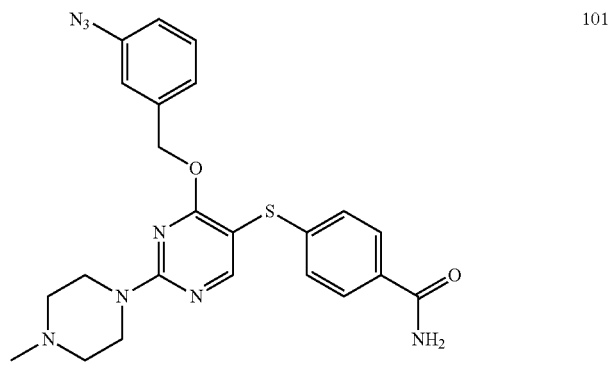
101
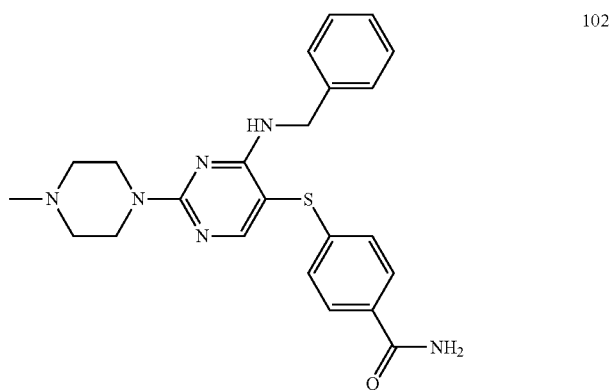
102
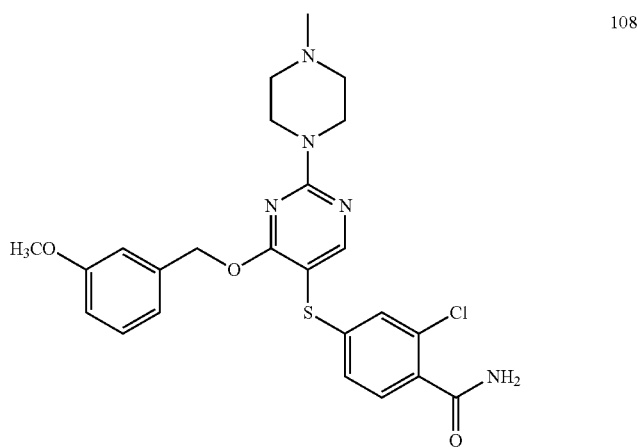
108

TABLE 5-continued
Exemplary componds of formula I.
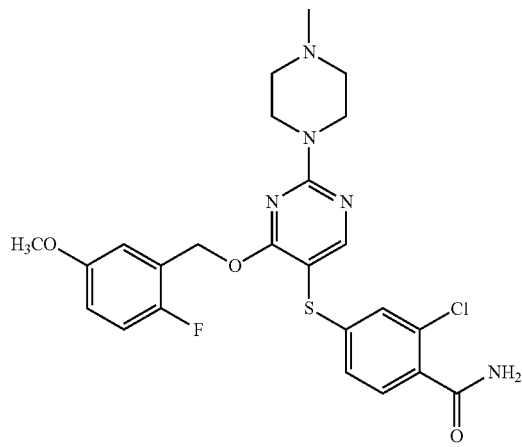 [SMILES: COc1ccc(F)c(COc2nc(N3CCN(C)CC3)ncc2Sc2ccc(C(N)=O)c(Cl)c2)c1]
109
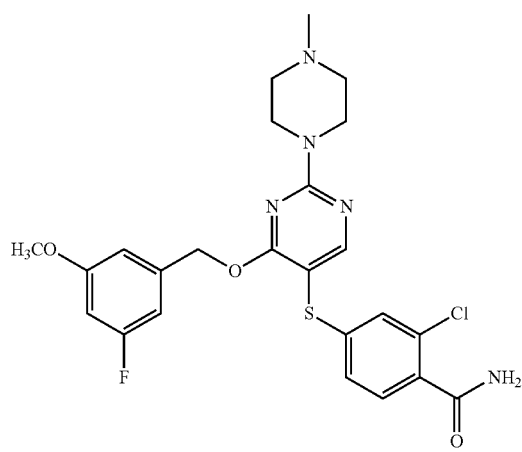 [SMILES: COc1cc(F)cc(COc2nc(N3CCN(C)CC3)ncc2Sc2ccc(C(N)=O)c(Cl)c2)c1]
110
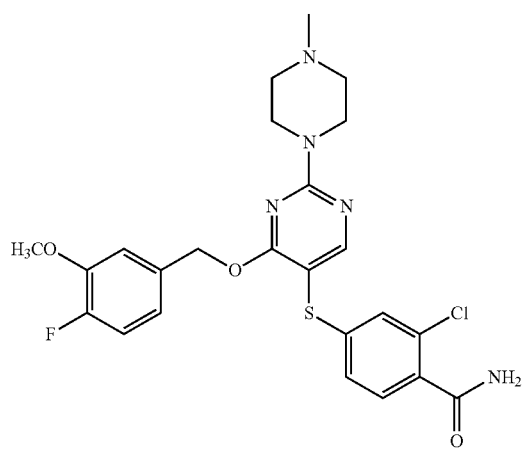 [SMILES: COc1cc(COc2nc(N3CCN(C)CC3)ncc2Sc2ccc(C(N)=O)c(Cl)c2)ccc1F]
111

TABLE 5-continued
Exemplary compounds of formula I.
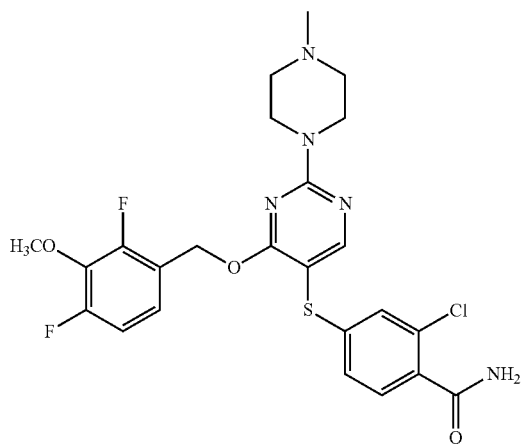 [SMILES: COc1c(F)ccc(COc2nc(N3CCN(C)CC3)ncc2Sc2ccc(C(N)=O)c(Cl)c2)c1F]
112
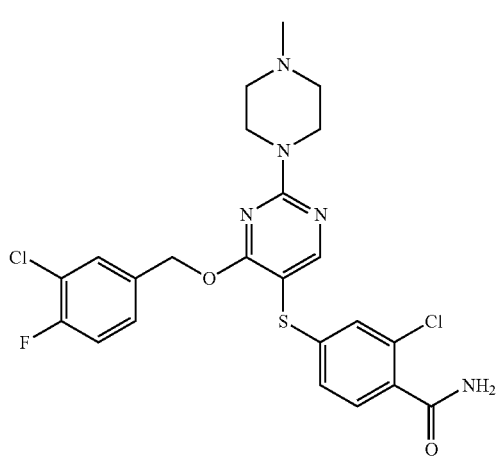 [SMILES: CN1CCN(c2ncc(Sc3ccc(C(N)=O)c(Cl)c3)c(OCc3ccc(F)c(Cl)c3)n2)CC1]
113
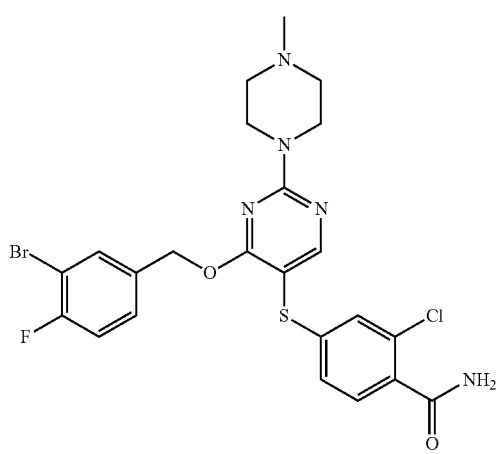 [SMILES: CN1CCN(c2ncc(Sc3ccc(C(N)=O)c(Cl)c3)c(OCc3ccc(F)c(Br)c3)n2)CC1]
114

TABLE 5-continued
Exemplary componds of formula I.
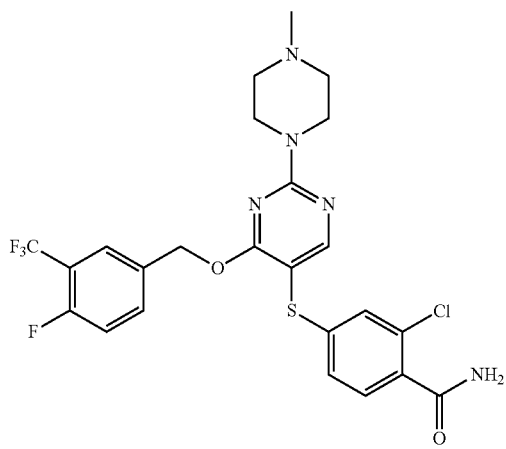 [SMILES: CN1CCN(c2ncc(Sc3ccc(C(N)=O)c(Cl)c3)c(OCc3ccc(F)c(C(F)(F)F)c3)n2)CC1]
115
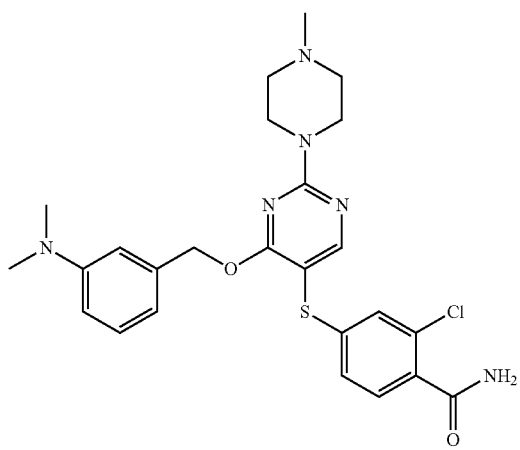 [SMILES: CN1CCN(c2ncc(Sc3ccc(C(N)=O)c(Cl)c3)c(OCc3cccc(N(C)C)c3)n2)CC1]
116
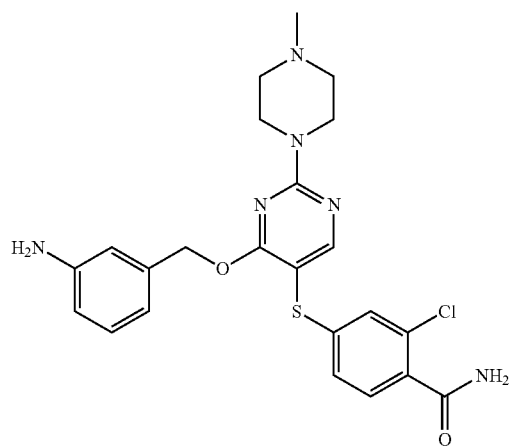 [SMILES: CN1CCN(c2ncc(Sc3ccc(C(N)=O)c(Cl)c3)c(OCc3cccc(N)c3)n2)CC1]
117

TABLE 5-continued
Exemplary compounds of formula I.
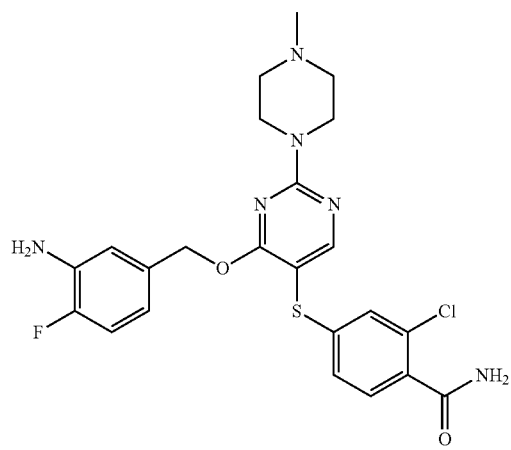 [SMILES: CN1CCN(c2ncc(Sc3ccc(C(N)=O)c(Cl)c3)c(OCc3ccc(F)c(N)c3)n2)CC1]
118
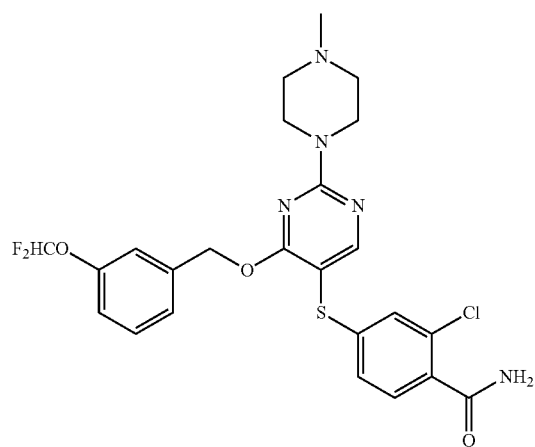 [SMILES: CN1CCN(c2ncc(Sc3ccc(C(N)=O)c(Cl)c3)c(OCc3cccc(OC(F)F)c3)n2)CC1]
121
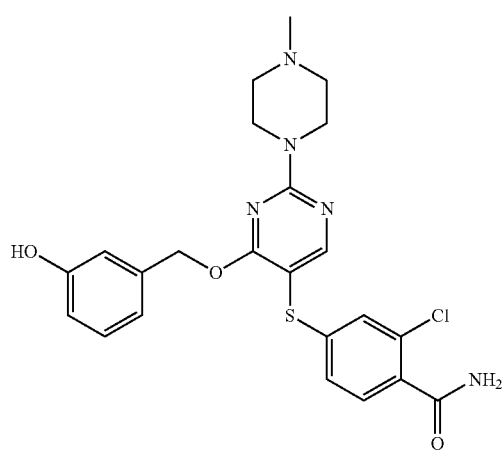 [SMILES: CN1CCN(c2ncc(Sc3ccc(C(N)=O)c(Cl)c3)c(OCc3cccc(O)c3)n2)CC1]
122

TABLE 5-continued
Exemplary componds of formula I.
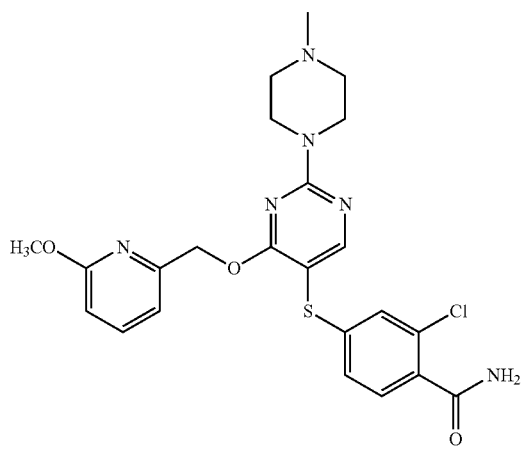 [SMILES: COc1cccc(COc2nc(N3CCN(C)CC3)ncc2Sc2ccc(C(N)=O)c(Cl)c2)n1]
123
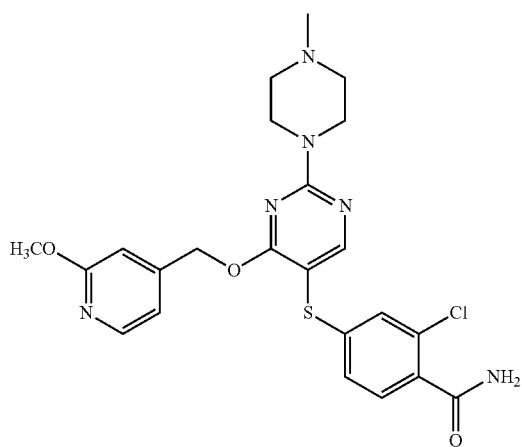 [SMILES: COc1cc(COc2nc(N3CCN(C)CC3)ncc2Sc2ccc(C(N)=O)c(Cl)c2)ccn1]
124
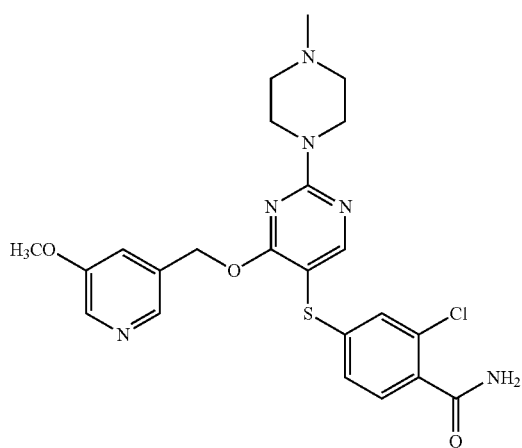 [SMILES: COc1cncc(COc2nc(N3CCN(C)CC3)ncc2Sc2ccc(C(N)=O)c(Cl)c2)c1]
125

TABLE 5-continued
Exemplary componds of formula I.
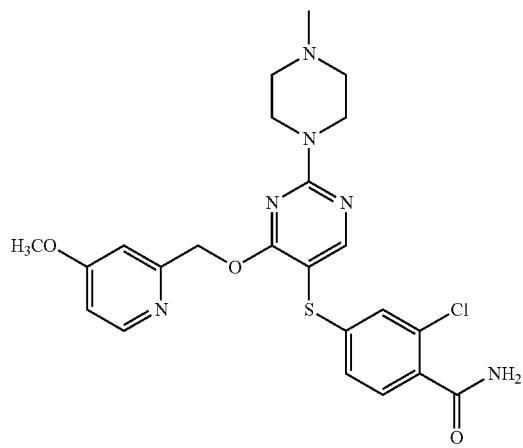 [SMILES: COc1ccnc(COc2nc(N3CCN(C)CC3)ncc2Sc2ccc(C(N)=O)c(Cl)c2)c1]
126
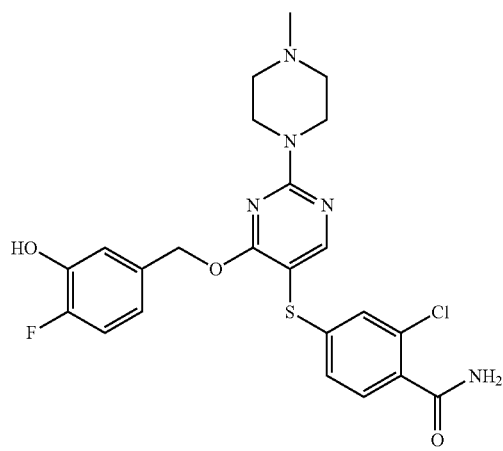 [SMILES: CN1CCN(c2ncc(Sc3ccc(C(N)=O)c(Cl)c3)c(OCc3ccc(F)c(O)c3)n2)CC1]
127
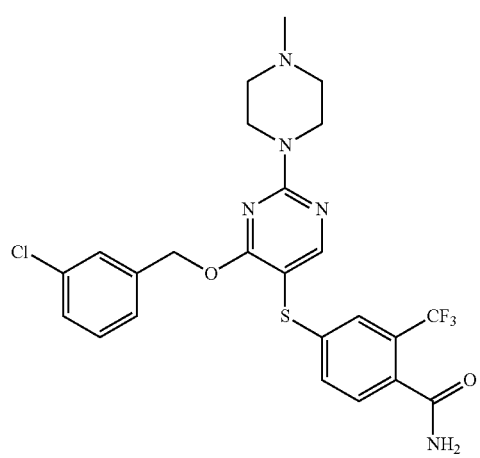 [SMILES: CN1CCN(c2ncc(Sc3ccc(C(N)=O)c(C(F)(F)F)c3)c(OCc3cccc(Cl)c3)n2)CC1]
131

TABLE 5-continued
Exemplary componds of formula I.
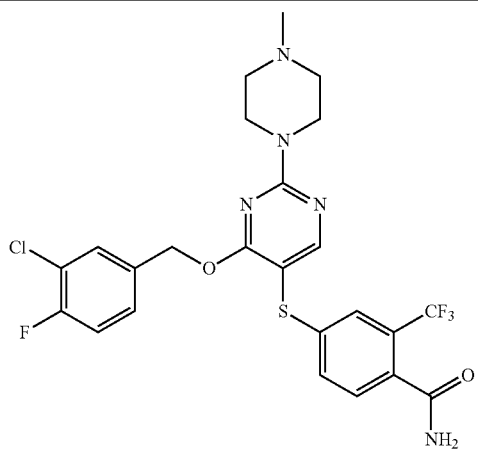
132
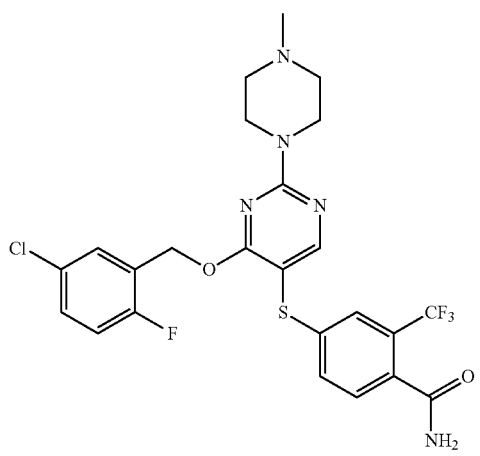 [SMILES: CN1CCN(c2ncc(Sc3ccc(C(N)=O)c(C(F)(F)F)c3)c(OCc3cc(Cl)ccc3F)n2)CC1]
133
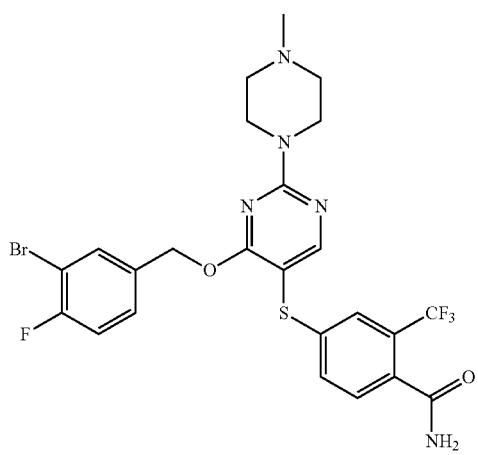 [SMILES: CN1CCN(c2ncc(Sc3ccc(C(N)=O)c(C(F)(F)F)c3)c(OCc3ccc(F)c(Br)c3)n2)CC1]
134

TABLE 5-continued
Exemplary compounds of formula I.
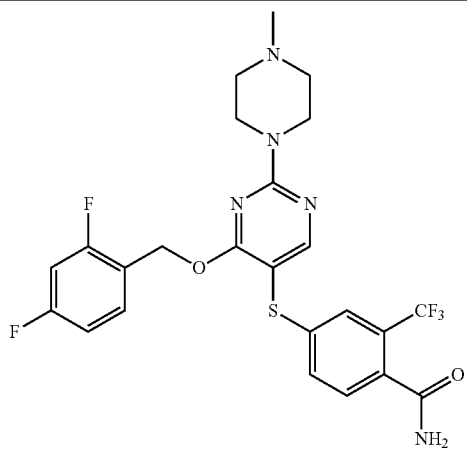
135
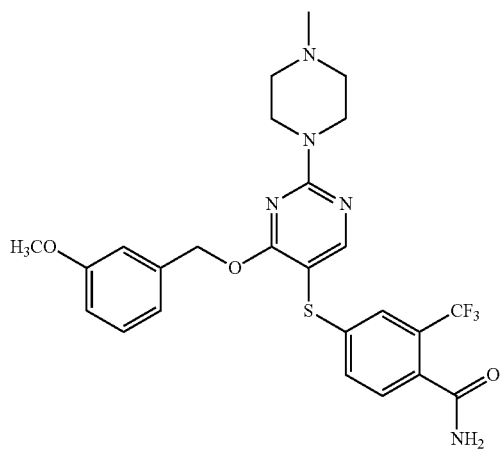 [SMILES: COc1cccc(COc2nc(N3CCN(C)CC3)ncc2Sc2ccc(C(N)=O)c(C(F)(F)F)c2)c1]
136
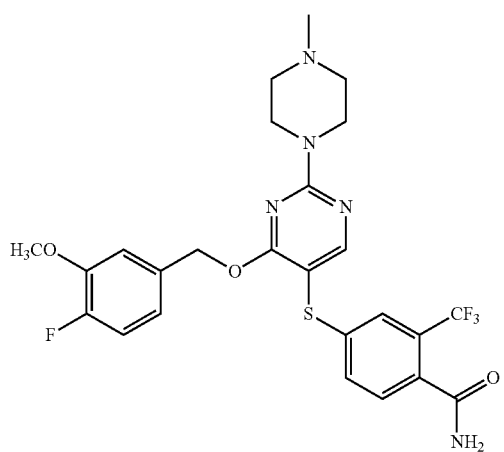 [SMILES: COc1cc(COc2nc(N3CCN(C)CC3)ncc2Sc2ccc(C(N)=O)c(C(F)(F)F)c2)ccc1F]
137

TABLE 5-continued
Exemplary componds of formula I.
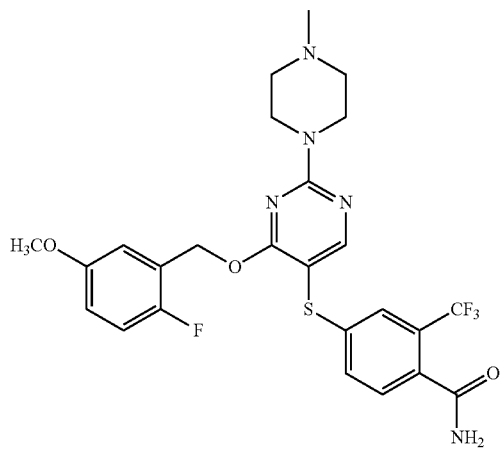 [SMILES: COc1ccc(F)c(COc2nc(N3CCN(C)CC3)ncc2Sc2ccc(C(N)=O)c(C(F)(F)F)c2)c1]
138
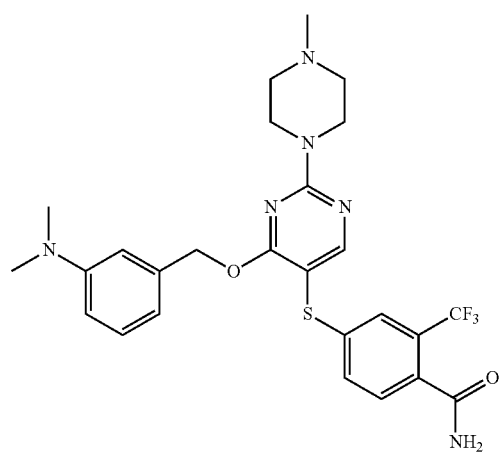 [SMILES: CN1CCN(c2ncc(Sc3ccc(C(N)=O)c(C(F)(F)F)c3)c(OCc3cccc(N(C)C)c3)n2)CC1]
139
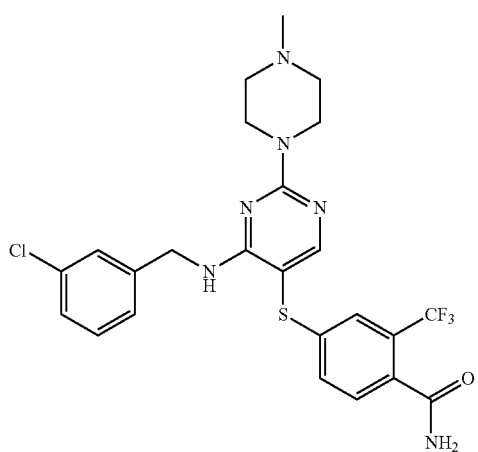 [SMILES: CN1CCN(c2ncc(Sc3ccc(C(N)=O)c(C(F)(F)F)c3)c(NCc3cccc(Cl)c3)n2)CC1]
141
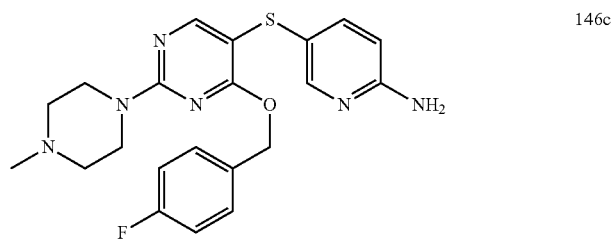
146c TABLE 5-continued
Exemplary compounds of formula I.
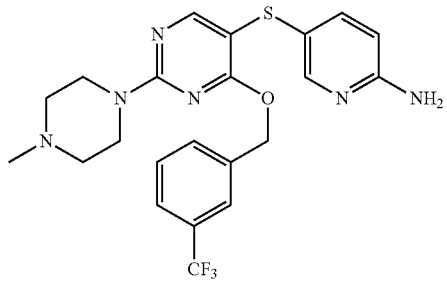 [SMILES: CN1CCN(c2ncc(Sc3ccc(N)nc3)c(OCc3cccc(C(F)(F)F)c3)n2)CC1]
146e
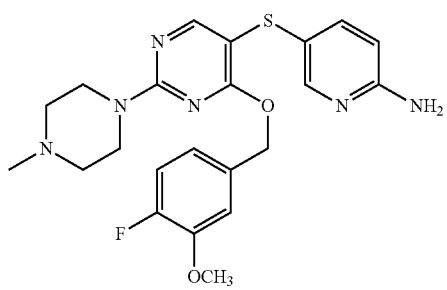
151
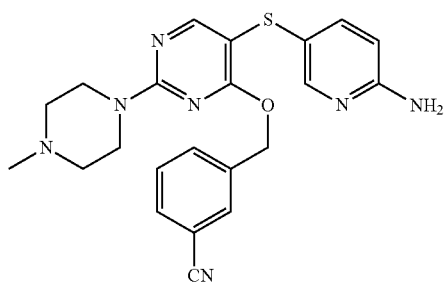 [SMILES: CN1CCN(c2ncc(Sc3ccc(N)nc3)c(OCc3cccc(C#N)c3)n2)CC1]
152
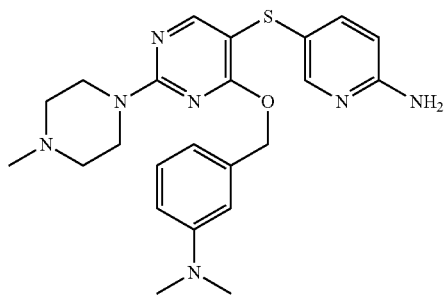 [SMILES: CN1CCN(c2ncc(Sc3ccc(N)nc3)c(OCc3cccc(N(C)C)c3)n2)CC1]
153
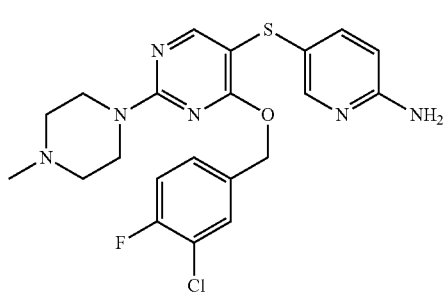 [SMILES: CN1CCN(c2ncc(Sc3ccc(N)nc3)c(OCc3ccc(F)c(Cl)c3)n2)CC1]
154

TABLE 5-continued
Exemplary componds of formula I.
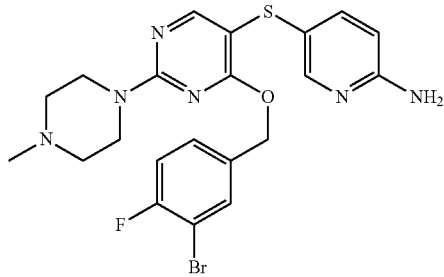 [SMILES: CN1CCN(c2ncc(Sc3ccc(N)nc3)c(OCc3ccc(F)c(Br)c3)n2)CC1]
155
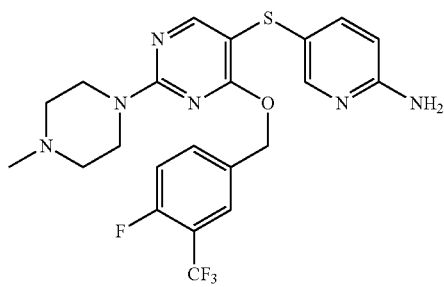 [SMILES: CN1CCN(c2ncc(Sc3ccc(N)nc3)c(OCc3ccc(F)c(C(F)(F)F)c3)n2)CC1]
156
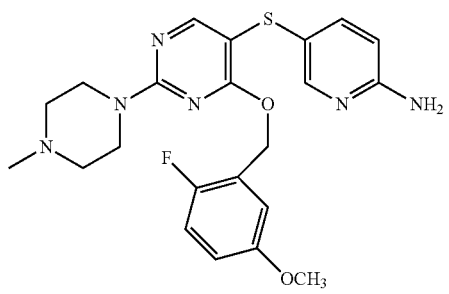 [SMILES: COc1ccc(F)c(COc2nc(N3CCN(C)CC3)ncc2Sc2ccc(N)nc2)c1]
157
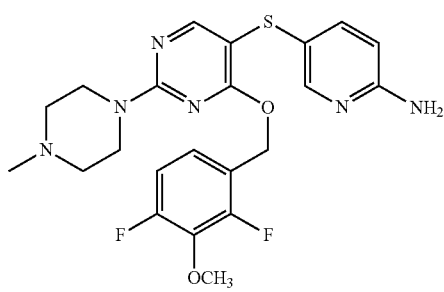 [SMILES: COc1c(F)ccc(COc2nc(N3CCN(C)CC3)ncc2Sc2ccc(N)nc2)c1F]
158
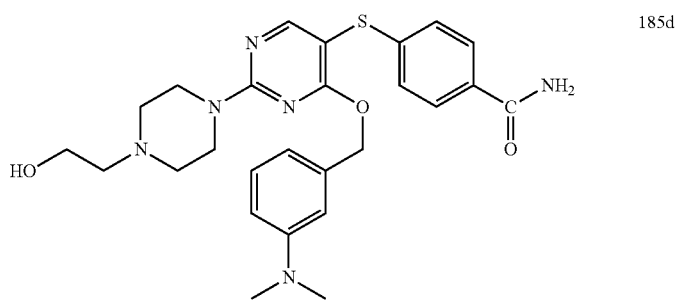
185d TABLE 5-continued
Exemplary componds of formula I.
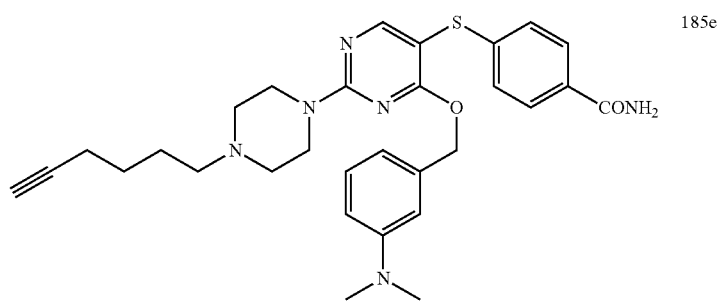
185e
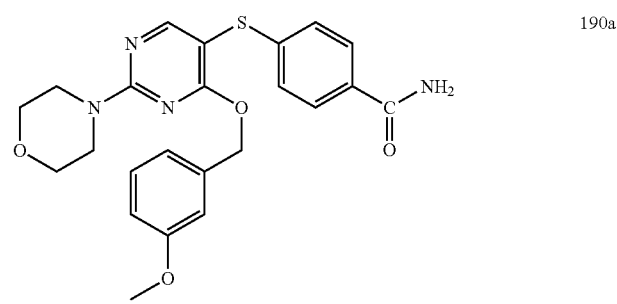
190a
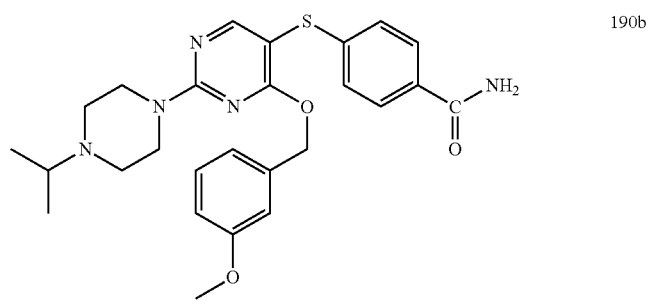
190b
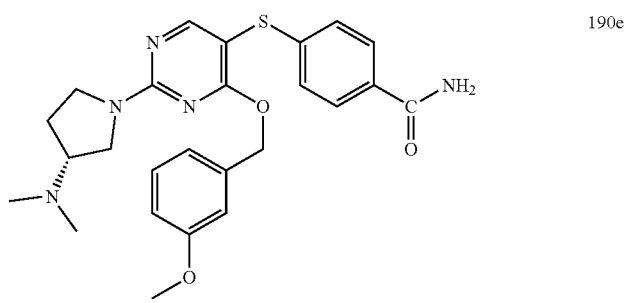
190e
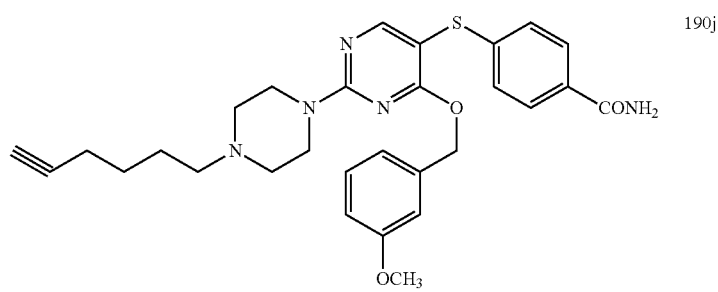
190j TABLE 5-continued
Exemplary compounds of formula I.
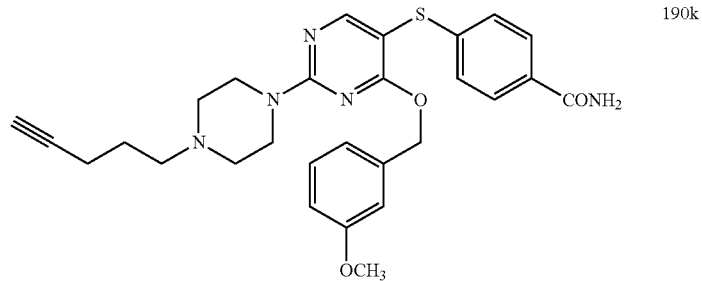
190k
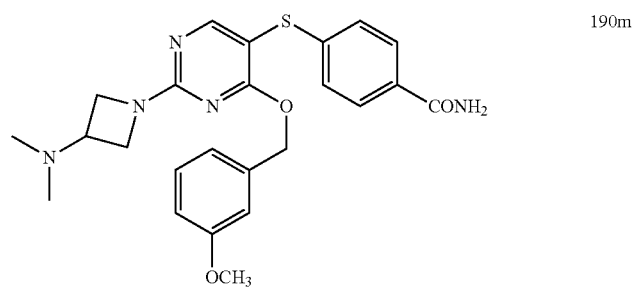
190m
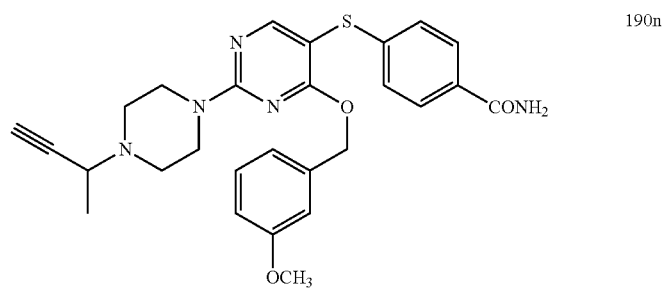
190n
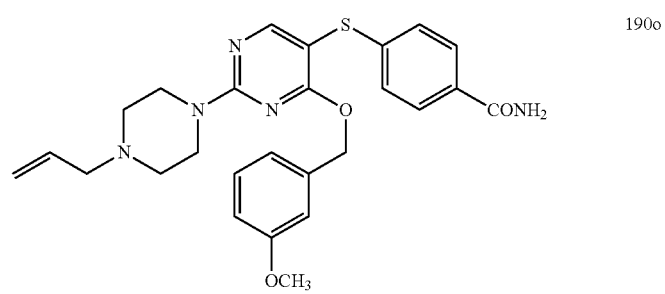
190o
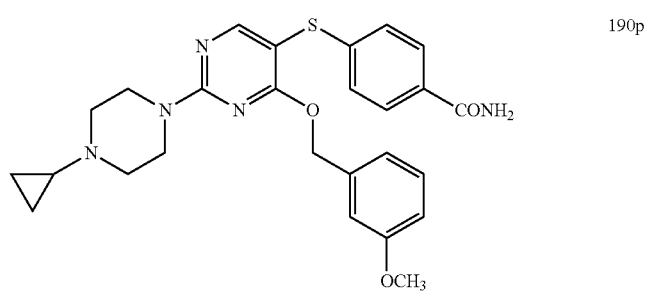
190p TABLE 5-continued
Exemplary compounds of formula I.
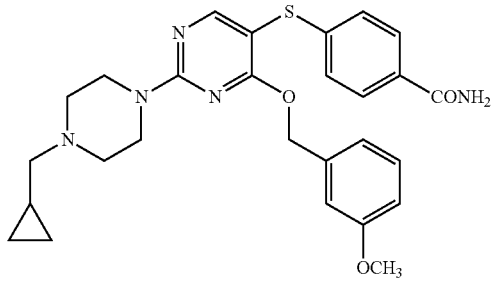 [SMILES: COc1cccc(COc2nc(N3CCN(CC4CC4)CC3)ncc2Sc2ccc(C(N)=O)cc2)c1]
190q
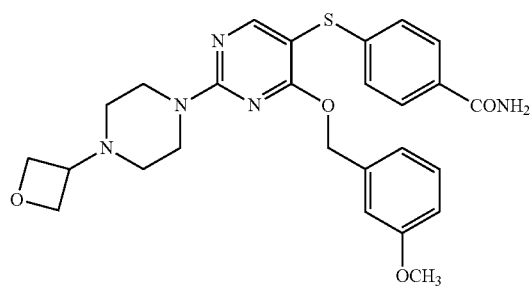
190r
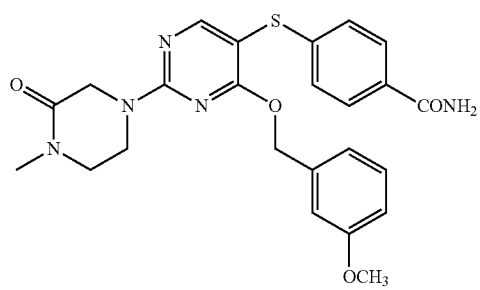 [SMILES: COc1cccc(COc2nc(N3CCN(C)C(=O)C3)ncc2Sc2ccc(C(N)=O)cc2)c1]
190t
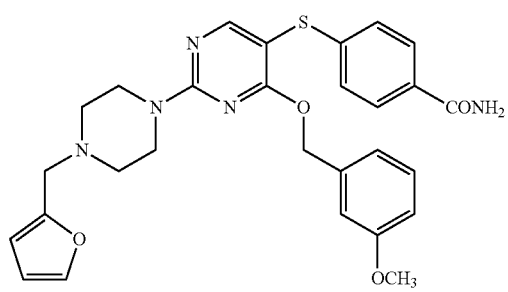 [SMILES: COc1cccc(COc2nc(N3CCN(Cc4ccco4)CC3)ncc2Sc2ccc(C(N)=O)cc2)c1]
190u
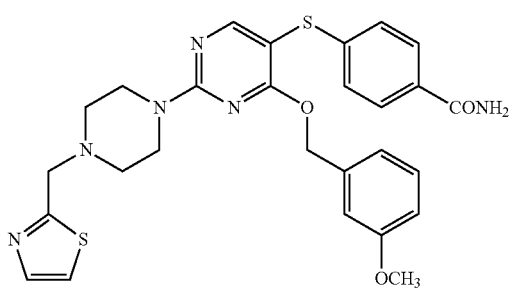 [SMILES: COc1cccc(COc2nc(N3CCN(Cc4nccs4)CC3)ncc2Sc2ccc(C(N)=O)cc2)c1]
190v TABLE 5-continued
Exemplary componds of formula I.
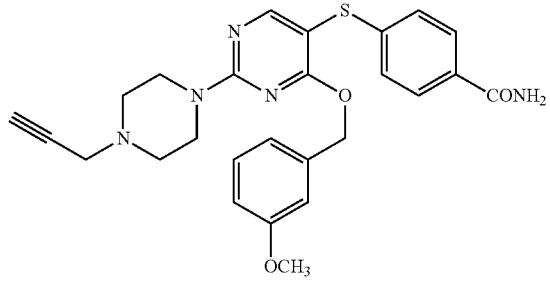 [SMILES: C#CCN1CCN(c2ncc(Sc3ccc(C(N)=O)cc3)c(OCc3cccc(OC)c3)n2)CC1] 198
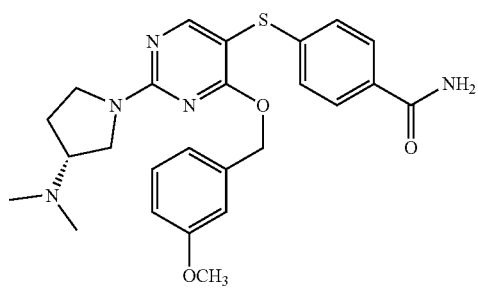 [SMILES: COc1cccc(COc2nc(N3CC[C@@H](N(C)C)C3)ncc2Sc2ccc(C(N)=O)cc2)c1] 205
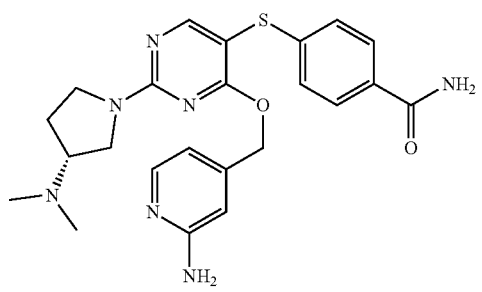 [SMILES: CN(C)[C@@H]1CCN(c2ncc(Sc3ccc(C(N)=O)cc3)c(OCc3ccnc(N)c3)n2)C1] 206
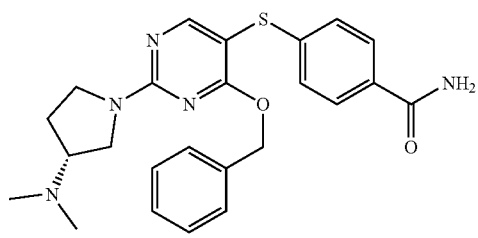 [SMILES: CN(C)[C@@H]1CCN(c2ncc(Sc3ccc(C(N)=O)cc3)c(OCc3ccccc3)n2)C1] 207
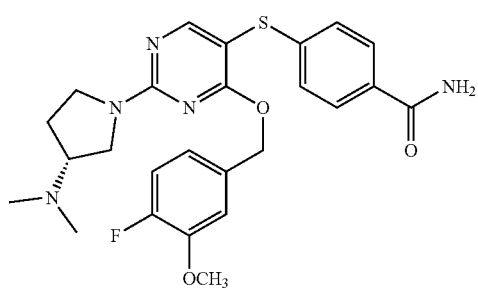 [SMILES: COc1cc(COc2nc(N3CC[C@@H](N(C)C)C3)ncc2Sc2ccc(C(N)=O)cc2)ccc1F] 208

TABLE 5-continued
Exemplary compunds of formula I.
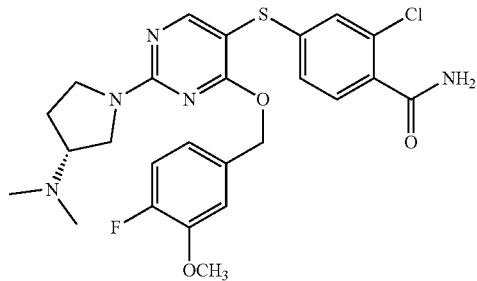 [SMILES: COc1cc(COc2nc(N3CC[C@@H](N(C)C)C3)ncc2Sc2ccc(C(N)=O)c(Cl)c2)ccc1F] 212
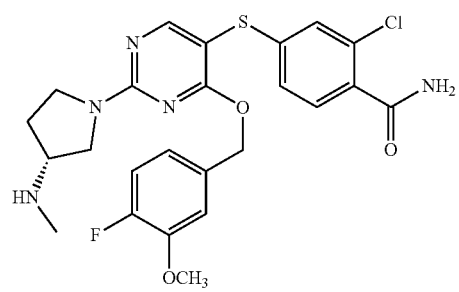 214
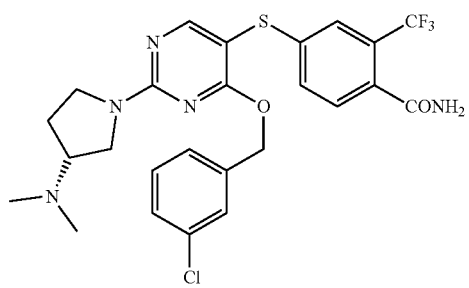 218
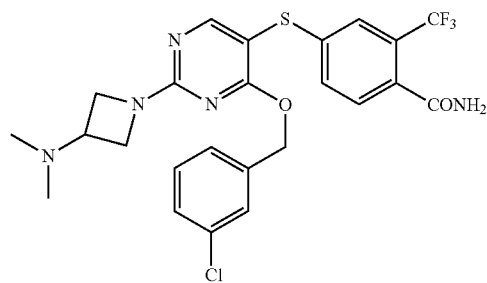 225
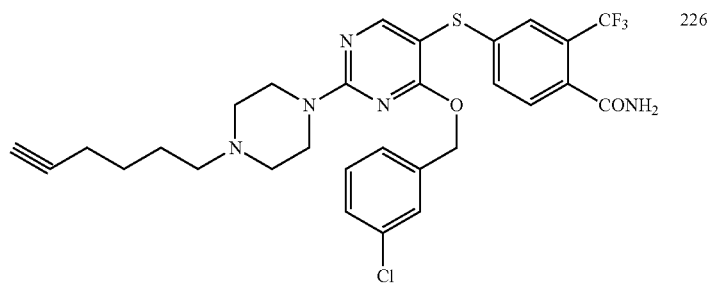 226

TABLE 5-continued
Exemplary compounds of formula I.
| | |
|---|---|
| 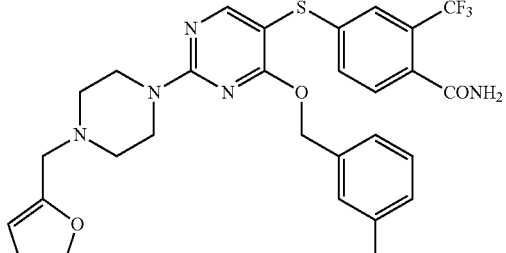 | 228 |
| 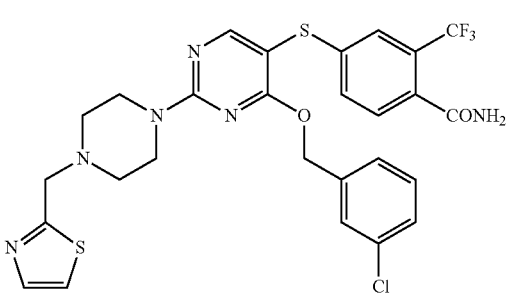 [SMILES: NC(=O)c1ccc(Sc2cnc(N3CCN(Cc4nccs4)CC3)nc2OCc2cccc(Cl)c2)cc1C(F)(F)F] | 229 |
| 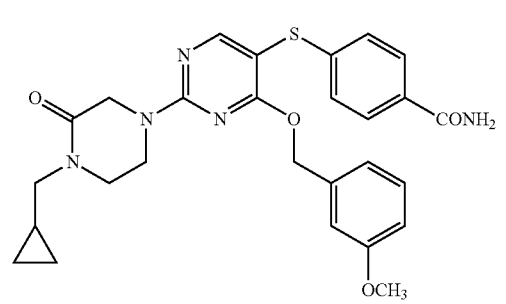 [SMILES: COc1cccc(COc2nc(N3CCN(CC4CC4)C(=O)C3)ncc2Sc2ccc(C(N)=O)cc2)c1] | 321 |
| 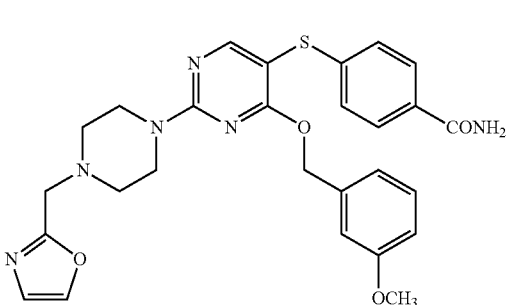 | 323 |
| 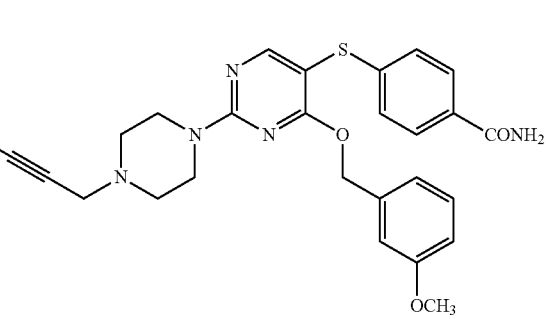 | 326 |

TABLE 5-continued
Exemplary componds of formula I.
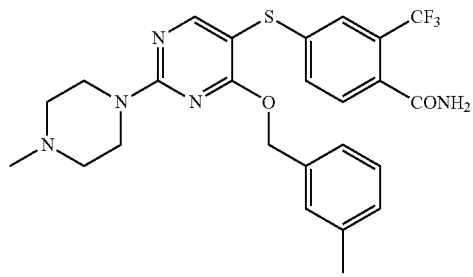 [SMILES: Cc1cccc(COc2nc(N3CCN(C)CC3)ncc2Sc2ccc(C(N)=O)c(C(F)(F)F)c2)c1]
329
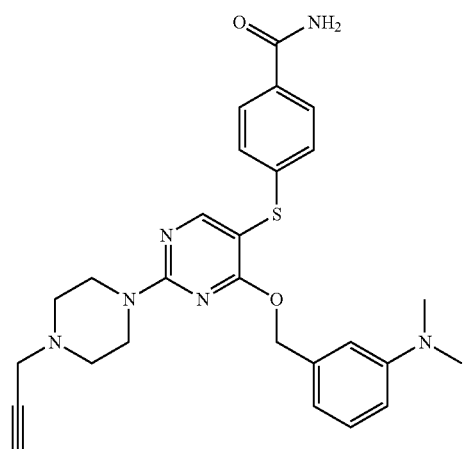 [SMILES: C#CCN1CCN(c2ncc(Sc3ccc(C(N)=O)cc3)c(OCc3cccc(N(C)C)c3)n2)CC1]
336
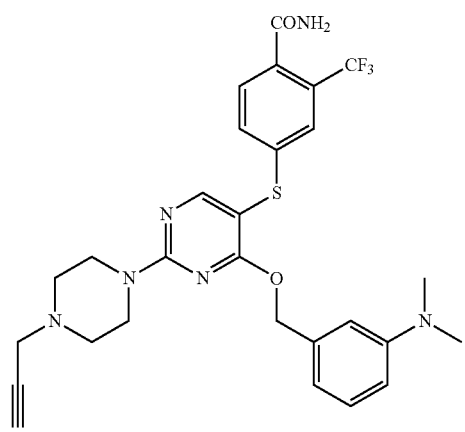 [SMILES: C#CCN1CCN(c2ncc(Sc3ccc(C(N)=O)c(C(F)(F)F)c3)c(OCc3cccc(N(C)C)c3)n2)CC1]
339
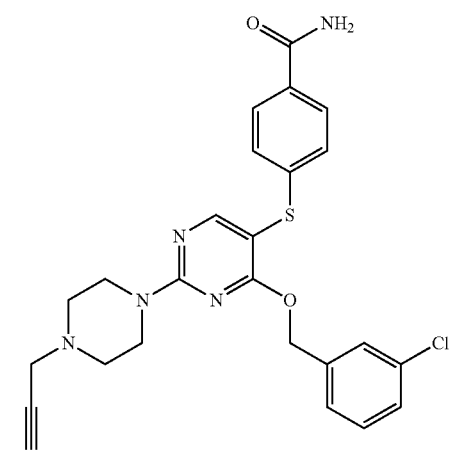 [SMILES: C#CCN1CCN(c2ncc(Sc3ccc(C(N)=O)cc3)c(OCc3cccc(Cl)c3)n2)CC1]
348

TABLE 5-continued
Exemplary compounds of formula I.
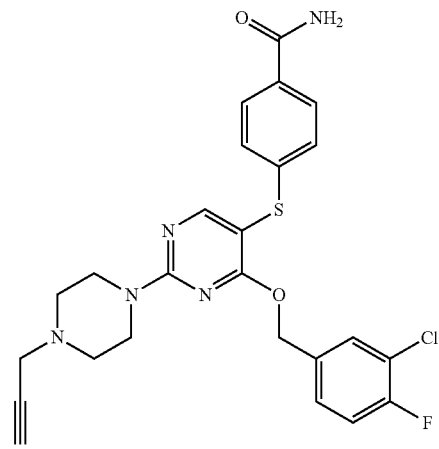 [SMILES: C#CCN1CCN(c2ncc(Sc3ccc(C(N)=O)cc3)c(OCc3ccc(F)c(Cl)c3)n2)CC1]
354
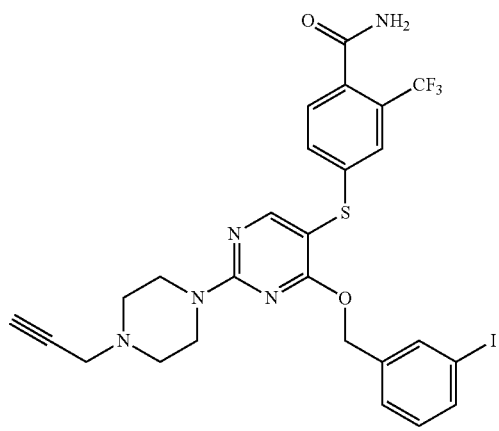 [SMILES: C#CCN1CCN(c2ncc(Sc3ccc(C(N)=O)c(C(F)(F)F)c3)c(OCc3cccc(I)c3)n2)CC1]
357
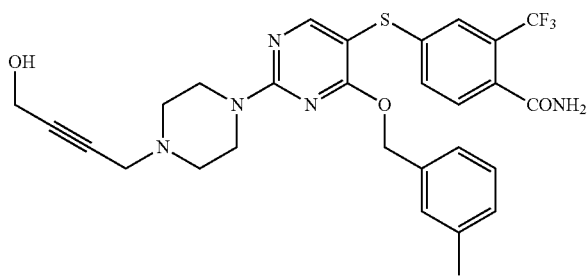 [SMILES: Cc1cccc(COc2nc(N3CCN(CC#CCO)CC3)ncc2Sc2ccc(C(N)=O)c(C(F)(F)F)c2)c1]
360
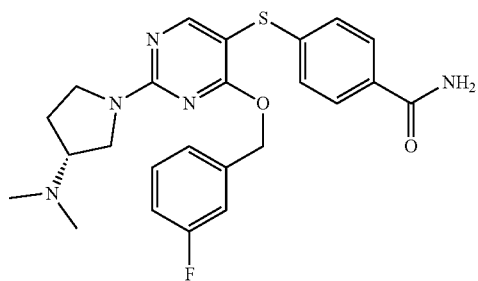 [SMILES: CN(C)[C@@H]1CCN(c2ncc(Sc3ccc(C(N)=O)cc3)c(OCc3cccc(F)c3)n2)C1]
363

TABLE 5-continued
Exemplary componds of formula I.
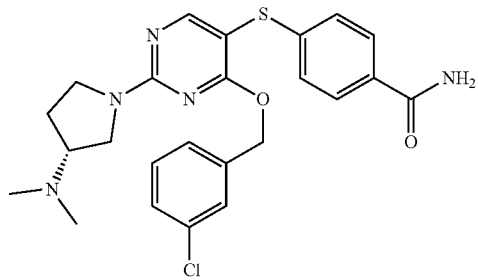
365
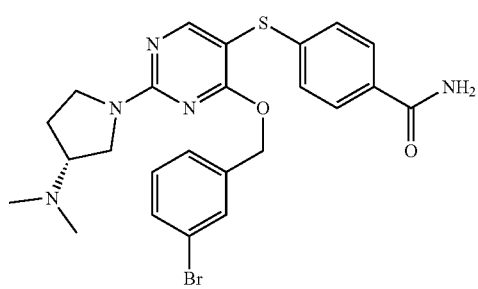 [SMILES: CN(C)[C@@H]1CCN(c2ncc(Sc3ccc(C(N)=O)cc3)c(OCc3cccc(Br)c3)n2)C1]
367
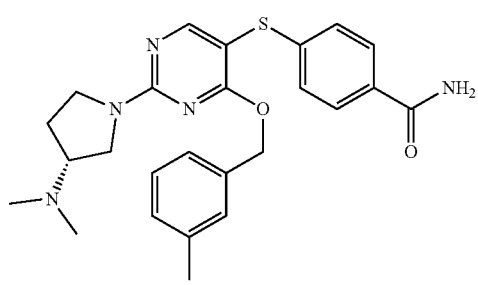 [SMILES: Cc1cccc(COc2nc(N3CC[C@@H](N(C)C)C3)ncc2Sc2ccc(C(N)=O)cc2)c1]
369
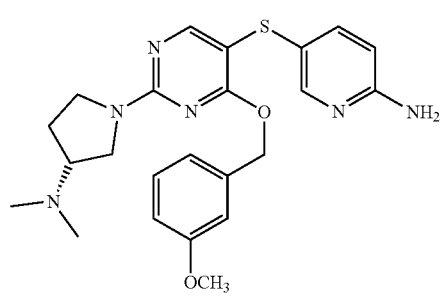
375
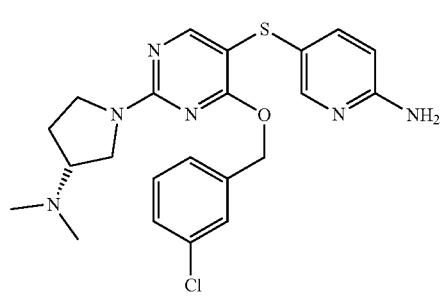
376

TABLE 5-continued

Exemplary componds of formula I.

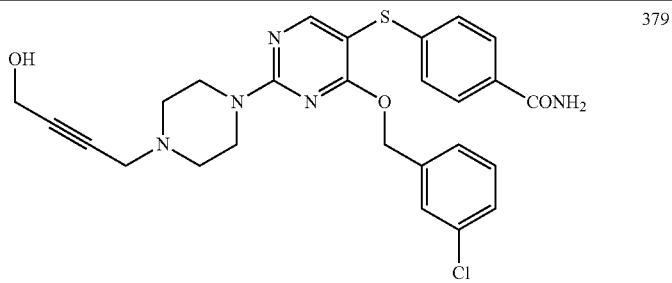

379

In certain embodiments, the present invention provides a compound of formula II or a pharmaceutically acceptable salt thereof.

In some embodiments, Y is —S—. In some embodiments, Y is —O—. In some embodiments, a compound of formula II is

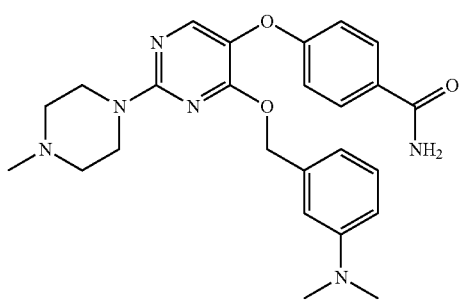 [SMILES: CN1CCN(c2ncc(Oc3ccc(C(N)=O)cc3)c(OCc3cccc(N(C)C)c3)n2)CC1]

or a pharmaceutically acceptable salt thereof. In some embodiments, Y is —CR$_2$—. In some embodiments, Y is —CH$_2$—. In some embodiments, a compound of formula II is

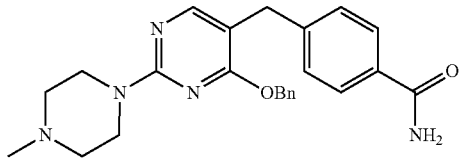 [SMILES: CN1CCN(c2ncc(Cc3ccc(C(N)=O)cc3)c(OCc3ccccc3)n2)CC1]

or a pharmaceutically acceptable salt thereof.

In some embodiments, Ring B is

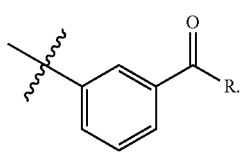

In some embodiments, Ring B is

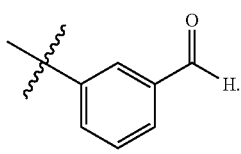

In some embodiments, Ring B is

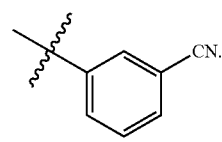 [SMILES: *c1cccc(C#N)c1]

In some embodiments, Ring B is

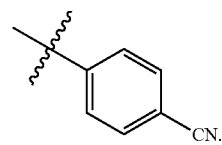 [SMILES: *c1ccc(C#N)cc1]

In some embodiments, Ring B is

In some embodiments, Ring B is

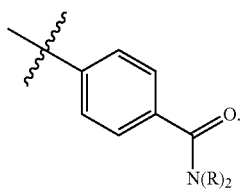

In some embodiments, Ring B is

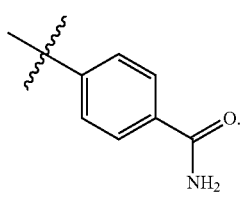 [SMILES: *c1ccc(C(N)=O)cc1]

In some embodiments, Ring B is

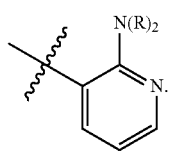

In some embodiments, Ring B is

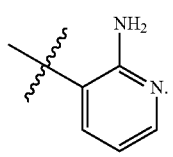 [SMILES: *c1cccnc1N]

In some embodiments, Ring B is thienyl optionally substituted with —C(O)R. In some embodiments, Ring B is thienyl optionally substituted with —C(O)Me. In some embodiments, Ring B is

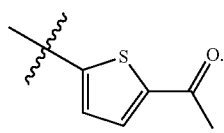 [SMILES: *c1ccc(C(C)=O)s1]

In some embodiments, Ring B is furanyl optionally substituted with —C(O)R. In some embodiments, Ring B is furanyl optionally substituted with —C(O)H. In some embodiments, Ring B is

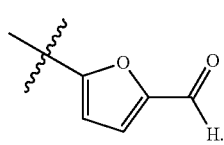

In some embodiments, a compound of formula II has the structure of formula II-a:

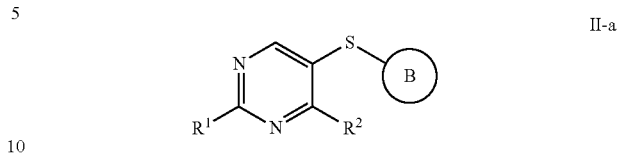

or a pharmaceutically acceptable salt thereof, wherein each variable is independently as described in classes and subclasses herein, both singly and in combination.

Exemplary compounds of formula II are depicted in below.

TABLE 6

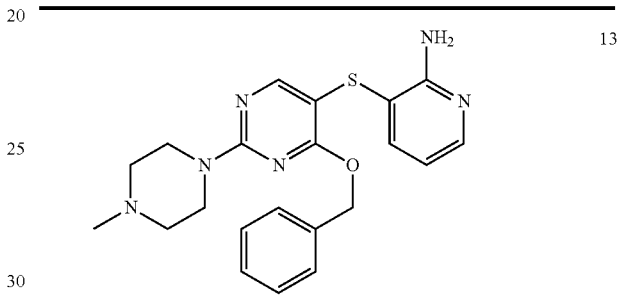

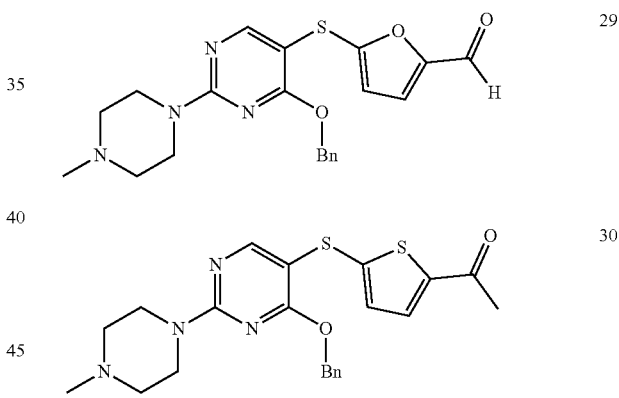

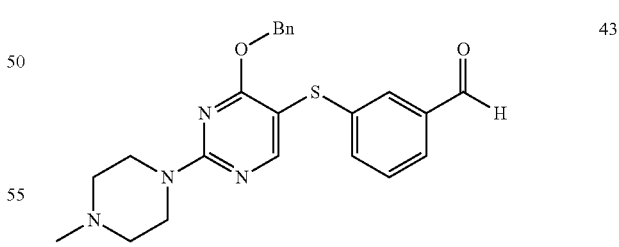

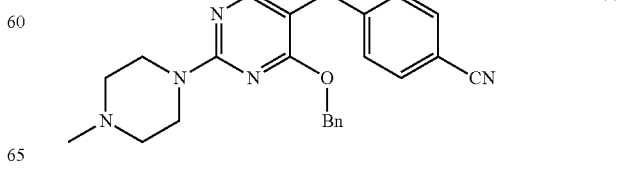

TABLE 6-continued

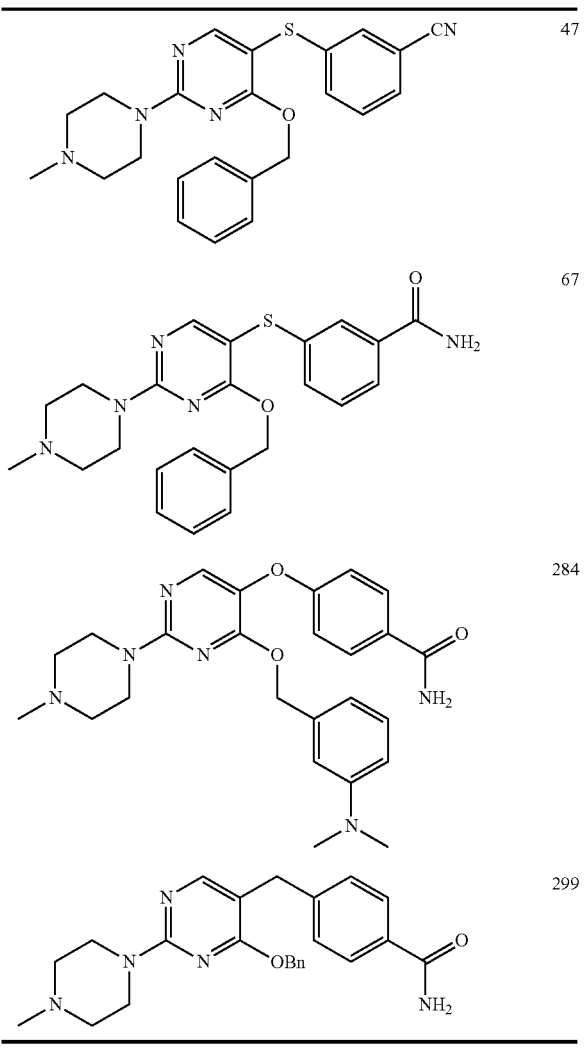

| | |
|---|---|
| | 47 |
| | 67 |
| | 284 |
| | 299 |

Uses

In some embodiments, the compounds of formulae I and/or II are useful in medicine. In some embodiments, the present invention provides a method of treating a subject suffering from or susceptible to a disease, disorder, or condition responsive to Hsp70 inhibition, the method comprising administering to the subject a therapeutically effective amount of a compound as described herein. In some embodiments, a disease, disorder, or condition is a proliferative disease, disorder, or condition. In some embodiments, a disease, disorder, or condition is cancer.

In certain embodiments, provided compounds have been found to possess anti-proliferative activity and are therefore believed to be of use in the treatment of proliferative disorders such as cancers and other disorders associated with uncontrolled cellular proliferation. As defined herein, an anti-proliferative effect within the scope of the present subject matter may be demonstrated, by way of nonlimiting example, by the ability to inhibit cell proliferation specific gene targets in vitro or in vivo, or inhibit cell proliferation in an in vitro whole cell assay, in an in vivo animal model, or in human clinical administration.

Provided compounds may be used in vitro or in vivo. In some embodiments, provided compounds may be particularly useful in the treatment of neoplasms or other proliferative diseases in vivo. However, provided compounds described above may also be used in vitro for research or clinical purposes (e.g., determining the susceptibility of a patient's disease to a provided compound, researching the mechanism of action, elucidating a cellular pathway or process). In certain embodiments, the neoplasm is a benign neoplasm. In other embodiments, the neoplasm is a malignant neoplasm.

In certain embodiments, the malignancy is a hematological malignancy. Hematological malignancies are types of cancers that affect the blood, bone marrow, and/or lymph nodes. Examples of hematological malignancies that may be treated using provided compounds include, but are not limited to, acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), Mantle cell lymphoma, B-cell lymphoma, acute lymphoblastic T cell leukemia (T-ALL), acute promyelocytic leukemia, and multiple myeloma. In certain embodiments, provided compounds are used to treat multiple myeloma, glioblastoma, epithelial carcinoma, cervical adenocarcinoma, or well-differentiated liposarcoma. In certain particular embodiments, the cancer is relapsed and/or refractory multiple myeloma. In other embodiments, provided compounds are used to treat chromic lymphocytic leukemia (CLL). In certain embodiments, provided compounds are used to treat acute lymphoblastic leukemia (ALL). In certain embodiments, provided compounds are used to treat acute myelogenous leukemia (AML). In certain embodiments, the cancer is a chronic myeloid leukemia (CML). In certain embodiments, the cancer is cutaneous T-cell lymphoma. In other embodiments, the cancer is peripheral T-cell lymphoma. provided compounds may also be used to treated a refractory or relapsed malignancy. In certain embodiments, the cancer is a refractory and/or relapsed hematological malignancy. In certain embodiments, the cancer is multidrug resistant. For example, the cancer may be resistant to a particular chemotherapeutic agent.

Other cancers besides hematological malignancies may also be treated using provided compounds. In certain embodiments, the cancer is a solid tumor. Exemplary cancers that may be treated using provided compounds include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, gallbladder cancer, laryngeal cancer, oral cancer, penile cancer, glandular tumors, rectal cancer, small intestine cancer, sarcoma, carcinoma, melanoma, urethral cancer, vaginal cancer, to name but a few.

In some embodiments, provided compounds may also be used to treat and/or kill cells in vitro. In certain embodiments, a cytotoxic concentration of a provided compound is contacted with the cells in order to kill them. In other embodiments, a sublethal concentration of a provided compound is used to treat the cells. In certain embodiments, the concentration of a provided compound ranges from 0.01 nM to 100 nM. In certain embodiments, the concentration of a provided compound ranges from 0.1 nM to 50 nM. In certain embodiments, the concentration of a provided compound ranges from 1 nM to 10 nM. In certain embodiments, the concentration of a provided compound ranges from 1 nM to 10 nM, more particularly 1 nM to 5 nM.

Any type of cell may be tested or killed with provided compound. The cells may be at any stage of differentiation or development. In certain embodiments, the cells are animal cells. In certain embodiments, the cells are vertebrate cells. In certain embodiments, the cells are mammalian cells. In certain embodiments, the cells are human cells. The cells may be derived from a male or female human in any stage of development. In certain embodiments, the cells are primate cells. In other embodiments, the cells are derived from a rodent (e.g., mouse, rat, guinea pig, hamster, gerbil). In certain embodiments, the cells are derived from a domesticated animal such as a dog, cat, cow, goat, pig, etc. The cells may also be derived from a genetically engineered animal or plant, such as a transgenic mouse.

The cells used may be wild type or mutant cells. The cells may be genetically engineered. In certain embodiments, the cells are normal cells. In certain embodiments, the cells are hematological cells. In certain embodiments, the cells are white blood cells. In certain particular embodiments, the cells are precursors of white blood cells (e.g., stem cells, progenitor cells, blast cells). In certain embodiments, the cells are neoplastic cells. In certain embodiments, the cells are cancer cells. In certain embodiments, the cells are derived from a hematological malignancy. In other embodiments, the cells are derived from a solid tumor. For example, the cells may be derived from a patient's tumor (e.g., from a biopsy or surgical excision). In certain embodiments, the cells are derived from a blood sample from the subject or from a bone marrow biopsy. In certain embodiments, the cells are derived from a lymph node biopsy. Such testing for cytotoxicity may be useful in determining whether a patient's disease will respond to a particular therapy. Such testing may also be useful in determining the dosage needed to treat the malignancy. This testing of the susceptibility of a patient's cancer to provided compound would prevent the unnecessary administration of drugs with no effect to the patient. The testing may also allow the use of lower dose of an inventive compound if the patient's cancer is particularly susceptible to the compound.

In some embodiments, the cells are derived from cancer cells lines. In certain embodiments, the cells are from hematological malignancies such as those discussed herein. Human leukemia cell lines include U937, HL-60, HL-60/RV+ (a P-glycoprotein over-expressing multidrug resistant HL-60 variant which was selected by continuous exposure to the vinca alkaloid vincristine), THP-1, Raji, CCRF-CEM, ALL3 (acute lymphoblastic leukemia isolated from a patient treated at Memorial Sloan Kettering Cancer Center and characterized as Philadelphia chromosome positive), and Jurkat. Exemplary CLL cell lines include JVM-3 and MEC-2. Exemplary myeloma cells lines include MM1.S, MM1.R (dexamethasone-resistant), RPMI8226, NCI-H929, and U266. Exemplary lymphoma cell lines include NCEB1 (Mantle cell lymphoma), JEKO (B cell lymphoma), Karpas, SUDH-6, SUDH-16, L428, KMH2, and Granta mantle lymphoma cell line. In certain embodiments, the cells are AML cells or multiple myeloma (CD138$^+$) cells. In certain embodiments, the cells are hematopoietic stem or progenitor cells. For example, in certain embodiments, the cells are hematopoietic progenitor cells such as CD34$^+$ bone marrow cells. In certain embodiments, the cells are MOLT-3 (acute lymphoblastic T-cell), SKNLP (neuroblastoma), PC9 (adenocarcinoma), H1650 (adeocarcinoma), H1975 (adeocarcinoma), H2030 (adeocarcinoma), H3255 (adeocarcinoma), TC71 (Ewing's sarcoma), HTP-15 (glioblastoma), A431 (epithelial carcinoma), HeLa (cervical adenocarcinoma), or WD0082 (well-differentiated liposarcoma) cells. In some embodiments, the cells are HL-60/RV+ cells. In certain embodiments, the cell lines are resistant to a particular chemotherapeutic agent.

In some embodiments, a cancer is refractory to treatment with Hsp90 inhibitors. Cancers resistant to Hsp90 inhibitors can be particularly difficult to treat. It is surprisingly found that a provided compound activates caspase, induced cell death and/or inhibited cell growth when administered to cells resistant to Hsp90 inhibitors. In some embodiments, the present invention provides a method for activating caspase in cells resistant to Hsp90 inhibitors, comprising administering to the cells a provided compound or a composition. In some embodiments, the present invention provides a method for inducing cell death in cells resistant to Hsp90 inhibitors, comprising administering to the cells a provided compound or a composition. In some embodiments, the present invention provides a method for inducing apoptosis in cells resistant to Hsp90 inhibitors, comprising administering to the cells a provided compound or a composition. In some embodiments, the present invention provides a method for inhibiting cell growth in cells resistant to Hsp90 inhibitors, comprising administering to the cells a provided compound or a composition.

In certain embodiments, provided compounds are useful in treating a subject in clinical remission, where the subject has been treated by surgery or has limited unresected disease. In some embodiments, a subject has been previously treated by Hsp90 inhibitor.

Pharmaceutical Compositions

In another aspect, the present invention provides pharmaceutical compositions comprising a compound of formulae I or II in combination with a pharmaceutically acceptable excipient (e.g., carrier).

The pharmaceutical compositions include optical isomers, diastereomers, or pharmaceutically acceptable salts of the compounds disclosed herein. A provided compound included in the pharmaceutical composition may be covalently attached to a carrier moiety, as described above. Alternatively, a provided compound included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be co-administered to the subject. Co-administration is meant to include simultaneous or sequential administration of the compounds individually or in combination (more than one compound). The preparations can also be combined, when desired, with other active substances (e.g. to reduce metabolic degradation).

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., a disease responsive to Hsp70 inhibition); presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of decreasing enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring inhibition and adjusting the dosage upwards or downwards, as described above. In certain embodiments, the administered dose is in the range of about 1 mg to about 1000 mg per day, either once, twice, or more than twice daily. In certain embodiments, the administered dose is in the range of about 0.001 to about 100 mg per kilogram per day. In certain embodiments, the administered dose is in the range of about 0.001 to about 10 mg per kilogram per day. In certain embodiments, the administered dose is in the range of about 0.0001 to about 100 mg per kilogram per day. In certain embodiments, the administered dose is in the range of about 0.0001 to about 10 mg per kilogram per day. In certain embodiments, the administered dose is in the range of about 0.01 to about 10 mg per kilogram per day.

In certain embodiments, the preferred therapeutically effective dosage will be the amount of a compound of the present subject matter required to obtain a serum, but more preferably tumor, concentration equivalent to the concentration to achieve phenotypic effects in any of the assays described herein, such as but not limited to induction of apoptosis as indicated by caspase. In some embodiments, such concentrations are selected from the group consisting of less than 200 uM; less than 100 uM; less than 50 uM; less than 25 uM; less than 15 uM; less than 10 uM; less than 5 uM; less than 2 uM; less than 1 uM; less than 500 nM; less than 200 nM; or less than 100 nM. In some embodiments, the phenotypic effect is the IC50 value for an assay.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

In some embodiments, pharmaceutical compositions in accordance with the subject matter described herein may be an intravenous form or an oral dosage form, for example, a capsule, a tablet, liquid, and/or a powder packaged in, for example, a multi-use or single-use package, including for example, a container or bottle, a blister package. Single dosage kits and packages containing once per day, or once per treatment, amount of the pharmaceutical composition may be prepared. Single dose, unit dose, and once-daily disposable containers of the present pharmaceutical compositions are contemplated as within the scope of the present subject matter.

Combination Therapy

In some embodiments, the present pharmaceutical compositions may be used in combination with an additional pharmaceutical dosage form to enhance their effectiveness in treating a disease, disorder, or condition as described herein. In this regard, the present compositions may be administered as part of a regimen additionally including any other pharmaceutical and/or pharmaceutical dosage form known in the art as effective for the treatment of a disease, disorder, or condition as described herein. Similarly, a pharmaceutically active ingredient other than those specified herein can be added to the present compositions to enhance their effectiveness in treating a disease, disorder, or condition as described herein. Accordingly, this additional pharmaceutically active ingredient or additional pharmaceutical dosage form can be administered to a patient either directly or indirectly, and concomitantly or sequentially, with the compositions described herein.

For example, other therapies, pharmaceutical dosage forms and/or anticancer agents that may be used in combination with the provided compounds and compositions of the present invention include surgery, radiotherapy (□-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. In certain embodiments, an anticancer agent is an epothilone, taxol, radicicol or TMC-95A/B. In certain embodiments, the epothilone is 12,13-desoxyepothilone B, (E)-9,10-dehydro-12,13-desoxyEpoB and 26-CF3-(E)-9,10-dehydro-12,13-desoxyEpoB. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof).

In some embodiments, a provided compound is administered in combination with one or more other anticancer agents. In some embodiments, an anticancer agent is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (e.g., TAXOL™, Bristol-Myers Squibb Oncology, Princeton, N.J.; ABRAXANE™, Celgene Corporation, Summit, N.J.), and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable agents for combination are suitable chemotherapeutic cell conditioners such as anti-hormonal agents that act to regulate or inhibit hormone action on tumors, including anti-estrogens, e.g., tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin. Additional anticancer agents for combination include chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). In some embodiments, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®.

In some embodiments, anti-cancer, anti-malignancy, or anti-proliferative disorder agents other than compounds discussed above are additionally contemplated as useful for combination therapy discussed herein. Combinations of any of the foregoing agents or their pharmaceutically acceptable salts or derivatives are contemplated herein.

In some embodiments, the present compositions and the additional pharmaceutical dosage form can be administered to a patient at the same time. In certain embodiments, one of the present compositions and the additional pharmaceutical dosage form can be administered in the morning and the other can be administered in the evening.

In some embodiments, the presently described compounds can be administered to a patient in need thereof in multiple pharmaceutical dosage forms. This combination therapy may maximize the effectiveness of the present composition in treating a cancer, malignancy, or proliferative disorder.

The following numbered embodiments, while non-limiting, are exemplary of certain aspects of the present disclosure:

1. A compound of formula I:

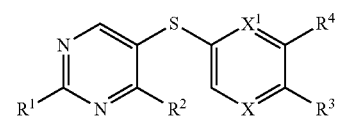

or a pharmaceutically acceptable salt thereof, wherein:
X is —N= or —CH=;
$X^1$ is —N= or —C($R^5$)=;
$R^1$ is

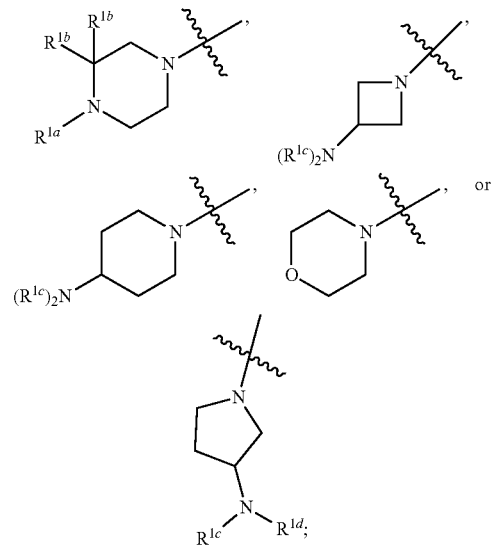

$R^{1a}$ is

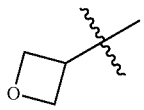

or $C_{1-6}$ aliphatic optionally substituted with one or more groups independently selected from —OH, cyclopropyl, or 5-membered heteroaryl having 1-2 heteroatoms independently selected from nitrogen, oxygen or sulfur;

each $R^{1b}$ is independently hydrogen, $C_{1-4}$ alkyl, or two $R^{1b}$ groups are optionally taken together to form an oxo group;

each of $R^{1c}$ and $R^{1d}$ is independently hydrogen or $C_{1-4}$ alkyl;

$R^2$ is —O—$CH_2$-Ring A, —NH—$CH_2$-Ring A, or —O—$CH_2CH_2$-Ring A;

Ring A is unsubstituted phenyl, unsubstituted furanyl,

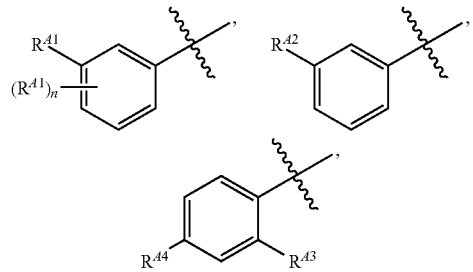

or pyridinyl optionally substituted with $R^{A5}$;

each of $R^{A1}$ is independently halogen, —CN, —C(O)N(R)$_2$, —N(R)$_2$, —OR, —C(O)R, —N$_3$, an optionally substituted 5- or 6-membered heterocyclyl or heteroaryl having one or two heteroatoms independently selected from nitrogen, oxygen, or sulfur, or $C_{1-4}$ alkyl optionally substituted with one or more halogen;

each R is independently hydrogen or $C_{1-4}$ alkyl optionally substituted with one or more halogen;

$R^{A2}$ is —Cl, —Br, —I, —CN, —C(O)N(R)$_2$, —N(R)$_2$, —OR, —C(O)R, —N$_3$, $C_{1-4}$ alkyl optionally substituted with one or more halogen, or an optionally substituted 5- or 6-membered heterocyclyl or heteroaryl having one or two heteroatoms independently selected from nitrogen, oxygen or sulfur;

n is 1 to 4;

$R^{A3}$ is —H or —F;

$R^{A4}$ is —F or —OR;

$R^{A5}$ is —OR or —N(R)$_2$;

$R^3$ is —C(O)N($R^{3a}$)$_2$, —OR$^{3b}$, —C(O)H, —C(O)OR, or —N($R^{3c}$)$_2$;

each $R^{3a}$ is independently hydrogen or $C_1$ alkyl optionally substituted with one or more groups independently selected from halogen or 1-pyrrolidinyl;

$R^{3b}$ is hydrogen or $C_{1-4}$ alkyl optionally substituted with one or more groups independently selected from halogen, $C_{1-4}$ alkyl, $C_{1-4}$ haloalkyl, oxo, or —N(R)$_2$;

each $R^{3c}$ is independently hydrogen or $C_{1-4}$ alkyl optionally substituted with one or more groups independently selected from halogen, $C_{1-4}$ alkyl, $C_{1-4}$ haloalkyl, oxo, or —N(R)$_2$;

$R^4$ is R, halogen, or —N(R)$_2$; and $R^5$ is hydrogen, methyl or —N(R)$_2$.

2. The compound of embodiment 1, wherein X is —N=.

3. The compound of embodiment 1, wherein X is —CH=.

4. The compound of any one of the preceding embodiments, wherein $R^3$ is —C(O)N($R^{3a}$)$_2$.

5. The compound of any one of the preceding embodiments, wherein $R^3$ is —C(O)NH$_2$.

6. The compound of embodiment 4, wherein one $R^{3a}$ is hydrogen, and the other R is $C_1$ alkyl optionally substituted with one or more groups independently selected from halogen or 1-pyrrolidinyl.

7. The compound of embodiment 4, wherein each $R^{3a}$ is methyl.

8. The compound of any one of embodiments 1-3, wherein $R^3$ is —OR$^{3b}$.

9. The compound of embodiment 8, wherein $R^{3b}$ is hydrogen.

10. The compound of embodiment 8, wherein $R^{3b}$ is $C_{1-4}$ alkyl optionally substituted with one or more groups independently selected from halogen, $C_{1-4}$ alkyl, $C_{1-4}$ haloalkyl, oxo, or —N(R)$_2$.

11. The compound of embodiment 8, wherein $R^{3b}$ is $C_{1-4}$ alkyl.

12. The compound of embodiment 11, wherein $R^{3b}$ is methyl.

13. The compound of embodiment 10, wherein $R^{3b}$ is —CH(CH$_3$)C(O)NH$_2$.

14. The compound of any one of embodiments 1-5, wherein $R^3$ is —C(O)H.

15. The compound of any one of embodiments 1-5, wherein $R^3$ is —C(O)OR.

16. The compound of any one of embodiments 1-5, wherein $R^3$ is —N($R^{3c}$)$_2$.

17. The compound of embodiment 16, wherein each $R^{3c}$ is hydrogen.

18. The compound of embodiment 16, wherein one $R^{3c}$ is hydrogen, and the other $R^{3c}$ is $C_{1-4}$ alkyl optionally substituted with one or more groups independently selected from halogen, $C_{1-4}$ alkyl, $C_{1-4}$ haloalkyl, oxo, or —N(R)$_2$;

19. The compound of any one of the preceding embodiments, wherein $R^4$ is R or halogen.

20. The compound of any one of the preceding embodiments, wherein $R^4$ is R.

21. The compound of any one of the preceding embodiments, wherein $R^4$ is hydrogen.

22. The compound of any one of embodiments 1-20, wherein $R^4$ is $C_{1-4}$ alkyl.

23. The compound of embodiment 22, wherein $R^4$ is methyl.

24. The compound of any one of embodiments 1-19, wherein $R^4$ is $C_{1-4}$ alkyl optionally substituted with one or more halogen.

25. The compound of embodiment 24, wherein $R^4$ is —CF$_3$.

26. The compound of any one of embodiments 1-19, wherein $R^4$ is halogen.

27. The compound of any one of embodiments 1-19, wherein $R^4$ is —F.

28. The compound of any one of embodiments 1-19, wherein $R^4$ is —Cl.

29. The compound of any one of embodiments 1-19, wherein $R^4$ is —Br.

30. The compound of any one of embodiments 1-19, wherein $R^4$ is —I.

31. The compound of any one of the preceding embodiments, wherein $X^1$ is —C($R^5$)=.

32. The compound of any one of the preceding embodiments, wherein $R^5$ is hydrogen.

33. The compound of any one of embodiments 1-31, wherein $R^5$ is methyl.
34. The compound of any one of embodiments 1-31, wherein $R^5$ is —$NH_2$.
35. The compound of any one of embodiments 1-30, wherein $X^1$ is —N=.
36. The compound of embodiment 1, wherein

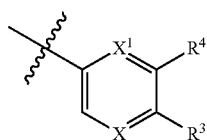

is a group selected from Table 4.
37. A compound of formula II:

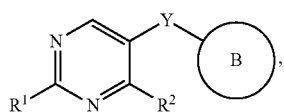

or a pharmaceutically acceptable salt thereof, wherein:
Y is —S—, —O—, or —$CR_2$—;
$R^1$ is

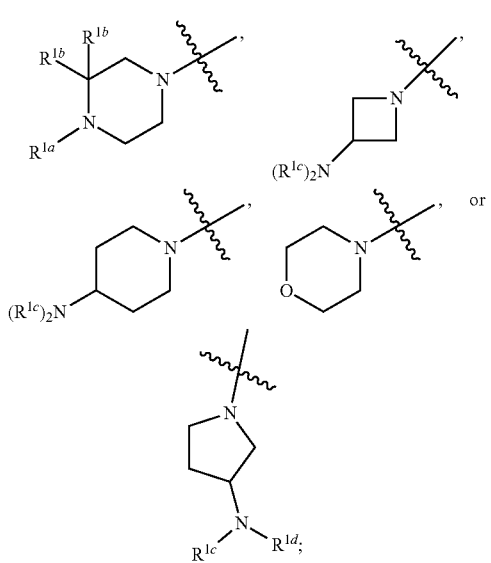

$R^{1a}$ is

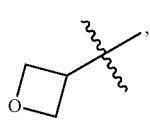

or $C_{1-6}$ aliphatic optionally substituted with one or more groups independently selected from —OH, cyclopropyl, or 5-membered heteroaryl having 1-2 heteroatoms independently selected from nitrogen, oxygen, or sulfur;

each $R^{1b}$ is independently hydrogen, $C_{1-4}$ alkyl, or two $R^{1b}$ groups are optionally taken together to form an oxo group;
each of $R^{1c}$ and $R^{1d}$ is independently hydrogen or $C_{1-4}$ alkyl;
$R^2$ is —O—$CH_2$-Ring A, —NH—$CH_2$-Ring A, or —O—$CH_2CH_2$-Ring A;
Ring A is unsubstituted phenyl, unsubstituted furanyl,

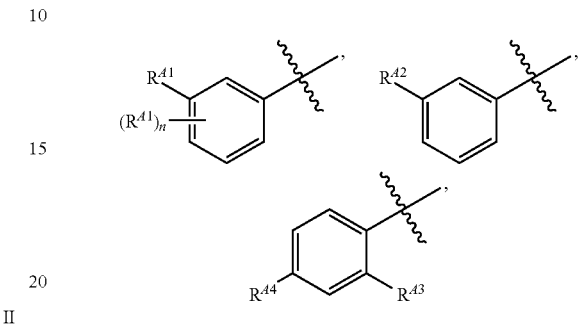

or pyridinyl optionally substituted with $R^{45}$;
each of $R^{41}$ is independently halogen, —CN, —C(O)N(R)$_2$, —N(R)$_2$, —OR, —C(O)R, —$N_3$, an optionally substituted 5- or 6-membered heterocyclyl or heteroaryl having one or two heteroatoms independently selected from nitrogen, oxygen, or sulfur, or $C_{1-4}$ alkyl optionally substituted with one or more halogen;
each R is independently hydrogen or $C_{1-4}$ alkyl optionally substituted with one or more halogen;
$R^{42}$ is —Cl, —Br, —I, —CN, —C(O)N(R)$_2$, —N(R)$_2$, —OR, —C(O)R, —$N_3$, $C_{1-4}$ alkyl optionally substituted with one or more halogen, or an optionally substituted 5- or 6-membered heterocyclyl or heteroaryl having one or two heteroatoms independently selected from nitrogen, oxygen or sulfur;
n is 1 to 4;
$R^{43}$ is —H or —F;
$R^{44}$ is —F or —OR;
$R^{45}$ is —OR or —N(R)$_2$; and
Ring B is

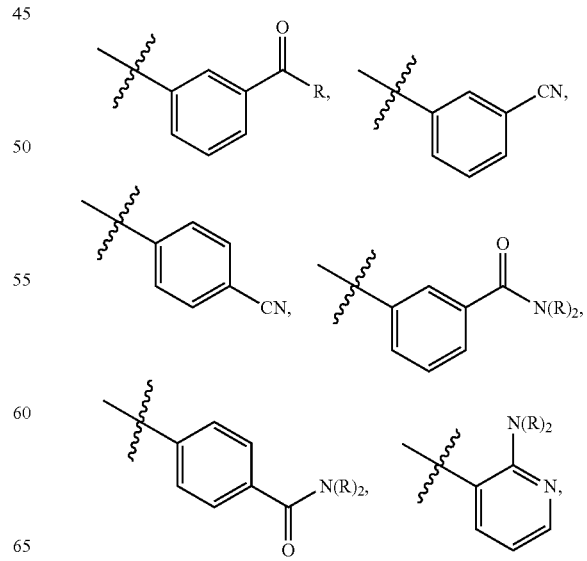

thienyl optionally substituted with —C(O)R, or furanyl optionally substituted with —C(O)R.

38. The compound of embodiment 37, wherein Y is —S—.
39. The compound of embodiment 37, wherein Y is —O—.
40. The compound of embodiment 37, wherein Y is —CH$_2$—.
41. The compound of embodiment 37, wherein Ring B is

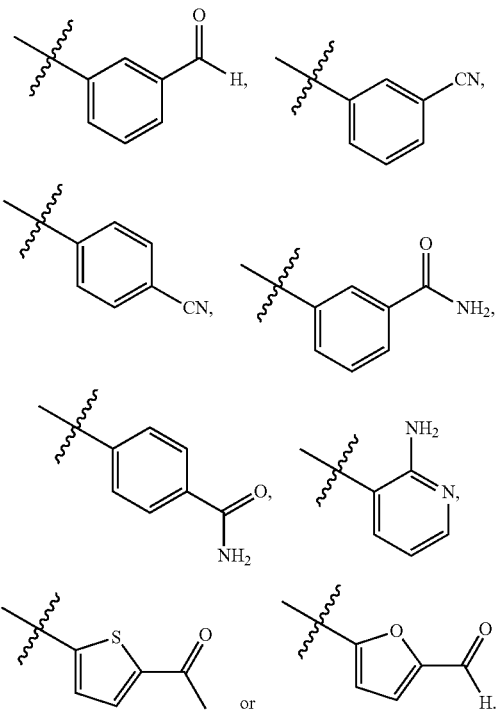

42. The compound of any one of the preceding embodiments, wherein R$^1$ is R$^1$ is

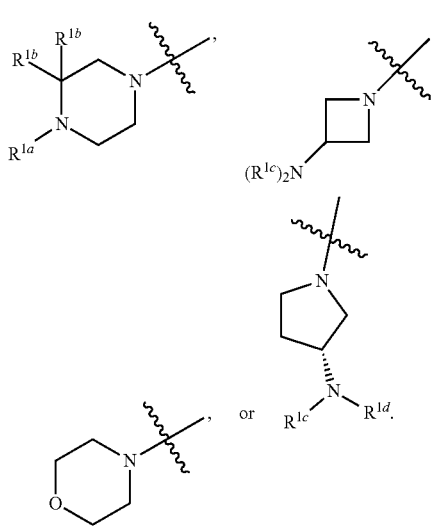

43. The compound of any one of the preceding embodiments, wherein R$^1$ is

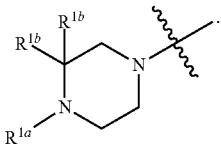

44. The compound of any one of the preceding embodiments, wherein each R$^{1b}$ is independently hydrogen, or two R$^{1b}$ groups are optionally taken together to form an oxo group.

45. The compound of any one of the preceding embodiments, wherein R$^{1a}$ is

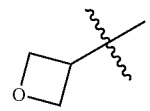

or C$_{1-4}$ straight chain aliphatic optionally substituted with one or more groups independently selected from —OH or 5-membered heteroaryl having 1-2 heteroatoms independently selected from nitrogen, oxygen or sulfur.

46. The compound of any one of embodiments 1-41, wherein R$^1$ is

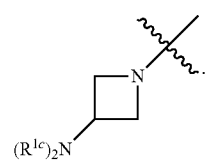

47. The compound of any one of embodiments 1-41, wherein R$^1$ is

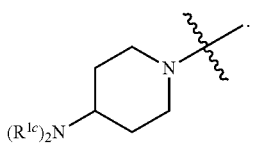

48. The compound of any one of embodiments 1-41, 46, and 47, wherein each R$^{1c}$ is independently C$_{1-4}$ alkyl.
49. The compound of any one of embodiments 1-41, 46, 47 and 48, wherein each R$^{1c}$ is methyl.
50. The compound of any one of embodiments 1-41, wherein R$^1$ is

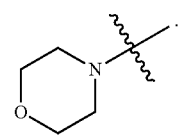

51. The compound of any one of embodiments 1-41, wherein R$^1$ is

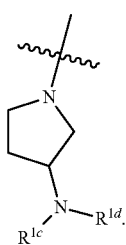

52. The compound of any one of embodiments 1-41, wherein $R^1$ is

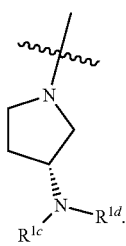

53. The compound of any one of embodiments 1-41 and 51-52, wherein each $R^{1c}$ is independently hydrogen or $C_{1-4}$ alkyl, and $R^{1d}$ is independently $C_{1-4}$ alkyl.
54. The compound of embodiment 51 or 52, wherein $R^1$ is

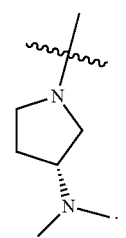

55. The compound of embodiment 51 or 52, wherein $R^1$ is

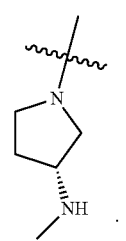 [SMILES: *N1CC[C@@H](NC)C1]

56. The compound of any one of embodiments 1-41, wherein $R^1$ is a group selected from Table 1.
57. The compound of any one of the preceding embodiments, wherein $R^2$ is —O—CH$_2$-Ring A.
58. The compound of any one of embodiments 1-56, wherein $R^2$ is —NH—CH$_2$-Ring A.
59. The compound of any one of embodiments 1-56, wherein $R^2$ is —O—CH$_2$CH$_2$-Ring A.
60. The compound of any one of embodiments 1-59, wherein Ring A is phenyl.
61. The compound of any one of embodiments 1-59, wherein Ring A is furanyl.

62. The compound of any one of embodiments 1-59, wherein Ring A is 1-furanyl.
63. The compound of any one of embodiments 1-59, wherein Ring A is 2-furanyl.
64. The compound of any one of embodiments 1-59, wherein Ring A is

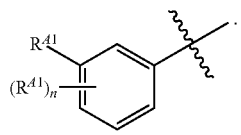

65. The compound of embodiment 64, wherein Ring A is

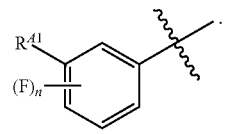

66. The compound of embodiment 65, wherein Ring A is

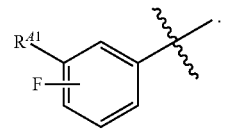

67. The compound of any one of embodiments 64-66, wherein $R^{41}$ is —Cl or —OR.
68. The compound of any one of embodiments 64-67, wherein $R^{41}$ is —OR, wherein R is $C_{1-4}$ alkyl.
69. The compound of any one of embodiments 64-68, wherein $R^{41}$ is —OCH$_3$.
70. The compound of any one of embodiments 1-66, wherein $R^{41}$ is —N(R)$_2$, wherein each R is independently $C_{1-4}$ alkyl.
71. The compound of any one of embodiments 1-66 and 70, wherein $R^{41}$ is —N(CH$_3$)$_2$.
72. The compound of any one of embodiments 1-59, wherein Ring A is

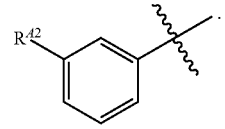

73. The compound of embodiment 72, wherein $R^{42}$ is —F, —Br, or —OR.
74. The compound of embodiment 72 or 73, wherein $R^{42}$ is —OR, wherein R is $C_{1-4}$ alkyl.
75. The compound of any one of embodiments 72-74, wherein $R^{42}$ is —OCH$_3$.
76. The compound of any one of embodiments 1-59, wherein Ring A is

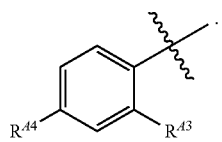

77. The compound of embodiment 76, wherein $R^{43}$ is —H or —F.
78. The compound of embodiment 76 or 77, wherein $R^{44}$ is —F or —OCH$_3$.
79. The compound of any one of embodiments 1-59, wherein Ring A is pyridinyl optionally substituted with $R^{45}$.
80. The compound of any one of embodiments 1-59, wherein Ring A is pyridinyl substituted with $R^{45}$.
81. The compound of embodiment 79 or 80, wherein $R^{45}$ is —N(R)$_2$.
82. The compound of embodiment 81, wherein $R^{45}$ is —NH$_2$.
83. The compound of embodiment 79 or 80, wherein $R^{45}$ is —OR.
84. The compound of embodiment 83, wherein R is $C_{1-4}$ alkyl.
85. The compound of embodiment 83 or 84, wherein R is methyl.
86. The compound of any of embodiments 1-56, wherein $R^2$ is a group selected from Table 3.
87. A compound selected from Table 5, or a pharmaceutically acceptable salt thereof.
88. A compound selected from Table 6, or a pharmaceutically acceptable salt thereof.
89. The compound of any one of the preceding embodiments, wherein the compound has an activity in a caspase cleaving assay at about 1.0 µM or below.
90. The compound of any one of the preceding embodiments, wherein the compound has an activity in a caspase cleaving assay below about 0.5 µM.
91. The compound of any one of the preceding embodiments, wherein the compound has an activity in a caspase cleaving assay below about 0.4 µM.
92. The compound of any one of the preceding embodiments, wherein the compound has an activity in a caspase cleaving assay below about 0.2 µM.
93. The compound of any one of the preceding embodiments, wherein the compound has an activity in a caspase cleaving assay below about 0.1 µM.
94. The compound of any one of the preceding embodiments, wherein the compound has an activity in a caspase cleaving assay below about 0.05 µM.
95. The compound of any one of the preceding embodiments, wherein the compound has an activity in a caspase cleaving assay below about 0.01 µM.
96. A pharmaceutical composition comprising a compound of any one of embodiments 1-95 and a pharmaceutically acceptable carrier.
97. A method of treating a subject suffering from or susceptible to a disease, disorder, or condition responsive to Hsp70 inhibition, the method comprising administering to the subject a therapeutically effective amount of a compound of any one of embodiments 1-95 or a composition thereof.
98. The method of embodiment 97, wherein the disease, disorder, or condition is a proliferative disease, disorder, or condition.
99. The method of embodiment 98, wherein the disease, disorder, or condition is cancer.
100. The method of embodiment 99, wherein the cancer is refractory to treatment with Hsp90 inhibitors.
101. The method of embodiment 99 or 100, further comprising administering to the subject a therapeutically effective amount of a second chemotherapeutic agent.
102. The method of any one of embodiments 99-101, wherein the subject is in clinical remission or, where the subject has been treated by surgery, has limited unresected disease.
103. A method of inhibiting Hsp70 activity, the method comprising contacting Hsp70 with a compound of any one of embodiments 1-95 or a composition thereof.
104. The method of embodiment 103, wherein the method is for the ex vivo inhibition of Hsp70.
105. The method of embodiment 103, wherein the method is for the inhibition of Hsp70 in a patient.
106. A method for treating or preventing cancer in a subject suffering therefrom, the method comprising administering to a patient in need thereof a therapeutically effective amount of a compound of any one of embodiments 1-95 or a composition thereof.
107. The method of embodiment 106, wherein the subject is in clinical remission or, where the subject has been treated by surgery, has limited unresected disease.
108. The method of embodiment 106 or 107, wherein the cancer is refractory to treatment with Hsp90 inhibitors.
109. A method for activating a caspase in cells, comprising administering to the cells a compound of any one of embodiments 1-95 or a composition thereof.
110. A method for inducing apoptosis in cells, comprising administering to the cells a compound of any one of embodiments 1-95 or a composition thereof.
111. A method for inhibiting cell growth, comprising administering to the cells a compound of any one of embodiments 1-95 or a composition thereof.
112. The method of any one of embodiments 109-111, wherein the cells are resistant to Hsp90 inhibitors.

In order that the invention described herein may be more fully understood, the following examples are set forth. It should be understood that these examples are for illustrative purposes only and are not to be construed as limiting this invention in any manner.

EXAMPLES

Chemical Synthesis and Purification

General. NMR spectra were recorded on a Bruker AV-III-500 or 600 MHz NMR spectrometer. Chemical shifts are reported in δ values in ppm downfield from TMS as the internal standard. $^1$H data are reported as follows: chemical shift, multiplicity (s=singlet, d=doublet, t=triplet, q=quartet, br=broad, m=multiplet), coupling constant (Hz), integration. $^{13}$C chemical shifts are reported in δ values in ppm downfield from TMS as the internal standard. High resolution mass spectra were recorded on a Waters LCT Premier system. Low resolution mass spectra were obtained on Waters Acquity Ultra Performance LC with electrospray ionization and SQ detector. Analytical HPLC was performed on a Waters Autopurification system with PDA, MicroMass ZQ and ELSD detector. Analytical thin layer chromatography was performed on 250 µM silica gel F$_{254}$ plates. Preparative thin layer chromatography was performed on 1000 µM silica gel F$_{254}$ plates. Flash column chromatography was performed employing 230-400 mesh silica gel. Solvents were HPLC grade. All reagents were purchased from Aldrich, Acros, Oakwood or Matrix Scientific and used without purification. All reactions were performed under argon protection.

Example 1

Scheme 2. Synthesis of 10, 11, 13, 14, 18, 19 and 22-25.

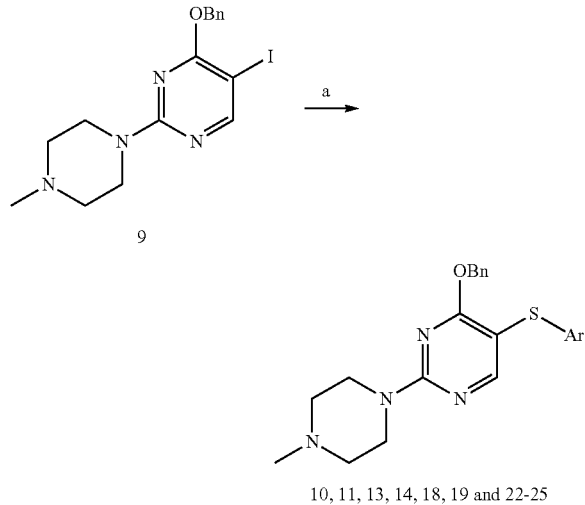

Reagents and conditions: a. arylthiol, copper(I)thiophene-2-carboxylate, K$_2$CO$_3$, DMF, 120-130° C., 3-24 h.

General procedure for the synthesis of 10, 11, 13, 14, 18, 19 and 22-25. A mixture of aryliodide 9 (1 equiv.), arylthiol (1.2 equiv.) and K$_2$CO$_3$ (2 equiv.) in DMF was evacuated and backfilled with argon three times. Copper(I)thiophene-2-carboxylate (0.4 equiv.) was added and evacuated and backfilled with argon two times. The reaction mixture was heated at 120° C. for 24 h or 130° C. for 3 h under argon. Solvent was removed under reduced pressure and the residue was purified by column chromatography to afford the desired product.

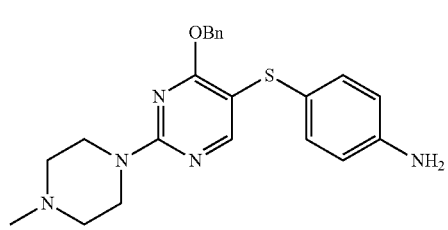

4-(4-(Benzyloxy)-2-(4-methylpiperazin-1-yl)pyrimidin-5-ylthio)aniline [10]. 10 was obtained in 75% yield following the general procedure above after heating at 120° C. for 24 h. $^1$H NMR (500 MHz, CDCl$_3$): δ 8.17 (s, 1H), 7.20-7.30 (m, 5H), 7.13 (d, J=8.4 Hz, 2H), 6.54 (d, J=8.4 Hz, 2H), 5.37 (s, 2H), 3.80 (m, 4H), 3.66 (br s, 2H), 2.42 (m, 4H), 2.32 (s, 3H); $^{13}$C NMR (125 MHz, CDCl$_3$): δ 167.8, 162.4, 161.0, 158.1, 145.7, 136.8, 132.4, 128.3, 127.7, 127.5, 123.9, 115.6, 67.6, 54.8, 46.2, 43.9; HRMS (ESI) m/z [M+H]$^+$ calcd. for C$_{22}$H$_{26}$N$_5$OS, 408.1858; found 408.1839.

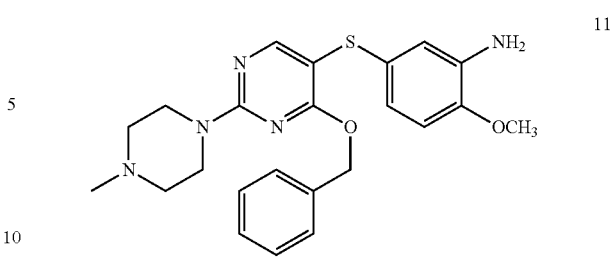

5-((4-(Benzyloxy)-2-(4-methylpiperazin-1-yl)pyrimidin-5-yl)thio)-2-methoxyaniline [11]. 11 was obtained in 64% yield following the general procedure above after heating at 120° C. for 24 h. $^1$H NMR (500 MHz, CDCl$_3$) δ 8.20 (s, 1H), 7.22-7.28 (m, 5H), 6.61-6.67 (m, 2H), 6.58 (s, 1H), 5.38 (s, 2H), 3.81-3.83 (m, 4H), 3.80 (s, 3H), 3.69 (br s, 2H), 2.43-2.45 (m, 4H), 2.33 (s, 3H); $^{13}$C NMR (125 MHz, CDCl$_3$): 168.3, 163.4, 161.3, 146.6, 137.0, 136.9, 128.5, 127.9, 127.8, 127.7, 120.0, 116.3, 110.9, 102.7, 67.8, 55.8, 55.0, 46.4, 44.0; MS (m/z): [M+H]$^+$ 438.2.

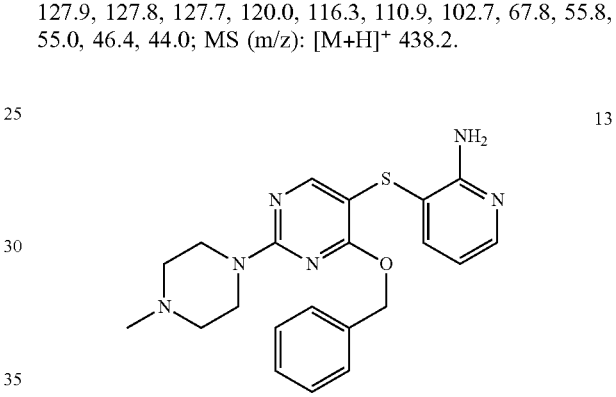

3-((4-(Benzyloxy)-2-(4-methylpiperazin-1-yl)pyrimidin-5-yl)thio)pyridin-2-amine [13]. 13 was obtained in 26% yield following the general procedure above after heating at 120° C. for 24 h. $^1$H NMR (500 MHz, CDCl$_3$) δ 8.19 (s, 1H), 7.95 (d, J=6.5 Hz, 1H), 7.51 (d, J=7.5 Hz, 1H), 7.31-7.36 (m, 5H), 6.50 (dd, J=7.5, 5.2 Hz, 1H), 5.36 (s, 2H), 5.01 (br s, 2H), 3.82-3.84 (m, 4H), 2.44-2.46 (m, 4H), 2.34 (s, 3H); HRMS (ESI) m/z [M+H]$^+$ calcd. for C$_{21}$H$_{25}$N$_6$OS, 409.1811; found 409.1804.

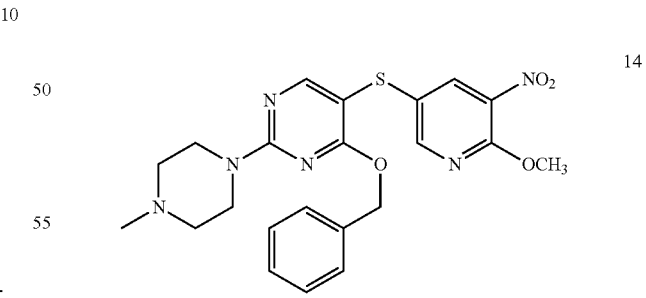

4-(Benzyloxy)-5-((6-methoxy-5-nitropyridin-3-yl)thio)-2-(4-methylpiperazin-1-yl)pyrimidine [14]. 14 was obtained in 63% yield following the general procedure above after heating at 120° C. for 24 h. $^1$H NMR (500 MHz, CDCl$_3$) δ 8.19 (s, 2H), 7.60 (s, 1H), 7.19-7.31 (m, 5H), 5.27 (s, 2H), 3.77-3.79 (m, 4H), 3.22 (s, 3H), 2.37-2.39 (m, 4H), 2.27 (s, 3H); $^{13}$C NMR (125 MHz, CDCl$_3$): 168.2, 162.7, 161.5, 153.9, 148.5, 143.0, 138.0, 136.1, 128.9, 128.8, 128.5, 110.2, 101.0, 68.5, 54.9, 46.3, 44.0, 38.6; HRMS (ESI) m/z [M+H]+ calcd. for C22H25N6O4S, 469.1658; found 469.1662.

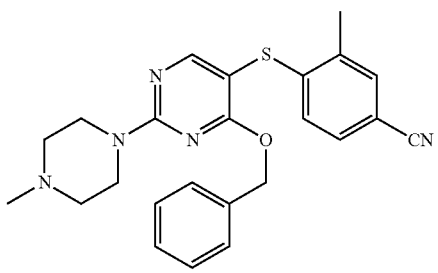

18

4-((4-(Benzyloxy)-2-(4-methylpiperazin-1-yl)pyrimidin-5-yl)thio)-3-methylbenzonitrile [18]. 18 was obtained in 76% yield following the general procedure above after heating at 120° C. for 24 h. 1H NMR (500 MHz, CDCl3): δ 8.24 (s, 1H), 7.39 (s, 1H), 7.12-7.32 (m, 6H), 6.76 (d, J=8.2 Hz, 1H), 5.39 (s, 2H), 3.86-3.94 (m, 4H), 2.46-2.52 (m, 4H), 2.43 (s, 3H), 2.38 (s, 3H); 13C NMR (125 MHz, CDCl3): δ 168.7, 165.2, 161.8, 144.7, 136.3, 135.7, 132.8, 129.6, 128.4, 128.0, 127.6, 125.4, 119.2, 107.8, 96.6, 67.8, 54.8, 46.2, 43.9, 19.7; HRMS (ESI) m/z [M+H]+ calcd. for C24H26N5OS, 432.1858; found 432.1840.

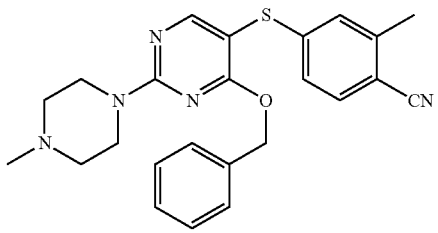

19

4-((4-(Benzyloxy)-2-(4-methylpiperazin-1-yl)pyrimidin-5-yl)thio)-2-methylbenzonitrile [19]. 19 was obtained in 78% yield following the general procedure above after heating at 120° C. for 24 h. 1H NMR (500 MHz, CDCl3): δ 8.24 (s, 1H), 7.36 (d, J=8.1 Hz, 1H), 7.23-7.30 (m, 3H), 7.11-7.18 (m, 2H), 6.96 (s, 1H), 6.90 (d, J=8.0 Hz, 1H), 5.30 (s, 2H), 3.85-3.93 (m, 4H), 2.44-2.50 (m, 4H), 2.41 (s, 3H), 2.35 (s, 3H); 13C NMR (125 MHz, CDCl3): δ 168.6, 165.0, 161.7, 145.2, 142.1, 136.3, 132.5, 128.4, 128.0, 127.5, 127.1, 123.5, 118.3, 108.9, 97.1, 67.8, 54.8, 46.2, 43.9, 20.4; HRMS (ESI) m/z [M+H]+ calcd. for C24H26N5OS, 432.1858; found 432.1840.

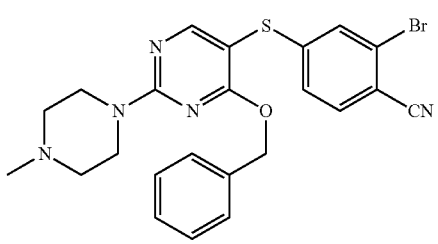

22

4-((4-(Benzyloxy)-2-(4-methylpiperazin-1-yl)pyrimidin-5-yl)thio)-2-bromobenzonitrile [22]. 22 was obtained in 52% yield following the general procedure above after heating at 120° C. for 24 h. 1H NMR (500 MHz, CDCl3): δ 8.22 (s, 1H), 7.38 (d, J=8.2 Hz, 1H), 7.24-7.31 (m, 4H), 7.14-7.19 (m, 2H), 6.85-7.04 (m, 1H), 5.37 (s, 2H), 3.83-3.97 (m, 4H), 2.44-2.54 (m, 4H), 2.37 (s, 3H); 13C NMR (125 MHz, CDCl3): δ 168.5, 165.1, 161.8, 147.6, 136.1, 133.8, 129.2, 128.5, 128.1, 127.5, 125.5, 124.6, 117.4, 111.4, 95.9, 68.0, 54.7, 46.1, 43.9; HRMS (ESI) m/z [M+H]+ calcd. for C23H22BrN5OS, 496.0807; found 496.0816.

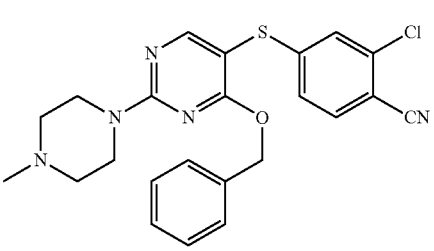

23

4-((4-(Benzyloxy)-2-(4-methylpiperazin-1-yl)pyrimidin-5-yl)thio)-2-chlorobenzonitrile [23]. 23 was obtained in 39% yield following the general procedure above after heating at 120° C. for 24 h. 1H NMR (500 MHz, CDCl3): δ 8.22 (s, 1H), 7.39 (d, J=8.3 Hz, 1H), 7.25-7.31 (m, 3H), 7.15-7.20 (m, 2H), 7.10 (d, J=1.7 Hz, 1H), 6.98 (dd, J=8.3, 1.7 Hz, 1H), 5.37 (s, 2H), 3.86-3.95 (m, 4H), 2.45-2.54 (m, 4H), 2.36 (s, 3H); 13C NMR (125 MHz, CDCl3): δ 168.5, 165.1, 161.8, 147.7, 137.1, 136.1, 133.5, 128.5, 128.1, 127.6, 126.2, 124.1, 116.2, 109.0, 95.9, 68.0, 54.7, 46.1, 43.9; HRMS (ESI) m/z [M+H]+ calcd. for C23H22ClN5OS, 452.1312; found 452.1303.

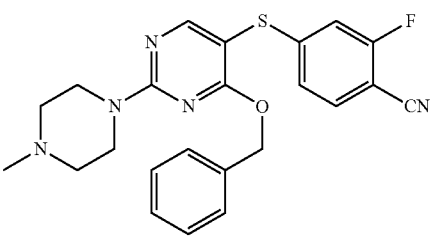

24

4-((4-(Benzyloxy)-2-(4-methylpiperazin-1-yl)pyrimidin-5-yl)thio)-2-fluorobenzonitrile [24]. 24 was obtained in 92% yield following the general procedure above after heating at 130° C. for 3 h. MS (ESI) m/z [M+H]+ 436.3.

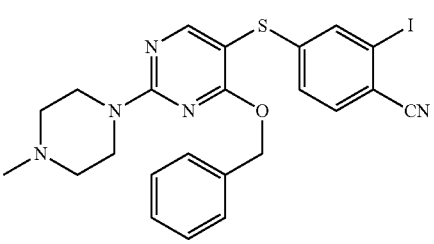

25

4-((4-(Benzyloxy)-2-(4-methylpiperazin-1-yl)pyrimidin-5-yl)thio)-2-iodobenzonitrile [25]. 25 was obtained in 57% yield following the general procedure above after heating at 130° C. for 3 h. MS (ESI) m/z [M+H]+ 544.2.

Example 2

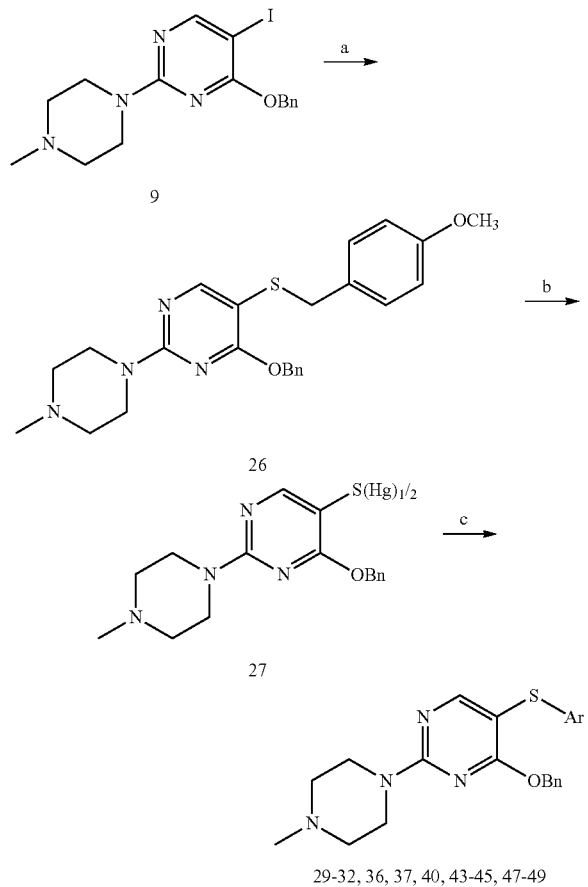

Scheme 3. Synthesis of 29-32, 36, 37, 40, 43-45, 47-49.

Reagents and conditions: a. (4-methoxyphenyl)methanethiol, copper(I) thiophene-2-carboxylate, CuI, K$_2$CO$_3$, DMF, 135° C., 18 h.; b. HgO, TFA, rt, 1 h.; c. aryliodide, K$_2$CO$_3$, neocuproine, CuI, DMF, 135° C., 1.5 h.

4-(Benzyloxy)-5-((4-methoxybenzyl)thio)-2-(4-methylpiperazin-1-yl)pyrimidine [26]. A mixture of 9 (0.400 g, 1.0 mmol) and K$_2$CO$_3$ (0.552 g, 4.0 mmol) in DMF (10 mL) was evacuated and backfilled with argon three times. Copper(I) thiophene-2-carboxylate (0.076 g, 0.4 mmol) and CuI (0.078 g, 0.4 mmol) was added and evacuated and backfilled with argon two times. (4-Methoxyphenyl)methanethiol (0.185 g, 1.2 mmol) was added and the reaction mixture was heated at 135° C. for 18 h. Solvent was removed under reduced pressure and the residue was purified by column chromatography (CH$_2$Cl$_2$:MeOH, 0-10% MeOH) to afford 0.340 mg (78%) of 26. HRMS (ESI) m/z [M+H]+ calcd. for C$_{24}$H$_{29}$N$_4$O$_2$S, 437.2011; found 437.2025.

bis((4-(Benzyloxy)-2-(4-methylpiperazin-1-yl)pyrimidin-5-yl)thio)mercury [27]. To a solution of 26 (5.0 g, 11.5 mmol) in TFA (30 mL) was added HgO (1.25 g, 5.7 mmol) and the mixture stirred for 1 h at rt. The reaction mixture was concentrated under reduced pressure and the resulting residue was purified by column chromatography (CH$_2$Cl$_2$: MeOH, 9:1) to afford 4.5 g (95%) of 27. $^1$H NMR (500 MHz, CDCl$_3$): δ 8.10 (s, 2H), 7.26-7.38 (m, 10H), 5.32 (s, 4H), 3.86 (m, 8H), 2.61 (m, 8H), 2.40 (s, 6H); MS (m/z): [M+H]+ 483.1.

General Procedure for Synthesis of 29-32, 36, 37, 40, 43-45, 47-49. The mixture of 27 (1 equiv.), aryliodide (1.2 equiv.), K$_2$CO$_3$ (4 equiv.), neocuproine (0.5 equiv.) and CuI (1 equiv.) in DMF was heated at 135° C. for 1.5 h under argon. Solvent was removed under reduced pressure and the residue was purified by column chromatography to afford the desired product.

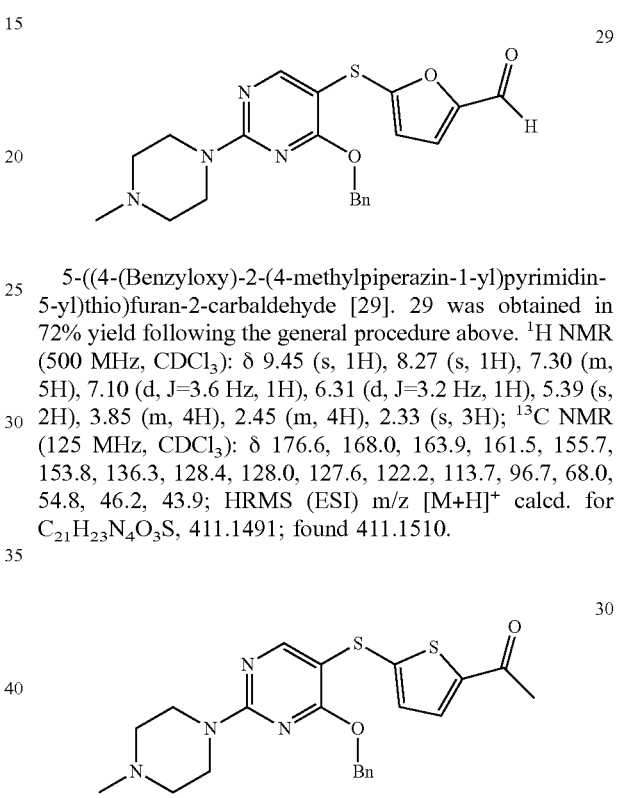

5-((4-(Benzyloxy)-2-(4-methylpiperazin-1-yl)pyrimidin-5-yl)thio)furan-2-carbaldehyde [29]. 29 was obtained in 72% yield following the general procedure above. $^1$H NMR (500 MHz, CDCl$_3$): δ 9.45 (s, 1H), 8.27 (s, 1H), 7.30 (m, 5H), 7.10 (d, J=3.6 Hz, 1H), 6.31 (d, J=3.2 Hz, 1H), 5.39 (s, 2H), 3.85 (m, 4H), 2.45 (m, 4H), 2.33 (s, 3H); $^{13}$C NMR (125 MHz, CDCl$_3$): δ 176.6, 168.0, 163.9, 161.5, 155.7, 153.8, 136.3, 128.4, 128.0, 127.6, 122.2, 113.7, 96.7, 68.0, 54.8, 46.2, 43.9; HRMS (ESI) m/z [M+H]+ calcd. for C$_{21}$H$_{23}$N$_4$O$_3$S, 411.1491; found 411.1510.

1-(5-((4-(Benzyloxy)-2-(4-methylpiperazin-1-yl)pyrimidin-5-yl)thio)thiophen-2-yl)ethanone [30]. 30 was obtained in 68% yield following the general procedure above. $^1$H NMR (500 MHz, CDCl$_3$): δ 8.26 (s, 1H), 7.45 (d, J=3.9 Hz, 1H), 7.25-7.32 (m, 5H), 6.90 (d, J=3.9 Hz, 1H), 5.39 (s, 2H), 3.84-3.90 (m, 4H), 2.44-2.49 (m, 7H), 2.35 (s, 3H); $^{13}$C NMR (125 MHz, CDCl$_3$): δ 189.6, 168.0, 164.1, 161.5, 150.4, 143.7, 136.3, 133.0, 128.4, 127.9, 127.6, 127.3, 100.1, 68.0, 54.8, 46.2, 43.9, 26.3; HRMS (ESI) m/z [M+H]+ calcd. for C$_{22}$H$_{25}$N$_4$O$_2$S$_2$, 441.1419; found 441.1418.

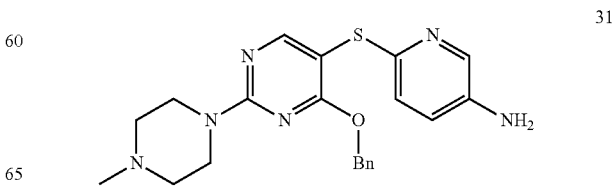

6-((4-(Benzyloxy)-2-(4-methylpiperazin-1-yl)pyrimidin-5-yl)thio)pyridin-3-amine [31]. 31 was obtained in 65% yield following the general procedure above. ¹H NMR (500 MHz, CDCl₃): δ 8.27 (s, 1H), 7.92 (s, 1H), 7.17-7.30 (m, 5H), 6.79 (s, 2H), 5.37 (s, 2H), 3.80-3.88 (m, 4H), 3.59 (br s, 2H), 2.42-2.49 (m, 4H), 2.34 (s, 3H); HRMS (ESI) m/z [M+H]⁺ calcd. for C₂₁H₂₅N₆OS, 409.1811; found 409.1806.

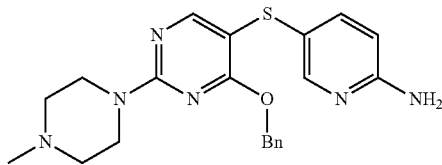

5-((4-(Benzyloxy)-2-(4-methylpiperazin-1-yl)pyrimidin-5-yl)thio)pyridin-2-amine [32]. 32 was obtained in 59% yield following the general procedure above. ¹H NMR (500 MHz, CDCl₃): δ 8.20 (s, 1H), 8.12 (s, 1H), 7.36-7.42 (m, 1H), 7.23-7.36 (m, 5H), 6.33 (d, J=8.5 Hz, 1H), 5.36 (s, 2H), 4.49 (br s, 2H), 3.77-3.84 (m, 4H), 2.38-2.47 (m, 4H), 2.37 (s, 3H); HRMS (ESI) m/z [M+H]⁺ calcd. for C₂₁H₂₅N₆OS, 409.1811; found 409.1810.

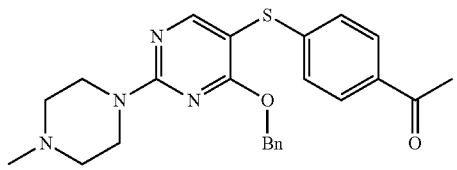

1-(4-((4-(Benzyloxy)-2-(4-methylpiperazin-1-yl)pyrimidin-5-yl)thio)phenyl)ethanone [36]. 36 was obtained in 52% yield following the general procedure above. ¹H NMR (500 MHz, CDCl₃): δ 8.26 (s, 1H), 7.77 (d, J=8.5 Hz, 2H), 7.23 (m, 3H), 7.14 (m, 2H), 7.12 (d, J=8.5 Hz, 2H), 5.36 (s, 2H), 3.88 (m, 4H), 2.54 (s, 3H), 2.47 (m, 4H), 2.35 (s, 3H); ¹³C NMR (125 MHz, CDCl₃): δ 197.2, 168.6, 165.0, 161.7, 145.3, 136.4, 134.0, 128.7, 128.3, 127.8, 127.4, 125.7, 97.7, 67.8, 54.8, 46.2, 43.9, 26.5; HRMS (ESI) m/z [M+H]⁺ calcd. for C₂₄H₂₇N₄O₂S, 435.1855; found 435.1866.

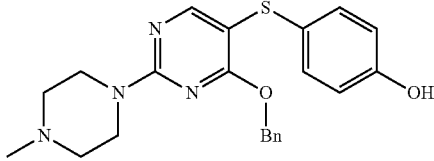

4-((4-(Benzyloxy)-2-(4-methylpiperazin-1-yl)pyrimidin-5-yl)thio)phenol [37]. 37 was obtained in 54% yield following the general procedure above. ¹H NMR (500 MHz, CDCl₃): δ 8.15 (s, 1H), 7.26 (m, 3H), 7.25 (m, 2H), 7.16 (d, J=8.5 Hz, 2H), 6.05 (d, J=8.5 Hz, 2H), 5.34 (s, 2H), 3.82 (m, 4H), 2.48 (m, 4H), 2.35 (s, 3H); ¹³C NMR (125 MHz, CDCl₃): δ 167.9, 162.3, 160.9, 155.8, 136.5, 132.3, 128.3, 127.8, 127.5, 125.9, 116.2, 103.6, 67.8, 54.7, 46.0, 43.6; HRMS (ESI) m/z [M+H]⁺ calcd. for C₂₂H₂₅N₄O₂S, 409.1698; found 409.1696.

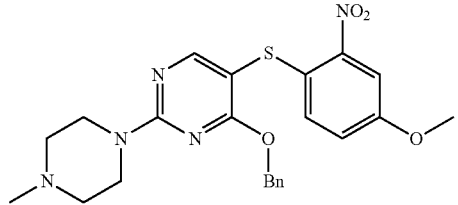

4-(Benzyloxy)-5-((4-methoxy-2-nitrophenyl)thio)-2-(4-methylpiperazin-1-yl)pyrimidine [40]. 40 was obtained in 59% yield following the general procedure above. ¹H NMR (500 MHz, CDCl₃): δ 8.26 (s, 1H), 7.72 (d, J=2.7 Hz, 1H), 7.22-7.28 (m, 3H), 7.12-7.18 (m, 2H), 6.91 (dd, J=9.0, 2.8 Hz, 1H), 6.81 (d, J=9.0 Hz, 1H), 5.35 (s, 2H), 3.86-3.94 (m, 4H), 3.84 (s, 3H), 2.46-2.51 (m, 4H), 2.36 (s, 3H); HRMS (ESI) m/z [M+H]⁺ calcd. for C₂₃H₂₆N₅O₄S, 468.1706; found 468.1697.

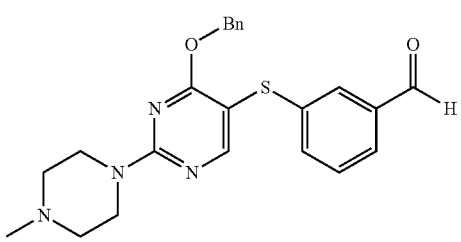

3-((4-(Benzyloxy)-2-(4-methylpiperazin-1-yl)pyrimidin-5-yl)thio)benzaldehyde [43]. 43 was obtained in 59% yield following the general procedure above. ¹H NMR (500 MHz, CDCl₃): δ 9.86 (s, 1H), 8.29 (s, 1H), 7.63 (d, J=7.2 Hz, 1H), 7.57 (s, 1H), 7.38 (m, 2H), 7.22 (m, 3H), 7.11 (m, 2H), 5.34 (s, 2H), 4.04 (m, 4H), 2.80 (m, 4H), 2.56 (s, 3H); ¹³C NMR (125 MHz, CDCl₃): δ 191.8, 168.6, 164.5, 161.3, 139.4, 130.9, 136.2, 132.9, 129.4, 128.4, 128.0, 127.9, 127.4, 126.9, 99.7, 68.0, 54.2, 45.3, 42.7; HRMS (ESI) m/z [M+H]⁺ calcd. for C₂₃H₂₅N₄O₂S, 421.1698; found 421.1703.

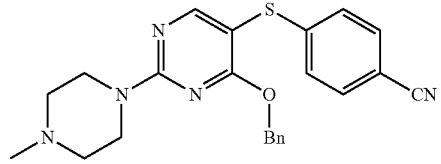

4-((4-(Benzyloxy)-2-(4-methylpiperazin-1-yl)pyrimidin-5-yl)thio)benzonitrile [44]. 44 was obtained in 72% yield following the general procedure above. ¹H NMR (500 MHz, CDCl₃): δ 8.24 (s, 1H), 7.42 (d, J=8.5 Hz, 2H), 7.25 (m, 3H), 7.13 (m, 2H), 7.10 (d, J=8.5 Hz, 2H), 5.36 (s, 2H), 3.95 (m, 4H), 2.60 (m, 4H), 2.40 (s, 3H); ¹³C NMR (125 MHz, CDCl₃): δ 168.0, 165.0, 161.7, 145.5, 136.1, 132.1, 128.4, 128.0, 127.5, 126.2, 118.9, 108.3, 97.3, 67.9, 54.2, 45.4, 43.2; HRMS (ESI) m/z [M+H]⁺ calcd. for C₂₃H₂₄N₅OS, 418.1702; found 418.1713.

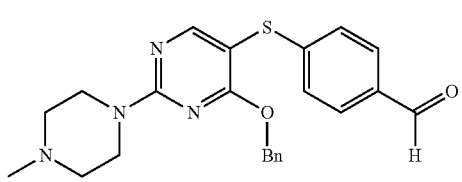

4-((4-(Benzyloxy)-2-(4-methylpiperazin-1-yl)pyrimidin-5-yl)thio)benzaldehyde [45]. 45 was obtained in 52% yield following the general procedure above. ¹H NMR (500 MHz, CDCl₃): δ 9.90 (s, 1H), 8.26 (s, 1H), 7.67 (d, J=8.3 Hz, 2H), 7.11-7.28 (m, 7H), 5.37 (s, 2H), 3.86-3.96 (m, 4H), 2.45-2.53 (m, 4H), 2.35 (s, 3H); ¹³C NMR (125 MHz, CDCl₃): δ 191.2, 168.7, 165.1, 161.7, 147.4, 136.3, 133.5, 130.0, 128.3, 127.9, 127.5, 125.8, 97.2, 67.8, 54.8, 46.2, 43.9; HRMS (ESI) m/z [M+H]⁺ calcd. for $C_{23}H_{25}N_4O_2S$, 421.1698; found 421.1690.

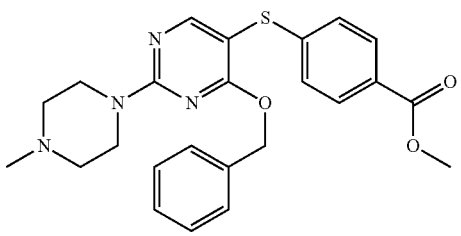

Methyl 4-((4-(benzyloxy)-2-(4-methylpiperazin-1-yl)pyrimidin-5-yl)thio)benzoate [49]. 49 was obtained in 72% yield following the general procedure above. ¹H NMR (500 MHz, CDCl₃, TMS) δ 8.26 (s, 1H), 7.84 (d, J=8.6 Hz, 2H), 7.23 (m, 3H), 7.11 (m, 4H), 5.36 (s, 2H), 3.89 (m, 7H), 2.48 (m, 4H), 2.36 (s, 3H); ¹³C NMR (125 MHz, CDCl₃) δ 168.6, 166.8, 165.0, 161.7, 144.9, 136.4, 129.9, 128.3, 127.8, 127.4, 126.8, 125.6, 97.9, 67.8, 54.8, 52.0, 46.2, 43.9; MS (m/z): 451.1 [M+H]⁺.

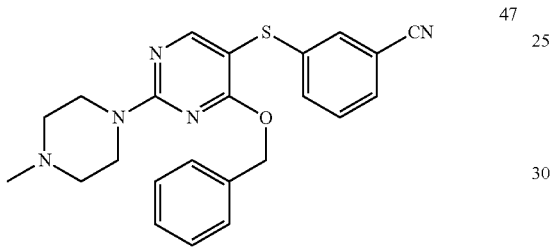

3-((4-(Benzyloxy)-2-(4-methylpiperazin-1-yl)pyrimidin-5-yl)thio)benzonitrile [47]. 47 was obtained in 70% yield following the general procedure above. ¹H NMR (500 MHz, CDCl₃): δ 8.27 (s, 1H), 7.37 (t, J=7.3 Hz, 1H), 7.36 (d, J=8.6 Hz, 1H), 7.23-7.33 (m, 5H), 7.14-7.18 (m, 2H), 5.37 (s, 2H), 3.85-3.91 (m, 4H), 2.37-2.61 (m, 4H), 2.37 (s, 3H); ¹³C NMR (125 MHz, CDCl₃): δ 168.5, 164.9, 161.6, 140.5, 136.2, 130.8, 129.5, 129.2, 128.7, 128.4, 128.0, 127.4, 118.5, 112.9, 97.4, 67.9, 54.8, 46.2, 43.9; MS (m/z): 418.2 [M+H]⁺.

Example 3

Scheme 5. Synthesis of 56.

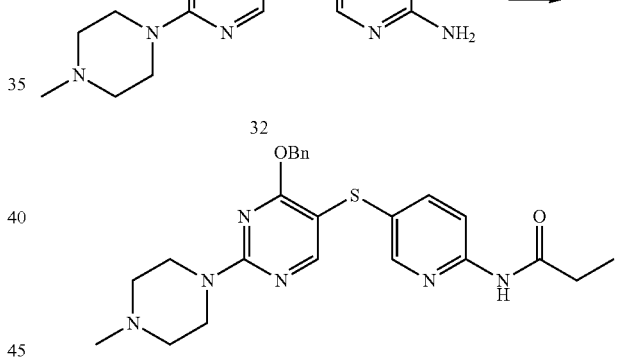

Reagents and conditions: a. acryloyl chloride, Et₃N, CH₂Cl₂, rt, 2 h.

N-(5-((4-(Benzyloxy)-2-(4-methylpiperazin-1-yl)pyrimidin-5-yl)thio)pyridin-2-yl)acrylamide [56]. To a solution of 32 (20 mg, 0.049 mmol) and Et₃N (49 mg, 0.49 mmol) in CH₂Cl₂ (0.5 mL) was added acryloyl chloride (44 mg, 0.49 mmol) and the mixture was stirred for 2 h at rt. Solvent was removed under reduced pressure and the resulting residue was purified by preparatory TLC (CH₂Cl₂:MeOH—NH₃, 15:1) to afford 15.9 mg (70%) of 56. ¹H NMR (500 MHz, CDCl₃): δ 8.27 (s, 1H), 8.16 (d, J=2.2 Hz, 1H), 8.14 (d, J=8.8 Hz, 1H), 8.08 (br s, 1H), 7.53 (dd, J=8.7, 2.4 Hz, 1H), 7.25-7.31 (m, 3H), 7.18-7.22 (m, 2H), 6.45 (dd, J=16.9, 0.8 Hz, 1H), 6.24 (dd, J=16.9, 10.3 Hz, 1H), 5.81 (dd, J=10.3, 0.8 Hz, 1H), 5.34 (s, 2H), 3.82-3.90 (m, 4H), 2.42-2.50 (m, 4H), 2.35 (s, 3H); ¹³C NMR (125 MHz, CDCl₃): δ 168.3, 163.8, 163.4, 161.4, 149.5, 148.0, 139.2, 136.3, 130.9, 129.4, 128.6, 128.4, 128.0, 127.6, 114.1, 100.1, 68.0, 54.7, 46.1, 43.8; HRMS (ESI) m/z [M+H]⁺ calcd. for $C_{24}H_{27}N_6O_2S$, 463.1916; found 463.1930.

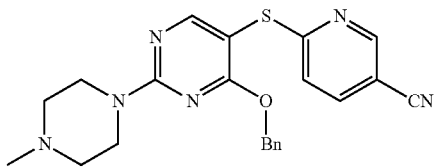

6-((4-(Benzyloxy)-2-(4-methylpiperazin-1-yl)pyrimidin-5-yl)thio)nicotinonitrile [48]. 48 was obtained in 65% yield following the general procedure above. ¹H NMR (500 MHz, CDCl₃): δ 8.57 (s, 1H), 8.25 (s, 1H), 7.59 (d, J=8.3 Hz, 1H), 7.21-7.31 (m, 5H), 6.98 (d, J=8.4 Hz, 1H), 5.40 (s, 2H), 3.90-3.94 (m, 4H), 2.45-2.52 (m, 4H), 2.38 (s, 3H); ¹³C NMR (125 MHz, CDCl₃): δ 168.5, 166.9, 164.9, 161.8, 152.1, 138.4, 136.3, 128.4, 128.0, 127.6, 119.8, 116.9, 104.9, 95.7, 67.8, 54.8, 46.2, 43.9; MS (m/z): 419.1 [M+H]⁺.

Example 4

Scheme 6. Synthesis of 58.

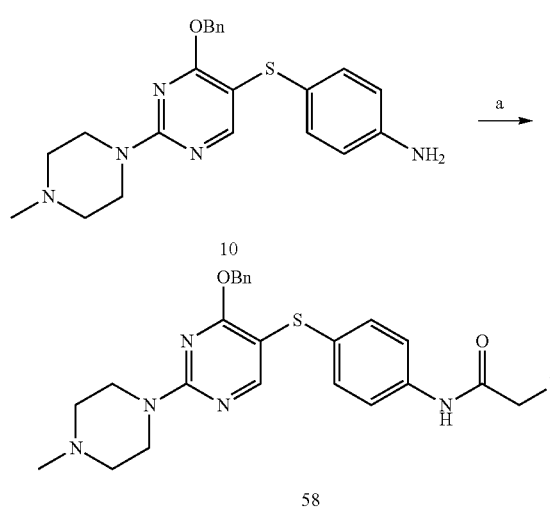

Reagents and conditions: a. Boc-glycine, DCC, THF, rt, overnight, then CH$_2$Cl$_2$:TFA (4:1), rt, 45 min.

2-Amino-N-(4-((4-(benzyloxy)-2-(4-methylpiperazin-1-yl)pyrimidin-5-yl)thio)phenyl)acetamide [58]. To a solution of 10 (19 mg, 0.047 mmol) in THF (1.5 mL) was added Boc-glycine (9.1 mg, 0.052 mmol) and DCC (10.7 mg, 0.052 mmol). After stirring overnight at rt, THF was evaporated and 1 mL of CH$_2$Cl$_2$:TFA (4:1) was added. The solution was stirred for 45 min., then concentrated to dryness under reduced pressure to give a residue which was purified by preparatory TLC (CH$_2$Cl$_2$:MeOH—NH$_3$ (7 N), 15:1) to afford 13.5 mg (62%) of 58. $^1$H NMR (500 MHz, CDCl$_3$): δ 9.34 (br s, 1H), 8.24 (s, 1H), 7.47 (d, J=8.6 Hz, 2H), 7.24-7.30 (m, 3H), 7.15-7.21 (m, 4H), 5.35 (s, 2H), 3.81-3.89 (m, 4H), 3.46 (s, 2H), 2.42-2.48 (m, 4H), 2.34 (s, 3H); $^{13}$C NMR (125 MHz, CDCl$_3$): δ 170.6, 168.4, 163.9, 161.3, 136.6, 135.9, 132.2, 129.1, 128.3, 127.7, 127.4, 119.9, 101.0, 67.7, 54.8, 46.2, 45.1, 43.9; HRMS (ESI) m/z [M+H]$^+$ calcd. for C$_{24}$H$_{29}$N$_6$O$_2$S, 465.2073; found 465.2076.

Example 5

Scheme 7. Synthesis of 62-63.

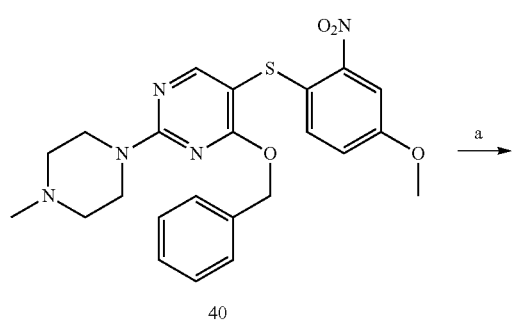

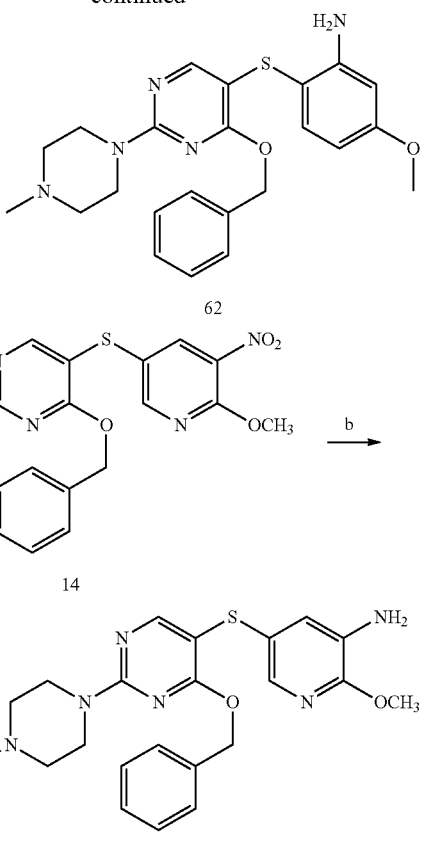

Reagents and conditions: a. Zn, AcOH, CH$_2$Cl$_2$, rt, 2 h; b. sodium hydrosulfite, dioxane, rt, 1 h.

2-((4-(Benzyloxy)-2-(4-methylpiperazin-1-yl)pyrimidin-5-yl)thio)-5-methoxyaniline [62]. A mixture of 40 (50 mg, 0.123 mmol), AcOH (50 μL) and Zn powder in CH$_2$Cl$_2$ (2 mL) was stirred at rt for 2 h. The reaction mixture was concentrated under reduced pressure to give a residue which was purified by column chromatography (CH$_2$Cl$_2$:MeOH, 9:1) to afford 44 mg (82%) of 62. $^1$H NMR (500 MHz, CDCl$_3$): δ 8.04 (s, 1H), 7.45 (m, 4H), 7.32 (m, 1H), 7.30 (m, 1H), 6.22 (m, 1H), 6.17 (m, 1H), 5.36 (s, 2H), 3.87 (m, 4H), 3.73 (s, 3H), 2.65 (m, 4H), 2.42 (s, 3H); $^{13}$C NMR (125 MHz, CDCl$_3$): δ 167.2, 161.7, 160.5, 160.3, 149.8, 137.9, 136.4, 128.5, 128.1, 128.0, 108.2, 105.0, 104.8, 100.3, 68.1, 55.2, 53.7, 44.7, 42.6; HRMS (ESI) m/z [M+H]$^+$ calcd. for C$_{23}$H$_{28}$N$_5$O$_2$S, 438.1964; found 438.1963.

5-((4-(Benzyloxy)-2-(4-methylpiperazin-1-yl)pyrimidin-5-yl)thio)-2-methoxypyridin-3-amine [63]. To a solution of 14 (10 mg, 0.021 mmol) in 2 mL of dry dioxane was added 12 mg (0.064 mmol) of sodium hydrosulfite. The resulting mixture was stirred at rt for 1 h. The reaction was then concentrated under reduced pressure and the residue was purified by preparatory TLC (CH$_2$Cl$_2$:MeOH—NH$_3$ (7 N), 15:1) to yield 5.8 mg (62%) of 63. $^1$H NMR (500 MHz, CDCl$_3$) δ 8.14 (s, 1H), 7.19-7.27 (m, 7H), 6.74 (s, 1H), 6.37 (s, 1H), 5.29 (s, 2H), 4.01 (s, 2H), 3.75-3.77 (m, 4H), 3.28 (s, 3H), 2.37-2.39 (m, 4H), 2.26 (s, 3H); HRMS (ESI) m/z [M+H]$^+$ calcd. for C$_{22}$H$_{27}$N$_6$O$_2$S, 439.1916; found 439.1909.

Example 6

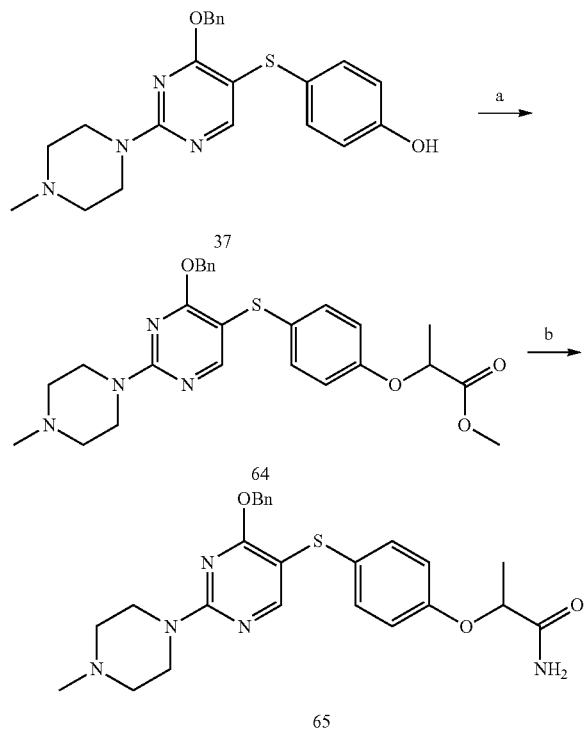

Reagents and conditions: a. methyl 2-bromopropanoate, K₂CO₃, CH₃CN, 80 °C, 1 h; b. MeOH—NH₃ (7N), rt, 12 h.

Methyl 2-(4-((4-(benzyloxy)-2-(4-methylpiperazin-1-yl)pyrimidin-5-yl)thio)phenoxy)propanoate [64]. A mixture of 37 (50 mg, 0.123 mmol), methyl 2-bromopropanoate (102 mg 0.613 mmol) and K₂CO₃ in acetonitrile (1 mL) was heated at 80° C. for 1 h. The reaction mixture was concentrated under reduced pressure to give a residue which was purified by preparatory TLC (CH₂Cl₂:MeOH, 20:1) to afford 42 mg (69%) of 64. $^1$H NMR (500 MHz, CDCl₃): δ 8.21 (s, 1H), 7.27 (m, 3H), 7.18 (m, 2H), 7.16 (d, J=8.6 Hz, 2H), 6.73 (d, J=8.6 Hz, 2H), 5.36 (s, 2H), 4.70 (q, J=6.5 Hz, 1H), 3.83 (m, 4H), 3.73 (s, 3H), 2.44 (m, 4H), 2.34 (s, 3H), 1.60 (d, J=6.2 Hz, 3H); $^{13}$C NMR (125 MHz, CDCl₃): δ 172.5, 168.2, 163.5, 161.2, 156.4, 136.6, 130.8, 128.9, 128.3, 127.7, 127.5, 115.7, 101.9, 72.8, 67.7, 54.8, 52.4, 46.2, 43.8, 18.6; HRMS (ESI) m/z [M+H]⁺ calcd. for C₂₆H₃₁N₄O₄S, 495.2066; found 495.2062.

2-(4-((4-(Benzyloxy)-2-(4-methylpiperazin-1-yl)pyrimidin-5-yl)thio)phenoxy)propanamide [65]. A solution of 64 (30 mg, 0.061 mmol) in 3 mL of MeOH—NH₃ (7 N) was stirred at rt for 12 h. The reaction mixture was concentrated under reduced pressure to give a residue which was purified by preparatory TLC (CH₂Cl₂:MeOH, 10:1) to afford 26 mg (89%) of 65. $^1$H NMR (500 MHz, CDCl₃): δ 8.22 (s, 1H), 7.25-7.30 (m, 3H), 7.15-7.23 (m, 4H), 6.76 (d, J=8.8 Hz, 2H), 6.32 (br s, 1H), 5.39 (br s, 1H), 5.36 (s, 2H), 4.60 (q, J=6.8 Hz, 1H), 3.80-3.87 (m, 4H), 2.43-2.48 (m, 4H), 2.34 (s, 3H), 1.57 (d, J=6.8 Hz, 3H); $^{13}$C NMR (125 MHz, CDCl₃): δ 174.6, 168.2, 163.6, 161.3, 155.6, 136.6, 130.7, 129.7, 128.3, 127.8, 127.4, 116.0, 103.5, 75.0, 67.7, 54.8, 46.2, 43.8, 18.6; HRMS (ESI) m/z [M+H]⁺ calcd. for C₂₅H₃₀N₅O₃S, 480.2069; found 480.2075.

Example 7

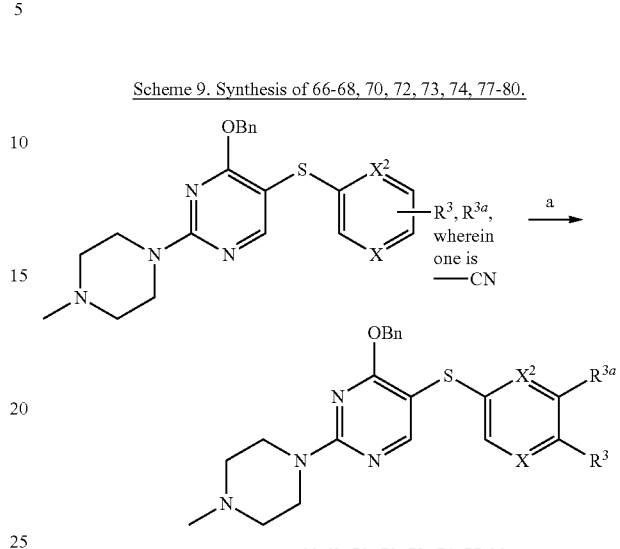

Reagents and conditions: a. KOH, t-BuOH, 80° C., 1 h.

General Procedure for the Synthesis of 66-80. A mixture of nitrile (1 equiv.) and KOH (25 eq.) in t-BuOH was heated at 80° C. for 1 h. Solvent was removed under reduced pressure and the residue was purified by preparatory TLC to afford the desired product.

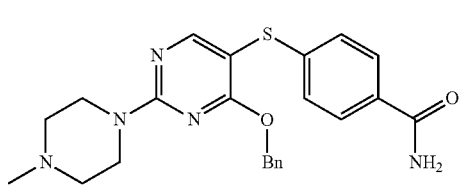

4-((4-(Benzyloxy)-2-(4-methylpiperazin-1-yl)pyrimidin-5-yl)thio)benzamide [66]. 66 was obtained in 83% yield following the general procedure above. $^1$H NMR (500 MHz, CDCl₃): δ 8.26 (s, 1H), 7.63 (d, J=8.4 Hz, 2H), 7.22-7.26 (m, 3H), 7.11-7.15 (m, 4H), 5.94 (br s, 1H), 5.56 (br s, 1H), 5.36 (s, 2H), 3.85-3.92 (m, 4H), 2.44-2.50 (m, 4H), 2.36 (s, 3H); HRMS (ESI) m/z [M+H]⁺ calcd. for C₂₃H₂₆N₅O₂S, 436.1807; found 436.1801.

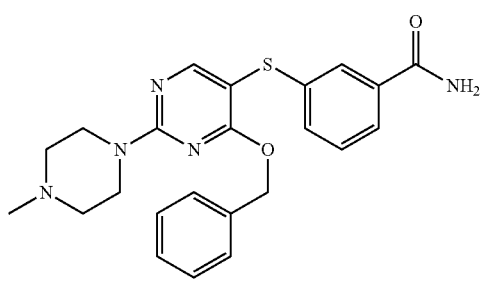

3-((4-(Benzyloxy)-2-(4-methylpiperazin-1-yl)pyrimidin-5-yl)thio)benzamide [67]. 67 was obtained in 78% yield following the general procedure above. $^1$H NMR (500 MHz, CDCl$_3$): δ 8.19 (s, 1H), 7.50 (s, 1H), 7.48 (t, J=5.5 Hz, 1H), 7.15-7.18 (m, 1H), 7.06 (d, J=7.3 Hz, 1H), 7.05 (d, J=5.8 Hz, 1H), 6.01 (br s, 2H), 5.27 (s, 2H), 3.77-3.79 (m, 4H), 2.37-2.39 (m, 4H), 2.26 (s, 3H); $^{13}$C NMR (125 MHz, CDCl$_3$): δ 169.0, 168.5, 164.5, 161.5, 138.8, 136.4, 134.1, 130.7, 129.0, 128.4, 127.9, 127.4, 126.1, 124.7, 99.1, 67.8, 54.7, 46.1, 43.8; MS (m/z): 436.2 [M+H]$^+$.

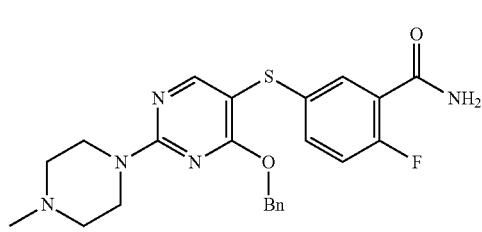

5-((4-(Benzyloxy)-2-(4-methylpiperazin-1-yl)pyrimidin-5-yl)thio)-2-fluorobenzamide [68]. 68 was obtained in 76% yield following the general procedure above. $^1$H NMR (500 MHz, CDCl$_3$): δ 8.19 (s, 1H), 7.87 (dd, J=7.2, 2.6 Hz, 1H), 7.13-7.22 (m, 4H), 7.08-7.12 (m, 2H), 6.87 (dd, J=11.4, 8.7 Hz, 1H), 6.51 (br s, 1H), 5.92 (br s, 1H), 5.28 (s, 2H), 3.78 (m, 4H), 2.38 (m, 4H), 2.27 (s, 3H); $^{13}$C NMR (125 MHz, CDCl$_3$): δ 168.4, 164.3, 164.2, 161.5, 159.3 (d, J=246 Hz), 136.4, 134.5 (d, J=2.5 Hz), 133.0 (d, J=9.1 Hz), 131.2, 128.3, 127.8, 127.5, 120.5 (d, J=12.5 Hz), 116.5 (d, J=26.3 Hz), 99.5, 67.8, 54.8, 46.2, 43.9. MS (m/z): 454.0 [M+H]$^+$.

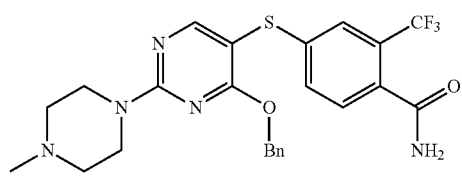

4-((4-(Benzyloxy)-2-(4-methylpiperazin-1-yl)pyrimidin-5-yl)thio)-2-(trifluoromethyl)benzamide [70]. 70 was obtained in 70% yield following the general procedure above. $^1$H NMR (500 MHz, CDCl$_3$): δ 8.18 (s, 1H), 7.36-7.39 (m, 1H), 7.31 (d, J=8.1 Hz, 1H), 7.17-7.23 (m, 3H), 7.11-7.15 (m, 1H), 7.06-7.10 (m, 2H), 6.02 (br s, 1H), 5.71 (br s, 1H), 5.28 (s, 2H), 3.81 (m, 4H), 2.39 (m, 4H), 2.27 (s, 3H); MS (m/z): 503.9 [M+H]$^+$.

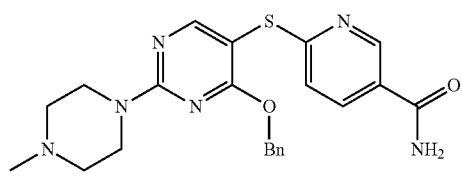

6-((4-(Benzyloxy)-2-(4-methylpiperazin-1-yl)pyrimidin-5-yl)thio)nicotinamide [72]. 72 was obtained in 84% yield following the general procedure above. $^1$H NMR (500 MHz, CDCl$_3$): δ 8.64 (s, 1H), 8.19 (s, 1H), 7.80 (dd, J=8.4, 2.0 Hz, 1H), 7.16-7.20 (m, 3H), 7.10-7.15 (m, 2H), 6.88 (d, J=8.4 Hz, 1H), 5.65 (br s, 2H), 5.31 (s, 2H), 3.83 (m, 4H), 2.42 (m, 4H), 2.30 (s, 3H); MS (m/z): 437.0 [M+H]$^+$.

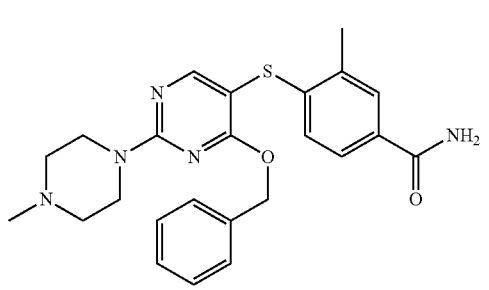

4-((4-(Benzyloxy)-2-(4-methylpiperazin-1-yl)pyrimidin-5-yl)thio)-3-methylbenzamide [73]. 73 was obtained in 88% yield following the general procedure above. $^1$H NMR (500 MHz, CDCl$_3$) δ 8.23 (s, 1H), 7.58 (s, 1H), 7.38 (dd, J=8.2, 1.4 Hz, 1H), 7.21-7.28 (m, 3H), 7.12-7.18 (m, 2H), 6.79 (d, J=8.2 Hz, 1H), 5.94 (br s, 1H), 5.61 (br s, 1H), 5.36 (s, 2H), 3.80-4.00 (m, 4H), 2.45-2.51 (m, 4H), 2.44 (s, 3H), 2.35 (s, 3H); MS (m/z): [M+H]$^+$ 450.2.

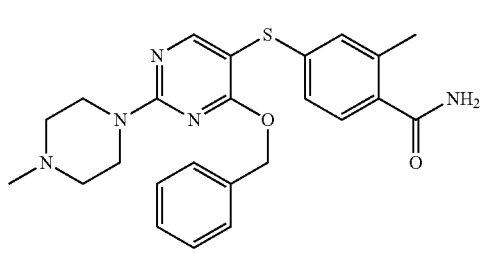

4-((4-(Benzyloxy)-2-(4-methylpiperazin-1-yl)pyrimidin-5-yl)thio)-2-methylbenzamide [74]. 74 was obtained in 81% yield following the general procedure above. $^1$H NMR (500 MHz, CDCl$_3$) δ 8.25 (s, 1H), 7.20-7.30 (m, 5H), 7.16 (d, J=6.7 Hz, 2H), 6.97 (s, 1H), 6.92 (d, J=8.1 Hz, 1H), 5.65 (br s, 2H), 5.37 (s, 2H), 3.87 (m, 4H), 2.48 (m, 4H), 2.41 (s, 3H), 2.35 (s, 3H); MS (m/z): [M+H]$^+$ 450.0.

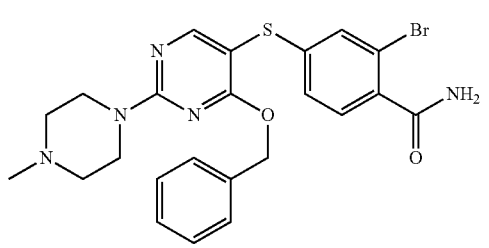

4-((4-(Benzyloxy)-2-(4-methylpiperazin-1-yl)pyrimidin-5-yl)thio)-2-bromobenzamide [77]. 77 was obtained in 49% yield following the general procedure above. $^1$H NMR (600 MHz, CD$_2$Cl$_2$/MeOH-d$_4$): δ 8.17 (s, 1H), 7.32 (d, J=8.2 Hz, 1H), 7.17-7.24 (m, 4H), 7.10-7.14 (m, 2H), 7.01 (dd, J=8.1, 1.8 Hz, 1H), 5.29 (s, 2H), 3.55-4.15 (m, 4H), 2.20-2.75 (m, 7H); HRMS (ESI) m/z [M+H]$^+$ calcd. for C$_{23}$H$_{24}$BrN$_5$O$_2$S, 514.0912; found 514.0902.

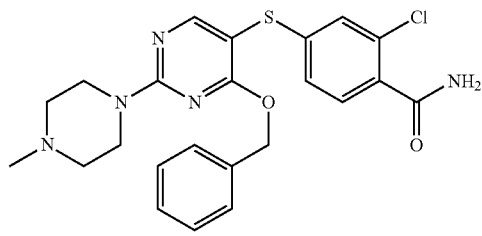

78

4-((4-(Benzyloxy)-2-(4-methylpiperazin-1-yl)pyrimidin-5-yl)thio)-2-chlorobenzamide [78]. 78 was obtained in 56% yield following the general procedure above. $^1$H NMR (500 MHz, CD$_2$Cl$_2$/MeOH-d$_4$): δ 8.16 (s, 1H), 7.41 (d, J=8.2 Hz, 1H), 7.15-7.25 (m, 3H), 7.09-7.14 (m, 2H), 7.02 (s, 1H), 6.97 (d, J=8.2 Hz, 1H), 5.26 (s, 2H), 3.77-3.88 (m, 4H), 2.40-2.53 (m, 4H), 2.29 (s, 3H); $^{13}$C NMR (125 MHz, CD$_2$Cl$_2$/MeOH-d$_4$): δ 169.2, 169.1, 165.2, 162.0, 143.7, 136.8, 131.8, 131.4, 130.5, 128.8, 128.3, 127.8, 127.5, 125.0, 98.1, 68.5, 54.8, 45.7, 43.7; HRMS (ESI) m/z [M+H]$^+$ calcd. for C$_{23}$H$_{24}$ClN$_5$O$_2$S, 470.1417; found 470.1422.

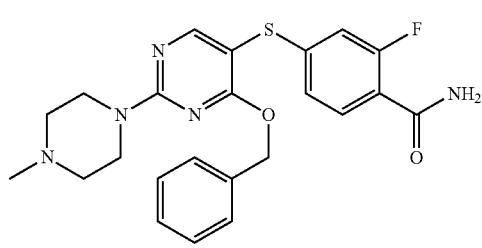

79

4-((4-(Benzyloxy)-2-(4-methylpiperazin-1-yl)pyrimidin-5-yl)thio)-2-fluorobenzamide [79]. 79 was obtained in 53% yield following the general procedure above. $^1$H NMR (500 MHz, CDCl$_3$) δ 8.25 (s, 1H), 7.94-7.97 (m, 1H), 7.26-7.27 (m, 3H), 7.17 (m, 2H), 6.96 (d, J=8.3 Hz, 1H), 6.77 (d, J=12.6 Hz, 1H), 6.57 (bs, 1H), 5.89 (bs, 1H), 5.38 (s, 2H), 3.92 (m, 4H), 2.52 (m, 4H), 2.39 (s, 3H); $^{13}$C NMR (125 MHz, CDCl$_3$) δ 168.8, 165.3, 164.6, 161.9, 146.9, 136.4, 132.6, 128.6, 128.2, 127.7, 122.2, 116.6, 113.2, 112.9, 97.3, 68.1, 54.9, 46.3, 44.0; HRMS (ESI) m/z [M+H]$^+$ calcd. for C$_{23}$H$_{25}$FN$_5$O$_2$S 454.1713; found 454.1713.

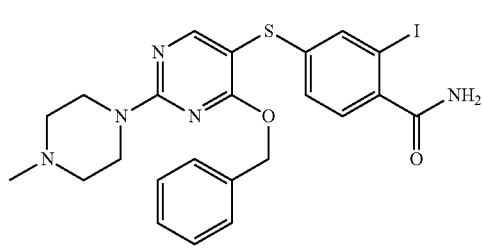

80

4-((4-(Benzyloxy)-2-(4-methylpiperazin-1-yl)pyrimidin-5-yl)thio)-2-iodobenzamide [80]. 80 was obtained in 52% yield following the general procedure above. $^1$H NMR (500 MHz, CDCl$_3$) δ 8.20 (s, 1H), 7.57 (s, 1H), 7.21-7.26 (m, 4H), 7.13 (d, J=7.4 Hz, 2H), 7.03 (d, J=8.0 Hz, 1H), 5.70 (br s, 2H), 5.31 (s, 2H), 3.91 (m, 4H), 2.55 (m, 4H), 2.37 (s, 3H); HRMS (ESI) m/z [M+H]$^+$ calcd. for C$_{23}$H$_{25}$IN$_5$O$_2$S 562.0774; found 562.0787.

Example 8

Scheme 10. Synthesis of 83-84.

4-((4-(Benzyloxy)-2-(4-methylpiperazin-1-yl)pyrimidin-5-yl)thio)benzoic acid [81]. A mixture of 49 (100 mg, 0.222 mmol) and LiOH (27 mg, 1.11 mmol) in 3 mL of THF:H$_2$O (2:1) was stirred at rt for 1.5 h. The reaction mixture was concentrated under reduced pressure to give a residue which was purified by column chromatography (CH$_2$Cl$_2$:MeOH, 9:1) to afford 93 mg (96%) of 81. $^1$H NMR (500 MHz, CDCl$_3$/MeOH-d$_4$): δ 8.18 (s, 1H), 7.76 (d, J=8.5 Hz, 2H), 7.10-7.15 (m, 3H), 6.95-7.02 (m, 4H), 5.23 (s, 2H), 3.40 (m, 4H), 2.81 (m, 4H), 2.18 (s, 3H); HRMS (ESI) m/z [M+H]+ calcd. for $C_{23}H_{25}N_4O_3S$, 437.1647; found 437.1654.

4-((4-(Benzyloxy)-2-(4-methylpiperazin-1-yl)pyrimidin-5-yl)thio)benzoyl chloride [82]. To a mixture of 81 (90 mg, 0.206 mmol) in $CH_2Cl_2$ was added oxalyl chloride (35 µL, 0.412 mmol) and the reaction mixture was stirred at rt for 5 h. The reaction mixture was concentrated under reduced pressure and dried to afford quantitative yield of 82, which was used without further purification.

General Procedure for Synthesis of 83-84. To a solution of 82 (1 equiv.) in $CH_2Cl_2$ (1 mL) was added amine (3 equiv.) and was stirred for 2 h at rt. Solvent was removed under reduced pressure and the resulting residue was purified by preparatory TLC.

4-((4-(Benzyloxy)-2-(4-methylpiperazin-1-yl)pyrimidin-5-yl)thio)-N-methylbenzamide [83]. 83 was obtained in 93% yield following the general procedure above. $^1$H NMR (500 MHz, $CDCl_3$): δ 8.29 (s, 1H), 7.61 (d, J=8.5 Hz, 2H), 7.24-7.28 (m, 3H), 7.12-7.17 (m, 4H), 6.14 (br s, 1H), 5.37 (s, 2H), 3.97 (m, 4H), 3.02 (d, J=4.8 Hz, 3H), 2.61 (m, 4H), 2.45 (s, 3H); $^{13}$C NMR (125 MHz, $CDCl_3$): δ 168.7, 167.6, 164.8, 161.5, 142.5, 136.3, 131.4, 128.4, 127.8, 127.4, 127.2, 126.3, 98.8, 67.9, 54.4, 45.6, 43.3, 26.8; MS (m/z): 450.2 [M+H]+

4-((4-(Benzyloxy)-2-(4-methylpiperazin-1-yl)pyrimidin-5-yl)thio)-N,N-dimethylbenzamide [84]. 84 was obtained in 88% yield following the general procedure above. $^1$H NMR (500 MHz, $CDCl_3$): δ 7.27 (s, 1H), 7.25-7.30 (m, 7H), 7.13 (d, J=6.9 Hz, 2H), 5.38 (s, 2H), 3.84-3.93 (m, 4H), 3.01 (s, 3H), 2.88 (s, 3H), 2.47-2.49 (m, 4H), 2.36 (s, 3H); $^{13}$C NMR (125 MHz, $CDCl_3$): δ 171.2, 168.6, 164.8, 161.5, 140.2, 136.4, 133.1, 129.8, 128.3, 127.7, 127.4, 126.3, 98.6, 67.8, 61.3, 54.8, 46.2, 43.8; MS (m/z): 464.0 [M+H]+.

Example 9

4-((4-(Benzyloxy)-2-(4-methylpiperazin-1-yl)pyrimidin-5-yl)thio)-N-(pyrrolidin-1-ylmethyl)benzamide [92]. To a solution of 66 (20 mg, 0.046 mmol) in t-BuOH (2 mL) was added pyrrolidine (8.3 µL, 0.10 mmol) and formalin (10 µL, 0.134 mmol). The reaction mixture was stirred at rt for 1 h and then refluxed for 2 h. Solvent was removed under reduced pressure and the residue was purified by preparatory TLC ($CH_2Cl_2$:MeOH—$NH_3$, 20:1) to afford 8.6 mg (36%) of 92. $^1$H NMR (500 MHz, $CDCl_3$) δ 8.26 (s, 1H), 7.60 (d, J=8.4 Hz, 2H), 7.23-7.24 (m, 3H), 7.11-7.14 (m, 4H), 6.55 (br s, 1H), 5.35 (s, 2H), 4.38 (d, J=6.0 Hz, 2H), 3.86-3.87 (m, 4H), 2.69-2.71 (m, 4H), 2.45-2.47 (m, 4H), 2.35 (s, 3H), 1.79-1.80 (m, 4H); $^{13}$C NMR (125 MHz, $CDCl_3$) δ 168.6, 167.0, 164.9, 161.6, 143.1, 136.4, 131.0, 128.5, 127.4, 127.2, 126.3, 126.0, 98.1, 67.8, 58.8, 54.8, 51.0, 46.2, 43.9, 23.7; HRMS (ESI) m/z [M+H]+ calcd. for $C_{28}H_{35}N_6O_2S$ 519.2542; found 519.2549.

4-((4-(Benzyloxy)-2-(4-methylpiperazin-1-yl)pyrimidin-5-yl)thio)-N-(piperidin-1-ylmethyl)benzamide [93]. To a solution of 66 (20 mg, 0.046 mmol) in t-BuOH (2 mL) was added piperidine (10 µL, 0.10 mmol) and formalin (10 µL, 0.134 mmol). The reaction mixture was stirred at rt for 1 h and then refluxed for 2 h. Solvent was removed under reduced pressure and the residue was purified by preparatory TLC ($CH_2Cl_2$:MeOH—$NH_3$, 20:1) to afford 9.1 mg (37%) of 93. $^1$H NMR (500 MHz, $CDCl_3$) δ 8.23 (s, 1H), 7.61 (d, J=8.4 Hz, 2H), 7.22-7.24 (m, 3H), 7.11-7.13 (m, 4H), 6.52 (br s, 1H), 5.36 (s, 2H), 4.25 (d, J=6.2 Hz, 2H), 3.86-3.88 (m, 4H), 2.56-2.58 (m, 4H), 2.45-2.47 (m, 4H), 2.35 (s, 3H), 1.57-1.62 (m, 4H), 1.44-1.45 (m, 2H); $^{13}$C NMR (125 MHz, $CDCl_3$) δ 168.6, 167.2, 164.9, 161.6, 143.1, 136.4, 130.9, 128.4, 127.4, 127.2, 126.3, 126.0, 98.1, 67.6, 62.5, 54.8, 51.5, 46.2, 43.9, 25.8, 24.1; HRMS (ESI) m/z [M+H]+ calcd. for $C_{29}H_{37}N_6O_2S$ 533.2699; found 533.2686.

Scheme 11. Synthesis of 92 and 93.

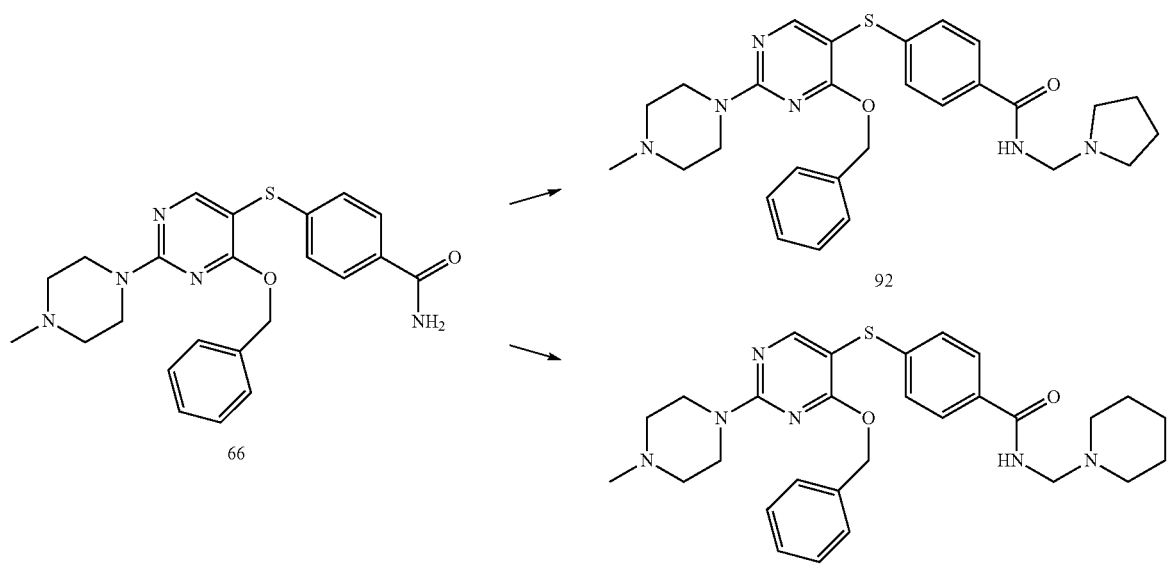

Reagents and conditions: a. t-BuOH, pyrrolidine, formalin, rt for 1 h then reflux for 2 h; b. t-BuOH, piperidine, formalin, rt for 1 h then reflux for 2 h.

Example 10

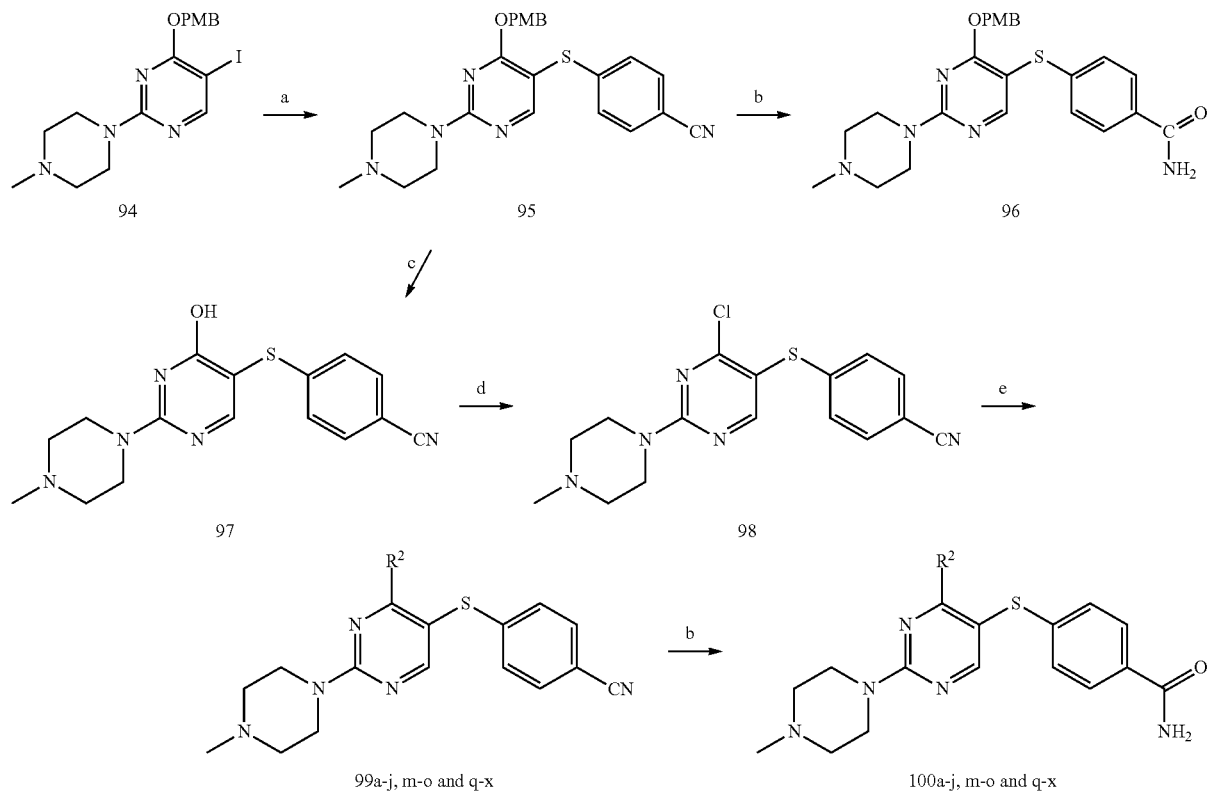

Scheme 12. Synthesis of 99a-j, m-o, and q-x and 100a-j, m-o, and q-x.

Reagents and conditions: a. 4-mercaptobenzonitrile, copper(I)thiophene-2-carboxylate, $K_2CO_3$, DMF, 120° C., 20 h; b. KOH, t-BuOH, 80° C., 1 h; c. TFA, $CH_2Cl_2$, rt, 12 h; d. $POCl_3$, 75° C., 1 h; e. ROH, NaH, $CH_3CN$, rt, 3 h.

4-(4-(4-Methoxybenzyloxy)-2-(4-methylpiperazin-1-yl)pyrimidin-5-ylthio)benzonitrile [95]. A mixture of 94 (1.0 g, 2.27 mmol) and $K_2CO_3$ (0.628 g, 4.54 mmol) in DMF (32 mL) was evacuated and backfilled with argon three times. Copper(I)thiophene-2-carboxylate (0.173 g, 0.908 mmol) was added and evacuated and backfilled with argon two times. 4-Mercaptobenzonitrile (0.496 g, 2.72 mmol) was added and the reaction mixture was heated at 120° C. for 20 h. Solvent was removed under reduced pressure and the residue was purified by column chromatography ($CH_2Cl_2$:MeOH, 200:1 to 40:1) to afford 0.867 g (85%) of 95. $^1$H NMR (500 MHz, $CDCl_3$): δ 8.22 (s, 1H), 7.39 (d, J=8.3 Hz, 2H), 7.03-7.11 (m, 4H), 6.78 (d, J=8.6 Hz, 2H), 5.30 (s, 2H), 3.90 (m, 4H), 3.79 (s, 3H), 2.49 (m, 4H), 2.36 (s, 3H); $^{13}$C NMR (125 MHz, $CDCl_3$): δ 168.6, 165.0, 161.8, 159.5, 145.7, 132.1, 129.4, 128.2, 126.1, 119.0, 113.7, 108.1, 96.9, 67.7, 55.3, 54.8, 46.2, 43.9; HRMS (ESI) m/z [M+H]$^+$ calcd. for $C_{24}H_{26}N_5O_2S$, 448.1807; found 448.1823.

4-((4-((4-Methoxybenzyl)oxy)-2-(4-methylpiperazin-1-yl)pyrimidin-5-yl)thio)benzamide [96]. A mixture of 95 (11.2 mg, 0.025 mmol) and KOH (20 mg, 0.357 mmol) in t-BuOH (500 μL) was heated at 80° C. for 1 h. Solvent was removed under reduced pressure and the residue was purified by preparatory TLC ($CH_2Cl_2$:MeOH—$NH_3$ (7 N), 20:1) to afford 9.8 mg (84%) of 96. $^1$H NMR (500 MHz, $CDCl_3$/MeOH-$d_4$): δ 8.19 (s, 1H), 7.56 (d, J=8.5 Hz, 2H), 6.97-7.06 (m, 4H), 6.72 (d, J=8.6 Hz, 2H), 5.24 (s, 2H), 3.80-3.88 (m, 4H), 3.73 (s, 3H), 2.41-2.49 (m, 4H), 2.32 (s, 3H); $^{13}$C NMR (125 MHz, $CDCl_3$): δ 169.5, 168.8, 164.9, 161.7, 159.5, 143.7, 130.0, 129.5, 128.5, 127.9, 126.2, 113.9, 98.5, 67.8, 55.4, 54.9, 46.2, 43.9; HRMS (ESI) m/z [M+H]$^+$ calcd. for $C_{24}H_{28}N_5O_3S$, 466.1913; found 466.1924.

4-((4-Hydroxy-2-(4-methylpiperazin-1-yl)pyrimidin-5-yl)thio)benzonitrile [97]. To a solution of 95 (0.800 g, 1.79 mmol) in $CH_2Cl_2$ (4 mL) was added TFA (4 mL) dropwise over 5 minutes and stirred at rt for 12 h. The reaction mixture was concentrated under reduced pressure to give a residue which was purified by column chromatography ($CH_2Cl_2$:MeOH, 10:1 to 7:1) to afford 0.546 g (93%) of 97. $^1$H NMR (500 MHz, $CDCl_3$/MeOH-$d_4$): δ 8.10 (s, 1H), 7.49 (d, J=8.5 Hz, 2H), 7.22 (d, J=8.5 Hz, 2H), 3.68-3.79 (m, 4H), 2.42-2.51 (m, 4H), 2.35 (s, 3H); $^{13}$C NMR (125 MHz, $CDCl_3$): δ 155.5, 145.8, 132.3, 131.2, 129.0, 126.0, 119.0, 108.1, 101.7, 54.3, 45.8, 44.4; HRMS (ESI) m/z [M+H]$^+$ calcd. for $C_{16}H_{18}N_5OS$, 328.1232; found 328.1234.

4-((4-Chloro-2-(4-methylpiperazin-1-yl)pyrimidin-5-yl)thio)benzonitrile [98]. 97 (0.419 g, 1.28 mmol) and $POCl_3$ (2 mL) were heated at 75° C. for 1 h. After cooling to rt, the reaction mixture was added to a beaker containing ice chips. Following complete quenching of $POCl_3$, solid $Na_2CO_3$ was carefully added until pH ~9. This was transferred to a seperatory funnel and extracted with $CH_2Cl_2$ (4×50 mL), dried over $MgSO_4$, filtered and concentrated to a solid which was purified by column chromatography ($CH_2Cl_2$:MeOH, 50:1 to 40:1) to afford 0.426 g (86%) of 98. $^1$H NMR (500 MHz, $CDCl_3$): δ 8.38 (s, 1H), 7.51 (d, J=8.5 Hz, 2H), 7.13 (d, J=8.4 Hz, 2H), 3.85-3.94 (m, 4H), 2.43-2.51 (m, 4H), 2.36 (s, 3H); MS (m/z): [M+H]$^+$ 346.0/348.0.

General Procedure for Synthesis of 99a-j, m-o and q-x. To alcohol (4.25 equiv.) dissolved in CH$_3$CN was added NaH (4 equiv.) and the resulting suspension was stirred for 10 min. at rt. Then 98 (1 equiv.) was added and the reaction mixture was stirred at rt for 3 h. Solvent was removed under reduced pressure and the residue was purified by column chromatography to afford the desired product.

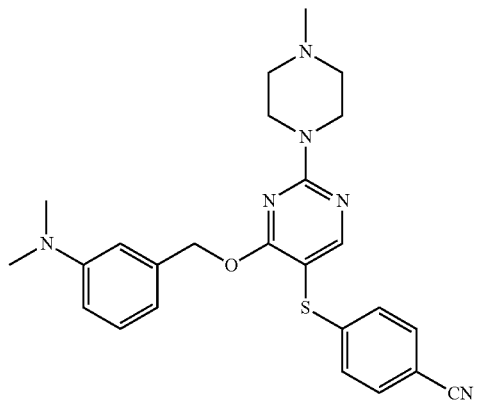

99a 4-((4-((3-(Dimethylamino)benzyl)oxy)-2-(4-methylpiperazin-1-yl)pyrimidin-5-yl)thio)benzonitrile [99a]. 99a was obtained contaminated with unreacted alcohol following the general procedure above. MS (m/z): [M+H]$^+$ 461.2.

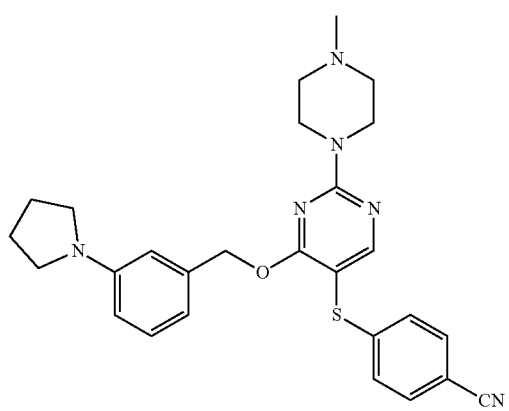

99b 4-((2-(4-Methylpiperazin-1-yl)-4-((3-(pyrrolidin-1-yl)benzyl)oxy)pyrimidin-5-yl)thio)benzonitrile [99b]. 99b was obtained in 89% yield following the general procedure above. $^1$H NMR (500 MHz, CDCl$_3$): δ 8.20 (s, 1H), 7.36 (d, J=8.4 Hz, 2H), 7.08 (t, J=7.8 Hz, 1H), 7.05 (d, J=8.4 Hz, 2H), 6.41-6.46 (m, 2H), 6.35 (br s, 1H), 5.31 (s, 2H), 3.81-3.95 (m, 4H), 3.06-3.13 (m, 4H), 2.43-2.48 (m, 4H), 2.34 (s, 3H), 1.91-2.00 (m, 4H); MS (m/z): [M+H]$^+$ 487.2.

99c 4-((4-((3-(Dimethylamino)-4-fluorobenzyl)oxy)-2-(4-methylpiperazin-1-yl)pyrimidin-5-yl)thio)benzonitrile [99c]. 99c was obtained contaminated with unreacted alcohol following the general procedure above. MS (m/z): [M+H]$^+$ 479.2.

99d 4-((4-(1-(3-(Dimethylamino)phenyl)ethoxy)-2-(4-methylpiperazin-1-yl)pyrimidin-5-yl)thio)benzonitrile [99d]. 99d was obtained contaminated with unreacted alcohol following the general procedure above. MS (m/z): [M+H]$^+$ 475.1.

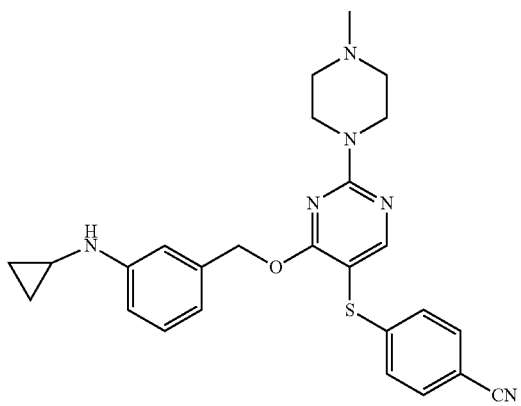

99e 4-((4-((3-(Cyclopropylamino)benzyl)oxy)-2-(4-methylpiperazin-1-yl)pyrimidin-5-yl)thio)benzonitrile [99e]. 99e was obtained contaminated with unreacted alcohol following the general procedure above. MS (m/z): [M+H]+ 473.3.

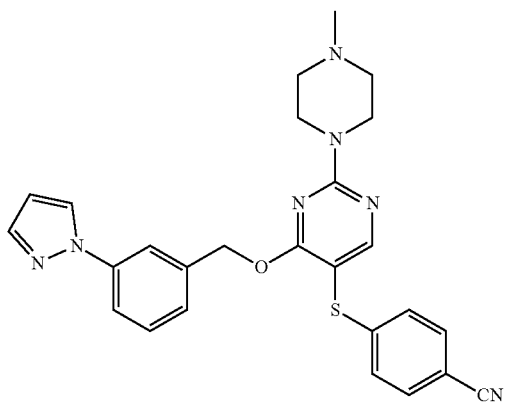

4-((4-((3-(1H-Pyrazol-1-yl)benzyl)oxy)-2-(4-methylpiperazin-1-yl)pyrimidin-5-yl)thio)benzonitrile [99f]. 99f was obtained in 98% yield following the general procedure above. $^1$H NMR (500 MHz, CDCl$_3$): δ 8.24 (s, 1H), 7.77 (d, J=2.5 Hz, 1H), 7.73 (d, J=1.6 Hz, 1H), 7.58-7.60 (m, 1H), 7.54-7.57 (m, 1H), 7.38 (d, J=8.5 Hz, 2H), 7.34 (t, J=7.9 Hz, 1H), 7.05-7.12 (m, 3H), 6.49 (t, J=2.2 Hz, 1H), 5.41 (s, 2H), 3.84-3.92 (m, 4H), 2.42-2.48 (m, 4H), 2.34 (s, 3H); MS (m/z): [M+H]+ 484.3.

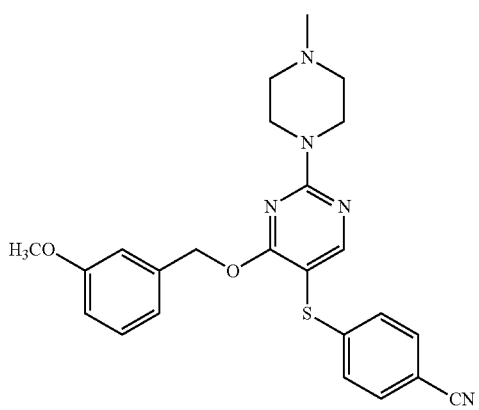

4-((4-((3-Methoxybenzyl)oxy)-2-(4-methylpiperazin-1-yl)pyrimidin-5-yl)thio)benzonitrile [99g]. 99g was obtained contaminated with unreacted alcohol following the general procedure above. MS (m/z): [M+H]+ 448.3.

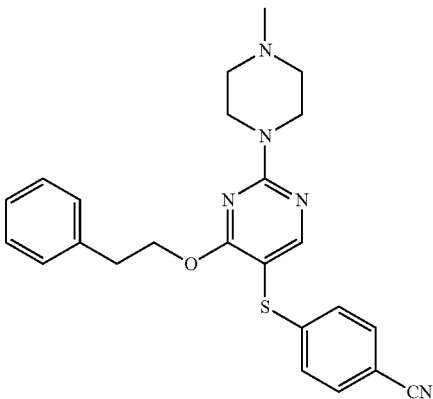

4-((2-(4-Methylpiperazin-1-yl)-4-phenethoxypyrimidin-5-yl)thio)benzonitrile [99h]. 99h was obtained in 89% yield following the general procedure above. $^1$H NMR (500 MHz, CDCl$_3$): δ 8.14 (s, 1H), 7.33 (d, J=8.3 Hz, 2H), 7.06-7.12 (m, 3H), 6.99-7.03 (m, 2H), 6.97 (d, J=8.4 Hz, 2H), 4.43 (t, J=6.8 Hz, 2H), 3.76-3.84 (m, 4H), 2.87 (t, J=6.8 Hz, 2H), 2.37-2.44 (m, 4H), 2.29 (s, 3H); MS (m/z): [M+H]+ 432.2.

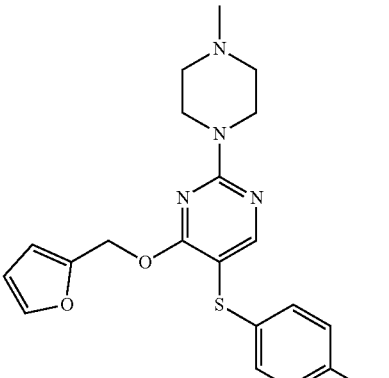

4-((4-(Furan-2-ylmethoxy)-2-(4-methylpiperazin-1-yl)pyrimidin-5-yl)thio)benzonitrile [99i]. 99i was obtained in 96% yield following the general procedure above. $^1$H NMR (500 MHz, CDCl$_3$): δ 8.16 (s, 1H), 7.33 (d, J=8.6 Hz, 2H), 7.26 (s, 1H), 6.97 (d, J=8.6 Hz, 2H), 6.21-6.27 (m, 1H), 6.20 (d, J=3.1 Hz, 1H), 5.27 (s, 2H), 3.79-3.90 (m, 4H), 2.37-2.46 (m, 4H), 2.30 (s, 3H); MS (m/z): [M+H]+ 408.2.

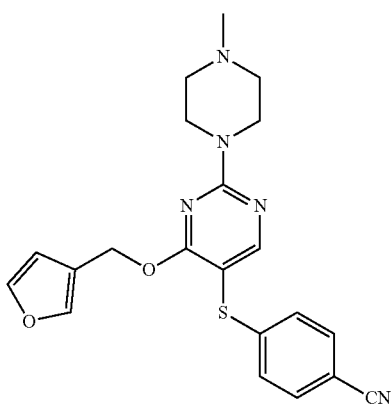

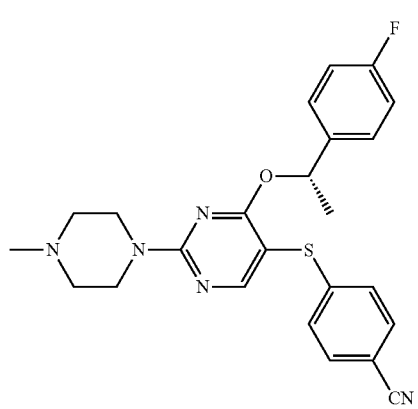

4-((4-(Furan-3-ylmethoxy)-2-(4-methylpiperazin-1-yl)pyrimidin-5-yl)thio)benzonitrile [99j]. 99j was obtained in 76% yield following the general procedure above. $^1$H NMR (500 MHz, CDCl$_3$): δ 8.17 (s, 1H), 7.35 (d, J=8.6 Hz, 2H), 7.22-7.28 (m, 2H), 7.00 (d, J=8.6 Hz, 2H), 6.12 (s, 1H), 5.18 (s, 2H), 3.78-3.88 (m, 4H), 2.37-2.48 (m, 4H), 2.30 (s, 3H); MS (m/z): [M+H]$^+$ 408.2.

(S)-4-((4-(1-(4-Fluorophenyl)ethoxy)-2-(4-methylpiperazin-1-yl)pyrimidin-5-yl)thio)benzonitrile [99n]. 99n was obtained in 55% yield following the general procedure above. $^1$H NMR (500 MHz, CDCl$_3$): δ 8.14 (s, 1H), 7.37 (d, J=8.2 Hz, 2H), 7.02-7.07 (m, 4H), 6.83-6.87 (m, 2H), 6.01-6.02 (m, 1H), 3.73-3.79 (m, 4H), 2.36-2.40 (m, 4H), 2.26 (s, 3H), 1.40 (d, J=6.5 Hz, 3H); $^{13}$C NMR (125 MHz, CDCl$_3$): δ 168.0, 164.9, 161.7, 145.8, 137.9, 132.1, 127.4, 126.2, 118.9, 115.3, 115.1, 108.2, 97.0, 73.6, 54.7, 46.2, 43.9, 22.7; MS (m/z): [M+H]$^+$ 450.1.

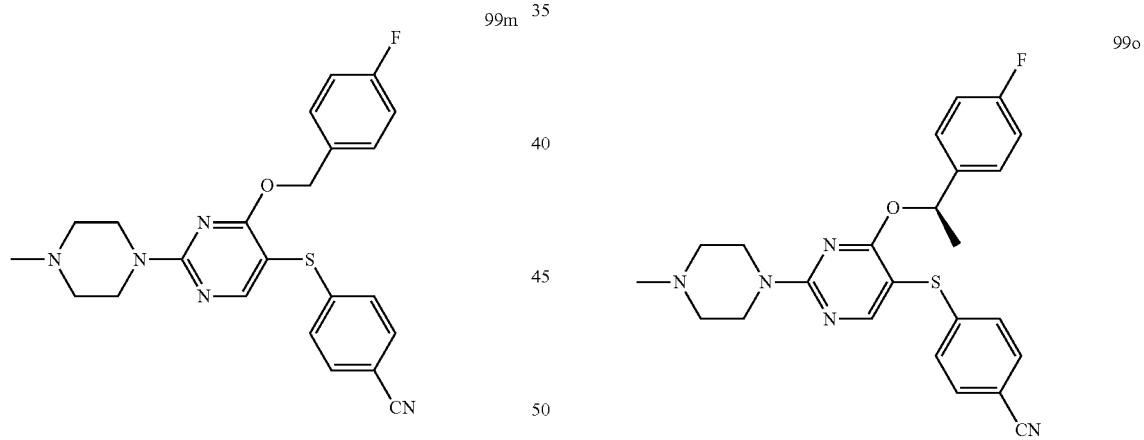

4-((4-((4-Fluorobenzyl)oxy)-2-(4-methylpiperazin-1-yl)pyrimidin-5-yl)thio)benzonitrile [99m]. 99m was obtained in 70% yield following the general procedure above. $^1$H NMR (500 MHz, CDCl$_3$): δ 8.17 (s, 1H), 7.35 (d, J=8.4 Hz, 2H), 7.04-7.07 (m, 4H), 7.01 (d, J=8.4 Hz, 2H), 6.86-6.88 (m, 2H), 5.24 (s, 2H), 3.81-3.85 (m, 4H), 2.40-2.45 (m, 4H), 2.30 (s, 3H); $^{13}$C NMR (125 MHz, CDCl$_3$): δ 168.5, 165.2, 161.7, 145.6, 132.1, 129.4, 129.3, 126.0, 118.9, 115.4, 115.2, 108.3, 96.8, 67.2, 54.7, 46.1, 43.8; MS (m/z): [M+H]$^+$ 436.0.

(R)-4-((4-(1-(4-Fluorophenyl)ethoxy)-2-(4-methylpiperazin-1-yl)pyrimidin-5-yl)thio)benzonitrile [99o]. 99o was obtained in 52% yield following the general procedure above. $^1$H NMR (500 MHz, CDCl$_3$): δ 8.14 (s, 1H), 7.37 (d, J=8.3 Hz, 2H), 7.02-7.05 (m, 4H), 6.83-6.87 (m, 2H), 5.99-6.02 (m, 1H), 3.73-3.79 (m, 4H), 2.36-2.39 (m, 4H), 2.27 (s, 3H), 1.39 (d, J=6.5 Hz, 3H); $^{13}$C NMR (125 MHz, CDCl$_3$): δ 168.0, 164.9, 161.7, 143.8, 137.9, 132.1, 127.5, 126.2, 118.9, 115.3, 115.1, 108.2, 97.0, 73.7, 54.7, 46.2, 43.9, 22.7; MS (m/z): [M+H]$^+$ 450.1.

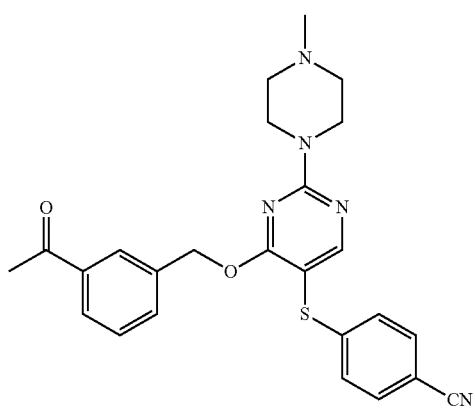

99q 4-((4-((3-Acetylbenzyl)oxy)-2-(4-methylpiperazin-1-yl)pyrimidin-5-yl)thio)benzonitrile [99q]. 99q was obtained contaminated with unreacted alcohol following the general procedure above. MS (m/z): [M+H]+ 460.2.

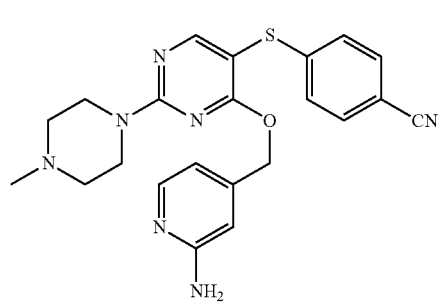

99r 4-((4-((2-Aminopyridin-4-yl)methoxy)-2-(4-methylpiperazin-1-yl)pyrimidin-5-yl)thio)benzonitrile [99r]. 99r was obtained contaminated with unreacted alcohol following the general procedure above. MS (m/z): [M+H]+ 434.2.

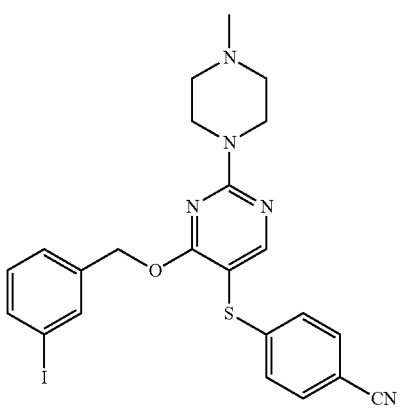

99s 4-((4-((3-Iodobenzyl)oxy)-2-(4-methylpiperazin-1-yl)pyrimidin-5-yl)thio)benzonitrile [99s]. 99s was obtained in 92% yield following the general procedure above. MS (m/z): [M+H]+ 444.2.

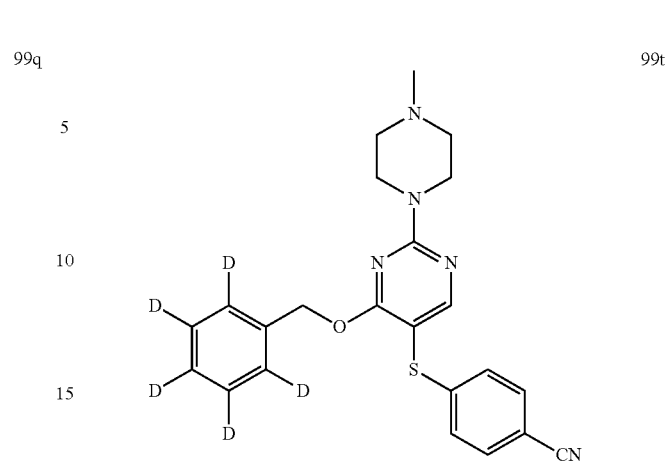

99t 4-((4-(Benzyloxy-d$_5$)-2-(4-methylpiperazin-1-yl)pyrimidin-5-yl)thio)benzonitrile [99t]. 99t was obtained in 82% yield following the general procedure above. MS (ESI) m/z [M+H]+ 423.4.

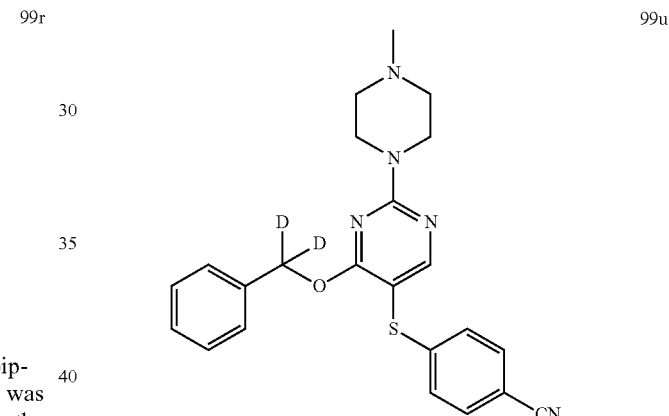

99u 4-((4-(Benzyloxy-d$_2$)-2-(4-methylpiperazin-1-yl)pyrimidin-5-yl)thio)benzonitrile [99u]. 99u was obtained in 78% yield following the general procedure above. MS (ESI) m/z [M+H]+ 420.4.

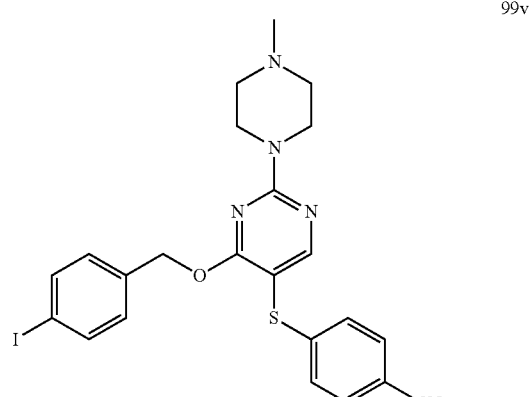

99v 4-((4-((4-Iodobenzyl)oxy)-2-(4-methylpiperazin-1-yl)pyrimidin-5-yl)thio)benzonitrile [99v]. 99v was obtained in 72% yield following the general procedure above. MS (ESI) m/z [M+H]+ 544.2.

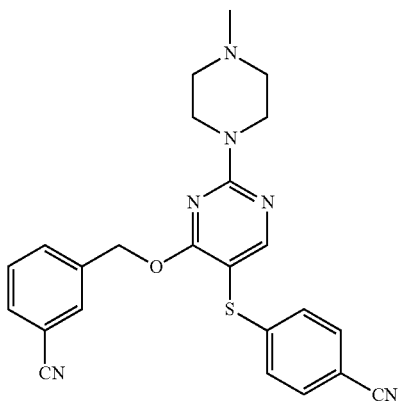

3-(((5-((4-Cyanophenyl)thio)-2-(4-methylpiperazin-1-yl)pyrimidin-4-yl)oxy)methyl)benzonitrile [99w]. 99w was obtained in 63% yield following the general procedure above. MS (ESI) m/z [M+H]+ 443.2.

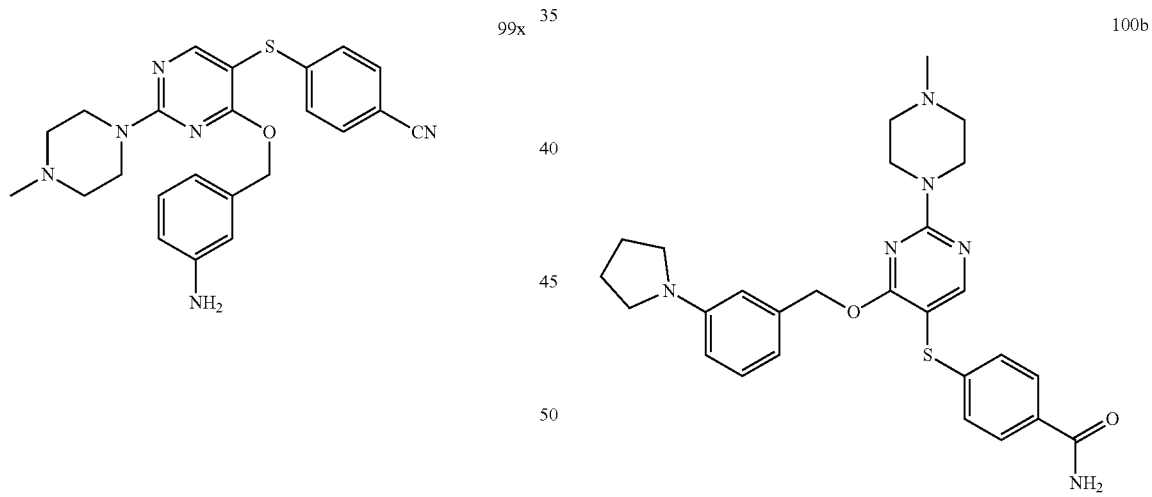

4-((4-((3-Aminobenzyl)oxy)-2-(4-methylpiperazin-1-yl)pyrimidin-5-yl)thio)benzonitrile [99x]. 99x was obtained in 96% yield following the general procedure above. $^1H$ NMR (500 MHz, CDCl$_3$): δ 8.16 (s, 1H), 7.35 (d, J=8.5 Hz, 2H), 7.02 (d, J=8.5 Hz, 2H), 6.96 (t, J=7.8 Hz, 1H), 6.50 (dd, J=7.9, 2.2 Hz, 1H), 6.47 (d, J=7.6 Hz, 1H), 6.33 (s, 1H), 5.20 (s, 2H), 3.82-3.85 (m, 4H), 3.51 (br s, 2H), 2.42-2.45 (m, 4H), 2.30 (s, 3H); MS (ESI) m/z [M+H]+ 433.1.

General Procedure for the Synthesis of 100a-j, m-o and q-x. A mixture of nitrile (1 equiv.) and KOH (25 equiv.) in t-BuOH was heated at 80° C. for 1 h. Solvent was removed under reduced pressure and the residue was purified by preparatory TLC to afford amide.

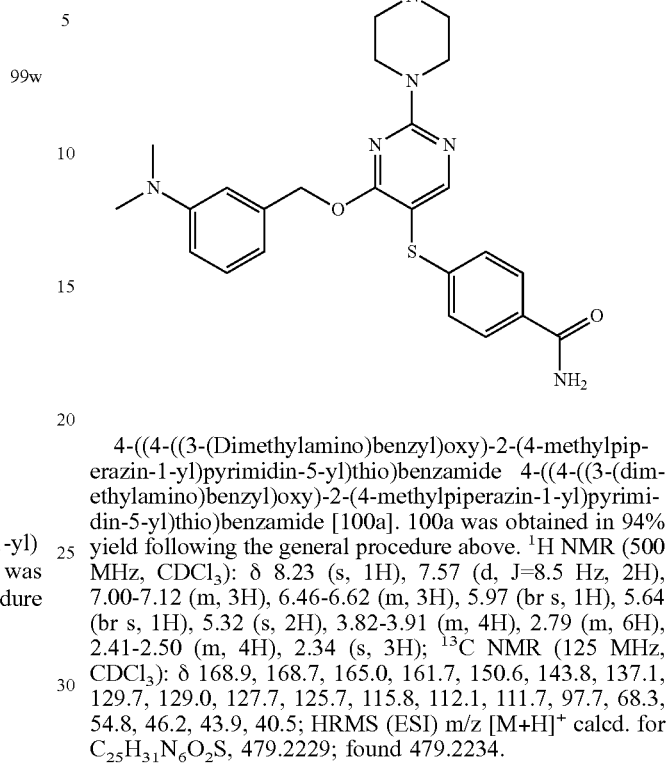

4-((4-((3-(Dimethylamino)benzyl)oxy)-2-(4-methylpiperazin-1-yl)pyrimidin-5-yl)thio)benzamide 4-((4-((3-(dimethylamino)benzyl)oxy)-2-(4-methylpiperazin-1-yl)pyrimidin-5-yl)thio)benzamide [100a]. 100a was obtained in 94% yield following the general procedure above. $^1$H NMR (500 MHz, CDCl$_3$): δ 8.23 (s, 1H), 7.57 (d, J=8.5 Hz, 2H), 7.00-7.12 (m, 3H), 6.46-6.62 (m, 3H), 5.97 (br s, 1H), 5.64 (br s, 1H), 5.32 (s, 2H), 3.82-3.91 (m, 4H), 2.79 (m, 6H), 2.41-2.50 (m, 4H), 2.34 (s, 3H); $^{13}$C NMR (125 MHz, CDCl$_3$): δ 168.9, 168.7, 165.0, 161.7, 150.6, 143.8, 137.1, 129.7, 129.0, 127.7, 125.7, 115.8, 112.1, 111.7, 97.7, 68.3, 54.8, 46.2, 43.9, 40.5; HRMS (ESI) m/z [M+H]+ calcd. for C$_{25}$H$_{31}$N$_6$O$_2$S, 479.2229; found 479.2234.

4-((2-(4-Methylpiperazin-1-yl)-4-((3-(pyrrolidin-1-yl)benzyl)oxy)pyrimidin-5-yl)thio)benzamide [100b]. 100b was obtained in 92% yield following the general procedure above. $^1$H NMR (500 MHz, CDCl$_3$): δ 8.23 (s, 1H), 7.58 (d, J=8.3 Hz, 2H), 7.04-7.10 (m, 3H), 6.45 (d, J=7.4 Hz, 1H), 6.41 (d, J=8.2 Hz, 1H), 6.39 (br s, 1H), 5.93 (br s, 1H), 5.60 (br s, 1H), 5.31 (s, 2H), 3.84-3.91 (m, 4H), 3.03-3.12 (m, 4H), 2.42-2.49 (m, 4H), 2.34 (s, 3H), 1.87-1.94 (m, 4H); $^{13}$C NMR (125 MHz, CDCl$_3$): δ 168.9, 168.6, 165.0, 161.8, 148.0, 143.9, 137.2, 129.6, 129.0, 128.0, 125.7, 114.5, 111.2, 110.6, 97.7, 68.4, 54.8, 47.5, 46.2, 43.9, 25.4; HRMS (ESI) m/z [M+H]+ calcd. for C$_{27}$H$_{33}$N$_6$O$_2$S, 505.2386; found 505.2362.

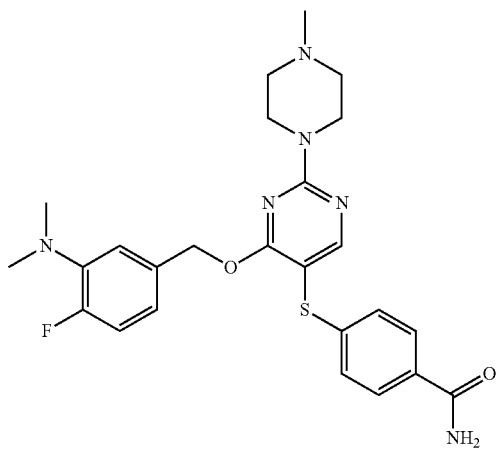

100c 4-((4-((3-(Dimethylamino)-4-fluorobenzyl)oxy)-2-(4-methylpiperazin-1-yl)pyrimidin-5-yl)thio)benzamide [100c]. 100c was obtained in 77% yield following the general procedure above. $^1$H NMR (500 MHz, CDCl$_3$): δ 8.23 (s, 1H), 7.56 (d, J=8.5 Hz, 2H), 7.02 (d, J=8.5 Hz, 2H), 6.82-6.88 (m, 1H), 6.71 (dd, J=8.6, 2.0 Hz, 1H), 6.61-6.67 (m, 1H), 6.10 (br s, 1H), 5.77 (br s, 1H), 5.27 (s, 2H), 3.82-3.92 (m, 4H), 2.67 (s, 6H), 2.42-2.50 (m, 4H), 2.34 (s, 3H); $^{13}$C NMR (125 MHz, CDCl$_3$): δ 168.8, 168.7, 165.1, 161.7, 154.6 (d, J=245 Hz), 143.6, 140.5 (d, J=9.0 Hz), 132.4 (d, J=3.6 Hz), 129.9, 127.7, 125.6, 120.3 (d, J=8.4 Hz), 117.8 (d, J=3.7 Hz), 115.9 (d, J=21.5 Hz), 97.7, 67.5, 54.8, 46.2, 43.9, 42.6 (d, J=3.8 Hz); HRMS (ESI) m/z [M+H]$^+$ calcd. for C$_{25}$H$_{30}$FN$_6$O$_2$S, 497.2135; found 497.2152.

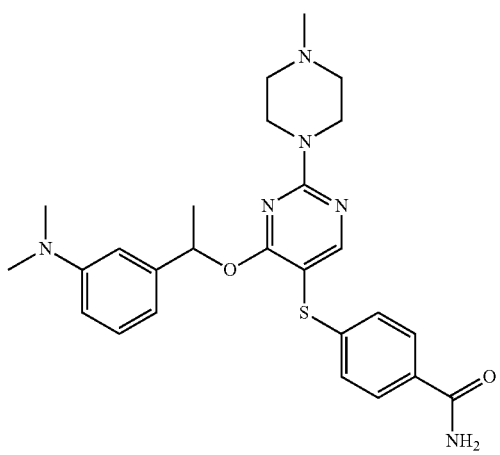

100d 4-((4-(1-(3-(Dimethylamino)phenyl)ethoxy)-2-(4-methylpiperazin-1-yl)pyrimidin-5-yl)thio)benzamide [100d]. 100d was obtained in 85% yield following the general procedure above. $^1$H NMR (600 MHz, CDCl$_3$): δ 8.20 (s, 1H), 7.59 (d, J=8.4 Hz, 2H), 7.05-7.11 (m, 3H), 6.54-6.58 (m, 2H), 6.48 (d, J=7.4 Hz, 1H), 6.05 (q, J=6.5 Hz, 1H), 6.04 (br s, 1H), 5.72 (br s, 1H), 3.75-3.87 (m, 4H), 2.81 (s, 6H), 2.38-2.47 (m, 4H), 2.32 (s, 3H), 1.48 (d, J=6.5 Hz, 3H); $^{13}$C NMR (150 MHz, CDCl$_3$): δ 168.8, 168.4, 164.8, 161.7, 150.5, 144.0, 143.2, 130.0, 129.0, 128.0, 126.0, 114.2, 111.8, 110.0, 98.1, 74.8, 54.8, 46.2, 43.8, 40.5, 22.9; HRMS (ESI) m/z [M+H]$^+$ calcd. for C$_{26}$H$_{33}$N$_6$O$_2$S, 493.2386; found 493.2394.

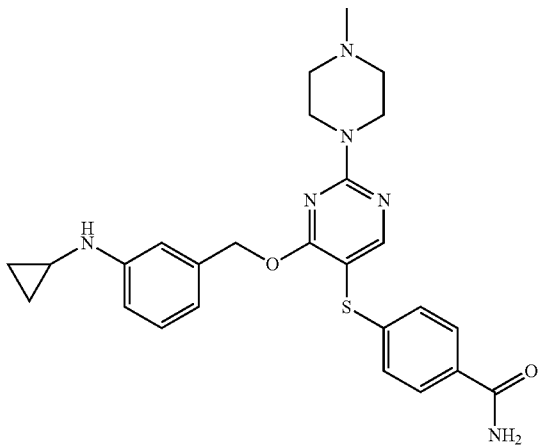

100e 4-((4-((3-(Cyclopropylamino)benzyl)oxy)-2-(4-methylpiperazin-1-yl)pyrimidin-5-yl)thio)benzamide [100e]. 100e was obtained in 75% yield following the general procedure above. $^{1H}$NMR (600 MHz, CDCl$_3$): δ 8.23 (s, 1H), 7.59 (d, J=8.5 Hz, 2H), 7.10 (d, J=8.5 Hz, 2H), 7.04 (t, J=7.8 Hz, 1H), 6.66 (dd, J=8.0, 1.7 Hz, 1H), 6.52 (d, J=7.5 Hz, 1H), 6.46 (s, 1H), 6.00 (br s, 1H), 5.60 (br s, 1H), 5.27 (s, 2H), 4.06 (br s, 1H), 3.80-3.93 (m, 4H), 2.43-2.50 (m, 4H), 2.34 (s, 3H), 2.25-2.30 (m, 1H), 0.62-0.67 (m, 2H), 0.41-0.45 (m, 2H); $^{13}$C NMR (150 MHz, CDCl$_3$): δ 168.75, 168.72, 164.9, 161.7, 148.8, 143.8, 137.3, 129.8, 129.0, 127.7, 126.0, 116.8, 112.5, 112.2, 97.9, 68.0, 54.8, 46.2, 43.8, 25.2, 7.4; HRMS (ESI) m/z [M+H]$^+$ calcd. for C$_{26}$H$_{31}$N$_6$O$_2$S, 491.2229; found 491.2243.

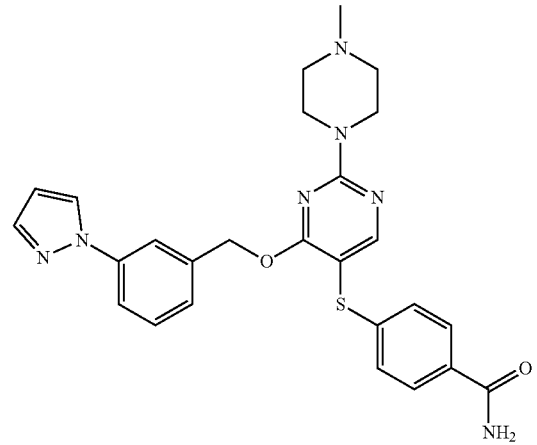

100f 4-((4-((3-(1H-Pyrazol-1-yl)benzyl)oxy)-2-(4-methylpiperazin-1-yl)pyrimidin-5-yl)thio)benzamide [100f]. 100f was obtained in 70% yield following the general procedure above. $^1$H NMR (500 MHz, CDCl$_3$): δ 8.27 (s, 1H), 7.73 (d, J=2.5 Hz, 1H), 7.70 (d, J=1.7 Hz, 1H), 7.53-7.59 (m, 4H), 7.32 (t, J=7.8 Hz, 1H), 7.10 (t, J=8.4 Hz, 2H), 7.06 (t, J=7.7

Hz, 1H), 6.45 (t, J=2.2 Hz, 1H), 6.07 (br s, 1H), 5.65 (br s, 1H), 5.41 (s, 2H), 3.84-3.93 (m, 4H), 2.43-2.50 (m, 4H), 2.34 (s, 3H); $^{13}$C NMR (125 MHz, CDCl$_3$): δ 168.7, 168.5, 165.0, 161.6, 143.4, 141.2, 140.2, 138.0, 130.0, 129.5, 127.8, 126.9, 125.9, 125.4, 118.7, 118.3, 107.8, 97.9, 67.3, 54.7, 46.1, 43.9; HRMS (ESI) m/z [M+H]$^+$ calcd. for C$_{26}$H$_{28}$N$_7$O$_2$S, 502.2025; found 502.2022.

(br s, 1H), 4.47 (t, J=7.0 Hz, 2H), 3.80-3.89 (m, 4H), 2.91 (t, J=7.0 Hz, 2H), 2.40-2.50 (m, 4H), 2.34 (s, 3H); $^{13}$C NMR (125 MHz, CDCl$_3$): δ 169.2, 168.9, 165.2, 162.0, 144.0, 138.1, 130.0, 129.2, 128.6, 127.9, 126.6, 125.8, 97.7, 67.4, 55.0, 46.4, 44.0, 35.3; HRMS (ESI) m/z [M+H]$^+$ calcd. for C$_{24}$H$_{28}$N$_5$O$_2$S, 450.1964; found 450.1951.

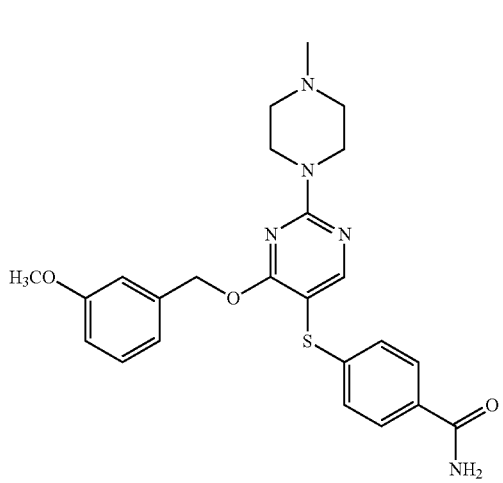

100g

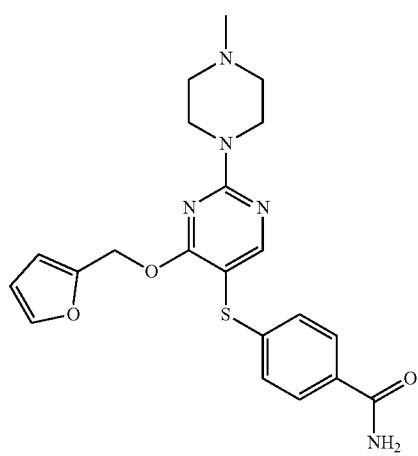

100i 4-((4-((3-Methoxybenzyl)oxy)-2-(4-methylpiperazin-1-yl)pyrimidin-5-yl)thio)benzamide [100g]. 100g was obtained in 60% yield following the general procedure above. $^1$H NMR (600 MHz, CDCl$_3$): δ 8.26 (s, 1H), 7.61 (d, J=8.3 Hz, 2H), 7.16 (t, J=7.8 Hz, 1H), 7.10 (d, J=8.2 Hz, 2H), 6.78 (d, J=8.2 Hz, 1H), 6.75 (d, J=7.5 Hz, 1H), 6.67 (s, 1H), 6.06 (br s, 1H), 5.65 (br s, 1H), 5.33 (s, 2H), 3.86-3.92 (m, 4H), 3.68 (s, 3H), 2.46-2.51 (m, 4H), 2.36 (s, 3H); $^{13}$C NMR (150 MHz, CDCl$_3$): δ 168.8, 168.6, 165.0, 161.7, 160.0, 143.6, 137.9, 129.9, 129.4, 127.8, 125.9, 119.8, 113.3, 113.2, 97.9, 67.7, 55.2, 54.8, 46.2, 43.9; HRMS (ESI) m/z [M+H]$^+$ calcd. for C$_{24}$H$_{28}$N$_5$O$_3$S, 466.1913; found 466.1904.

4-((4-(Furan-2-ylmethoxy)-2-(4-methylpiperazin-1-yl)pyrimidin-5-yl)thio)benzamide [100i]. 100i was obtained in 76% yield following the general procedure above. $^1$H NMR (500 MHz, CDCl$_3$): δ 8.23 (s, 1H), 7.57 (d, J=8.4 Hz, 2H), 7.30 (s, 1H), 7.05 (d, J=8.4 Hz, 2H), 6.26-6.29 (m, 1H), 6.24 (d, J=3.2 Hz, 1H), 5.94 (br s, 1H), 5.62 (br s, 1H), 5.31 (s, 2H), 3.84-3.93 (m, 4H), 2.43-2.52 (m, 4H), 2.35 (s, 3H); $^{13}$C NMR (125 MHz, CDCl$_3$): δ 168.9, 168.7, 165.3, 161.7, 150.0, 143.7, 143.1, 130.0, 127.9, 126.2, 110.6, 110.4, 98.2, 60.1, 55.0, 46.4, 44.1; HRMS (ESI) m/z [M+H]$^+$ calcd. for C$_{21}$H$_{24}$N$_5$O$_3$S, 426.1600; found 426.1598.

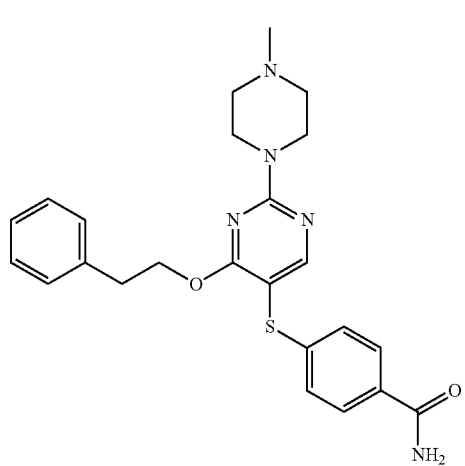

100h

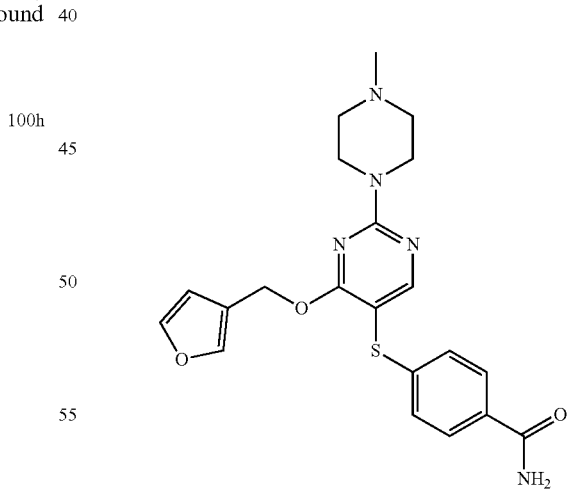

100j 4-((2-(4-Methylpiperazin-1-yl)-4-phenethoxypyrimidin-5-yl)thio)benzamide [100h]. 100h was obtained in 99% yield following the general procedure above. $^1$H NMR (500 MHz, CDCl$_3$): δ 8.22 (s, 1H), 7.60 (d, J=8.7 Hz, 2H), 7.11-7.17 (m, 3H), 7.02-7.10 (m, 4H), 5.95 (br s, 1H), 5.72

4-((4-(Furan-3-ylmethoxy)-2-(4-methylpiperazin-1-yl)pyrimidin-5-yl)thio)benzamide [100j]. 100j was obtained in 82% yield following the general procedure above. $^1$H NMR (500 MHz, CDCl$_3$/MeOH-d$_4$): δ 8.17 (s, 1H), 7.57 (d, J=8.5 Hz, 2H), 7.18-7.26 (m, 2H), 7.02 (d, J=8.5 Hz, 2H), 6.12 (br s, 1H), 5.17 (s, 2H), 3.78-3.87 (m, 4H), 2.42-2.49 (m, 4H), 2.31 (s, 3H); $^{13}$C NMR (125 MHz, CDCl$_3$): δ 169.8, 168.7, 164.9, 161.6, 143.5, 143.3, 141.1, 129.9, 127.9, 126.0, 120.7, 110.3, 98.4, 60.0, 54.8, 46.0, 43.7; HRMS (ESI) m/z [M+H]+ calcd. for C21H24N5O3S, 426.1600; found 426.1596.

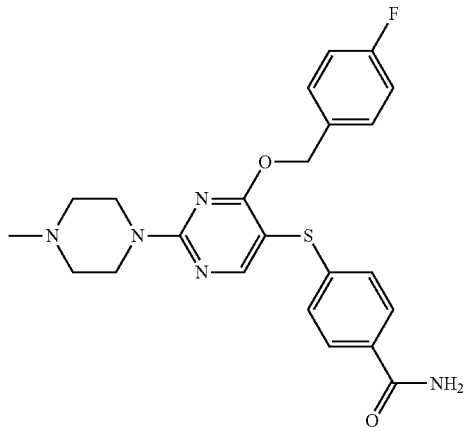

4-((4-((4-Fluorobenzyl)oxy)-2-(4-methylpiperazin-1-yl)pyrimidin-5-yl)thio)benzamide [100m]. 100m was obtained in 85% yield following the general procedure above. $^1$H NMR (500 MHz, CDCl$_3$): δ 8.19 (s, 1H), 7.55 (d, J=8.4 Hz, 2H), 7.01-7.05 (m, 4H), 6.80-6.88 (m, 2H), 5.92 (br s, 1H), 5.70 (br s, 1H), 5.24 (s, 2H), 3.80-3.85 (m, 4H), 2.40-2.43 (m, 4H), 2.29 (s, 3H); $^{13}$C NMR (125 MHz, CDCl$_3$): δ 168.6, 168.5, 164.9, 161.6, 143.6, 132.1, 129.9, 129.3, 127.7, 126.0, 115.3, 115.2, 98.0, 67.1, 54.8, 46.2, 43.9; MS (m/z): [M+H]+ 454.1.

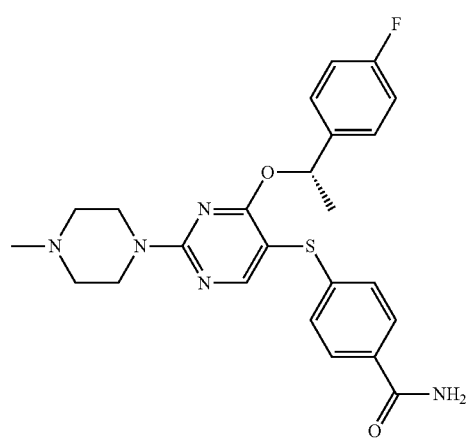

(S)-4-((4-(1-(4-Fluorophenyl)ethoxy)-2-(4-methylpiperazin-1-yl)pyrimidin-5-yl)thio)benzamide [100n]. 100n was obtained in 83% yield following the general procedure above. $^1$H NMR (600 MHz, CDCl$_3$): δ 8.16 (s, 1H), 7.57 (d, J=8.5 Hz, 2H), 7.06 (d, J=8.5 Hz, 2H), 6.99-7.02 (m, 2H), 6.81-6.85 (m, 2H), 5.98-6.02 (m, 1H), 3.68-3.79 (m, 4H), 2.37-2.39 (m, 4H), 2.27 (s, 3H), 1.39 (d, J=6.6 Hz, 3H); $^{13}$C NMR (150 MHz, CDCl$_3$): δ 168.7, 168.0, 164.7, 161.6, 143.8, 138.0, 129.9, 127.7, 127.5, 126.2, 115.2, 115.1, 98.2, 73.6, 54.7, 46.2, 43.8, 22.8; MS (m/z): [M+H]+468.2.

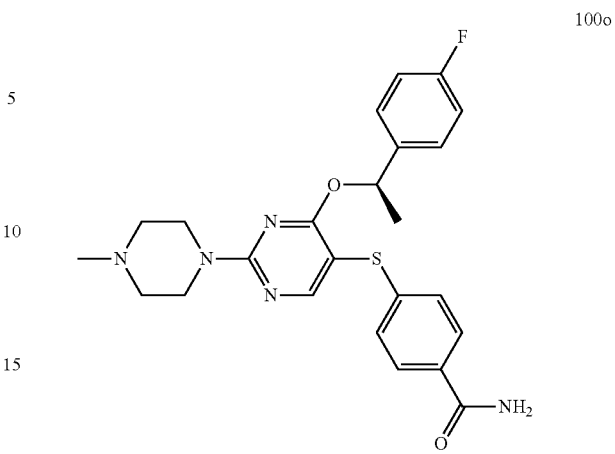

(R)-4-((4-(1-(4-Fluorophenyl)ethoxy)-2-(4-methylpiperazin-1-yl)pyrimidin-5-yl)thio)benzamide [100o]. 100o was obtained in 78% yield following the general procedure above. $^1$H NMR (600 MHz, CDCl$_3$): δ 8.16 (s, 1H), 7.57 (d, J=8.5 Hz, 2H), 7.06 (d, J=8.5 Hz, 2H), 6.99-7.02 (m, 2H), 6.81-6.85 (m, 2H), 5.98-6.02 (m, 1H), 3.72-3.79 (m, 4H), 2.37-2.40 (m, 4H), 2.27 (s, 3H), 1.39 (d, J=6.6 Hz, 3H); $^{13}$C NMR (150 MHz, CDCl$_3$): δ 168.7, 168.0, 164.7, 161.5, 143.8, 138.0, 129.9, 127.7, 127.4, 126.2, 115.2, 115.0, 98.3, 73.6, 54.7, 46.2, 43.8, 22.8; MS (m/z): [M+H]+468.2.

4-((4-((3-Acetylbenzyl)oxy)-2-(4-methylpiperazin-1-yl)pyrimidin-5-yl)thio)benzamide [100q]. 100q was obtained in 55% yield following the general procedure above. $^1$H NMR (600 MHz, CDCl$_3$): δ 8.28 (s, 1H), 7.81-7.83 (m, 1H), 7.78 (s, 1H), 7.63-7.67 (m, 2H), 7.37 (d, J=5.0 Hz, 2H), 7.09-7.13 (m, 2H), 6.43 (br s, 1H), 5.54 (br s, 1H), 5.39 (s, 2H), 3.89 (m, 4H), 2.54 (s, 3H), 2.51 (m, 4H), 2.38 (s, 3H); HRMS (ESI) m/z [M+H]+ calcd. for C25H27N5O3S, 478.1913; found 478.1911.

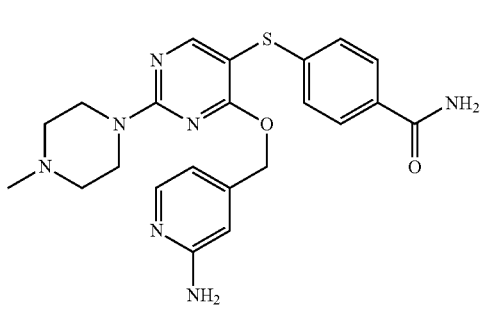

4-((4-((2-Aminopyridin-4-yl)methoxy)-2-(4-methylpiperazin-1-yl)pyrimidin-5-yl)thio)benzamide [100r]. 100r was obtained in 48% yield following the general procedure above. $^1$H NMR (600 MHz, CDCl$_3$/MeOH-d$_4$): δ 8.29 (s, 1H), 7.89 (d, J=5.3 Hz, 1H), 7.67 (d, J=8.3 Hz, 2H), 7.17 (d, J=8.5 Hz, 2H), 6.42 (d, J=5.2 Hz, 1H), 5.94 (s, 1H), 5.23 (s, 2H), 3.86 (m, 4H), 2.48 (m, 4H), 2.36 (s, 3H); $^{13}$C NMR (150 MHz, CDCl$_3$/MeOH-d$_4$): δ 169.3, 168.2, 164.9, 161.7, 158.7, 147.8, 147.6, 143.6, 130.4, 127.9, 126.5, 112.1, 98.2, 66.2, 54.9, 46.3, 43.9; HRMS (ESI) m/z [M+H]$^+$ calcd. for C$_{22}$H$_{26}$N$_7$O$_2$S, 452.1869; found 452.1860.

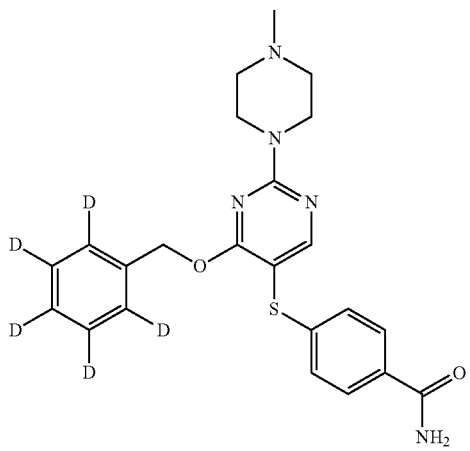

4-((4-(Benzyloxy-d$_5$)-2-(4-methylpiperazin-1-yl)pyrimidin-5-yl)thio)benzamide [100t]. 100t was obtained in 67% yield following the general procedure above. $^1$H NMR (600 MHz, CDCl$_3$) δ 8.26 (s, 1H), 7.62 (d, J=8.4 Hz, 1H), 7.12 (d, J=8.4 Hz, 2H), 6.02 (br s, 1H), 5.73 (br s, 1H), 5.36 (s, 2H), 3.87-3.89 (m, 4H), 2.46-2.48 (m, 4H), 2.35 (s, 3H); $^{13}$C NMR (150 MHz, CDCl$_3$) δ 168.7, 168.6, 164.9, 161.6, 143.7, 136.2, 129.8, 127.8, 127.7, 127.3, 127.0, 126.0, 97.9, 67.7, 54.8, 46.2, 43.9; HRMS (ESI) m/z [M+H]$^+$ calcd. for C$_{23}$H$_{21}$D$_5$N$_5$O$_2$S 441.2121; found 441.2122.

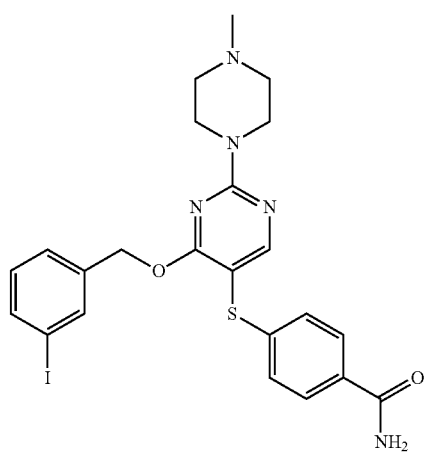

4-((4-((3-Iodobenzyl)oxy)-2-(4-methylpiperazin-1-yl)pyrimidin-5-yl)thio)benzamide [100s]. 100s was obtained in 35% yield following the general procedure above. $^1$H NMR (500 MHz, CDCl$_3$) δ 8.27 (s, 1H), 7.66 (d, J=8.3 Hz, 2H), 7.57 (d, J=7.8 Hz, 1H), 7.52 (s, 1H), 7.13 (d, J=8.3 Hz, 2H), 7.08 (d, J=7.6 Hz, 1H), 6.98 (t, J=7.8 Hz, 1H), 6.02 (br s, 1H), 5.67 (br s, 1H), 5.28 (s, 2H), 3.86-3.88 (m, 4H), 2.47-2.49 (m, 4H), 2.36 (s, 3H); $^{13}$C NMR (150 MHz, CDCl$_3$) δ 168.7, 168.3, 165.0, 161.6, 143.4, 138.7, 136.9, 136.3, 130.1, 130.0, 127.9, 126.6, 125.9, 97.8, 94.2, 66.8, 54.8, 46.2, 43.9; HRMS (ESI) m/z [M+H]$^+$ calcd. for C$_{23}$H$_{25}$IN$_5$O$_2$S 562.0774; found 562.0758.

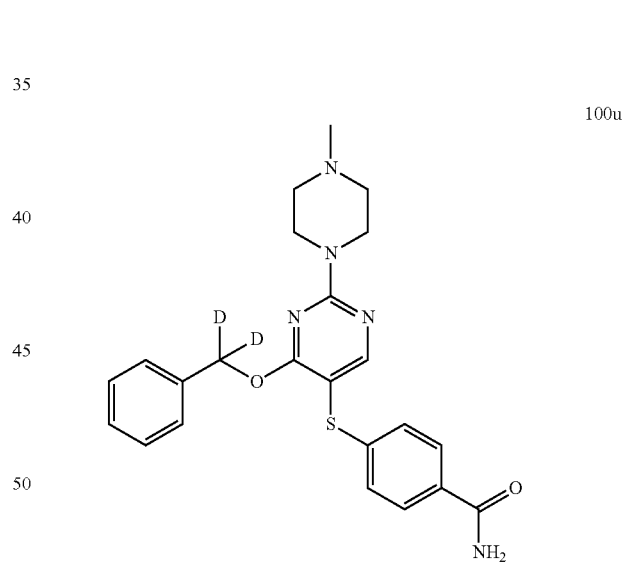

4-((4-(Benzyloxy-d$_2$)-2-(4-methylpiperazin-1-yl)pyrimidin-5-yl)thio)benzamide [100u]. 100u was obtained in 77% yield following the general procedure above. $^1$H NMR (600 MHz, CDCl$_3$) δ 8.26 (s, 1H), 7.62 (d, J=8.3 Hz, 2H), 7.24-7.25 (m, 3H), 7.11-7.14 (m, 4H), 6.03 (br s, 1H), 5.76 (br s, 1H), 3.86-3.88 (m, 4H), 2.46-2.48 (m, 4H), 2.35 (s, 3H); $^{13}$C NMR (150 MHz, CDCl$_3$) δ 168.7, 168.6, 164.9, 161.6, 143.7, 136.2, 129.8, 128.3, 127.9, 127.7, 127.5, 126.0, 97.9, 67.6, 54.8, 46.2, 43.9; HRMS (ESI) m/z [M+H]$^+$ calcd. for C$_{23}$H$_{24}$D$_2$N$_5$O$_2$S 438.1933; found 438.1928.

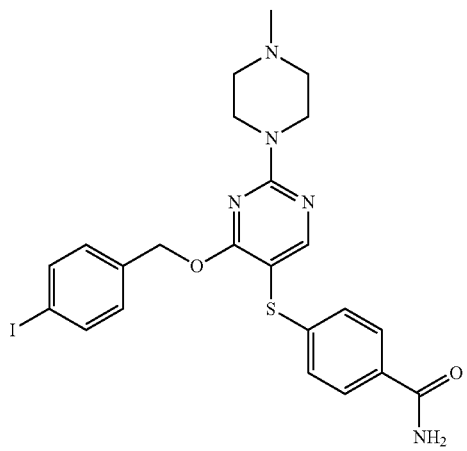

100v 4-((4-((4-Iodobenzyl)oxy)-2-(4-methylpiperazin-1-yl)pyrimidin-5-yl)thio)benzamide [100v]. 100v was obtained in 68% yield following the general procedure above. $^1$H NMR (600 MHz, CDCl$_3$/MeOD-d$_4$) δ 8.24 (s, 1H), 7.63 (d, J=8.4 Hz, 2H), 7.54 (d, J=8.2 Hz, 2H), 7.08 (d, J=8.4 Hz, 2H), 6.84 (d, J=8.2 Hz, 2H), 5.26 (s, 2H), 3.87 (s, 4H), 2.51 (s, 4H), 2.20 (s, 3H); $^{13}$C NMR (150 MHz, CDCl$_3$/MeOD-d$_4$) δ 169.2, 168.4, 164.9, 161.4, 143.4, 137.4, 136.0, 129.9, 129.2, 127.8, 126.0, 93.4, 67.2, 54.5, 45.9, 43.5; HRMS (ESI) m/z [M+H]$^+$ calcd. for C$_{23}$H$_{25}$IN$_5$O$_2$S 562.0774; found 562.0797.

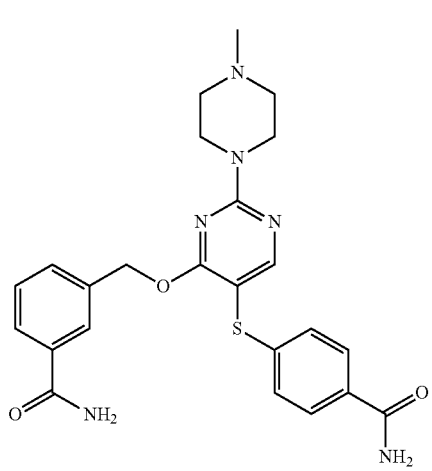

100w 3-(((5-((4-Carbamoylphenyl)thio)-2-(4-methylpiperazin-1-yl)pyrimidin-4-yl)oxy)methyl)benzamide [100w]. 100w was obtained in 53% yield following the general procedure above. $^1$H NMR (600 MHz, CDCl$_3$/MeOH-d$_4$) δ 8.24 (s, 1H), 7.63-7.69 (m, 4H), 7.25-7.29 (m, 2H), 7.05 (d, J=8.5 Hz, 2H), 5.36 (s, 2H), 3.96 (m, 4H), 2.79 (m, 4H), 2.55 (s, 3H); HRMS (ESI) m/z [M+H]$^+$ calcd. for C$_{24}$H$_{27}$N$_6$O$_3$S 479.1865; found 479.1855.

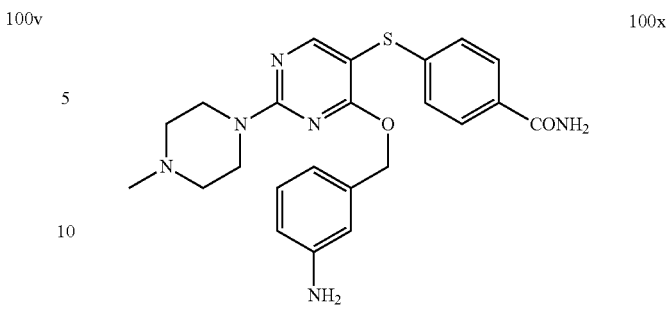

100x 4-((4-((3-Aminobenzyl)oxy)-2-(4-methylpiperazin-1-yl)pyrimidin-5-yl)thio)benzamide [100x]. 100x was obtained in 64% yield following the general procedure above. $^1$H NMR (600 MHz, CDCl$_3$/MeOD-d$_4$) δ 8.25 (s, 1H), 7.63 (d, J=8.5 Hz, 2H), 7.10 (d, J=8.5 Hz, 2H), 7.01 (t, J=7.7 Hz, 1H), 6.53-6.57 (m, 2H), 6.22 (s, 1H), 5.24 (s, 2H), 3.91 (m, 4H), 2.55 (m, 4H), 2.39 (s, 3H); $^{13}$C NMR (150 MHz, CDCl$_3$/MeOD-d$_4$) δ 169.6, 168.7, 164.7, 161.6, 146.5, 143.5, 137.5, 130.2, 129.3, 127.9, 126.3, 118.0, 115.0, 114.2, 98.6, 68.0, 54.7, 45.9, 43.6; HRMS (ESI) m/z [M+H]$^+$ calcd. for C$_{23}$H$_{27}$N$_6$O$_2$S 451.1916; found 451.1908.

Example 11

Scheme 13. Synthesis of 101.

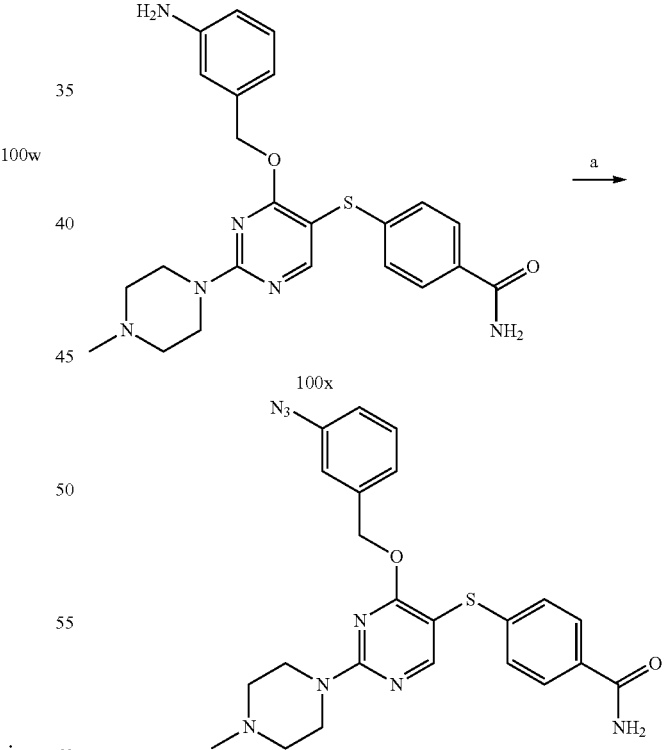

Reagents and conditions: a. NaNO$_2$, NaN$_3$, p-TsOH, CH$_3$CN, H$_2$O, rt, 4 h.

4-((4-((3-Azidobenzyl)oxy)-2-(4-methylpiperazin-1-yl)pyrimidin-5-yl)thio)benzamide [101]. To a solution of 100x (20 mg, 0.044 mmol) and p-TsOH (22 mg, 0.131 mmol) in CH₃CN (1 mL) and H₂O (2 drops) was added NaNO₂ (8 mg, 0.118 mmol) and NaN₃ (15 mg, 0.231) and was stirred at rt for 4 h. The reaction mixture was concentrated to dryness under reduced pressure to give a residue which was purified by preparatory TLC (CH₂Cl₂:MeOH—NH₃ (7 N), 15:1) to afford 5.5 mg (26%) of 101. ¹H NMR (600 MHz, CDCl₃) δ 8.29 (s, 1H), 7.65 (d, J=8.5 Hz, 2H), 7.24 (t, J=7.9 Hz, 1H), 7.12 (d, J=8.6 Hz, 2H), 6.91-6.94 (m, 2H), 6.80 (s, 1H), 6.04 (br s, 1H), 5.64 (br s, 1H), 5.24 (s, 2H), 4.00 (m, 4H), 2.70 (m, 4H), 2.49 (s, 3H); ¹³C NMR (150 MHz, CDCl₃) δ 168.8, 168.7, 165.2, 161.6, 143.4, 140.4, 138.5, 130.3, 130.0, 128.1, 126.2, 124.0, 118.7, 118.1, 98.9, 67.5, 54.6, 53.7, 43.3; HRMS (ESI) m/z [M+H]⁺ calcd. for $C_{23}H_{25}N_8O_2S$ 477.1821; found 477.1811.

Example 12

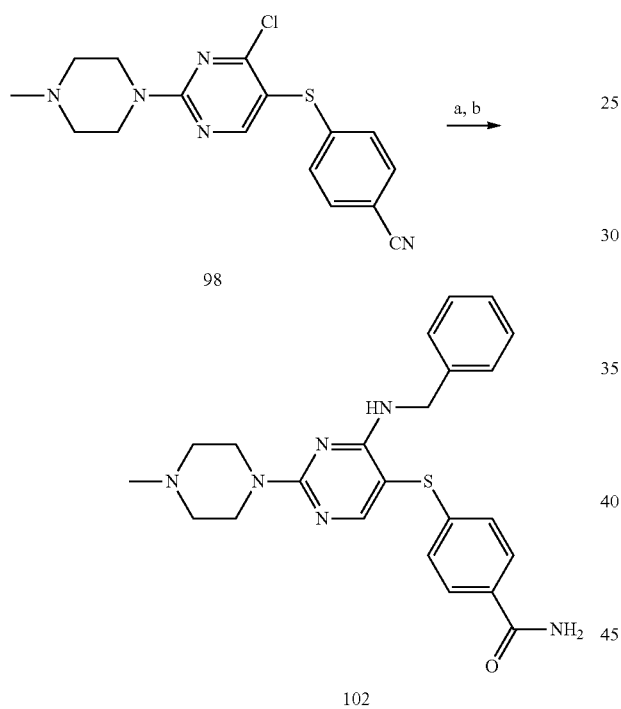

Reagents and conditions: a. benzylamine, CH₃CN, 80° C., 2 h; b. KOH, t-BuOH, 80° C., 1 h.

4-((4-(Benzylamino)-2-(4-methylpiperazin-1-yl)pyrimidin-5-yl)thio)benzamide [102]. A mixture of 98 (20 mg, 0.058 mmol) and benzylamine (18.6 mg, 0.174 mmol) in acetonitrile (500 μL) was heated at 80° C. for 2 h. Solvent was removed under reduced pressure and the residue was purified by preparatory TLC (CH₂Cl₂:MeOH—NH₃ (7 N), 20:1) to afford a residue. To this was added t-BuOH (650 μL) and KOH (81 mg, 1.45 mmol) and the mixture heated at 80° C. for 1 h. Solvent was removed under reduced pressure and the residue was purified by preparatory TLC (CH₂Cl₂: MeOH—NH₃ (7 N), 15:1) to afford 16.4 mg (65%) of 102. ¹H NMR (600 MHz, CDCl₃): δ 8.03 (s, 1H), 7.59 (d, J=8.5 Hz, 2H), 7.14-7.21 (m, 3H), 7.04-7.09 (m, 4H), 5.93 (br s, 1H), 5.83 (t, J=5.8 Hz, 1H), 5.53 (br s, 1H), 4.53 (d, J=5.8 Hz, 2H), 3.74-3.83 (m, 4H), 2.33-2.42 (m, 4H), 2.28 (s, 3H); ¹³C NMR (150 MHz, CDCl₃): δ 168.5, 163.5, 162.0, 161.8, 142.8, 138.8, 130.2, 128.6, 128.0, 127.30, 127.29, 125.3, 93.8, 54.9, 46.2, 44.5, 43.7; MS (m/z): [M+H]⁺ 435.0.

Example 13

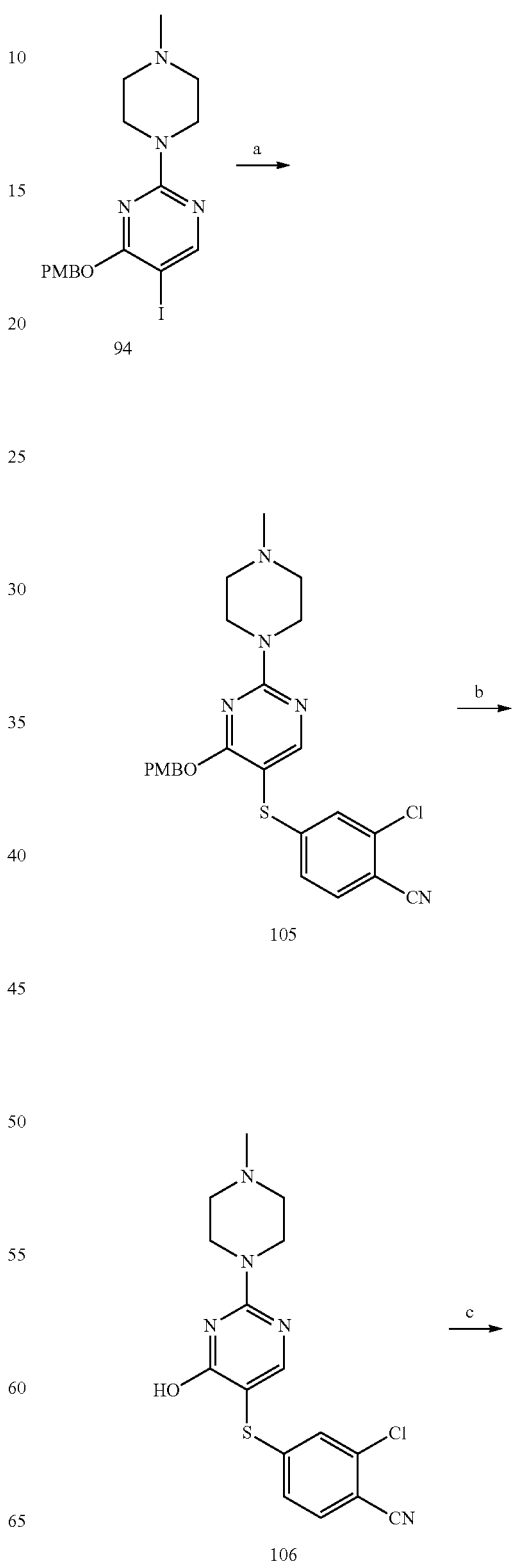

Scheme 16. Synthesis of 108-118 and 121-126.

-continued

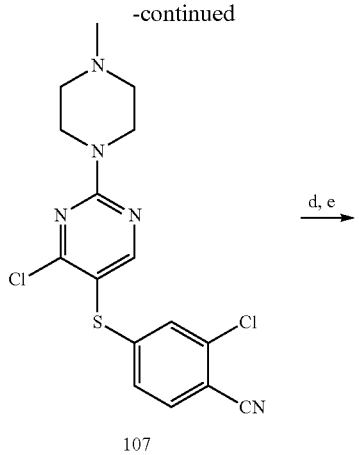

107

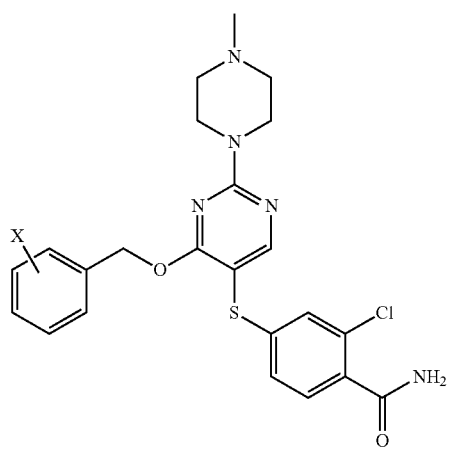

108-118, 121-126

Reagents and conditions: a. 2-chloro-4-mercaptobenzonitrile, copper(I)thiophene-2-carboxylate, K₂CO₃, DMF, 120° C., 17 h; b. TFA, CH₂Cl₂, rt, 12 h; c. POCl₃, 75° C., 1 h; d. ROH, NaH, CH₃CN, rt, 3 h; e. KOH, t-BuOH, 80° C., 1 h.

2-Chloro-4-((4-((4-methoxybenzyl)oxy)-2-(4-methylpiperazin-1-yl)pyrimidin-5-yl)thio)benzonitrile [105]. A mixture of 94 (0.920 g, 2.09 mmol) and K₂CO₃ (0.866 g, 6.27 mmol) in DMF (27 mL) was evacuated and backfilled with argon three times. Copper(I)thiophene-2-carboxylate (0.159 g, 0.832 mmol) was added and evacuated and backfilled with argon two times. 2-Chloro-4-mercaptobenzonitrile (0.425 g, 2.51 mmol) was added and the reaction mixture was heated at 120° C. for 17 h. Solvent was removed under reduced pressure and the residue was purified by column chromatography (CH₂Cl₂:MeOH, 0-10% MeOH) to afford 0.504 g (50%) of 105. $^1$H NMR (600 MHz, CDCl₃): δ 8.21 (s, 1H), 7.39 (d, J=8.3 Hz, 1H), 7.09-7.13 (m, 2H), 7.06 (d, J=1.7 Hz, 1H), 6.97 (dd, J=8.3, 1.8 Hz, 1H), 6.79-6.83 (m, 2H), 5.30 (s, 2H), 3.91-3.96 (m, 4H), 3.80 (s, 3H), 2.51-2.56 (m, 4H), 2.39 (s, 3H); $^{13}$C NMR (150 MHz, CDCl₃): δ 168.5, 165.0, 161.8, 159.5, 147.6, 137.0, 133.4, 129.5, 128.0, 126.2, 124.1, 116.2, 113.8, 108.9, 96.0, 67.8, 55.3, 54.7, 46.1, 43.8; HRMS (ESI) m/z [M+H]⁺ calcd. for C₂₄H₂₄ClN₅O₂S, 482.1417; found 482.1406.

2-Chloro-4-((4-hydroxy-2-(4-methylpiperazin-1-yl)pyrimidin-5-yl)thio)benzonitrile [106]. To a solution of 105 (0.500 g, 1.04 mmol) in CH₂Cl₂ (4 mL) was added TFA (4 mL) dropwise over 5 minutes and stirred at rt for 12 h. The reaction mixture was concentrated under reduced pressure to give a residue which was purified by column chromatography (CH₂Cl₂:MeOH, 0-15% MeOH) to afford 0.354 g (94%) of 106. $^1$H NMR (500 MHz, CDCl₃/MeOH-d₄): δ 8.14 (s, 1H), 7.50 (d, J=8.3 Hz, 1H), 7.18 (d, J=1.7 Hz, 1H), 7.11 (dd, J=8.3, 1.7 Hz, 1H), 3.85-4.28 (m, 4H), 3.09-3.27 (m, 4H), 2.82 (s, 3H); MS (ESI) m/z 362.2/364.3 [M+H]⁺.

2-Chloro-4-((4-chloro-2-(4-methylpiperazin-1-yl)pyrimidin-5-yl)thio)benzonitrile [107]. 106 (0.354 g, 0.978 mmol) and POCl₃ (2 mL) were heated at 75° C. for 1 h. After cooling to rt, the reaction mixture was added to a beaker containing ice chips. Following complete quenching of POCl₃, solid Na₂CO₃ was carefully added until pH ~9. This was transferred to a seperatory funnel and extracted with CH₂Cl₂ (3×100 mL), dried over MgSO₄, filtered and concentrated to a give 0.337 g (91%) of 107 which was used without further purification. $^1$H NMR (500 MHz, CDCl₃): δ 8.38 (s, 1H), 7.51 (d, J=8.3 Hz, 1H), 7.13 (d, J=1.8 Hz, 1H), 7.02 (dd, J=8.3, 1.8 Hz, 1H), 3.90-4.00 (m, 4H), 2.47-2.58 (m, 4H), 2.38 (s, 3H); MS (ESI) m/z 380.1/382.1 [M+H]⁺.

General Procedure for Synthesis of 108-118 and 121-126. To alcohol (4.25 equiv.) dissolved in CH₃CN was added NaH (4 equiv.) and the resulting suspension was stirred for 10 min. at rt. Then 107 (1 equiv.) was added and the reaction mixture was stirred at rt for 3 h. Solvent was removed under reduced pressure and the residue was purified by column chromatography to afford intermediate nitrile. A mixture of the nitrile (1 equiv.) and KOH (25 equiv.) in t-BuOH was heated at 80° C. for 1 h. Solvent was removed under reduced pressure and the residue was purified by preparatory TLC to afford desired amide.

108

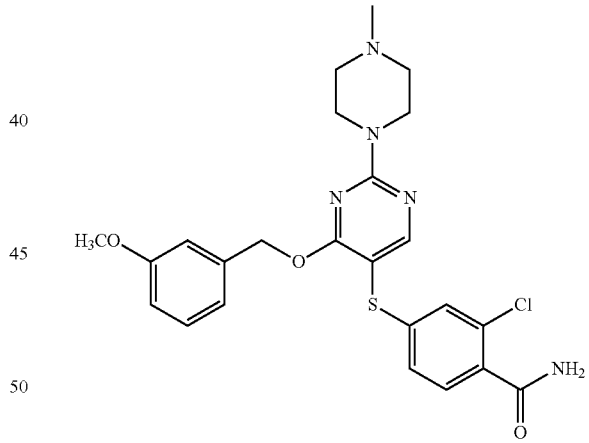

2-Chloro-4-((4-((3-methoxybenzyl)oxy)-2-(4-methylpiperazin-1-yl)pyrimidin-5-yl)thio)benzamide [108]. 108 was obtained in 26% yield following the general procedure above. $^1$H NMR (600 MHz, CDCl₃): δ 8.25 (s, 1H), 7.65 (d, J=8.2 Hz, 1H), 7.20 (t, J=7.9 Hz, 1H), 7.08 (d, J=1.8 Hz, 1H), 7.00 (dd, J=8.3, 1.9 Hz, 1H), 6.77-6.82 (m, 2H), 6.66 (s, 1H), 6.52 (br s, 1H), 5.98 (br s, 1H), 5.34 (s, 2H), 3.87-3.93 (m, 4H), 3.72 (s, 3H), 2.47-2.52 (m, 4H), 2.36 (s, 3H); $^{13}$C NMR (150 MHz, CDCl₃): δ 168.5, 167.5, 164.9, 161.7, 159.5, 143.9, 137.8, 131.3, 131.1, 129.8, 129.4, 127.0, 124.5, 119.8, 113.23, 113.20, 97.1, 67.7, 55.2, 54.7, 46.2, 43.8; HRMS (ESI) m/z [M+H]⁺ calcd. for C₂₄H₂₆ClN₅O₃S, 500.1523; found 500.1510.

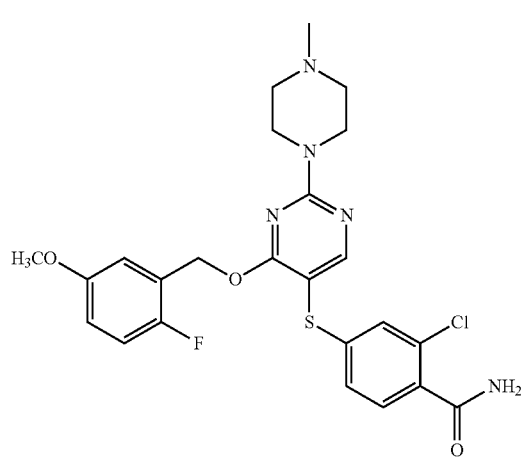

2-Chloro-4-((4-(2-fluoro-5-methoxybenzyl)oxy)-2-(4-methylpiperazin-1-yl)pyrimidin-5-yl)thio)benzamide [109]. 109 was obtained in 50% yield following the general procedure above. $^1$H NMR (600 MHz, CDCl$_3$): δ 8.24 (s, 1H), 7.62 (d, J=8.2 Hz, 1H), 7.06 (d, J=1.8 Hz, 1H), 6.98 (dd, J=8.2, 1.8 Hz, 1H), 6.88-6.93 (m, 1H), 6.69-6.74 (m, 1H), 6.54-6.58 (m, 1H), 6.47 (br s, 1H), 5.97 (br s, 1H), 5.37 (s, 2H), 3.91-4.02 (m, 4H), 3.63 (s, 3H), 2.52-2.65 (m, 4H), 2.42 (s, 3H); HRMS (ESI) m/z [M+H]$^+$ calcd. for C$_{24}$H$_{25}$ClFN$_5$O$_3$S, 518.1429; found 518.1432.

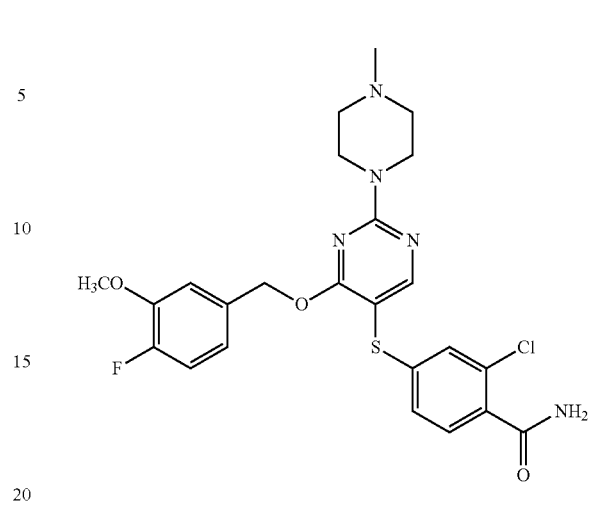

2-Chloro-4-((4-((4-fluoro-3-methoxybenzyl)oxy)-2-(4-methylpiperazin-1-yl)pyrimidin-5-yl)thio)benzamide [111]. 111 was obtained in 62% yield following the general procedure above. $^1$H NMR (600 MHz, CDCl$_3$/MeOH-d$_4$): δ 8.28 (s, 1H), 7.55 (d, J=8.2 Hz, 1H), 7.08 (s, 1H), 7.00-7.06 (m, 2H), 6.86-6.91 (m, 1H), 6.77-6.81 (m, 1H), 5.35 (s, 2H), 3.89-3.97 (m, 4H), 3.76 (s, 3H), 2.51-2.57 (m, 4H), 2.38 (s, 3H); $^{13}$C NMR (150 MHz, CDCl$_3$/MeOH-d$_4$): δ 168.9, 168.5, 165.5, 162.1, 152.4 (d, J=244 Hz), 147.93, 147.86, 144.0, 133.2 (d, J=3.8 Hz), 131.8, 131.0, 130.7, 127.1, 124.6, 120.4 (d, J=7.0 Hz), 116.1 (d, J=18.4 Hz), 113.3 (d, J=2.0 Hz), 67.9, 56.4, 54.9, 46.0, 43.9; HRMS (ESI) m/z [M+H]$^+$ calcd. for C$_{24}$H$_{25}$ClFN$_5$O$_3$S, 518.1429; found 518.1418.

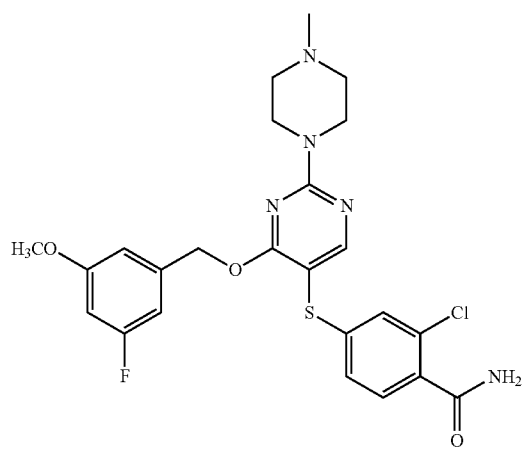

2-Chloro-4-((4-((3-fluoro-5-methoxybenzyl)oxy)-2-(4-methylpiperazin-1-yl)pyrimidin-5-yl)thio)benzamide [110]. 110 was obtained in 43% yield following the general procedure above. $^1$H NMR (600 MHz, CD$_2$Cl$_2$/MeOH-d$_4$): δ 8.18 (s, 1H), 7.48 (d, J=8.2 Hz, 1H), 7.02 (d, J=1.8 Hz, 1H), 6.97 (dd, J=8.2, 1.8 Hz, 1H), 6.42-6.46 (m, 2H), 6.36-6.39 (m, 1H), 5.22 (s, 2H), 3.79-3.85 (m, 4H), 3.63 (s, 3H), 2.40-2.47 (m, 4H), 2.28 (s, 3H); HRMS (ESI) m/z [M+H]$^+$ calcd. for C$_{24}$H$_{25}$ClFN$_5$O$_3$S, 518.1429; found 518.1423.

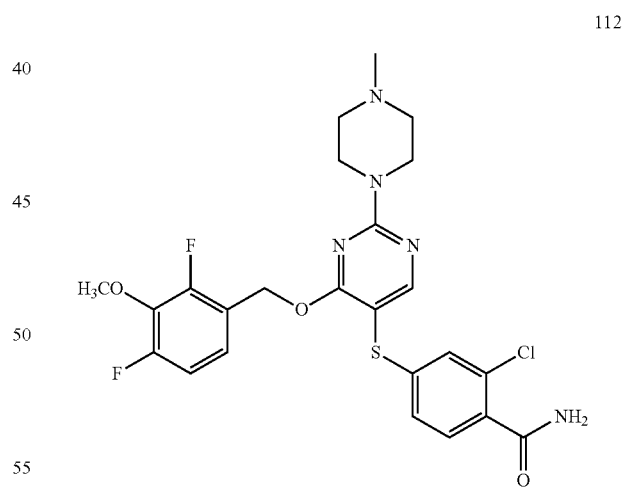

2-Chloro-4-((4-((2,4-difluoro-3-methoxybenzyl)oxy)-2-(4-methylpiperazin-1-yl)pyrimidin-5-yl)thio)benzamide [112]. 112 was obtained in 62% yield following the general procedure above. $^1$H NMR (600 MHz, CDCl$_3$): δ 8.19 (s, 1H), 7.58 (d, J=8.0 Hz, 1H), 6.93-6.99 (m, 2H), 6.68-6.77 (m, 2H), 6.43 (br s, 1H), 5.97 (br s, 1H), 5.30 (s, 2H), 3.85-3.97 (m, 7H), 2.47-2.58 (m, 4H), 2.36 (s, 3H); $^{13}$C NMR (150 MHz, CDCl$_3$): δ 168.3, 167.4, 165.0, 161.5, 155.6 (dd, J=247.8, 4.9 Hz), 153.8 (dd, J=248.4, 5.5 Hz), 143.6, 136.3 (t, J=14.1 Hz), 131.3, 131.1, 130.1, 127.1, 124.7, 122.8, 120.4 (dd, J=12.9, 3.4 Hz), 112.0 (dd, J=19.4, 3.5 Hz), 97.5, 62.0, 61.2, 54.6, 45.8, 43.5; HRMS (ESI) m/z [M+H]+ calcd. for $C_{24}H_{24}ClF_2N_5O_3S$, 536.1335; found 536.1337.

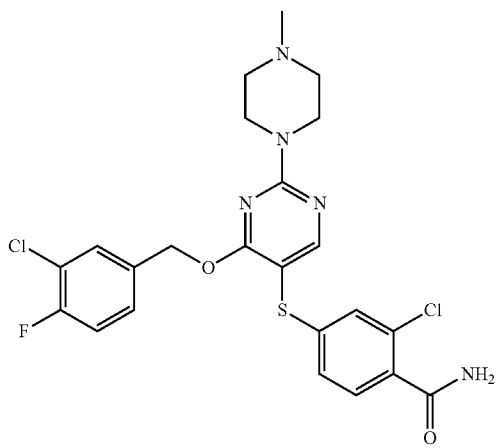

2-Chloro-4-((4-((3-chloro-4-fluorobenzyl)oxy)-2-(4-methylpiperazin-1-yl)pyrimidin-5-yl)thio)benzamide [113]. 113 was obtained in 48% yield following the general procedure above. $^1$H NMR (500 MHz, CDCl$_3$): δ 8.25 (s, 1H), 7.69 (d, J=8.3 Hz, 1H), 7.20 (dd, J=7.0, 1.8 Hz, 1H), 6.97-7.07 (m, 4H), 6.41 (br s, 1H), 5.92 (br s, 1H), 5.26 (s, 2H), 3.87-4.02 (m, 4H), 2.53-2.68 (m, 4H), 2.43 (s, 3H); $^{13}$C NMR (125 MHz, CDCl$_3$): δ 168.5, 167.3, 165.3, 161.7, 157.9 (d, J=248.1 Hz), 143.8, 133.5 (d, J=3.9 Hz), 131.7, 130.2, 130.0, 127.5, 127.43, 127.37, 124.9, 121.2 (d, J=17.9 Hz), 116.9 (d, J=21.2 Hz), 97.9, 66.8, 54.7, 45.9, 43.6; HRMS (ESI) m/z [M+H]+ calcd. for $C_{23}H_{22}Cl_2FN_5O_2S$, 522.0934; found 522.0920.

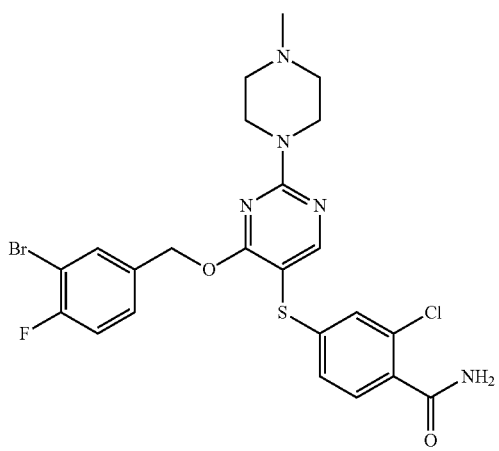

4-((4-((3-Bromo-4-fluorobenzyl)oxy)-2-(4-methylpiperazin-1-yl)pyrimidin-5-yl)thio)-2-chlorobenzamide [114]. 114 was obtained in 47% yield following the general procedure above. $^1$H NMR (500 MHz, CDCl$_3$): δ 8.25 (s, 1H), 7.70 (d, J=8.2 Hz, 1H), 7.37 (dd, J=6.5, 1.9 Hz, 1H), 6.98-7.08 (m, 4H), 6.41 (br s, 1H), 5.91 (br s, 1H), 5.26 (s, 2H), 3.89-4.05 (m, 4H), 2.53-2.70 (m, 4H), 2.45 (s, 3H); $^{13}$C NMR (125 MHz, CDCl$_3$): δ 168.5, 167.3, 165.3, 161.7, 158.9 (d, J=246.6 Hz), 143.8, 133.8 (d, J=3.8 Hz), 133.0, 131.69, 131.66, 130.2, 128.3 (d, J=7.4 Hz), 127.4, 124.9, 116.8 (d, J=22.3 Hz), 109.2 (d, J=21.2 Hz), 98.0, 66.7, 54.6, 45.8, 43.5; HRMS (ESI) m/z [M+H]+ calcd. for $C_{23}H_{22}BrClFN_5O_2S$, 566.0428; found 566.0413.

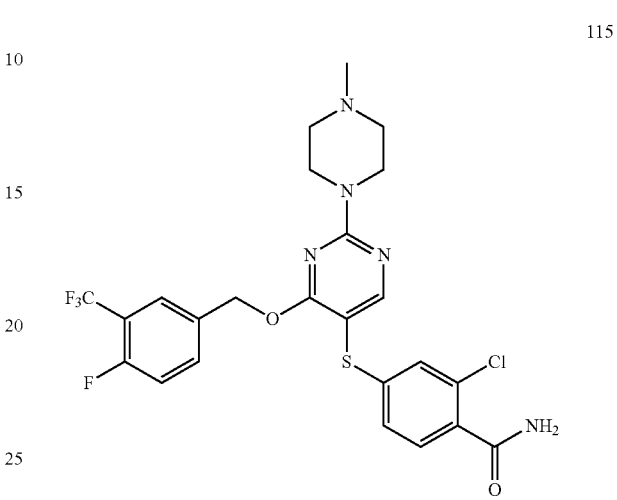

2-Chloro-4-((4-((4-fluoro-3-(trifluoromethyl)benzyl)oxy)-2-(4-methylpiperazin-1-yl)pyrimidin-5-yl)thio)benzamide [115]. 115 was obtained in 52% yield following the general procedure above. $^1$H NMR (600 MHz, CDCl$_3$): δ 8.24 (s, 1H), 7.66 (d, J=8.2 Hz, 1H), 7.48 (dd, J=6.5, 1.6 Hz, 1H), 7.28-7.32 (m, 1H), 7.09-7.14 (m, 1H), 7.02 (d, J=1.8 Hz, 1H), 6.99 (dd, J=8.3, 1.9 Hz, 1H), 6.40 (br s, 1H), 6.09 (br s, 1H), 5.32 (s, 2H), 3.83-3.99 (m, 4H), 2.48-2.59 (m, 4H), 2.39 (s, 3H); $^{13}$C NMR (150 MHz, CDCl$_3$): δ 168.3, 167.3, 165.2, 161.5, 159.3 (d, J=255.5 Hz), 143.7, 133.0 (d, J=8.6 Hz), 132.5 (d, J=3.8 Hz), 131.4, 131.3, 130.0, 127.0, 126.4, 124.5, 122.4 (q, J=270.8 Hz), 118.2, 117.3 (d, J=20.8 Hz), 97.2, 66.5, 54.5, 45.9, 43.6; HRMS (ESI) m/z [M+H]+ calcd. for $C_{24}H_{22}ClF_4N_5O_2S$, 556.1197; found 556.1182.

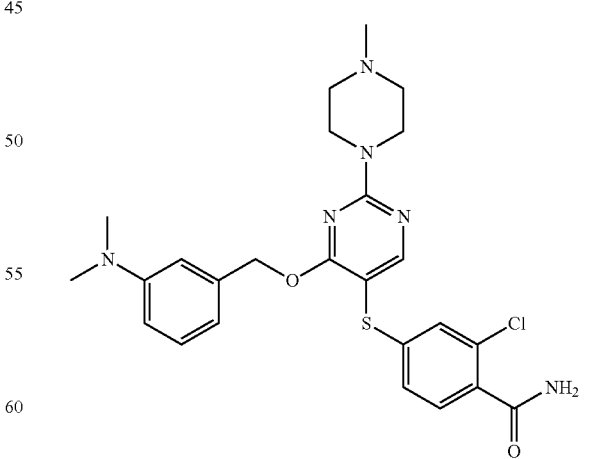

2-Chloro-4-((4-((3-(dimethylamino)benzyl)oxy)-2-(4-methylpiperazin-1-yl)pyrimidin-5-yl)thio)benzamide [116]. 116 was obtained in 67% yield following the general procedure above. $^1$H NMR (600 MHz, CDCl$_3$): δ 8.22 (s, 1H), 7.61 (d, J=8.2 Hz, 1H), 7.10-7.14 (m, 1H), 7.04 (d, J=1.8 Hz, 1H), 6.96 (dd, J=8.2, 1.8 Hz, 1H), 6.61 (dd, J=8.3, 2.4 Hz, 1H), 6.57 (s, 1H), 6.54 (d, J=7.5 Hz, 1H), 6.47 (br s, 1H), 5.99 (br s, 1H), 5.31 (s, 2H), 3.88-3.97 (m, 4H), 2.82 (s, 6H), 2.49-2.58 (m, 4H), 2.38 (s, 3H); $^{13}$C NMR (150 MHz, CDCl$_3$): δ 169.0, 167.6, 165.2, 161.9, 150.8, 144.3, 137.2, 131.5, 131.4, 129.8, 129.3, 127.0, 124.6, 115.9, 112.4, 111.8, 97.4, 68.7, 54.8, 46.1, 43.8, 40.7; HRMS (ESI) m/z [M+H]$^+$ calcd. for C$_{25}$H$_{29}$ClN$_6$O$_2$S, 513.1839; found 513.1833.

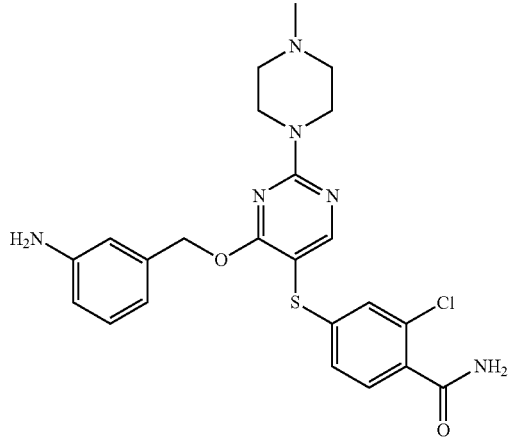

4-((4-((3-Aminobenzyl)oxy)-2-(4-methylpiperazin-1-yl)pyrimidin-5-yl)thio)-2-chlorobenzamide [117]. 117 was obtained in 29% yield following the general procedure above. $^1$H NMR (600 MHz, CD$_2$Cl$_2$/MeOH-d$_4$): δ 8.15 (s, 1H), 7.35 (d, J=8.2 Hz, 1H), 7.03 (d, J=1.7 Hz, 1H), 6.93-6.99 (m, 4H), 6.50-6.56 (m, 2H), 6.28 (s, 1H), 5.17 (s, 2H), 3.75-3.88 (m, 4H), 2.40-2.52 (m, 4H), 2.27 (s, 3H); $^{13}$C NMR (150 MHz, CD$_2$Cl$_2$/MeOH-d$_4$): δ 168.8, 167.9, 163.8, 161.0, 146.3, 142.3, 136.7, 130.8, 130.6, 129.0, 128.5, 126.4, 123.9, 117.0, 114.3, 113.4, 97.1, 67.5, 53.8, 44.8, 42.7; HRMS (ESI) m/z [M+H]$^+$ calcd. for C$_{23}$H$_{25}$ClN$_6$O$_2$S, 485.1526; found 485.1527.

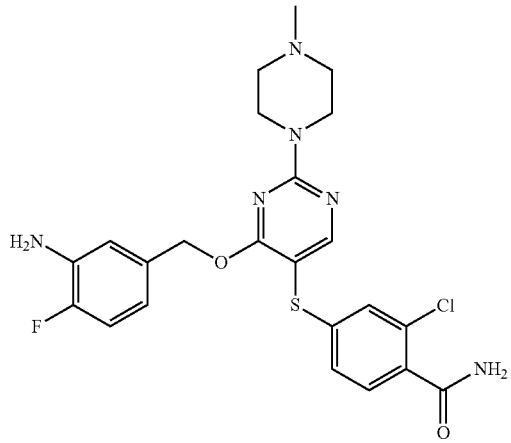

4-((4-((3-Amino-4-fluorobenzyl)oxy)-2-(4-methylpiperazin-1-yl)pyrimidin-5-yl)thio)-2-chlorobenzamide [118]. 118 was obtained in 53% yield following the general procedure above. $^1$H NMR (500 MHz, CD$_2$Cl$_2$/MeOH-d$_4$): δ 8.15 (s, 1H), 7.34 (d, J=8.1 Hz, 1H), 7.01 (d, J=1.5 Hz, 1H), 6.94 (dd, J=8.1, 1.5 Hz, 1H), 6.75-6.82 (m, 1H), 6.43-6.49 (m, 1H), 6.35-6.41 (m, 1H), 5.13 (s, 2H), 3.75-3.84 (m, 4H), 2.40-2.46 (m, 4H), 2.26 (s, 3H); HRMS (ESI) m/z [M+H]$^+$ calcd. for C$_{23}$H$_{24}$ClFN$_6$O$_2$S, 503.1432; found 503.1430.

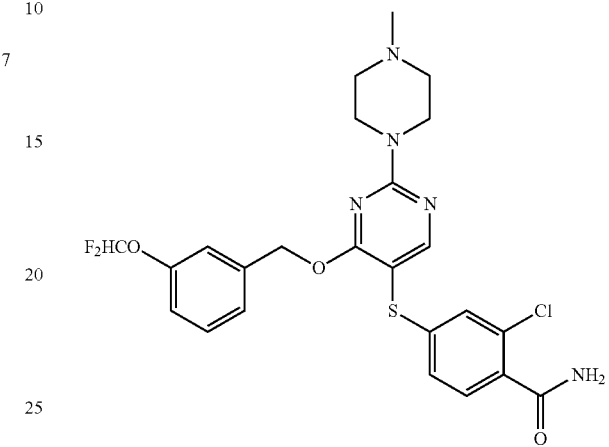

2-Chloro-4-((4-((3-(difluoromethoxy)benzyl)oxy)-2-(4-methylpiperazin-1-yl)pyrimidin-5-yl)thio)benzamide [121]. 121 was obtained in 46% yield following the general procedure above. $^1$H NMR (600 MHz, CDCl$_3$): δ 8.20 (s, 1H), 7.62 (d, J=8.2 Hz, 1H), 7.21 (t, J=7.9 Hz, 1H), 7.02 (d, J=1.8 Hz, 1H), 6.93-6.97 (m, 3H), 6.85-6.88 (m, 1H), 6.39 (t, J=73.7 Hz, 1H), 6.36 (br s, 1H), 5.77 (br s, 1H), 5.28 (s, 2H), 3.78-3.86 (m, 4H), 2.39-2.45 (m, 4H), 2.30 (s, 3H); HRMS (ESI) m/z [M+H]$^+$ calcd. for C$_{24}$H$_{24}$ClF$_2$N$_5$O$_3$S, 536.1335; found 536.1324.

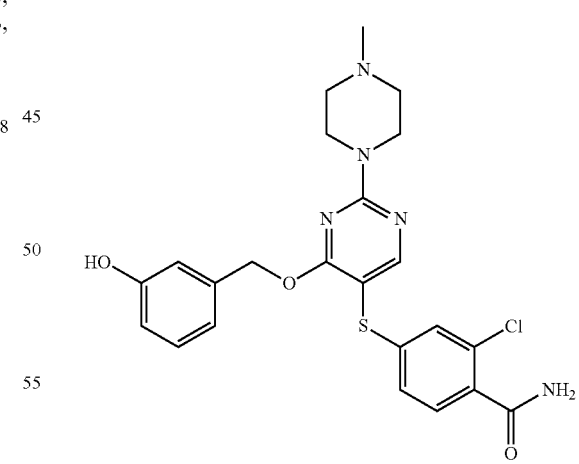

2-Chloro-4-((4-((3-hydroxybenzyl)oxy)-2-(4-methylpiperazin-1-yl)pyrimidin-5-yl)thio)benzamide [122]. 122 was obtained in 52% yield as a byproduct from the synthesis of 121. $^1$H NMR (600 MHz, CDCl$_3$): δ 8.18 (s, 1H), 7.44 (s, 1H), 7.08-7.11 (m, 1H), 7.04 (t, J=7.9 Hz, 1H), 6.94 (dd, J=8.2, 1.7 Hz, 1H), 6.66-6.70 (m, 2H), 6.39 (br s, 1H), 6.07-6.13 (m, 1H), 5.99 (d, J=1.7 Hz, 1H), 5.11 (s, 2H), 3.78-3.86 (m, 4H), 2.44-2.47 (m, 4H), 2.30 (s, 3H); $^{13}$C NMR (150 MHz, CDCl$_3$): δ 169.2, 167.9, 163.6, 161.6, 156.5, 143.5, 137.3, 131.0, 130.5, 130.1, 129.3, 128.0, 125.7, 120.1, 116.1, 114.8, 98.4, 68.2, 54.7, 46.1, 43.7; HRMS (ESI) m/z [M+H]$^+$ calcd. for C$_{23}$H$_{24}$ClN$_5$O$_3$S, 486.1367; found 486.1361.

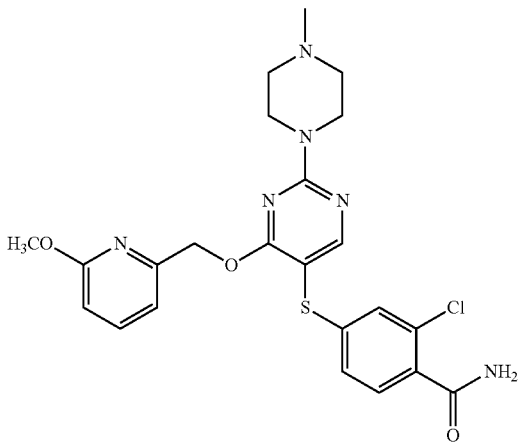

2-Chloro-4-((4-((6-methoxypyridin-2-yl)methoxy)-2-(4-methylpiperazin-1-yl)pyrimidin-5-yl)thio)benzamide [123]. 123 was obtained in 49% yield following the general procedure above. $^1$H NMR (600 MHz, CDCl$_3$): δ 8.20 (s, 1H), 7.62 (d, J=8.2 Hz, 1H), 7.37-7.42 (m, 1H), 7.04 (d, J=1.7 Hz, 1H), 7.00 (dd, J=8.2, 1.8 Hz, 1H), 6.57 (d, J=7.3 Hz, 1H), 6.53 (d, J=8.2 Hz, 1H), 6.38 (br s, 1H), 6.00 (br s, 1H), 3.76-3.83 (m, 7H), 2.36-2.41 (m, 4H), 2.28 (s, 3H); $^{13}$C NMR (150 MHz, CDCl$_3$): δ 168.5, 167.4, 165.2, 163.5, 161.7, 154.1, 144.1, 139.1, 131.4, 131.3, 129.8, 127.0, 124.6, 113.2, 109.4, 96.8, 68.3, 54.7, 53.4, 46.2, 43.8; HRMS (ESI) m/z [M+H]$^+$ calcd. for C$_{23}$H$_{25}$ClN$_6$O$_3$S, 501.1476; found 501.1472.

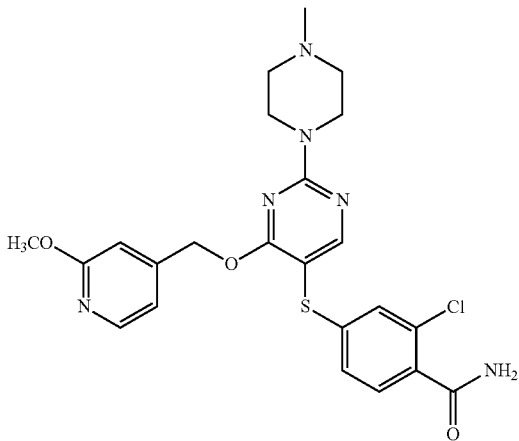

2-Chloro-4-((4-((2-methoxypyridin-4-yl)methoxy)-2-(4-methylpiperazin-1-yl)pyrimidin-5-yl)thio)benzamide [124]. 124 was obtained in 46% yield following the general procedure above. $^1$H NMR (600 MHz, CDCl$_3$): δ 8.21 (s, 1H), 7.99 (d, J=5.3 Hz, 1H), 7.63 (d, J=8.2 Hz, 1H), 7.04 (d, J=1.8 Hz, 1H), 6.99 (dd, J=8.2, 1.9 Hz, 1H), 6.60 (dd, J=5.3, 1.3 Hz, 1H), 6.44 (br s, 1H), 6.34 (s, 1H), 5.95 (br s, 1H), 5.23 (s, 2H), 3.83 (s, 3H), 3.79 (m, 4H), 2.40 (m, 4H), 2.28 (s, 3H); $^{13}$C NMR (150 MHz, CDCl$_3$): δ 168.1, 167.5, 165.1, 164.4, 161.6, 148.2, 147.0, 143.6, 131.5, 131.2, 130.2, 127.2, 124.7, 114.8, 108.4, 97.2, 66.0, 54.7, 53.5, 46.2, 43.9; HRMS (ESI) m/z [M+H]$^+$ calcd. for C$_{23}$H$_{25}$ClN$_6$O$_3$S, 501.1476; found 501.1462.

2-Chloro-4-((4-((5-methoxypyridin-3-yl)methoxy)-2-(4-methylpiperazin-1-yl)pyrimidin-5-yl)thio)benzamide [125]. 125 was obtained in 49% yield following the general procedure above. $^1$H NMR (600 MHz, CDCl$_3$): δ 8.22 (s, 1H), 8.08 (br s, 1H), 7.49 (br s, 2H), 7.42 (d, J=8.1 Hz, 1H), 7.00 (d, J=1.7 Hz, 1H), 6.95 (dd, J=8.1, 1.8 Hz, 1H), 6.91-6.93 (m, 1H), 5.94 (br s, 1H), 5.25 (s, 2H), 3.87-3.94 (m, 4H), 3.72 (s, 3H), 2.51-2.59 (m, 4H), 2.38 (s, 3H); $^{13}$C NMR (150 MHz, CDCl$_3$): δ 168.3, 167.8, 164.3, 161.4, 155.4, 142.4, 141.1, 136.5, 132.4, 131.8, 131.4, 130.2, 127.8, 125.4, 120.4, 98.9, 65.1, 55.6, 54.5, 45.8, 43.4; HRMS (ESI) m/z [M+H]$^+$ calcd. for C$_{23}$H$_{25}$ClN$_6$O$_3$S, 501.1476; found 501.1467.

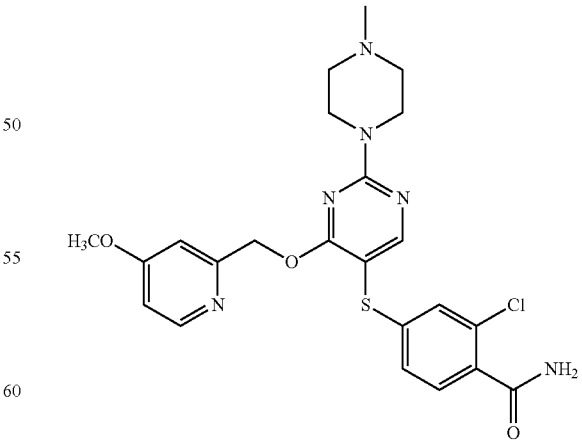

2-Chloro-4-((4-((4-methoxypyridin-2-yl)methoxy)-2-(4-methylpiperazin-1-yl)pyrimidin-5-yl)thio)benzamide [126]. 126 was obtained in 39% yield following the general procedure above. $^1$H NMR (600 MHz, CDCl$_3$): δ 8.25 (d, J=5.7

Hz, 1H), 8.22 (s, 1H), 7.63 (d, J=8.3 Hz, 1H), 7.09 (d, J=1.8 Hz, 1H), 7.01 (dd, J=8.3, 1.8 Hz, 1H), 6.61 (dd, J=5.8, 2.5 Hz, 1H), 6.52 (d, J=2.3 Hz, 1H), 6.40 (br s, 1H), 5.98 (br s, 1H), 5.36 (s, 2H), 3.81-3.92 (m, 4H), 3.65 (s, 3H), 2.45-2.55 (m, 4H), 2.35 (s, 3H); $^{13}$C NMR (150 MHz, CDCl$_3$): δ 167.3, 166.2, 165.4, 164.2, 160.6, 157.1, 149.3, 142.9, 130.5, 130.4, 128.9, 125.9, 123.4, 107.5, 105.6, 96.0, 67.3, 54.0, 53.5, 44.7, 42.3; HRMS (ESI) m/z [M+H]$^+$ calcd. for C$_{23}$H$_{25}$ClN$_6$O$_3$S, 501.1476; found 501.1487.

Example 14

Scheme 17. Synthesis of 127.

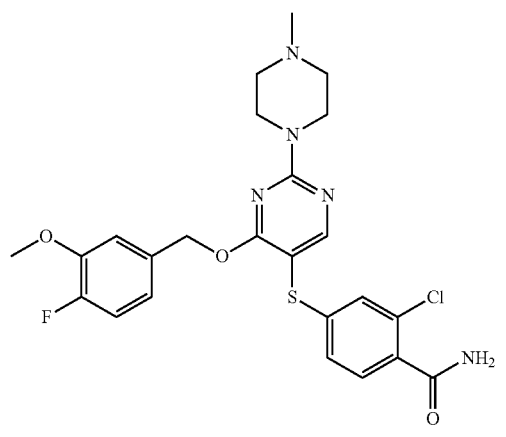

111

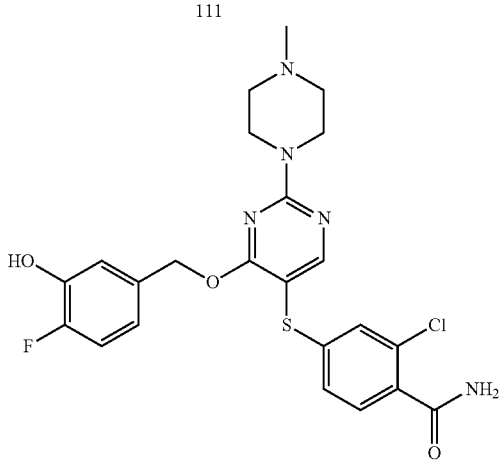

127

Reagents and conditions: a. BCl$_3$·S(CH$_3$)$_2$, 1,2-dichloroethane, 80° C., overnight.

2-Chloro-4-((4-((4-fluoro-3-hydroxybenzyl)oxy)-2-(4-methylpiperazin-1-yl)pyrimidin-5-yl)thio)benzamide [127]. A mixture of 111 (19 mg, 0.0367 mmol) and boron trichloride methyl sulfide complex (26 mg, 0.147 mmol) in 1,2-dichloroethane (1 mL) was heated at 80° C. overnight. Solvents were removed under reduced pressure and the resulting residue was purified by column chromatography (CH$_2$Cl$_2$:MeOH, 0-10% MeOH) to give 2.8 mg (15%) of 127. $^1$H NMR (600 MHz, CDCl$_3$): δ 8.25 (s, 1H), 7.55 (d, J=8.2 Hz, 1H), 7.12 (d, J=1.7 Hz, 1H), 7.01 (dd, J=8.2, 1.8 Hz, 1H), 6.91-6.96 (m, 1H), 6.66-6.70 (m, 1H), 6.41 (br s, 1H), 6.31 (d, J=8.3 Hz, 1H), 5.99 (br s, 1H), 5.17 (s, 2H), 3.86-3.93 (m, 4H), 2.48-2.52 (m, 4H), 2.36 (s, 3H); HRMS (ESI) m/z [M+H]$^+$ calcd. for C$_{23}$H$_{23}$ClFN$_5$O$_3$S, 504.1272; found 504.1263.

Example 15

Scheme 18. Synthesis of 131-139.

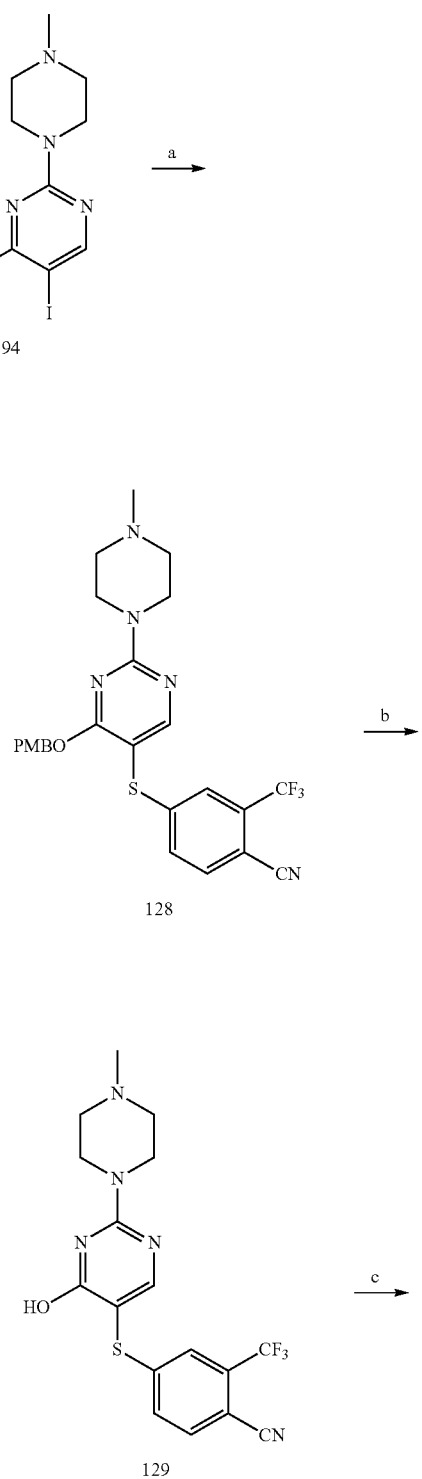

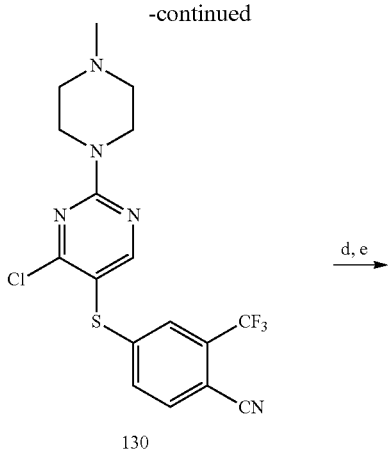

130

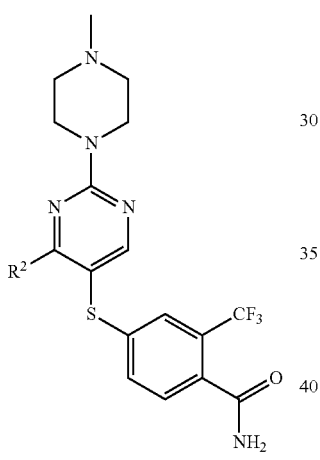

131-139

Reagents and conditions: a. 4-mercapto-2-(trifluoromethyl)benzonitrile, copper(I)thiophene-2-carboxylate, K₂CO₃, DMF, 120° C., 23 h; b. TFA, CH₂Cl₂, rt, 5 h; c. POCl₃, 75° C., 1 h; d. ROH, NaH, CH₃CN, rt, 3 h; e. KOH, t-BuOH, 80° C., 1 h.

4-((4-((4-Methoxybenzyl)oxy)-2-(4-methylpiperazin-1-yl)pyrimidin-5-yl)thio)-2-(trifluoromethyl)benzonitrile [128]. A mixture of 94 (1.5 g, 3.4 mmol) and K₂CO₃ (1.41 g, 10.2 mmol) in DMF (44 mL) was evacuated and backfilled with argon three times. Copper(I)thiophene-2-carboxylate (0.259 g, 1.36 mmol) was added and evacuated and backfilled with argon two times. 4-Mercapto-2-(trifluoromethyl)benzonitrile (0.829 g, 4.08 mmol) was added and the reaction mixture was heated at 120° C. for 23 h. Solvent was removed under reduced pressure and the residue was purified by column chromatography (CH₂Cl₂:MeOH, 0-10% MeOH) to afford 1.66 g (95%) of 128. ¹H NMR (600 MHz, CDCl₃): δ 8.29 (s, 1H), 7.57 (d, J=8.2 Hz, 1H), 7.44 (s, 1H), 7.19 (d, J=8.2 Hz, 1H), 7.08 (d, J=8.5 Hz, 2H), 6.82 (d, J=8.6 Hz, 2H), 5.31 (s, 2H), 3.70-3.88 (m, 7H), 2.73 (m, 4H), 1.60 (s, 3H); MS (ESI) m/z 516.2 [M+H]⁺.

4-((4-Hydroxy-2-(4-methylpiperazin-1-yl)pyrimidin-5-yl)thio)-2-(trifluoromethyl)benzonitrile [129]. To a solution of 128 (1.66 g, 3.2 mmol) in CH₂Cl₂ (15 mL) was added TFA (15 mL) dropwise over 5 minutes and stirred at rt for 5 h. The reaction mixture was concentrated under reduced pressure to give a residue which was purified by column chromatography (CH₂Cl₂:MeOH, 0-20% MeOH) to afford 1.21 g (95%) of 129. ¹H NMR (500 MHz, CDCl₃/MeOH-d₄): δ 8.11 (s, 1H), 7.64 (d, J=8.2 Hz, 1H), 7.48 (d, J=2.7 Hz, 1H), 7.34 (dd, J=8.2, 1.6 Hz, 1H), 3.91 (m, 4H), 2.73 (m, 4H), 2.54 (s, 1H); MS (ESI) m/z 396.1 [M+H]⁺.

4-((4-Chloro-2-(4-methylpiperazin-1-yl)pyrimidin-5-yl)thio)-2-(trifluoromethyl)benzonitrile [130]. 129 (0.826 g, 2.09 mmol) and POCl₃ (5 mL) were heated at 75° C. for 1 h. After cooling to rt, the reaction mixture was added to a beaker containing ice chips. Following complete quenching of POCl₃, solid Na₂CO₃ was carefully added until pH ~9. This was transferred to a seperatory funnel and extracted with CH₂Cl₂ (3×100 mL), dried over MgSO₄, filtered and concentrated to a give 0.707 g (82%) of 130 which was used without further purification. ¹H NMR (500 MHz, CDCl₃): δ 8.36 (s, 1H), 7.61 (d, J=8.2 Hz, 1H), 7.39 (s, 1H), 7.17 (d, J=8.2 Hz, 1H), 3.90 (m, 4H), 2.59 (m, 4H), 1.48 (s, 3H); MS (ESI) m/z 414.1 [M+H]⁺.

General Procedure for Synthesis of 131-139. To alcohol (4.25 equiv.) dissolved in CH₃CN was added NaH (4 equiv.) and the resulting suspension was stirred for 10 min. at rt. Then 130 (1 equiv.) was added and the reaction mixture was stirred at rt for 3 h. Solvent was removed under reduced pressure and the residue was purified by column chromatography to afford intermediate nitrile. A mixture of the nitrile (1 equiv.) and KOH (25 equiv.) in t-BuOH was heated at 80° C. for 1 h. Solvent was removed under reduced pressure and the residue was purified by preparatory TLC to afford the desired amide.

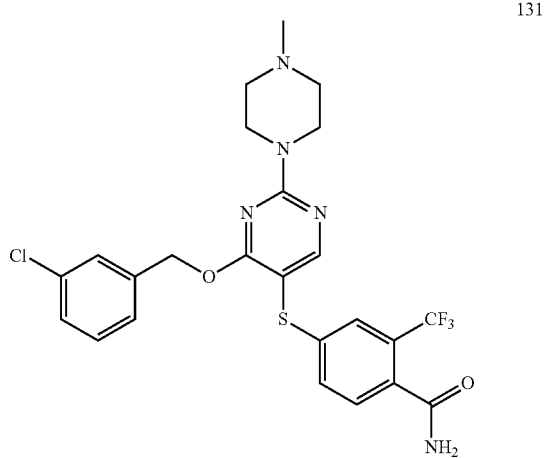 [SMILES: CN1CCN(c2ncc(Sc3ccc(C(N)=O)c(C(F)(F)F)c3)c(OCc3cccc(Cl)c3)n2)CC1]

131

4-((4-((3-Chlorobenzyl)oxy)-2-(4-methylpiperazin-1-yl)pyrimidin-5-yl)thio)-2-(trifluoromethyl)benzamide [131]. 131 was obtained in 47% yield following the general procedure above. ¹H NMR (600 MHz, CDCl₃): δ 8.21 (s, 1H), 7.36-7.39 (m, 2H), 7.13-7.17 (m, 3H), 7.07 (s, 1H), 6.95-6.98 (m, 1H), 5.87 (br s, 1H), 5.73 (br s, 1H), 5.24 (s, 2H), 3.82-3.97 (m, 4H), 2.47-2.60 (m, 4H), 2.37 (s, 3H); ¹³C NMR (150 MHz, CDCl₃): δ 169.1, 168.4, 165.0, 161.5, 141.9, 138.2, 134.2, 131.6, 129.9, 129.21, 129.18, 128.1, 127.8 (d, J=31.9 Hz), 127.5, 125.4, 123.9 (q, J=5.2 Hz), 123.2 (q, J=272.4 Hz), 97.5, 67.1, 54.5, 45.7, 43.4; HRMS (ESI) m/z [M+H]⁺ calcd. for C₂₄H₂₃ClF₃N₅O₂S, 538.1291; found 538.1287.

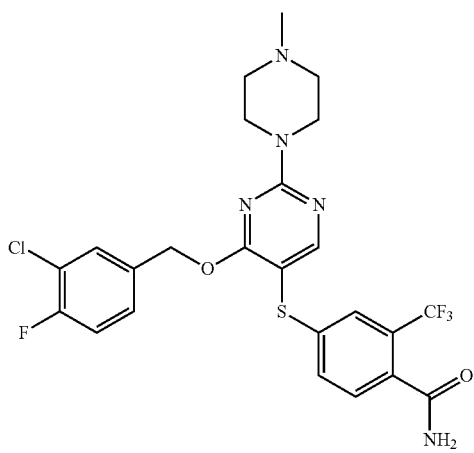

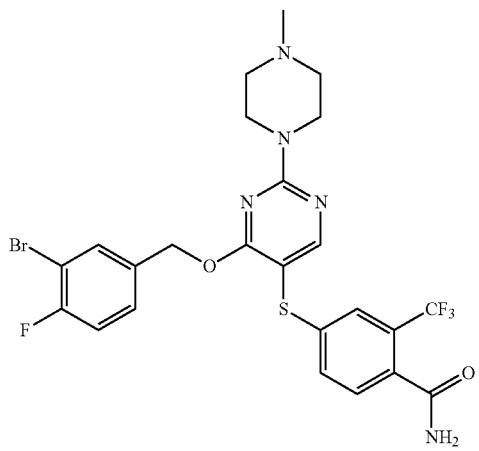

4-((4-((3-Chloro-4-fluorobenzyl)oxy)-2-(4-methylpiperazin-1-yl)pyrimidin-5-yl)thio)-2-(trifluoromethyl)benzamide [132]. 132 was obtained in 48% yield following the general procedure above. ¹H NMR (600 MHz, CDCl₃): δ 8.21 (s, 1H), 7.34-7.39 (m, 2H), 7.13-7.17 (m, 2H), 6.98-7.02 (m, 1H), 6.93-6.97 (m, 1H), 5.91 (br s, 1H), 5.73 (br s, 1H), 5.21 (s, 2H), 3.83-3.98 (m, 4H), 2.48-2.64 (m, 4H), 2.37 (s, 3H); ¹³C NMR (150 MHz, CDCl₃): δ 169.1, 168.3, 165.1, 161.5, 158.5, 156.9, 141.9, 133.2 (d, J=3.9 Hz), 131.6, 129.8, 129.2, 127.6 (q, J=32.0 Hz), 127.3 (d, J=7.2 Hz), 123.9 (q, J=5.2 Hz), 123.2 (q, J=272.3 Hz), 120.9 (d, J=17.8 Hz), 116.7 (d, J=21.0 Hz), 97.4, 66.6, 54.5, 45.8, 43.4; HRMS (ESI) m/z [M+H]⁺ calcd. for C₂₄H₂₂ClF₄N₅O₂S, 556.1197; found 556.1200.

4-((4-((3-Bromo-4-fluorobenzyl)oxy)-2-(4-methylpiperazin-1-yl)pyrimidin-5-yl)thio)-2-(trifluoromethyl)benzamide [134]. 134 was obtained in 51% yield following the general procedure above. ¹H NMR (600 MHz, CDCl₃): δ 8.21 (s, 1H), 7.38 (d, J=8.1 Hz, 1H), 7.35 (d, J=1.4 Hz, 1H), 7.33 (dd, J=6.7, 1.7 Hz, 1H), 7.14 (dd, J=8.1, 1.6 Hz, 1H), 6.96-7.01 (m, 2H), 5.89 (br s, 1H), 5.73 (br s, 1H), 5.21 (s, 2H), 3.83-4.02 (m, 4H), 2.49-2.67 (m, 4H), 2.40 (s, 3H); ¹³C NMR (150 MHz, CDCl₃): δ 169.1, 168.3, 165.1, 161.5, 159.5, 157.9, 141.8, 133.6 (d, J=3.8 Hz), 132.7, 131.6, 129.2 (d, J=5.1 Hz), 128.1 (d, J=7.3 Hz), 127.8 (q, J=32.0 Hz), 123.9 (q, J=5.2 Hz), 123.2 (q, J=272.3 Hz), 116.6 (d, J=22.4 Hz), 108.9 (d, J=21.3 Hz), 97.5, 66.6, 54.4, 45.7, 43.3; HRMS (ESI) m/z [M+H]⁺ calcd. for C₂₄H₂₂BrF₄N₅O₂S, 600.0692; found 600.0697.

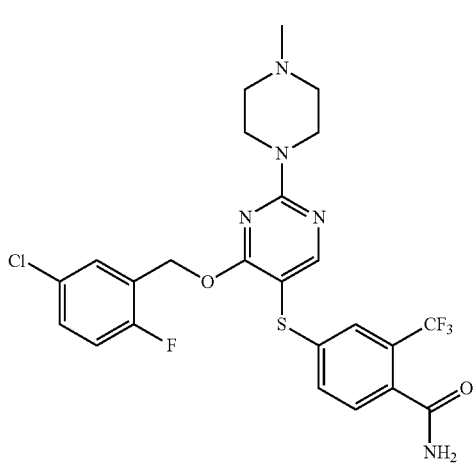

4-((4-((5-Chloro-2-fluorobenzyl)oxy)-2-(4-methylpiperazin-1-yl)pyrimidin-5-yl)thio)-2-(trifluoromethyl)benzamide [133]. 133 was obtained in 53% yield following the general procedure above. ¹H NMR (500 MHz, CDCl₃): δ 8.22 (s, 1H), 7.36-7.42 (m, 2H), 7.12-7.18 (m, 2H), 7.01-7.05 (m, 1H), 6.87-6.93 (m, 1H), 5.90 (br s, 1H), 5.73 (br s, 1H), 5.30 (s, 2H), 3.88-4.06 (m, 4H), 2.55-2.72 (m, 4H), 2.43 (s, 3H); HRMS (ESI) m/z [M+H]⁺ calcd. for C₂₄H₂₂ClF₄N₅O₂S, 556.1197; found 556.1199.

4-((4-((2,4-Difluorobenzyl)oxy)-2-(4-methylpiperazin-1-yl)pyrimidin-5-yl)thio)-2-(trifluoromethyl)benzamide [135]. 135 was obtained in 57% yield following the general procedure above. ¹H NMR (600 MHz, CDCl₃): δ 8.20 (s, 1H), 7.33-7.37 (m, 2H), 7.14-7.18 (m, 1H), 6.98-7.04 (m, 1H), 6.67-6.75 (m, 2H), 5.87 (br s, 1H), 5.71 (br s, 1H), 5.29 (s, 2H), 3.80-4.05 (m, 4H), 2.46-2.68 (m, 4H), 2.38 (3, 3H); ¹³C NMR (150 MHz, CDCl₃): δ 169.1, 168.3, 165.0, 162.8 (dd, J=248.3, 11.9 Hz), 161.5, 160.6 (dd, J=248.9, 12.0 Hz), 141.9, 131.6, 130.7 (dd, J=9.7, 5.4 Hz), 129.5, 129.1, 127.7

(q, J=31.9 Hz), 124.2 (q, J=5.1 Hz), 123.2 (q, J=272.3 Hz), 119.3 (dd, J=14.5, 3.8 Hz), 111.5 (dd, J=21.1, 3.5 Hz), 103.8 (t, J=25.4 Hz), 97.7, 61.2, 54.5, 45.7, 43.3; HRMS (ESI) m/z [M+H]+ calcd. for $C_{24}H_{22}F_5N_5O_2S$, 540.1493; found 540.1476.

7.10 (dd, J=8.1, 1.7 Hz, 1H), 7.34 (d, J=8.2 Hz, 1H), 7.41 (d, J=1.7 Hz, 1H), 8.27 (s, 1H); 13C NMR (150 MHz, CDCl3) δ 43.9, 46.2, 54.9, 56.5, 67.6, 97.2, 113.4, 116.1, 120.6, 123.9, 127.9, 128.9, 129.2, 131.7, 132.7, 142.3, 147.6, 151.5, 53.1, 161.9, 165.3, 168.7, 169.3; HRMS (ESI) m/z [M+H]+ calcd. for $C_{25}H_{26}F_4N_5O_3S$ 552.1692; found 552.1687.

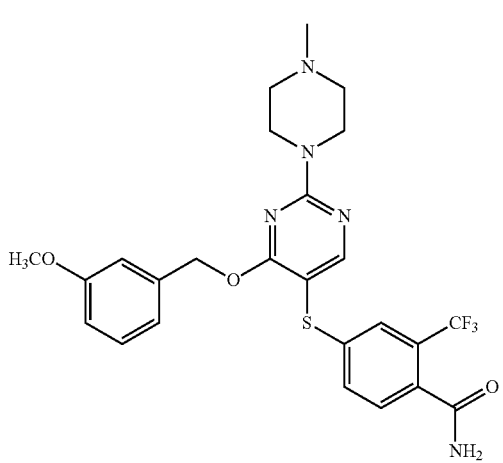

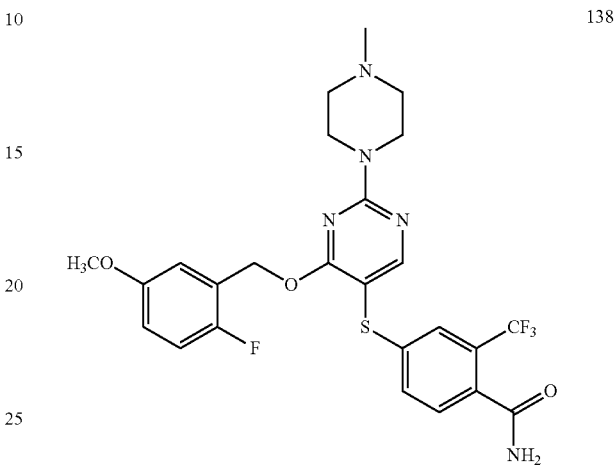

4-((4-((3-Methoxybenzyl)oxy)-2-(4-methylpiperazin-1-yl)pyrimidin-5-yl)thio)-2-(trifluoromethyl)benzamide [136]. 136 was obtained in 52% yield following the general procedure above. 1H NMR (600 MHz, CDCl3): δ 8.20 (s, 1H), 7.38 (d, J=1.4 Hz, 1H), 7.30 (d, J=8.1 Hz, 1H), 7.11-7.15 (m, 1H), 7.09 (dd, J=8.1, 1.5 Hz, 1H), 6.68-6.74 (m, 2H), 6.49 (s, 1H), 5.92 (br s, 1H), 5.87 (br s, 1H), 5.24 (s, 2H), 3.82-3.97 (m, 4H), 3.64 (s, 3H), 2.46-2.58 (m, 4H), 2.36 (s, 3H); 13C NMR (150 MHz, CDCl3): δ 169.3, 168.4, 164.8, 161.6, 159.4, 142.5, 137.7, 131.5, 129.5, 129.1, 129.0, 127.7 (q, J=32.0 Hz), 124.0 (q, J=5.2 Hz), 123.2 (q, J=272.4 Hz), 119.9, 113.5, 113.1, 97.6, 67.8, 55.2, 54.5, 45.8, 43.5; HRMS (ESI) m/z [M+H]+ calcd. for $C_{25}H_{26}F_3N_5O_3S$, 534.1787; found 534.1787.

4-((4-((2-Fluoro-5-methoxybenzyl)oxy)-2-(4-methylpiperazin-1-yl)pyrimidin-5-yl)thio)-2-(trifluoromethyl)benzamide [138]. 138 was obtained in 60% yield following the general procedure above. 1H NMR (600 MHz, CDCl3): δ 8.21 (s, 1H), 7.39 (d, J=1.6 Hz, 1H), 7.32 (d, J=8.1 Hz, 1H), 7.10 (dd, J=8.1, 1.7 Hz, 1H), 6.86 (m, 1H), 6.65-6.69 (m, 1H), 6.41-6.44 (m, 1H), 5.93 (br s, 1H), 5.88 (br s, 1H), 5.30 (s, 2H), 3.90 (m, 4H), 3.59 (s, 3H), 2.53 (s, 4H), 2.37 (s, 3H); HRMS (ESI) m/z [M+H]+ calcd. for $C_{25}H_{25}F_4N_5O_3S$, 552.1692; found 552.1699.

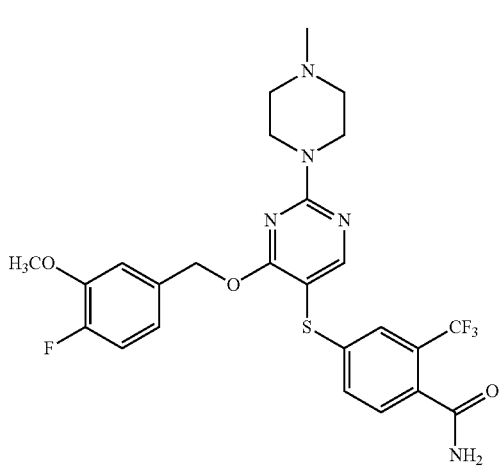

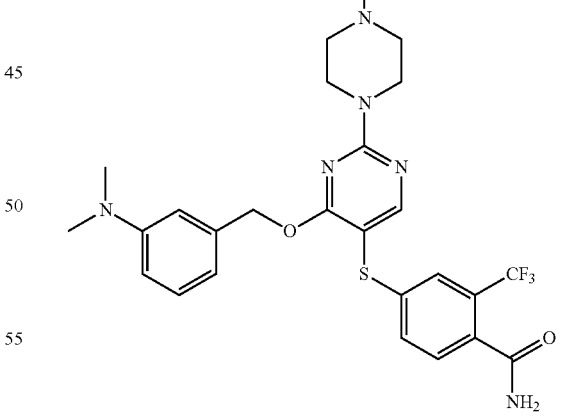

4-((4-((4-Fluoro-3-methoxybenzyl)oxy)-2-(4-methylpiperazin-1-yl)pyrimidin-5-yl)thio)-2-(trifluoromethyl)benzamide [137]. 137 was obtained in 63% yield following the general procedure above. 1H NMR (600 MHz, CDCl3) δ 2.40 (s, 3H), 2.54 (m, 4H), 3.72 (s, 3H), 3.94 (m, 4H), 5.31 (s, 2H), 5.95 (bs, 2H), 6.74-6.77 (m, 2H), 6.97-7.00 (m, 1H), 4-((4-((3-(Dimethylamino)benzyl)oxy)-2-(4-methylpiperazin-1-yl)pyrimidin-5-yl)thio)-2-(trifluoromethyl)benzamide [139]. 139 was obtained in 68% yield following the general procedure above. 1H NMR (600 MHz, CDCl3): δ 8.18 (s, 1H), 7.37 (d, J=1.5 Hz, 1H), 7.24 (d, J=8.1 Hz, 1H), 7.05-7.09 (m, 1H), 7.03 (dd, J=8.1, 1.6 Hz, 1H), 6.56-6.59 (m, 1H), 6.47-6.52 (m, 2H), 5.88 (br s, 1H), 5.84 (br s, 1H), 5.26 (s, 2H), 3.83-3.96 (m, 4H), 2.76 (s, 6H), 2.45-2.55 (m, 4H), 2.35 (s, 3H); FIRMS (ESI) m/z [M+H]+ calcd. for $C_{26}H_{29}F_3N_6O_2S$, 547.2103; found 547.2090.

Example 16

Scheme 19. Synthesis of 141.

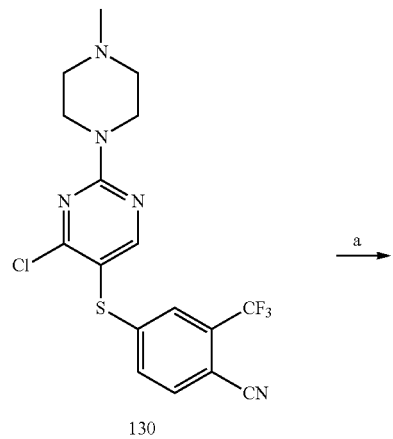

Reagents and conditions: a. 3-chlorobenzylamine, CH$_3$CN, 75° C., 3 h; b. KOH, t-BuOH, 80° C., 1 h.

4-((4-((3-Chlorobenzyl)amino)-2-(4-methylpiperazin-1-yl)pyrimidin-5-yl)thio)-2-(trifluoromethyl)benzamide [140]. A solution of 130 (15 mg, 0.036245 mmol), 3-chlorobenzylamine (22.1 µL, 0.181 mmol) in CH$_3$CN (500 µL) was heated at 75° C. for 3 h. The reaction mixture was concentrated under reduced pressure to give a residue which was purified by preparatory TLC (CH$_2$Cl$_2$:MeOH—NH$_3$ (7 N), 10:1) to afford 6 mg (32%) of 140. $^1$H NMR (500 MHz, CDCl$_3$/MeOH-d$_4$): δ 8.00 (s, 1H), 7.58 (d, J=8.3 Hz, 1H), 7.42 (d, J=1.3 Hz, 1H), 7.11-7.19 (m, 3H), 7.07 (s, 1H), 6.95-7.00 (m, 1H), 5.90 (t, J=5.9 Hz, 1H), 4.50 (d, J=5.9 Hz, 2H), 3.75-3.89 (m, 4H), 2.40-2.45 (m, 4H), 2.29 (s, 3H); MS (ESI) m/z 519.1 [M+H]+.

4-((4-((3-Chlorobenzyl)amino)-2-(4-methylpiperazin-1-yl)pyrimidin-5-yl)thio)-2-(trifluoromethyl)benzamide [141]. A mixture of 140 (6 mg, 0.0116 mmol) and KOH (49 mg, 0. mmol) in t-BuOH (400 µL) was heated at 80° C. for 1 h. Solvent was removed under reduced pressure and the residue was purified by preparatory TLC (CH$_2$Cl$_2$:MeOH—NH$_3$ (7 N), 10:1) to afford 4.6 mg (74%) of 141. $^1$H NMR (600 MHz, CDCl$_3$): δ 8.05 (s, 1H), 7.43 (d, J=8.1 Hz, 1H), 7.36 (d, J=1.3 Hz, 1H), 7.11-7.16 (m, 3H), 7.07 (s, 1H), 6.95-6.99 (m, 1H), 5.90-5.95 (t, J=5.5 Hz, 1H), 5.78 (br s, 1H), 5.72 (br s, 1H), 4.49 (d, J=5.9 Hz, 2H), 3.99 (m, 4H), 2.72 (m, 4H), 2.52 (s, 3H); HRMS (ESI) m/z [M+H]+ calcd. for $C_{24}H_{24}ClF_3N_6OS$, 537.1451; found 537.1459.

Example 17

Scheme 20. Synthesis of 146c, e, g, h.

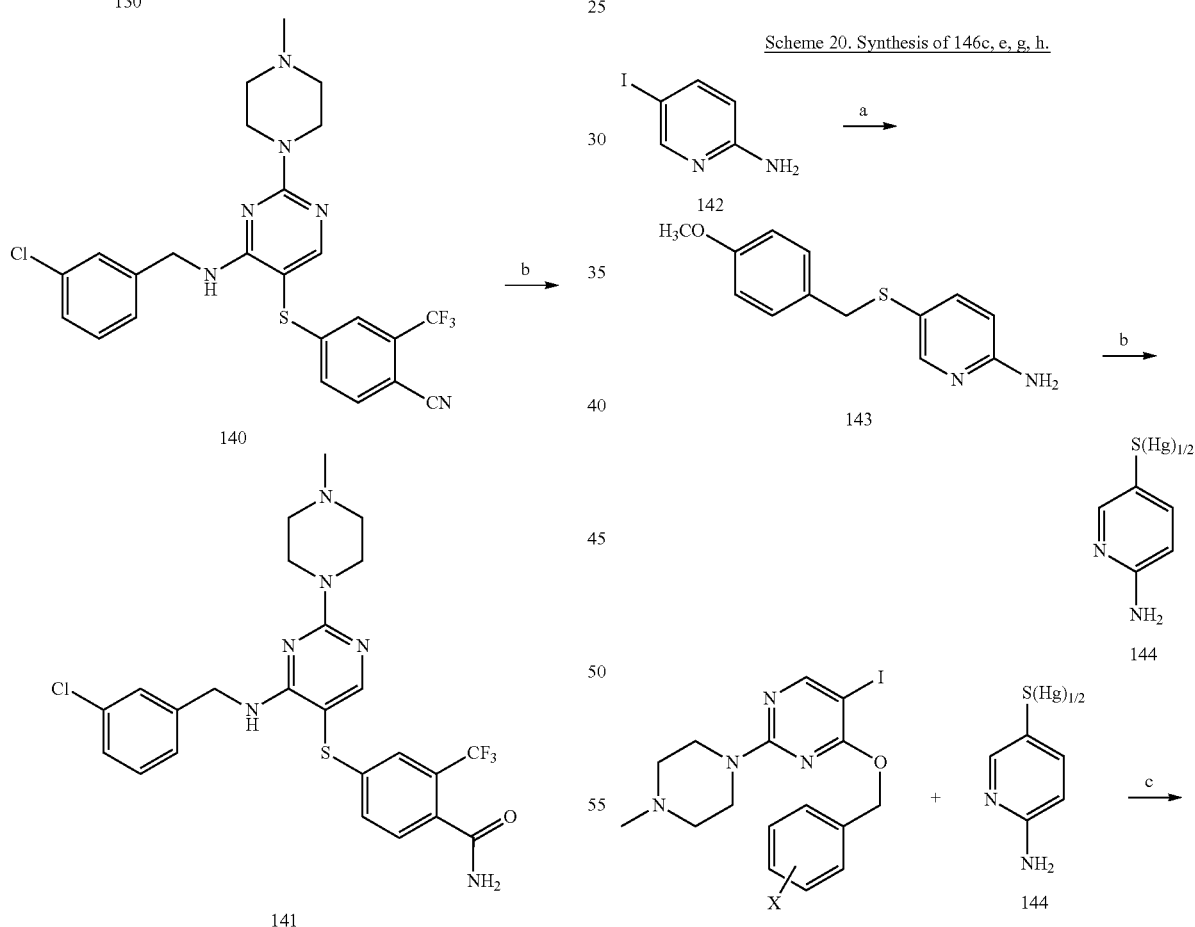

145c YK232 4-F
145e YK234 3-CF$_3$
145g YK244 3, 4-F
145h YK245 3, 5-CF$_3$

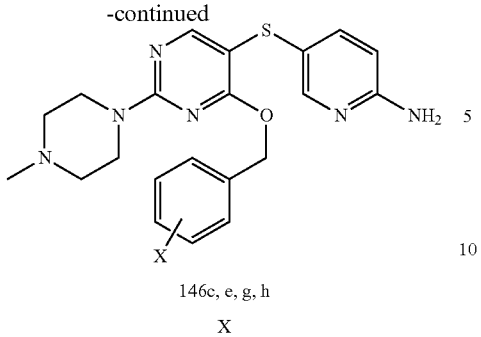

146c, e, g, h

| X | | |
|---|---|---|
| 146c | YK232 | 4-F |
| 146e | YK234 | 3-CF₃ |
| 146g | YK244 | 3, 4-F |
| 146h | YK245 | 3, 5-CF₃ |

Reagents and conditions: a. (4-methoxyphenyl)methanethiol, CuI, neocuproine, K₂CO₃, DMF, 135° C., 18 h; b. HgO, TFA, 60° C., 1 h; c. CuI, neocuproine, K₂CO₃, DMF, 140° C., 1 h.

5-((4-Methoxybenzyl)thio)pyridin-2-amine [143]. A mixture of 142 (0.220 g, 1.0 mmol), K₂CO₃ (0.552 g, 4.0 mmol), CuI (0.078 g, 0.4 mmol) and neocuproine (0.090 g, 0.4 mmol) in DMF (5 mL) was evacuated and backfilled with argon three times. (4-methoxyphenyl)methanethiol (0.185 g, 1.2 mmol) was added and the reaction mixture was heated at 135° C. for 18 h. Solvent was removed under reduced pressure and the residue was purified by column chromatography (CH₂Cl₂:MeOH, 0-10% MeOH) to afford 185 mg (75%) of 143. MS (m/z): [M+H]⁺ 247.1.

Bis((6-aminopyridin-3-yl)thio)mercury [144]. To a solution of 143 (1.0 g, 4.1 mmol) in TFA (10 mL) was added HgO (0.45 g, 2.05 mmol) and the mixture was heated to 60° C. for 1 h. The reaction mixture was concentrated under reduced pressure and the resulting residue was purified by column chromatography (CH₂Cl₂:MeOH, 9:1) to afford 0.85 g (92%) of 144.

General Procedure for the Synthesis of 146c/e/g/h. A mixture of 145c/e/g/h (1 equiv.), 144 (1.2 equiv.), K₂CO₃ (4 equiv.), CuI (1.0 equiv.) and neocuproine (0.2 equiv.) in DMF was heated at 140° C. for 1 h under argon. The reaction mixture was concentrated under reduced pressure and purified by preparatory TLC.

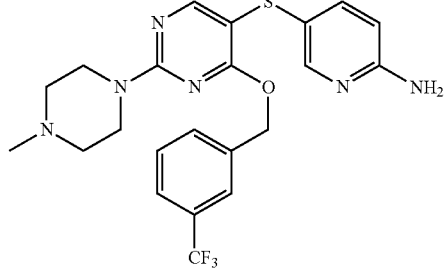

5-((2-(4-Methylpiperazin-1-yl)-4-((3-(trifluoromethyl) benzyl)oxy)pyrimidin-5-yl)thio)pyridin-2-amine [146e]. 146e was obtained in 52% yield following the general procedure above. ¹H NMR (600 MHz, CDCl₃): δ 8.17 (s, 1H), 8.07 (s, 1H), 7.57 (d, J=7.6 Hz, 1H), 7.40 (t, J=7.5 Hz, 1H), 7.37 (dd, J=8.6, 2.3 Hz, 1H), 7.28-7.32 (m, 2H), 6.31 (d, J=8.5 Hz, 1H), 5.32 (s, 2H), 4.39 (s, 2H), 3.67-3.70 (m, 4H), 2.28-2.33 (m, 4H), 2.24 (s, 3H); ¹³C NMR (150 MHz, CDCl₃): δ 167.5, 162.8, 160.9, 157.5, 151.1, 141.5, 135.4, 132.1, 128.0, 127.5, 126.9, 125.7, 120.7, 108.8, 63.6, 54.7, 46.2, 43.8; MS (m/z): [M+H]⁺ 477.0.

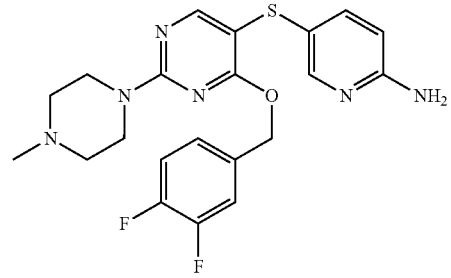

5-((4-((3,4-Difluorobenzyl)oxy)-2-(4-methylpiperazin-1-yl)pyrimidin-5-yl)thio)pyridin-2-amine [146g]. 146g was obtained in 68% yield following the general procedure above. MS (m/z): [M+H]⁺ 444.9.

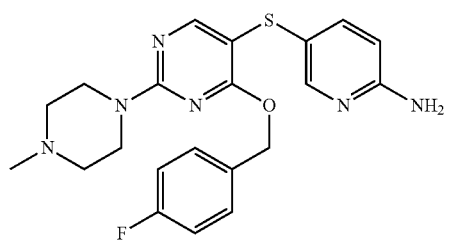

5-((4-((4-Fluorobenzyl)oxy)-2-(4-methylpiperazin-1-yl) pyrimidin-5-yl)thio)pyridin-2-amine [146c]. 146c was obtained in 63% yield following the general procedure above. ¹H NMR (500 MHz, CDCl₃): δ 8.13 (s, 1H), 8.03 (s, 1H), 7.30 (dd, J=8.5, 1.8 Hz, 1H), 7.15-7.19 (m, 2H), 6.92-6.95 (m, 2H), 6.26 (d, J=8.5 Hz, 1H), 5.24 (s, 2H), 4.38 (s, 2H), 3.74-3.76 (m, 4H), 2.27-2.39 (m, 4H), 2.27 (s, 3H); MS (m/z): [M+H]⁺ 427.0.

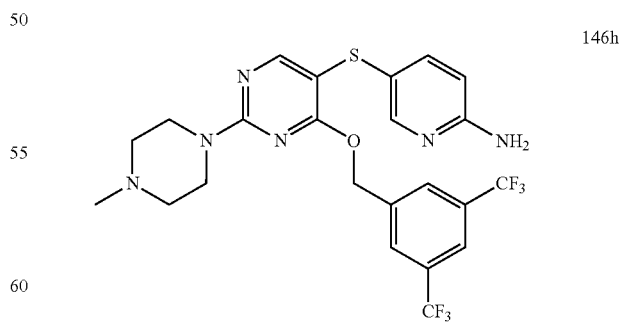

5-((4-((3,5-Bis(trifluoromethyl)benzyl)oxy)-2-(4-methylpiperazin-1-yl)pyrimidin-5-yl)thio)pyridin-2-amine [146h]. 146h was obtained in 47% yield following the general procedure above. MS (m/z): [M+H]⁺ 545.0.

Example 18

Scheme 21. Synthesis of 151-158.

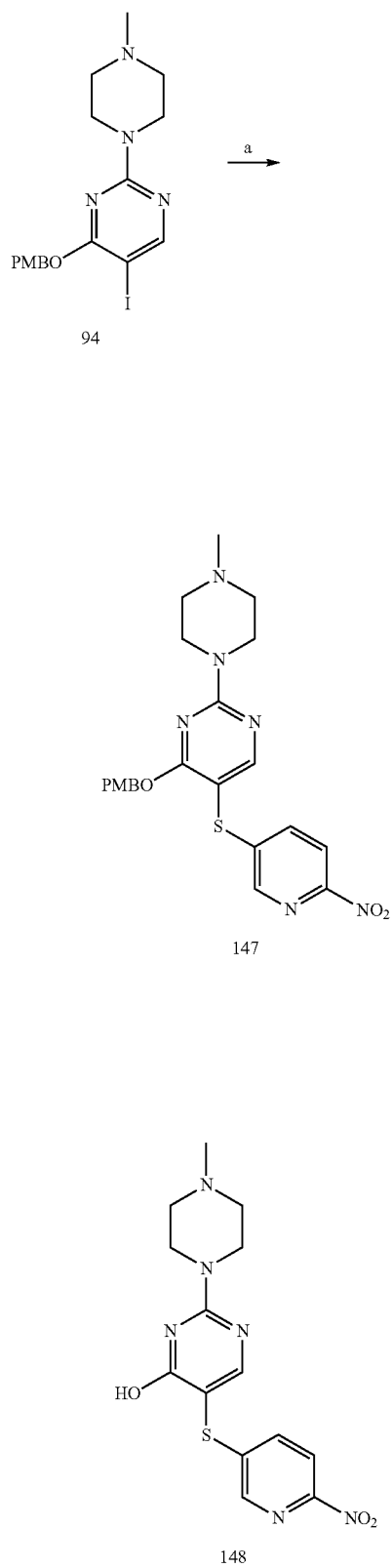

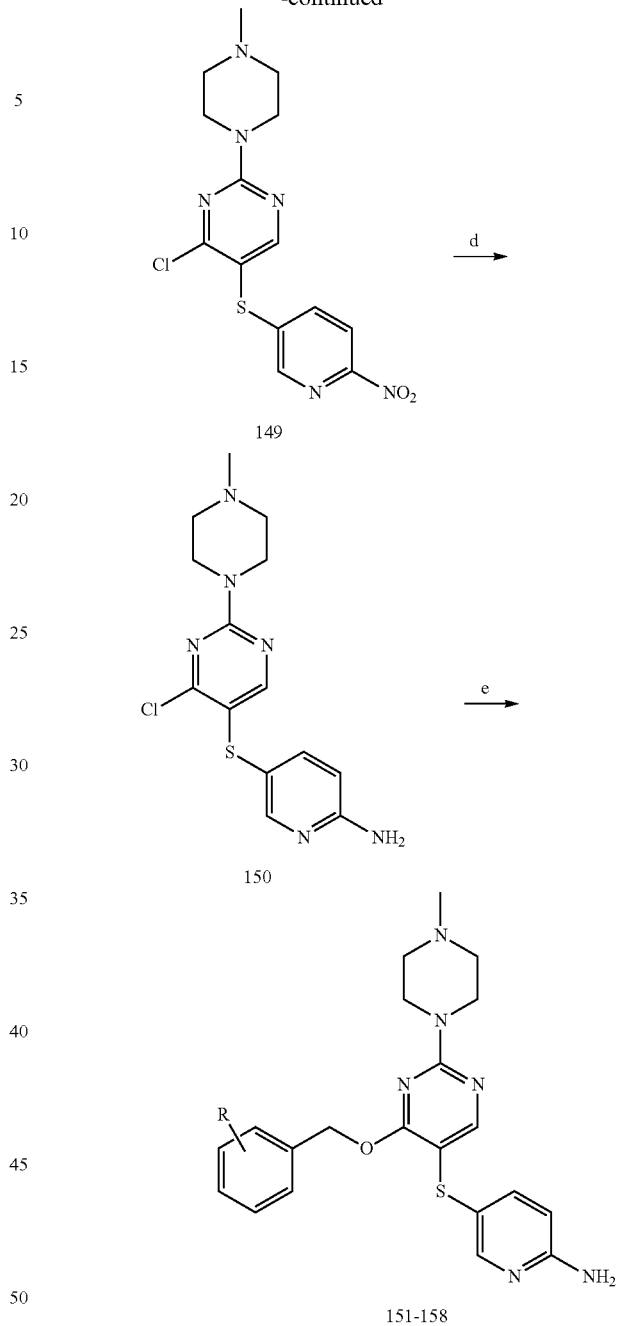

Reagents and conditions: a. 6-Nitropyridine-3-thiol, Copper(I)thiophene-2-carboxylate, K₂CO₃, DMF, 130° C., 3 h; b. TFA, CH₂Cl₂, rt, overnight; c. POCl₃, 80° C., 1 h; d. iron, AcOH, rt, 2 h; e. ROH, NaH, CH₃CN, rt, 3 h.

4-((4-Methoxybenzyl)oxy)-2-(4-methylpiperazin-1-yl)-5-((6-nitropyridin-3-yl)thio)pyrimidine [147]. A mixture of 94 (0.760 g, 1.726 mmol) and K₂CO₃ (0.714 g, 5.178 mmol) in DMF (20 mL) was evacuated and backfilled with argon three times. Copper(I)thiophene-2-carboxylate (0.132 g, 0.690 mmol) was added and evacuated and backfilled with argon two times. 6-Nitropyridine-3-thiol (0.350 g, 2.24 mmol) was added and the reaction mixture was heated at 130° C. for 3 h. Solvent was removed under reduced pressure and the residue was purified by column chromatography (CH₂Cl₂:MeOH, 0-10% MeOH) to afford 0.600 g (74%) of 147. MS (m/z): [M+H]⁺ 469.0.

2-(4-Methylpiperazin-1-yl)-5-((6-nitropyridin-3-yl)thio)pyrimidin-4-ol [148]. To a solution of 147 (0.600 g, 1.28 mmol) in CH$_2$Cl$_2$ (10 mL) was added TFA (1 mL) dropwise over 5 minutes and stirred at rt for overnight. The reaction mixture was concentrated under reduced pressure to give a residue which was purified by column chromatography (CH$_2$Cl$_2$:MeOH, 0-20% MeOH) to afford 0.280 g (63%) of 148. $^1$H NMR (500 MHz, DMSO-d$_6$): δ 8.37 (d, J=2.4 Hz, 1H), 8.22 (s, 1H), 8.19 (d, J=8.7 Hz, 1H), 7.80 (dd, J=8.6, 2.5 Hz, 1H), 3.25-3.28 (m, 4H), 2.78 (s, 3H), 2.49-2.51 (m, 4H); MS (m/z): [M+H]$^+$ 349.1.

4-Chloro-2-(4-methylpiperazin-1-yl)-5-((6-nitropyridin-3-yl)thio)pyrimidine [149]. 148 (0.240 g, 0.69 mmol) and POCl$_3$ (5 mL) were heated at 80° C. for 1 h. After cooling to rt, the reaction mixture was added to a beaker containing ice chips. Following complete quenching of POCl$_3$, solid Na$_2$CO$_3$ was carefully added until pH ~9. This was transferred to a separatory funnel and extracted with CH$_2$Cl$_2$ (3×75 mL), dried over MgSO$_4$, filtered and concentrated to a give 0.180 g (71%) of 149 which was used without further purification. MS (ESI) m/z [M+H]$^+$ 367.1.

5-((4-Chloro-2-(4-methylpiperazin-1-yl)pyrimidin-5-yl)thio)pyridin-2-amine [150]. A mixture of 149 (140 mg, 0.382 mmol), iron (10 mg, 0.179 mmol) in AcOH (1 mL) was stirred at rt for 2 h. The reaction mixture was concentrated under reduced pressure to give a residue which was purified by column chromatography (CH$_2$Cl$_2$:MeOH, 0-10% MeOH) to afford 70 mg (54%) of 150. MS (ESI) m/z [M+H]$^+$ 337.1.

General Procedure for Synthesis of 151-158. To alcohol (4.25 equiv.) dissolved in CH$_3$CN was added NaH (4 equiv.) and the resulting suspension was stirred for 10 min. at rt. Then 150 (1 equiv.) was added and the reaction mixture was stirred at rt for 3 h. Solvent was removed under reduced pressure and the residue was purified by preparatory TLC to afford the desired product.

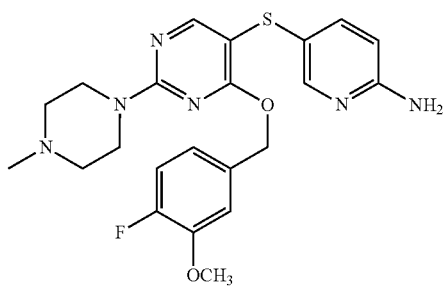

151

5-((4-((4-Fluoro-3-methoxybenzyl)oxy)-2-(4-methylpiperazin-1-yl)pyrimidin-5-yl)thio)pyridin-2-amine [151]. 151 was obtained in 81% yield following the general procedure above. $^1$H NMR (500 MHz, CDCl$_3$) δ 8.22 (s, 1H), 8.11 (s, 1H), 7.38-7.40 (m, 1H), 7.01-7.05 (m, 1H), 6.93-6.95 (m, 1H), 6.82-6.84 (m, 1H), 6.32 (d, J=8.5 Hz, 1H), 5.31 (s, 2H), 4.49 (br s, 2H), 3.85 (m, 7H), 2.49-2.52 (m, 4H), 2.38 (s, 3H); $^{13}$C NMR (125 MHz, CDCl$_3$) δ 168.0, 162.7, 161.2, 157.7, 151.3, 147.8, 141.7, 133.0, 120.7, 120.3, 116.1, 115.9, 113.1, 108.9, 103.4, 67.6, 56.4, 54.9, 46.2, 43.8; FIRMS (ESI) m/z [M+H]$^+$ calcd. for C$_{22}$H$_{26}$FN$_6$O$_2$S 457.1822; found 457.1809.

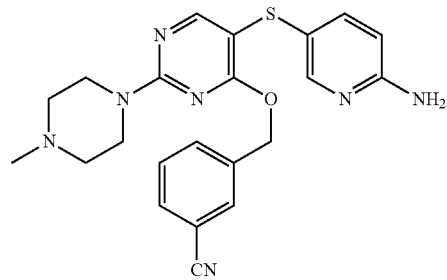

152

3-(((5-((6-Aminopyridin-3-yl)thio)-2-(4-methylpiperazin-1-yl)pyrimidin-4-yl)oxy)methyl)benzonitrile [152]. 152 was obtained in 70% yield following the general procedure above. $^1$H NMR (500 MHz, CDCl$_3$) δ 8.26 (s, 1H), 8.10 (d, J=2.2 Hz, 1H), 7.58 (d, J=7.6 Hz, 1H), 7.50 (m, 1H), 7.41-7.46 (m, 2H), 7.39 (s, 1H), 6.45 (d, J=8.5 Hz, 1H), 5.37 (s, 2H), 4.56 (br s, 2H), 3.85 (m, 4H), 2.51 (m, 4H), 2.39 (s, 3H); $^{13}$C NMR (125 MHz, CDCl$_3$) δ 167.6, 162.8, 161.0, 157.9, 151.3, 141.5, 138.4, 131.9, 131.7, 131.1, 129.4, 120.4, 118.8, 112.8, 109.2, 103.2, 66.6, 54.8, 46.1, 43.7; HRMS (ESI) m/z [M+H]$^+$ calcd. for C$_{22}$H$_{24}$N$_7$O$_2$S 434.1763; found 434.1751.

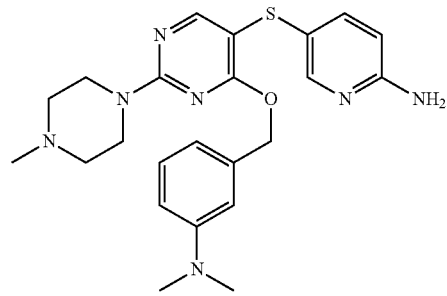

153

5-((4-((3-(Dimethylamino)benzyl)oxy)-2-(4-methylpiperazin-1-yl)pyrimidin-5-yl)thio)pyridin-2-amine [153]. 153 was obtained in 75% yield following the general procedure above. $^1$H NMR (500 MHz, CDCl$_3$) δ 8.19 (s, 1H), 8.14 (d, J=2.0 Hz, 1H), 7.42 (dd, J=8.5, 2.4 Hz, 1H), 7.20 (t, J=7.9 Hz, 1H), 6.74 (s, 1H), 6.66-6.68 (m, 2H), 6.33 (d, J=8.5 Hz, 1H), 5.34 (s, 2H), 4.46 (br s, 2H), 3.86 (m, 4H), 2.94 (s, 6H), 2.47-2.49 (m, 4H), 2.37 (s, 3H); $^{13}$C NMR (125 MHz, CDCl$_3$) δ 168.2, 162.6, 161.2, 157.7, 151.4, 150.9, 141.9, 137.5, 129.3, 120.9, 116.1, 112.2, 111.9, 108.9, 103.4, 68.7, 54.9, 46.2, 43.8, 40.8; HRMS (ESI) m/z [M+H]$^+$ calcd. for C$_{23}$H$_{30}$N$_7$OS 452.2233; found 452.2215.

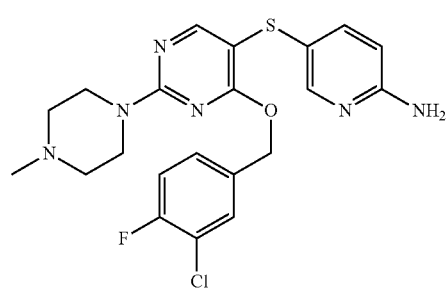

154

5-((4-((3-Chloro-4-fluorobenzyl)oxy)-2-(4-methylpiperazin-1-yl)pyrimidin-5-yl)thio)pyridin-2-amine [154]. 154 was obtained in 80% yield following the general procedure above. $^1$H NMR (500 MHz, CDCl$_3$) δ 8.22 (s, 1H), 8.10 (d, J=2.1 Hz, 1H), 7.39 (dd, J=8.5, 2.4 Hz, 1H), 7.30 (dd, J=7.0, 1.9 Hz, 1H), 7.07-7.14 (m, 2H), 6.36 (d, J=8.5 Hz, 1H), 5.29 (s, 2H), 4.48 (br s, 2H), 3.80-3.82 (m, 4H), 2.43-2.45 (m, 4H), 2.33 (s, 3H); $^{13}$C NMR (125 MHz, CDCl$_3$) δ 167.7, 162.8, 161.1, 157.8, 156.9, 151.3, 141.6, 133.9, 130.2, 127.7, 120.7, 116.8, 116.7, 108.9, 103.2, 66.5, 55.0, 46.4, 44.1; HRMS (ESI) m/z [M+H]$^+$ calcd. for C$_{21}$H$_{23}$ClFN$_6$OS 461.1327; found 461.1316.

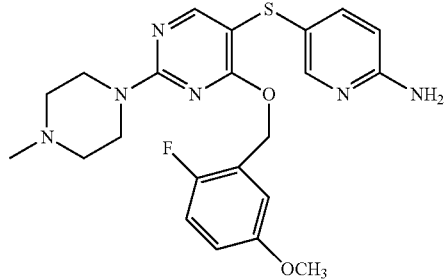

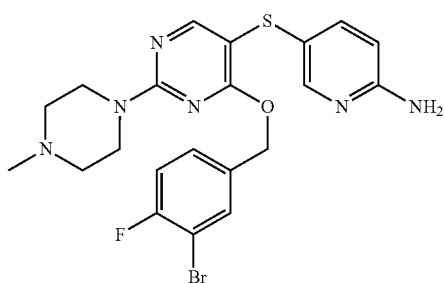

5-((4-((3-Bromo-4-fluorobenzyl)oxy)-2-(4-methylpiperazin-1-yl)pyrimidin-5-yl)thio)pyridin-2-amine [155]. 155 was obtained in 73% yield following the general procedure above. $^1$H NMR (500 MHz, CDCl$_3$) δ 8.22 (s, 1H), 8.11 (s, 1H), 7.48 (dd, J=6.5, 1.9 Hz, 1H), 7.40 (dd, J=8.5, 2.3 Hz, 1H), 7.17-7.20 (m, 1H), 7.07 (t, J=8.4 Hz, 1H), 6.39 (d, J=8.5 Hz, 1H), 5.29 (s, 2H), 4.50 (br s, 2H), 3.86 (m, 4H), 2.51 (m, 4H), 2.38 (s, 3H); $^{13}$C NMR (125 MHz, CDCl$_3$) δ 167.7, 162.7, 161.0, 157.9, 157.8, 151.4, 141.7, 134.2, 133.1, 128.6, 128.5, 116.7, 116.6, 109.2, 109.1, 66.5, 54.8, 46.1, 43.8; HRMS (ESI) m/z [M+H]$^+$ calcd. for C$_{21}$H$_{23}$BrFN$_6$OS 505.0821; found 505.0821.

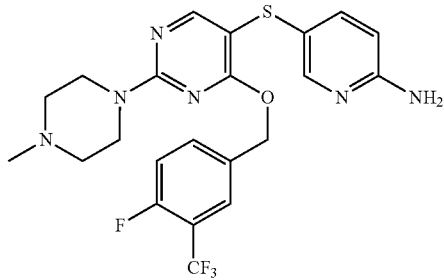

5-((4-((4-Fluoro-3-(trifluoromethyl)benzyl)oxy)-2-(4-methylpiperazin-1-yl)pyrimidin-5-yl)thio)pyridin-2-amine [156]. 156 was obtained in 68% yield following the general procedure above. $^1$H NMR (500 MHz, CDCl$_3$) δ 8.21 (s, 1H), 8.08 (d, J=2.0 Hz, 1H), 7.55 (d, J=6.6 Hz, 1H), 7.40-7.43 (m, 1H), 7.37 (dd, J=8.5, 2.3 Hz, 1H), 7.16 (t, J=9.3 Hz, 1H), 6.34 (d, J=8.5 Hz, 1H), 5.34 (s, 2H), 4.49 (br s, 2H), 3.84 (m, 4H), 2.48-2.50 (m, 4H), 2.37 (s, 3H); HRMS (ESI) m/z [M+H]$^+$ calcd. for C$_{22}$H$_{23}$F$_4$N$_6$OS 495.1590; found 495.1577.

5-((4-((2-Fluoro-5-methoxybenzyl)oxy)-2-(4-methylpiperazin-1-yl)pyrimidin-5-yl)thio)pyridin-2-amine [157]. 157 was obtained in 96% yield following the general procedure above. $^1$H NMR (500 MHz, CDCl$_3$) δ 8.19 (s, 1H), 8.12 (s, 1H), 7.42 (dd, J=8.5, 2.2 Hz, 1H), 6.96 (t, J=9.2 Hz, 1H), 6.84-6.86 (m, 1H), 6.76-6.79 (m, 1H), 6.34 (d, J=8.5 Hz, 1H), 5.40 (s, 2H), 4.48 (br s, 2H), 3.83 (m, 4H), 3.73 (s, 3H), 2.45-2.47 (m, 4H), 2.34 (s, 3H); $^{13}$C NMR (125 MHz, CDCl$_3$) δ 167.9, 162.8, 161.1, 157.8, 155.9, 151.4, 141.8, 124.6, 120.7, 116.0, 115.9, 114.9, 114.3, 109.0, 103.3, 61.7, 56.0, 54.9, 46.2, 43.9; HRMS (ESI) m/z [M+H]$^+$ calcd. for C$_{22}$H$_{26}$FN$_6$O$_2$S 457.1822; found 457.1817.

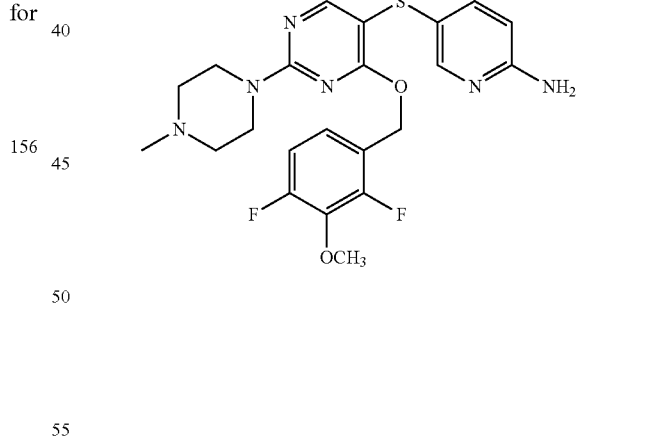

5-((4-((2,4-Difluoro-3-methoxybenzyl)oxy)-2-(4-methylpiperazin-1-yl)pyrimidin-5-yl)thio)pyridin-2-amine [158]. 158 was obtained in 95% yield following the general procedure above. $^1$H NMR (500 MHz, CDCl$_3$) δ 8.21 (s, 1H), 8.10 (s, 1H), 7.40 (dd, J=8.5, 2.2 Hz, 1H), 6.80-6.91 (m, 2H), 6.35 (d, J=8.5 Hz, 1H), 5.38 (s, 2H), 4.49 (br s, 2H), 4.00 (s, 3H), 3.85 (m, 4H), 2.49-2.50 (m, 4H), 2.37 (s, 3H); HRMS (ESI) m/z [M+H]$^+$ calcd. for C$_{22}$H$_{25}$F$_2$N$_6$O$_2$S 475.1728; found 475.1718.

Example 19

Scheme 23. Synthesis of 166-168.

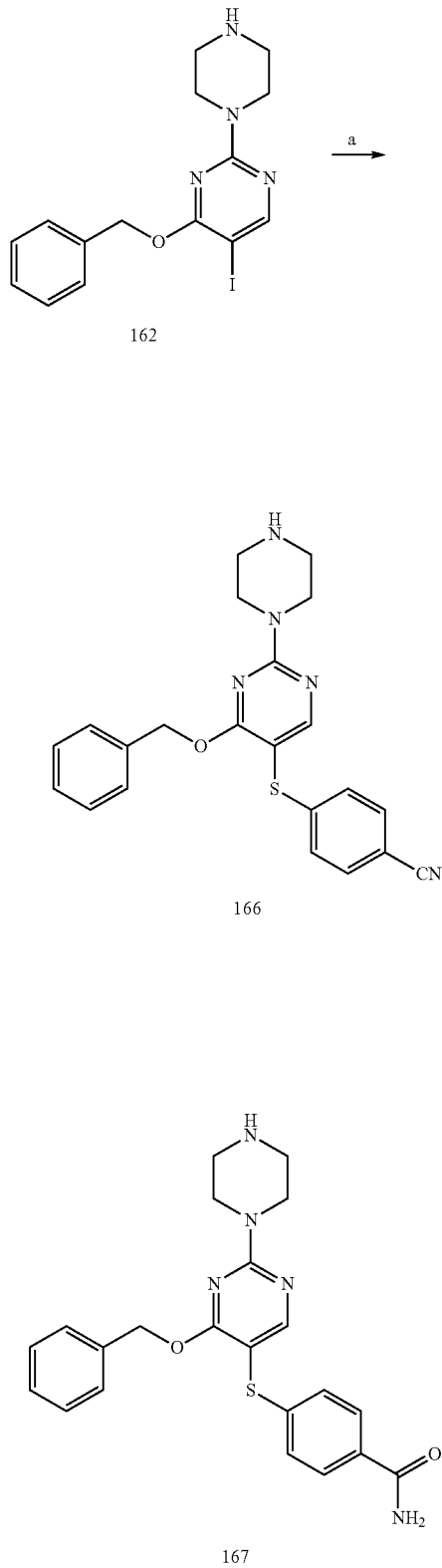

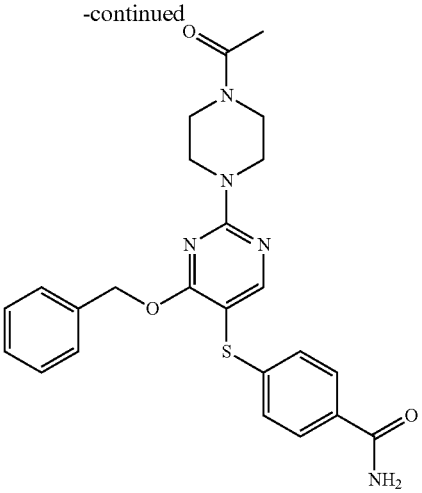

Reagents and conditions: a. 4-mercaptobenzonitrile, CuI, neocuproine, K₂CO₃, DMF, 120° C., 20 h; b. KOH, t-BuOH, 80° C., 1 h; c. acetic anhydride, DMAP, 110° C. for 2 h.

4-((4-(Benzyloxy)-2-(piperazin-1-yl)pyrimidin-5-yl)thio) benzonitrile [166]. A mixture of 162 (75 mg, 0.189 mmol), K₂CO₃ (52.2 mg, 0.378 mmol), neocuproine (11.8 mg, 0.0567 mmol), CuI (10.8 mg, 0.0567 mmol) and 4-mercaptobenzonitrile (31.9 mg, 0.236 mmol) in DMF (2 mL) was heated at 120° C. for 20 h. Solvent was removed under reduced pressure and the residue was purified by preparatory TLC (CH₂Cl₂:MeOH—NH₃ (7 N), 15:1) to afford 24.6 mg (32%) of 166. ¹H NMR (500 MHz, CDCl₃): δ 8.17 (s, 1H), 7.34 (d, J=8.3 Hz, 2H), 7.15-7.21 (m, 3H), 7.05-7.09 (m, 2H), 7.02 (d, J=8.3 Hz, 2H), 5.29 (s, 2H), 3.74-3.80 (m, 4H), 2.84-2.89 (m, 4H); ¹³C NMR (125 MHz, CDCl₃): δ 168.6, 165.1, 161.8, 145.7, 136.3, 132.1, 128.4, 128.0, 127.5, 126.1, 119.0, 108.2, 96.7, 67.8, 45.9, 45.2; HRMS (ESI) m/z [M+H]⁺ calcd. for C₂₂H₂₂N₅OS, 404.1545; found 404.1537.

4-((4-(Benzyloxy)-2-(piperazin-1-yl)pyrimidin-5-yl)thio) benzamide [167]. A mixture of 166 (18.5 mg, 0.0458 mmol) and KOH (56.5 mg, 1.01 mmol) in t-BuOH (500 µL) was heated at 80° C. for 1 h. Solvent was removed under reduced pressure and the residue was purified by preparatory TLC (CH₂Cl₂:MeOH—NH₃ (7 N), 15:1) to afford 15 mg (78%) of 167. ¹H NMR (500 MHz, CDCl₃): δ 8.26 (s, 1H), 7.62 (d, J=8.3 Hz, 2H), 7.21-7.25 (m, 3H), 7.10-7.16 (m, 4H), 5.97 (br s, 1H), 5.80 (br s, 1H), 5.36 (s, 2H), 3.80-3.87 (m, 4H), 2.90-2.97 (m, 4H); ¹³C NMR (125 MHz, CDCl₃): δ 168.8, 168.6, 164.9, 161.7, 143.7, 136.4, 129.9, 128.3, 127.8, 127.7, 127.4, 126.1, 97.9, 67.8, 45.9, 45.1; HRMS (ESI) m/z [M+H]⁺ calcd. for C₂₂H₂₄N₅O₂S, 422.1651; found 422.1644.

4-((2-(4-Acetylpiperazin-1-yl)-4-(benzyloxy)pyrimidin-5-yl)thio)benzamide [168]. A solution of 167 (10 mg, 0.023 mmol) and DMAP (0.001 mmol, 2 mg) in 2 mL of acetic anhydride was stirred at 110° C. for 2 h. Solvent was removed under reduced pressure and the residue was purified by preparatory TLC (CH₂Cl₂:hexane:EtOAc:MeOH—NH₃ (7 N), 4:4:2:1) to yield 6.8 mg (61%) of 168. ¹H NMR (600 MHz, CDCl₃): δ 8.21 (s, 1H), 7.62 (d, J=8.6 Hz, 2H), 7.17-7.20 (m, 3H), 7.05-7.07 (m, 4H), 5.95 (br s, 1H), 5.75 (br s, 1H), 5.29 (s, 2H), 3.80-3.83 (m, 2H), 3.76-3.83 (m, 2H), 3.61-3.63 (m, 4H), 3.45-3.48 (m, 2H), 2.09 (s, 3H); ¹³C NMR (150 MHz, CDCl₃): δ 169.3, 168.7, 168.6, 164.8, 161.5, 143.3, 136.2, 130.0, 128.4, 127.9, 127.8, 127.3, 126.2, 99.0, 68.0, 45.9, 43.7, 41.1. HRMS (ESI) m/z [M+H]+ calcd. for $C_{24}H_{26}N_5O_2S$, 464.1721; found 464.1728.

Example 20

Scheme 25. Synthesis of 179a and c.

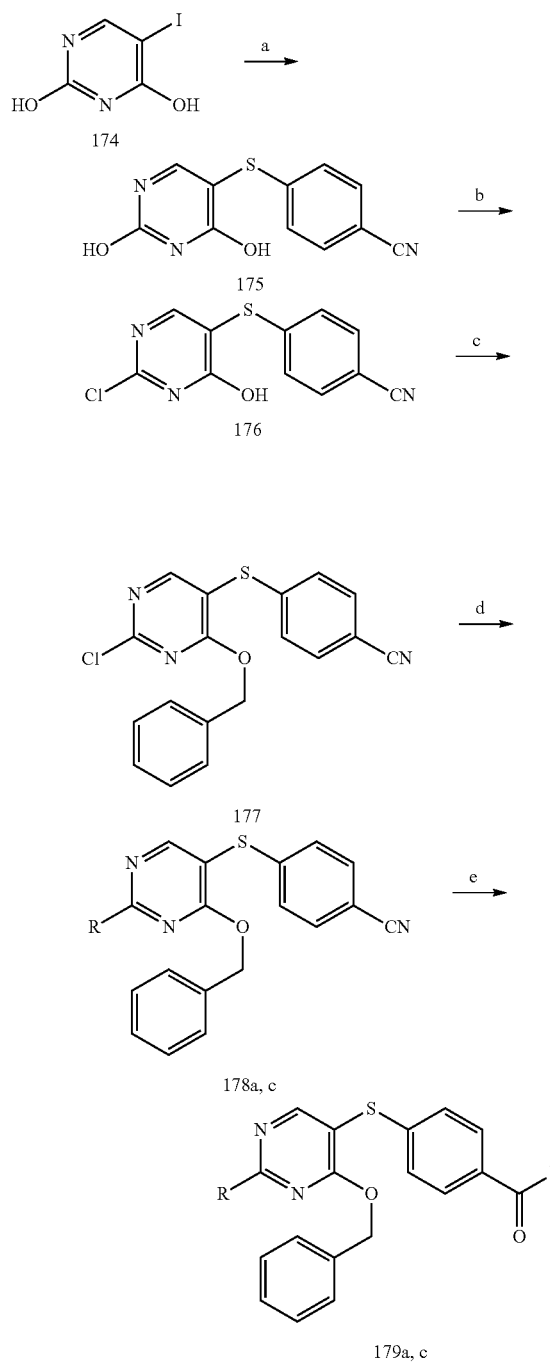

Reagents and conditions: a. 4-mercaptobenzonitrile, copper(I)thiophene-2-carboxylate, $K_2CO_3$, DMF, 130° C., 16 h; b. $POCl_3$, DIEA, 100° C., 1 h; c. BnOH, KOH, 18-crown-6, rt, 12 h, toluene; d. amine, DMF, 90° C., 2 h; e. KOH, t-BuOH, 80° C., 1 h.

4-((2,4-Dihydroxypyrimidin-5-yl)thio)benzonitrile [175]. A mixture of 5-iodopyrimidine-2,4-diol 174 (1 g, 4.2 mmol), 4-mercaptobenzonitrile (0.68 g, 5.04 mmol) and $K_2CO_3$ (1.74 g, 12.6 mmol) in DMF (30 mL) was evacuated and backfilled with argon three times. Copper(I)thiophene-2-carboxylate (0.32 g, 1.68 mmol) was added and evacuated and backfilled with argon two times and the reaction mixture was heated at 130° C. for 16 h. Solvent was removed under reduced pressure and purified by column chromatography ($CH_2Cl_2$:$CH_3OH$:$CH_3COOH$, 25:1:0.3) to give 0.65 g (63%) of 175. $^1$H NMR (500 MHz, DMSO-$d_6$): δ 8.03 (s, 1H), 7.69 (d, J=7.9 Hz, 2H), 7.31 (d, J=8.6 Hz, 2H); $^{13}$C NMR (125 MHz, DMSO-$d_6$): δ 162.6, 151.6, 150.8, 144.9, 132.4, 125.7, 118.8, 107.2, 99.1; HRMS (ESI) m/z [M−H]+ calcd. for $C_{11}H_6N_3O_2S$, 244.0181; found 244.0178.

4-((2,4-Dichloropyrimidin-5-yl)thio)benzonitrile [176]. In a 100 mL round bottomed flask containing 0.65 g (2.65 mmol) of 175 was added 12.1 mL of $POCl_3$ (20.34 g, 132.65 mmol) with stirring. To this mixture 1.15 mL of DIEA (0.85 g, 6.63 mmol) was added slowly and the reaction was heated at 100° C. for 1 h. After cooling to rt, the reaction mixture was added to a beaker containing ice chips. Following complete quenching of $POCl_3$, solid $Na_2CO_3$ was carefully added until pH ~9. This was transferred to a seperatory funnel and extracted with $CH_2Cl_2$ (4×75 mL), dried over $MgSO_4$, filtered and concentrated to a solid which was purified by column chromatography (hexane:EtOAc, 80:20) to afford 0.56 g (86%) of 176. $^1$H NMR (500 MHz, $CDCl_3$): δ 8.34 (s, 1H), 7.61 (d, J=8.2 Hz, 2H), 7.34 (d, J=8.2 Hz, 2H); $^{13}$C NMR (125 MHz, $CDCl_3$): δ 163.5, 161.9, 159.9, 137.9, 133.5, 131.1, 128.8, 118.0, 112.5; MS (ESI) m/z [M+H]+ 282.1.

4-((4-(Benzyloxy)-2-chloropyrimidin-5-yl)thio)benzonitrile [177]. To 176 (0.16 g, 0.57 mmol) dissolved in toluene (10 mL) was added benzylalcohol (59 μL, 61.5 mg, 0.57 mmol). KOH (32 mg, 0.57 mmol) was added followed by 18-crown-6 (7.5 mg, 0.03 mmol) and reaction was stirred at rt for 12 h. Then the reaction mixture was concentrated under reduced pressure to give a residue to which 50 mL EtOAc was added. This was transferred to a seperatory funnel and washed with 0.1 N HCl (30 mL) followed by $H_2O$ (2×30 mL), dried over $MgSO_4$, filtered and concentrated to a solid which was purified by column chromatography (hexane:EtOAc, 90:10 to 80:20) to afford 67 mg (34%) of 177. MS (m/z): [M+H]+ 354.2.

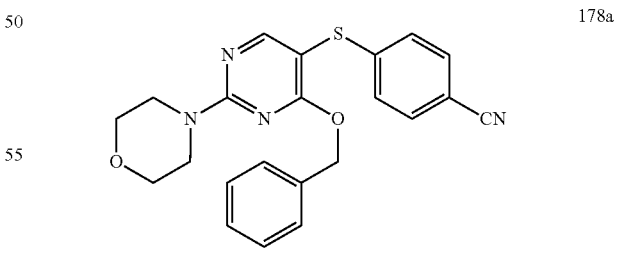

178a 4-((4-(Benzyloxy)-2-morpholinopyrimidin-5-yl)thio)benzonitrile [178a]. To 177 (15.0 mg, 0.039 mmol) was added morpholine (4.1 mg, 0.047 mmol) in DMF (2 mL) and heated at 90° C. for 2 h. Solvent was removed under reduced pressure and the residue was purified by preparatory TLC (hexane:EtOAc, 75:25) to afford 7.8 mg (45%) of 178a. MS (m/z): [M+H]+ 405.5.

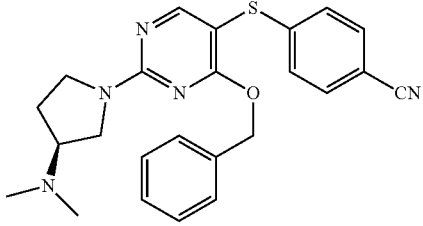

(S)-4-((4-(Benzyloxy)-2-(3-(dimethylamino)pyrrolidin-1-yl)pyrimidin-5-yl)thio)benzonitrile [178c]. To 177 (10.0 mg, 0.028 mmol) was added (S)—N,N-dimethylpyrrolidin-3-amine (3.9 mg, 0.034 mmol) in DMF (2 mL) and heated at 90° C. for 2 h. Solvent was removed under reduced pressure and the residue was purified by Prep TLC (CH$_2$Cl$_2$: MeOH, 10:1) to afford 5.8 mg (48%) of 178c. MS (m/z): [M+H]$^+$ 432.3.

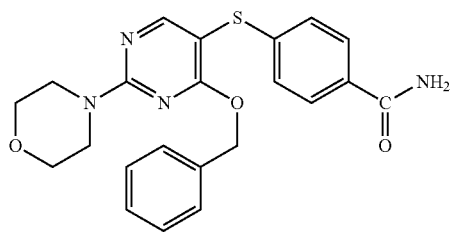

4-((4-((4-(Benzyloxy)-2-morpholinopyrimidin-5-yl)thio)benzamide [179a]. A mixture of 178a (7.8 mg, 0.019 mmol) and KOH (23.8 mg, 0.425 mmol) in t-BuOH (1 mL) was heated at 80° C. for 1 h. Solvent was removed under reduced pressure and the residue was purified by preparatory TLC (hexane:EtOAc, 75:25, two times) to afford 4.7 mg (59%) of 179a. $^1$H NMR (600 MHz, CDCl$_3$): δ 8.21 (s, 1H), 7.56 (d, J=8.5 Hz, 2H), 7.17-7.19 (m, 3H), 7.04-7.06 (m, 4H), 5.91 (br s, 1H), 5.51 (br s, 1H), 5.29 (s, 2H), 3.76-3.79 (m, 4H), 3.69-3.70 (m, 4H); $^{13}$C NMR (150 MHz, CDCl$_3$): δ 168.9, 168.8, 165.1, 161.9, 143.8, 136.5, 130.1, 128.6, 128.1, 127.9, 127.6, 126.3, 98.8, 68.1, 66.9, 44.6; HRMS (ESI) m/z [M+H]$^+$ calcd. for C$_{22}$H$_{23}$N$_4$O$_3$S, 423.1491; found 423.1481.

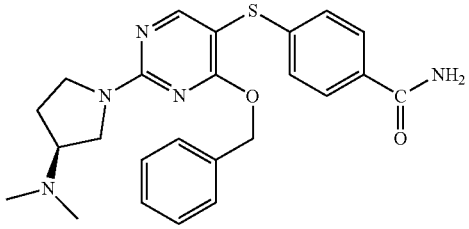

(S)-4-((4-(Benzyloxy)-2-(3-(dimethylamino)pyrrolidin-1-yl)pyrimidin-5-yl)thio)benzamide (179c). A mixture of 178c (5.8 mg, 0.014 mmol) and KOH (16.6 mg, 0.30 mmol) in t-BuOH (1 mL) was heated at 80° C. for 1 h. Solvent was removed under reduced pressure and the residue was purified by preparatory TLC (CH$_2$Cl$_2$:MeOH—NH$_3$ (7 N), 10:1) to afford 4.1 mg (63%) of 179c. $^1$H NMR (600 MHz, CDCl$_3$): δ 8.27 (s, 1H), 7.62 (d, J=8.5 Hz, 2H), 7.24 (t, J=8.5 Hz, 3H), 7.16 (s, 2H), 7.11 (J=8.4 Hz, 2H), 5.98 (br s, 1H), 5.58 (br s, 1H), 5.39 (s, 2H), 3.82-3.98 (m, 2H), 3.49-3.54 (m, 1H), 3.31-3.36 (m, 1H), 2.78-2.82 (m, 1H), 2.34 (s, 3H), 2.32 (s, 3H), 2.20-2.25 (m, 1H), 1.88-1.95 (m, 1H); $^{13}$C NMR (150 MHz, CDCl$_3$): δ 168.6, 168.5, 164.9, 160.2, 143.9, 136.6, 136.5, 129.7, 128.3, 127.8, 127.7, 127.6, 125.8, 97.4, 67.8, 65.4, 51.3, 46.1, 44.4, 30.4; FIRMS (ESI) m/z [M+H]$^+$ calcd. for C$_{24}$H$_{28}$N$_5$O$_2$S, 450.1964; found 450.1956.

Example 21

Scheme 26. Synthesis of 182.

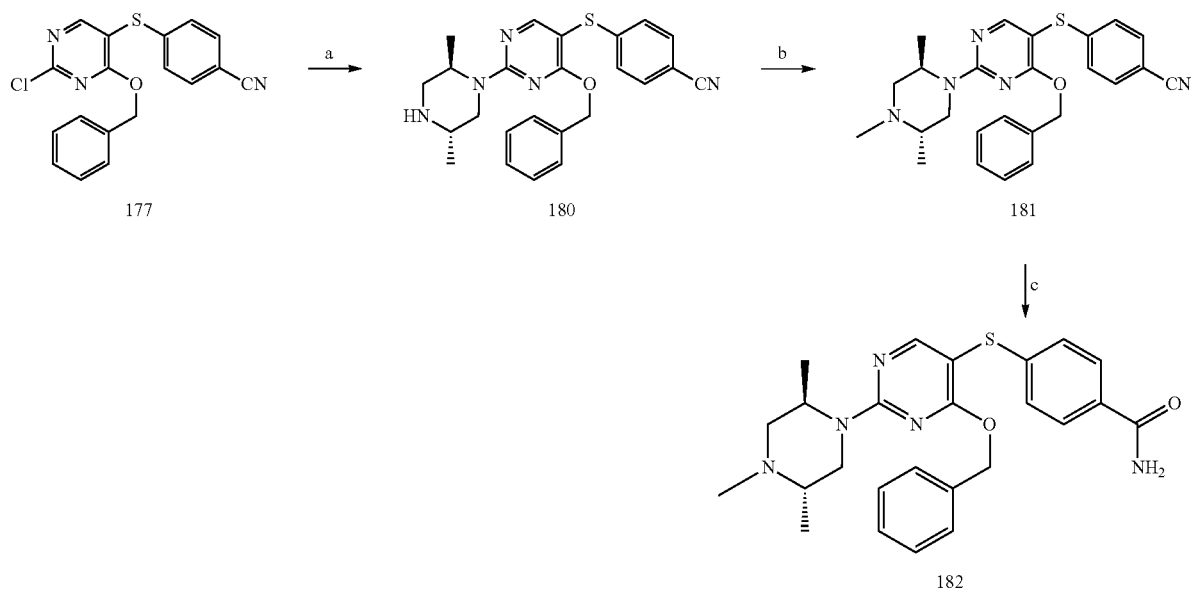

Reagents and conditions: a. trans-2,5-dimethylpiperazine, Et$_3$N, DMF, 90° C., 2 h; b. formaldehyde, NaBH$_3$CN, NaOAc, MeOH, 50° C., 5 h; c. KOH, tBuOH, 80° C., 1 h.

4-((4-(Benzyloxy)-2-((2R,5S)-2,5-dimethylpiperazin-1-yl)pyrimidin-5-yl)thio)benzonitrile [180]. To 177 (20 mg, 0.056 mmol) was added trans-2,5-dimethylpiperazine (8 mg, 0.0672 mmol) and Et$_3$N (15 µL, 0.11 mmol) in DMF (3 mL) and heated at 90° C. for 2 h. Solvent was removed under reduced pressure and the residue was purified by preparative TLC (CH$_2$Cl$_2$:MeOH, 10:1) to afford 20 mg (82%) of 180. $^1$H NMR (500 MHz, CDCl$_3$): δ 8.24 (s, 1H), 7.42 (d, J=8.3 Hz, 2H), 7.23-7.27 (m, 3H), 7.10-7.16 (m, 4H), 5.41 (d, J=12.6 Hz, 1H), 5.31 (d, J=12.6 Hz, 1H), 4.76 (m, 1H), 4.29 (d, J=13.4 Hz, 1H), 3.29-3.39 (m, 3H), 2.64 (d, J=13.0 Hz, 1H), 1.83-1.87 (m, 1H), 1.27 (d, J=6.5 Hz, 3H), 1.19 (d, J=6.7 Hz, 3H); MS (m/z): [M+H]$^+$ 432.0.

4-((4-(Benzyloxy)-2-((2R,5S)-2,4,5-trimethylpiperazin-1-yl)pyrimidin-5-yl)thio)benzonitrile [181]. To a solution of 180 (20 mg, 0.046 mmol) in MeOH (3 mL) was added formalin (20 µL, 0.269 mmol), sodium acetate (20 mg, 0.244 mmol) and sodium cyanoborohydride (20 mg, 0.095 mmol) and was heated at 50° C. for 5 h. Solvent was removed under reduced pressure and the residue was purified by preparative TLC (CH$_2$Cl$_2$:MeOH, 10:1) to afford 16 mg (77%) of 181. MS (ESI) m/z [M+H]$^+$ 446.4.

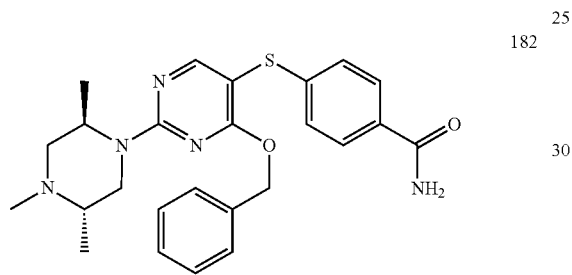

182

4-((4-(Benzyloxy)-2-((2R,5S)-2,4,5-trimethylpiperazin-1-yl)pyrimidin-5-yl)thio)benzamide [182]. A mixture of 181 (16 mg, 0.036 mmol) and KOH (40 mg, 0.71 mmol) in t-BuOH (3 mL) was heated at 80° C. for 1 h. Solvent was removed under reduced pressure and the residue was purified by preparatory TLC (CH$_2$Cl$_2$:MeOH, 20:1) to afford 9 mg (54%) of 182. $^1$H NMR (600 MHz, CDCl$_3$) δ 8.19 (s, 1H), 7.56 (d, J=8.4 Hz, 2H), 7.16-7.19 (m, 3H), 7.06-7.08 (m, 4H), 5.95 (br s, 1H), 5.62 (br s, 1H), 5.33 (d, J=12.6 Hz, 1H), 5.22 (d, J=12.6 Hz, 1H), 4.79 (s, 1H), 4.35 (d, J=13.2 Hz, 1H), 3.38 (d, J=12.0 Hz, 1H), 2.97 (s, 1H), 2.74 (dd, J=12.0, 4.6 Hz, 1H), 2.34 (d, J=10.9 Hz, 1H), 2.30 (s, 3H), 1.24 (d, J=6.6 Hz, 3H), 0.88 (d, J=6.5 Hz, 3H); $^{13}$C NMR (150 MHz, CDCl$_3$) δ 168.7, 168.6, 165.0, 162.1, 143.8, 136.5, 129.8, 128.3, 127.8, 127.7, 127.3, 126.0, 97.4, 67.7, 54.3, 52.0, 46.9, 44.0, 42.8, 15.7, 7.8; HRMS (ESI) m/z [M+H]$^+$ calcd. for C$_{25}$H$_{30}$N$_5$O$_2$S 464.2120; found 464.2104.

Example 22

Scheme 27. Synthesis of 185a, b, d and e.

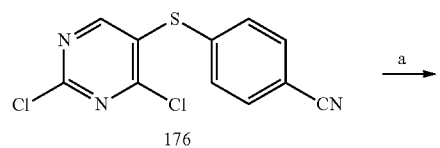

176

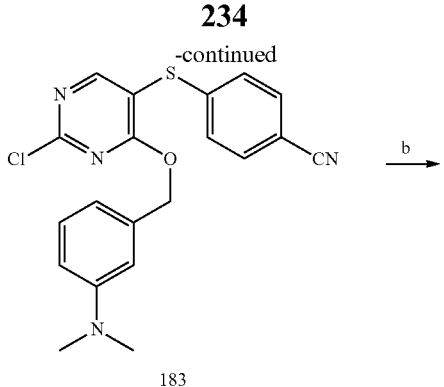

183

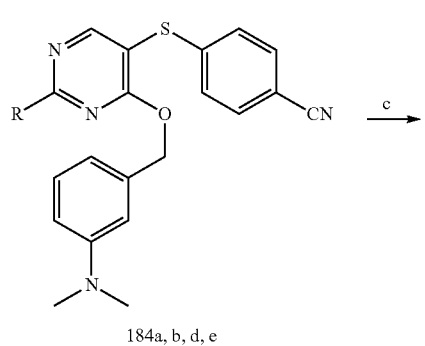

184a, b, d, e

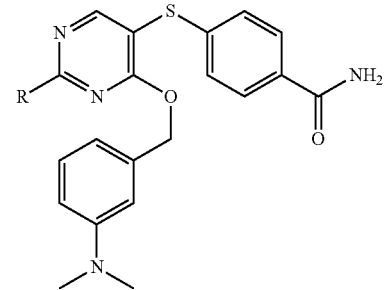

185a, b, d, e

Reagents and conditions: a. 3- dimethylaminobenzylalcohol, KOH, 18-crown-6, toluene, rt, 12 h; b. amine, DMF, 90° C., 2 h; c. KOH, t-BuOH, 80° C., 1 h.

4-((2-Chloro-4-((3-(dimethylamino)benzyl)oxy)pyrimidin-5-yl)thio)benzonitrile [183]. To 176 (0.26 g, 0.935 mmol) dissolved in toluene (12 mL) was added 3-dimethylaminobenzylalcohol (134 µL, 141.0 mg, 0.935 mmol). KOH (78 mg, 1.4 mmol) was added followed by 18-crown-6 (12 mg, 0.047 mmol) and reaction was stirred at rt for 12 h. Then the reaction mixture was concentrated under reduced pressure to give a residue to which 100 mL EtOAc was added. This was transferred to a seperatory funnel and washed with 0.1 N HCl (50 mL) followed by H$_2$O (2×50 mL), dried over MgSO$_4$, filtered and concentrated to a solid which was purified by column chromatography (hexane: EtOAc, 90:10 to 80:20) to afford 0.11 g (30%) of 183. $^1$H NMR (500 MHz, CDCl$_3$): δ 8.36 (s, 1H), 7.35 (d, J=8.4 Hz, 2H), 7.09 (t, J=8.0 Hz, 1H), 7.07 (d, J=8.4 Hz, 2H), 6.61 (dd, J=8.6, 2.3 Hz, 1H), 6.52 (s, 1H), 6.42 (d, J=7.3 Hz, 1H), 5.32 (s, 2H), 2.84 (s, 6H); MS (ESI) m/z [M+H]$^+$ 397.2.

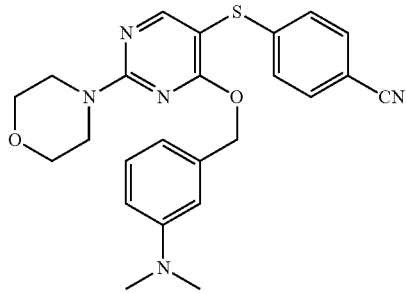

184a 4-((4-((3-(Dimethylamino)benzyl)oxy)-2-morpholinopyrimidin-5-yl)thio)benzonitrile [184a]. To 183 (10.0 mg, 0.0252 mmol) was added morpholine (2.64 mg, 0.0303 mmol) in DMF (2 mL) and heated at 90° C. for 2 h. Solvent was removed under reduced pressure and the residue was purified by preparatory TLC (hexane:EtOAc, 7:3) to afford 6.2 mg (64%) of 184a. MS (m/z): [M+H]$^+$ 448.3.

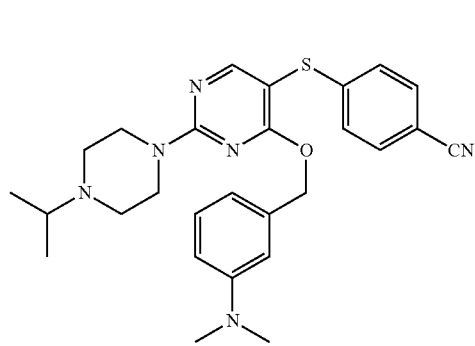

184b 4-((4-((3-(Dimethylamino)benzyl)oxy)-2-(4-isopropylpiperazin-1-yl)pyrimidin-5-yl)thio)benzonitrile [184b]. To 183 (10.0 mg, 0.0252 mmol) was added N-isopropylpiperazine (4.2 mg, 0.033 mmol) in DMF (2 mL) and heated at 90° C. for 2 h. Solvent was removed under reduced pressure and the residue was used in the next step without further purification. MS (m/z): [M+H]$^+$ 489.4.

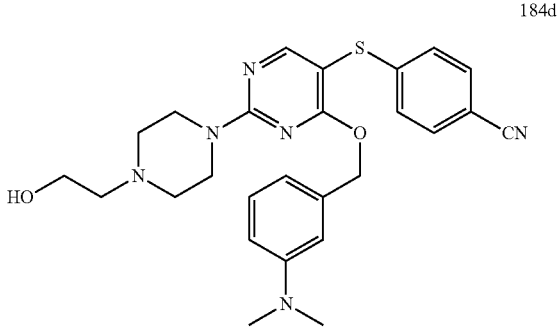 [SMILES: CN(C)c1cccc(COc2nc(N3CCN(CCO)CC3)ncc2Sc2ccc(C#N)cc2)c1]

184d 4-((4-((3-(Dimethylamino)benzyl)oxy)-2-(4-(2-hydroxyethyl)piperazin-1-yl)pyrimidin-5-yl)thio)benzonitrile [184d]. To 183 (10.0 mg, 0.0252 mmol) was added 2-(piperazin-1-yl)ethanol (4.3 mg, 0.033 mmol) in DMF (2 mL) and heated at 90° C. for 2 h. Solvent was removed under reduced pressure and the residue was used in the next step without further purification. MS (m/z): [M+H]$^+$ 491.4.

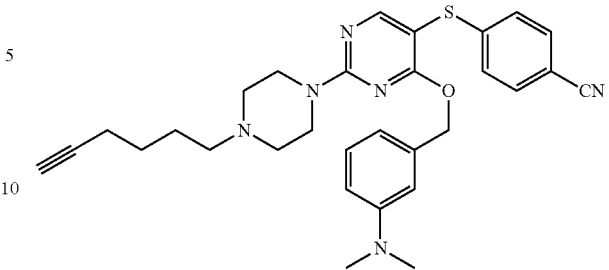

184e 4-((4-((3-(Dimethylamino)benzyl)oxy)-2-(4-(hex-5-yn-1-yl)piperazin-1-yl)pyrimidin-5-yl)thio)benzonitrile [184e]. To 183 (10.0 mg, 0.0252 mmol) was added 1-(hex-5-yn-1-yl)piperazine (5.5 mg, 0.033 mmol) and Et$_3$N (100 µL) in DMF (2 mL) and was stirred at rt for overnight. Solvent was removed under reduced pressure and the residue was used in the next step without further purification. $^1$H NMR (500 MHz, CDCl$_3$) δ 8.22 (s, 1H), 7.39 (d, J=8.5 Hz, 2H), 7.13 (t, J=7.8 Hz, 1H), 7.06 (d, J=8.5 Hz, 2H), 6.63 (dd, J=8.3, 2.2 Hz, 1H), 6.50-6.56 (m, 2H), 5.33 (s, 2H), 3.90 (m, 4H), 2.84 (s, 6H), 2.52 (m, 4H), 2.42 (t, J=7.0 Hz, 2H), 2.25 (td, J=7.0, 2.6 Hz, 2H), 1.97 (t, J=2.5 Hz, 1H), 1.66-1.71 (m, 2H), 1.57-1.62 (m, 2H); MS (m/z): [M+H]$^+$ 527.1.

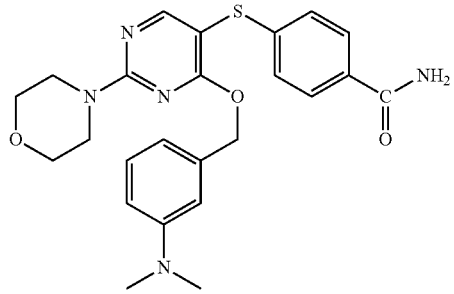

185a 4-((4-((3-(Dimethylamino)benzyl)oxy)-2-morpholinopyrimidin-5-yl)thio)benzamide [185a]. A mixture of 184a (6.2 mg, 0.014 mmol) and KOH (17.1 mg, 0.305 mmol) in t-BuOH (1 mL) was heated at 80° C. for 1 h. Solvent was removed under reduced pressure and the residue was purified by preparatory TLC (hexane:EtOAc, 1:1) to afford 4.1 mg (63%) of 185a. $^1$H NMR (600 MHz, CDCl$_3$): δ 8.19 (s, 1H), 7.53 (d, J=8.4 Hz, 2H), 7.05 (t, J=8.4 Hz, 1H), 7.02 (d, J=8.4 Hz, 2H), 6.56 (dd, J=8.9, 2.6 Hz, 1H), 6.50 (s, 1H), 6.46 (d, J=7.4 Hz, 1H), 5.97 (br s, 1H), 5.49 (br s, 1H), 5.27 (s, 2H), 3.78-3.79 (m, 4H), 3.69-3.71 (m, 4H), 2.75 (s, 6H); $^{13}$C NMR (150 MHz, CDCl$_3$): δ 168.9, 168.6, 164.9, 161.8, 150.6, 143.6, 137.1, 129.7, 129.0, 127.7, 125.7, 115.7, 112.1, 111.6, 98.2, 68.4, 66.7, 44.4, 40.5; HRMS (ESI) m/z [M+H]$^+$ calcd. for C$_{24}$H$_{25}$N$_5$O$_3$S, 466.1913; found 466.1901.

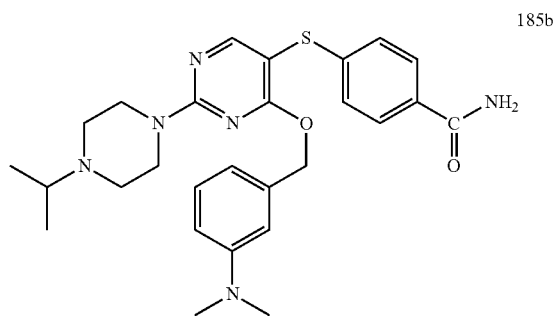 [SMILES: CC(C)N1CCN(c2ncc(Sc3ccc(C(N)=O)cc3)c(OCc3cccc(N(C)C)c3)n2)CC1]

185b

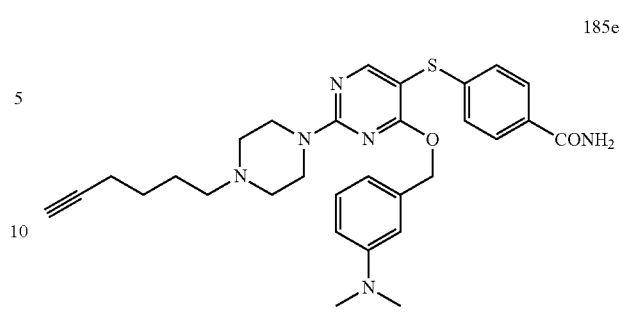

185e 4-((4-((3-(Dimethylamino)benzyl)oxy)-2-(4-isopropylpiperazin-1-yl)pyrimidin-5-yl)thio)benzamide [185b]. A mixture of 184b and KOH (31.0 mg, 0.055 mmol) in t-BuOH (1.5 mL) was heated at 80° C. for 1 h. Solvent was removed under reduced pressure and the residue was purified by preparatory TLC (CH$_2$Cl$_2$: MeOH—NH$_3$ (7 N), 10:1) to afford 9.2 mg (72%) of 185b. $^1$H NMR (600 MHz, CDCl$_3$): δ 8.17 (s, 1H), 7.52 (d, J=10.0 Hz, 2H), 7.04 (t, J=9.6 Hz, 1H), 7.01 (d, J=10.4 Hz, 2H), 6.55 (dd, J=10.0, 2.9 Hz, 1H), 6.51 (s, 1H), 6.47 (d, J=9.2 Hz, 1H), 5.95 (br s, 1H), 5.47 (br s, 1H), 5.26 (s, 2H), 3.82-3.84 (m, 4H), 2.74 (s, 6H), 2.66-2.70 (m, 1H), 2.52-2.54 (m, 4H), 1.02 (d, J=7.9 Hz, 6H); $^{13}$C NMR (150 MHz, CDCl$_3$): δ 168.9, 168.8, 164.9, 161.6, 150.6, 143.8, 137.1, 129.7, 128.9, 127.7, 125.7, 115.8, 112.1, 111.7, 97.6, 68.3, 54.7, 48.5, 44.2, 40.5, 18.4; HRMS (ESI) m/z [M+H]$^+$ calcd. for C$_{27}$H$_{35}$N$_6$O$_2$S, 507.2542; found 507.2543.

4-((4-((3-(Dimethylamino)benzyl)oxy)-2-(4-(hex-5-yn-1-yl)piperazin-1-yl)pyrimidin-5-yl)thio)benzamide [185e]. A mixture of 184e (12 mg, 0.023 mmol) and KOH (28 mg, 0.5 mmol) in t-BuOH (2 mL) was heated at 80° C. for 1 h. Solvent was removed under reduced pressure and the residue was purified by preparatory TLC (CH$_2$Cl$_2$: MeOH—NH$_3$ (7 N), 10:1) to afford 5.7 mg (46%) of 185e. $^1$H NMR (600 MHz, CDCl$_3$) δ 8.25 (s, 1H), 7.59 (d, J=8.4 Hz, 2H), 7.12 (t, J=7.9 Hz, 1H), 7.07 (d, J=8.4 Hz, 2H), 6.61-6.63 (m, 1H), 6.57 (s, 1H), 6.54 (d, J=7.5 Hz, 1H), 6.09 (br s, 1H), 5.68 (br s, 1H), 5.34 (s, 2H), 3.90 (m, 4H), 2.81 (s, 6H), 2.53 (m, 4H), 2.40-2.45 (m, 2H), 2.25 (td, J=7.0, 2.6 Hz, 2H), 1.98 (t, J=2.6 Hz, 1H), 1.64-1.71 (m, 2H), 1.55-1.63 (m, 2H); $^{13}$C NMR (150 MHz, CDCl$_3$) δ 168.8, 165.0, 161.6, 150.5, 143.8, 137.1, 129.5, 129.0, 127.7, 125.5, 115.8, 112.0, 111.6, 97.4, 84.2, 68.6, 68.2, 58.0, 52.9, 43.8, 40.5, 26.3, 25.8, 18.3; HRMS (ESI) m/z [M+H]$^+$ calcd. for C$_{30}$H$_{37}$N$_6$O$_2$S 545.2699; found 545.2701.

Example 23

Scheme 28. Synthesis of 187.

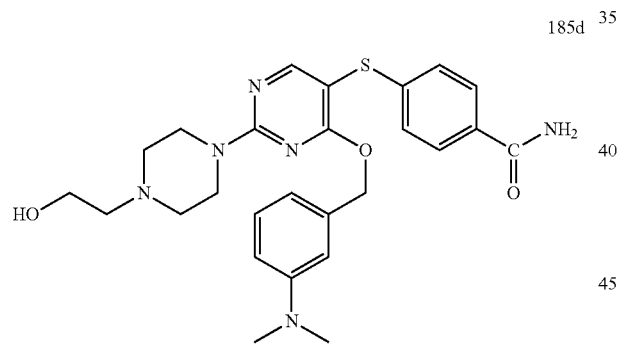

185d

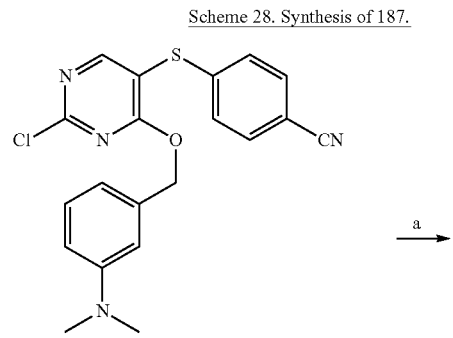

183

4-((4-((3-(Dimethylamino)benzyl)oxy)-2-(4-(2-hydroxyethyl)piperazin-1-yl)pyrimidin-5-yl)thio)benzamide [185d]. A mixture of 184d and KOH (31.0 mg, 0.055 mmol) in t-BuOH (1.5 mL) was heated at 80° C. for 1 h. Solvent was removed under reduced pressure and the residue was purified by preparatory TLC (CH$_2$Cl$_2$: MeOH—NH$_3$ (7 N), 10:1) to afford 10.2 mg (80%) of 185d. $^1$H NMR (600 MHz, CDCl$_3$): δ 8.18 (s, 1H), 7.53 (d, J=8.5 Hz, 2H), 7.05 (t, J=7.5 Hz, 1H), 7.02 (d, J=8.5 Hz, 2H), 6.56 (dd, J=8.5, 2.3 Hz, 1H), 6.51 (s, 1H), 6.47 (d, J=7.6 Hz, 1H), 5.26 (s, 2H), 3.83-3.84 (m, 4H), 3.62-3.63 (m, 4H), 2.74 (s, 6H), 2.53-2.57 (m, 6H); $^{13}$C NMR (150 MHz, CDCl$_3$): δ 169.1, 168.9, 164.9, 161.6, 150.6, 143.7, 137.1, 129.7, 128.9, 127.7, 125.7, 115.8, 112.2, 111.7, 97.9, 68.4, 59.6, 57.7, 43.8, 40.5; HRMS (ESI) m/z [M+H]$^+$ calcd. for C$_{26}$H$_{33}$N$_6$O$_3$S, 509.2335; found 509.2336.

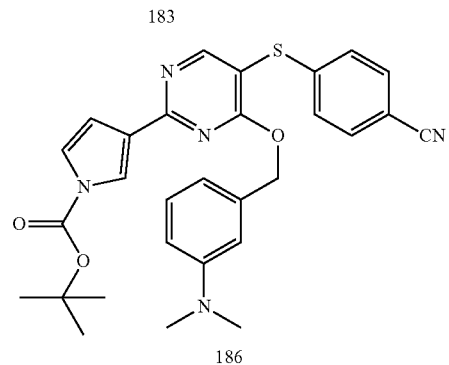

186

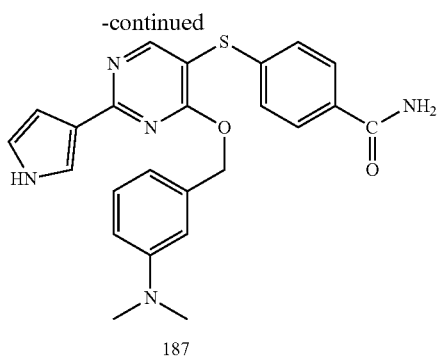

187

Reagents and conditions: a. tert-butyl 3-(4,4,5,5-tetramethyl-1,3,2-dioxaborolan-2-yl)-1H-pyrrole-1-carboxylate, NaHCO₃, PdCl₂(PPh₃)₂, DMF, H₂O, 90° C., 16 h; b. TFA, CH₂Cl₂, rt, 20 h; c. KOH, t-BuOH, 80° C., 1 h.

tert-Butyl 3-(5-((4-cyanophenyl)thio)-4-((3-(dimethylamino)benzyl)oxy)pyrimidin-2-yl)-1H-pyrrole-1-carboxylate [186]. To a solution of 183 (20 mg, 0.038 mmol) in DMF (2 mL) in a round bottomed flask, was added tert-butyl 3-(4,4,5,5-tetramethyl-1,3,2-dioxaborolan-2-yl)-1H-pyrrole-1-carboxylate (18.0 mg, 0.076 mmol) followed by NaHCO₃ (9.5 mg, 0.113 mmol). Then vacuum was applied to the reaction mixture followed by back filling the flask with argon. This vacuum-argon cycle was performed for two more times. Then PdCl₂(PPh₃)₂ (5.3 mg, 0.0076 mmol), and 0.1 mL of degassed distilled H₂O were added to the reaction mixture. The reaction mixture was then subjected to vacuum-argon cycle for two more times and heated at 90° C. for 16 h. Solvent was removed under reduced pressure and the resulting residue was purified by preparatory TLC (hexane: EtOAc, 8:2) to give 10 mg (71%) of 186. MS (m/z): [M+H]⁺ 528.1.

4-((4-((3-(Dimethylamino)benzyl)oxy)-2-(1H-pyrrol-3-yl)pyrimidin-5-yl)thio)benzamide [187]. To 186 (10 mg, 0.019 mmol) dissolved in CH₂Cl₂ (2 mL) was added 140 µL of TFA and the reaction mixture was stirred at rt for 20 h. Solvent was removed under reduced pressure to get residue (MS (m/z): [M+H]⁺ 428.20) and t-BuOH (1 mL) was added followed by KOH (20 mg, 0.36 mmol) and the reaction mixture was heated at 80° C. for 1 h. Solvent was removed under reduced pressure and the residue was purified by preparatory TLC (CH₂Cl₂:MeOH—NH₃ (7 N), 10:1) to afford 5.3 mg (61%) of 187. ¹H NMR (600 MHz, CDCl₃): δ 8.75 (s, 1H), 7.70-7.71 (m, 1H), 7.60 (d, J=8.5 Hz, 2H), 7.14 (d, J=8.5 Hz, 2H), 7.13 (t, J=9.1 Hz, 1H), 6.97-6.98 (m, 1H), 6.85-6.86 (m, 1H), 6.66 (s, 1H), 6.64 (dd, J=9.1, 2.2 Hz, 1H), 6.61 (d, J=9.1, 2.2 Hz, 1H), 5.49 (s, 2H), 2.84 (s, 6H); ¹³C NMR (150 MHz, CDCl₃): δ 173.5, 168.9, 167.9, 163.6, 162.6, 150.6, 141.4, 136.8, 129.1, 127.8, 127.1, 123.9, 121.5, 119.2, 116.4, 112.4, 112.3, 108.9, 108.5, 68.7, 40.6; HRMS (ESI) m/z [M+H]⁺ calcd. for C₂₄H₂₄N₅O₂S, 446.1651; found 446.1647.

Example 24

Scheme 29. Synthesis of 190a, b, d-h, j, k, and m-v.

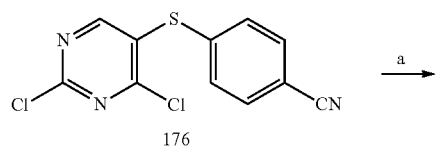

176

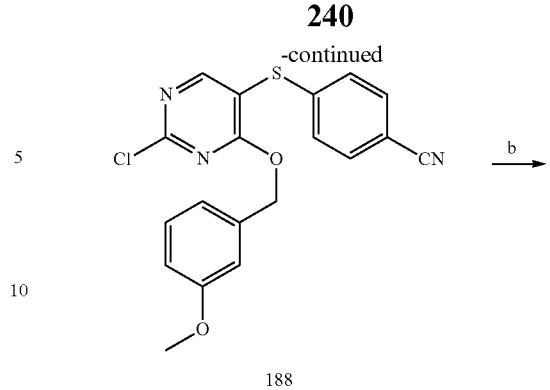

188

Reagents and conditions: a. 3- methoxybenzylalcohol, KOH, 18-crown-6, toluene, rt, 12 h; b. amine, Et₃N, DMF, 90° C., 2 h; c. KOH, t-BuOH, 80° C., 1 h.

4-((2-Chloro-4-((3-methoxybenzyl)oxy)pyrimidin-5-yl)thio)benzonitrile [188]. To 176 (0.3 g, 1.07 mmol) dissolved in toluene (18 mL) was added 3-methoxybenzylalcohol (133 µL, 147.3 mg, 1.07 mmol). KOH (68 mg, 1.28 mmol) was added followed by 18-crown-6 (14.1 mg, 0.054 mmol) and reaction was stirred at rt for 12 h. Then the reaction mixture was concentrated under reduced pressure to give a residue to which 120 mL EtOAc was added. This was transferred to a seperatory funnel and washed with 0.1 N HCl (60 mL) followed by H₂O (2×60 mL), dried over MgSO₄, filtered and concentrated to a solid which was purified by column chromatography (hexane:EtOAc, 90:10 to 80:20) to afford 0.13 g (32%) of 188. ¹H NMR (600 MHz, CDCl₃): δ 8.41 (s, 1H), 7.43 (d, J=8.6 Hz, 2H), 7.18 (t, J=8.2 Hz, 1H), 7.16 (d, J=8.6 Hz, 2H), 6.82 (dd, J=8.2, 1.8 Hz, 1H), 6.70 (d, J=7.7 Hz, 1H), 6.62 (s, 1H), 5.36 (s, 2H), 3.75 (s, 3H); ¹³C NMR (150 MHz, CDCl₃): δ 168.6, 162.7, 160.8, 159.7, 140.7, 135.9, 132.7, 129.7, 128.8, 120.6, 118.5, 114.4, 113.7, 113.4, 110.4, 69.9, 55.3. MS (ESI) m/z [M+H]⁺ 384.2.

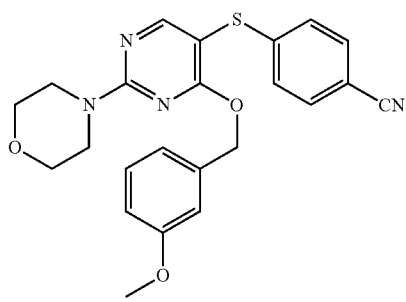

189a 4-((4-((4-((3-Methoxybenzyl)oxy)-2-morpholinopyrimidin-5-yl)thio)benzonitrile [189a]. To 188 (10.0 mg, 0.026 mmol) was added morpholine (2.7 mg, 0.031 mmol) in DMF (2 mL) and heated at 90° C. for 2 h. Solvent was removed under reduced pressure and the residue was used in the next step without further purification. MS (m/z): [M+H]+ 435.37.

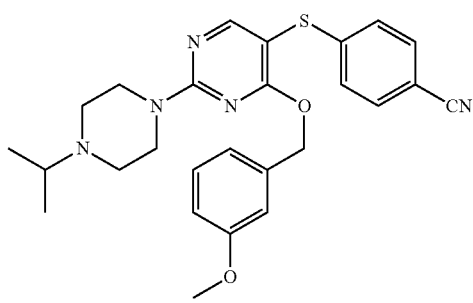

189b 4-((2-(4-Isopropylpiperazin-1-yl)-4-((3-methoxybenzyl)oxy)pyrimidin-5-yl)thio)benzonitrile [189b]. To 188 (10.0 mg, 0.026 mmol) was added N-isopropylpiperazine (4.0 mg, 0.031 mmol) in DMF (2 mL) and heated at 90° C. for 2 h. Solvent was removed under reduced pressure and the residue was used in the next step without further purification. MS (m/z): [M+H]+ 476.2.

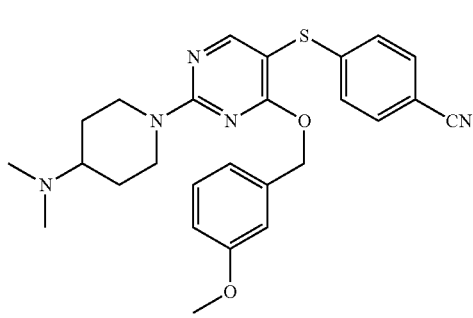

189d 4-((2-(4-(Dimethylamino)piperidin-1-yl)-4-((3-methoxybenzyl)oxy)pyrimidin-5-yl)thio)benzonitrile [189d]. To 188 (9.0 mg, 0.023 mmol) was added N,N-dimethylpiperidin-4-amine (3.9 m g, 0.03 mmol) in DMF (2 mL) and heated at 90° C. for 2 h. Solvent was removed under reduced pressure and and the residue was used in the next step without further purification. MS (m/z): [M+H]+476.2.

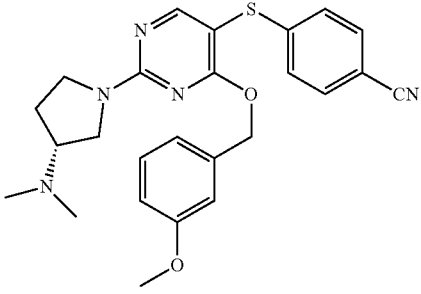

189e (R)-4-((2-(3-(Dimethylamino)pyrrolidin-1-yl)-4-((3-methoxybenzyl)oxy)pyrimidin-5-yl)thio)benzonitrile [189e]. To 188 (9.0 mg, 0.023 mmol) was added (R)—N,N-dimethylpyrrolidin-3-amine (3.4 mg, 0.03 mmol) in DMF (2 mL) and heated at 90° C. for 2 h. Solvent was removed under reduced pressure and the residue was purified by preparatory TLC (CH$_2$Cl$_2$:MeOH, 10:1) to afford 9.7 mg (89%) of 189e. MS (m/z): [M+H]+ 462.1.

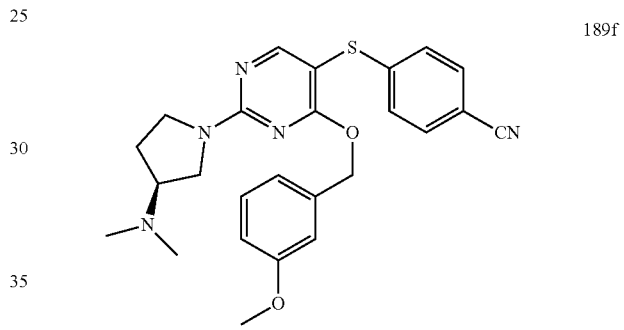

189f (S)-4-((2-(3-(Dimethylamino)pyrrolidin-1-yl)-4-((3-methoxybenzyl)oxy)pyrimidin-5-yl)thio)benzonitrile [189f]. To 188 (9.0 mg, 0.023 mmol) was added (S)—N,N-dimethylpyrrolidin-3-amine (3.4 mg, 0.03 mmol) in DMF (2 mL) and heated at 90° C. for 2 h. Solvent was removed under reduced pressure and the residue was purified by prepatory TLC (CH$_2$Cl$_2$:MeOH, 10:1) to afford 9.5 mg (88%) of 189f. MS (m/z): [M+H]+ 462.2.

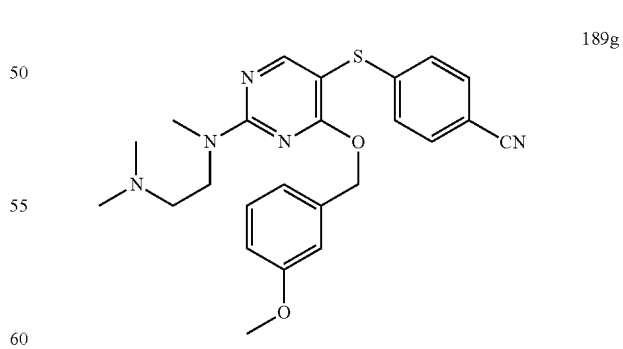

189g 4-((2-((2-(Dimethylamino)ethyl)(methyl)amino)-4-((3-methoxybenzyl)oxy)pyrimidin-5-yl)thio)benzonitrile [189g]. To 188 (9.0 mg, 0.023 mmol) was added N$^1$,N$^1$,N$^2$-trimethylethane-1,2-diamine (3.1 mg, 0.03 mmol) in DMF (2 mL) and heated at 90° C. for 2 h. Solvent was removed under reduced pressure and the residue was purified by prepatory TLC (CH$_2$Cl$_2$:MeOH—NH$_3$ (7 N), 20:1) to afford 7 mg (66%) of 189g. MS (m/z): [M+H]$^+$ 450.2.

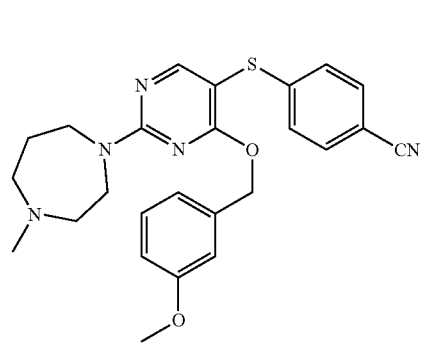

189h 4-((4-((3-Methoxybenzy)oxy)-2-(4-methyl-1,4-diazepan-1-yl)pyrimidin-5-yl)thio)benzonitrile [189h]. To 188 (9.0 mg, 0.023 mmol) was added 1-methyl-1,4-diazepane (3.9 mg, 0.03 mmol) in DMF (2 mL) and heated at 90° C. for 2 h. Solvent was removed under reduced pressure and the residue was purified by preparatory TLC (CH$_2$Cl$_2$:MeOH, 10:1) to afford 10.1 mg (93%) of 189h. MS (m/z): [M+H]$^+$ 462.1.

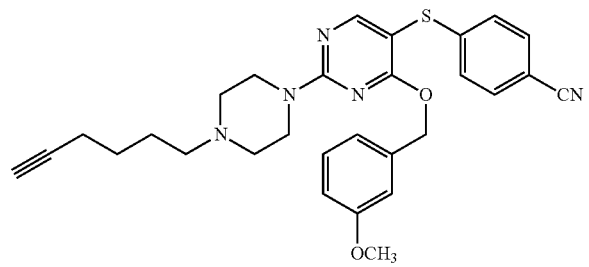

189j 4-((2-(4-(Hex-5-yn-1-yl)piperazin-1-yl)-4-((3-methoxybenzyl)oxy)pyrimidin-5-yl)thio)benzonitrile [189j]. To 188 (20 mg, 0.0521 mmol) was added 1-(hex-5-yn-1-yl)piperazine (17.3 mg, 0.104 mmol) and Et$_3$N (100 µL, 0.72 mmol) in DMF (3 mL) and stirred at rt for overnight. Solvent was removed under reduced pressure and the residue was purified by preparatory TLC (CH$_2$Cl$_2$:MeOH, 10:1) to afford 24.6 mg (92%) of 189j. $^1$H NMR (500 MHz, CDCl$_3$): δ 8.16 (s, 1H), 7.34 (d, J=8.6 Hz, 2H), 7.10 (t, J=7.9 Hz, 1H), 7.02 (d, J=8.6 Hz, 2H), 6.72 (dd, J=8.2, 2.5 Hz, 1H), 6.66 (d, J=7.6 Hz, 1H), 6.59 (s, 1H), 5.22 (s, 2H), 3.79-3.81 (m, 4H), 3.65 (s, 3H), 2.43-2.45 (m, 4H), 2.35 (t, J=7.6 Hz, 2H), 2.17 (td, J=7.0, 2.7 Hz, 2H), 1.89 (t, J=2.6 Hz, 1H), 1.60 (m, 2H), 1.52 (m, 2H); MS (m/z): [M+H]$^+$ 514.3.

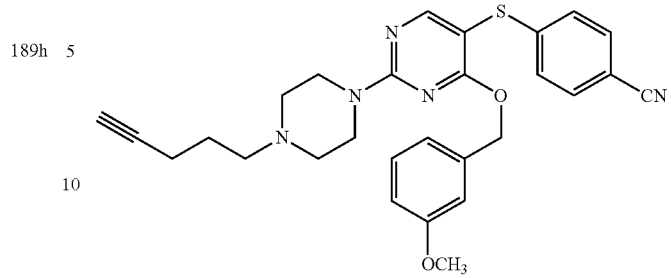

189k 4-((4-((3-Methoxybenzyl)oxy)-2-(4-(pent-4-yn-1-yl)piperazin-1-yl)pyrimidin-5-yl)thio)benzonitrile [189k]. To 188 (15 mg, 0.039 mmol) was added 1-(pent-4-yn-1-yl)piperazine (7.6 mg, 0.05 mmol) and Et$_3$N (10 µL, 0.072 mmol) in DMF (3 mL) and heated at 90° C. for 3 h. Solvent was removed under reduced pressure and the residue was purified by preparatory TLC (CH$_2$Cl$_2$:MeOH, 30:1) to afford 18 mg (92%) of 189k. MS (ESI) m/z [M+H]$^+$ 500.3.

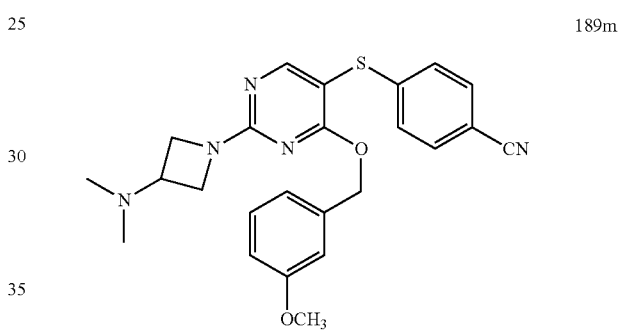

189m 4-((2-(3-(Dimethylamino)azetidin-1-yl)-4-((3-methoxybenzyl)oxy)pyrimidin-5-yl)thio)benzonitrile [189m]. To 188 (10 mg, 0.026 mmol) was added N,N-dimethylazetidin-3-amine (13 mg, 0.13 mmol) and Et$_3$N (20 µl, 0.144 mmol) in DMF (3 mL) and heated at 90° C. for 3 h. Solvent was removed under reduced pressure and the residue was purified by preparatory TLC (CH$_2$Cl$_2$:MeOH, 30:1) to afford 189m in quantitative yield. $^1$H NMR (500 MHz, CDCl$_3$): δ 8.15 (s, 1H), 7.34 (d, J=8.5 Hz, 2H), 7.10 (t, J=7.9 Hz, 1H), 6.99 (d, J=8.5 Hz, 2H), 6.72 (dd, J=8.2, 2.4, 1H), 6.67 (d, J=7.6 Hz, 1H), 6.61 (s, 1H), 5.26 (s, 2H), 4.12 (dd, J=9.4, 8.5 Hz, 2H), 3.96 (dd, J=9.4, 7.3 Hz, 2H), 3.66 (s, 3H), 3.16 (quintet, J=5.5 Hz, 1H), 2.19 (s, 6H); MS (ESI) m/z [M+H]$^+$ 448.0.

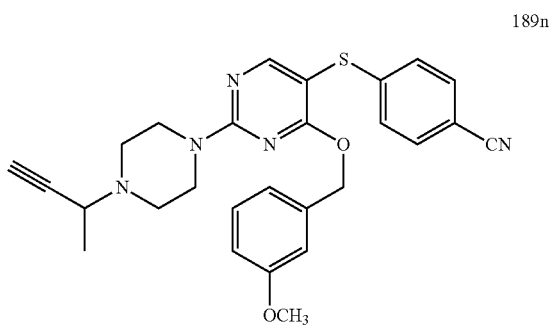 [SMILES: C#CC(C)N1CCN(c2ncc(Sc3ccc(C#N)cc3)c(OCc3cccc(OC)c3)n2)CC1]

189n

4-((2-(4-(But-3-yn-2-yl)piperazin-1-yl)-4-((3-methoxybenzyl)oxy)pyrimidin-5-yl)thio)benzonitrile [189n].

To 188 (10 mg, 0.026 mmol) was added 1-(but-3-yn-2-yl)piperazine (18 mg, 0.13 mmol) and Et$_3$N (200 µl, 1.44 mmol) in DMF (3 mL) and heated at 90° C. for 3 h. Solvent was removed under reduced pressure and the residue was purified by preparatory TLC (CH$_2$Cl$_2$:MeOH, 30:1) to afford 12 mg (94%) of 189n. $^1$H NMR (500 MHz, CDCl$_3$): δ 8.24 (s, 1H), 7.42 (d, J=8.5 Hz, 2H), 7.18 (t, J=7.9 Hz, 1H), 7.10 (d, J=8.5 Hz, 2H), 6.80 (dd, J=8.3, 2.4, 1H), 6.74 (d, J=7.6 Hz, 1H), 6.67 (m, 1H), 5.34 (s, 2H), 3.86-3.95 (m, 4H), 3.72 (s, 3H), 3.55-3.60 (m, 1H), 2.71-2.76 (m, 2H), 2.53-2.57 (m, 2H), 2.29 (d, J=2.1 Hz, 1H), 1.41 (d, J=7.1 Hz, 3H); MS (ESI) m/z [M+H]$^+$ 486.3.

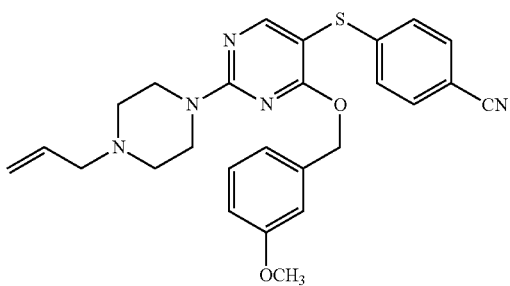

4-((2-(4-Allylpiperazin-1-yl)-4-((3-methoxybenzyl)oxy)pyrimidin-5-yl)thio)benzonitrile [189o].

To 188 (10 mg, 0.026 mmol) was added 1-allylpiperazine (16.4 mg, 0.13 mmol) and Et$_3$N (200 µL, 1.44 mmol) in DMF (3 mL) and heated at 90° C. for 3 h. Solvent was removed under reduced pressure and the residue was purified by preparatory TLC (CH$_2$Cl$_2$:MeOH, 30:1) to afford 11 mg (89%) of 189o. $^1$H NMR (500 MHz, CDCl$_3$): δ 8.24 (s, 1H), 7.42 (d, J=8.4 Hz, 2H), 7.17 (t, J=7.9 Hz, 1H), 7.09 (d, J=8.4 Hz, 2H), 6.79 (dd, J=8.2, 2.2 Hz, 1H), 6.73 (d, J=7.5 Hz, 1H), 6.67 (m, 1H), 5.86-5.93 (m, 1H), 5.33 (s, 2H), 5.17-5.22 (m, 2H), 3.88-3.90 (m, 4H), 3.72 (s, 3H), 3.05 (d, J=6.6 Hz, 2H), 2.50-2.53 (m, 4H); MS (ESI) m/z [M+H]$^+$ 474.1.

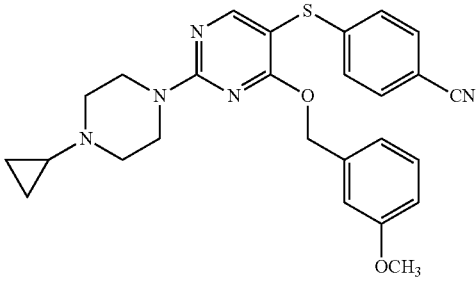

4-((2-(4-Cyclopropylpiperazin-1-yl)-4-((3-methoxybenzyl)oxy)pyrimidin-5-yl)thio) benzonitrile [189p].

To 188 (10 mg, 0.026 mmol) was added 1-cyclopropylpiperazine dihydrochloride (26 mg, 0.130 mmol), DMF (1 mL) and Et$_3$N (50 µL, 0.358 mmol) and the reaction mixture was heated at 90° C. for 2 h. Solvent was removed under reduced pressure and the residue was purified by preparatory TLC (hexane:EtOAc, 1:1) to afford 12 mg (97%) of 189p. MS (m/z): [M+H]$^+$ 474.2.

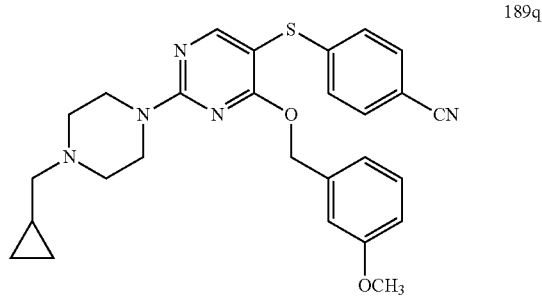 [SMILES: COc1cccc(COc2nc(N3CCN(CC4CC4)CC3)ncc2Sc2ccc(C#N)cc2)c1]

4-((2-(4-(Cyclopropylmethyl)piperazin-1-yl)-4-((3-methoxybenzyl)oxy)pyrimidin-5-yl)thio)benzonitrile [189q].

To 188 (10 mg, 0.026 mmol) in DMF (1 mL) was added 1-(cyclopropylmethyl)piperazine (19.3 µL, 0.130 mmol) and the reaction mixture was heated at 90° C. for 2 h. Solvent was removed under reduced pressure and the residue was purified by preparatory TLC (CH$_2$Cl$_2$:MeOH—NH$_3$ (7 N), 20:1) to afford 9.6 mg (76%) of 189q. MS (m/z): [M+H]$^+$ 488.3.

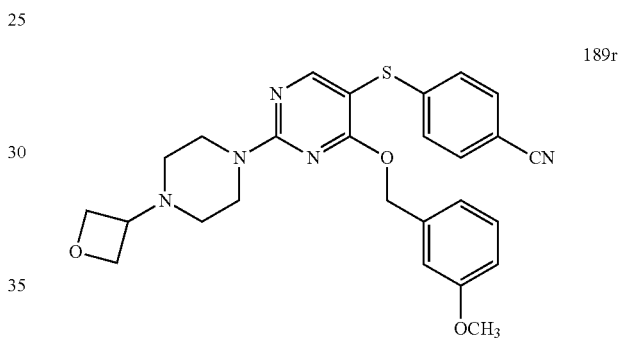

4-((4-((3-Methoxybenzyl)oxy)-2-(4-(oxetan-3-yl)piperazin-1-yl)pyrimidin-5-yl)thio) benzonitrile [189r].

To 188 (14 mg, 0.036 mmol) in DMF (1 mL) was added 1-(oxetan-3-yl)piperazine ditrifluoroacetate (184 mg, 0.50 mmol), and lastly Et$_3$N (50 µL, 0.358 mmol) and the reaction mixture was heated at 90° C. for 4 h. The solvent was removed under reduced pressure and the residue was purified by preparatory TLC (CH$_2$Cl$_2$:MeOH—NH$_3$ (7 N), 40:1) to afford 10 mg (57%) of 189r. MS (m/z): [M+H]$^+$ 490.0.

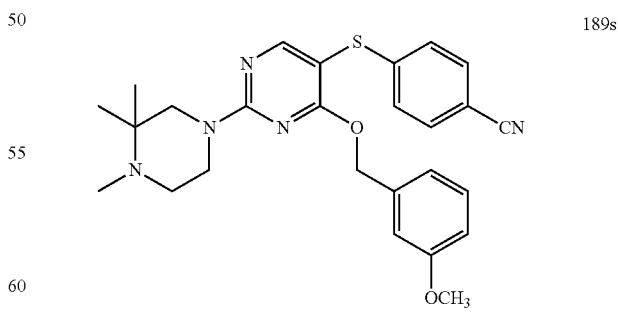

4-((4-((3-Methoxybenzyl)oxy)-2-(3,3,4-trimethylpiperazin-1-yl)pyrimidin-5-yl)thio) benzonitrile [189s].

To 188 (10 mg, 0.026 mmol), 1,2,2-trimethylpiperazine (67 mg, 0.52 mmol) was added DMF (1 mL) and the reaction mixture was heated at 90° C. for 2 h. Solvent was removed under reduced pressure and the residue was purified by preparatory TLC (CH₂Cl₂:MeOH—NH₃ (7 N), 20:1) to afford 7.4 mg (60%) of 189s. MS (m/z): [M+H]⁺ 476.2.

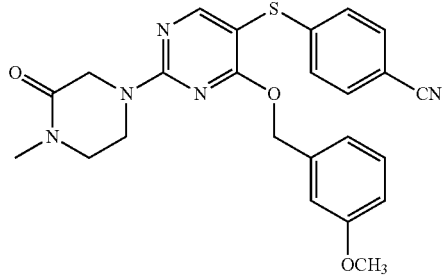

189t 4-((4-((3-Methoxybenzyl)oxy)-2-(4-methyl-3-oxopiperazin-1-yl)pyrimidin-5-yl)thio) benzonitrile [189t]. To 188 (10 mg, 0.026 mmol) in DMF (800 µL) was added 1-methylpiperazin-2-one (14.8 mg, 0.130 mmol) and the reaction mixture was heated at 90° C. for 2 h. Solvent was removed under reduced pressure and the residue was purified by preparatory TLC (CH₂Cl₂:MeOH—NH₃ (7 N), 20:1) to afford 10 mg (83%) of 189t. MS (m/z): [M+H]⁺ 462.1.

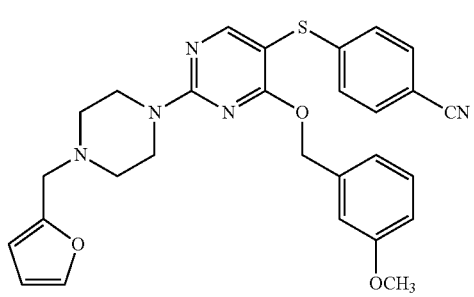

189u 4-((2-(4-(Furan-2-ylmethyl)piperazin-1-yl)-4-((3-methoxybenzyl)oxy)pyrimidin-5-yl)thio)benzonitrile [189u]. To 188 (10 mg, 0.026 mmol) was added 1-(furan-2-ylmethyl)piperazine ditrifluoroacetate (36.4 mg, 0.092 mmol), DMF (1 mL) and Et₃N (50 µL, 0.358 mmol) and the reaction mixture was heated at 90° C. for 2 h. Solvent was removed under reduced pressure and the residue was purified by preparatory TLC (hexane:EtOAc, 1:1) to afford 10 mg (75%) of 189u. MS (m/z): [M+H]⁺ 514.3.

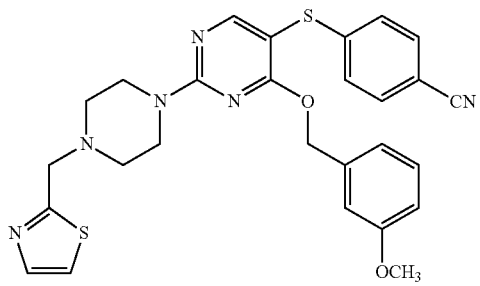

189v 4-((4-((3-Methoxybenzyl)oxy)-2-(4-(thiazol-2-ylmethyl) piperazin-1-yl)pyrimidin-5-yl)thio)benzonitrile [189v]. To 188 (10 mg, 0.026 mmol) was added 2-(piperidin-4-ylmethyl)thiazole ditrifluoroacetate (38.6 mg, 0.094 mmol), DMF (1 mL), and Et₃N (50 µL, 0.358 mmol) and the reaction mixture was heated at 90° C. for 2 h. Solvent was removed under reduced pressure and the residue was purified by preparatory TLC (hexane:EtOAc, 1:1) to afford 12 mg (87%) of 189v. MS (m/z): [M+H]⁺ 531.1.

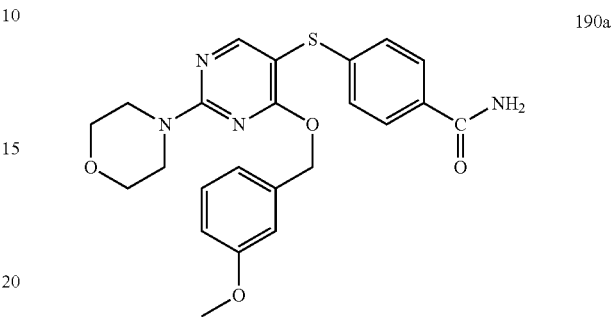

190a 4-((4-((3-Methoxybenzyl)oxy)-2-morpholinopyrimidin-5-yl)thio)benzamide [190a]. A mixture of intermediate 189a (11 mg, 0.025 mmol) and KOH (32.0 mg, 0.057 mmol) in t-BuOH (1.5 mL) was heated at 80° C. for 1 h. Solvent was removed under reduced pressure and the residue was purified by preparatory TLC (CH₂Cl₂: MeOH—NH₃ (7 N), 20:1) to afford 9.4 mg (80%) of 190a. ¹H NMR (600 MHz, CDCl₃): δ 8.28 (s, 1H), 7.62 (d, J=8.6 Hz, 2H), 7.17 (t, J=7.8 Hz, 1H), 7.10 (d, J=8.4 Hz, 2H), 6.78 (d, J=8.1 Hz, 1H), 6.74 (d, J=7.6 Hz, 1H), 6.67 (s, 1H), 6.06 (br s, 1H), 5.68 (br s, 1H), 5.33 (s, 2H), 3.83-3.85 (m, 4H), 3.75-3.77 (m, 4H), 3.68 (s, 3H); ¹³C NMR (150 MHz, CDCl₃): δ 168.8, 168.6, 164.8, 161.7, 159.5, 143.4, 137.8, 129.9, 129.4, 127.7, 125.9, 119.7, 113.2, 113.1, 98.4, 67.7, 66.7, 55.2, 44.3; HRMS (ESI) m/z [M+H]⁺ calcd. for C₂₃H₂₅N₄O₄S, 453.1597; found 453.1599.

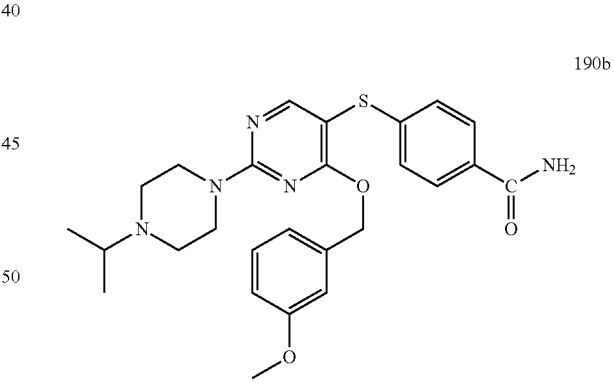

190b 4-((2-(4-Isopropylpiperazin-1-yl)-4-((3-methoxybenzyl) oxy)pyrimidin-5-yl)thio)benzamide [190b]. A mixture of 189b and KOH (32.0 mg, 0.057 mmol) in t-BuOH (1.5 mL) was heated at 80° C. for 1 h. Solvent was removed under reduced pressure and the residue was purified by preparatory TLC (CH₂Cl₂: MeOH—NH₃ (7 N), 20:1) to afford 8.1 mg (64%) of 190b. ¹H NMR (600 MHz, CDCl₃): δ 8.26 (s, 1H), 7.61 (d, J=8.3 Hz, 2H), 7.16 (t, J=7.9 Hz, 1H), 7.10 (d, J=8.4 Hz, 2H), 6.78 (dd, J=8.2, 2.4 Hz, 1H), 6.75 (d, J=7.6 Hz, 1H), 6.68 (s, 1H), 6.05 (br s, 1H), 5.63 (br s, 1H), 5.34 (s, 2H), 3.87-3.88 (m, 4H), 3.68 (s, 3H), 2.75 (septet, J=6.4, 1H), 2.57-2.59 (m, 4H), 1.08 (d, J=6.5 Hz, 6H); ¹³C NMR (150 MHz, CDCl₃): δ 169.0, 168.8, 165.2, 161.8, 159.7, 143.9, 138.1, 130.1, 129.5, 127.9, 126.0, 119.9, 113.5, 113.3, 97.7, 67.8, 55.4, 54.8, 48.6, 44.5, 18.7; HRMS (ESI) m/z [M+H]⁺ calcd. for C₂₆H₃₂N₅O₃S, 494.2226; found 494.2215.

NMR (150 MHz, CDCl₃): δ 168.8, 168.5, 164.9, 160.2, 159.5, 143.8, 138.2, 129.8, 129.3, 127.7, 125.7, 119.9, 113.3, 113.2, 97.3, 67.6, 65.4, 55.2, 51.3, 46.1, 44.4, 30.4; HRMS (ESI) m/z [M+H]⁺ calcd. for C₂₅H₃₀N₅O₃S, 480.2069; found 480.2079.

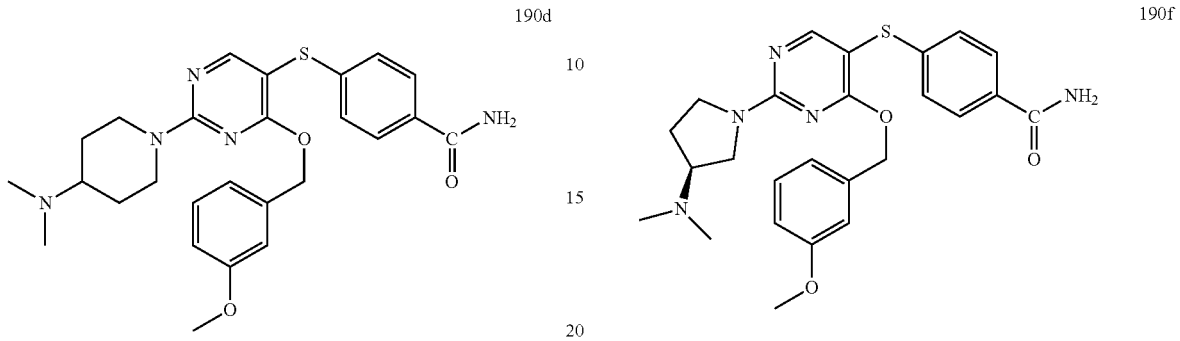

4-((2-(4-(Dimethylamino)piperidin-1-yl)-4-((3-methoxybenzyl)oxy)pyrimidin-5-yl)thio)benzamide [190d]. A mixture of intermediate 189d and KOH (26.0 mg, 0.046 mmol) in t-BuOH (1.5 mL) was heated at 80° C. for 1 h. Solvent was removed under reduced pressure and the residue was purified by preparatory TLC (CH₂Cl₂: MeOH—NH₃ (7 N), 20:1×2) to afford 5.3 mg (53%) of 190d. ¹H NMR (600 MHz, CDCl₃): δ 8.26 (s, 1H), 7.62 (d, J=8.4 Hz, 2H), 7.16 (t, J=7.9 Hz, 1H), 7.11 (d, J=8.3 Hz, 2H), 6.78 (dd, J=8.3, 2.4 Hz, 1H), 6.76 (d, J=8.5 Hz, 1H), 6.68 (s, 1H), 6.05 (br s, 1H), 5.57 (br s, 1H), 5.34 (s, 2H), 4.81 (d, J=13.2 Hz, 2H), 3.68 (s, 3H), 2.88-2.96 (m, 2H), 2.47-2.51 (m, 1H), 2.34 (s, 6H), 1.93-1.95 (m, 2H), 1.43-1.49 (m, 2H); ¹³C NMR (150 MHz, CDCl₃): δ 169.2, 168.6, 164.9, 161.4, 159.5, 143.6, 137.9, 129.8, 129.3, 127.7, 125.8, 119.7, 113.2, 113.1, 97.6, 67.6, 62.5, 55.1, 43.4, 41.3, 27.8; HRMS (ESI) m/z [M+H]⁺ calcd. for C₂₆H₃₂N₅O₃S, 494.2226; found 494.2232.

(S)-4-((2-(3-(Dimethylamino)pyrrolidin-1-yl)-4-((3-methoxybenzyl)oxy)pyrimidin-5-yl)thio)benzamide [190f]. A mixture of 189f (9.5 mg, 0.021 mmol) and KOH (24.0 mg, 0.42 mmol) in t-BuOH (1 mL) was heated at 80° C. for 1 h. Solvent was removed under reduced pressure and the residue was purified by preparatory TLC (CH₂Cl₂:MeOH—NH₃ (7 N), 20:1) to afford 6.4 mg (64%) of 190f. ¹H NMR (600 MHz, CDCl₃): δ 8.27 (s, 1H), 7.61 (d, J=8.3 Hz, 2H), 7.16 (t, J=7.9 Hz, 1H), 7.09 (d, J=8.5 Hz, 2H), 6.77 (dd, J=8.1, 2.2 Hz, 2H), 6.69 (s, 1H), 6.06 (br s, 1H), 5.63 (br s, 1H), 5.36 (s, 2H), 3.84-3.96 (m, 2H), 3.68 (s, 3H), 3.49-3.54 (m, 1H), 3.32-3.35 (m, 1H), 2.77-2.79 (m, 1H), 2.34 (s, 3H), 2.33 (s, 3H), 2.20-2.24 (m, 1H), 1.89-1.93 (m, 1H); ¹³C NMR (150 MHz, CDCl₃): δ 168.8, 168.4, 164.9, 160.2, 159.5, 143.8, 138.2, 129.8, 129.3, 127.7, 125.7, 119.9, 113.3, 113.2, 97.3, 67.6, 65.5, 55.1, 51.3, 46.1, 44.4, 30.4; HRMS (ESI) m/z [M+H]⁺ calcd. for C₂₅H₃₀N₅O₃S, 480.2069; found 480.2063.

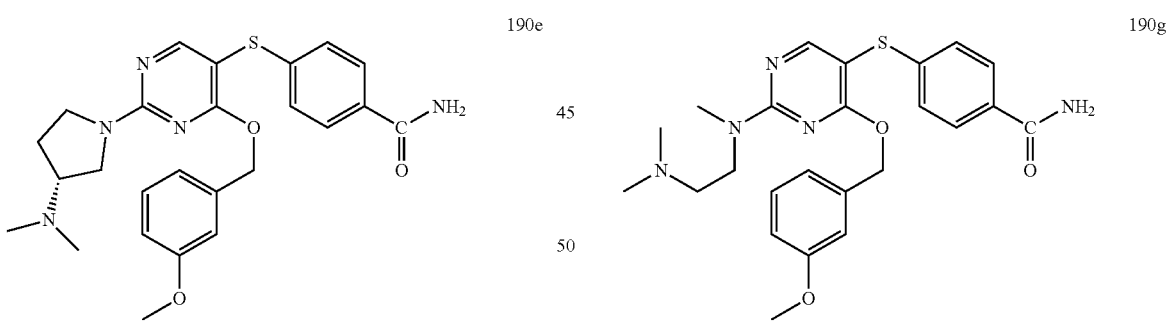

(R)-4-((2-(3-(dimethylamino)pyrrolidin-1-yl)-4-((3-methoxybenzyl)oxy)pyrimidin-5-yl)thio)benzamide [190e]. A mixture of 189e (9.7 mg, 0.021 mmol) and KOH (24.0 mg, 0.42 mmol) in t-BuOH (1 mL) was heated at 80° C. for 1 h. Solvent was removed under reduced pressure and the residue was purified by preparatory TLC (CH₂Cl₂:MeOH—NH₃ (7 N), 20:1) to afford 7.0 mg (70%) of 190e. ¹H NMR (600 MHz, CDCl₃): δ 8.27 (s, 1H), 7.61 (d, J=8.1 Hz, 2H), 7.16 (t, J=8.0 Hz, 1H), 7.09 (d, J=8.0 Hz, 2H), 6.77 (dd, J=8.0, 2.0 Hz, 2H), 6.69 (s, 1H), 6.05 (br s, 1H), 5.61 (br s, 1H), 5.36 (s, 2H), 3.82-3.96 (m, 2H), 3.67 (s, 3H), 3.49-3.55 (m, 1H), 3.31-3.35 (m, 1H), 2.76-2.82 (m, 1H), 2.34 (s, 3H), 2.33 (s, 3H), 2.21-2.24 (m, 1H), 1.88-1.95 (m, 1H); ¹³C 4-((2-((2-(Dimethylamino)ethyl)(methyl)amino)-4-((3-methoxybenzyl)oxy)pyrimidin-5-yl)thio)benzamide [190g]. A mixture of 189g (7.0 mg, 0.018 mmol) and KOH (22.5 mg, 0.40 mmol) in t-BuOH (1 mL) was heated at 80° C. for 1 h. Solvent was removed under reduced pressure and the residue was purified by preparatory TLC (CH₂Cl₂:MeOH—NH₃ (7 N), 20:1 then 15:1) to afford 4.7 mg (64%) of 190g. ¹H NMR (600 MHz, CDCl₃): δ 8.26 (s, 1H), 7.63 (d, J=8.1 Hz, 2H), 7.16 (t, J=7.8 Hz, 1H), 7.12 (d, J=7.8 Hz, 2H), 6.78 (dd, J=8.2, 2.3 Hz, 2H), 6.67 (s, 1H), 6.07 (br s, 1H), 5.62 (br s, 1H), 5.36 (s, 2H), 3.81-3.90 (m, 2H), 3.68 (s, 3H), 3.22 (s, 3H), 2.63-2.84 (m, 2H), 2.54 (s, 3H), 2.38 (s, 3H); ¹³C NMR (150 MHz, CDCl₃): δ 168.9, 168.7, 165.0, 162.2, 159.8, 143.8, 138.2, 130.1, 129.6, 127.9, 126.1, 119.4, 113.3, 113.2, 97.9, 67.7, 56.1, 55.4, 45.4, 45.0, 36.2; HRMS (ESI) m/z [M+H]$^+$ calcd. for C$_{25}$H$_{30}$N$_5$O$_3$S, 468.2069; found 468.2074.

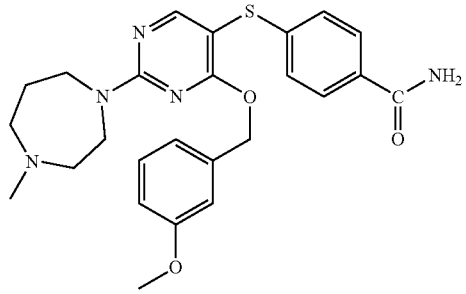

(4-((4-((3-Methoxybenzyl)oxy)-2-(4-methyl-1,4-diazepan-1-yl)pyrimidin-5-yl)thio)benzamide [190h]. A mixture of 189h (10.1 mg, 0.022 mmol) and KOH (24.5 mg, 0.44 mmol) in t-BuOH (1 mL) was heated at 80° C. for 1 h. Solvent was removed under reduced pressure and the residue was purified by preparatory TLC (CH$_2$Cl$_2$:MeOH—NH$_3$ (7 N), 20:1 then 15:1) to afford 6.5 mg (62%) of 190h. $^1$H NMR (600 MHz, CDCl$_3$): δ 8.18 (s, 1H), 7.61 (d, J=8.2 Hz, 2H), 7.09 (t, J=7.8 Hz, 1H), 7.05 (d, J=7.5 Hz, 2H), 6.73 (dd, J=8.2, 2.4 Hz, 1H), 6.67 (d, J=8.5 Hz, 1H), 6.65 (s, 1H), 5.26 (s, 2H), 3.73-3.81 (m, 4H), 3.58 (s, 3H), 3.16-3.17 (m, 2H), 2.61-2.67 (m, 2H), 2.54-2.56 (m, 2H), 2.28 (s, 3H); $^{13}$C NMR (150 MHz, CDCl$_3$): δ 170.0, 169.8, 166.4, 163.1, 160.9, 144.4, 139.8, 131.7, 130.7, 129.3, 126.5, 120.9, 114.5, 114.1, 98.2, 68.9, 58.5, 57.9, 56.0, 47.3, 47.1, 46.8, 27.8; HRMS (ESI) m/z [M+H]$^+$ calcd. for C$_{25}$H$_{30}$N$_5$O$_3$5, 480.2069; found 480.2069.

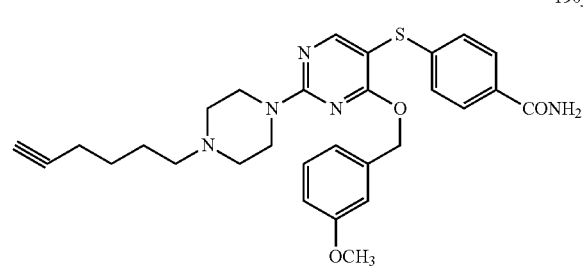

4-((2-(4-(Hex-5-yn-1-yl)piperazin-1-yl)-4-((3-methoxybenzyl)oxy)pyrimidin-5-yl)thio)benzamide [190j]. A mixture of 189j (20 mg, 0.039 mmol) and KOH (48 mg, 0.86 mmol) in t-BuOH (3 mL) was heated at 80° C. for 1 h. Solvent was removed under reduced pressure and the residue was purified by preparatory TLC (CH$_2$Cl$_2$:MeOH—NH$_3$ (7 N), 20:1) to afford 17.2 mg (83%) of 190j. $^1$H NMR (500 MHz, CDCl$_3$) δ 8.26 (s, 1H), 7.61 (d, J=8.5 Hz, 2H), 7.17 (t, J=7.9 Hz, 1H), 7.09 (d, J=8.5 Hz, 2H), 6.77 (dd, J=8.2, 2.5 Hz, 1H), 6.75 (d, J=7.6 Hz, 1H), 6.67 (s, 1H), 6.15 (br s, 1H), 5.93 (br s, 1H), 5.33 (s, 2H), 3.88 (m, 4H), 3.67 (s, 3H), 2.52 (m, 4H), 2.40-2.43 (m, 2H), 2.25 (td, J=7.2, 2.6 Hz, 2H), 1.98 (t, J=2.6 Hz, 1H), 1.63-1.71 (m, 2H), 1.57-1.61 (m, 2H); $^{13}$C NMR (125 MHz, CDCl$_3$) δ 169.1, 168.7, 165.1, 161.7, 159.6, 143.7, 138.0, 130.0, 129.5, 127.9, 125.9, 119.9, 113.4, 113.3, 97.8, 84.4, 68.8, 67.8, 58.2, 55.3, 53.1, 44.0, 26.5, 26.0, 18.5; HRMS (ESI) m/z [M+H]$^+$ calcd. for C$_{29}$H$_{34}$N$_5$O$_3$S 532.2382; found 532.2366.

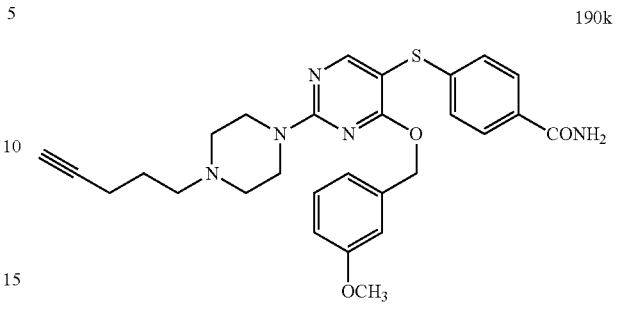

4-((4-((3-Methoxybenzyl)oxy)-2-(4-(pent-4-yn-1-yl)piperazin-1-yl)pyrimidin-5-yl)thio)benzamide [190k]. A mixture of 189k (18 mg, 0.0360 mmol) and KOH (44 mg, 0.792 mmol) in t-BuOH (3 mL) was heated at 80° C. for 1 h. Solvent was removed under reduced pressure and the residue was purified by preparatory TLC (CH$_2$Cl$_2$:MeOH—NH$_3$ (7 N), 20:1) to afford 12.4 mg (67%) of 190k. $^1$H NMR (500 MHz, CDCl$_3$) δ 8.27 (s, 1H), 7.62 (d, J=8.5 Hz, 2H), 7.17 (t, J=7.9 Hz, 1H), 7.11 (d, J=8.5 Hz, 2H), 6.78 (dd, J=8.3, 2.4 Hz, 1H), 6.75 (d, J=7.6 Hz, 1H), 6.69 (s, 1H), 6.05 (br s, 1H), 5.68 (br s, 1H), 5.34 (s, 2H), 3.91 (m, 4H), 3.69 (s, 3H), 2.56 (m, 6H), 2.30 (td, J=7.0, 2.5 Hz, 2H), 1.98 (t, J=2.6 Hz, 1H), 1.80 (m, 2H); $^{13}$C NMR (125 MHz, CDCl$_3$) δ 169.0, 168.8, 165.1, 161.8, 159.8, 143.7, 138.1, 130.2, 129.6, 128.0, 126.1, 120.0, 113.5, 113.4, 84.0, 69.0, 67.9, 57.4, 55.4, 53.6, 53.1, 43.9, 16.6; HRMS (ESI) m/z [M+H]$^+$ calcd. for C$_{28}$H$_{32}$N$_5$O$_3$S 518.2226; found 518.2233.

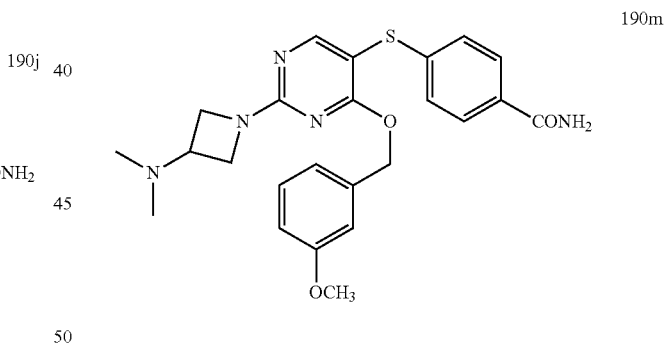

4-((2-(3-(Dimethylamino)azetidin-1-yl)-4-((3-methoxybenzyl)oxy)pyrimidin-5-yl)thio)benzamide [190m]. A mixture of 189m (11.5 mg, 0.026 mmol) and KOH (32 mg, 0.57 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 20:1) to afford 7.1 mg (59%) of 190m. $^1$H NMR (600 MHz, CDCl$_3$) δ 8.25 (s, 1H), 7.61 (d, J=8.5 Hz, 2H), 7.17 (t, J=7.9 Hz, 1H), 7.07 (d, J=8.5 Hz, 2H), 6.74-6.81 (m, 2H), 6.69 (s, 1H), 6.10 (br s, 1H), 5.71 (br s, 1H), 5.34 (s, 2H), 4.19-4.23 (m, 2H), 4.04-4.07 (m, 2H), 3.69 (s, 3H), 3.27 (m, 1H), 2.28 (s, 6H); $^{13}$C NMR (150 MHz, CDCl$_3$) δ 169.03, 168.98, 165.1, 162.7, 159.7, 143.6, 138.0, 130.1, 129.5, 128.0, 126.0, 120.3, 113.7, 113.5, 98.8, 67.9, 56.0, 55.4, 54.3, 42.0; HRMS (ESI) m/z [M+H]$^+$ calcd. for C$_{24}$H$_{28}$N$_5$O$_3$S 466.1913; found 466.1927.

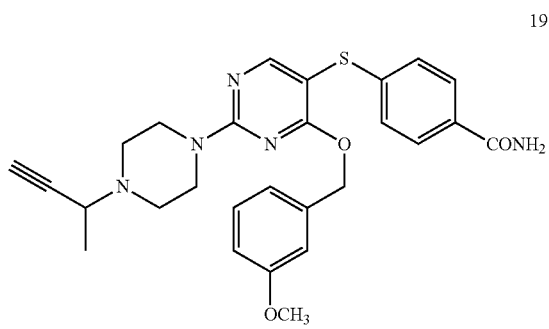

190n 4-((2-(4-(But-3-yn-2-yl)piperazin-1-yl)-4-((3-methoxybenzyl)oxy)pyrimidin-5-yl)thio)benzamide [190n]. A mixture of 189n (12 mg, 0.025 mmol) and KOH (30 mg, 0.54 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 20:1) to afford 8.6 mg (68%) of 190n. $^1$H NMR (600 MHz, CDCl$_3$) δ 8.27 (s, 1H), 7.62 (d, J=8.5 Hz, 2H), 7.17 (t, J=7.9 Hz, 1H), 7.11 (d, J=8.5 Hz, 2H), 6.77-6.80 (m, 1H), 6.75 (d, J=7.5 Hz, 1H), 6.68 (s, 1H), 6.06 (br s, 1H), 5.68 (br s, 1H), 5.34 (s, 2H), 3.85-3.96 (m, 4H), 3.68 (s, 3H), 3.55-3.61 (m, 1H), 2.70-2.77 (m, 2H), 2.52-2.59 (m, 2H), 2.29 (d, J=2.2 Hz, 1H), 1.40 (d, J=7.0 Hz, 3H); $^{13}$C NMR (150 MHz, CDCl$_3$) δ 168.8, 168.6, 164.9, 161.5, 159.5, 143.6, 137.9, 129.9, 129.3, 127.7, 125.8, 119.8, 113.3, 113.1, 97.7, 81.8, 73.1, 67.6, 55.1, 51.8, 48.7, 43.9, 19.1; HRMS (ESI) m/z [M+H]$^+$ calcd. for C$_{27}$H$_{30}$N$_5$O$_3$S 504.2069; found 504.2090.

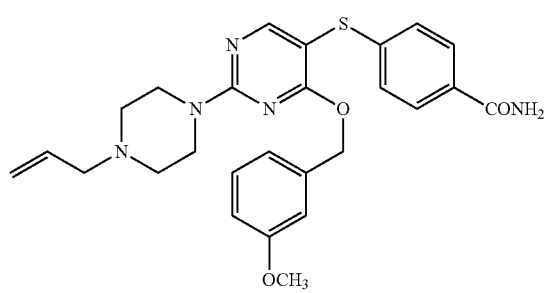

190o 4-((2-(4-Allylpiperazin-1-yl)-4-((3-methoxybenzyl)oxy)pyrimidin-5-yl)thio)benzamide [190o]. A mixture of 189o (11 mg, 0.023 mmol) and KOH (28.3 mg, 0.51 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 20:1) to afford 10.2 mg (90%) of 190o. $^1$H NMR (500 MHz, CDCl$_3$) δ 8.26 (s, 1H), 7.61 (d, J=8.4 Hz, 2H), 7.16 (t, J=7.9 Hz, 1H), 7.10 (d, J=8.4 Hz, 2H), 6.74-6.80 (m, 2H), 6.68 (s, 1H), 6.05 (br s, 1H), 5.85-5.95 (m, 1H), 5.74 (br s, 1H), 5.33 (s, 2H), 5.19-5.24 (m, 2H), 3.87-3.89 (m, 4H), 3.68 (s, 3H), 3.05 (d, J=6.5 Hz, 2H), 2.51-2.53 (m, 4H); $^{13}$C NMR (125 MHz, CDCl$_3$) δ 168.8, 168.6, 164.9, 161.6, 159.6, 143.6, 137.9, 134.6, 130.0, 129.3, 127.7, 125.9, 119.8, 118.5, 113.3, 113.1, 97.8, 67.6, 61.8, 55.2, 52.8, 43.9; HRMS (ESI) m/z [M+H]$^+$ calcd. for C$_{26}$H$_{30}$N$_5$O$_3$S 492.2069; found 492.2052.

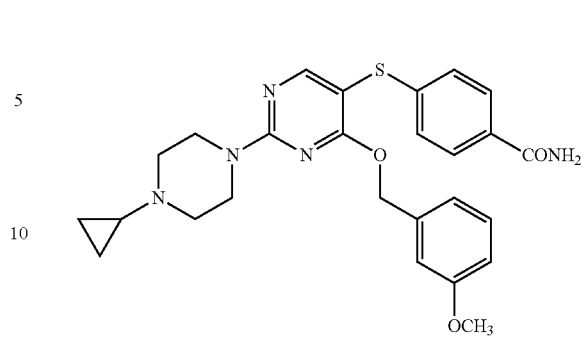

190p 4-((2-(4-Cyclopropylpiperazin-1-yl)-4-((3-methoxybenzyl)oxy)pyrimidin-5-yl)thio) benzamide [190p]. A mixture of 189p (12 mg, 0.025 mmol) and KOH (28.4 mg, 0.50 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 20:1) to afford 8.2 mg (67%) of 190p. $^1$H NMR (600 MHz, CDCl$_3$): δ 8.26 (s, 1H), 7.62 (d, J=8.5 Hz, 2H), 7.16 (t, J=7.9 Hz, 1H), 7.11 (d, J=8.5 Hz, 2H), 6.78 (dd, J=8.2, 2.4 Hz, 1H), 6.76 (d, J=7.6 Hz, 1H), 6.68 (s, 1H), 6.05 (br s, 1H), 5.57 (br s, 1H), 5.34 (s, 2H), 3.83 (m, 4H), 3.68 (s, 3H), 2.67 (m, 4H), 1.65 (m, 1H), 0.48-0.52 (m, 4H); $^{13}$C NMR (150 MHz, CDCl$_3$): δ 168.7, 168.5, 164.9, 161.6, 159.5, 143.6, 137.9, 129.8, 129.3, 127.7, 125.8, 119.7, 113.2, 113.1, 97.6, 67.6, 55.1, 53.1, 43.9, 38.5, 5.9; HRMS (ESI) m/z [M+H]$^+$ calcd. for C$_{26}$H$_{30}$N$_5$O$_3$S, 492.2069; found 492.2051.

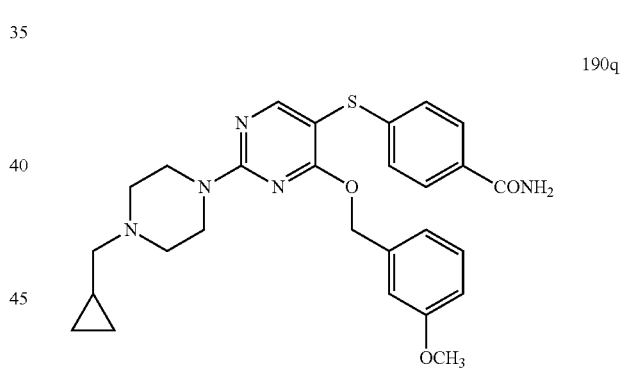

190q 4-((2-(4-(Cyclopropylmethyl)piperazin-1-yl)-4-((3-methoxybenzyl)oxy)pyrimidin-5-yl)thio)benzamide [190q]. A mixture of 189q (9.6 mg, 0.0196 mmol) and KOH (22 mg, 0.392 mmol) in t-BuOH (2 mL) was heated at 80° C. for 2 h. Solvent was removed under reduced pressure and the residue was purified by preparatory TLC (CH$_2$Cl$_2$:MeOH—NH$_3$ (7 N), 20:1) to afford 8.0 mg (81%) of 190q. $^1$H NMR (600 MHz, CDCl$_3$): δ 8.26 (s, 1H), 7.62 (d, J=8.5 Hz, 2H), 7.16 (t, J=7.9 Hz, 1H), 7.11 (d, J=8.5 Hz, 2H), 6.78 (dd, J=8.2, 2.3 Hz, 1H), 6.76 (d, J=7.6 Hz, 1H), 6.68 (s, 1H), 6.03 (br s, 1H), 5.57 (br s, 1H), 5.33 (s, 2H), 3.91 (m, 4H), 3.68 (s, 3H), 2.61 (m, 4H), 2.33 (m, 2H), 0.92 (m, 1H), 0.56 (m, 2H), 0.15 (m, 2H); $^{13}$C NMR (150 MHz, CDCl$_3$): δ 168.7, 168.5, 164.9, 161.5, 159.5, 143.5, 137.8, 129.8, 129.3, 127.7, 125.8, 119.7, 113.2, 113.1, 97.7, 67.6, 63.7, 55.1, 52.9, 43.8, 8.2, 4.0; HRMS (ESI) m/z [M+H]$^+$ calcd. for C$_{27}$H$_{32}$N$_5$O$_3$S, 506.2226; found 506.2209.

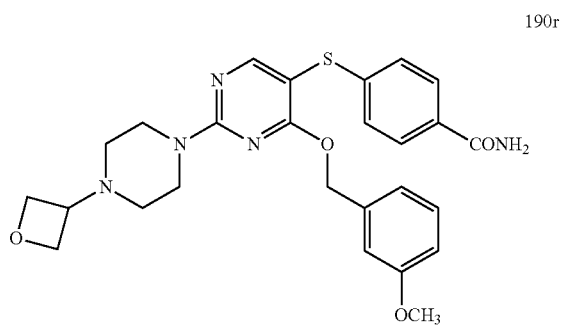 [SMILES: COc1cccc(COc2nc(N3CCN(C4COC4)CC3)ncc2Sc2ccc(C(N)=O)cc2)c1]

190r

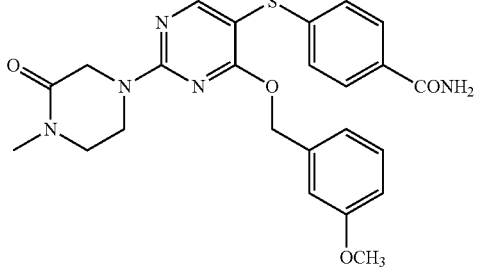

190t 4-((4-((3-Methoxybenzyl)oxy)-2-(4-(oxetan-3-yl)piperazin-1-yl)pyrimidin-5-yl)thio)benzamide [190r]. A mixture of 189r (10 mg, 0.020 mmol) and KOH (22.4 mg, 0.4 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 20:1) to afford 4.5 mg (44%) of 190r. $^1$H NMR (600 MHz, MeOH-d$_4$): δ 8.25 (s, 1H), 7.72 (d, J=3.3 Hz, 2H), 7.14 (t, J=7.9 Hz, 1H), 7.10 (d, J=8.5 Hz, 2H), 6.78 (dd, J=8.1, 2.4 Hz, 1H), 6.72 (d, J=8.1 Hz, 1H), 6.68 (s, 1H), 5.32 (s, 2H), 4.71 (t, J=6.7 Hz, 2H), 4.64 (t, J=6.2 Hz, 2H), 3.90 (m, 4H) 3.64 (s, 3H), 3.51-3.55 (m, 1H), 2.42 (m, 4H); $^{13}$C NMR (150 MHz, MeOH-d$_4$): δ 171.7, 170.1, 165.9, 162.9, 161.1, 144.6, 139.4, 131.7, 130.4, 129.2, 126.8, 120.6, 114.3, 113.9, 99.8, 76.5, 68.9, 60.3, 55.6, 50.4, 44.6; HRMS (ESI) m/z [M+H]$^+$ calcd. for C$_{26}$H$_{30}$N$_5$O$_4$S, 508.2019; found 508.2014.

4-((4-((3-Methoxybenzyl)oxy)-2-(4-methyl-3-oxopiperazin-1-yl)pyrimidin-5-yl)thio) benzamide [190t]. A mixture of 189t (10 mg, 0.021 mmol) and KOH (24.2 mg, 0.433 mmol) in t-BuOH (2 mL) was heated at 80° C. for 45 minutes. Solvent was removed under reduced pressure and the residue was purified by preparatory TLC (CH$_2$Cl$_2$:MeOH—NH$_3$ (7 N), 20:1) to afford 3.0 mg (30%) of 190t. $^1$H NMR (600 MHz, MeOH-d$_4$): δ 8.30 (s, 1H), 7.72 (d, J=8.6 Hz, 2H), 7.14 (t, J=7.9 Hz, 1H), 7.11 (d, J=8.6 Hz, 2H), 6.78 (dd, J=8.2, 2.3 Hz, 1H), 6.72 (d, J=7.6 Hz, 1H), 6.69 (s, 1H), 5.36 (s, 2H), 4.40 (s, 2H), 4.10 (t, J=5.4 Hz, 2H), 3.65 (s, 3H), 3.47 (t, J=5.4 Hz, 2H), 3.01 (s, 3H); $^{13}$C NMR (150 MHz, MeOH-d$_4$): δ 171.6, 170.2, 168.4, 165.9, 162.2, 161.2, 144.3, 139.3, 131.8, 130.4, 129.3, 126.9, 120.6, 114.5, 113.8, 100.9, 69.1, 55.6, 41.7, 34.7; HRMS (ESI) m/z [M+H]$^+$ calcd. for C$_{24}$H$_{26}$N$_5$O$_4$S, 480.1706; found 480.1702.

190s

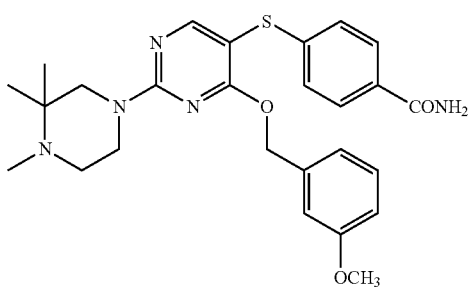

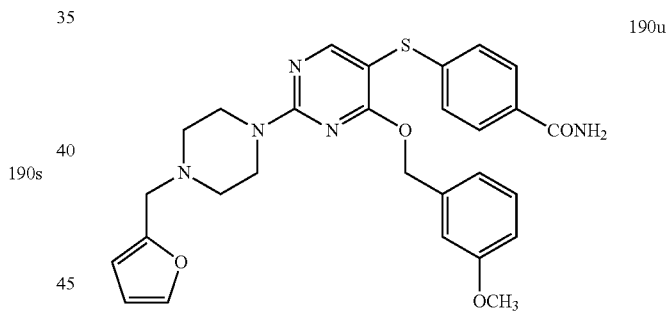

190u 4-((4-((3-Methoxybenzyl)oxy)-2-(3,3,4-trimethylpiperazin-1-yl)pyrimidin-5-yl)thio) benzamide [190s]. A mixture of 189s (7.4 mg, 0.015 mmol) and KOH (16.8 mg, 0.3 mmol) in t-BuOH (1.5 mL) was heated at 80° C. for 1h. Solvent was removed under reduced pressure and the residue was purified by preparatory TLC (CH$_2$Cl$_2$:MeOH—NH$_3$ (7 N), 15:1) to afford 6.9 mg (93%) of 190s. MS (m/z): [M+H]$^+$ 494.1.

4-((2-(4-(Furan-2-ylmethyl)piperazin-1-yl)-4-((3-methoxybenzyl)oxy)pyrimidin-5-yl)thio)benzamide [190u]. A mixture of 189u (10 mg, 0.0194 mmol) and KOH (22 mg, 0.39 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 20:1) to afford 8.8 mg (85%) of 190u. $^1$H NMR (600 MHz, CDCl$_3$): δ 8.26 (s, 1H), 7.62 (d, J=8.5 Hz, 2H), 7.41 (m, 1H), 7.16 (t, J=7.9 Hz, 1H), 7.10 (d, J=8.5 Hz, 2H), 6.78 (dd, J=8.2, 2.3 Hz, 1H), 6.74 (d, J=7.6 Hz, 1H), 6.66 (s, 1H), 6.34 (m, 1H), 6.24 (d, J=3.0 Hz, 1H), 6.03 (br s, 1H), 5.60 (br s, 1H), 5.44 (s, 2H), 3.90 (m, 4H), 3.66 (s, 3H), 3.61 (s, 2H), 2.54 (m, 4H); $^{13}$C NMR (150 MHz, CDCl$_3$): δ 168.7, 168.5, 164.9, 161.5, 159.5, 143.5, 142.4, 137.8, 129.8, 129.3, 127.7, 125.8, 119.7, 113.2, 113.1, 110.1, 109.1, 97.7, 67.6, 55.1, 54.8, 52.8, 43.7; HRMS (ESI) m/z [M+H]$^+$ calcd. for C$_{28}$H$_{30}$N$_5$O$_4$S, 532.2019; found 532.2020.

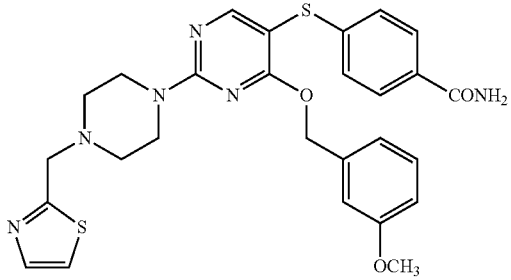

190v 4-((4-((3-Methoxybenzyl)oxy)-2-(4-(thiazol-2-ylmethyl) piperazin-1-yl)pyrimidin-5-yl)thio)benzamide [190v]. A mixture of 189u (12 mg, 0.023 mmol) and KOH (25.2 mg, 0.45 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 20:1) to afford 9.6 mg (76%) of 190v. $^1$H NMR (600 MHz, CDCl$_3$): δ 8.26 (s, 1H), 7.74 (d, J=3.3 Hz, 1H), 7.62 (d, J=8.5 Hz, 2H), 7.33 (d, J=3.3 Hz, 1H), 7.16 (t, J=7.9 Hz, 1H), 7.11 (d, J=8.5 Hz, 2H), 6.78 (dd, J=8.2, 2.3 Hz, 1H), 6.74 (d, J=7.6 Hz, 1H), 6.68 (s, 1H), 6.05 (br s, 1H), 5.51 (br s, 1H), 5.44 (s, 2H), 4.05 (s, 2H), 3.90 (m, 4H), 3.66 (s, 3H), 2.66 (m, 4H); $^{13}$C NMR (150 MHz, CDCl$_3$): δ 169.4, 168.7, 168.5, 164.9, 161.5, 159.5, 143.5, 142.5, 137.8, 129.9, 129.3, 127.7, 125.8, 119.7, 113.2, 113.1, 97.8, 67.6, 59.5, 55.1, 52.8, 43.9; HRMS (ESI) m/z [M+H]$^+$ calcd. for C$_{27}$H$_{29}$N$_6$O$_3$S$_2$, 549.1743; found 549.1761.

Example 25

Scheme 30. Synthesis of 193.

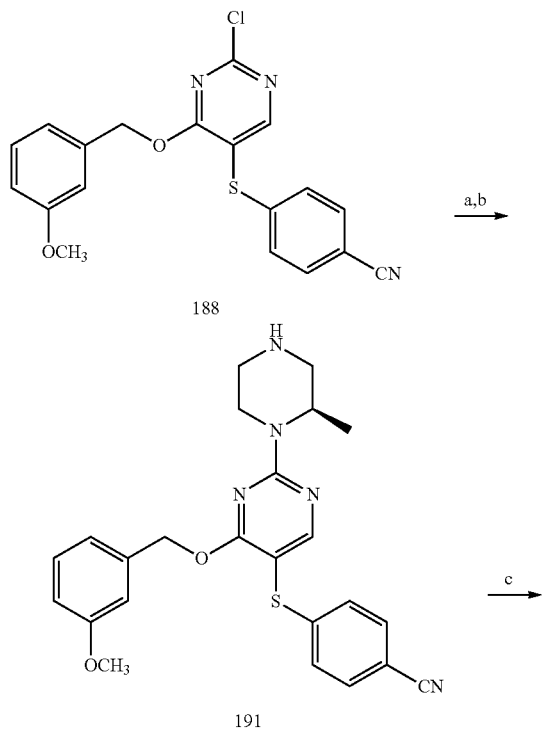

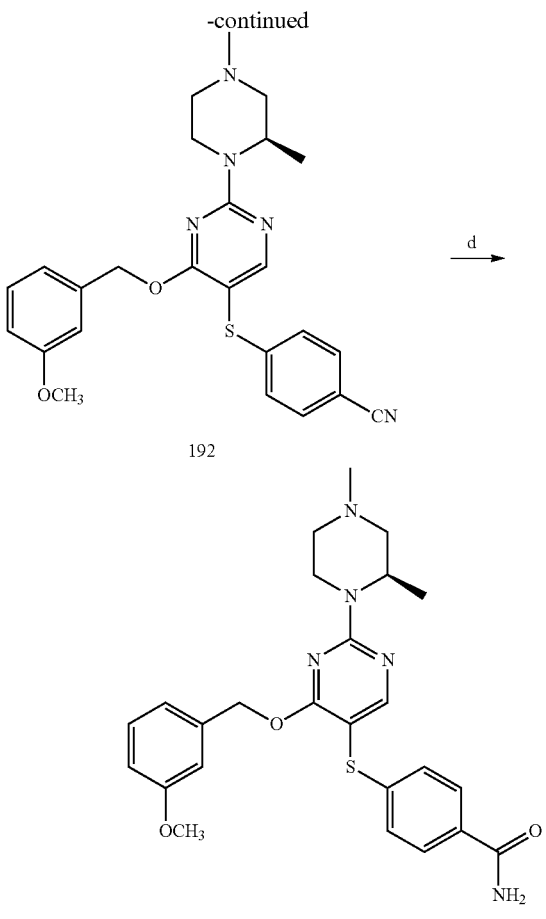

Reagents and conditions: a. (S)-1-N-Boc-2-methylpiperazine, DMF, Et$_3$N, 90° C., 2 h; b. TFA, CH$_2$Cl$_2$, rt, 4 h; c. formalin, sodium cyanoborohydride, sodium acetate, MeOH, 50° C., 5 h; d. KOH, t-BuOH, 80° C., 1 h.

(R)-4-((4-((3-methoxybenzyl)oxy)-2-(2-methylpiperazin-1-yl)pyrimidin-5-yl)thio)benzonitrile [191]. To 188 (15 mg, 0.039 mmol) in DMF (3 mL) was added (S)-1-N-Boc-2-methylpiperazine (9.4 mg, 0.047 mmol) and Et$_3$N (10 μL, 0.072 mmol) and heated at 90° C. for 2 h. Solvent was removed under reduced pressure and the residue was purified by preparatory TLC (CH$_2$Cl$_2$:MeOH, 10:1) to afford Boc-protected intermediate in quantitative yield. To this was added 1 mL of a solution of CH$_2$Cl$_2$:TFA (7:3) and stirred at rt for 4 h. Solvent was removed under reduced pressure and the residue was purified by preparatory TLC (CH$_2$Cl$_2$: MeOH—NH$_3$ (7 N), 20:1) to afford 17 mg (98%) of 191. $^1$H NMR (500 MHz, CDCl$_3$): δ 8.17 (s, 1H), 7.35 (d, J=8.4 Hz, 2H), 7.10 (t, J=7.8 Hz, 1H), 7.04 (d, J=8.4 Hz, 2H), 6.72 (dd, J=8.1, 1.7, 1H), 6.67 (d, J=7.5 Hz, 1H), 6.60 (s, 1H), 5.29 (d, J=12.7 Hz, 1H), 5.24 (d, J=12.7 Hz, 1H), 4.76 (m, 1H), 4.42-4.47 (m, 1H), 3.65 (s, 3H), 3.00-3.12 (m, 2H), 2.84-2.94 (m, 2H), 2.67-2.73 (m, 1H), 1.22 (d, J=6.8 Hz, 3H); MS (ESI) m/z [M+H]$^+$ 448.3.

(R)-4-((2-(2,4-dimethylpiperazin-1-yl)-4-((3-methoxybenzyl)oxy)pyrimidin-5-yl)thio)benzonitrile [192]. To a solution of 191 (17 mg, 0.038 mmol) in MeOH (5 mL) was added formalin (20 μL, 0.269 mmol), sodium acetate (20 mg, 0.244 mmol) and sodium cyanoborohydride (20 mg, 0.095 mmol) and was heated at 50° C. for 5 h. Solvent was removed under reduced pressure and the residue was purified by preparative TLC (CH$_2$Cl$_2$:MeOH, 10:1) to afford 15 mg (86%) of 192. MS (ESI) m/z [M+H]$^+$ 462.2.

(R)-4-((2-(2,4-dimethylpiperazin-1-yl)-4-((3-methoxybenzyl)oxy)pyrimidin-5-yl)thio)benzamide [193]. A mixture of 192 (15 mg, 0.0325 mmol) and KOH (40 mg, 0.71 mmol) in t-BuOH (3 mL) was heated at 80° C. for 1 h. Solvent was removed under reduced pressure and the residue was purified by preparatory TLC (CH$_2$Cl$_2$:MeOH—NH$_3$ (7 N), 20:1) to afford 12.2 mg (78%) of 193. $^1$H NMR (500 MHz, CDCl$_3$) δ 8.28 (s, 1H), 7.62 (d, J=8.2 Hz, 2H), 7.12-7.18 (m, 3H), 6.75-6.79 (m, 2H), 6.69 (s, 1H), 6.07 (br s, 1H), 5.81 (br s, 1H), 5.35 (d, J=12.0 Hz, 1H), 5.29 (d, J=12.0 Hz, 1H), 4.87 (s, 1H), 4.53 (d, J=13.0 Hz, 1H), 3.69 (s, 3H), 3.28 (t, J=12.6 Hz, 1H), 2.90 (d, J=10.6 Hz, 1H), 2.76 (d, J=11.2 Hz, 1H), 2.32 (s, 3H), 2.23 (d, J=10.6 Hz, 1H), 2.03 (t, J=11.5 Hz, 1H), 1.31 (d, J=6.6 Hz, 3H); $^{13}$C NMR (125 MHz, CDCl$_3$) δ 169.1, 168.8, 165.2, 161.5, 159.8, 143.8, 138.2, 130.1, 129.5, 128.0, 126.1, 119.9, 113.4, 113.2, 97.8, 67.8, 60.1, 55.4, 55.3, 47.1, 46.7, 39.3, 15.6; HRMS (ESI) m/z [M+H]$^+$ calcd. for C$_{25}$H$_{30}$N$_5$O$_3$S 480.2069; found 480.2054.

Example 26

4-((4-((3-Methoxybenzyl)oxy)-2-(5-methyl-2,5-diazabicyclo[2.2.1]heptan-2-yl)pyrimidin-5-yl)thio)benzonitrile [194]. To 188 (15.0 mg, 0.039 mmol) in DMF (2 mL) was added a tert-butyl 2,5-diazabicyclo[2.2.1]heptane-2-carboxylate (11.6 mg, 0.0585 mmol) and heated at 90° C. for 2 h. Solvent was removed under reduced pressure and to the residue was added CH$_2$Cl$_2$ (3 mL) followed by TFA (1 mL) dropwise over 5 minutes and the reaction mixture was stirred at rt for 2 h. The reaction mixture was concentrated under reduced pressure and dried under high vacuum overnight. This residue was taken up into CH$_3$OH (3 mL) and to this was added 37% formaldehyde (40 μL, 15 mg, 0.495 mmol), sodium triacetoxyborohydride (35 mg, 0.165 mmol) and sodium acetate (27 mg, 0.330 mmol) and the reaction was heated at 50° C. for 5 h. Solvent was removed under reduced pressure and the residue was purified by preparatory TLC (CH$_2$Cl$_2$:MeOH, 10:1) to afford 16.2 mg (91%) of 194. MS (m/z): [M+H]$^+$ 460.18.

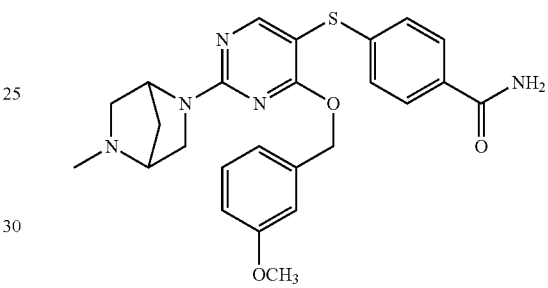

195

4-((4-((2-Aminopyridin-4-yl)methoxy)-2-(5-methyl-2,5-diazabicyclo[2.2.1]heptan-2-yl)pyrimidin-5-yl)thio)benzamide [195]. A mixture of 194 (16.2 mg, 0.0353 mmol) and KOH (39.5 mg, 0.706 mmol) in t-BuOH (3 mL) was heated at 80° C. for 1 h. Solvent was removed under reduced pressure and the residue was purified by preparatory TLC (CH$_2$Cl$_2$:MeOH—NH$_3$ (7 N), 20:1) to afford 10.0 mg (60%) of 195. $^1$H NMR (600 MHz, CDCl$_3$): δ 8.19 (s, 1H), 7.55 (d, J=8.2 Hz, 2H), 7.09 (t, J=7.9 Hz, 1H), 7.03 (d, J=8.2 Hz, 2H), 6.68-6.72 (m, 2H), 6.61 (s, 1H), 5.99 (br s, 1H), 5.62 (br s, 1H), 5.52 (s, 2H), 4.73-4.78 (m, 1H), 3.35-3.74 (m, 3H), 3.61 (s, 3H), 2.96 (m, 1H), 2.50-2.70 (m, 1H), 2.41 (s, 3H), 1.78-1.99 (m, 2H); HRMS (ESI) m/z [M+H]$^+$ calcd. for C$_{25}$H$_{28}$N$_5$O$_3$S, 478.1913; found 478.1897.

Example 27

Scheme 32. Synthesis of 198.

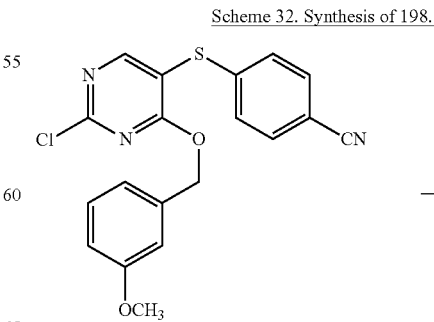

188

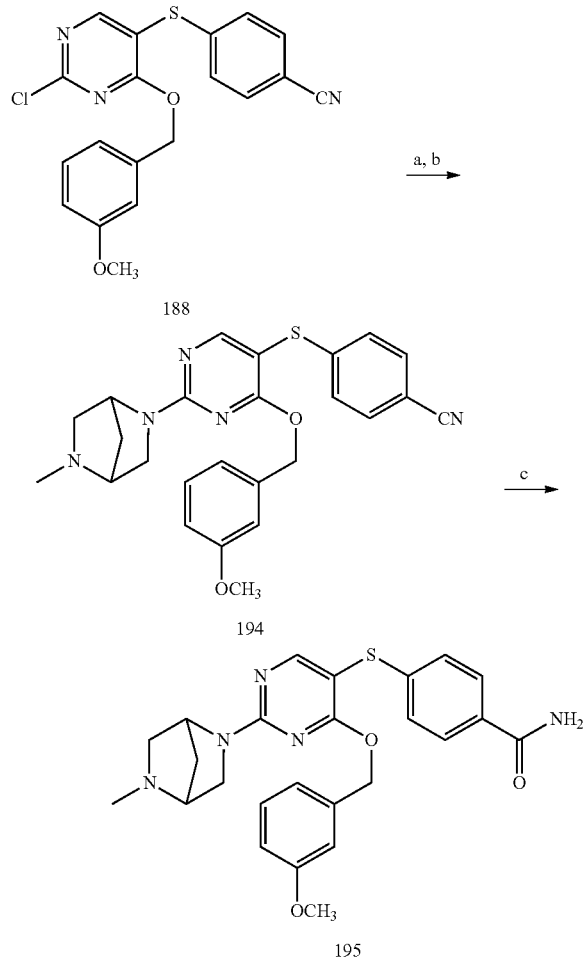

Scheme 31. Synthesis of 195.

Reagents and conditions: a. (i) tert-butyl 2,5-diazabicyclo[2.2.1]heptane-2-carboxylate, DMF, 90° C., 2 h; (ii) TFA, CH$_2$Cl$_2$, rt, 2 h; b. 37% formaldehyde, NaBH(OAc)$_3$, CH$_3$COONa, CH$_3$OH, 50° C., 5 h; c. KOH, t-BuOH, 80° C., 1 h.

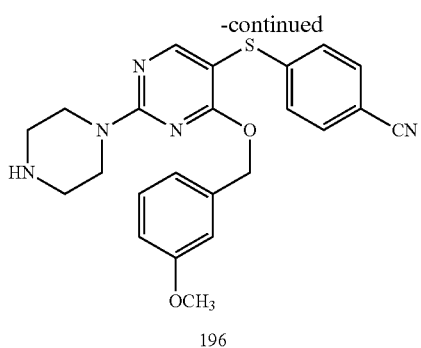

196

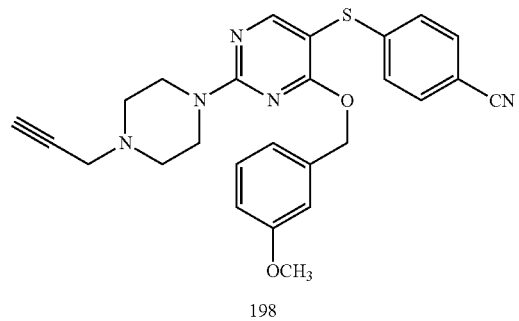

197

198

Reagents and conditions: a.(i) piperazine, Et₃N, DMF. DMF, 90° C., 2 h. (ii) TFA, CH₂Cl₂, rt, 2 h; b. propargyl bromide, Et₃N, DMF, 90° C., 1 h; c. KOH, t-BuOH, 80° C., 1 h.

4-((4-((3-Methoxybenzyl)oxy)-2-(piperazin-1-yl)pyrimidin-5-yl)thio)benzonitrile [196]. To 188 (75 mg, 0.195 mmol) was added piperazine (47 mg, 0.254 mmol) and Et₃N (50 μL, 0.36 mmol) in DMF (4 mL) and heated at 90° C. for 2 h. Solvent was removed under reduced pressure and the residue was purified by preparatory TLC (CH₂Cl₂:MeOH, 10:1) to afford Boc-protected intermediate in quantitative yield. To this was added 5 mL of a solution of CH₂Cl₂:TFA (7:3) and stirred at rt for 2 h. Solvent was removed under reduced pressure and the residue was purified by preparatory TLC (CH₂Cl₂:MeOH—NH₃ (7 N), 20:1) to afford 58 mg (69%) of 196. MS (ESI) m/z [M+H]⁺ 434.3.

4-((4-((3-Methoxybenzyl)oxy)-2-(4-(prop-2-yn-1-yl)piperazin-1-yl)pyrimidin-5-yl)thio)benzonitrile [197]. A mixture of 196 (20 mg, 0.046 mmol), propargyl bromide (80% in toluene; 8.2 mg, 0.055 mol,) and Et₃N (14 mg, 0.138 mmol) in DMF (1 mL) was heated at 90° C. for 1 h. Solvent was removed under reduced pressure and the residue was purified by preparatory TLC (CH₂Cl₂:MeOH—NH₃ (7 N), 30:1) to afford 14 mg (63%) of 197. MS (ESI) m/z [M+H]⁺ 472.3.

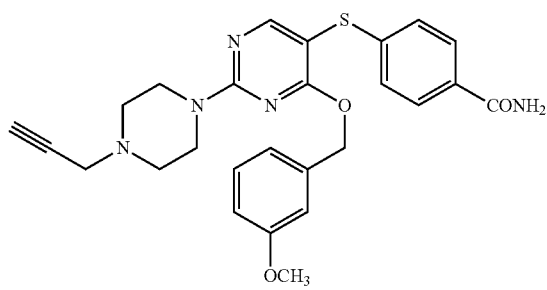

4-((4-((3-Methoxybenzyl)oxy)-2-(4-(prop-2-yn-1-yl)piperazin-1-yl)pyrimidin-5-yl)thio)benzamide [198]. A mixture of 197 (10 mg, 0.021 mmol) and KOH (26 mg, 0.466 mmol) in t-BuOH (3 mL) was heated at 80° C. for 1 h. Solvent was removed under reduced pressure and the residue was purified by preparatory TLC (CH₂Cl₂:MeOH—NH₃ (7 N), 20:1) to afford 3.6 mg (35%) of 198. ¹H NMR (500 MHz, CDCl₃) δ 8.29 (s, 1H), 7.63 (d, J=8.5 Hz, 2H), 7.18 (t, J=7.9 Hz, 1H), 7.12 (d, J=8.5 Hz, 2H), 6.79 (dd, J=8.2, 2.3 Hz, 1H), 6.75 (d, J=7.6 Hz, 1H), 6.68 (s, 1H), 6.04 (br s, 1H), 5.60 (br s, 1H), 5.34 (s, 2H), 4.06 (m, 4H), 3.70 (s, 3H), 3.57 (s, 2H), 2.85 (m, 4H), 2.42 (s, 1H); FIRMS (ESI) m/z [M+H]⁺ calcd. for $C_{26}H_{28}N_5O_3S$ 490.1913; found 490.1899.

Example 28

Scheme 33. Synthesis of 205-208.

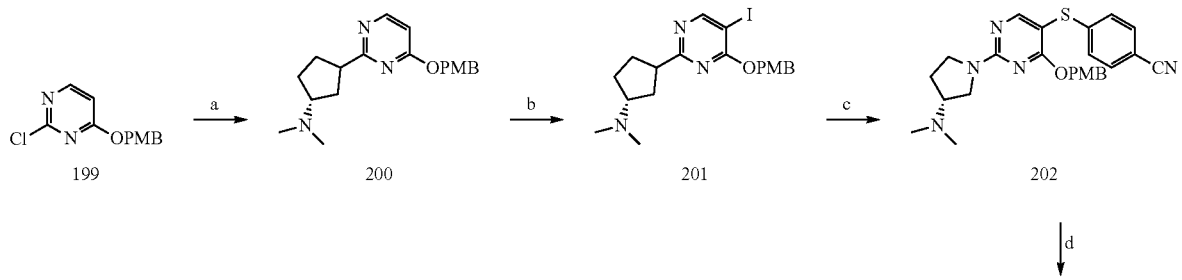

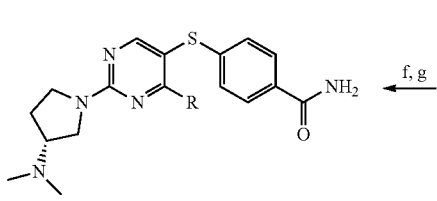 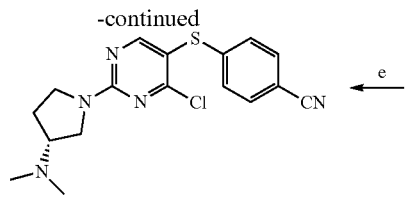 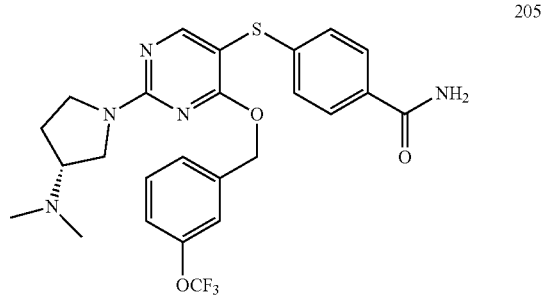 [SMILES: CN(C)[C@@H]1CCN(c2ncc(Sc3ccc(C(N)=O)cc3)c(OCc3cccc(OC(F)(F)F)c3)n2)C1]

Reagents and conditions: a. (R)-N,N-dimethylpyrrolidin-3-amine, DMF, 90° C., 2 h; b. NIS, TFA, ACN, rt; c. 4-mercaptobenzonitrile, copper (I)thiophene-2-carboxylate, $K_2CO_3$, DMF, 120° C., 20 h; d. TFA, $CH_2Cl_2$, rt, 12 h; e. $POCl_3$, 100° C., 1 h; f. ROH, NaH, $CH_3CN$, rt, 3 h; g. KOH, t-BuOH, 80° C., 1 h.

(R)-1-(4-((4-Methoxybenzyl)oxy)pyrimidin-2-yl)-N,N-dimethylpyrrolidin-3-amine [200]. To a solution of 2-chloro-4-((4-methoxybenzyl)oxy)pyrimidine (199; 0.9 g, 3.60 mmol) in DMF (10 mL) was added (R)—N,N-dimethylpyrrolidin-3-amine (0.67 mL, 0.62 g, 5.4 mmol) and heated at 90° C. for 2 h. Solvent was removed under reduced pressure and the crude product was purified by column chromatography ($CH_2Cl_2$:MeOH—$NH_3$ (7 N), 50:1) to give 1.12 g (86%) of an oil 200. $^1$H NMR (500 MHz, $CDCl_3$): δ 8.05 (d, J=5.7 Hz, 1H), 7.37 (d, J=8.5 Hz, 2H), 6.89 (d, J=8.5 Hz, 2H), 5.99 (d, J=5.7, 2H), 5.31 (s, 2H), 3.91-3.96 (m, 1H), 3.83-3.88 (m, 1H), 3.81 (s, 3H), 3.46-3.53 (m, 1H), 3.28-3.32 (m, 1H), 2.73-2.81 (m, 1H), 2.33 (s, 6H), 2.18-2.24 (m, 1H), 1.84-1.95 (m, 1H); $^{13}$C NMR (125 MHz, $CDCl_3$): δ 169.4, 160.3, 159.6, 158.2, 130.1, 129.2, 114.0, 96.4, 67.2, 65.7, 55.5, 51.1, 45.9, 44.6, 30.6; MS (ESI) m/z [M+H]$^+$ 329.2.

(R)-1-(5-Iodo-4-((4-methoxybenzyl)oxy)pyrimidin-2-yl)-N,N-dimethylpyrrolidin-3-amine [201]. To 200 (1.12 g, 3.41 mmol) in acetonitrile (17 mL) was added N-iodosuccinimide (0.917 g, 4.09 mmol) and TFA (1.02 mL, 1.56 g, 13.65 mmol), and the reaction mixture was stirred at rt for 1.5 h. The reaction mixture was basified with $Na_2CO_3$ (pH ~8), concentrated to dryness and the residue was taken up into EtOAc (150 mL) and washed with 10% sodium thiosulfate (50 mL) and brine (2×40 mL). The organic layer was dried over $MgSO_4$, filtered and concentrated to give a residue which was purified by column chromatography ($CH_2Cl_2$:MeOH—$NH_3$ (7 N), 50:1) to yield 1.13 g (76%) of 201. $^1$H NMR (500 MHz, $CDCl_3$): δ 8.26 (s, 1H), 7.38 (d, J=8.6 Hz, 2H), 6.89 (d, J=8.6 Hz, 2H), 5.36 (s, 2H), 3.83-3.89 (m, 1H), 3.81 (s, 3H), 3.73-3.79 (m, 1H), 3.43-3.51 (m, 1H), 3.28-3.33 (m, 1H), 2.78-2.84 (m, 1H), 2.34 (s, 6H), 2.18-2.24 (m, 1H), 1.86-1.96 (m, 1H); MS (ESI) m/z [M+H]$^+$ 455.1.

(R)-4-((2-(3-(dimethylamino)pyrrolidin-1-yl)-4-((4-methoxybenzyl)oxy)pyrimidin-5-yl)thio)benzonitrile [202]. A mixture of 201 (0.7 g, 1.54 mmol), 4-mercaptobenzonitrile (0.25 g, 1.85 mmol) and $K_2CO_3$ (0.64 g, 4.62 mmol) in DMF (20 mL) was evacuated and backfilled with argon three times. Copper(I)thiophene-2-carboxylate (0.12 g, 0.61 mmol) was added and evacuated and backfilled with argon two times and the reaction mixture was heated at 130° C. for 16 h. Solvent was removed under reduced pressure and purified by column chromatography ($CH_2Cl_2$:$CH_3OH$, 10:1) to give 0.42 g (58%) of 202. MS (ESI) m/z [M+H]$^+$ 462.1.

(R)-4-((2-(3-(Dimethylamino)pyrrolidin-1-yl)-4-hydroxypyrimidin-5-yl)thio)benzonitrile [203].3 mL of $CH_2Cl_2$ and 4 mL of TFA was added to 202 (0.42 g, 0.9 mmol) and stirred at rt for 2 h. The reaction mixture was concentrated under reduced pressure and the residue was purified by column chromatography ($CH_2Cl_2$:$CH_3OH$, 10:1) to give 0.30 g (97%) of 203. MS (m/z): [M+H]$^+$ 342.1.

(R)-4-((4-Chloro-2-(3-(dimethylamino)pyrrolidin-1-yl)pyrimidin-5-yl)thio)benzonitrile [204].203 (0.12 g, 0.35 mmol) and $POCl_3$ (2 mL) were heated at 100° C. for 1 h. After cooling to rt, the reaction mixture was added to a beaker containing ice chips. Following complete quenching of $POCl_3$, solid $Na_2CO_3$ was carefully added until pH ~9. This was transferred to a seperatory funnel and extracted with $CH_2Cl_2$ (4×50 mL), dried over $MgSO_4$, filtered and concentrated to a solid which was purified by column chromatography ($CH_2Cl_2$:MeOH, 40:1 to 20:1) to afford 0.12 g (95%) of 204. $^1$H NMR (500 MHz, $CDCl_3$): δ 8.40 (s, 1H), 7.51 (d, J=8.3 Hz, 2H), 7.12 (d, J=8.4 Hz, 2H), 3.94-3.99 (m, 1H), 3.83-3.91 (m, 1H), 3.53-3.60 (m, 1H), 3.41-3.45 (m, 1H), 2.84-2.91 (m, 1H), 2.37 (s, 6H), 2.24-2.30 (m, 1H), 1.96-2.03 (m, 1H); MS (ESI) m/z [M+H]$^+$ 360.10.

(R)-4-((2-(3-(Dimethylamino)pyrrolidin-1-yl)-4-((3-(trifluoromethoxy)benzyl)oxy)pyrimidin-5-yl)thio)benzamide [205]. To (3-(trifluoromethoxy)phenyl)methanol (6.3 μL, 8.1 mg, 0.042 mmol) dissolved in $CH_3CN$ (1 mL) was added NaH (2.8 mg, 0.116 mmol) and the resulting suspension was stirred for 10 min. at rt. Then 204 (10 mg, 0.0289 mmol) was added and the reaction mixture was stirred at rt for 2.5 h. MeOH (1 mL) was added and stirred for 5 minutes then the reaction mixture was concentrated under reduced pressure to give a residue which was partially purified by preparatory TLC ($CH_2Cl_2$:MeOH—$NH_3$ (7 N), 20:1) to afford 8.2 mg of intermediate nitrile (MS (m/z): [M+H]$^+$ 516.2). A mixture of this and KOH (20.0 mg, 0.35 mmol) in t-BuOH (1 mL) was heated at 80° C. for 1 h. Solvent was removed under reduced pressure and the residue was purified by preparatory TLC ($CH_2Cl_2$:MeOH—$NH_3$ (7 N), 10:1) to afford 6.6 mg (78%) of 205. $^1$H NMR (600 MHz, $CDCl_3$): δ 8.23 (s, 1H), 7.64 (d, J=8.5 Hz, 2H), 7.25 (d, J=7.9 Hz, 1H), 7.12 (d, J=8.5 Hz, 2H), 7.09 (d, J=8.7, 1H), 7.07 (t, J=7.3, 1H), 7.05 (s, 1H), 6.00 (br s, 1H), 5.62 (br s, 1H), 5.37 (s, 2H), 3.93-3.99 (m, 1H), 3.78-3.87 (m, 1H), 3.45-3.56 (m, 1H), 3.03-3.40 (m, 1H), 2.77-2.86 (m, 1H), 2.34 (s, 6H), 2.20-2.25 (m, 1H), 1.90-1.96 (m, 1H); $^{13}$C NMR (150 MHz, CDCl$_3$+CD$_3$OD): δ 168.6, 168.2, 165.1, 160.2, 149.1, 143.7, 138.9, 129.9, 129.7, 127.8, 125.7, 125.6, 125.5, 121.9 (q, J=255.6 Hz), 120.2, 119.9, 97.3, 66.7, 65.4, 51.1, 45.9, 44.3, 30.1; HRMS (ESI) m/z [M+H]$^+$ calcd. for C$_{25}$H$_{27}$F$_3$N$_5$O$_3$S, 534.1787; found 534.1782.

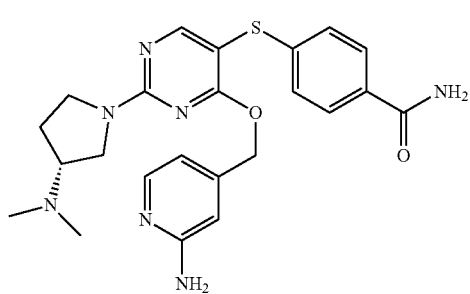

206

(R)-4-((4-((2-Aminopyridin-4-yl)methoxy)-2-(3-(dimethylamino)pyrrolidin-1-yl)pyrimidin-5-yl)thio)benzamide [206]. To ((2-aminopyridin-4-yl)methanol (5.4 mg, 0.042 mmol) dissolved in CH$_3$CN (1 mL) was added NaH (2.8 mg, 0.116 mmol) and the resulting suspension was stirred for 10 min. at rt. Then 204 (10 mg, 0.0289 mmol) was added and the reaction mixture was stirred at rt for 2.5 h. MeOH (1 mL) was added and stirred for 5 minutes then the reaction mixture was concentrated under reduced pressure to give a residue which was purified by preparatory TLC (CH$_2$Cl$_2$:MeOH—NH$_3$ (7 N), 20:1) to afford 8.0 mg of intermediate nitrile (MS (m/z): [M+H]$^+$ 448.2). A mixture of this and KOH (22.0 mg, 0.39 mmol) in t-BuOH (1 mL) was heated at 80° C. for 1 h. Solvent was removed under reduced pressure and the residue was purified by preparatory TLC (CH$_2$Cl$_2$:MeOH—NH$_3$ (7 N), 10:1) to afford 4.8 mg (58%) of 206. $^1$H NMR (600 MHz, CDCl$_3$): δ 8.31 (s, 1H), 7.92 (s, 1H), 7.66 (d, J=8.3 Hz, 2H), 7.17 (d, J=8.2 Hz, 2H), 6.43 (m, 1H), 6.10 (br s, 1H), 5.93 (m, 1H), 5.62 (br s, 1H), 5.25 (s, 2H), 4.46 (br s, 2H), 3.75-3.98 (m, 2H), 3.42-3.56 (m, 1H), 3.27-3.38 (m, 1H), 2.75-2.82 (m, 1H), 2.33 (s, 6H), 2.20-2.25 (m, 1H), 1.86-1.96 (m, 1H); HRMS (ESI) m/z [M+H]$^+$ calcd. for C$_{23}$H$_{28}$N$_7$O$_2$5, 466.2025; found 466.2020.

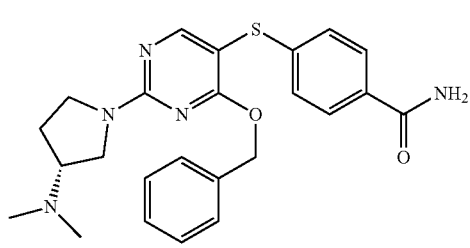

207

(R)-4-((4-(Benzyloxy)-2-(3-(dimethylamino)pyrrolidin-1-yl)pyrimidin-5-yl)thio)benzamide [207]. To benzylalcohol (4.34 μL, 4.54 mg, 0.042 mmol) dissolved in CH$_3$CN (1 mL) was added NaH (2.8 mg, 0.116 mmol) and the resulting suspension was stirred for 10 min. at rt. Then 204 (10 mg, 0.0289 mmol) was added and the reaction mixture was stirred at rt for 2.5 h. MeOH (1 mL) was added and stirred for 5 minutes then the reaction mixture was concentrated under reduced pressure to give a residue which was purified by preparatory TLC (CH$_2$Cl$_2$:MeOH—NH$_3$ (7 N), 20:1) to afford 8.0 mg of intermediate nitrile (MS (m/z): [M+H]$^+$ 432.2). A mixture of this and KOH (22.0 mg, 0.39 mmol) in t-BuOH (1 mL) was heated at 80° C. for 1 h. Solvent was removed under reduced pressure and the residue was purified by preparatory TLC (CH$_2$Cl$_2$:MeOH—NH$_3$ (7 N), 20:1) to afford 5.2 mg (63%) of 207. $^1$H NMR (600 MHz, CDCl$_3$): δ 8.27 (s, 1H), 7.62 (d, J=8.5 Hz, 2H), 7.22-7.24 (m, 3H0, 7.15 (m, 2H), 7.11 (d, J=8.5 Hz, 2H), 5.99 (br s, 1H), 5.62 (br s, 1H), 5.39 (s, 2H), 3.81-3.98 (m, 2H), 3.48-3.55 (m, 1H), 3.31-3.37 (m, 1H), 2.76-2.83 (m, 1H), 2.34 (s, 6H), 2.19-2.25 (m, 1H), 1.88-1.96 (m, 1H); HRMS (ESI) m/z [M+H]$^+$ calcd. for C$_{24}$H$_{28}$N$_5$O$_2$S, 450.1964; found 450.1962.

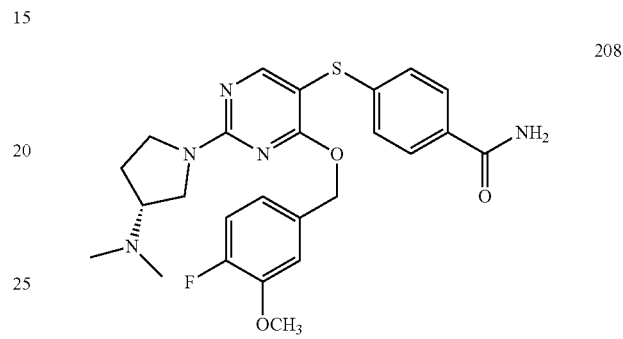

208

(R)-4-((2-(3-(Dimethylamino)pyrrolidin-1-yl)-4-((4-fluoro-3-methoxybenzyl)oxy)pyrimidin-5-yl)thio)benzamide [208]. To (4-fluoro-3-methoxyphenyl)methanol (5.52 μL, 6.6 mg, 0.042 mmol) dissolved in CH$_3$CN (1 mL) was added NaH (2.8 mg, 0.116 mmol) and the resulting suspension was stirred for 10 min. at rt. Then 204 (10 mg, 0.0289 mmol) was added and the reaction mixture was stirred at rt for 2.5 h. MeOH (1 mL) was added and stirred for 5 minutes then the reaction mixture was concentrated under reduced pressure to give a residue which was purified by preparatory TLC (CH$_2$Cl$_2$:MeOH—NH$_3$ (7 N), 20:1) to afford 7.2 mg of intermediate nitrile (MS (m/z): [M+H]$^+$ 480.2). A mixture of this and KOH (18.5 mg, 0.33 mmol) in t-BuOH (1 mL) was heated at 80° C. for 1 h. Solvent was removed under reduced pressure and the residue was purified by preparatory TLC (CH$_2$Cl$_2$:MeOH—NH$_3$ (7 N), 20:1) to afford 4.1 mg (55%) of 208. $^1$H NMR (600 MHz, CDCl$_3$): δ 8.28 (s, 1H), 7.60 (d, J=8.5 Hz, 2H), 7.06 (d, J=8.5 Hz, 2H), 6.93-6.97 (m, 1H), 6.74-6.79 (m, 2H), 6.01 (br s, 1H), 5.55 (br s, 1H), 5.34 (s, 2H), 3.83-3.99 (m, 2H), 3.52-3.57 (m, 1H), 3.35-3.40 (m, 1H), 2.79-2.85 (m, 1H), 2.35 (s, 6H), 2.20-2.27 (m, 1H), 1.92-2.05 (m, 1H); $^{13}$C NMR (150 MHz, CDCl$_3$): δ 168.5, 165.1, 160.3, 152.8, 151.2, 147.5, 143.9, 132.8, 129.7, 127.7, 125.4, 120.6, 115.6, 113.0, 97.1, 67.3, 65.3, 56.1, 51.1, 45.9, 44.3, 30.1; HRMS (ESI) m/z [M+H]$^+$ calcd. for C$_{25}$H$_{29}$FN$_5$O$_3$S, 498.1975; found 498.1980.

Example 29

Scheme 34. Synthesis of 212-214.

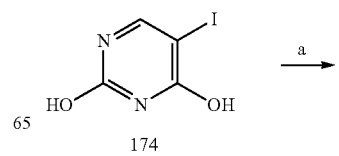

174

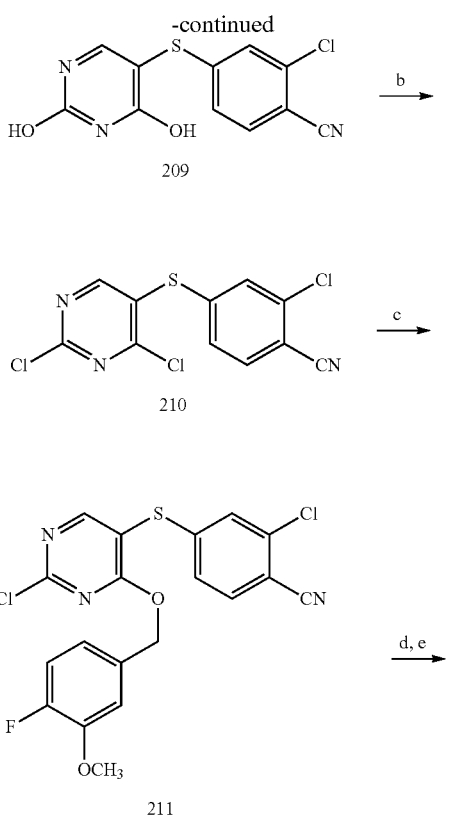

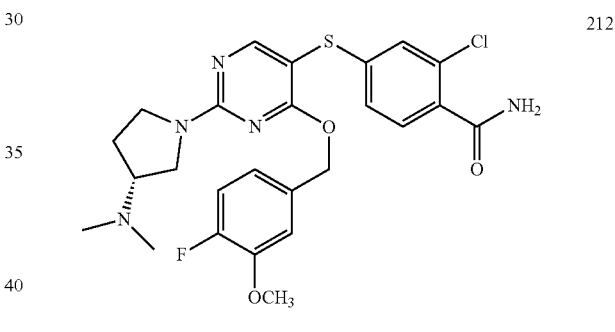

Reagents and conditions: a. 2-chloro-4-mercaptobenzonitrile, copper(I)thiophene-2-carboxylate, K₂CO₃, DMF, 130° C., 16 h; b. POCl₃, DIEA, 100° C., 4 h; c. (4-fluoro-3-methoxyphenyl)methanol, NaH, CH₃CN, rt, 2.5 h; d. amine, Et₃N, DMF, 90° C., 2 h; e. KOH, t-BuOH, 80° C., 1 h.

2-Chloro-4-((2,4-dihydroxypyrimidin-5-yl)thio)benzonitrile [209]. A mixture of 5-iodopyrimidine-2,4-diol (174; 2.7 g, 0.011 mmol), 2-chloro-4-mercaptobenzonitrile (2.5 g, 0.015 mmol) and K₂CO₃ (4.71 g, 0.034 mmol) in DMF (80 mL) was evacuated and backfilled with argon three times. Copper(I)thiophene-2-carboxylate (0.865 g, 0.0046 mmol) was added and evacuated and backfilled with argon two times and the reaction mixture was heated at 130° C. for 16 h. Solvent was removed under reduced pressure and purified by column chromatography (CH₂Cl₂:CH₃OH:CH₃COOH, 15:1:0.1) to give 2.0 g (65%) of 209. MS (ESI) m/z 278.0 [M−H]⁻.

2-Chloro-4-((2,4-dichloropyrimidin-5-yl)thio)benzonitrile [210]. To a mixture of 209 (2.0 g, 7.14 mmol) and POCl₃ (25 mL) was added DIEA (3.11 mL, 2.31 g, 17.9 mmol) and the reaction was heated at 100° C. for 4 h. After cooling to rt, the reaction mixture was added to a beaker containing ice chips. Following complete quenching of POCl₃, solid Na₂CO₃ was carefully added until pH ~9. This was transferred to a seperatory funnel and extracted with CH₂Cl₂ (4×100 mL), dried over MgSO₄, filtered and concentrated to a solid which was purified by column chromatography (hexane:EtOAc, 80:20) to afford 0.935 g (41%) of 210.

2-Chloro-4-((2-chloro-4-((4-fluoro-3-methoxybenzyl)oxy)pyrimidin-5-yl)thio)benzonitrile [211]. To (4-fluoro-3-methoxyphenyl)methanol (75.9 µL, 90.7 mg, 0.5809 mmol) dissolved in CH₃CN (5 mL) was added NaH (17.0 mg, 0.6971 mmol) and the resulting suspension was stirred for 10 min. at rt. Then 210 (183 mg, 0.5809 mmol) was added and the reaction mixture was stirred at rt for 2.5 h. MeOH (1 mL) was added and stirred for 5 minutes then the reaction mixture was concentrated under reduced pressure to give a residue which was purified by preparatory TLC (n-hexane:EtOAc, 8:2) to afford 59.2 mg of 211. ¹H NMR (500 MHz, CDCl₃): δ 8.42 (s, 1H), 7.41 (d, J=8.2 Hz, 1H), 7.09 (s, 1H), 6.92-6.98 (m, 2H), 6.86 (d, J=8.0 Hz, 1H), 6.66-6.84 (m, 1H), 5.32 (s, 2H), 3.79 (s, 3H); ¹³C NMR (125 MHz, CDCl₃): δ 168.7, 163.7, 161.5, 153.7, 151.7, 147.7, 142.8, 134.1, 130.6, 128.4, 126.1, 121.5, 116.4, 115.7, 114.3, 112.1, 111.1, 70.0, 56.4; MS (ESI) m/z [M+H]⁺ 436.0.

(R)-2-Chloro-4-((2-(3-(dimethylamino)pyrrolidin-1-yl)-4-((4-fluoro-3-methoxybenzyl)oxy)pyrimidin-5-yl)thio)benzamide [212]. To 211 (10.0 mg, 0.023 mmol) was added a (R)—N,N-dimethylpyrrolidin-3-amine (11 µL, 10.5 mg, 0.0919 mmol) in DMF (2 mL) and heated at 90° C. for 2 h. Solvent was removed under reduced pressure to give a residue which was purified by preparatory TLC (CH₂Cl₂:MeOH—NH₃ (7 N), 20:1) to afford 8.7 mg (74%) of intermediate nitrile (MS (m/z): [M+H]⁺ 514.1). A mixture of this and KOH (18.0 mg, 0.318 mmol) in t-BuOH (2 mL) was heated at 80° C. for 1 h. Solvent was removed under reduced pressure and the residue was purified by preparatory TLC (CH₂Cl₂:MeOH—NH₃ (7 N), 20:1) to afford 7.2 mg (80%) of 212. ¹H NMR (600 MHz, CD₂Cl₂): δ 8.16 (s, 1H), 7.48 (d, J=8.1 Hz, 1H), 6.90-6.94 (m, 2H), 6.88 (d, J=8.2 Hz, 1H), 6.76 (dd, J=8.2, 1.6 Hz, 1H), 6.71 (s, 1H), 6.27 (br s, 1H), 5.81 (br s, 1H), 5.27 (s, 2H), 3.73-3.88 (m, 2H), 3.63 (s, 3H), 3.42-3.46 (m, 1H), 3.26-3.33 (m, 1H), 2.76-2.80 (m, 1H), 2.26 (s, 3H), 2.25 (s, 3H), 2.12-2.15 (m, 1H), 1.86-2.90 (m, 1H); ¹³C NMR (150 MHz, CD₂Cl₂): δ 168.8, 165.6, 160.9, 153.2, 151.2, 147.8, 144.5, 133.4, 131.7, 131.1, 130.6, 126.9, 124.5, 120.6, 116.1, 113.4, 96.5, 67.7, 65.6, 56.5, 51.3, 46.4, 44.3, 30.2; FIRMS (ESI) m/z [M+H]⁺ calcd. for C₂₅H₂₈ClFN₅O₃S, 532.1585; found 532.1592.

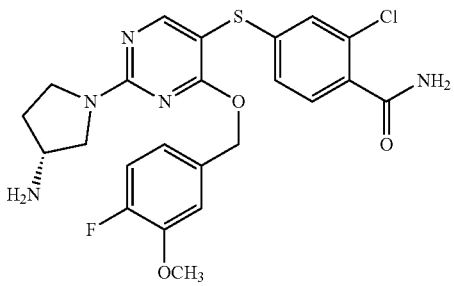

(R)-4-((2-(3-Aminopyrrolidin-1-yl)-4-((4-fluoro-3-methoxybenzyl)oxy)pyrimidin-5-yl)thio)-2-chlorobenzamide [213]. To 211 (30.0 mg, 0.069 mmol) was added a (R)—N,N-dimethylpyrrolidin-3-amine (18.1 μL, 17.8 mg, 0.206 mmol) in DMF (2 mL) and heated at 90° C. for 2 h. Solvent was removed under reduced pressure to give a residue which was purified by preparatory TLC (CH$_2$Cl$_2$: MeOH—NH$_3$ (7 N), 15:1) to afford 28.0 mg (84%) of intermediate nitrile (MS (m/z): [M+H]$^+$ 486.1). A mixture of this and KOH (64.6 mg, 1.154 mmol) in t-BuOH (5 mL) was heated at 80° C. for 1 h. Solvent was removed under reduced pressure and the residue was purified by preparatory TLC (CH$_2$Cl$_2$:MeOH—NH$_3$ (7 N), 10:1) to afford 25.7 mg (86%) of 213. $^1$H NMR (600 MHz, CDCl$_3$/MeOH-d$_4$): δ 8.15 (s, 1H), 7.45 (d, J=8.1 Hz, 1H), 6.84-6.92 (m, 3H), 6.67-6.76 (m, 2H), 5.27 (s, 2H), 3.73-3.80 (m, 2H), 3.67 (s, 3H), 3.58-3.62 (m, 1H), 3.27-3.34 (m, 2H), 2.10-2.14 (m, 1H), 1.78-1.82 (m, 1H); $^{13}$C NMR (150 MHz, CDCl$_3$/MeOH-d$_4$): δ 168.5, 164.7, 160.3, 152.8, 151.2, 147.4, 143.7, 132.5, 131.4, 130.4, 130.2, 126.6, 124.1, 120.2, 115.7, 112.9, 96.7, 67.4, 56.1, 54.5, 50.5, 45.1, 33.2; HRMS (ESI) m/z [M+H]$^+$ calcd. for C$_{23}$H$_{24}$ClFN$_5$O$_3$S, 504.1272; found 504.1275.

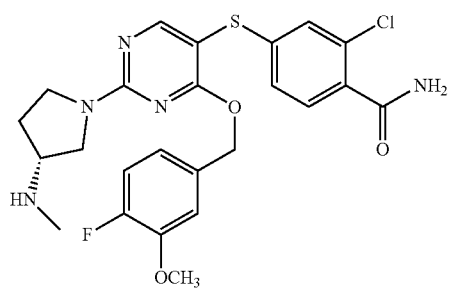

(R)-2-Chloro-4-((4-((4-fluoro-3-methoxybenzyl)oxy)-2-(3-(methylamino)pyrrolidin-1-yl)pyrimidin-5-yl)thio)benzamide [214]. To 211 (12.0 mg, 0.0276 mmol) was added a (R)—N-methylpyrrolidin-3-amine (9.7 μL, 9.1 mg, 0.206 mmol) in DMF (2 mL) and heated at 90° C. for 2 h. Solvent was removed under reduced pressure to give a residue which was purified by preparatory TLC (CH$_2$Cl$_2$:MeOH—NH$_3$ (7 N), 20:1) to afford 11.6 mg (84%) of intermediate nitrile (MS (m/z): [M+H]$^+$ 500.1). A mixture of this and KOH (26.0 mg, 0.465 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 15:1) to afford 7.6 mg (64%) of 214. $^1$H NMR (500 MHz, CD$_2$Cl$_2$/MeOH-d$_4$): δ 8.15 (s, 1H), 7.45 (d, J=8.1 Hz, 1H), 6.90-6.94 (m, 2H), 6.77 (dd, J=1.9 and 8.1 Hz, 1H), 6.68-6.72 (m, 1H), 5.27 (s, 2H), 3.63-3.76 (m, 2H), 3.65 (s, 3H), 3.55-3.56 (m, 1H), 3.25-3.41 (m, 2H), 2.41 (s, 3H), 2.12-2.19 (m, 1H), 1.82-1.86 (m, 1H); HRMS (ESI) m/z [M+H]$^+$ calcd. for C$_{24}$H$_{26}$ClFN$_5$O$_3$S, 518.1278; found 518.1280.

Example 30

Scheme 35. Synthesis of 218 and 225-229.

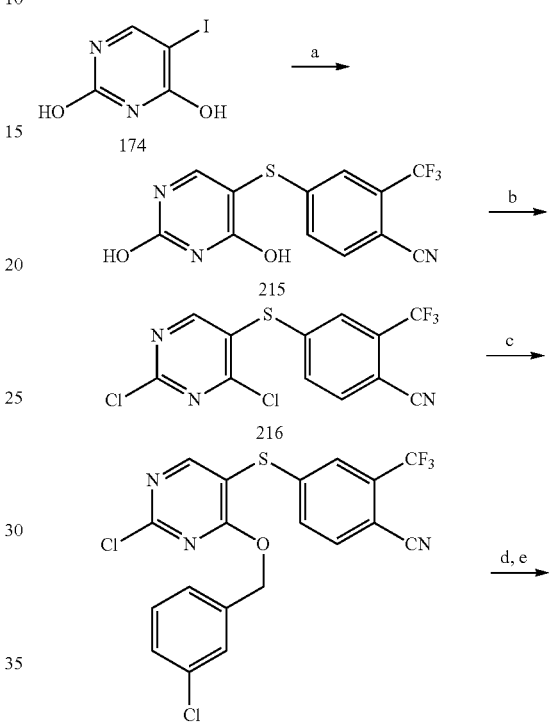

218 and 225-229

Reagents and conditions: a. 4-mercapto-2-(trifluoromethyl)benzonitrile, copper(I)thiophene-2-carboxylate, K$_2$CO$_3$, DMF, 130° C., 16 h; b. POCl$_3$, DIEA, 100° C. for 4 h; c. 3-chlorobenzylalcohol, CH$_3$CN, NaH, rt for 4 h; d. amine, Et$_3$N, DMF, 90° C., 2 h; e. KOH, t-BuOH, 80° C., 1 h.

4-((2,4-Dihydroxypyrimidin-5-yl)thio)-2-(trifluoromethyl)benzonitrile [215]. A mixture of 5-iodopyrimidine-2,4-diol 174 (3.77 g, 15.8 mmol), 4-mercapto-2-(trifluoromethyl)benzonitrile (3.86 g, 19.0 mmol) and K$_2$CO$_3$ (6.55 g, 47.4 mmol) in DMF (100 mL) was evacuated and backfilled with argon three times. Copper(I)thiophene-2-carboxylate (1.21 g, 6.32 mmol) was added and evacuated and backfilled with argon two times and the reaction mixture was heated at 130° C. for 16 h. Solvent was removed under reduced pressure and purified by column chromatography (CH$_2$Cl$_2$: CH$_3$OH:CH$_3$COOH, 25:1:0.3) to give 2.54 g (51%) of 215. MS (ESI) m/z 312.0 [M−H]$^-$.

4-((2,4-Dichloropyrimidin-5-yl)thio)-2-(trifluoromethyl)benzonitrile [216]. 0.320 g (1.022 mmol) of 215 was added 7 mL of POCl$_3$ (4 g, 25.55 mmol) with stirring. To this mixture 450 µL of DIEA (0.33 g, 2.55 mmol) was added slowly and the reaction was heated at 100° C. for 4 h. After cooling to rt, the reaction mixture was added to a beaker containing ice chips. Following complete quenching of POCl$_3$, solid Na$_2$CO$_3$ was carefully added until pH ~9. This was transferred to a seperatory funnel and extracted with CH$_2$Cl$_2$ (4×75 mL), dried over MgSO$_4$, filtered and concentrated to a solid which was purified by column chromatography (hexane:EtOAc, 80:20) to afford 0.25 g (70%) of 216. $^1$H NMR (600 MHz, CDCl$_3$): δ 8.64 (s, 1H), 7.83 (d, J=8.2 Hz, 1H), 7.69 (d, J=1.7 Hz, 1H), 7.45 (dd, J=1.7, 8.2 Hz, 1H); MS (ESI) m/z 383.8/385.8 [M+Cl]$^-$.

4-((2-Chloro-4-((3-chlorobenzyl)oxy)pyrimidin-5-yl)thio)-2-(trifluoromethyl)benzonitrile [217]. To 3-chlorobenzylalcohol (101 mg, 0.71 mmol) dissolved in CH$_3$CN (2 mL) was added NaH (22 mg, 0.923 mmol) and the resulting suspension was stirred for 10 min. at rt. Then 216 (0.250 g, 0.71 mmol) was added and the reaction mixture was stirred at rt for 4 h. The reaction mixture was concentrated under reduced pressure to give a residue which was purified by preparatory TLC (hexane:CH$_2$Cl$_2$, 40:60) to afford 110 mg (34%) of 217. MS (ESI) m/z [M+H]$^+$ 456.1.

General Procedure for Synthesis of 218 and 225-229. To 217 (1 equiv.) was added amine (1.5 equiv.) and Et$_3$N (2 equiv.) in DMF and heated at 90° C. for 2 h. Solvent was removed under reduced pressure and the residue was purified by prepatory TLC to afford intermediate nitrile. A mixture of the nitrile (1 equiv.) and KOH (25 equiv.) in t-BuOH was heated at 80° C. for 1 h. Solvent was removed under reduced pressure and the residue was purified by preparatory TLC to afford desired amide.

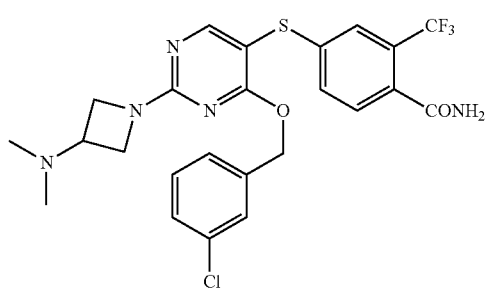

4-((4-((3-Chlorobenzyl)oxy)-2-(3-(dimethylamino)azetidin-1-yl)pyrimidin-5-yl)thio)-2-(trifluoromethyl)benzamide [225]. 225 was obtained in 36% yield following the general procedure above. $^1$H NMR (600 MHz, CD$_2$Cl$_2$) δ 8.25 (s, 1H), 7.44 (d, J=1.5 Hz, 1H), 7.41 (d, J=8.2 Hz, 1H), 7.22-7.26 (m, 2H), 7.18-7.22 (m, 2H), 7.06-7.09 (m, 1H), 5.77 (br s, 2H), 5.33 (s, 2H), 4.16-4.19 (m, 2H), 4.03 (m, 2H), 3.28 (br s, 1H), 2.26 (s, 6H); $^{13}$C NMR (150 MHz, CD$_2$Cl$_2$) δ 169.2, 169.1, 165.7, 163.2, 142.5, 139.1, 134.4, 132.3, 130.3, 129.6, 129.5, 128.5, 128.4, 128.2 (q, J=31.9 Hz), 126.4, 124.4 (q, J=5.1 Hz), 123.9 (q, J=272.3 Hz), 98.0, 67.7, 56.4, 54.6, 42.0; HRMS (ESI) m/z [M+H]$^+$ calcd. for C$_{24}$H$_{24}$ClF$_3$N$_5$O$_2$S 538.1291; found 538.1306.

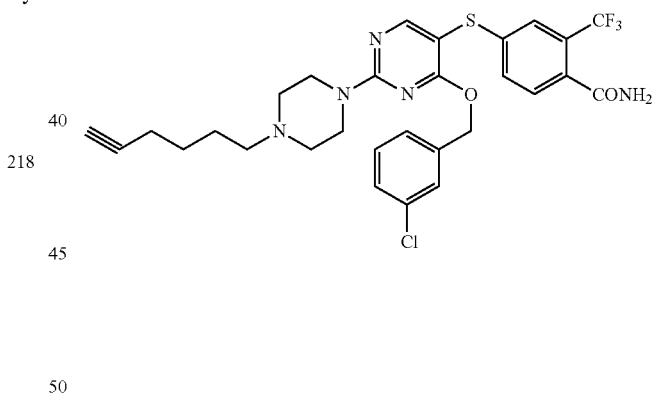

(R)-4-((4-((3-Chlorobenzyl)oxy)-2-(3-(dimethylamino)pyrrolidin-1-yl)pyrimidin-5-yl)thio)-2-(trifluoromethyl)benzamide [218]. 218 was obtained in 51% yield following the general procedure above. $^1$H NMR (600 MHz, CDCl$_3$) δ 8.28 (s, 1H), 7.41-7.45 (m, 2H), 7.16-7.24 (m, 4H), 7.03-7.07 (m, 1H), 5.96 (br s, 1H), 5.83 (br s, 1H), 5.29-5.38 (m, 2H), 3.81-4.00 (m, 2H), 3.48-3.56 (m, 1H), 3.35-3.43 (m, 1H), 2.88-2.89 (m, 1H), 2.38 (d, J=12.1 Hz, 6H), 2.23-2.27 (m, 1H), 1.94-2.03 (m, 1H); HRMS (ESI) m/z [M+H]$^+$ calcd. for C$_{25}$H$_{26}$ClF$_3$N$_5$O$_2$S 552.1448; found 552.1457.

4-((4-((3-Chlorobenzyl)oxy)-2-(4-(hex-5-yn-1-yl)piperazin-1-yl)pyrimidin-5-yl)thio)-2-(trifluoromethyl)benzamide [226]. 226 was obtained in 48% yield following the general procedure above. $^1$H NMR (600 MHz, CDCl$_3$) δ 8.27 (s, 1H), 7.42-7.46 (m, 2H), 7.18-7.26 (m, 3H), 7.14 (s, 1H), 7.01-7.06 (m, 1H), 5.93 (br s, 1H), 5.82 (br s, 1H), 5.32 (s, 2H), 3.88 (m, 4H), 2.52 (m, 4H), 2.40-2.45 (m, 2H), 2.25 (td, J=7.0, 2.6 Hz, 2H), 1.98 (t, J=2.6 Hz, 1H), 1.64-1.70 (m, 2H), 1.56-1.62 (m, 2H); $^{13}$C NMR (150 MHz, CDCl$_3$) δ 169.4, 168.5, 165.3, 161.7, 142.2, 138.5, 134.3, 131.6, 130.0, 129.3, 129.1, 128.3, 128.0 (q, J=29.7 Hz), 127.7, 125.6, 124.0 (q, J=5.2 Hz), 123.4 (q, J=271.3 Hz), 96.9, 84.4, 68.8, 67.2, 58.2, 53.0, 44.1, 26.5, 25.9, 18.5; HRMS (ESI) m/z [M+H]$^+$ calcd. for C$_{29}$H$_{30}$ClF$_3$N$_5$O$_2$S 604.1761; found 604.1786.

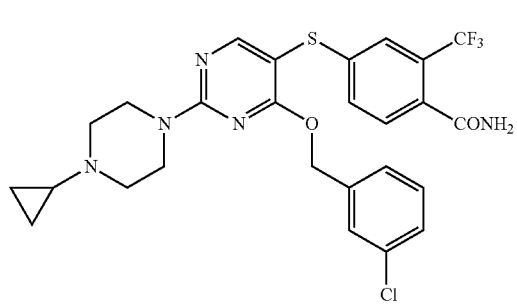

227

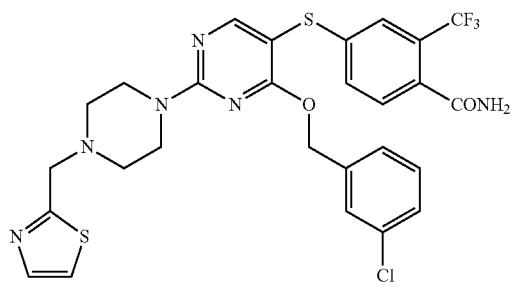

229

4-((4-((3-Chlorobenzyl)oxy)-2-(4-cyclopropylpiperazin-1-yl)pyrimidin-5-yl)thio)-2-(trifluoromethyl)benzamide [227]. 227 was obtained in 69% yield following the general procedure above. $^1$H NMR (600 MHz, CDCl$_3$) δ 8.27 (s, 1H), 7.45 (m, 1H), 7.43 (d, J=8.2 Hz, 1H), 7.20-7.24 (m, 3H), 7.15 (s, 1H), 7.04 (m, 1H), 5.79-5.81 (d, J=8.4 Hz, 2H), 5.32 (s, 2H), 3.82 (m, 4H), 2.67 (m, 4H), 1.65 (m, 1H), 0.48-0.52 (m, 4H); $^{13}$C NMR (150 MHz, CDCl$_3$) δ 169.1, 168.3, 165.1, 161.6, 142.1, 138.3, 134.1, 131.4, 129.8, 129.2, 129.0, 128.1, 127.8 (q, J=31.9 Hz), 127.5, 125.4, 123.8 (q, J=5.3 Hz), 123.2 (q, J=272.3 Hz), 96.7, 67.0, 53.0, 44.0, 31.0, 5.9; HRMS (ESI) m/z [M+H]$^+$ calcd. for C$_{26}$H$_{26}$ClF$_3$N$_5$O$_2$S 564.1448; found 564.1456.

4-((4-((3-Chlorobenzyl)oxy)-2-(4-(thiazol-2-ylmethyl)piperazin-1-yl)pyrimidin-5-yl)thio)-2-(trifluoromethyl)benzamide [229]. 229 was obtained in 48% yield following the general procedure above. $^1$H NMR (600 MHz, CDCl$_3$) δ 8.27 (s, 1H), 7.74 (d, J=3.1 Hz, 1H), 7.43-7.44 (m, 2H), 7.35 (d, J=3.1 Hz, 1H), 7.20-7.24 (m, 3H), 7.13 (s, 1H), 7.02-7.03 (m, 1H), 5.78-5.80 (d, J=12.8 Hz, 2H), 5.30 (s, 2H), 3.94 (s, 2H), 3.91 (m, 4H), 2.65-2.67 (m, 4H); $^{13}$C NMR (150 MHz, CDCl$_3$) δ 169.4, 169.0, 168.3, 165.1, 161.6, 142.5, 142.0, 138.3, 134.1, 131.5, 129.8, 129.2, 129.1, 128.1, 127.8 (q, J=32.0 Hz), 127.4, 125.4, 123.8 (q, J=5.0 Hz), 123.2 (q, J=272.6 Hz), 119.7, 97.0, 67.0, 59.5, 52.8, 44.0; HRMS (ESI) m/z [M+H]$^+$ calcd. for C$_{27}$H$_{25}$ClF$_3$N$_6$O$_2$S$_2$ 621.1121; found 621.1139.

Example 31

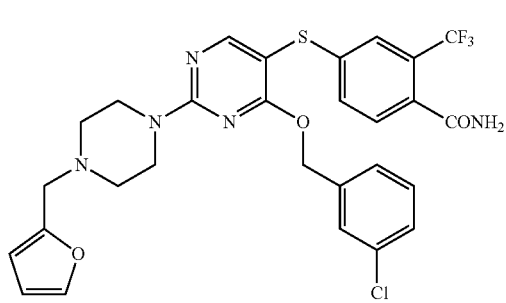

228

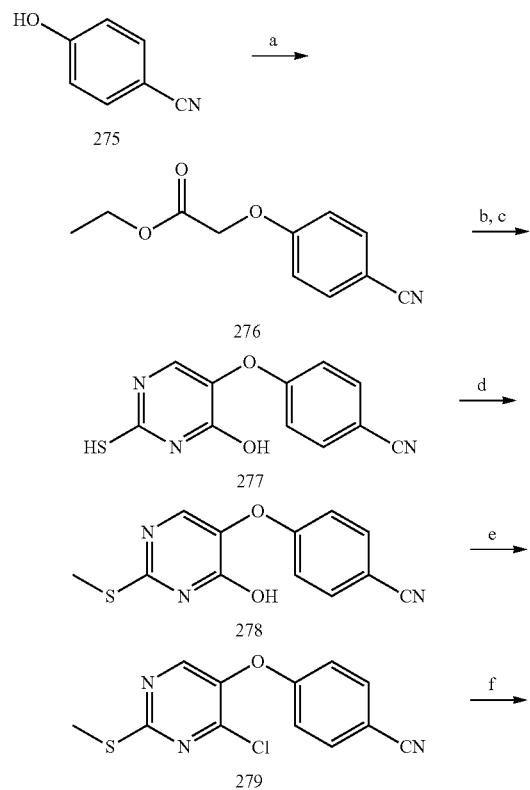

Scheme 44. Synthesis of 282.

4-((4-((3-Chlorobenzyl)oxy)-2-(4-(furan-2-ylmethyl)piperazin-1-yl)pyrimidin-5-yl)thio)-2-(trifluoromethyl)benzamide [228]. 228 was obtained in 47% yield following the general procedure above. $^1$H NMR (600 MHz, CDCl$_3$) δ 8.26 (s, 1H), 7.41-7.44 (m, 3H), 7.19-7.26 (m, 3H), 7.13 (s, 1H), 7.02-7.03 (m, 1H), 6.34 (m, 1H), 6.24 (d, J=3.0 Hz, 1H), 5.78 (br s, 2H), 5.30 (s, 2H), 3.89 (m, 4H), 3.60 (s, 2H), 2.53-2.55 (m, 4H); $^{13}$C NMR (150 MHz, CDCl$_3$) δ 169.1, 168.3, 165.1, 161.6, 151.0, 142.5, 142.1, 138.3, 134.1, 131.4, 129.8, 129.2, 129.0, 128.1, 127.8 (q, J=32.0 Hz), 127.5, 125.4, 123.8 (q, J=5.3 Hz), 123.2 (q, J=272.6 Hz), 110.1, 109.2, 96.8, 67.0, 54.9, 52.4, 43.8; HRMS (ESI) m/z [M+H]$^+$ calcd. for C$_{28}$H$_{26}$ClF$_3$N$_5$O$_3$S 604.1397; found 604.1404.

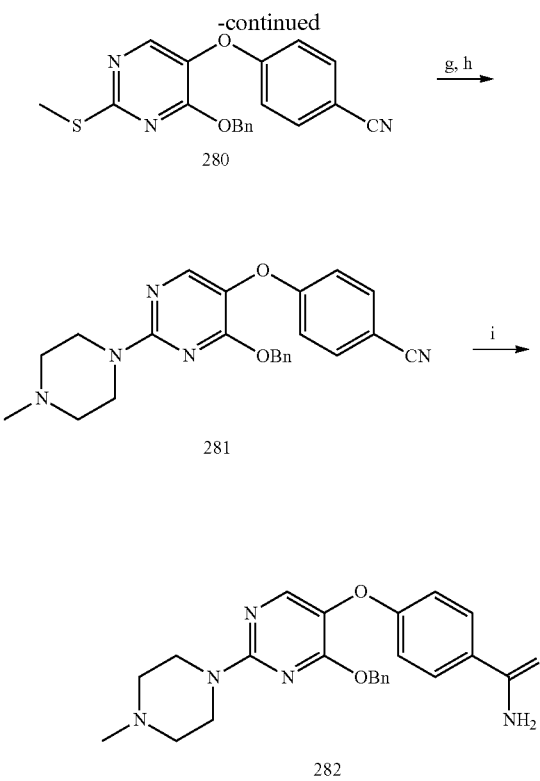

Reagents and conditions: a. ethyl bromoacetate, K₂CO₃, CH₃CN, 80° C., 12 h; b. ethyl formate, NaH, THF, 0° C. to rt, 20 h; c. ethanol, thiourea, reflux, 18 h, then 1M HCl (aq.); d. Et₃N, DMF, 0° C. to rt, overnight; e. POCl₃, 75° C., 1 h; f. BnOH, NaH, CH₃CN, rt, 2.5 h; g. m-CPBA, CH₂Cl₂, rt for 3 h; h. N-methylpiperazine, DMF, 80° C., 1 h; i. KOH, t-BuOH, 80° C., 1 h.

Ethyl 2-(4-cyanophenoxy)acetate [276]. A mixture of 4-cyanophenol (275; 4.0 g, 33.6 mmol), ethyl bromoacetate (5.05 g, 30.2 mmol) and K₂CO₃ (5.8 g, 42.2 mmol) in acetonitrile (50 mL) was heated to 80° C. for 12 h. The reaction mixture was concentrated under reduced pressure and purified by column chromatography (hexane:EtOAc, 0-40% EtOAc) to give 4.7 g (75%) of 276. $^1$H NMR (500 MHz, CDCl₃): δ 7.63 (d, J=8.8 Hz, 2H), 6.99 (d, J=8.8 Hz, 2H), 4.69 (s, 2H), 4.31 (q, J=7.2 Hz, 2H), 1.32 (t, J=7.2 Hz, 3H); $^{13}$C NMR (125 MHz, CDCl₃): δ 167.9, 161.0, 134.1, 118.9, 115.4, 105.2, 65.2, 61.7, 14.1; MS (m/z): [M+H]⁺ 205.9.

4-((4-Hydroxy-2-mercaptopyrimidin-5-yl)oxy)benzonitrile [277]. A solution of 276 (2.05 g, 10 mmol) and ethyl formate (2.70 g, 45 mmol) in THF (50 mL) was added dropwise to a suspension of NaH (0.36 g, 15 mmol) in THF (10 mL) at 0° C. over 1h. Afterwords, the ice-bath was removed and stirring continued at rt for 20 h. Solvent was removed under reduced pressure and the resulting residue was dissolved in ethanol (10 mL) and combined with thiourea (0.91 g, 12 mmol) and the reaction was refluxed for 18 h. Then 1 M HCl (aq.) was added and the precipitated solid was filtered, washed with water and hexane to give 1.66 g (71%) of 277. $^1$H NMR (500 MHz, CDCl₃/MeOH-d₄): δ 7.76 (d, J=8.0 Hz, 2H), 7.75 (s, 1H), 7.18 (d, J=8.0 Hz, 2H); $^{13}$C NMR (125 MHz, CDCl₃): δ 174.4, 160.5, 157.2, 134.4, 134.2, 132.6, 118.8, 116.4, 104.9; MS (m/z): [M−H]⁻ 244.1.

4-((4-Hydroxy-2-(methylthio)pyrimidin-5-yl)oxy)benzonitrile [278]. To a mixture of 277 (500 mg, 2 mmol) and Et₃N (212 mg, 2.1 mmol) in DMF (5 mL) at 0° C. was added methyl iodide (282 mg, 2 mmol). Afterwords the ice-bath was removed and stirring continued overnight at rt. Solvent was removed under reduced pressure and purified by column chromatography (CH₂Cl₂:MeOH, 0-10% MeOH) to give 461 mg (89%) of 278. $^1$H NMR (500 MHz, CDCl₃/MeOH-d₄): δ 7.72 (s, 1H), 7.50 (d, J=8.8 Hz, 2H), 6.92 (d, J=8.8 Hz, 2H), 2.47 (s, 3H); $^{13}$C NMR (125 MHz, CDCl₃): δ; MS (m/z): [M+H]⁺ 260.0.

4-((4-Chloro-2-(methylthio)pyrimidin-5-yl)oxy)benzonitrile [279]. 278 (0.200 g, 0.77 mmol) and POCl₃ (1 mL) were heated at 75° C. for 1 h. After cooling to rt, the reaction mixture was added to a beaker containing ice chips. Following complete quenching of POCl₃, solid Na₂CO₃ was carefully added until pH ~9. This was transferred to a seperatory funnel and extracted with CH₂Cl₂ (4×25 mL), dried over MgSO₄, filtered and concentrated to a solid which was purified by column chromatography (CH₂Cl₂:MeOH, 50:1 to 40:1) to afford 0.173 g (81%) of 279. MS (m/z): [M+H]⁺ 277.9/279.9.

4-((4-(Benzyloxy)-2-(methylthio)pyrimidin-5-yl)oxy)benzonitrile [280]. To benzylalcohol (46.7 mg, 0.432 mmol) dissolved in CH₃CN (500 μL) was added NaH (10.4 mg, 0.432 mmol) and the resulting suspension was stirred for 10 min. at rt. Then 279 (30 mg, 0.108 mmol 0.0289 mmol) was added and the reaction mixture was stirred at rt for 2.5 h. MeOH (1 mL) was added and stirred for 5 minutes then the reaction mixture was concentrated under reduced pressure to give a residue which was partially purified by preparatory TLC (CH₂Cl₂:MeOH—NH₃ (7 N), 20:1) to afford 28.5 mg of 280. $^1$H NMR (500 MHz, CDCl₃): δ 8.21 (s, 1H), 7.58 (d, J=8.9 Hz, 2H), 7.31-7.39 (m, 3H), 7.16-7.18 (m, 2H), 6.94 (d, J=8.8 Hz, 2H), 5.45 (s, 2H), 2.60 (s, 3H); $^{13}$C NMR (125 MHz, CDCl₃): δ 168.2, 160.9, 149.8, 140.9, 135.3, 134.1, 133.8, 128.6, 128.5, 128.4, 127.9, 127.7, 127.0, 118.6, 116.6, 106.4, 68.6, 14.7; MS (m/z): [M+H]⁺ 350.0.

4-((4-(Benzyloxy)-2-(4-methylpiperazin-1-yl)pyrimidin-5-yl)oxy)benzonitrile [281]. 280 (35 mg, 0.1 mmol) and m-CPBA (34.4 mg, 0.2 mmol) in CH₂Cl₂ (2 mL) was stirred at rt for 3 h. Then solvent was removed under reduced pressure and the resulting residue was dissolved in DMF (1 mL) and reacted with N-methylpiperazine (26 mg, 0.3 mmol) at 80° C. for 1 h. Solvent was removed under reduced pressure and purified by column chromatography (CH₂Cl₂:MeOH—NH₃ (7 N), 100:1 to 50:1) to give 26 mg (65%) of 281. $^1$H NMR (500 MHz, CDCl₃): δ 7.92 (s, 1H), 7.47 (d, J=7.4 Hz, 2H), 7.18-7.21 (m, 3H), 7.06-7.09 (m, 2H), 6.85 (d, J=7.4 Hz, 2H), 5.27 (s, 2H), 3.73-3.78 (m, 4H), 2.39-2.43 (m, 4H), 2.29 (s, 3H); $^{13}$C NMR (125 MHz, CDCl₃): δ 162.1, 161.3, 158.9, 150.8, 136.1, 133.9, 128.4, 128.1, 127.6, 127.4, 127.0, 118.8, 116.1, 105.6, 67.7, 54.9, 46.2, 43.1; MS (m/z): [M+H]⁺ 402.2.

4-((4-(Benzyloxy)-2-(4-methylpiperazin-1-yl)pyrimidin-5-yl)oxy)benzamide [282]. A mixture of 281 (10 mg, 0.025 mol) and KOH (35 mg, 0.62 mmol) in t-BuOH (500 μL) was heated at 80° C. for 1 h. Solvent was removed under reduced pressure and the residue was purified by preparatory TLC (CH₂Cl₂:MeOH—NH₃ (7 N), 15:1) to afford 8.8 mg (84%) of 282. $^1$H NMR (500 MHz, CDCl₃): δ 7.93 (s, 1H), 7.66 (d, J=8.8 Hz, 2H), 7.16-7.19 (m, 3H), 7.07-7.09 (m, 2H), 6.84 (d, J=8.8 Hz, 2H), 5.83 (br s, 1H), 5.54 (br s, 1H), 5.28 (s, 2H), 3.74-3.78 (m, 4H), 2.42-2.45 (m, 4H), 2.30 (s, 3H); $^{13}$C NMR (125 MHz, CDCl₃): δ 168.5, 161.7, 161.5, 158.6, 150.8, 136.3, 129.2, 128.3, 128.1, 128.0, 127.5, 127.0, 115.4, 67.6, 54.8, 46.1, 44.0; MS (m/z): [M+H]⁺ 420.2.

Compounds 283 and 284 were synthesized in a similar manner to 282 shown in Scheme 44.

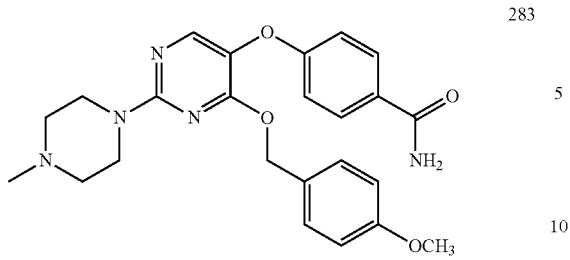

283

4-((4-((4-Methoxybenzyl)oxy)-2-(4-methylpiperazin-1-yl)pyrimidin-5-yl)oxy)benzamide [283]. $^1$H NMR (500 MHz, CDCl$_3$): δ 7.91 (s, 1H), 7.65 (d, J=8.7 Hz, 2H), 7.04 (d, J=8.6 Hz, 2H), 6.82 (d, J=8.7 Hz, 2H), 6.72 (d, J=8.6 Hz, 2H), 5.73 (br s, 2H), 5.23 (s, 2H), 3.75 (m, 4H), 3.71 (s, 3H), 2.42 (m, 4H), 2.32 (s, 3H); $^{13}$C NMR (125 MHz, CDCl$_3$): δ 168.6, 161.7, 161.6, 159.4, 158.6, 150.7, 129.4, 129.2, 128.3, 128.1, 127.0, 115.4, 113.7, 67.4, 55.3, 54.9, 46.2, 44.1; MS (m/z): [M+H]$^+$ 450.2.

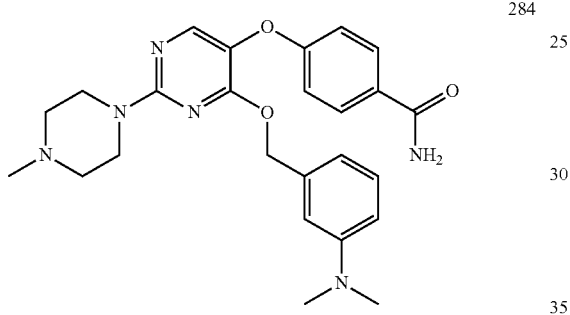

284

4-((4-((3-(Dimethylamino)benzyl)oxy)-2-(4-methylpiperazin-1-yl)pyrimidin-5-yl)oxy)benzamide [284]. $^1$H NMR (500 MHz, CDCl$_3$): δ 7.92 (s, 1H), 7.64 (d, J=8.7 Hz, 2H), 7.05 (t, J=8.6 Hz, 1H), 6.83 (d, J=8.7 Hz, 2H), 6.54 (dd, J=8.0, 2.1 Hz, 1H), 6.47 (s, 2H), 5.86 (br s, 1H), 5.48 (br s, 1H), 5.24 (s, 2H), 3.74-3.77 (m, 4H), 2.76 (s, 6H), 2.39-2.42 (m, 4H), 2.28 (s, 3H); $^{13}$C NMR (125 MHz, CDCl$_3$): δ 168.5, 161.7, 161.5, 158.7, 150.7, 150.6, 137.0, 129.2, 129.0, 127.9, 126.9, 115.7, 115.3, 112.1, 111.6, 68.1, 54.9, 46.3, 44.2, 40.5.

Example 32

Scheme 45. Synthesis of 299.

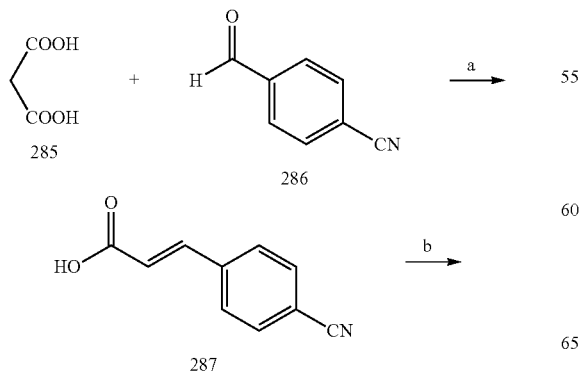

285    286

287

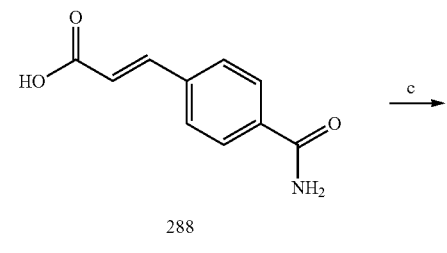

288

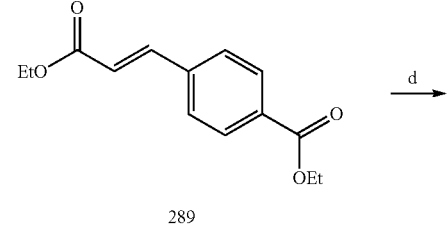

289

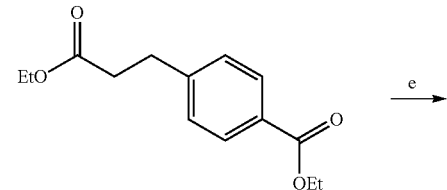

290

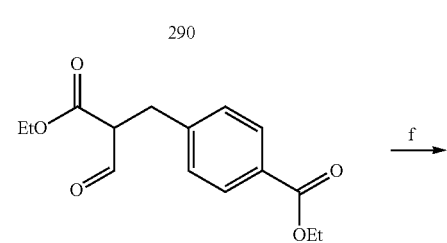

291

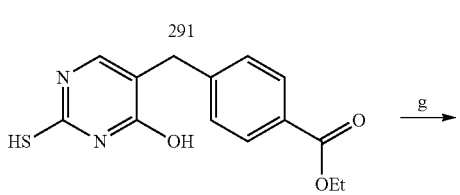

292

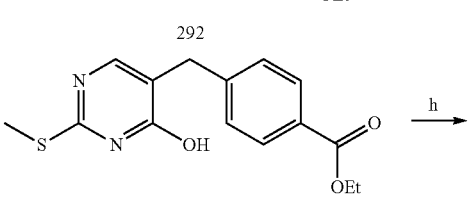

293

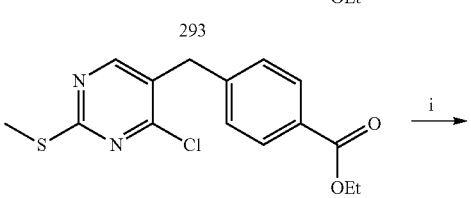

294

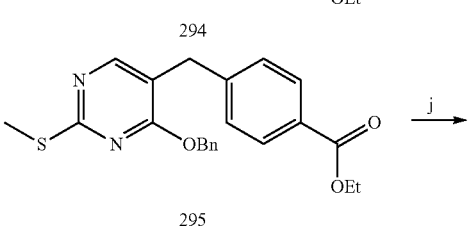

295

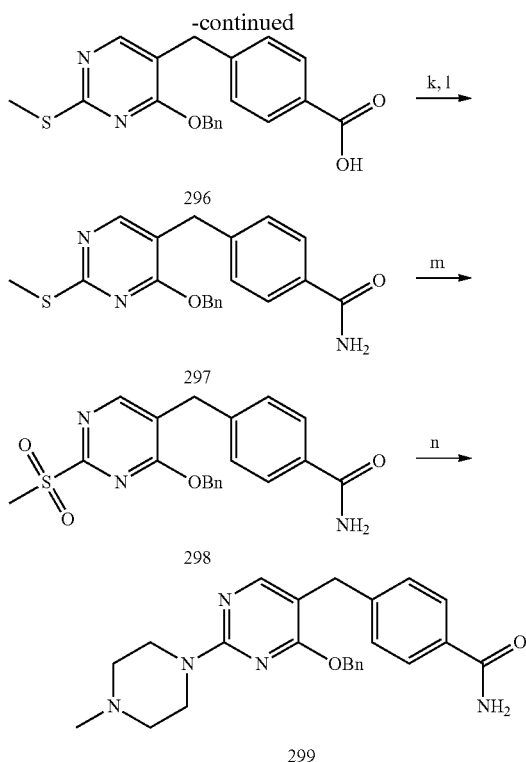

Reagents and conditions: a. pyridine, piperidine, 110° C., 2 h; b. KOH, t-BuOH, 80° C., 3 h; c. H₂SO₄, EtOH, 80° C., 12 h; d. EtOH, Pd/C (10%), rt, 12 h; e. HCOOEt, NaH, THF, 0° C. to rt, 24 h; f. thiourea, EtOH, reflux, 8 h; g. CH₃I, Et₃N, DMF, rt, 2 h; h. POCl₃, 80° C., 1 h; i. BnOH, NaH, CH₃CN, rt, 2.5 h; j. NaOH, EtOH, reflux, 8 h; k. oxalyl chloride, DMF, rt, 5 h; l. NH₃ (g), -78° C. to rt, 30 min; m. m-CPBA, CH₂Cl₂, stir, 2 h; n. N-methylpiperazine, K₂CO₃, DMF, 100° C., 1 h.

(E)-3-(4-Cyanophenyl)acrylic acid [287]. To a mixture of malonic acid (285; 2.02 g, 19.47 mmol), 4-formylbenzonitrile (286; 2.55 g, 19.47 mmol) and pyridine was added piperidine (0.2 mL). The reaction mixture was heated at 110° C. for 2 h. Solvent was removed under reduced pressure and the residue was purified by column chromatography (CH₂Cl₂: MeOH, 50:1 to 10:1) to afford 3.2 g (95%) of 287. MS m/z [M+H]⁺ 174.3.

(E)-3-(4-Carbamoylphenyl)acrylic acid [288]. A mixture of 287 (3.2 g, 18.5 mmol) and KOH (6.0 g, 107.14 mmol) in t-BuOH (50 mL) was heated at 80° C. for 3 h. Solvent was removed under reduced pressure and the residue was purified by column chromatography (CH₂Cl₂:MeOH:CH₃COOH, 15:1:0.1) to afford 2.5 g (72%) of 288. MS m/z [M+H]⁺ 192.3.

(E)-Ethyl 4-(3-ethoxy-3-oxoprop-1-en-1-yl)benzoate [289]. A mixture of 288 (2.5 g, 13.1 mmol) and H₂SO₄ (6.0 g, 107.14 mmol) in EtOH (100 mL) was heated at 80° C. for 12 h. Solvent was removed under reduced pressure and the residue was taken up into CH₂Cl₂ (150 mL) and washed with water (50 mL) and brine (2×50 mL), dried over MgSO₄, filtered and concentrated to give an oil that was purified by column chromatography (hexane:EtOAc:1:1) to afford 0.72 g (23%) of 289. MS m/z [M+H]⁺ 249.1.

Ethyl 4-(3-ethoxy-3-oxopropyl)benzoate [290]. To 289 (0.72 g, 2.90 mmol) in EtOH (50 mL) was added Pd/C (10%) (80 mg) and stirred at room temperature for 12 h. Solvent was removed under reduced pressure and the residue was purified by column chromatography (CH₂Cl₂: MeOH, 50:1 to 10:1) to afford 0.71 g (97%) of 290. MS m/z [M+H]⁺ 251.4.

Ethyl 4-(3-ethoxy-2-formyl-3-oxopropyl)benzoate [291]. A mixture of 290 (0.5 g, 2 mmol) and ethylformate (0.67 g, 9 mmol) in 3 mL of THF was added over a period of 30 min to a suspension of NaH (0.1 g, 4.1 mmol) in 2 mL THF at 0° C. At the end of addition the reaction mixture was stirred at room temperature for 24 h. Solvent was removed under reduced pressure and the residue was purified by column chromatography (hexane: EtOAc, 1:1) to afford 0.43 g (78%) of 291. MS m/z [M+H]⁺ 279.2.

Ethyl 4-((4-hydroxy-2-mercaptopyrimidin-5-yl)methyl)benzoate [292]. A mixture of 291 (0.4 g, 1.43 mmol) and thiourea (0.11 g, 1.43 mmol) in 40 mL of EtOH was refluxed for 8 h. Solvent was removed under reduced pressure and the residue was purified by column chromatography (CH₂Cl₂: MeOH:CH₃COOH, 40:1:0.1 to 10:1:0.1) to afford 0.13 g (30%) of 292. MS m/z [M+H]⁺ 291.1.

Ethyl 4-((4-hydroxy-2-(methylthio)pyrimidin-5-yl)methyl)benzoate [293]. To 292 (0.12 g, 0.414 mmol) in DMF (5 mL) was added Et₃N (0.2 mL) and allowed to stir for 10 min. Then to the reaction mixture was added methyliodide (62 mg, 0.43 mmol) and the reaction mixture was stirred at rt for 2 h. Solvent was removed under reduced pressure and the residue was purified by preparative TLC (CH₂Cl₂: MeOH, 10:1) to afford 60 mg (49%) of 293. MS m/z [M+H]⁺ 305.1.

Ethyl 4-((4-chloro-2-(methylthio)pyrimidin-5-yl)methyl)benzoat [294]. A mixture of 293 (60 mg, 0.197 mmol) and POCl₃ (2 mL) were heated at 80° C. for 1 h. After cooling to rt, the reaction mixture was added to a beaker containing ice chips. Following complete quenching of POCl₃, solid Na₂CO₃ was carefully added until pH ~9. This was transferred to a seperatory funnel and extracted with CH₂Cl₂ (4×25 mL), dried over MgSO₄, filtered and concentrated to a solid which was purified by preparative TLC (hexane: EtOAc, 8:2) to afford 56 mg (88%) of 294. MS (m/z): [M+H]⁺ 323.0/325.0.

Ethyl 4-((4-(benzyloxy)-2-(methylthio)pyrimidin-5-yl)methyl)benzoate [295]. To benzyl alcohol (10.7 μL, 11.3 mg, 0.104 mmol) dissolved in CH₃CN (500 μL) was added NaH (2.8 mg, 0.116 mmol) and the resulting suspension was stirred for 10 min. at rt. Then 294 (28 mg, 0.0869 mmol) was added and the reaction mixture was stirred at rt for 2.5 h. MeOH (1 mL) was added and stirred for 5 minutes then the reaction mixture was concentrated under reduced pressure to give a residue which was purified by preparatory TLC (CH₂Cl₂:MeOH—NH₃ (7 N), 20:1) to afford 31.2 mg (91%) of 295. (MS (m/z): [M+H]⁺ 395.2.

4-((4-(Benzyloxy)-2-(methylthio)pyrimidin-5-yl)methyl)benzoic acid [296]. A mixture of 295 (31 mg, 0.0786 mmol) and NaOH (9.5 mg, 0.236 mmol) in 10 mL of EtOH was refluxed for 8 h. Solvent was removed under reduced pressure and the residue was used in the next step without further purification. MS m/z [M+H]⁺ 367.1.

4-((4-(Benzyloxy)-2-(methylthio)pyrimidin-5-yl)methyl)benzamide [297]. To 296 (28 mg, 0.0765 mmol) in DMF (2 mL) was added oxalyl chloride (6.6 μL, 9.6 mg, 0.0765 mmol) at rt and allowed to stir for 5 h resulting in acid chloride. Then to the reaction mixture NH₃ (g) was bubbled at −78° C. and the reaction mixture was stirred at room temperature for 30 min. Solvent was removed under reduced pressure and the residue was purified by preparative TLC (CH₂Cl₂: MeOH—NH₃ (7 N), 20:1) to afford 24 mg (86%) of 297. MS m/z [M+H]⁺ 366.2.

4-((4-(Benzyloxy)-2-(methylsulfonyl)pyrimidin-5-yl)methyl)benzamide [298]. To 297 (24 mg, 0.0655 mmol) in CH₂Cl₂ (5 mL) was added m-CPBA (22.6 mg, 0.1314 mmol) and allowed to stir for 2 h at rt. Solvent was removed under reduced pressure and the resulting sulfone was further reacted without additional purification. MS m/z [M+H]+ 398.1.

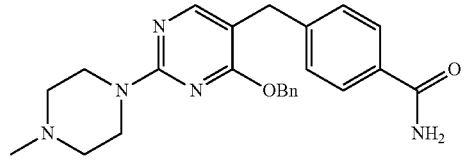

299

4-((4-(Benzyloxy)-2-(4-methylpiperazin-1-yl)pyrimidin-5-yl)methyl)benzamide [299]. To a solution of 298 (26 mg, 0.0656 mmol) in DMF (2 mL) was added N-methylpiperazine (20.5 µL, 18.1 mg, 0.181 mmol) and K$_2$CO$_3$ (7.3 mg, 0.1312 mmol) and heated at 100° C. for 1 h. Solvent was removed under reduced pressure and the residue was was purified by preparative TLC (CH$_2$Cl$_2$:MeOH—NH$_3$ (7 N), 20:1) to afford 20 mg (69%) of 299. $^1$H NMR (500 MHz, CDCl$_3$): δ 7.86 (s, 1H), 7.60 (d, J=8.2 Hz, 2H), 7.12-7.23 (m, 7H), 5.24 (s, 2H), 3.64-3.75 (m, 6H), 2.34-2.41 (m, 4H), 2.26 (s, 3H); $^{13}$C NMR (125 MHz, CDCl$_3$): δ 169.1, 167.1, 160.9, 157.5, 144.9, 136.8, 131.0, 128.9, 128.4, 127.9, 127.7, 127.4, 108.4, 67.3, 54.9, 46.2, 43.9, 32.8; MS m/z [M+H]+ 418.1.

Example 33

Scheme 46. Synthesis of 304.

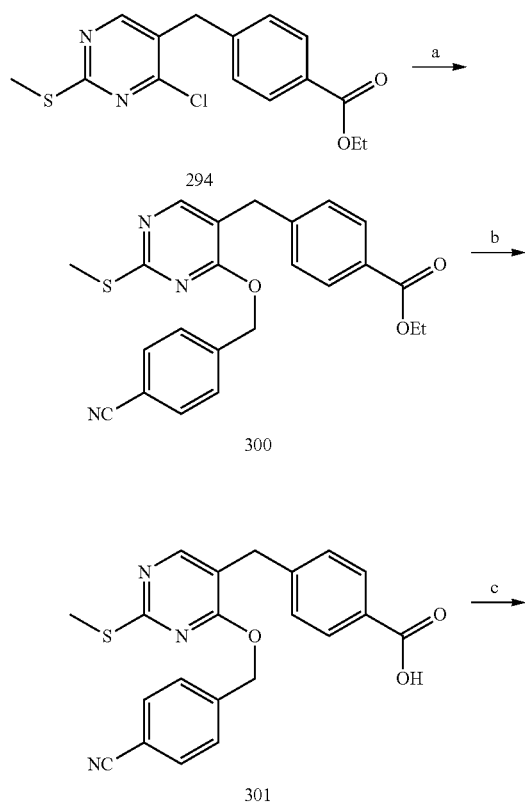

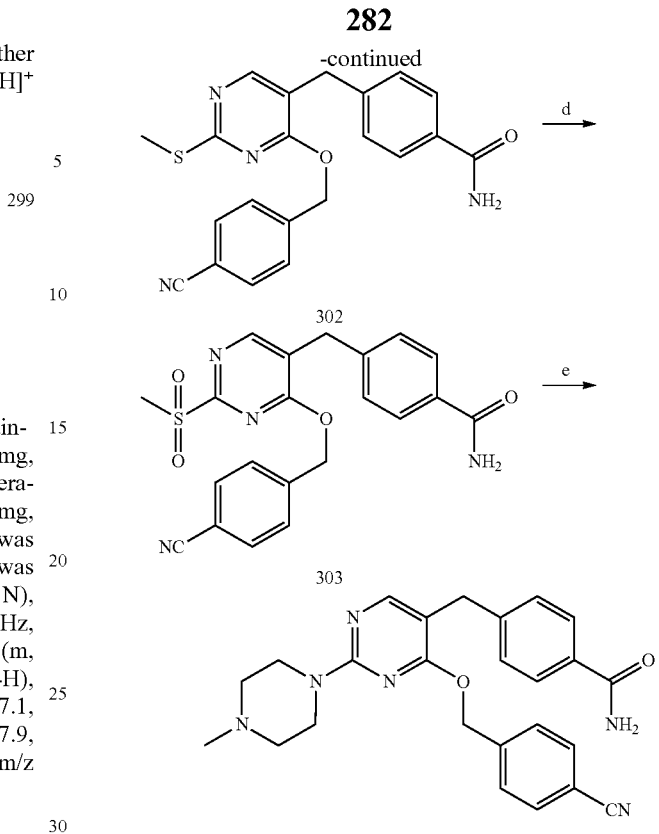

Reagents and conditions: a. 4-CNBnOH, NaH, CH$_3$CN, rt, 2.5 h; b. NaOH, EtOH, reflux, 8 h; b. oxalyl chloride, DMF, rt, 5 h; c. NH$_3$ (g), -78° C. to rt, 30 min; d. m-CPBA, CH$_2$Cl$_2$, rt, 2 h; e. N-methylpiperazine, K$_2$CO$_3$, DMF, 100° C., 1 h.

Ethyl 4-((4-((4-cyanobenzyl)oxy)-2-(methylthio)pyrimidin-5-yl)methyl)benzoate [300]. To 4-cyanobenzylalcohol (11.9 µL, 13.8 mg, 0.104 mmol) dissolved in CH$_3$CN (500 µL) was added NaH (2.8 mg, 0.116 mmol) and the resulting suspension was stirred for 10 min. at rt. Then 294 (28 mg, 0.0869 mmol) was added and the reaction mixture was stirred at rt for 2.5 h. MeOH (1 mL) was added and stirred for 5 minutes then the reaction mixture was concentrated under reduced pressure to give a residue which was purified by preparatory TLC (CH$_2$Cl$_2$:MeOH—NH$_3$ (7 N), 20:1) to afford 29.2 mg (81%) of 300 (MS (m/z): [M+H]+ 420.2.

4-((4-((4-Cyanobenzyl)oxy)-2-(methylthio)pyrimidin-5-yl)methyl)benzoic acid [301]. A mixture of 300 (29 mg, 0.0692 mmol) and NaOH (8.3 mg, 0.2076 mmol) in 10 mL of EtOH was refluxed for 8 h. Solvent was removed under reduced pressure and the residue was used in the next step without further purification. MS m/z [M+H]+ 392.1.

4-((4-((4-Cyanobenzyl)oxy)-2-(methylthio)pyrimidin-5-yl)methyl)benzamide [302]. To 301 (27 mg, 0.069 mmol) in DMF (2 mL) was added oxalyl chloride (5.9 µL, 8.7 mg, 0.069 mmol) at rt and allowed to stir for 5 h resulting in acid chloride. Then to the reaction mixture NH$_3$ (g) was bubbled at -78° C. and the reaction mixture was stirred at room temperature for 30 min. Solvent was removed under reduced pressure and the residue was purified by preparative TLC (CH$_2$Cl$_2$: MeOH—NH$_3$ (7 N), 20:1) to afford 23 mg (85%) of 302. MS m/z [M+H]+ 391.2.

4-((4-((4-Cyanobenzyl)oxy)-2-(methylsulfonyl)pyrimidin-5-yl)methyl)benzamide [303]. To 302 (23 mg, 0.0588 mmol) in CH$_2$Cl$_2$ (5 mL) was added m-CPBA (20.2 mg, 0.1176 mmol) and allowed to stir for 2 h at rt. Solvent was removed under reduced pressure and the resulting sulfone was further reacted without additional purification. MS m/z [M+H]$^+$ 423.1.

4-((4-((4-Cyanobenzyl)oxy)-2-(4-methylpiperazin-1-yl)pyrimidin-5-yl)methyl)benzamide [304]. To a solution of 303 (25 mg, 0.0591 mmol) in DMF (2 mL) was added N-methylpiperazine (19.7 µL, 17.7 mg, 0.177 mmol) and K$_2$CO$_3$ (6.6 mg, 0.1182 mmol) and the mixture was heated at 100° C. for 1 h. Solvent was removed under reduced pressure and the residue was was purified by preparative TLC (CH$_2$Cl$_2$:MeOH—NH$_3$ (7 N), 20:1) to afford 17 mg (65%) of 304. $^1$H NMR (500 MHz, CDCl$_3$): δ 7.87 (s, 1H), 7.66 (d, J=8.4 Hz, 2H), 7.51 (d, J=8.4 Hz, 2H), 7.18 (d, J=8.4 Hz, 2H), 7.16 (d, J=8.4 Hz, 2H), 5.29 (s, 2H), 3.75 (s, 2H), 3.66-3.71 (m, 4H), 2.37-2.43 (m, 4H), 2.27 (s, 3H); MS m/z [M+H]$^+$ 443.1.

Example 34

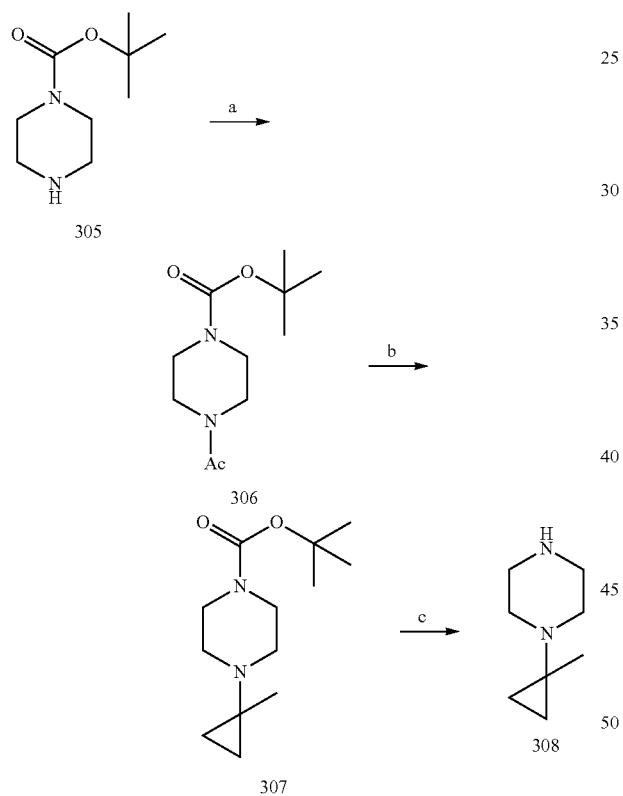

Scheme 47. Synthesis of 306-308.

Reagents and conditions: a. Ac$_2$O, CH$_2$Cl$_2$, 0° C., 30 min.; b. EtMgBr, MeTi(O-i-Pr)$_3$, THF, -78° C. to rt; c. TFA, CH$_2$Cl$_2$, rt, 24 h.

tert-Butyl 4-acetylpiperazine-1-carboxylate [306]. To a solution of 305 (1 g, 5.36 mmol) in CH$_2$Cl$_2$ (10 mL) cooled to 0° C. was added acetic anhydride (557 µL, 5.9 mmol) over a period of two minutes. The reaction mixture was stirred at 0° C. for 30 minutes. The solvent was removed under reduced pressure and the crude was treated with saturated NaHCO$_3$ (40 mL) and extracted with diethyl ether (3×30 mL). The combined organic extracts were dried over MgSO$_4$ and the solvent was concentrated to give 0.86 g (70%) of 306 as a clear oil that was used without further purification. MS (m/z): [M+Na]$^+$251.5.

tert-Butyl 4-(1-methylcyclopropyl)piperazine-1-carboxylate [307]. 306 (850 mg, 3.72 mmol) is dissolved in dry THF (10 mL) and cooled to −78° C. under argon. To this was added a solution of MeTi(O-i-Pr)$_3$ (4.5 mL of 1M in THF) over a period of 3 minutes followed by EtMgBr (4.8 mL of 3M in Et$_2$O) over a period of 7 minutes. The reaction mixture was allowed to warm to rt and stirred for an additional 30 minutes then carefully diluted with water (10 mL) and a solution of Rochelle salt (30 mL, 20% aq.). The mixture was stirred vigorously for 15 minutes then extracted with EtOAc (3×) and the combined organic layers were dried under MgSO$_4$. Solvent was removed under reduced pressure and the residue was purified by chromatography (0-20% EtOAc in hexanes) to afford 307 (0.358 g, 40%). MS (m/z): [M+H]$^+$ 241.1.

1-(1-Methylcyclopropyl)piperazine [308]. To a solution of 307 (300 mg, 1.24 mmol) in CH$_2$Cl$_2$ (6 mL) was added TFA (800 µL) and the reaction mixture was stirred at rt for 24 h. The solvent was concentrated to give 308 as its diTFA salt in quantitative yield and used without any further purification. MS (m/z): [M+H]$^+$ 141.8.

Example 35

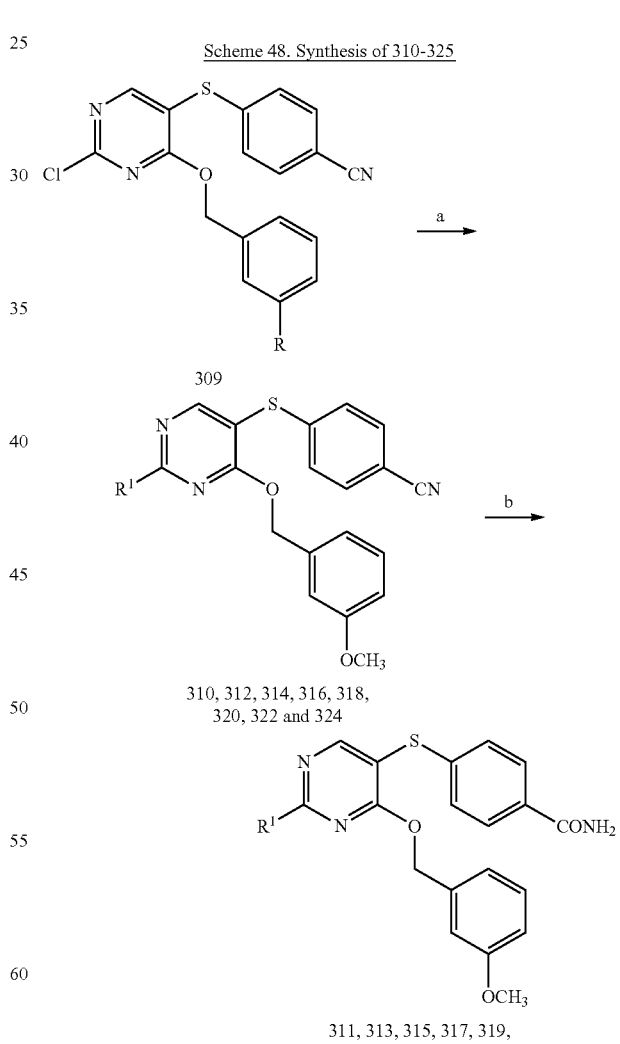

Scheme 48. Synthesis of 310-325

310, 312, 314, 316, 318, 320, 322 and 324

311, 313, 315, 317, 319, 321, 323 and 325

Reagents and conditions: a. amine, Et$_3$N, DMF, 90° C., 2 h; b. KOH, t-BuOH, 80° C., 1 h.

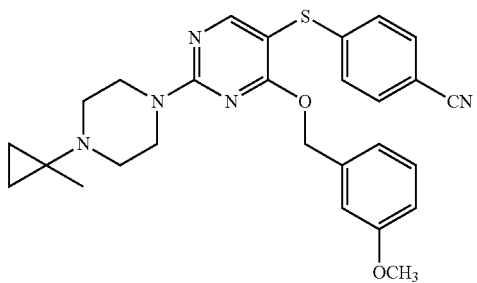

310

4-((4-((3-Methoxybenzyl)oxy)-2-(4-(1-methylcyclopropyl)piperazin-1-yl)pyrimidin-5-yl)thio)benzonitrile [310]. To 309 (8.2 mg, 0.021 mmol) was added 308 (106.6 mg, 0.29 mmol) and Et₃N (50 μL) in DMF (1 mL) and heated at 90° C. for 2 h. Solvent was removed under reduced pressure and the residue was purified by preparatory TLC (hexane: EtOAc, 8:2) to afford 8.6 mg (84%) of 310. MS (ESI) m/z [M+H]⁺ 488.2.

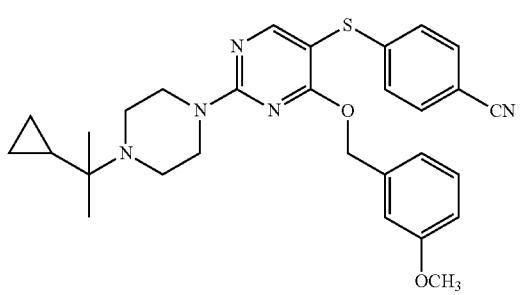

312

4-((2-(4-(2-Cyclopropylpropan-2-yl)piperazin-1-yl)-4-((3-methoxybenzyl)oxy)pyrimidin-5-yl)thio)benzonitrile [312]. To 309 (10 mg, 0.026 mmol) was added 1-(2-cyclopropylpropan-2-yl)piperazine (8.8 mg, 0.052 mmol) in DMF (1.5 mL) and heated at 90° C. for 1 h. Solvent was removed under reduced pressure and the residue was purified by preparatory TLC (CH₂Cl₂:MeOH, 40:1) to afford 6 mg (45%) of 312. MS (ESI) m/z [M+H]⁺ 516.2.

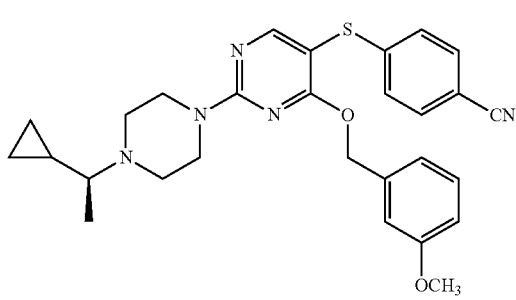

314

(S)-4-((2-(4-(1-Cyclopropylethyl)piperazin-1-yl)-4-((3-methoxybenzyl)oxy)pyrimidin-5-yl)thio)benzonitrile [314]. To 309 (10 mg, 0.026 mmol) was added (S)-1-(1-cyclopropylethyl)piperazine (20.1 mg, 0.130 mmol) in DMF (2 mL) and heated at 90° C. for 1 h. Solvent was removed under reduced pressure and the residue was purified by preparatory TLC (CH₂Cl₂:MeOH, 40:1) to afford 12 mg (92%) of 314. MS (ESI) m/z [M+H]⁺ 502.2.

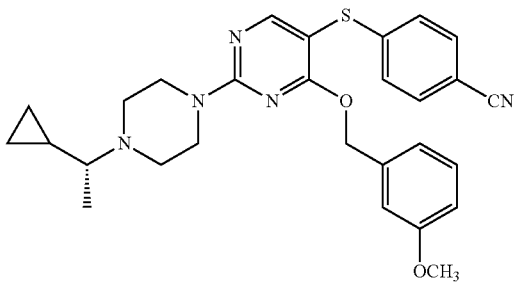

316

(R)-4-((2-(4-(1-Cyclopropylethyl)piperazin-1-yl)-4-((3-methoxybenzyl)oxy)pyrimidin-5-yl)thio)benzonitrile [316]. To 309 (10 mg, 0.026 mmol) was added (R)-1-(1-cyclopropylethyl)piperazine (20.1 mg, 0.130 mmol) in DMF (2 mL) and heated at 90° C. for 1 h. Solvent was removed under reduced pressure and the residue was purified by preparatory TLC (CH₂Cl₂:MeOH, 40:1) to afford 8.5 mg (65%) of 316. MS (ESI) m/z [M+H]⁺ 502.2.

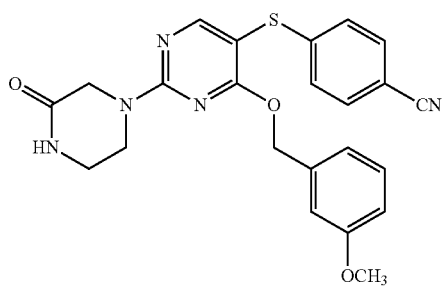

318

4-((4-((3-Methoxybenzyl)oxy)-2-(3-oxopiperazin-1-yl)pyrimidin-5-yl)thio)benzonitrile [318]. To 309 (11.1 mg, 0.0289 mmol) was added piperizine-2-one (14.5 mg, 0.145 mmol) and Et₃N (21 μL, 0.145 mmol) in DMF (1 mL) and heated at 90° C. for 1 h. Solvent was removed under reduced pressure and the residue was purified by preparatory TLC (CH₂Cl₂:MeOH, 20:1) to afford 9.7 mg (75%) of 318. MS (ESI) m/z [M+H]⁺ 448.0.

287

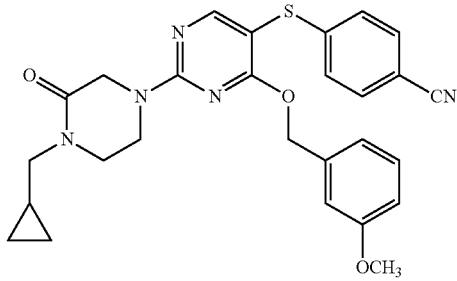

4-((2-(4-(Cyclopropylmethyl)-3-oxopiperazin-1-yl)-4-((3-methoxybenzyl)oxy)pyrimidin-5-yl)thio)benzonitrile [320]. To 309 (9.9 mg, 0.0258 mmol) was added 1-(cyclopropylmethyl)piperazin-2-one (36 mg, 0.129 mmol) and Et$_3$N (50 µL) in DMF (1 mL) and heated at 90° C. for 1 h. Solvent was removed under reduced pressure and the residue was purified by preparatory TLC (CH$_2$Cl$_2$:MeOH, 20:1) to afford 10.3 mg (80%) of 320. MS (ESI) m/z [M+H]$^+$ 502.0.

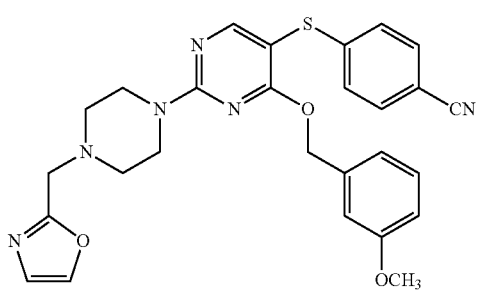

4-((4-((3-Methoxybenzyl)oxy)-2-(4-(oxazol-2-ylmethyl)piperazin-1-yl)pyrimidin-5-yl)thio)benzonitrile [322]. To 309 (13.8 mg, 0.0360 mmol) was added 2-(piperazin-1-ylmethyl)oxazole (30.1 mg, 0.18 mmol) and Et$_3$N (50 µL) in DMF (1 mL) and heated at 90° C. for 1 h. Solvent was removed under reduced pressure and the residue was purified by preparatory TLC (CH$_2$Cl$_2$:MeOH, 40:1) to afford 15.5 mg (84%) of 322. MS (ESI) m/z [M+H]$^+$ 515.1.

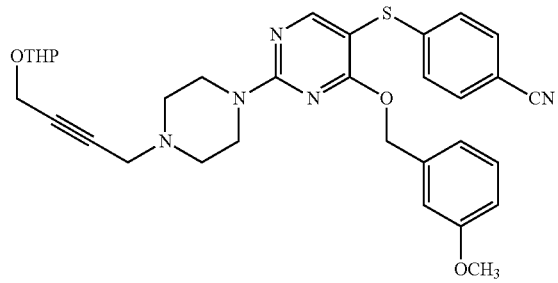

4-((4-((3-Methoxybenzyl)oxy)-2-(4-(4-((tetrahydro-2H-pyran-2-yl)oxy)but-2-yn-1-yl)piperazin-1-yl)pyrimidin-5-yl)thio)benzonitrile [324]. To 309 (14.9 mg, 0.0389 mmol) was added 1-(4-((tetrahydro-2H-pyran-2-yl)oxy)but-2-yn-1-yl)piperazine (37.1 mg, 0.1995 mmol) and Et$_3$N (50 µL) in DMF (1 mL) and heated at 90° C. for 1 h. Solvent was removed under reduced pressure and the residue was purified by preparatory TLC (hexane:EtOAc, 1:4) to afford 12.3 mg (54%) of 324. MS (ESI) m/z [M+H]$^+$ 586.1.

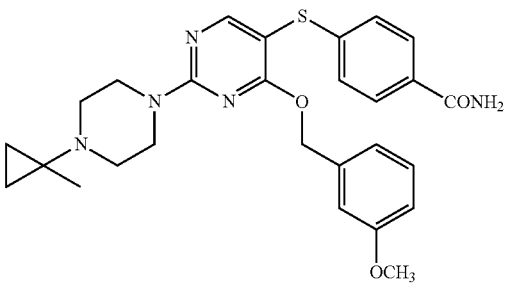

4-((4-((3-Methoxybenzyl)oxy)-2-(4-(1-methylcyclopropyl)piperazin-1-yl)pyrimidin-5-yl)thio)benzamide [311]. A mixture of 310 (8.6 mg, 0.0176 mmol) and KOH (19.7 mg, 0.352 mmol) in t-BuOH (1.5 mL) was heated at 80° C. for 1 h. Solvent was removed under reduced pressure and the residue was purified by preparatory TLC (CH$_2$Cl$_2$:MeOH—NH$_3$ (7 N), 20:1) to afford 6.1 mg (68%) of 311. $^1$H NMR (600 MHz, CDCl$_3$): δ 8.30 (s, 1H), 7.64 (d, J=8.3 Hz, 2H), 7.19 (t, J=7.9 Hz, 1H), 7.14 (d, J=8.3 Hz, 2H), 6.80 (d, J=8.3 Hz, 1H), 6.73 (d, J=7.6 Hz, 1H), 6.62 (s, 1H), 6.49 (br s, 1H), 6.25 (br s, 1H), 5.44 (s, 2H), 4.89 (m, 2H), 3.71 (s, 3H), 3.53 (m, 4H), 3.09 (m, 2H), 1.59 (t, J=6.1 Hz, 2H), 1.37 (s, 3H), 0.78 (t, J=6.2 Hz, 2H); $^{13}$C NMR (150 MHz, CDCl$_3$): δ 170.0, 168.8, 164.4, 161.4, 160.8, 159.6, 143.3, 137.5, 129.5, 127.9, 126.4, 119.6, 113.3, 113.1, 100.5, 68.2, 55.2, 49.2, 43.8, 40.8, 15.8, 12.7; HRMS (ESI) m/z [M+H]$^+$ calcd. for C$_{27}$H$_{32}$N$_5$O$_3$S, 506.2226; found 506.2208.

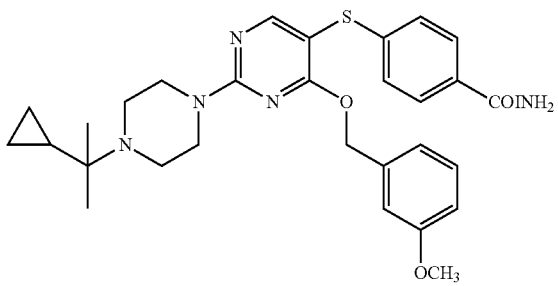

4-((2-(4-(2-Cyclopropylpropan-2-yl)piperazin-1-yl)-4-((3-methoxybenzyl)oxy)pyrimidin-5-yl)thio)benzamide [313]. A mixture of 312 (6 mg, 0.0116 mmol) and KOH (13 mg, 0.232 mmol) in t-BuOH (2 mL) was heated at 70° C. for 1.5 h. Solvent was removed under reduced pressure and the residue was purified by preparatory TLC (CH$_2$Cl$_2$:MeOH—NH$_3$ (7 N), 20:1) to afford 5.8 mg (94%) of 313. $^1$H NMR (600 MHz, CDCl$_3$): δ 8.26 (s, 1H), 7.62 (d, J=8.4 Hz, 2H), 7.17 (t, J=7.9 Hz, 1H), 7.11 (d, J=8.5 Hz, 2H), 6.79 (d, J=8.2 Hz, 1H), 6.76 (d, J=7.5 Hz, 1H), 6.69 (s, 1H), 6.04 (br s, 1H), 5.50 (br s, 1H), 5.34 (s, 2H), 3.87 (m, 4H), 3.68 (s, 3H), 2.77 (m, 4H), 1.22 (m, 1H), 0.88 (s, 6H), 0.45 (m, 2H), 0.25 (m, 2H); HRMS (ESI) m/z [M+H]$^+$ calcd. for C$_{29}$H$_{36}$N$_5$O$_3$S, 534.2539; found 534.2537.

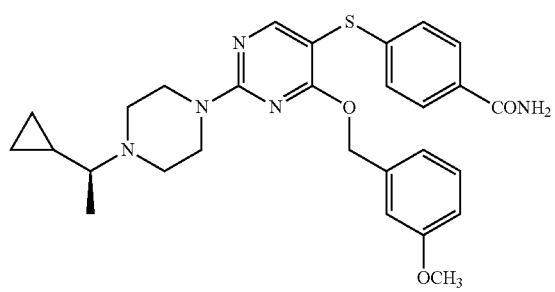

(S)-4-((2-(4-(1-Cyclopropylethyl)piperazin-1-yl)-4-((3-methoxybenzyl)oxy)pyrimidin-5-yl)thio)benzamide [315]. A mixture of 314 (12 mg, 0.0239 mmol) and KOH (27 mg, 0.478 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 20:1) to afford 12 mg (97%) of 315. $^1$H NMR (600 MHz, CDCl$_3$): δ 8.26 (s, 1H), 7.62 (d, J=8.8 Hz, 2H), 7.17 (t, J=6.6 Hz, 1H), 7.11 (d, J=8.8 Hz, 2H), 6.74-6.80 (m, 2H), 6.69 (s, 1H), 6.03 (br s, 1H), 5.60 (br s, 1H), 5.34 (s, 2H), 3.89 (m, 4H), 3.68 (s, 3H), 2.81 (m, 2H), 2.64 (m, 2H), 1.72 (m, 1H), 1.20 (d, J=6.5 Hz, 3H), 0.73-0.80 (m, 1H), 0.59-0.67 (m, 1H), 0.46-0.53 (m, 1H), 0.27-0.34 (m, 1H), 0.01-0.08 (m, 1H); HRMS (ESI) m/z [M+H]$^+$ calcd. for C$_{28}$H$_{34}$N$_5$O$_3$S, 520.2382; found 520.2360.

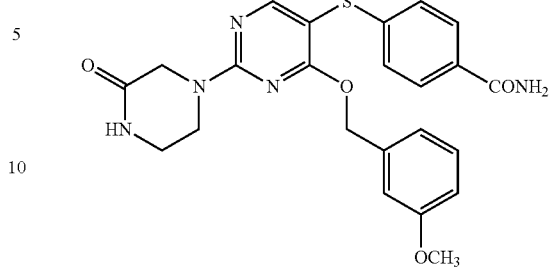

4-((4-((3-Methoxybenzyl)oxy)-2-(3-oxopiperazin-1-yl)pyrimidin-5-yl)thio)benzamide [319]. A mixture of 318 (9.7 mg, 0.0217 mmol) and KOH (24.3 mg, 0.433 mmol) in t-BuOH (2 mL) was heated at 70° C. for 1.5 h. Solvent was removed under reduced pressure and the residue was purified by preparatory TLC (CH$_2$Cl$_2$:MeOH—NH$_3$ (7 N), 10:1) to afford 6.6 mg (65%) of 319. $^1$H NMR (600 MHz, MeOH-d$_4$): δ 8.23 (s, 1H), 7.63 (d, J=6.7 Hz, 2H), 7.05 (t, J=7.8 Hz, 1H), 7.02 (d, J=6.7 Hz, 2H), 6.66-6.70 (m, 1H), 6.64 (d, J=7.6 Hz, 1H), 6.60 (s, 1H), 5.27 (s, 2H), 4.30 (s, 2H), 3.94-3.98 (m, 2H), 3.55 (s, 3H), 3.28-3.33 (m, 2H); $^{13}$C NMR (150 MHz, MeOH-d$_4$): 171.7, 170.6, 170.2, 165.9, 162.3, 161.2, 144.3, 139.3, 131.8, 130.4, 129.3, 126.9, 120.7, 114.5, 113.8, 100.9, 69.2, 55.6, 49.6, 41.6, 41.4; HRMS (ESI) m/z [M+H]$^+$ calcd. for C$_{23}$H$_{24}$N$_5$O$_4$S, 466.1549; found 466.1550.

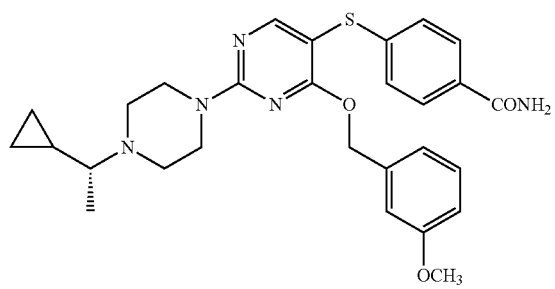

(R)-4-((2-(4-(1-Cyclopropylethyl)piperazin-1-yl)-4-((3-methoxybenzyl)oxy)pyrimidin-5-yl)thio)benzamide [317]. A mixture of 316 (8.5 mg, 0.0169 mmol) and KOH (19 mg, 0.338 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 20:1) to afford 8 mg (91%) of 317. $^1$H NMR (600 MHz, CDCl$_3$): δ 8.26 (s, 1H), 7.62 (d, J=6.8 Hz, 2H), 7.17 (t, J=7.9 Hz, 1H), 7.11 (d, J=8.7 Hz, 2H), 6.79 (dd, J=8.2, 2.5 Hz, 1H), 6.76 (d, J=7.6 Hz, 1H), 6.69 (s, 1H), 6.01 (br s, 1H), 5.51 (br s, 1H), 5.34 (s, 2H), 3.89 (m, 4H), 3.68 (s, 3H), 2.81 (m, 2H), 2.64 (m, 2H), 1.72 (m, 1H), 1.21 (m, 3H), 0.77 (m, 1H), 0.63 (m, 1H), 0.49 (m, 1H), 0.31 (m, 1H), 0.05 (m, 1H); HRMS (ESI) m/z [M+H]$^+$ calcd. for C$_{28}$H$_{34}$N$_5$O$_3$S, 520.2382; found 520.2396.

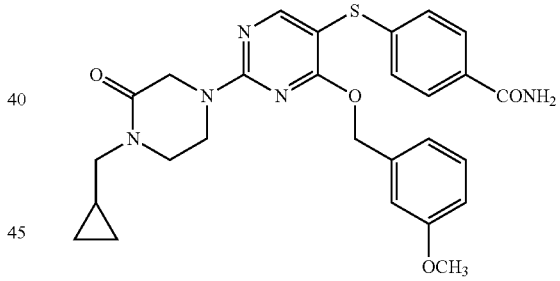

4-((2-(4-(Cyclopropylmethyl)-3-oxopiperazin-1-yl)-4-((3-methoxybenzyl)oxy)pyrimidin-5-yl)thio)benzamide [321]. A mixture of 320 (10.3 mg, 0.0205 mmol) and KOH (23.1 mg, 0.411 mmol) in t-BuOH (2 mL) was heated at 70° C. for 1.5 h. Solvent was removed under reduced pressure and the residue was purified by preparatory TLC (CH$_2$Cl$_2$:MeOH—NH$_3$ (7 N), 20:1) to afford 6.6 mg (62%) of 321. $^1$H NMR (600 MHz, CDCl$_3$): δ 8.31 (s, 1H), 7.64 (d, J=8.4 Hz, 2H), 7.17 (t, J=9.5 Hz, 1H), 7.12 (d, J=8.0 Hz, 2H), 6.74-6.80 (m, 2H), 6.68 (s, 1H), 6.00 (br s, 1H), 5.50 (br s, 1H), 5.41 (s, 2H), 4.48 (s, 2H), 4.10-4.13 (m, 2H), 3.73 (s, 3H), 3.52-3.56 (m, 2H), 3.37 (d, J=7.0 Hz, 2H), 0.98-1.04 (m, 1H), 0.50-0.58 (m, 2H), 0.27-0.31 (m, 2H); $^{13}$C NMR (150 MHz, CDCl$_3$): 168.7, 168.6, 165.5, 164.8, 160.6, 159.6, 143.1, 137.9, 130.1, 129.4, 127.8, 126.1, 119.7, 113.5, 112.9, 99.4, 67.9, 55.2, 51.1, 48.2, 45.9, 40.9, 9.1, 3.6; HRMS (ESI) m/z [M+H]$^+$ calcd. for C$_{27}$H$_{30}$N$_5$O$_4$S, 520.2019; found 520.1994.

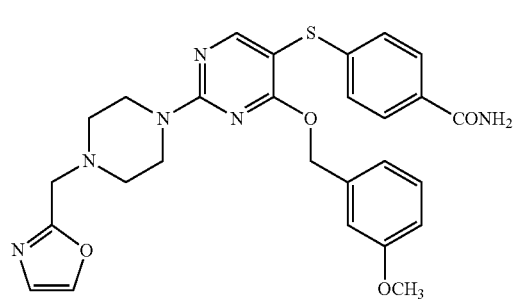

323

4-((4-((3-Methoxybenzyl)oxy)-2-(4-(oxazol-2-ylmethyl)piperazin-1-yl)pyrimidin-5-yl)thio)benzamide [323]. A mixture of 322 (15.5 mg, 0.0301 mmol) and KOH (16.9 mg, 0.301 mmol) in t-BuOH (2 mL) was heated at 70° C. for 1.5 h. Solvent was removed under reduced pressure and the residue was purified by preparatory TLC (CH$_2$Cl$_2$:MeOH—NH$_3$ (7 N), 15:1) to afford 10 mg (63%) of 323. $^1$H NMR (600 MHz, CDCl$_3$): δ 8.26 (s, 1H), 7.67 (s, 1H), 7.61 (d, J=8.4 Hz, 2H), 7.16 (t, J=7.8 Hz, 1H), 7.08-7.13 (m, 3H), 6.78 (d, J=8.2 Hz, 1H), 6.74 (d, J=7.5 Hz, 1H), 6.66 (s, 1H), 6.06 (br s, 1H), 5.63 (br s, 1H), 5.32 (s, 2H), 3.90-3.93 (m, 4H), 3.79 (s, 2H), 3.68 (s, 3H), 2.61-2.64 (m, 4H); $^{13}$C NMR (150 MHz, CDCl$_3$): 168.8, 168.6, 164.9, 161.5, 160.9, 159.5, 143.5, 139.2, 139.8, 129.9, 129.3, 127.7, 127.2, 125.9, 119.7, 113.2, 113.1, 97.9, 67.6, 55.1, 54.7, 52.6, 43.7; HRMS (ESI) m/z [M+H]$^+$ calcd. for C$_{27}$H$_{29}$N$_6$O$_4$S, 533.1971; found 533.1979.

325

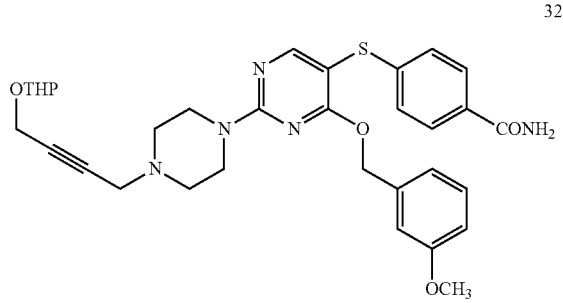

4-((4-((3-Methoxybenzyl)oxy)-2-(4-(4-((tetrahydro-2H-pyran-2-yl)oxy)but-2-yn-1-yl)piperazin-1-yl)pyrimidin-5-yl)thio)benzamide [325]. A mixture of 324 (12.3 mg, 0.0210 mmol) and KOH (11.8 mg, 0.210 mmol) in t-BuOH (2 mL) was heated at 70° C. for 1.5 h. Solvent was removed under reduced pressure and the residue was purified by preparatory TLC (CH$_2$Cl$_2$:MeOH—NH$_3$ (7 N), 15:1) to afford 7.6 mg (60%) of 325. MS (ESI) m/z [M+H]$^+$ 604.1.

Example 36

Scheme 49. Synthesis of 326.

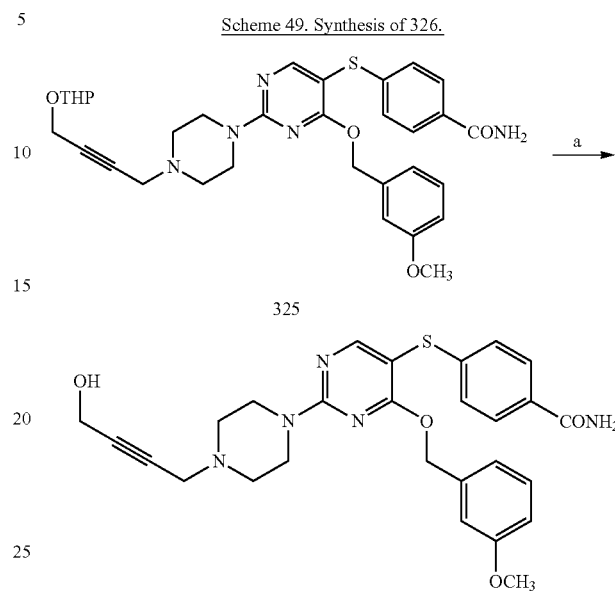

Reagents and conditions: a. PPTS, EtOH, 60° C., overnight.

4-((2-(4-(4-Hydroxybut-2-yn-1-yl)piperazin-1-yl)-4-((3-methoxybenzyl)oxy)pyrimidin-5-yl)thio)benzamide [326]. A mixture of 325 (7.6 mg, 0.0126) in EtOH (1 mL) was added PPTS (1 mg, 0.004 mmol) and the reaction stirred at 60° C. for overnight. Solvent was removed under reduced pressure and the residue was purified by preparatory TLC (CH$_2$Cl$_2$:MeOH—NH$_3$ (7 N), 10:1) to afford 3.7 mg (57%) of 326. $^1$H NMR (600 MHz, CDCl$_3$/MeOH-d$_4$): δ 8.24 (s, 1H), 7.72 (d, J=8.6 Hz, 1H), 7.16 (t, J=7.9 Hz, 1H), 7.12 (d, J=8.6 Hz, 2H), 6.78 (d, J=8.2 Hz, 1H), 6.74 (d, J=7.5 Hz, 1H), 6.70 (s, 1H), 5.34 (s, 2H), 4.23 (s, 2H), 3.90-3.93 (m, 4H), 3.67 (s, 3H), 3.41 (t, J=1.7 Hz, 2H), 2.65-2.68 (m, 4H); $^{13}$C NMR (150 MHz, CDCl$_3$/MeOH-d$_4$): 171.7, 170.2, 166.1, 162.9, 161.1, 144.7, 139.4, 131.5, 130.6, 129.3, 126.9, 120.9, 114.6, 113.9, 99.9, 85.7, 79.9, 69.1, 55.9, 52.9, 51.0, 48.1, 44.8; HRMS (ESI) m/z [M+H]$^+$ calcd. for C$_{27}$H$_{30}$N$_5$O$_4$S, 520.2019; found 520.2003.

Example 37

Scheme 50. Synthesis of 328-333.

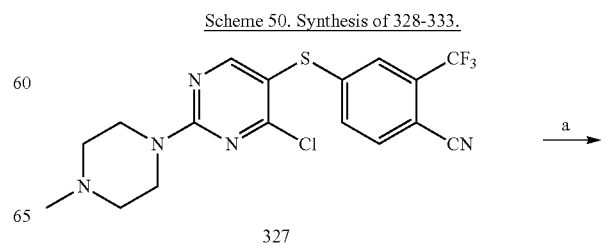

327

-continued

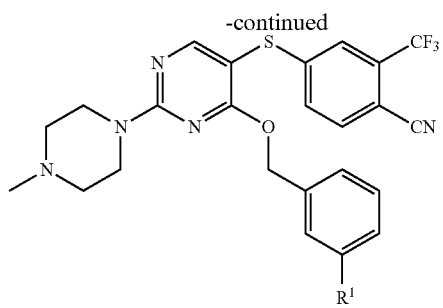

328, 330 and 332

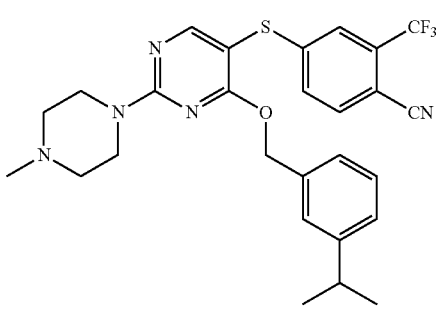

4-((4-((3-Isopropylbenzyl)oxy)-2-(4-methylpiperazin-1-yl)pyrimidin-5-yl)thio)-2-(trifluoromethyl)benzonitrile [330]. To a solution of (3-isopropylphenyl)methanol (17.9 mg, 0.119 mmol) in CH$_3$CN (1 mL) was added NaH (2.5 mg, 0.106 mmol) and the resulting suspension was stirred for 10 min. at rt. Then 327 (11 mg, 0.0265 mmol) was added and the reaction mixture was stirred at rt for 3 h. The reaction mixture was concentrated under reduced pressure to give a residue which was purified by preparatory TLC (CH$_2$Cl$_2$:MeOH—NH$_3$ (7 N), 20:1) to afford 13.5 mg (97%) of 330. MS(ESI) m/z [M+H]$^+$ 528.2.

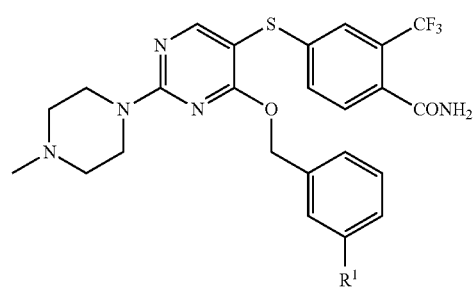

329, 331 and 333

Reagents and conditions: a. ROH, NaH, CH$_3$CN, rt, 3 h; b. KOH, t-BuOH, 80° C., 1 h.

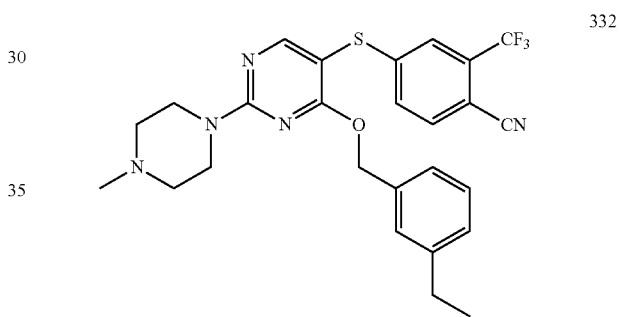

4-((4-((3-Ethylbenzyl)oxy)-2-(4-methylpiperazin-1-yl)pyrimidin-5-yl)thio)-2-(trifluoromethyl)benzonitrile [332]. To (3-ethylphenyl)methanol (16.2 mg, 0.119 mmol) dissolved in CH$_3$CN (1 mL) was added NaH (2.5 mg, 0.106 mmol) and the resulting suspension was stirred for 10 min. at rt. Then 327 (11 mg, 0.0265 mmol) was added and the reaction mixture was stirred at rt for 3 h. The reaction mixture was concentrated under reduced pressure to give a residue which was purified by preparatory TLC (CH$_2$Cl$_2$:MeOH—NH$_3$ (7 N), 20:1) to afford 9.4 mg (69%) of 332. MS (ESI) m/z [M+H]$^+$ 514.2.

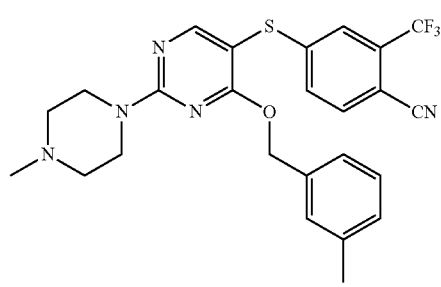

4-((4-((3-Methylbenzyl)oxy)-2-(4-methylpiperazin-1-yl)pyrimidin-5-yl)thio)-2-(trifluoromethyl)benzonitrile [328]. To a solution of m-tolylmethanol (20.5 µL, 0.170 mmol) in CH$_3$CN (1 mL) was added NaH (3.5 mg, 0.148 mmol) and the resulting suspension was stirred for 10 min. at rt. Then 327 (15.6 mg, 0.037 mmol) was added and the reaction mixture was stirred at rt for 3 h. The reaction mixture was concentrated under reduced pressure to give a residue which was purified by preparatory TLC (CH$_2$Cl$_2$:MeOH—NH$_3$ (7 N), 20:1) to afford 7.5 mg (41%) of 328. MS (ESI) m/z [M+H]$^+$ 500.0.

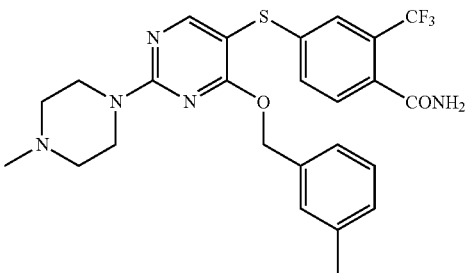

4-((4-((3-Methylbenzyl)oxy)-2-(4-methylpiperazin-1-yl)pyrimidin-5-yl)thio)-2-(trifluoromethyl)benzamide [329]. A mixture of 328 (7.5 mg, 0.015 mmol) and KOH (16.8 mg, 0.30 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 20:1) to afford 4.7 mg (61%) of 329. $^1$H NMR (600 MHz, CDCl$_3$): δ 8.26 (s, 1H), 7.45 (s, 1H), 7.41 (d, J=8.2 Hz, 1H), 7.20 (d, J=8.1 Hz, 1H), 7.17 (t, J=7.6 Hz, 1H), 7.07 (d, J=7.6 Hz, 1H), 7.02 (s, 1H), 6.96 (d, J=7.6 Hz, 1H), 5.68-5.80 (m, 2H), 5.32 (s, 2H), 3.90 (m, 4H), 2.49 (m, 4H), 2.37 (s, 3H), 2.28 (s, 3H); $^{13}$C NMR (150 MHz, CDCl$_3$): δ 169.0, 168.6, 164.9, 161.7, 142.3, 138.0, 136.1, 131.3, 129.2, 129.1, 128.7, 128.32, 128.28, 127.6 (q, J=31.9 Hz), 123.9 (q, J=5.1 Hz), 123.2 (q, J=272.5 Hz), 97.0, 68.0, 54.7, 46.2, 43.8, 21.4; HRMS (ESI) m/z [M+H]$^+$ calcd. for C$_{25}$H$_{27}$F$_3$N$_5$O$_2$S, 518.1838; found 518.1834.

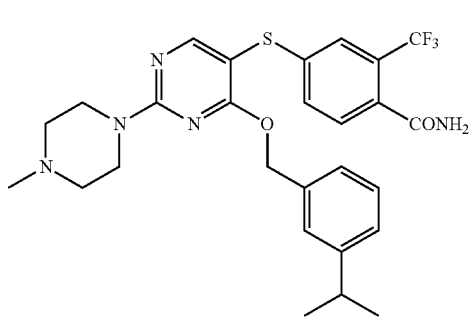

331

4-((4-((3-Isopropylbenzyl)oxy)-2-(4-methylpiperazin-1-yl)pyrimidin-5-yl)thio)-2-(trifluoromethyl)benzamide [331]. A mixture of 330 (13.5 mg, 0.0255 mmol) and KOH (28.6 mg, 0.511 mmol) in t-BuOH (2 mL) was heated at 80° C. for 1 h. Solvent was removed under reduced pressure and the residue was purified by preparatory TLC (CH$_2$Cl$_2$:MeOH—NH$_3$ (7 N), 20:1) to afford 7.8 mg (56%) of 331. $^1$H NMR (600 MHz, CDCl$_3$): δ 8.27 (s, 1H), 7.46 (s, 1H), 7.41 (d, J=8.2 Hz, 1H), 7.20 (t, J=7.8 Hz, 2H), 7.10-7.15 (m, 2H), 6.97 (d, J=7.6 Hz, 1H), 5.80 (br s, 1H), 5.73 (br s, 1H), 5.35 (s, 2H), 3.90 (m, 4H), 2.83 (septet, J=6.9 Hz, 1H), 2.49 (m, 4H), 2.36 (s, 3H), 1.19 (d, J=6.9 Hz, 6H); $^{13}$C NMR (150 MHz, CDCl$_3$): δ 169.1, 168.7, 165.0, 161.8, 149.0, 142.4, 136.2, 131.3, 129.2, 129.0, 128.4, 127.7 (q, J=31.8 Hz), 126.0, 125.5, 124.8, 123.8 (q, J=5.3 Hz), 123.2 (q, J=272.3 Hz), 96.9, 68.2, 54.7, 46.2, 43.8, 34.0, 23.9; HRMS (ESI) m/z [M+H]$^+$ calcd. for C$_{27}$H$_{31}$F$_3$N$_5$O$_2$S, 546.2151; found 546.2159.

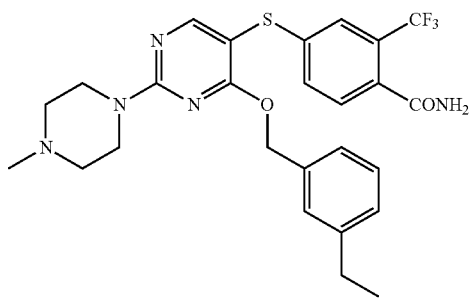

333

4-((4-((3-Ethylbenzyl)oxy)-2-(4-methylpiperazin-1-yl)pyrimidin-5-yl)thio)-2-(trifluoromethyl)benzamide [333]. A mixture of 332 (9.4 mg, 0.0183 mmol) and KOH (21 mg, 0.366 mmol) in t-BuOH (1.5 mL) was heated at 80° C. for 1 h. Solvent was removed under reduced pressure and the residue was purified by preparatory TLC (CH$_2$Cl$_2$:MeOH—NH$_3$ (7 N), 20:1) to afford 5 mg (52%) of 333. $^1$H NMR (600 MHz, CDCl$_3$): δ 8.27 (s, 1H), 7.45 (s, 1H), 7.41 (d, J=8.1 Hz, 1H), 7.16-7.23 (m, 2H), 7.10 (d, J=7.6 Hz, 1H), 7.07 (s, 1H), 6.97 (d, J=7.6 Hz, 1H), 5.77 (br s, 1H), 5.72 (br s, 1H), 5.34 (s, 2H), 3.90 (m, 4H), 2.58 (q, J=7.6 Hz, 2H), 2.49 (m, 4H), 2.37 (s, 3H), 1.18 (t, J=7.6 Hz, 3H); $^{13}$C NMR (150 MHz, CDCl$_3$): δ 169.0, 168.7, 165.0, 161.7, 144.4, 142.3, 136.2, 131.3, 129.14, 129.08, 128.4, 127.7 (q, J=31.9 Hz), 127.5, 127.0, 124.7, 123.8 (q, J=5.3 Hz), 123.2 (q, J=272.3 Hz), 97.0, 68.1, 54.7, 46.1, 43.8, 28.7, 15.5; HRMS (ESI) m/z [M+H]$^+$ calcd. for C$_{26}$H$_{29}$F$_3$N$_5$O$_2$S, 532.1994; found 532.1994.

Example 38

Scheme 51. Synthesis of 335 and 336.

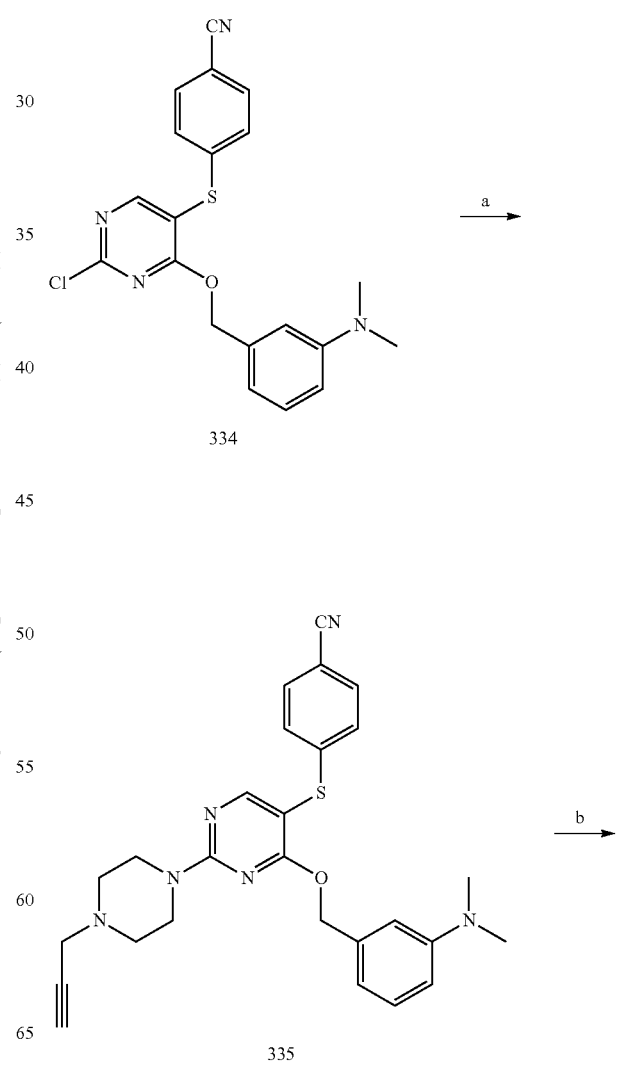

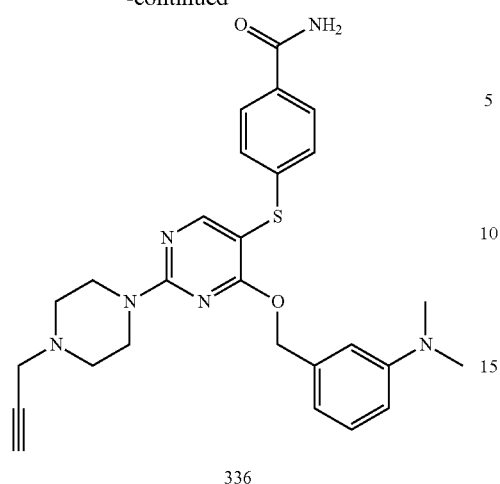

Reagents and conditions: a. 1-(prop-2-yn-1-yl)piperazine, Et₃N, DMF, 90° C., 1 h; b. KOH, t-BuOH, 80° C., 1.5 h.

4-((4-((3-(Dimethylamino)benzyl)oxy)-2-(4-(prop-2-yn-1-yl)piperazin-1-yl)pyrimidin-5-yl)thio)benzonitrile [335]. To 334 (16.5 mg, 0.0416 mmol) was added 1-(prop-2-yn-1-yl)piperazine (46 mg, 0.208 mmol) and Et₃N (75 μL) in DMF (1 mL) and heated at 90° C. for 1 h. Solvent was removed under reduced pressure and the residue was purified by preparatory TLC (CH₂Cl₂:MeOH, 40:1) to afford 14.4 mg (71%) of 335. MS (ESI) m/z [M+H]⁺ 485.1.

4-((4-((3-(Dimethylamino)benzyl)oxy)-2-(4-(prop-2-yn-1-yl)piperazin-1-yl)pyrimidin-5-yl)thio)benzamide [336]. A mixture of 335 (14.4 mg, 0.03 mmol) and KOH (33.3 mg, 0.594 mmol) in t-BuOH (2 mL) was heated at 80° C. for 1.5 h. Solvent was removed under reduced pressure and the residue was purified by preparatory TLC (CH₂Cl₂:MeOH—NH₃ (7N), 20:1) to afford 10.9 mg (73%) of 336. ¹H NMR (600 MHz, CDCl₃): δ 8.26 (s, 1H), 7.59 (d, J=8.4 Hz, 2H), 7.12 (t, J=7.9 Hz, 1H), 7.07 (d, J=7.7 Hz, 2H), 6.62 (d, J=8.3 Hz, 1H), 6.58 (s, 1H), 6.54 (d, J=7.4 Hz, 1H), 6.02 (br s, 1H), 5.58 (br s, 1H), 5.34 (s, 2H), 3.91-3.94 (m, 4H), 3.38 (s, 2H), 2.81 (s, 6H), 2.63-2.67 (m, 4H), 2.29 (t, J=2.3 Hz, 1H); ¹³C NMR (150 MHz, CDCl₃): δ 168.8, 168.7, 164.9, 161.7, 150.6, 143.7, 137.1, 129.6, 129.0, 127.7, 125.7, 115.7, 112.1, 111.7, 97.8, 78.4, 73.7, 68.3, 51.6, 47.0, 43.9, 40.6; MS (ESI) m/z [M+H]⁺ 503.1.

Example 39

Scheme 52. Synthesis of 338-345.

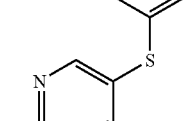

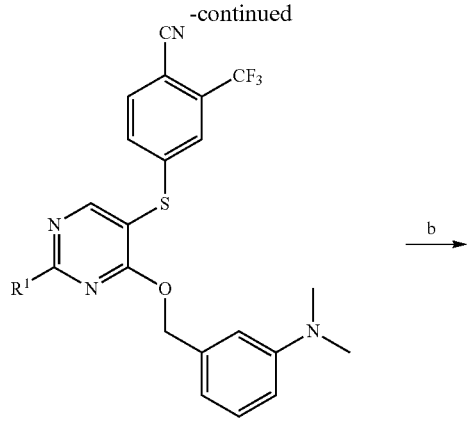

338, 340, 342 and 344

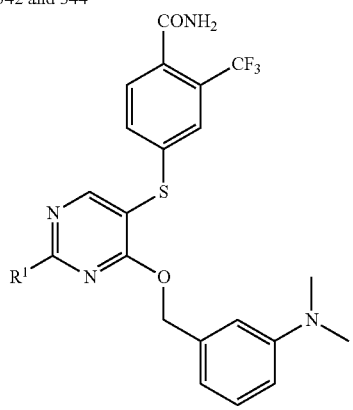

339, 341, 343 and 345

Reagents and conditions: a. amine, Et₃N, DMF, 90° C., 1 h; b. KOH, t-BuOH, 80° C., 1.5 h.

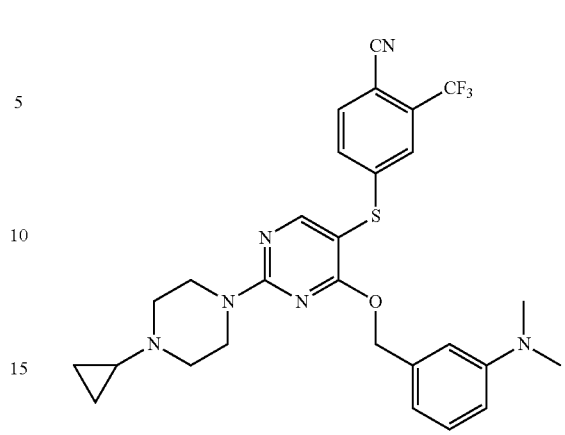

4-((2-(4-Cyclopropylpiperazin-1-yl)-4-((3-(dimethylamino)benzyl)oxy)pyrimidin-5-yl)thio)-2-(trifluoromethyl)benzonitrile [340]. To 337 (28.6 mg, 0.0615 mmol) was added 1-cyclopropylpiperazine (61.2 mg, 0.3076 mmol) and Et₃N (100 µL) in DMF (1 mL) and heated at 90° C. for 1 h. Solvent was removed under reduced pressure and the residue was purified by preparatory TLC (CH₂Cl₂:MeOH, 20:1) to afford 25.7 mg (75%) of 340. MS (ESI) m/z [M+H]⁺ 555.1.

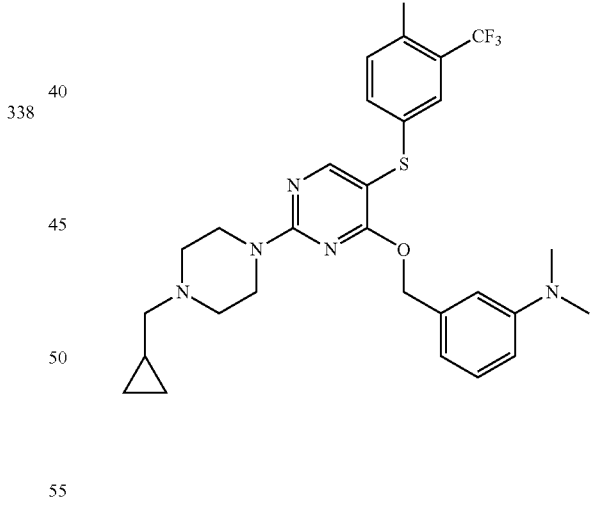

4-((2-(4-(Cyclopropylmethyl)piperazin-1-yl)-4-((3-(dimethylamino)benzyl)oxy)pyrimidin-5-yl)thio)-2-(trifluoromethyl)benzonitrile [342]. To 337 (24.5 mg, 0.0527 mmol) was added 1-cyclopropylmethyl)piperazine (36.9 mg, 0.263 mmol) and Et₃N (50 µL) in DMF (1 mL) and heated at 90° C. for 1 h. Solvent was removed under reduced pressure and the residue was purified by preparatory TLC (CH₂Cl₂:MeOH, 20:1) to afford 23.7 mg (79%) of 342. MS (ESI) m/z [M+H]⁺ 569.1.

4-((4-((3-(Dimethylamino)benzyl)oxy)-2-(4-(prop-2-yn-1-yl)piperazin-1-yl)pyrimidin-5-yl)thio)-2-(trifluoromethyl)benzonitrile [338]. To 337 (23.2 mg, 0.05 mmol) was added 1-(prop-2-yn-1-yl)piperazine (88 mg, 0.250 mmol) and Et₃N (50 µL) in DMF (1 mL) and heated at 90° C. for 1 h. Solvent was removed under reduced pressure and the residue was purified by preparatory TLC (CH₂Cl₂:MeOH, 20:1) to afford 19.7 mg (72%) of 338. MS (ESI) m/z [M+H]⁺ 553.0.

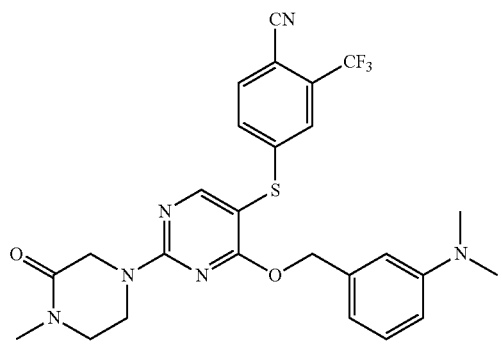

344

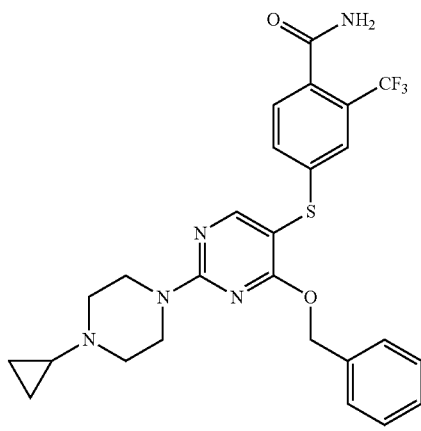

341

4-((4-((3-(Dimethylamino)benzyl)oxy)-2-(4-methyl-3-oxopiperazin-1-yl)pyrimidin-5-yl)thio)-2-(trifluoromethyl)benzonitrile [344]. To 337 (31.8 mg, 0.0684 mmol) was added 1-methylpiperazin-2-one (51.5 mg, 0.342 mmol) and Et$_3$N (50 µL) in DMF (1 mL) and heated at 90° C. for 1 h. Solvent was removed under reduced pressure and the residue was purified by preparatory TLC (CH$_2$Cl$_2$:MeOH, 20:1) to afford 31.8 mg (86%) of 344. MS (ESI) m/z [M+H]$^+$ 543.1.

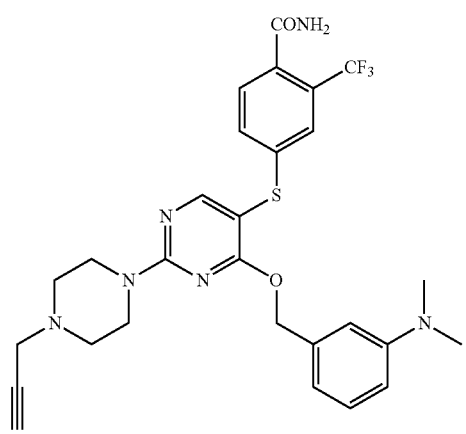

339

4-((4-((3-(Dimethylamino)benzyl)oxy)-2-(4-(prop-2-yn-1-yl)piperazin-1-yl)pyrimidin-5-yl)thio)-2-(trifluoromethyl)benzamide [339]. A mixture of 338 (19.7 mg, 0.0356 mmol) and KOH (40 mg, 0.713 mmol) in t-BuOH (2 mL) was heated at 80° C. for 1.5 h. Solvent was removed under reduced pressure and the residue was purified by preparatory TLC (CH$_2$Cl$_2$:MeOH—NH$_3$ (7 N), 20:1) to afford 7.8 mg (38%) of 339. $^1$H NMR (600 MHz, CDCl$_3$): δ 8.25 (s, 1H), 7.44 (s, 1H), 7.31 (d, J=8.1 Hz, 1H), 7.14 (t, J=7.8 Hz, 1H), 7.11 (d, J=8.1 Hz, 1H), 6.64 (d, J=8.3 Hz, 1H), 6.55-6.58 (m, 2H), 5.93 (br s, 1H), 5.79 (br s, 1H), 5.33 (s, 2H), 3.92-3.95 (m, 4H), 3.39 (s, 2H), 2.82 (s, 6H), 2.64-2.66 (m, 4H), 2.28 (t, J=2.3 Hz, 1H); $^{13}$C NMR (150 MHz, CDCl$_3$): 169.2, 168.7, 164.9, 161.7, 150.6, 142.2, 136.9, 131.2, 129.1, 129.0, 128.8, 127.6 (q, J=31.9 Hz), 123.7 (q, J=5.0 Hz), 123.2 (q, J=272.3 Hz), 116.1, 112.4, 111.9, 97.0, 78.3, 73.6, 68.4, 51.6, 46.9, 43.8, 40.6; HRMS (ESI) m/z [M+H]$^+$ calcd. for C$_{28}$H$_{30}$F$_3$N$_6$O$_2$S, 571.2103; found 571.2086.

4-((2-(4-Cyclopropylpiperazin-1-yl)-4-((3-(dimethylamino)benzyl)oxy)pyrimidin-5-yl)thio)-2-(trifluoromethyl)benzamide [341]. A mixture of 340 (25.7 mg, 0.0463 mmol) and KOH (52 mg, 0.927 mmol) in t-BuOH (2 mL) was heated at 80° C. for 1.5 h. Solvent was removed under reduced pressure and the residue was purified by preparatory TLC (CH$_2$Cl$_2$:MeOH—NH$_3$ (7 N), 20:1) to afford 19 mg (72%) of 341. $^1$H NMR (600 MHz, CDCl$_3$): δ 8.25 (s, 1H), 7.45 (s, 1H), 7.31 (d, J=8.1 Hz, 1H), 7.14 (t, J=7.9 Hz, 1H), 7.10 (dd, J=8.1, 1.4 Hz, 1H), 6.65 (dd, J=8.2, 2.2 Hz, 1H), 6.55-6.59 (m, 2H), 5.93 (s, 1H), 5.84 (s, 1H), 5.34 (s, 2H), 3.86 (m, 4H), 2.83 (s, 6H), 2.69 (m, 4H), 1.63-1.69 (m, 1H), 0.46-0.53 (m, 4H); $^{13}$C NMR (150 MHz, CDCl$_3$): δ 169.3, 168.7, 164.9, 161.7, 150.6, 142.3, 137.0, 131.2, 129.05, 128.99, 128.8, 127.6 (q, J=31.9 Hz), 123.7 (q, J=5.0 Hz), 123.2 (q, J=272.3 Hz), 116.1, 112.4, 112.0, 96.7, 68.3, 53.1, 43.9, 40.6, 38.5, 5.9; HRMS (ESI) m/z [M+H]$^+$ calcd. for C$_{28}$H$_{32}$F$_3$N$_6$O$_2$S, 573.2260; found 573.2264.

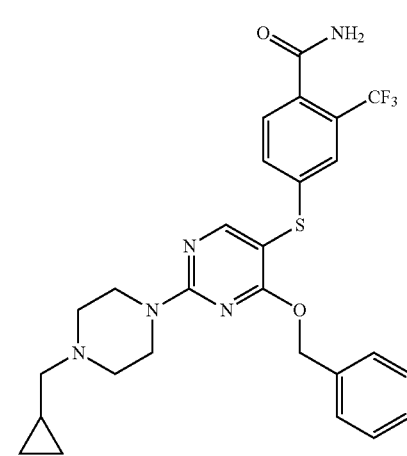

343

4-((2-(4-(Cyclopropylmethyl)piperazin-1-yl)-4-((3-(dimethylamino)benzyl)oxy)pyrimidin-5-yl)thio)-2-(trifluoromethyl)benzamide [343]. A mixture of 342 (23.7 mg, 0.0417 mmol) and KOH (46.8 mg, 0.833 mmol) in t-BuOH (2 mL) was heated at 80° C. for 1.5 h. Solvent was removed under reduced pressure and the residue was purified by preparatory TLC (CH$_2$Cl$_2$:MeOH—NH$_3$ (7 N), 20:1) to afford 15.4 mg (63%) of 343. $^1$H NMR (600 MHz, CDCl$_3$): δ 8.25 (s, 1H), 7.45 (s, 1H), 7.31 (d, J=8.1 Hz, 1H), 7.14 (t, J=7.9 Hz, 1H), 7.10 (dd, J=8.0, 1.5 Hz, 1H), 6.64 (dd, J=8.2, 2.3 Hz, 1H), 6.55-6.59 (m, 2H), 5.94 (s, 1H), 5.88 (s, 1H), 5.34 (s, 2H), 3.93 (m, 4H), 2.83 (s, 6H), 2.61 (m, 4H), 2.33 (d, J=6.6 Hz, 2H), 0.88-0.95 (m, 1H), 0.54-0.59 (m, 2H), 0.13-0.16 (m, 2H); $^{13}$C NMR (150 MHz, CDCl$_3$): δ 169.3, 168.7, 164.9, 161.7, 150.6, 142.2, 137.0, 131.2, 129.1, 129.0, 128.8, 127.6 (q, J=31.8 Hz), 123.7 (q, J=5.0 Hz), 123.2 (q, J=272.4 Hz), 116.1, 112.4, 112.0, 96.7, 68.3, 63.8, 53.0, 43.9, 40.6, 8.3, 4.0; HRMS (ESI) m/z [M+H]$^+$ calcd. for C$_{29}$H$_{34}$F$_3$N$_6$O$_2$S, 587.2416; found 587.2416.

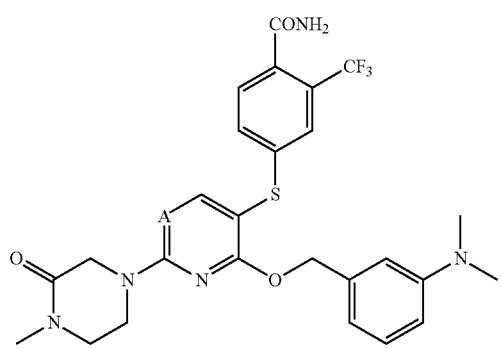

345

4-((4-((3-(Dimethylamino)benzyl)oxy)-2-(4-methyl-3-oxopiperazin-1-yl)pyrimidin-5-yl)thio)-2-(trifluoromethyl)benzamide [345]. A mixture of 344 (31.8 mg, 0.0586 mmol) and KOH (65.8 mg, 1.172 mmol) in t-BuOH (2 mL) was heated at 80° C. for 1.5 h. Solvent was removed under reduced pressure and the residue was purified by preparatory TLC (CH$_2$Cl$_2$:MeOH—NH$_3$ (7 N), 20:1) to afford 22.7 mg (69%) of 345. $^1$H NMR (600 MHz, CDCl$_3$): δ 8.29 (s, 1H), 7.44 (s, 1H), 7.33 (d, J=8.1 Hz, 1H), 7.15 (t, J=7.9 Hz, 1H), 7.12 (d, J=8.1 Hz, 1H), 6.65 (d, J=8.3 Hz, 1H), 6.58 (s, 1H), 6.54 (d, J=7.5 Hz, 1H), 5.92 (br s, 1H), 5.68 (br s, 1H), 5.35 (s, 2H), 4.47 (s, 2H), 4.11-4.14 (m, 2H), 3.45-3.47 (m, 2H), 3.06 (s, 3H), 2.85 (s, 6H); HRMS (ESI) m/z [M+H]$^+$ calcd. for C$_{26}$H$_{28}$F$_3$N$_6$O$_3$S, 561.1896; found 561.1902.

Example 40

Scheme 53. Synthesis of 347 and 348.

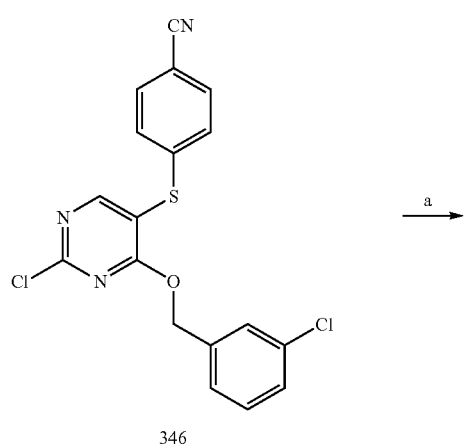

346

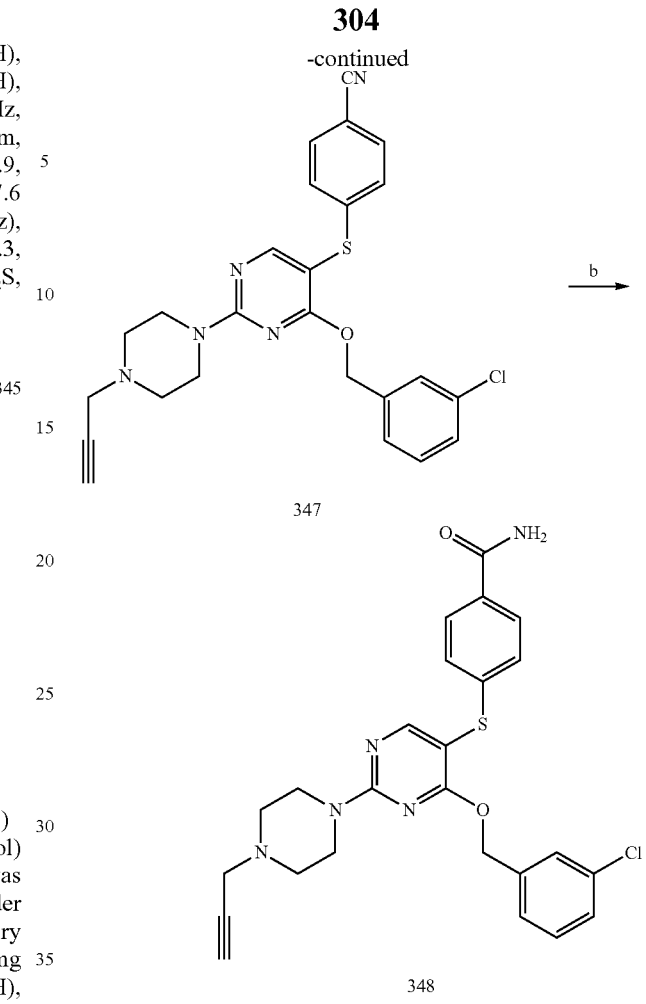

347

348

Reagents and conditions: a. 1-(prop-2-yn-1-yl)piperazine, Et$_3$N, DMF, 90° C., 1 h; b. KOH, t-BuOH, 80° C., 1.5 h.

4-((4-((3-Chlorobenzyl)oxy)-2-(4-(prop-2-yn-1-yl)piperazin-1-yl)pyrimidin-5-yl)thio)benzonitrile [347]. To 346 (24.2 mg, 0.0623 mmol) was added 1-(prop-2-yn-1-yl)piperazine (68.9 mg, 0.3116 mmol) and Et$_3$N (50 μL) in DMF (1 mL) and heated at 90° C. for 1 h. Solvent was removed under reduced pressure and the residue was purified by preparatory TLC (CH$_2$Cl$_2$:MeOH, 40:1) to afford 17.5 mg (59%) of 347. MS (ESI) m/z [M+H]$^+$ 476.0.

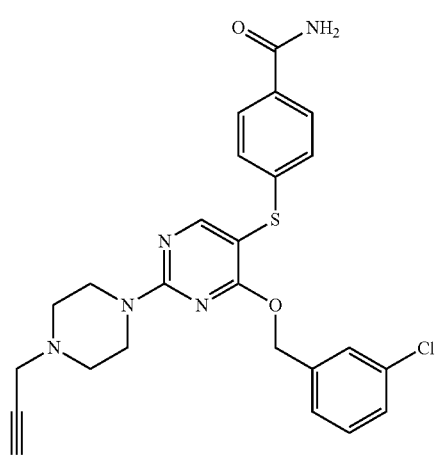

348

4-((4-((3-Chlorobenzyl)oxy)-2-(4-(prop-2-yn-1-yl)piperazin-1-yl)pyrimidin-5-yl)thio)benzamide [348]. A mixture of 347 (17.5 mg, 0.0368 mmol) and KOH (41.3 mg, 0.735 mmol) in t-BuOH (2 mL) was heated at 80° C. for 1.5 h. Solvent was removed under reduced pressure and the residue was purified by preparatory TLC (CH$_2$Cl$_2$:MeOH—NH$_3$ (7 N), 20:1) to afford 9.4 mg (52%) of 348. $^1$H NMR (600 MHz, CDCl$_3$): δ 8.27 (s, 1H), 7.66 (d, J=8.4 Hz, 2H), 7.17-7.32 (m, 2H), 7.14 (d, J=8.4 Hz, 2H), 7.09 (s, 1H), 7.02 (d, J=7.5 Hz, 1H), 6.01 (br s, 1H), 5.61 (br s, 1H), 5.31 (s, 2H), 3.98-4.02 (m, 4H), 3.38 (s, 2H), 2.60-2.65 (m, 4H), 2.28 (t, J=2.3 Hz, 1H); $^{13}$C NMR (150 MHz, CDCl$_3$): δ 168.7, 168.3, 164.9, 161.5, 143.4, 138.4, 134.2, 129.9, 129.6, 128.0, 127.8, 127.4, 125.9, 125.4, 97.9, 78.4, 73.7, 66.9, 51.6, 46.8, 43.8; HRMS (ESI) m/z [M+H]$^+$ calcd. for C$_{25}$H$_{25}$ClN$_5$O$_2$S, 494.1417; found 494.1411.

Example 41

Scheme 54. Synthesis of 350-351.

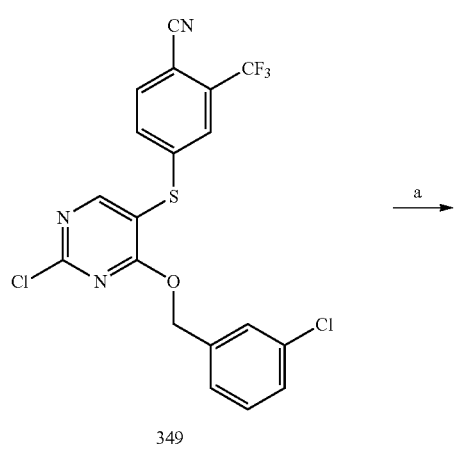

349

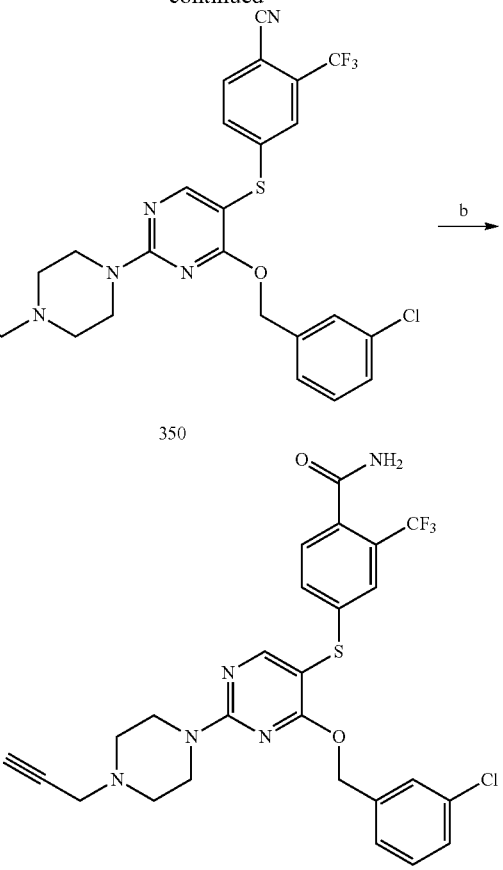

Reagents and conditions: a. 1-(prop-2-yn-1-yl)piperazine, Et$_3$N, DMF, 90° C., 1 h; b. KOH, t-BuOH, 80° C., 1.5 h.

4-((4-((3-Chlorobenzyl)oxy)-2-(4-(prop-2-yn-1-yl)piperazin-1-yl)pyrimidin-5-yl)thio)-2-(trifluoromethyl)benzonitrile [350]. To 349 (12.5 mg, 0.0274 mmol) was added 1-(prop-2-yn-1-yl)piperazine (30.3 mg, 0.137 mmol) and Et$_3$N (50 μL) in DMF (1 mL) and heated at 90° C. for 1 h. Solvent was removed under reduced pressure and the residue was purified by preparatory TLC (CH$_2$Cl$_2$:MeOH, 40:1) to afford 12.5 mg (84%) of 350. MS (ESI) m/z [M+H]$^+$ 544.0.

4-((4-((3-Chlorobenzyl)oxy)-2-(4-(prop-2-yn-1-yl)piperazin-1-yl)pyrimidin-5-yl)thio)-2-(trifluoromethyl)benzamide [351]. A mixture of 350 (12.5 mg, 0.023 mmol) and KOH (26 mg, 0.459 mmol) in t-BuOH (2 mL) was heated at 80° C. for 1.5 h. Solvent was removed under reduced pressure and the residue was purified by preparatory TLC (CH$_2$Cl$_2$:MeOH—NH$_3$ (7 N), 20:1) to afford 6.2 mg (48%) of 351. $^1$H NMR (600 MHz, CDCl$_3$): δ 8.27 (s, 1H), 7.40-7.45 (m, 2H), 7.20-7.25 (m, 3H), 7.14 (s, 1H), 7.04 (d, J=6.7 Hz, 1H), 5.79 (br s, 2H), 5.32 (s, 2H), 3.88-3.92 (m, 4H), 3.38 (s, 2H), 2.62-2.65 (m, 4H), 2.28 (t, J=2.2 Hz, 1H); $^{13}$C NMR (150 MHz, CDCl$_3$): δ 169.1, 168.3, 165.1, 161.6, 142.0, 138.2, 134.2, 131.4, 129.8, 129.2, 129.1, 128.1, 127.7 (q, J=31.9 Hz), 127.5, 125.4, 123.8 (q, J=5.1 Hz), 123.2 (q, J=272.3 Hz), 96.9, 78.3, 73.6, 67.0, 51.5, 46.9, 43.8; HRMS (ESI) m/z [M+H]$^+$ calcd. for C$_{26}$H$_{24}$ClF$_3$N$_5$O$_2$S, 562.1291; found 562.1298.

Example 42

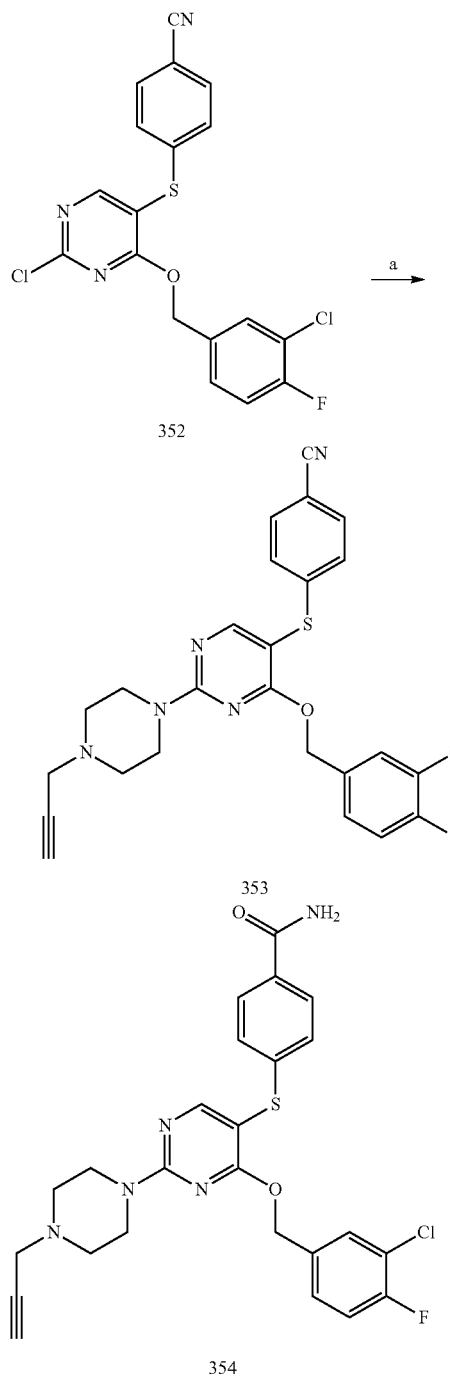

Reagents and conditions: a. 1-(prop-2-yn-1-yl)piperazine, Et₃N, DMF, 90° C., 1 h; b. KOH, t-BuOH, 80° C., 1.5 h.

4-((4-((3-Chloro-4-fluorobenzyl)oxy)-2-(4-(prop-2-yn-1-yl)piperazin-1-yl)pyrimidin-5-yl)thio)benzonitrile [353]. To 352 (24.7 mg, 0.0608 mmol) was added 1-(prop-2-yn-1-yl)piperazine (67.2 mg, 0.304 mmol) and Et₃N (100 µL) in DMF (1 mL) and heated at 90° C. for 1 h. Solvent was removed under reduced pressure and the residue was purified by preparatory TLC (CH₂Cl₂:MeOH, 40:1) to afford 24.5 mg (82%) of 353. MS (ESI) m/z [M+H]⁺ 494.0.

4-((4-((3-Chloro-4-fluorobenzyl)oxy)-2-(4-(prop-2-yn-1-yl)piperazin-1-yl)pyrimidin-5-yl)thio)benzamide [354]. A mixture of 353 (24.5 mg, 0.05 mmol) and KOH (56 mg, 0.99 mmol) in t-BuOH (2 mL) was heated at 80° C. for 1.5 h. Solvent was removed under reduced pressure and the residue was purified by preparatory TLC (CH₂Cl₂:MeOH—NH₃ (7 N), 20:1) to afford 19.1 mg (75%) of 354. $^1$H NMR (600 MHz, CDCl₃): δ 8.28 (s, 1H), 7.67 (d, J=8.4 Hz, 2H), 7.14 (d, J=7.0 Hz, 1H), 7.12 (d, J=8.4 Hz, 2H), 6.98-7.03 (m, 2H), 6.02 (br s, 1H), 5.70 (br s, 1H), 5.27 (s, 2H), 3.90-3.95 (m, 4H), 3.39 (s, 2H), 2.62-2.66 (m, 4H), 2.29 (t, J=2.3 Hz, 1H); $^{13}$C NMR (150 MHz, CDCl₃): δ 168.4 (d, J=52.7 Hz), 165.0, 161.4, 158.4, 156.8, 143.4, 133.4, 130.1, 129.7, 127.9, 127.2 (d, J=11.9 Hz), 125.9, 120.9 (d, J=17.9 Hz), 116.4 (d, J=23.9 Hz), 98.0, 78.3, 73.8, 66.5, 51.7, 47.2, 43.9; HRMS (ESI) m/z [M+H]⁺ calcd. for C₂₅H₂₄ClFN₅O₂S, 512.1323; found 512.1330.

Example 43

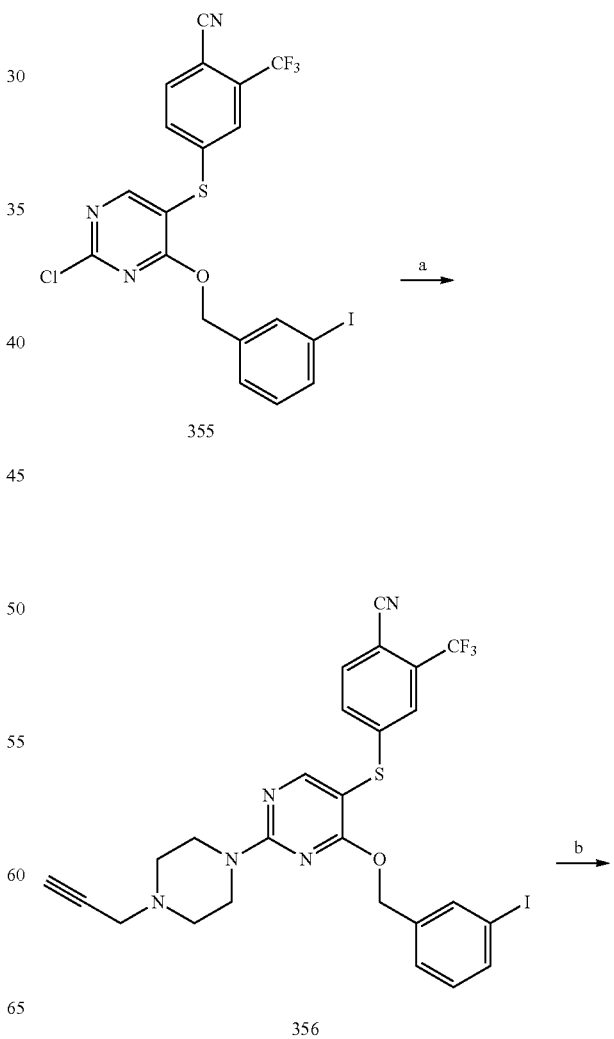

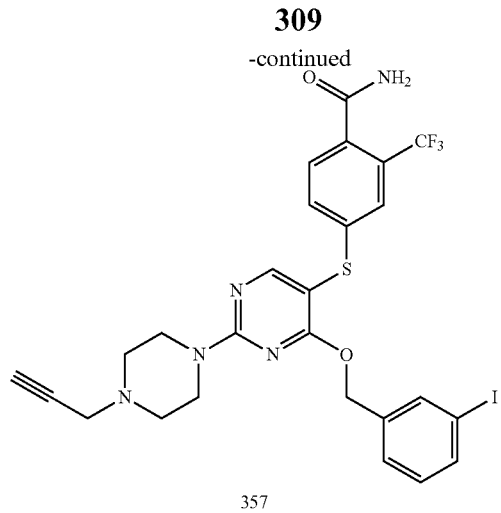

357

Reagents and conditions: a. 1-(prop-2-yn-1-yl)piperazine, Et₃N, DMF, 90° C., 1 h; b. KOH, t-BuOH, 80° C., 1.5 h.

4-((4-((3-Iodobenzyl)oxy)-2-(4-(prop-2-yn-1-yl)piperazin-1-yl)pyrimidin-5-yl)thio)-2-(trifluoromethyl)benzonitrile [356]. To 355 (46.7 mg, 0.0853 mmol) was added 1-(prop-2-yn-1-yl)piperazine (94.3 mg, 0.426 mmol) and Et₃N (100 µL) in DMF (1 mL) and heated at 90° C. for 1 h. Solvent was removed under reduced pressure and the residue was purified by preparatory TLC (CH₂Cl₂:MeOH, 40:1) to afford 37.5 mg (69%) of 356. MS (ESI) m/z [M+H]⁺ 636.2.

4-((4-((3-Iodobenzyl)oxy)-2-(4-(prop-2-yn-1-yl)piperazin-1-yl)pyrimidin-5-yl)thio)-2-(trifluoromethyl)benzamide [357]. A mixture of 356 (37.5 mg, 0.059 mmol) and KOH (66.2 mg, 1.18 mmol) in t-BuOH (2 mL) was heated at 80° C. for 1.5 h. Solvent was removed under reduced pressure and the residue was purified by preparatory TLC (CH₂Cl₂:MeOH—NH₃ (7 N), 20:1) to afford 21.7 mg (56%) of 357. ¹H NMR (600 MHz, CDCl₃): δ 8.28 (s, 1H), 7.59 (d, J=8.0 Hz, 1H), 7.58 (s, 1H), 7.43-7.47 (m, 2H), 7.21 (d, J=8.1 Hz, 1H), 7.11 (d, J=7.7 Hz, 1H), 7.03 (t, J=7.7 Hz, 1H), 5.80 (br s, 1H), 5.78 (br s, 1H), 5.29 (s, 2H), 3.89-3.92 (m, 4H), 3.39 (s, 2H), 2.63-2.66 (m, 4H), 2.28 (t, J=2.4 Hz, 1H); ¹³C NMR (150 MHz, CDCl₃): δ 169.0, 168.4, 165.1, 161.6, 142.1, 138.6, 136.9, 136.4, 131.4, 130.3, 129.3, 128.9, 127.7 (q, J=31.9 Hz), 126.5, 123.8 (q, J=5.2 Hz), 123.2 (q, J=272.6 Hz), 96.9, 94.1, 78.3, 73.6, 66.9, 51.5, 46.9, 43.8; HRMS (ESI) m/z [M+H]⁺ calcd. for C₂₆H₂₄F₃IN₅O₂S, 654.0648; found 654.0644.

Example 44

Scheme 57. Synthesis of 358-360.

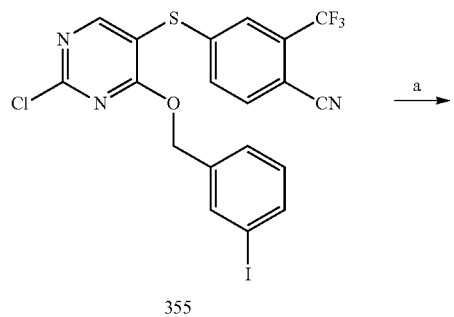

355

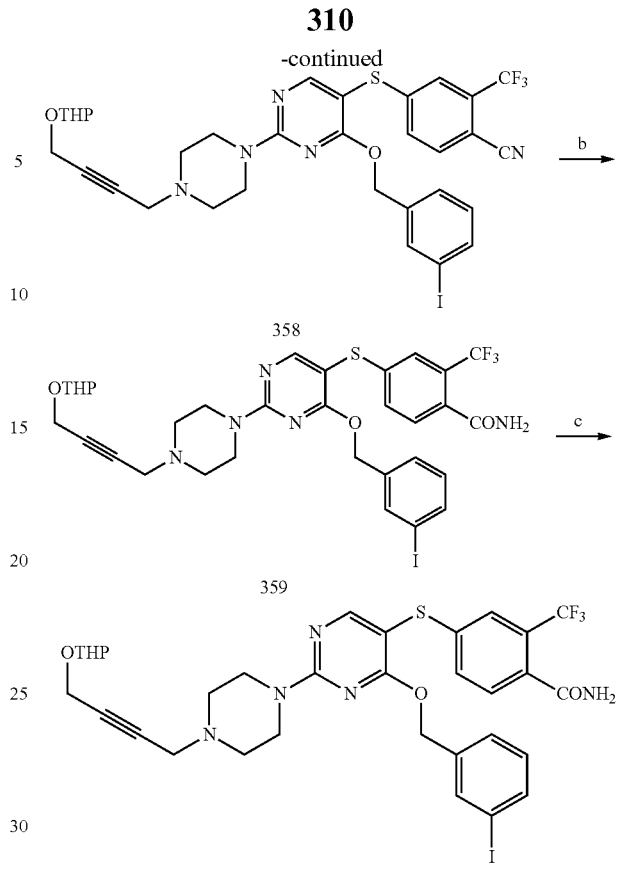

Reagents and conditions: a. 1-(4-((tetrahydro-2H-pyran-2-yl)oxy)but-2-yn-1-yl)piperazine, Et₃N, DMF, 90° C., 1 h; b. KOH, t-BuOH, 70° C., 1.5 h; c. PPTS, EtOH, 60° C., overnight.

4-((4-((3-Iodobenzyl)oxy)-2-(4-(4-((tetrahydro-2H-pyran-2-yl)oxy)but-2-yn-1-yl)piperazin-1-yl)pyrimidin-5-yl)thio)-2-(trifluoromethyl)benzonitrile [358]. To 355 (45.8 mg, 0.0836 mmol) was added 1-(4-((tetrahydro-2H-pyran-2-yl)oxy)but-2-yn-1-yl)piperazine (79.7 mg, 0.33 mmol) and Et₃N (100 µL) in DMF (1 mL) and heated at 90° C. for 1 h. Solvent was removed under reduced pressure and the residue was purified by preparatory TLC (hexane:EtOAc, 1:4) to afford 45.9 mg (73%) of 358. MS (ESI) m/z [M+H]⁺ 750.2.

4-((4-((3-Iodobenzyl)oxy)-2-(4-(4-((tetrahydro-2H-pyran-2-yl)oxy)but-2-yn-1-yl)piperazin-1-yl)pyrimidin-5-yl)thio)-2-(trifluoromethyl)benzamide [359]. A mixture of 358 (45.9 mg, 0.0612 mmol) and KOH (68.7 mg, 1.22 mmol) in t-BuOH (2 mL) was heated at 70° C. for 1.5 h. Solvent was removed under reduced pressure and the residue was purified by preparatory TLC (CH₂Cl₂:MeOH—NH₃ (7 N), 15:1) to afford 22.9 mg (49%) of 359. MS (ESI) m/z [M+H]⁺ 768.1.

4-((2-(4-(4-Hydroxybut-2-yn-1-yl)piperazin-1-yl)-4-((3-iodobenzyl)oxy)pyrimidin-5-yl)thio)-2-(trifluoromethyl)benzamide [360]. A mixture of 359 (22.9 mg, 0.03 mmol) in EtOH (1 mL) was added PPTS (1 mg, 0.004 mmol) and the reaction stirred at 60° C. for overnight. Solvent was removed under reduced pressure and the residue was purified by preparatory TLC (CH₂Cl₂:MeOH—NH₃ (7 N), 10:1) to afford 12.0 mg (59%) of 360. ¹H NMR (600 MHz, CDCl₃): δ 8.27 (s, 1H), 7.57-7.61 (m, 2H), 7.44-7.47 (m, 2H), 7.21 (d, J=8.0 Hz, 1H), 7.11 (d, J=7.7 Hz, 1H), 7.03 (t, J=7.7, 1H), 5.78 (br s, 2H), 5.29 (s, 2H), 4.31 (s, 2H), 3.89-3.95 (m, 4H), 3.41 (s, 2H), 2.61-2.65 (m, 4H); $^{13}$C NMR (150 MHz, CDCl$_3$): δ 169.0, 168.4, 165.1, 161.6, 142.1, 138.5, 136.9, 136.4, 131.4, 130.3, 129.3, 129.0, 127.7 (q, J=31.9 Hz), 126.6, 123.8 (q, J=5.0 Hz), 123.2 (q, J=272.4 Hz), 96.9, 94.1, 83.7, 80.5, 66.9, 51.7, 51.2, 47.3, 43.8; HRMS (ESI) m/z [M+H]$^+$ calcd. for C$_{27}$H$_{26}$F$_3$IN$_5$O$_3$S, 684.0753; found 684.0753.

Example 45

Scheme 58. Synthesis of 362-369.

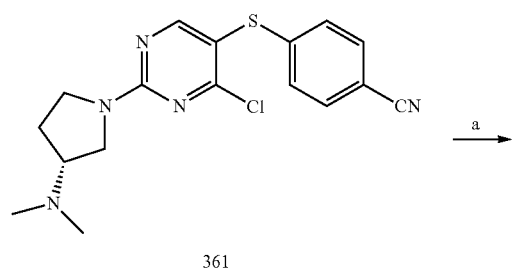

361

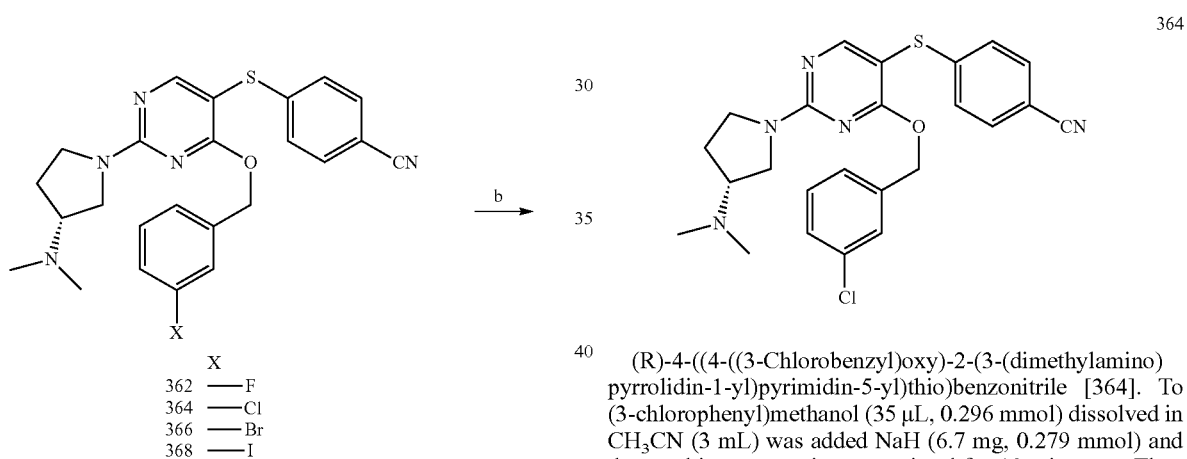

| X | |
|---|---|
| 362 | —F |
| 364 | —Cl |
| 366 | —Br |
| 368 | —I |

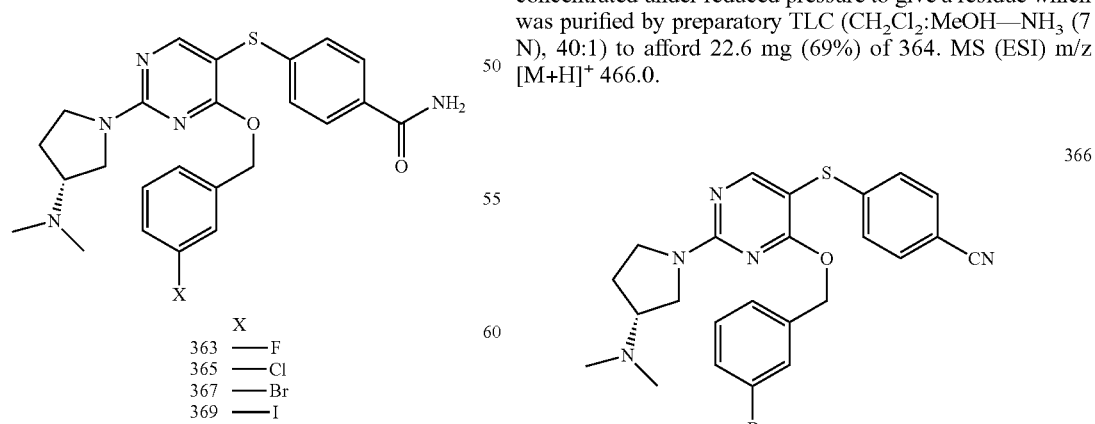

| X | |
|---|---|
| 363 | —F |
| 365 | —Cl |
| 367 | —Br |
| 369 | —I |

Reagents and conditions: a. (3-fluorophenyl)methanol, NaH, CH$_3$CN, rt, 3 h; b. KOH, t-BuOH, 70° C., 1 h.

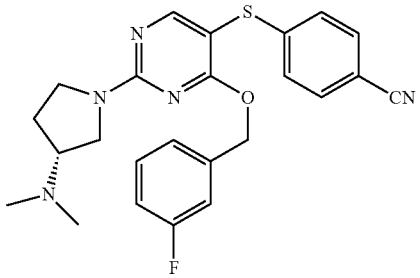

362

(R)-4-((2-(3-(Dimethylamino)pyrrolidin-1-yl)-4-((3-fluorobenzyl)oxy)pyrimidin-5-yl)thio)benzonitrile [362]. To (3-fluorophenyl)methanol (34 μL, 0.311 mmol) dissolved in CH$_3$CN (3 mL) was added NaH (7.0 mg, 0.292 mmol) and the resulting suspension was stirred for 10 min. at rt. Then 361 (26.3 mg, 0.0731 mmol) was added and the reaction mixture was stirred at rt for 3 h. The reaction mixture was concentrated under reduced pressure to give a residue which was purified by preparatory TLC (CH$_2$Cl$_2$:MeOH—NH$_3$ (7 N), 40:1) to afford 24.8 mg (77%) of 362. MS (ESI) m/z [M+H]$^+$ 450.0.

364

(R)-4-((4-((3-Chlorobenzyl)oxy)-2-(3-(dimethylamino)pyrrolidin-1-yl)pyrimidin-5-yl)thio)benzonitrile [364]. To (3-chlorophenyl)methanol (35 μL, 0.296 mmol) dissolved in CH$_3$CN (3 mL) was added NaH (6.7 mg, 0.279 mmol) and the resulting suspension was stirred for 10 min. at rt. Then 361 (25.1 mg, 0.07 mmol) was added and the reaction mixture was stirred at rt for 3 h. The reaction mixture was concentrated under reduced pressure to give a residue which was purified by preparatory TLC (CH$_2$Cl$_2$:MeOH—NH$_3$ (7 N), 40:1) to afford 22.6 mg (69%) of 364. MS (ESI) m/z [M+H]$^+$ 466.0.

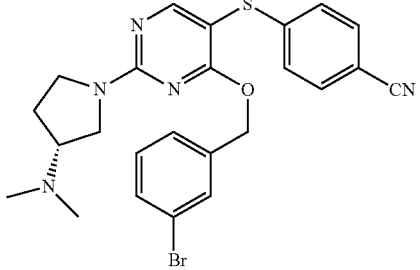

366

(R)-4-((4-((3-Bromobenzyl)oxy)-2-(3-(dimethylamino)pyrrolidin-1-yl)pyrimidin-5-yl)thio)benzonitrile [366]. To (3-bromophenyl)methanol (35 µL, 0.296 mmol) dissolved in CH₃CN (3 mL) was added NaH (6.7 mg, 0.279 mmol) and the resulting suspension was stirred for 10 min. at rt. Then 361 (25.1 mg, 0.07 mmol) was added and the reaction mixture was stirred at rt for 3 h. The reaction mixture was concentrated under reduced pressure to give a residue which was purified by preparatory TLC (CH₂Cl₂:MeOH—NH₃ (7 N), 40:1) to afford 29.3 mg (82%) of 366. MS (ESI) m/z [M+H]⁺ 510.0/512.0.

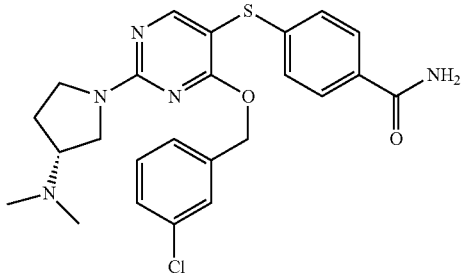

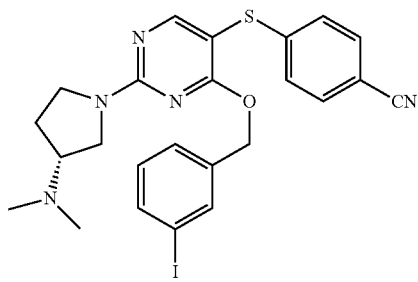

(R)-4-((2-(3-(Dimethylamino)pyrrolidin-1-yl)-4-((3-iodobenzyl)oxy)pyrimidin-5-yl)thio)benzonitrile [368]. To a solution of (3-iodophenyl)methanol (40 µL, 0.311 mmol) in CH₃CN (3 mL) was added NaH (7.0 mg, 0.292 mmol) and the resulting suspension was stirred for 10 min. at rt. Then 361 (26.3 mg, 0.0731 mmol) was added and the reaction mixture was stirred at rt for 3 h. The reaction mixture was concentrated under reduced pressure to give a residue which was purified by preparatory TLC (CH₂Cl₂:MeOH—NH₃ (7 N), 40:1) to afford 33.8 mg (83%) of 368. MS (ESI) m/z [M+H]⁺ 558.1.

(R)-4-((4-((3-Chlorobenzyl)oxy)-2-(3-(dimethylamino)pyrrolidin-1-yl)pyrimidin-5-yl)thio)benzamide [365]. A mixture of 364 (22.6 mg, 0.0485 mmol) and KOH (54.43 mg, 0.97 mmol) in t-BuOH (2 mL) was heated at 70° C. for 1.5 h. Solvent was removed under reduced pressure and the residue was purified by preparatory TLC (CH₂Cl₂:MeOH—NH₃ (7 N), 15:1) to afford 17.4 mg (74%) of 365. ¹H NMR (600 MHz, CDCl₃): δ 8.29 (s, 1H), 7.66 (d, J=8.4 Hz, 2H), 7.21-7.22 (m, 1H), 7.17 (t, J=7.6 Hz, 1H), 7.10-7.13 (m, 3H), 7.02 (d, J=7.3 Hz, 1H), 6.04 (br s, 1H), 5.69 (br s, 1H), 5.33 (s, 2H), 3.93-3.97 (m, 1H), 3.79-3.87 (m, 1H), 3.47-3.53 (m, 1H), 3.29-3.37 (m, 1H), 2.79-2.82 (m, 1H), 2.34 (d, J=9.4 Hz, 6H), 2.21-2.25 (m, 1H), 1.88-1.96 (m, 1H); ¹³C NMR (150 MHz, CDCl₃): δ 168.8, 168.2, 164.9, 160.2, 143.6, 138.7, 134.2, 129.9, 129.6, 127.9, 127.8, 127.6, 125.8, 125.6, 97.4, 66.9, 65.3, 51.2, 45.9, 44.3, 30.2; HRMS (ESI) m/z [M+H]⁺ calcd. for C₂₄H₂₇ClN₅O₂S, 484.1574; found 484.1588.

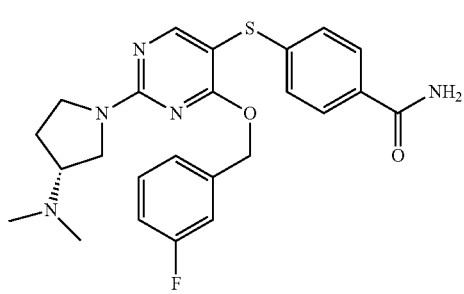

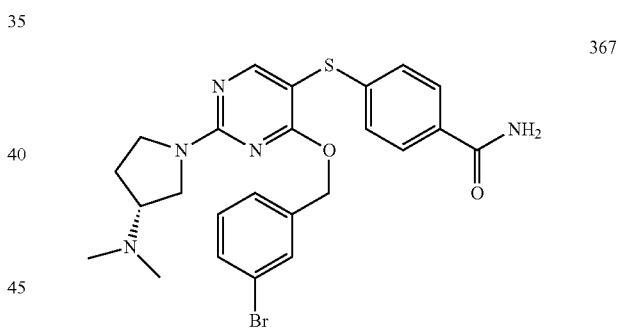

(R)-4-((2-(3-(Dimethylamino)pyrrolidin-1-yl)-4-((3-fluorobenzyl)oxy)pyrimidin-5-yl)thio)benzamide [363]. A mixture of 362 (24.8 mg, 0.0552 mmol) and KOH (61.91 mg, 1.1033 mmol) in t-BuOH (2 mL) was heated at 70° C. for 1.5 h. Solvent was removed under reduced pressure and the residue was purified by preparatory TLC (CH₂Cl₂:MeOH—NH₃ (7 N), 15:1) to afford 21.1 mg (82%) of 363. ¹H NMR (600 MHz, CDCl₃): δ 8.29 (s, 1H), 7.65 (d, J=8.4 Hz, 2H), 7.18-7.23 (m, 1H), 7.12 (d, J=8.4 Hz, 2H), 6.89-6.94 (m, 2H), 6.75 (d, J=9.2 Hz, 1H), 6.05 (br s, 1H), 5.72 (br s, 1H), 5.35 (s, 2H), 3.93-3.97 (m, 1H), 3.79-3.86 (m, 1H), 3.48-3.53 (m, 1H), 3.30-3.37 (m, 1H), 2.79-2.82 (m, 1H), 2.33 (s, 6H), 2.20-2.25 (m, 1H), 1.90-1.95 (m, 1H); ¹³C NMR (150 MHz, CDCl₃): δ 168.8, 168.2, 164.9, 163.5, 161.9, 160.2, 143.6, 139.2, 129.8 (d, J=27.8 Hz), 127.8, 125.9, 122.9, 114.6 (d, J=24.9 Hz), 114.2 (d, J=27.8 Hz), 97.6, 66.8, 65.3, 51.3, 45.9, 44.3, 30.1; MS (ESI) m/z [M+H]⁺468.1.

(R)-4-((4-((3-Bromobenzyl)oxy)-2-(3-(dimethylamino)pyrrolidin-1-yl)pyrimidin-5-yl)thio)benzamide [367]. A mixture of 366 (29.3 mg, 0.0574 mmol) and KOH (64.4 mg, 1.148 mmol) in t-BuOH (2 mL) was heated at 70° C. for 1.5 h. Solvent was removed under reduced pressure and the residue was purified by preparatory TLC (CH₂Cl₂:MeOH—NH₃ (7 N), 15:1) to afford 15.9 mg (52%) of 367. ¹H NMR (600 MHz, CDCl₃): δ 8.29 (s, 1H), 7.66 (d, J=8.4 Hz, 2H), 7.36 (d, J=7.8 Hz, 1H), 7.29 (s, 1H), 7.06-7.13 (m, 4H), 6.04 (br s, 1H), 5.67 (br s, 1H), 5.32 (s, 2H), 3.93-3.97 (m, 1H), 3.79-3.87 (m, 1H), 3.49-3.53 (m, 1H), 3.30-3.36 (m, 1H), 2.78-2.82 (m, 1H), 2.34 (d, J=10.9 Hz, 6H), 2.22-2.25 (m, 1H), 1.90-1.95 (m, 1H); ¹³C NMR (150 MHz, CDCl₃): δ 168.7, 168.2, 164.9, 160.2, 143.6, 138.9, 130.9, 130.6, 130.5, 129.9, 127.8, 126.1, 125.7, 122.3, 97.3, 66.8, 65.3, 51.2, 45.9, 44.3, 30.4; HRMS (ESI) m/z [M+H]⁺ calcd. for C₂₄H₂₇BrN₅O₂S, 528.1069; found 528.1052.

315

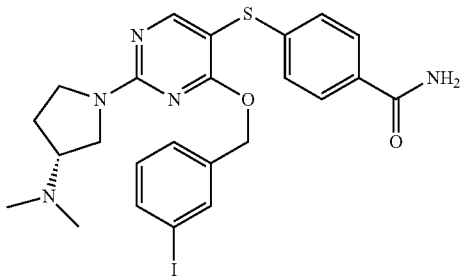

369

(R)-4-((2-(3-(Dimethylamino)pyrrolidin-1-yl)-4-((3-iodobenzyl)oxy)pyrimidin-5-yl)thio)benzamide [369]. A mixture of 368 (33.8 mg, 0.0606 mmol) and KOH (68.04 mg, 1.212 mmol) in t-BuOH (2 mL) was heated at 70° C. for 1.5 h. Solvent was removed under reduced pressure and the residue was purified by preparatory TLC (CH$_2$Cl$_2$:MeOH—NH$_3$ (7 N), 15:1) to afford 18.8 mg (54%) of 369. $^1$H NMR (600 MHz, CDCl$_3$): δ 8.28 (s, 1H), 7.67 (d, J=8.3 Hz, 2H), 7.57 (d, J=7.9 Hz, 1H), 7.53 (s, 1H), 7.08-7.18 (m, 3H), 6.98 (t, J=7.7 Hz, 1H), 6.07 (s, 1H), 5.77 (s, 1H), 5.30 (s, 2H), 3.95 (m, 1H), 3.84 (m, 1H), 3.51 (m, 1H), 3.33 (m, 1H), 2.80 (m, 1H), 2.34 (d, J=13.4 Hz, 6H), 2.23 (m, 1H), 1.92 (m, 1H); HRMS (ESI) m/z [M+H]$^+$ calcd. for C$_{24}$H$_{27}$IN$_5$O$_2$S, 576.0930; found 576.0952.

Example 46

Scheme 59. Synthesis of 371-375.

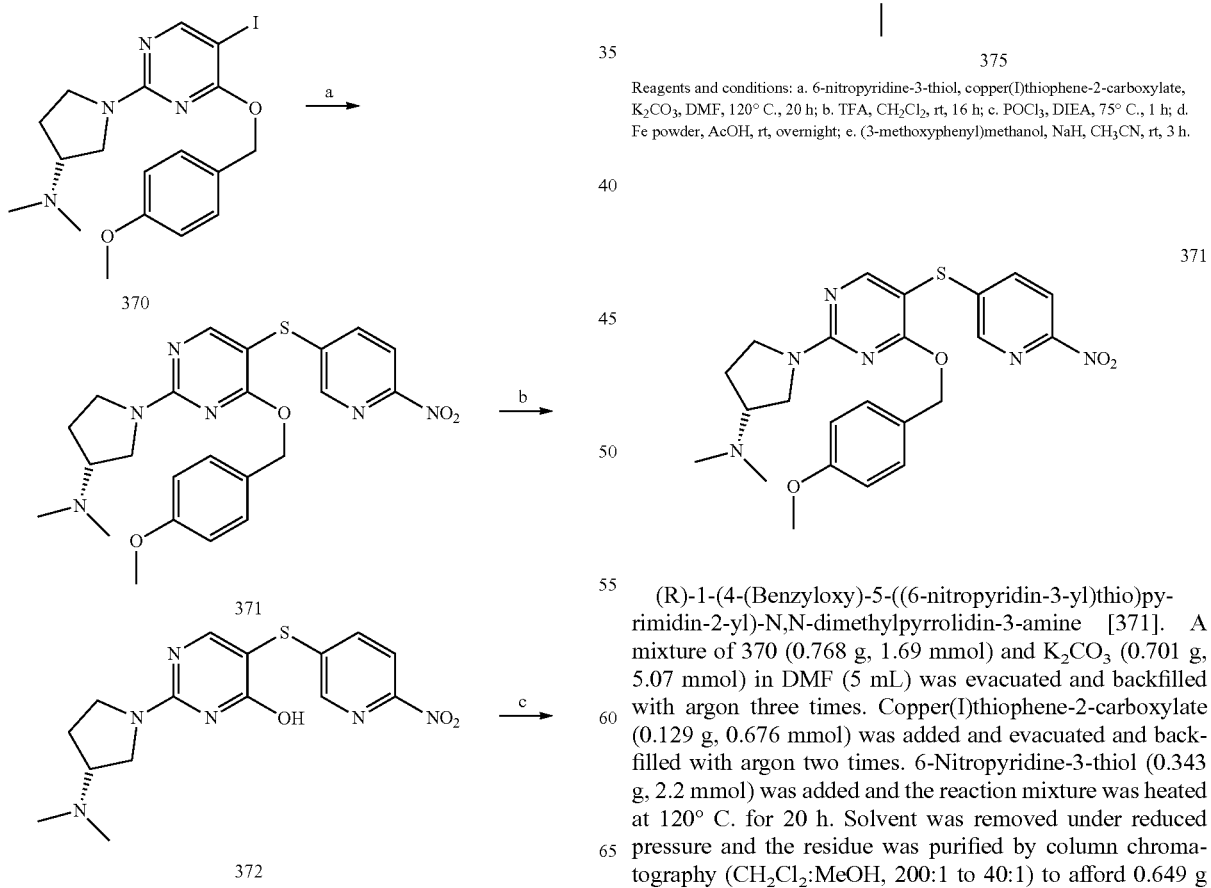

Reagents and conditions: a. 6-nitropyridine-3-thiol, copper(I)thiophene-2-carboxylate, K$_2$CO$_3$, DMF, 120° C., 20 h; b. TFA, CH$_2$Cl$_2$, rt, 16 h; c. POCl$_3$, DIEA, 75° C., 1 h; d. Fe powder, AcOH, rt, overnight; e. (3-methoxyphenyl)methanol, NaH, CH$_3$CN, rt, 3 h.

(R)-1-(4-(Benzyloxy)-5-((6-nitropyridin-3-yl)thio)pyrimidin-2-yl)-N,N-dimethylpyrrolidin-3-amine [371]. A mixture of 370 (0.768 g, 1.69 mmol) and K$_2$CO$_3$ (0.701 g, 5.07 mmol) in DMF (5 mL) was evacuated and backfilled with argon three times. Copper(I)thiophene-2-carboxylate (0.129 g, 0.676 mmol) was added and evacuated and backfilled with argon two times. 6-Nitropyridine-3-thiol (0.343 g, 2.2 mmol) was added and the reaction mixture was heated at 120° C. for 20 h. Solvent was removed under reduced pressure and the residue was purified by column chromatography (CH$_2$Cl$_2$:MeOH, 200:1 to 40:1) to afford 0.649 g (80%) of 371. MS (ESI) m/z [M+H]$^+$ 483.2.

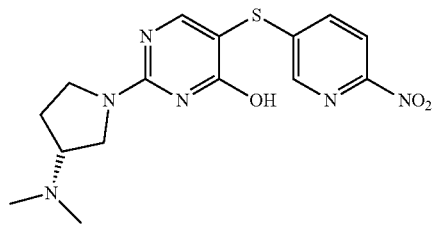

372

(R)-2-(3-(Dimethylamino)pyrrolidin-1-yl)-5-((6-nitropyridin-3-yl)thio)pyrimidin-4-ol [372]. To a solution of 371 (0.649 g, 1.34 mmol) in $CH_2Cl_2$ (4 mL) was added TFA (4 mL) dropwise over 5 minutes and stirred at rt for 16 h. The reaction mixture was concentrated under reduced pressure to give a residue which was purified by column chromatography ($CH_2Cl_2$:MeOH, 9:1 to 8:2) to afford 0.351 g (72%) of 372. MS (ESI) m/z [M+H]$^+$ 363.2.

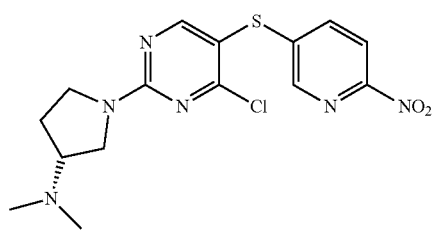

373

(R)-1-(4-Chloro-5-((6-nitropyridin-3-yl)thio)pyrimidin-2-yl)-N,N-dimethylpyrrolidin-3-amine [373]. 372 (0.351 g, 0.968 mmol), $POCl_3$ (3.4 mL) and DIEA (0.423 mL, 2.42 mmol) were heated at 75° C. for 1 h. After cooling to rt, the reaction mixture was added to a beaker containing ice chips. Following complete quenching of $POCl_3$, solid $Na_2CO_3$ was carefully added until pH ~9. This was transferred to a seperatory funnel and extracted with $CH_2Cl_2$ (4×50 mL), dried over $MgSO_4$, filtered and concentrated to a solid which was purified by column chromatography ($CH_2Cl_2$:MeOH, 100:0 to 95:5) to afford 139.5 mg (38%) of 373. MS (ESI) m/z [M+H]$^+$ 381.0.

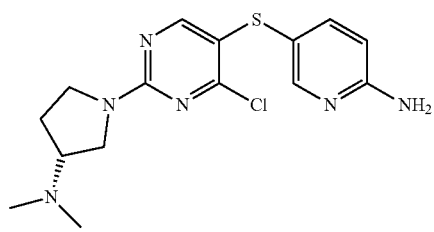

374

(R)-5-((4-Chloro-2-(3-(dimethylamino)pyrrolidin-1-yl)pyrimidin-5-yl)thio)pyridin-2-amine [374]. A mixture of 373 (139.5 mg, 0.366 mmol) and iron powder (82 mg, 1.465 mmol) in acetic acid (1 mL) was stirred at rt for overnight. The reaction mixture was concentrated under reduced pressure and purified by column chromatography ($CH_2Cl_2$:MeOH, 100:0 to 90:10) to afford 78.1 mg (61%) of 374. MS (ESI) m/z [M+H]$^+$ 351.1.

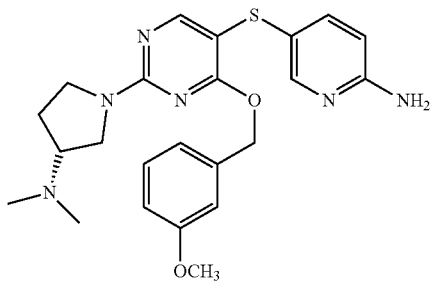

375

(R)-5-((2-(3-(Dimethylamino)pyrrolidin-1-yl)-4-((3-methoxybenzyl)oxy)pyrimidin-5-yl)thio)pyridin-2-amine [375]. To a solution of (3-methoxyphenyl)methanol (42 µL, 0.338 mmol) in $CH_3CN$ (3 mL) was added NaH (9.5 mg, 0.394 mmol) and the resulting suspension was stirred for 10 min. at rt. Then 374 (39.5 mg, 0.113 mmol) was added and the reaction mixture was stirred at rt for 3 h. The reaction mixture was concentrated under reduced pressure to give a residue which was purified by preparatory TLC ($CH_2Cl_2$: MeOH—$NH_3$ (7 N), 20:1) to afford 12 mg (23%) of 375. $^1$H NMR (600 MHz, $CDCl_3$): δ 8.23 (s, 1H), 8.13 (s, 1H), 7.40 (dd, J=8.5, 2.3 Hz, 1H), 7.23 (t, J=7.9 Hz, 1H), 6.85-6.90 (m, 2H), 6.82 (dd, J=8.3, 2.2 Hz, 1H), 6.34 (d, J=8.5 Hz, 1H), 5.37 (s, 2H), 4.45 (s, 2H), 3.79 (s, 3H), 3.46 (m, 1H), 3.27 (m, 1H), 2.74 (m, 1H), 2.31 (s, 6H), 2.19 (s, 1H), 1.76-1.88 (m, 3H); HRMS (ESI) m/z [M+H]$^+$ calcd. for $C_{23}H_{29}N_6O_2S$, 453.2073; found 453.2051.

Example 47

Scheme 60. Synthesis of 376.

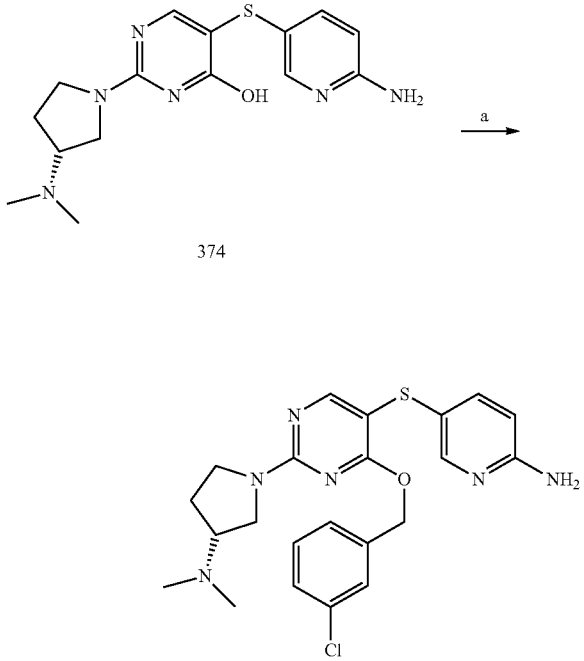

Reagents and conditions: a. (3-chlorophenyl)methanol, NaH, $CH_3CN$, rt, 3 h.

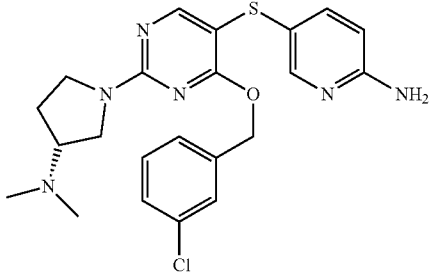

(R)-5-((4-((3-Chlorobenzyl)oxy)-2-(3-(dimethylamino) pyrrolidin-1-yl)pyrimidin-5-yl)thio)pyridin-2-amine [376]. To a solution of (3-chlorophenyl)methanol (41 μL, 0.351 mmol) in CH$_3$CN (3 mL) was added NaH (9.8 mg, 0.410 mmol) and the resulting suspension was stirred for 10 min. at rt. Then 374 (41.1 mg, 0.117 mmol) was added and the reaction mixture was stirred at rt for 3 h. The reaction mixture was concentrated under reduced pressure to give a residue which was purified by preparatory TLC (CH$_2$Cl$_2$: MeOH—NH$_3$ (7 N), 20:1) to afford 9 mg (17%) of 376. $^1$H NMR (600 MHz, CDCl$_3$): δ 8.25 (s, 1H), 8.12 (s, 1H), 7.39 (d, J=8.5 Hz, 1H), 7.22-7.26 (m, 3H), 7.13-7.16 (m, 1H), 6.37 (d, J=8.5 Hz, 1H), 5.34 (s, 2H), 4.46 (br s, 2H), 3.75-3.88 (m, 2H), 3.41-3.44 (m, 1H), 3.25-3.28 (m, 1H), 2.73-2.79 (m, 1H), 2.31 (s, 6H), 2.16-2.21 (m, 1H), 1.83-1.91 (m, 1H); HRMS (ESI) m/z [M+H]$^+$ calcd. for C$_{22}$H$_{26}$ClN$_6$OS, 457.1577; found 457.1561.

Example 48

Scheme 61. Synthesis of 377-379.

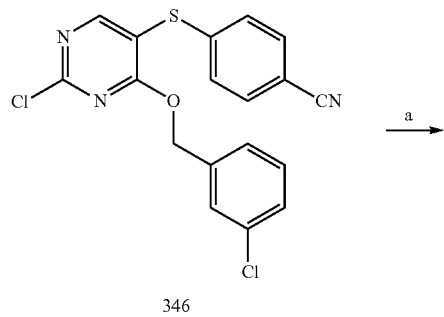

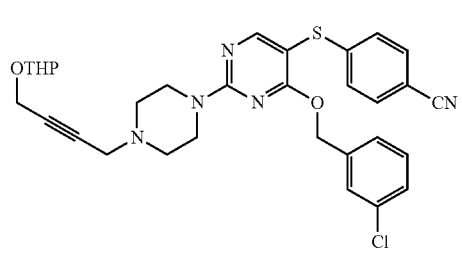

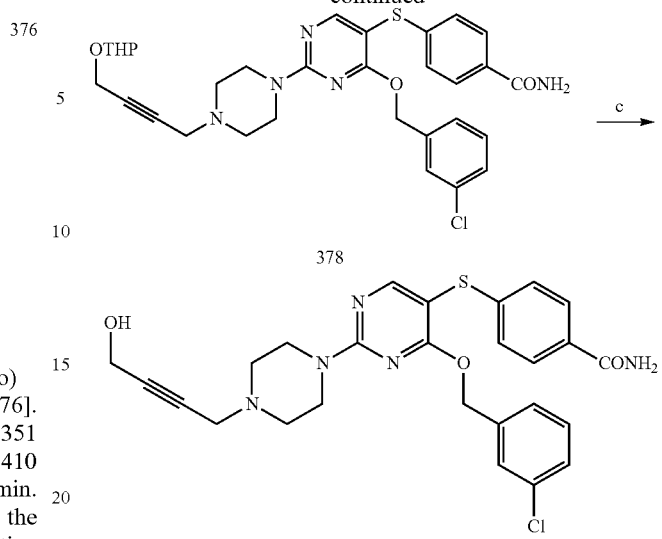

Reagents and conditions: a. 1-(4-((tetrahydro-2H-pyran-2-yl)oxy)but-2-yn-1-yl)piperazine, Et$_3$N, DMF, 90° C., 1 h; b. KOH, t-BuOH, 70° C., 1.5 h; c. PPTS, EtOH, 60° C., overnight.

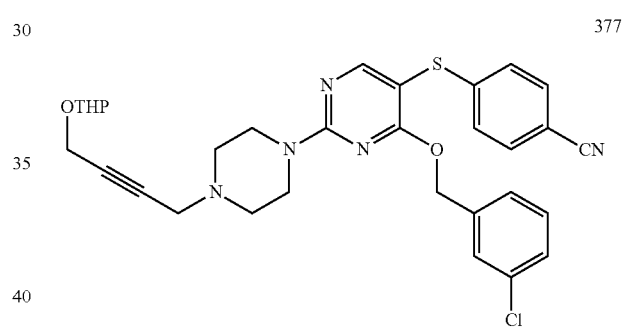

4-((4-((3-Chlorobenzyl)oxy)-2-(4-(4-((tetrahydro-2H-pyran-2-yl)oxy)but-2-yn-1-yl)piperazin-1-yl)pyrimidin-5-yl)thio)benzonitrile [377]. To 346 (24.9 mg, 0.065 mmol) was added 1-(4-((tetrahydro-2H-pyran-2-yl)oxy)but-2-yn-1-yl)piperazine (55.5 mg, 0.233 mmol) and Et$_3$N (100 μL) in DMF (1 mL) and heated at 90° C. for 1 h. Solvent was removed under reduced pressure and the residue was purified by preparatory TLC (hexane:EtOAc, 1:4) to afford 28.2 mg (73%) of 377. MS (ESI) m/z [M+H]$^+$ 590.1.

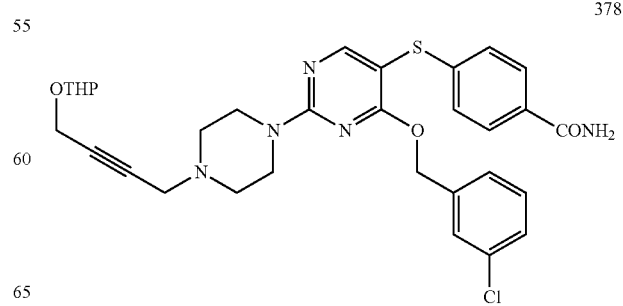

4-((4-((3-Chlorobenzyl)oxy)-2-(4-(4-((tetrahydro-2H-pyran-2-yl)oxy)but-2-yn-1-yl)piperazin-1-yl)pyrimidin-5-yl)thio)benzamide [378]. A mixture of 377 (28.2 mg, 0.0478 mmol) and KOH (26.8 mg, 0.478 mmol) in t-BuOH (2 mL) was heated at 70° C. for 1.5 h. Solvent was removed under reduced pressure and the residue was purified by preparatory TLC (CH$_2$Cl$_2$:MeOH—NH$_3$ (7 N), 15:1) to afford 22 mg (46%) of 378. MS (ESI) m/z [M+H]$^+$ 608.3.

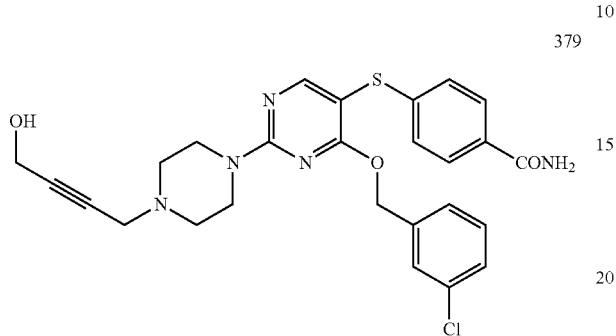

379

4-((4-((3-Chlorobenzyl)oxy)-2-(4-(4-hydroxybut-2-yn-1-yl)piperazin-1-yl)pyrimidin-5-yl)thio)benzamide [379]. A mixture of 378 (13.4 mg, 0.022 mmol) in EtOH (1 mL) was added PPTS (1 mg, 0.004 mmol) and the reaction stirred at 60° C. for overnight. Solvent was removed under reduced pressure and the residue was purified by preparatory TLC (CH$_2$Cl$_2$:MeOH—NH$_3$ (7 N), 10:1) to afford 6.2 mg (54%) of 379. $^1$H NMR (600 MHz, CDCl$_3$/MeOH-d$_4$): δ 8.26 (s, 1H), 7.74-7.77 (m, 2H), 7.19-7.24 (m, 2H), 7.14 (d, J=8.8 Hz, 2H), 7.11 (m, 1H), 7.04 (m, 1H), 5.34 (s, 2H), 4.23 (s, 2H), 3.91 (m, 4H), 3.41 (s, 2H), 2.66 (m, 4H); $^{13}$C NMR (150 MHz, CDCl$_3$/MeOH-d$_4$): δ 171.3, 169.4, 165.4, 162.3, 144.0, 139.6, 135.0, 131.2, 130.5, 129.0, 128.6, 128.1, 126.6, 126.2, 99.5, 85.3, 79.4, 67.9, 52.3, 50.6, 47.6, 44.3; HRMS (ESI) m/z [M+H]$^+$ calcd. for C$_{26}$H$_{27}$ClN$_5$O$_3$S, 524.1523; found 524.1508.

Example 49

Caspase Cleavage Assay

Caspase3, 7 Activation. MOLM-13 cells (30,000 cells/well) were plated in black 96-well plates (Corning Cat. #3603) in 40 µL of RPMI media, and left in an incubator (37° C., 5% CO$_2$) for up to 24 h. Cells were treated for 16 h with compounds or DMSO (control) at desired concentrations in 50 µL of media. Drugs were added in triplicate wells. Following exposure of cells to Hsp70 inhibitors, 50 µL of buffer containing 10 mM HEPES (pH 7.5), 2 mM EDTA, 0.1% CHAPS and the caspase substrate Z-DEVD-R110 at 25 µM was added to each well. Plates were incubated until the signal stabilized and then the fluorescence signal of each well was measured in an Analyst GT microplate reader. The percentage increase in apoptotic cells was calculated by comparison of the fluorescence reading obtained from treated versus control cells.

Exemplary results are described in Table 7, below.

TABLE 7

Exemplary results of caspase activation assay.

| Compounds | c* |
|---|---|
| 10 | C |
| 11 | B |
| 13 | C |
| 29 | C |
| 30 | C |
| 32 | B |
| 36 | D |
| 37 | C |
| 43 | C |
| 44 | C |
| 45 | B |
| 47 | C |
| 49 | B |
| 56 | E |
| 58 | C |
| 62 | C |
| 63 | E |
| 65 | C |
| 66 | B |
| 67 | B |
| 68 | D |
| 70 | A |
| 73 | D |
| 74 | C |
| 77 | B |
| 78 | C |
| 79 | B |
| 80 | C |
| 81 | D |
| 83 | C |
| 84 | B |
| 92 | C |
| 93 | D |
| 96 | C |
| 100a | A |
| 100b | B |
| 100c | A |
| 100d | E |
| 100e | A |
| 100f | C |
| 100g | A |
| 100h | B |
| 100i | C |
| 100j | B |
| 100m | B |
| 100n | E |
| 100o | E |
| 100q | C |
| 100r | D |
| 100s | B |
| 100t | C |
| 100u | C |
| 100v | E |
| 100w | C |
| 100x | A |
| 101 | A |
| 102 | B |
| 108 | A |
| 109 | A |
| 110 | B |
| 111 | A |
| 112 | A |
| 113 | A |
| 114 | A |
| 115 | B |
| 116 | A |
| 117 | B |
| 118 | C |
| 121 | B |
| 122 | B |
| 123 | B |
| 124 | A |
| 125 | A |
| 126 | B |
| 127 | C |
| 131 | A |
| 132 | A |

TABLE 7-continued

Exemplary results of caspase activation assay.

| Compounds | c* |
|---|---|
| 133 | A |
| 134 | B |
| 135 | B |
| 136 | A |
| 137 | A |
| 138 | A |
| 139 | A |
| 141 | D |
| 146c | B |
| 146e | C |
| 151 | A |
| 152 | B |
| 153 | A |
| 154 | A |
| 155 | A |
| 156 | B |
| 157 | A |
| 158 | A |
| 167 | E |
| 168 | E |
| 179a | E |
| 179c | E |
| 182 | E |
| 185a | D |
| 185b | D |
| 185d | C |
| 185e | A |
| 187 | D |
| 190a | B |
| 190b | B |
| 190e | A |
| 190g | E |
| 190h | E |
| 190j | A |
| 190k | A |
| 190m | A |
| 190n | B |
| 190o | A |
| 190p | A |
| 190q | A |
| 190r | B |
| 190t | A |
| 190u | A |
| 190v | A |
| 193 | E |
| 195 | E |
| 198 | A |
| 205 | C |
| 206 | C |
| 207 | C |
| 208 | A |
| 212 | A |
| 213 | E |
| 214 | C |
| 218 | A |
| 225 | B |
| 226 | B |
| 227 | E |
| 228 | A |
| 229 | B |
| 282 | E |
| 283 | E |
| 284 | C |
| 299 | B |
| 304 | E |
| 311 | E |
| 313 | E |
| 315 | D |
| 317 | E |
| 319 | E |
| 321 | A |
| 323 | A |
| 326 | A |
| 329 | C |
| 331 | E |
| 333 | D |
| 336 | A |
| 339 | C |
| 341 | E |
| 343 | E |
| 345 | D |
| 348 | C |
| 351 | D |
| 354 | A |
| 357 | B |
| 360 | B |
| 363 | B |
| 365 | B |
| 367 | B |
| 369 | B |
| 375 | A |
| 376 | A |
| 379 | A |

*Concentration at which 50% of the maximum signal was achieved.

A: $c < 0.2\ \mu M$;

B: $0.2\ \mu M \leq c < 0.4\ \mu M$;

C: $0.4\ \mu M \leq c < 1.0\ \mu M$;

D: $1.0\ \mu M \leq c < 1.2\ \mu M$; and

E: $c \geq 1.2\ \mu M$

Example 50

Effects of Hsp70 Inhibitors on Cells with Resistance to Hsp 90 Inhibitor.

Cell lines: MDA-MB-468 cells were obtained from the American Type Culture Collection. DLBCL cells were described in Cerchietti L C, et al. *BCL6 repression of EP300 in human diffuse large B cell lymphoma cells provides a basis for rational combinatorial therapy*. J Clin Invest. Dec. 1, 2010; 120(12): 4569-4582; and Cerchietti L C, et al. *A purine scaffold Hsp90 inhibitor destabilizes BCL-6 and has specific antitumor activity in BCL-6-dependent B cell lymphomas*. Nat Med. 2009 December; 15(12):1369-76. MDA-MB-468 cells were grown in DME/F12 with 10% FBS and 1% penicillin and streptomycin. OCI-LY1R cells were developed by continuous incubation of OCI-LY1 cells with suboptimal concentrations of PU-H71 (depicted below) with subsequent selection of resistant clones. OCI-LY1, OCI-LY1R and OCI-LY7 cells were cultured in IMDM supplemented with 20% FBS, 1% glutamax and 1% penicillin and streptomycin. OCI-LY3, FARAGE, HBL1, Karpas422, MD901, U2932, SU-DHL4, SU-DHL6, RCK8 and TMD8 cells were grown in RPMI with 10% FBS, 1% glutamax and 1% penicillin and streptomycin.

PU-H71

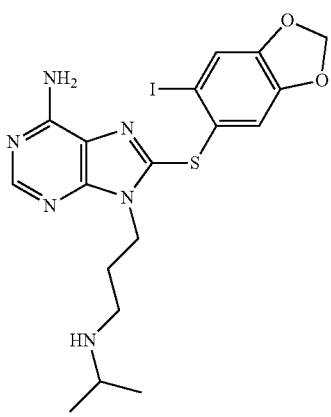

Western blot: Cells were plated and treated next day with indicated drug concentrations for 24h. Cells were collected and protein was extracted in 20 mM Tris pH 7.4, 25 mM NaCl, 1% NP-40 buffer. 30-50m of total protein was subjected to SDS-PAGE, transferred onto nitrocellulose membrane and incubated with indicated antibodies. P-Akt, BID, Mcl1, Caspase 9, caspase 3, caspase 7 and Bcl-XL antibodies were purchased from Cell Signaling Technology; Bax antibody from Santa Cruz Biotechnology; cleaved PARP Ab from Promega; and β-actin Ab from Sigma. Blots were washed with TB S-0.1% Tween 20 and incubated with the appropriate HRP-conjugated secondary antibody. The chemiluminescent signal was detected using the Enhanced Chemiluminescence Detection System (Amersham Biosciences) according to the manufacturer's instructions.

Growth inhibition: 5,000 cells per well were plated in black 96-well microtiter plates and treated next day with indicated compounds at 1/2 serial dilutions. The plate was incubated for 72h after which growth was measured using the CellTiter-Glo Luminescent Cell Viability Assay (Promega) according to manufacture's instructions. The percentage cell growth inhibition was calculated by comparing luminescence readings obtained from treated versus control cells, accounting for initial cell population. The luminescence signal in each well was measured using the Analyst GT microplate reader (Molecular Devices).

It was surprisingly found that provided compounds of the present invention can activate caspases, induce cell death and inhibit cell growth in cancer cells resistant to Hsp90 inhibitors (FIG. 1).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A method of treating cancer in a patient in need thereof, wherein cancer is a hematological malignancy or a solid tumor; and
wherein the method comprises administering to the patient a therapeutically effective amount of a compound of Formula I:

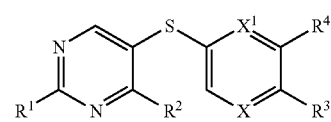

or a pharmaceutically acceptable salt thereof, wherein:
X is —N= or —CH=;
$X^1$ is —N= or —C($R^5$)=;
$R^1$ is

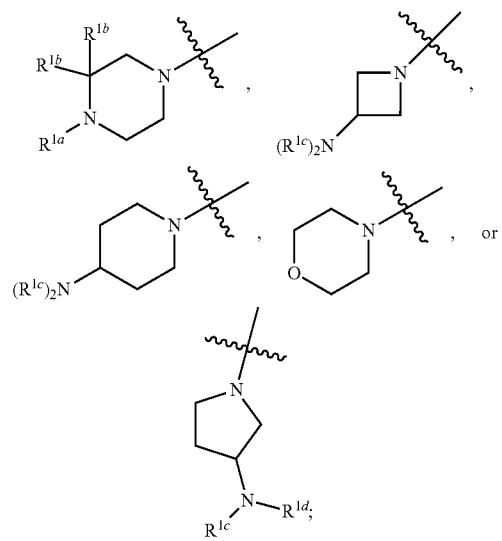

$R^{1a}$ is

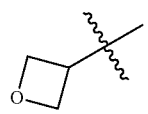 [SMILES: *C1COC1]

or $C_{1-6}$ aliphatic optionally substituted with one or more groups independently selected from —OH, cyclopropyl, or 5-membered heteroaryl having 1-2 heteroatoms independently selected from nitrogen, oxygen or sulfur;

each $R^{1b}$ is independently hydrogen, $C_{1-4}$ alkyl, or two $R^{1b}$ groups are optionally taken together to form an oxo group;

each of $R^{1c}$ and $R^{1d}$ is independently hydrogen or $C_{1-4}$ alkyl;

$R^2$ is —O—CH$_2$-Ring A, —NH—CH$_2$-Ring A, or —O—CH$_2$CH$_2$-Ring A;

Ring A is unsubstituted phenyl, unsubstituted furanyl,

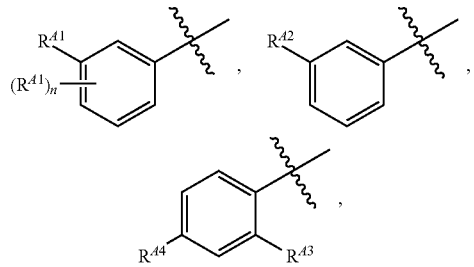

or pyridinyl optionally substituted with $R^{45}$;

each of $R^{41}$ is independently halogen, —CN, —C(O)N(R)$_2$, —N(R)$_2$, —OR, —C(O)R, —N$_3$, an optionally substituted 5- or 6-membered heterocyclyl or heteroaryl having one or two heteroatoms independently selected from nitrogen, oxygen, or sulfur, or $C_{1-4}$ alkyl optionally substituted with one or more halogen;

each R is independently hydrogen or $C_{1-4}$ alkyl optionally substituted with one or more halogen;

$R^{42}$ is —Cl, —Br, —I, —CN, —C(O)N(R)$_2$, —N(R)$_2$, —OR, —C(O)R, —N$_3$, $C_{1-4}$ alkyl optionally substituted with one or more halogen, or an optionally substituted 5- or 6-membered heterocyclyl or heteroaryl having one or two heteroatoms independently selected from nitrogen, oxygen or sulfur;

n is 1 to 4;

$R^{43}$ is —H or —F;

$R^{44}$ is —F or —OR;

$R^{45}$ is —OR or —N(R)$_2$;

$R^3$ is —C(O)N(R$^{3a}$)$_2$, —OR$^{3b}$, —C(O)H, —C(O)OR, or —N(R$^{3c}$)$_2$;

each $R^{3a}$ is independently hydrogen or $C_1$ alkyl optionally substituted with one or more groups independently selected from halogen or 1-pyrrolidinyl;

$R^{3b}$ is hydrogen or $C_{1-4}$ alkyl optionally substituted with one or more groups independently selected from halogen, $C_{1-4}$ alkyl, $C_{1-4}$ haloalkyl, oxo, or —N(R)$_2$;

each $R^{3c}$ is independently hydrogen or $C_{1-4}$ alkyl optionally substituted with one or more groups independently selected from halogen, $C_{1-4}$ alkyl, $C_{1-4}$ haloalkyl, oxo, or —N(R)$_2$;

$R^4$ is R, halogen, or —N(R)$_2$; and $R^5$ is hydrogen, methyl or —N(R)$_2$.

2. The method of claim 1, wherein X is —N=.
3. The method of claim 1, wherein X is —CH=.
4. The method of claim 1, wherein $R^3$ is —C(O)NH$_2$.
5. The method of claim 1, wherein $R^3$ is —N(R$^{3c}$)$_2$.
6. The method of claim 1, wherein $R^4$ is —CF$_3$.
7. The method of claim 1, wherein $R^4$ is halogen.
8. The method of claim 1, wherein $X^1$ is —C(R$^5$)=.
9. The method of claim 1, wherein $X^1$ is —N=.

10. The method of claim 1, wherein $R^1$ is

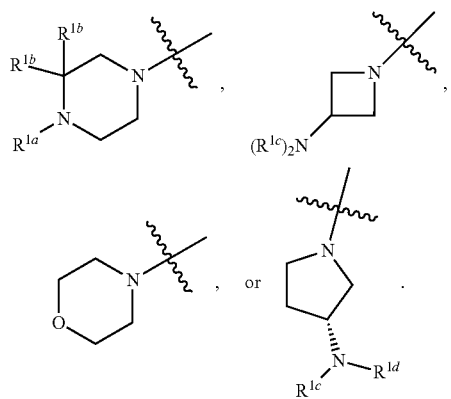

11. The method of claim 1, wherein $R^2$ —O—CH$_2$-Ring A.

12. The method of claim 1, wherein Ring A is phenyl,

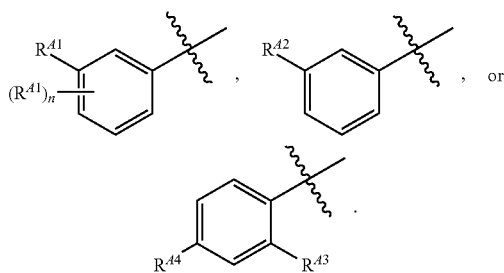

13. The method of claim 1, wherein the compound of Formula I is selected from the group consisting of:

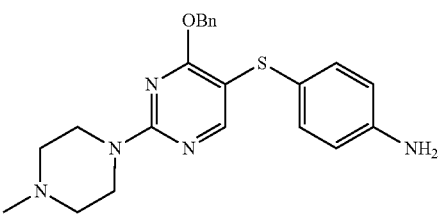

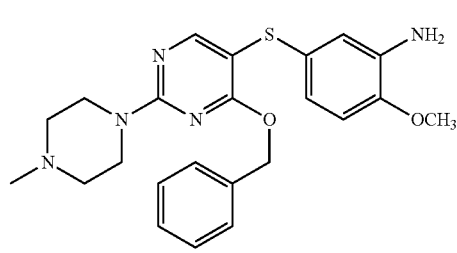

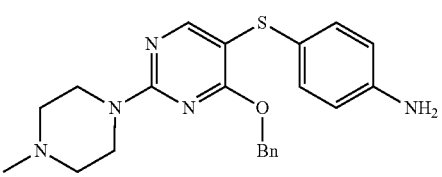

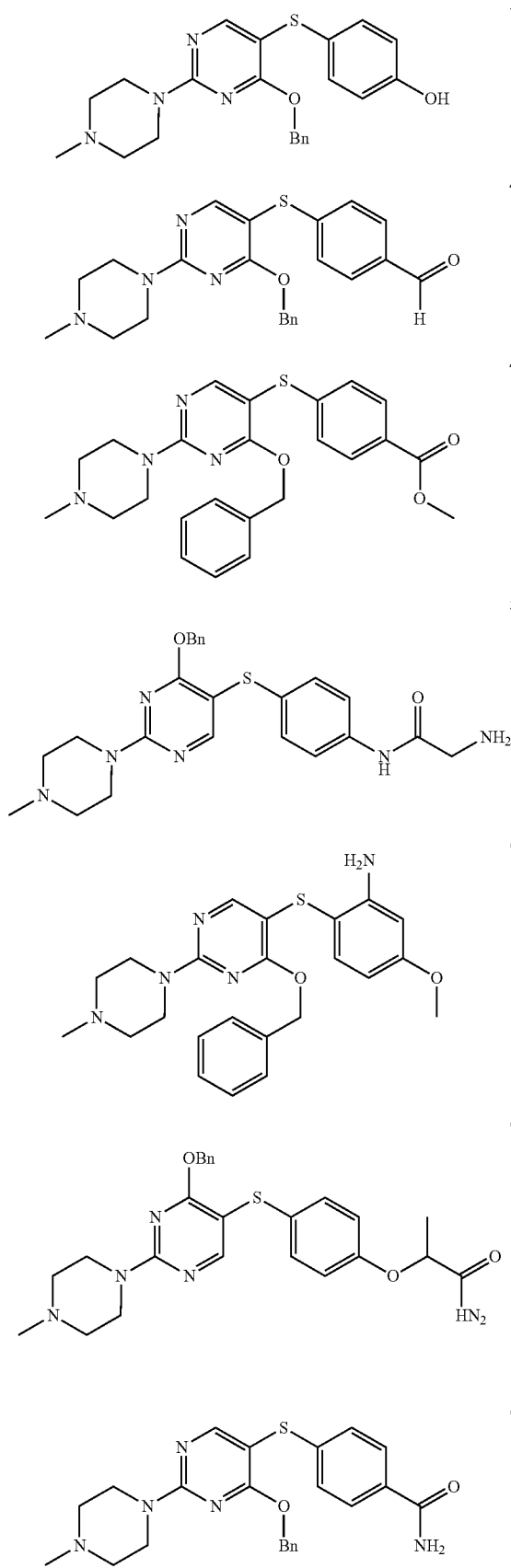
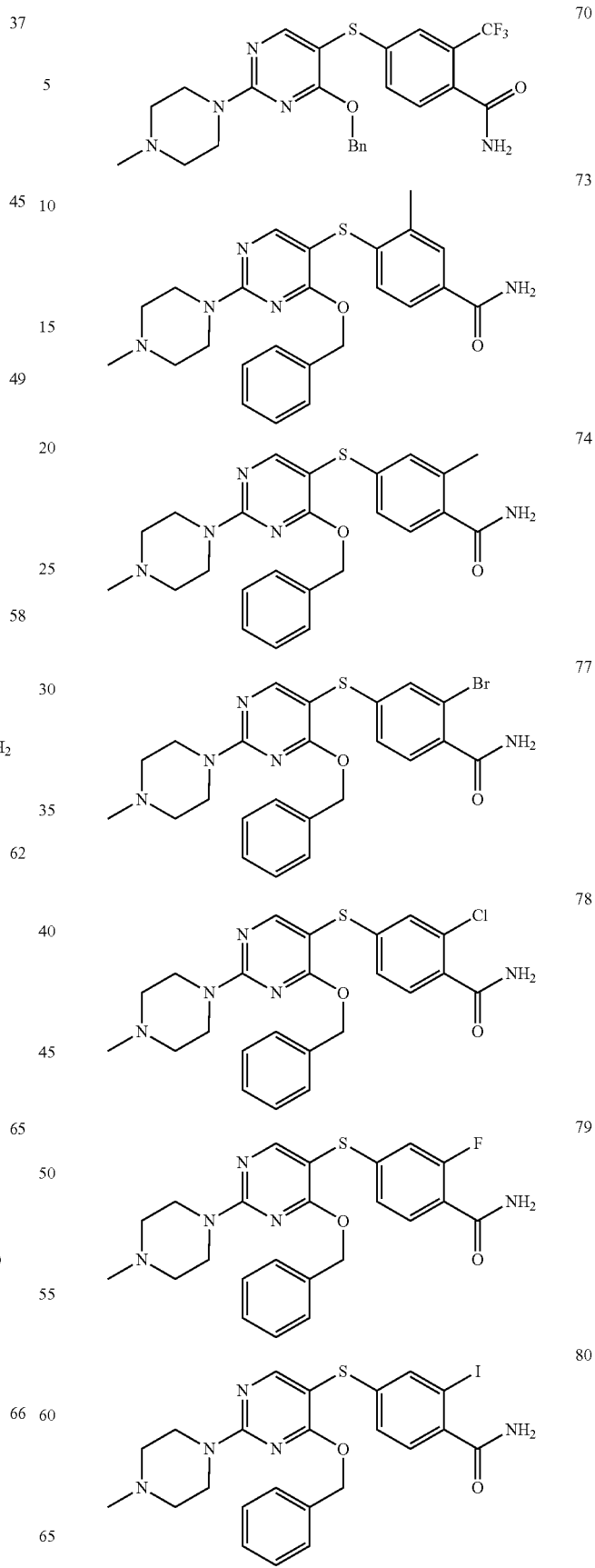

331
-continued
83
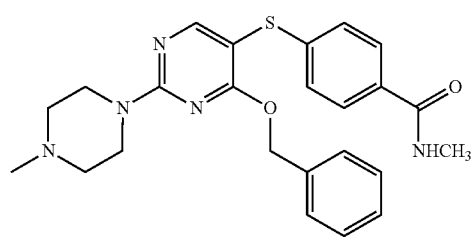
84
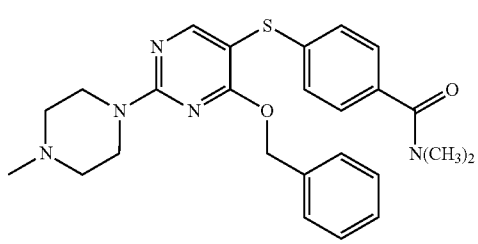
92
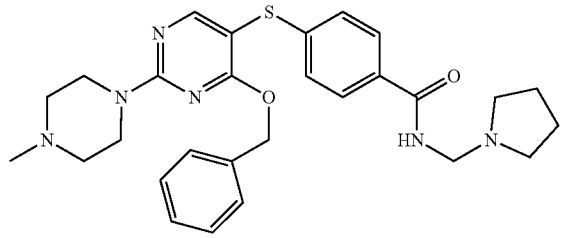
100a
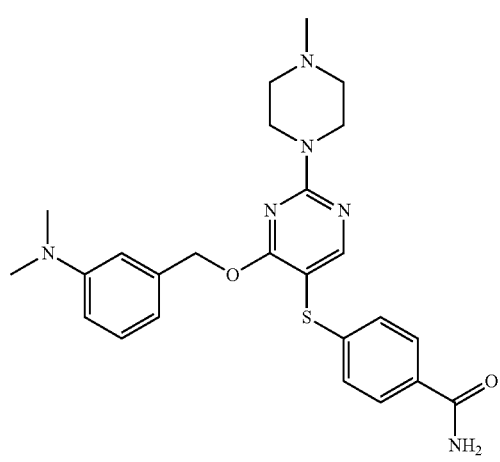
332
-continued
100b
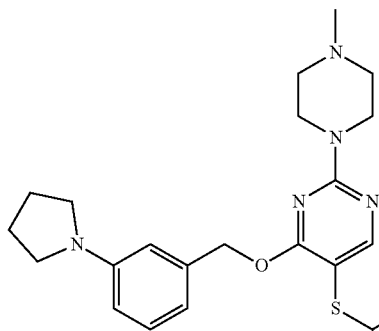
100c
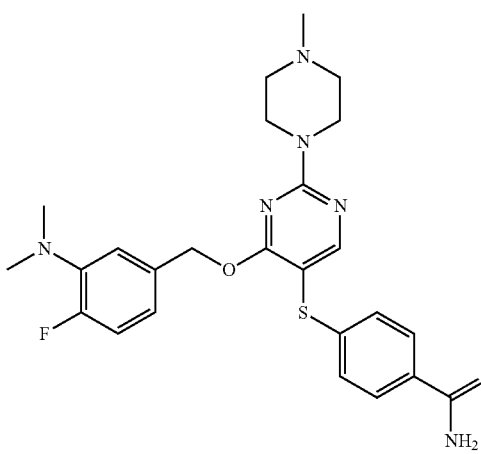
100e
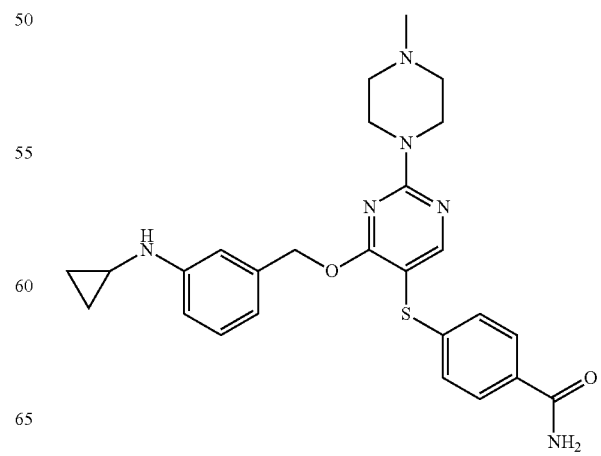

100f
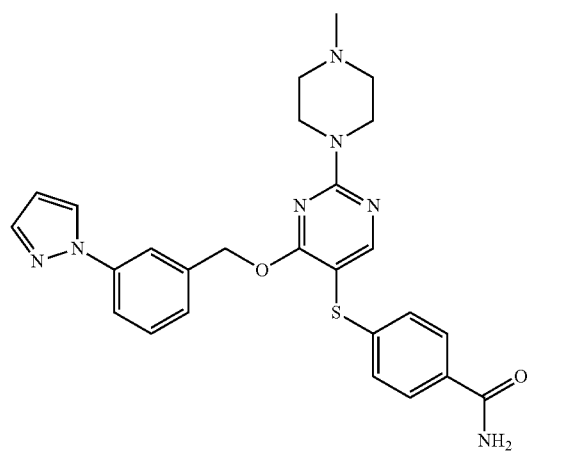
100i
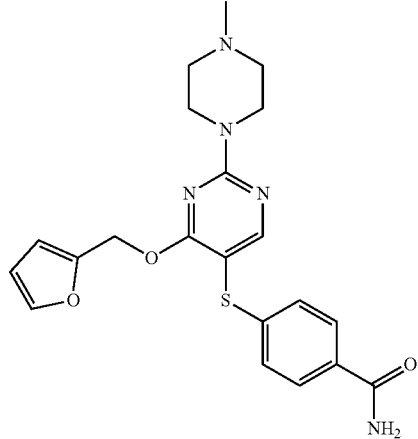
100g
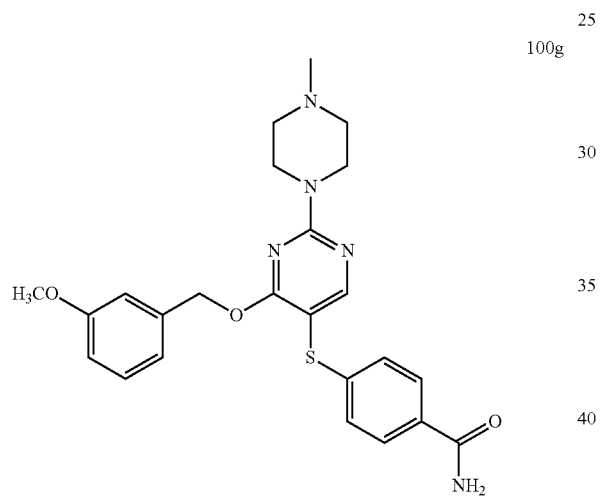
100j
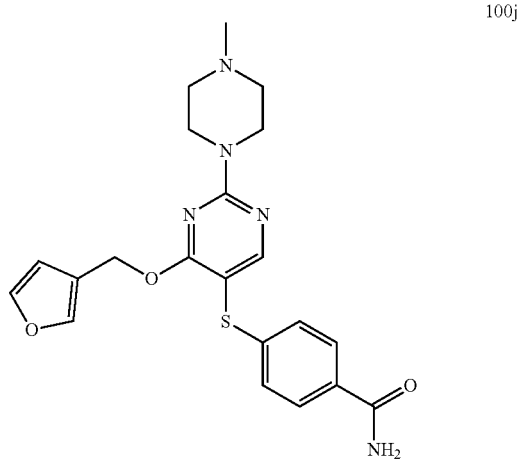
100h
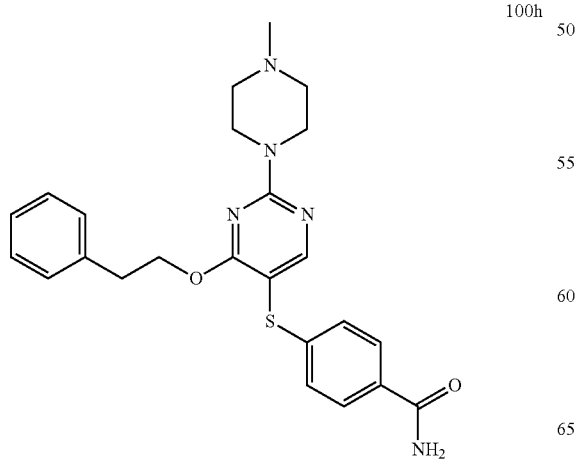
100m
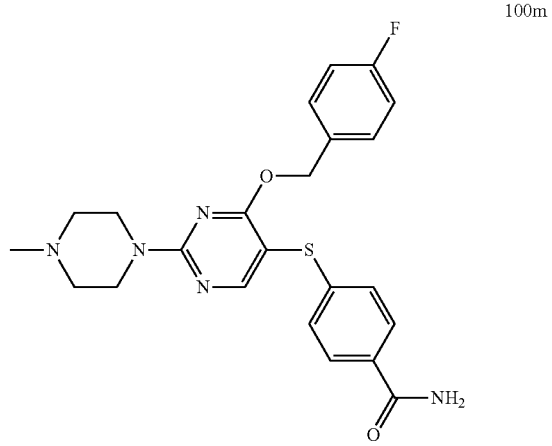

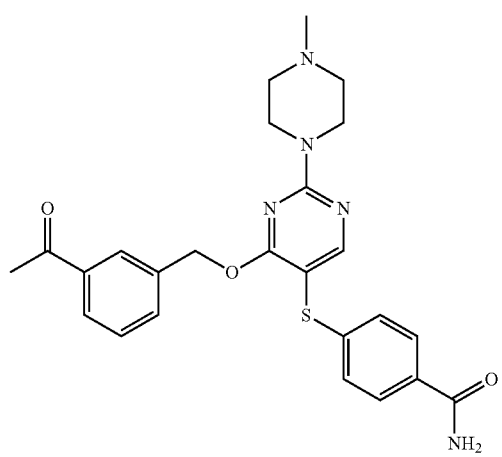
100q
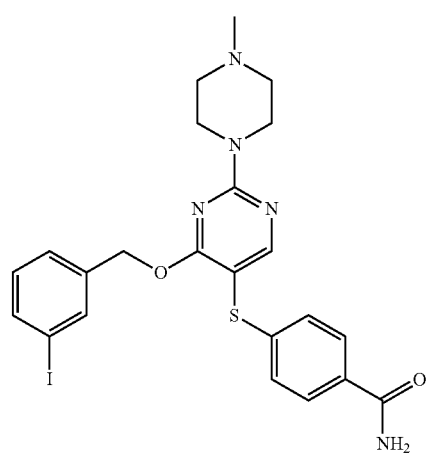
100s
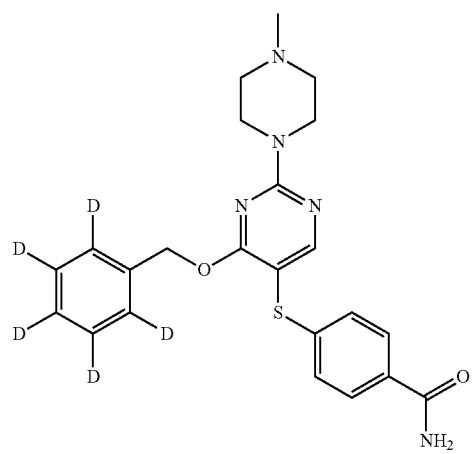
100t
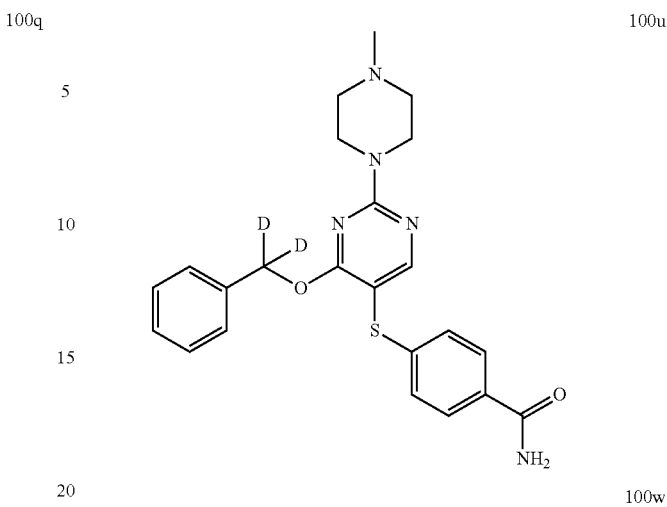
100u
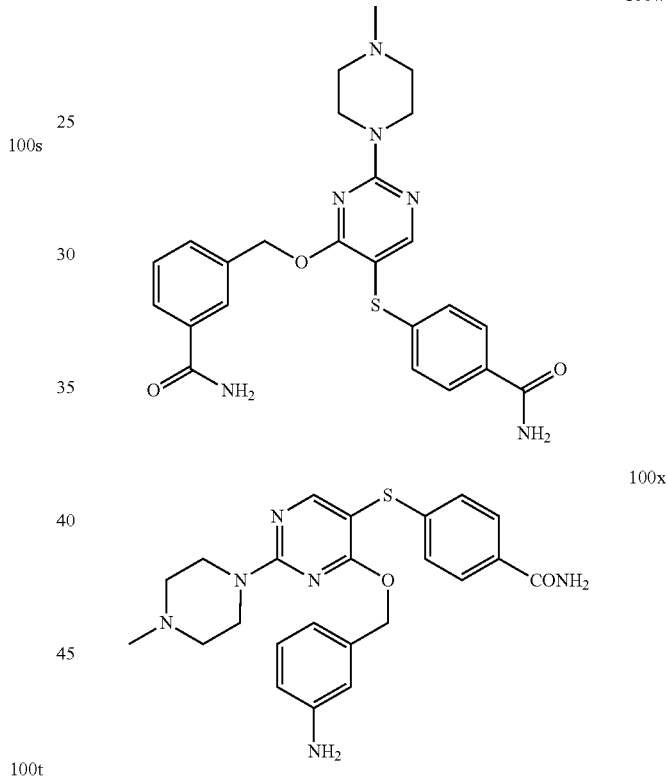
100w
100x
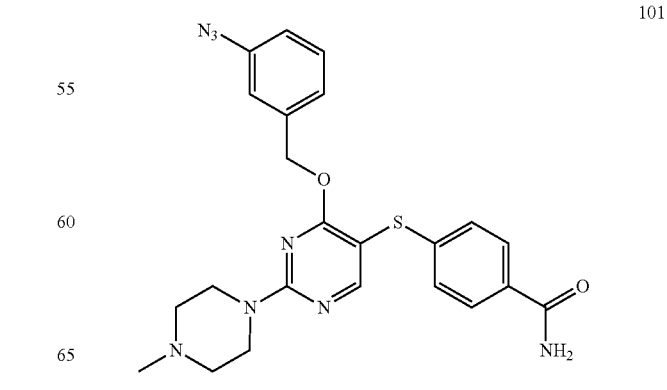
101

337
102
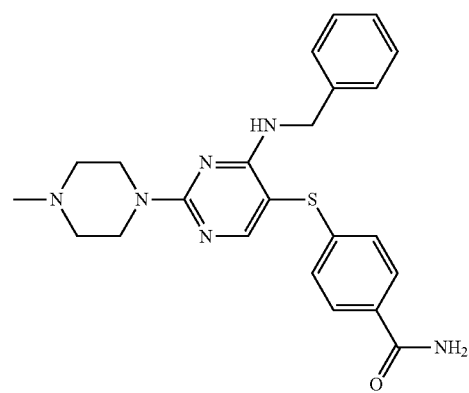
108
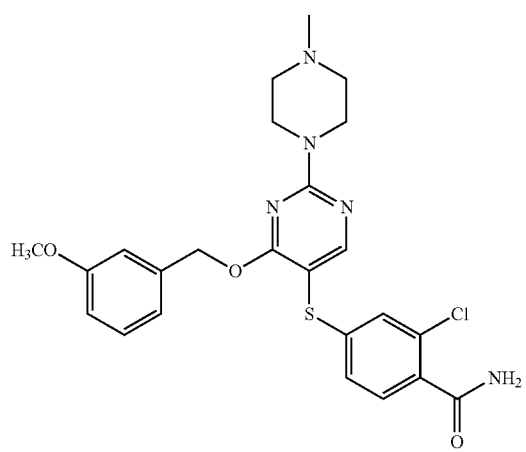
109
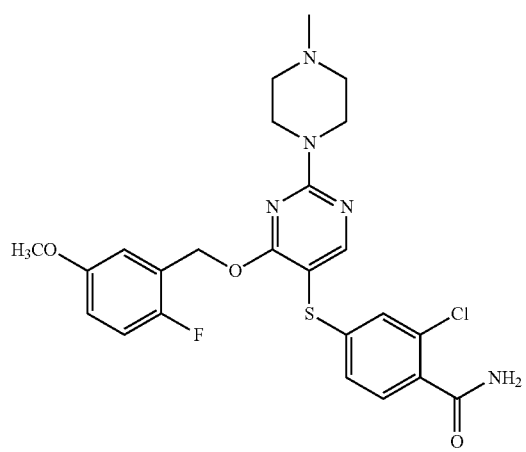
338
110
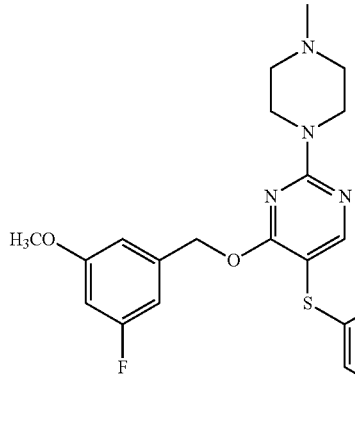
111
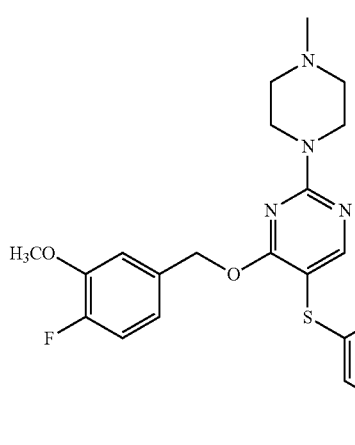
112
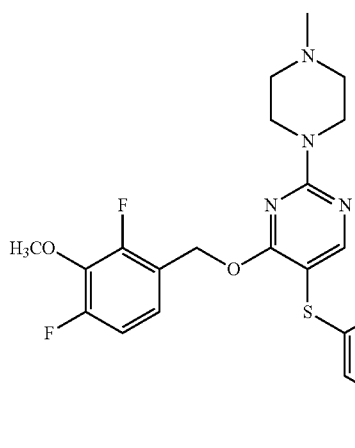

-continued
113
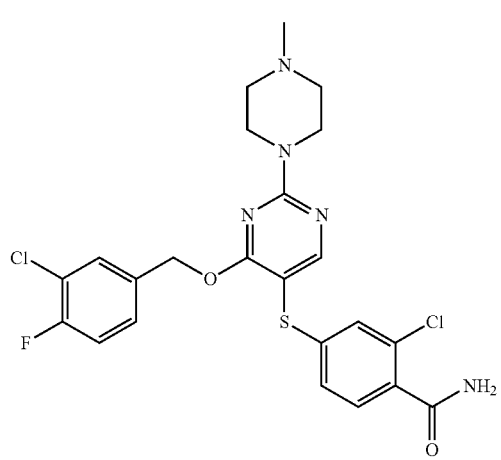
114
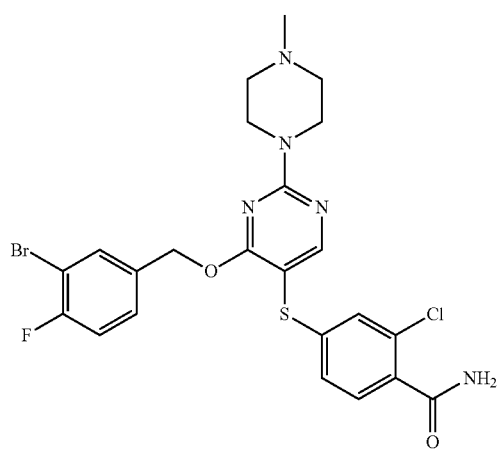
115
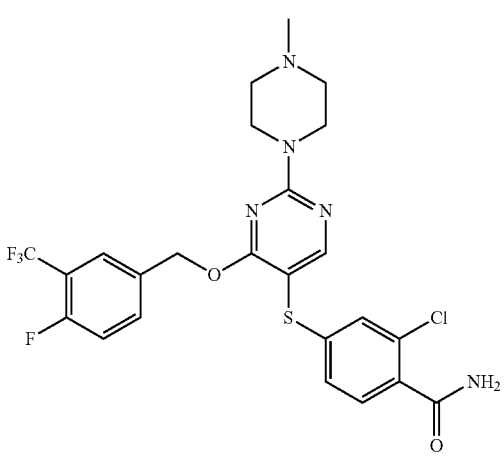
-continued
116
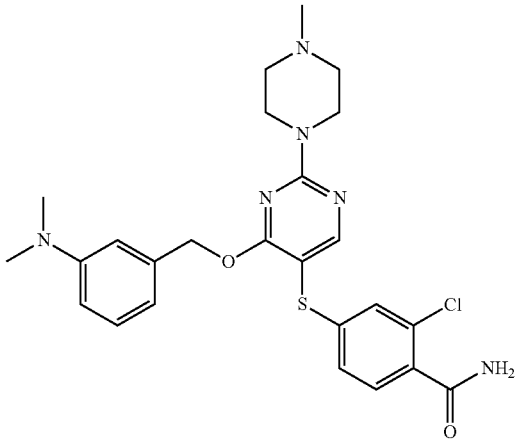
117
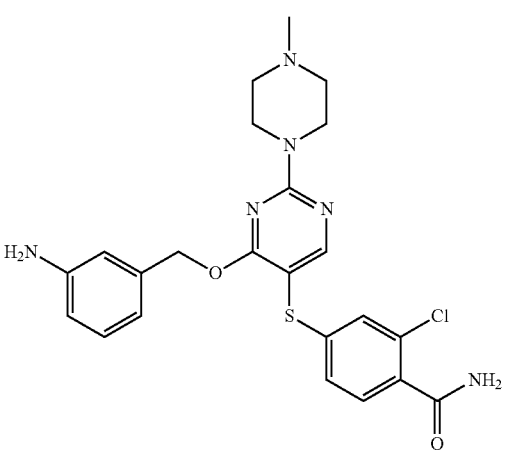
118
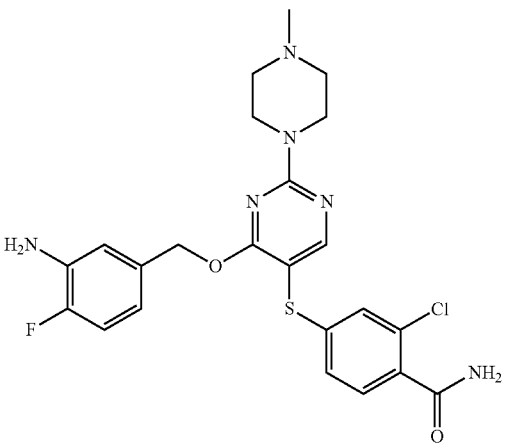

121
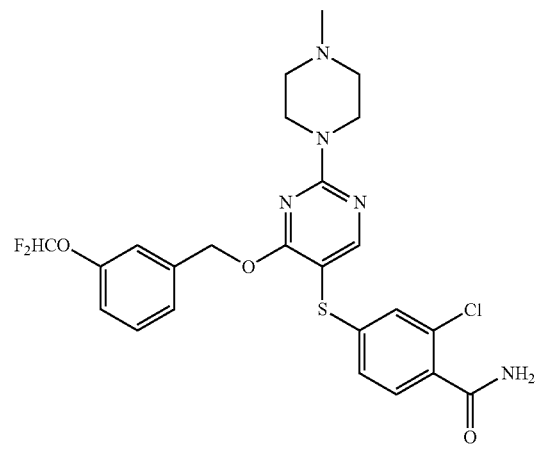
124
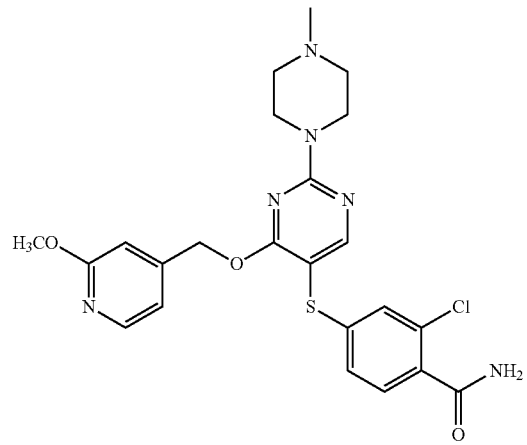
122
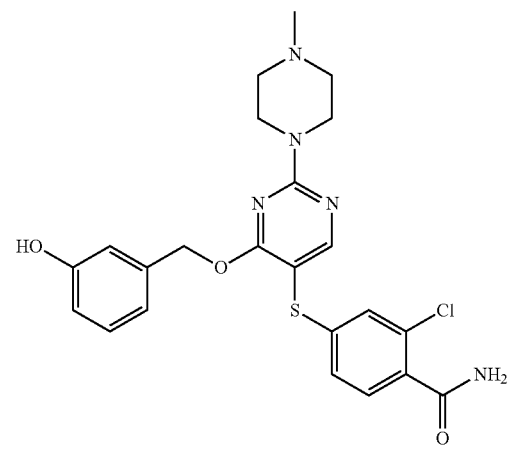
125
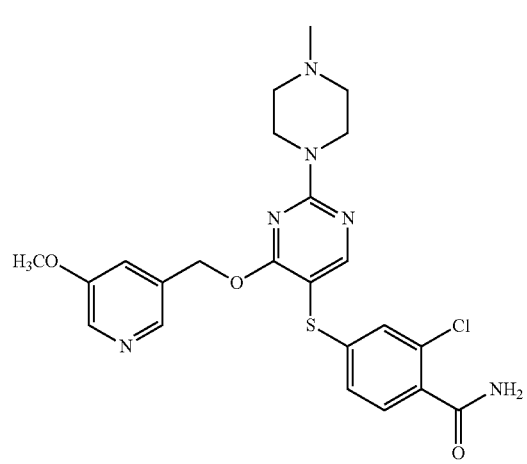
123
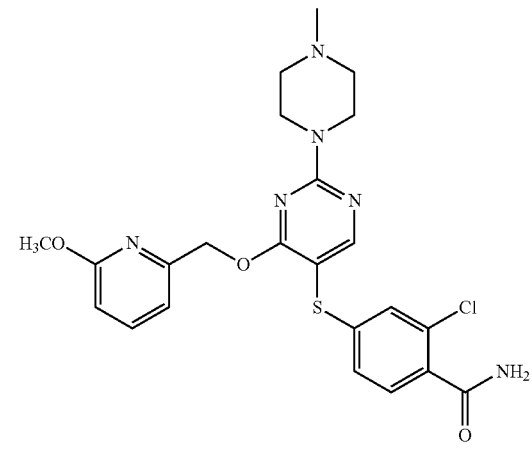
126
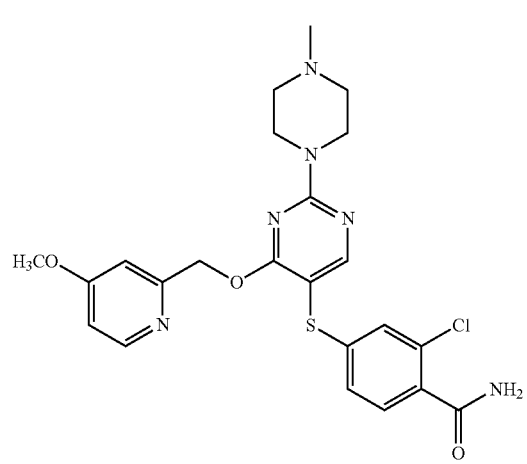

127
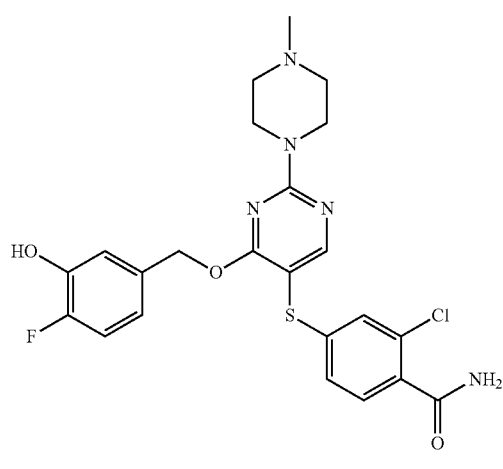
131
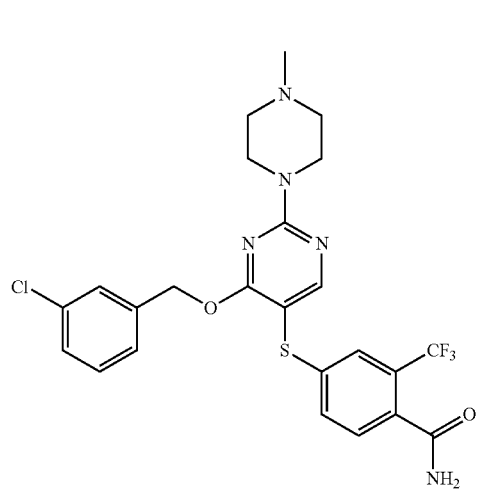
132
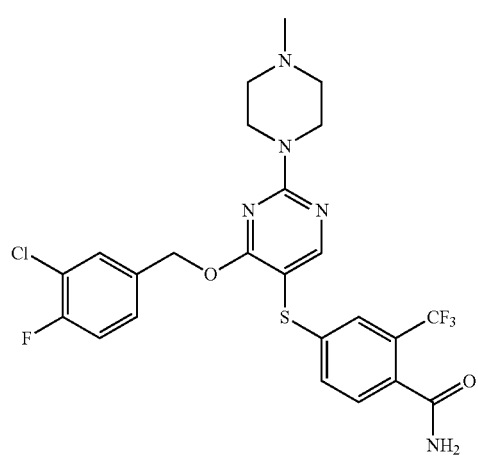
133
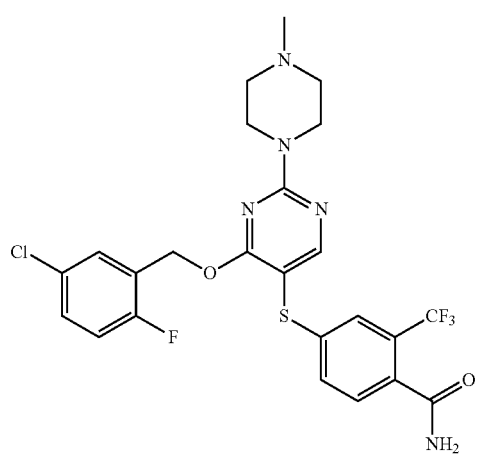
134
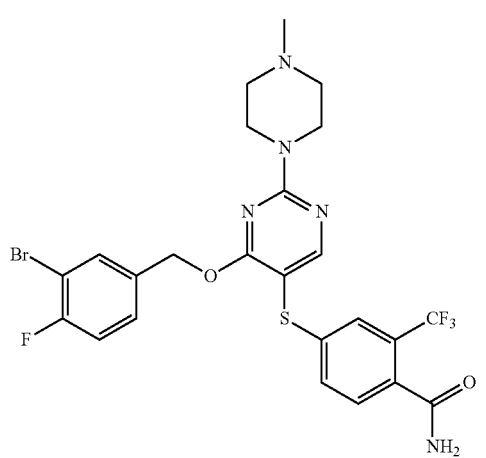
135
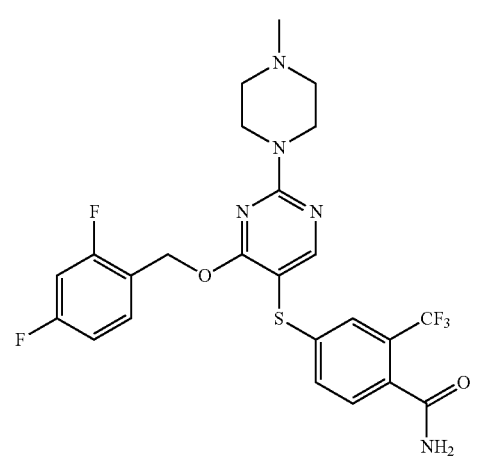

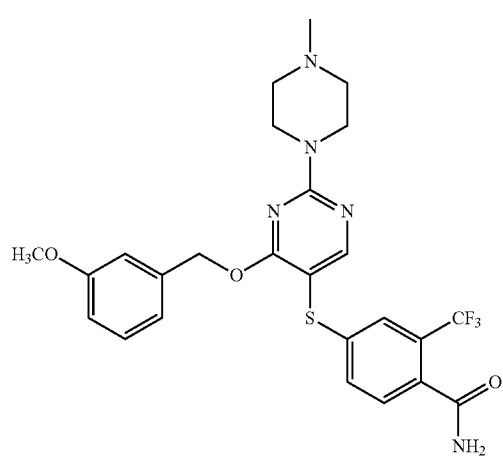
136
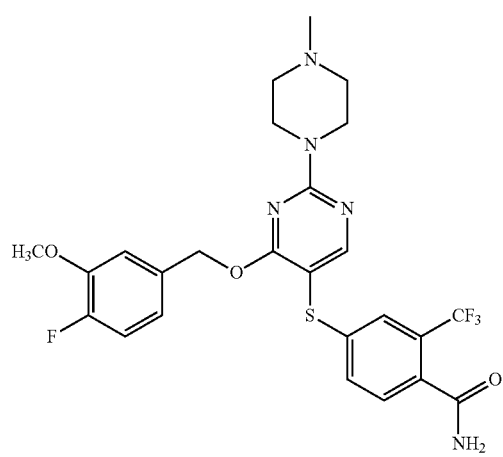
137
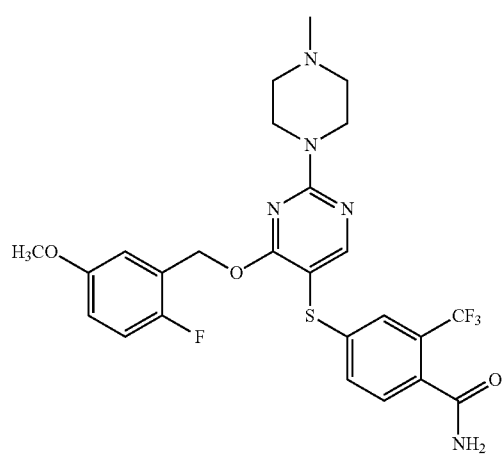
138
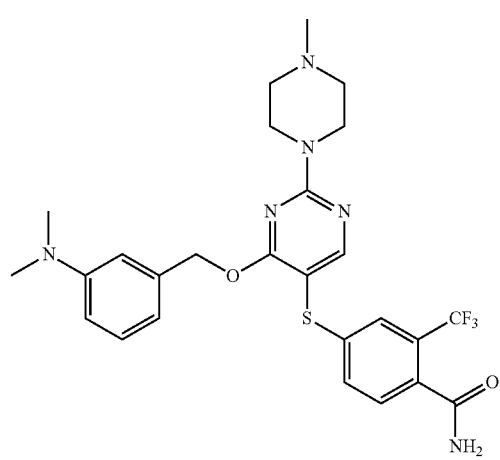
139
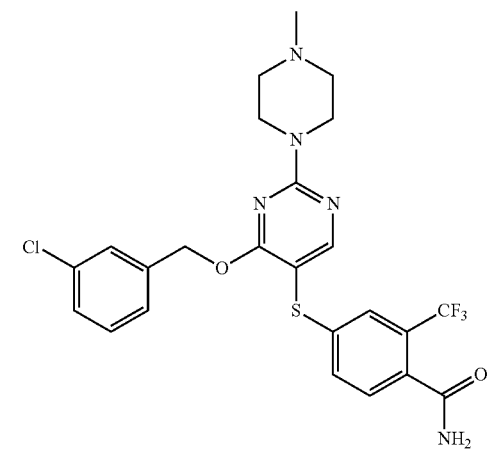
141
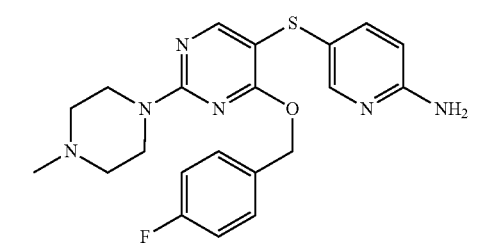
146c
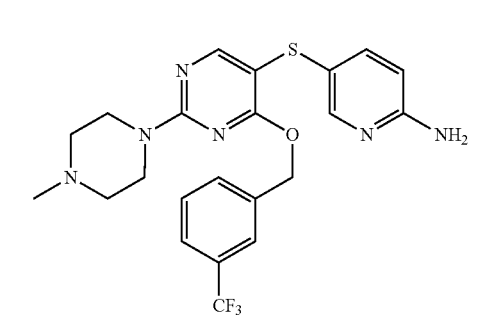
146e 151 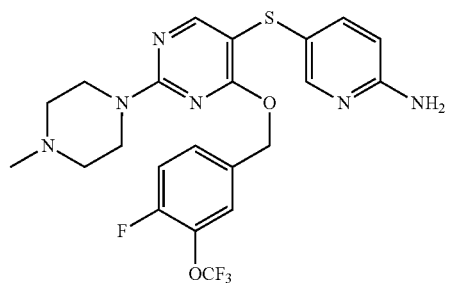
152 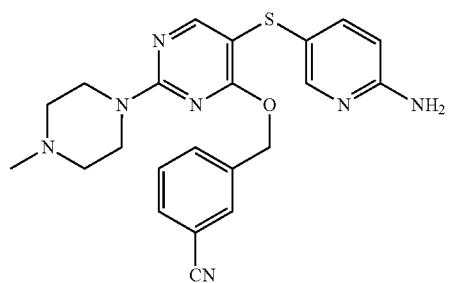
153 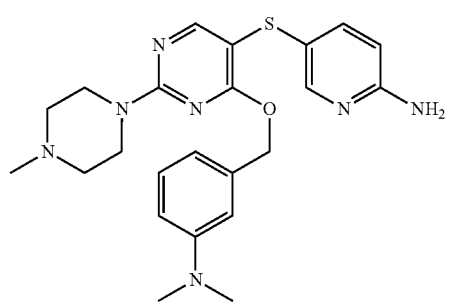
154 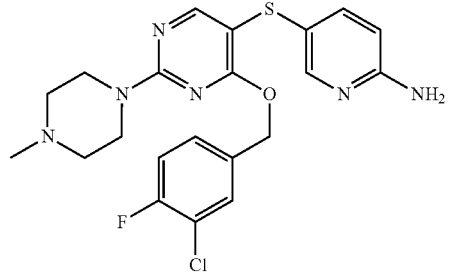
155 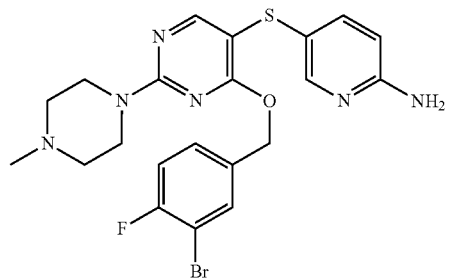
156 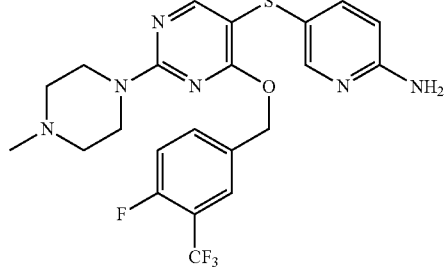
157 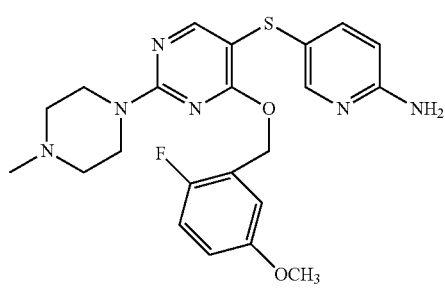
158 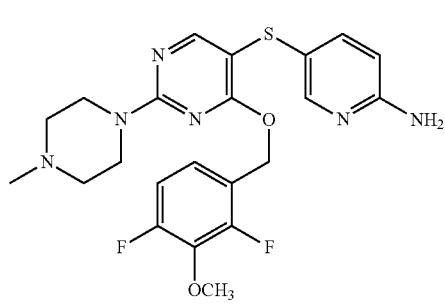
185d 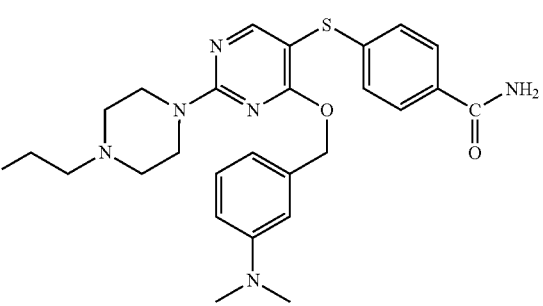
185e 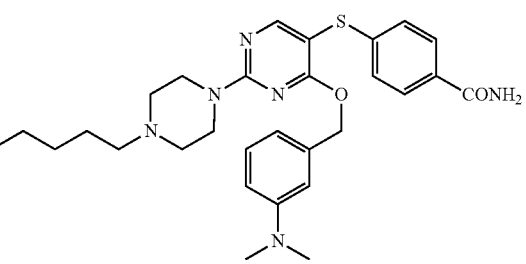

-continued
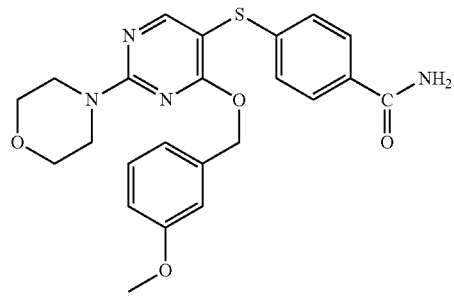
190a
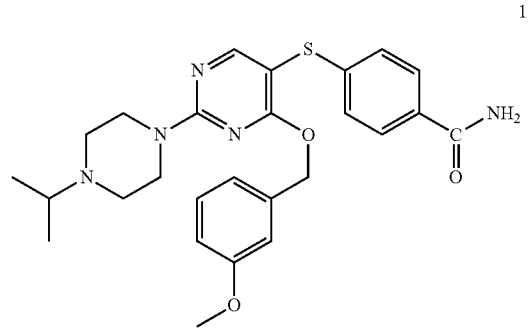
190b
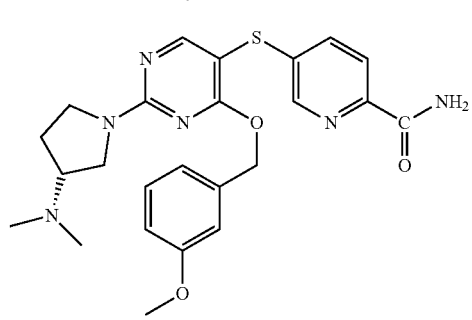
190e
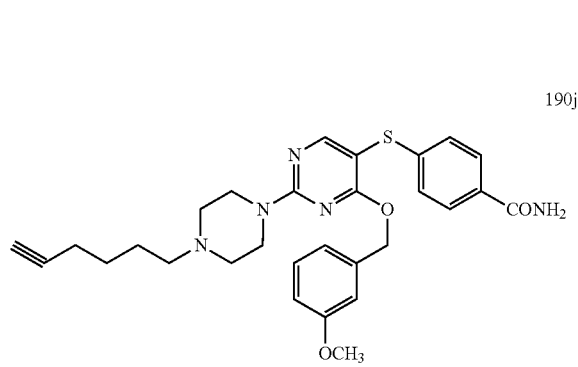
190j
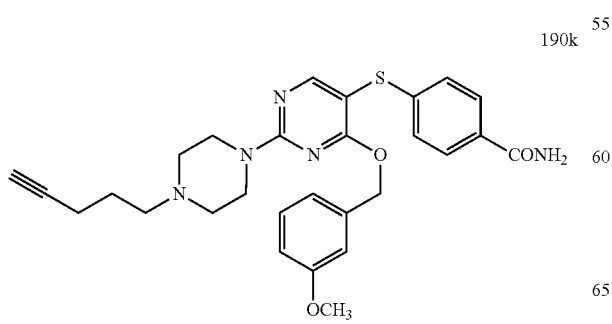
190k
-continued
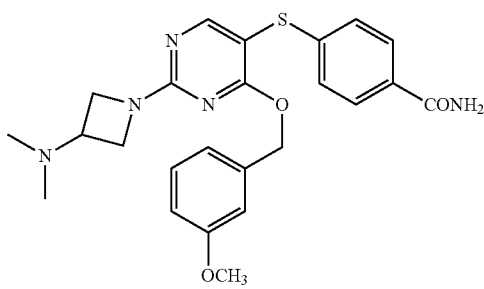
190m
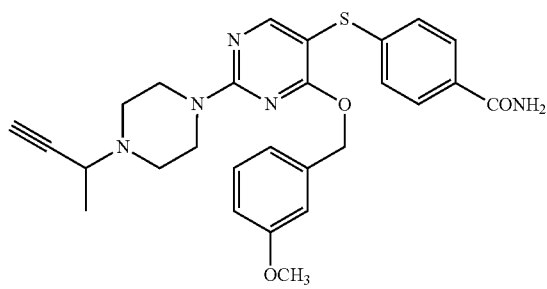
190n
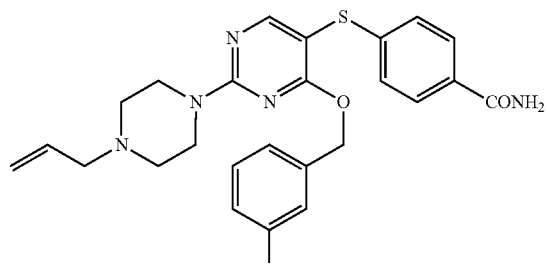
190o
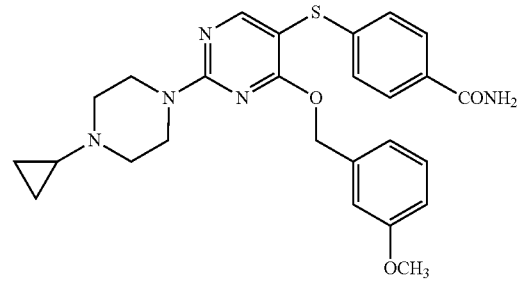
190p
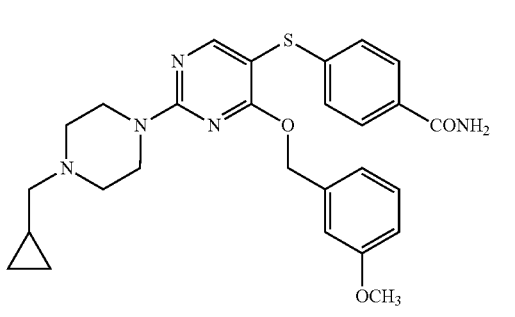
190q 190r 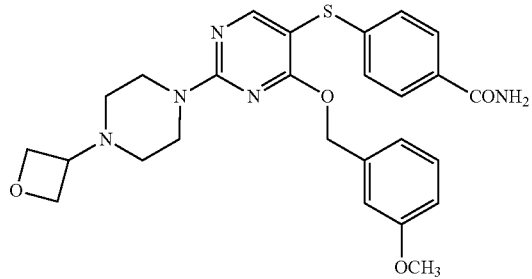
205 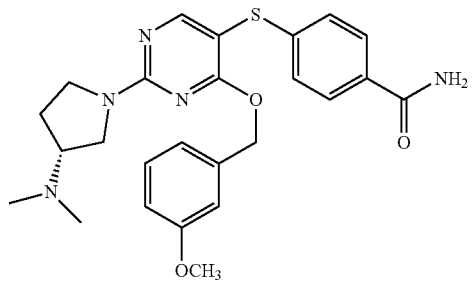
190t 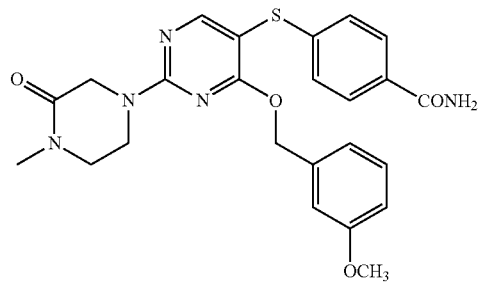
206 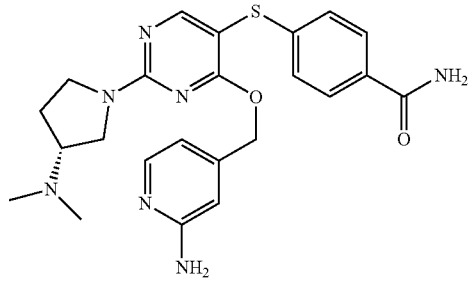
190u 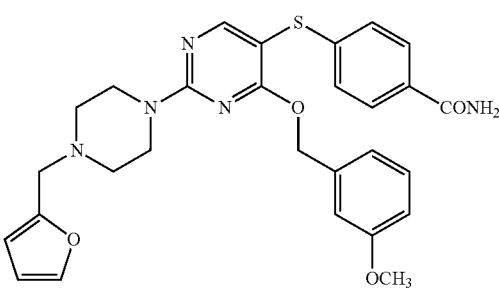
207 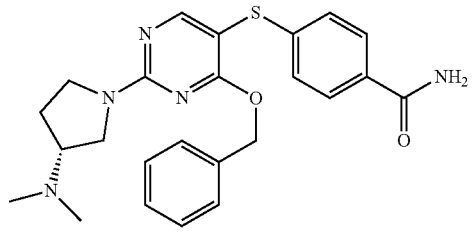
190v 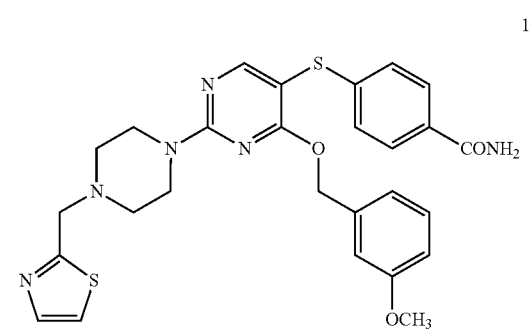
208 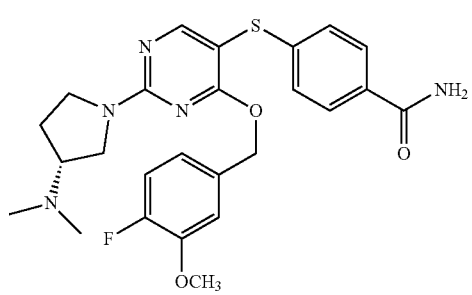
198 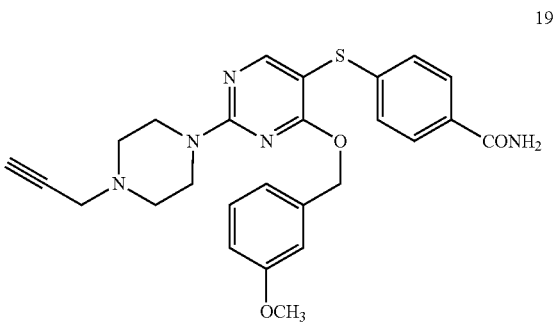
212 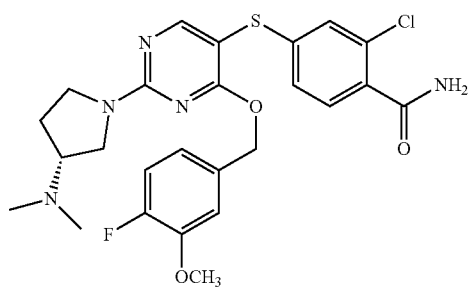

353
-continued
214
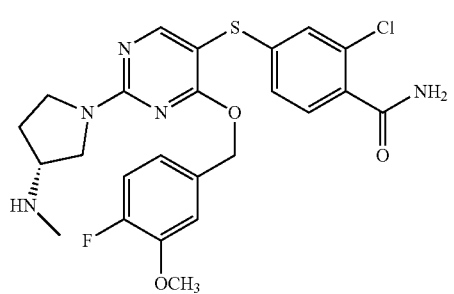
218
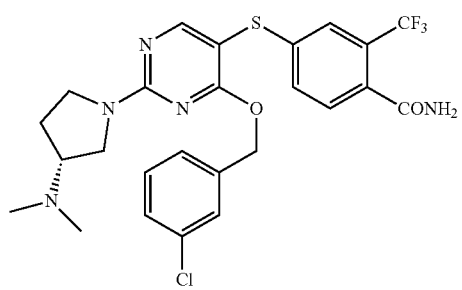
225
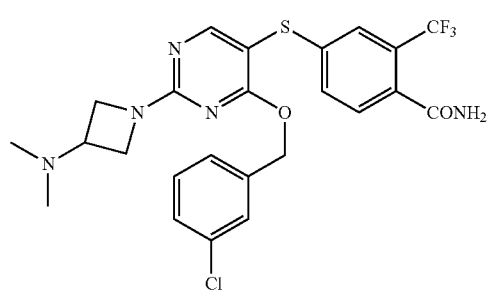
226
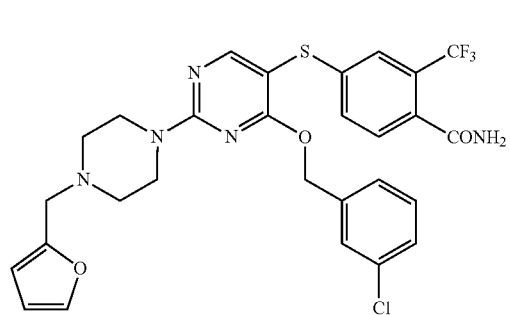
354
-continued
229
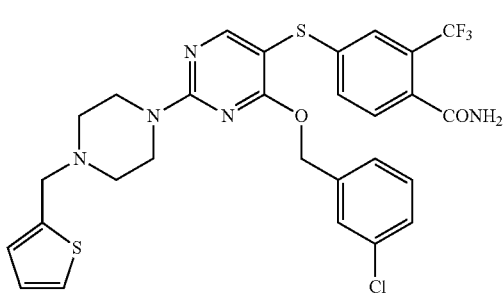
321
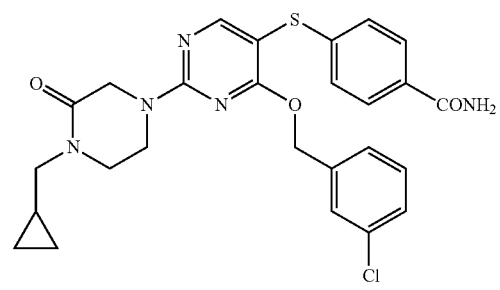
323
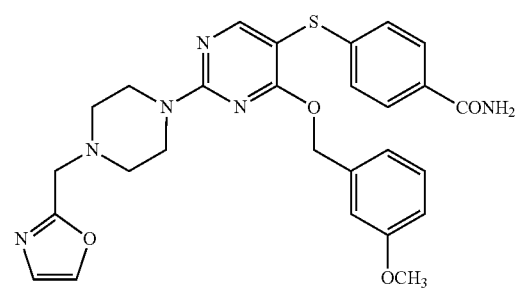
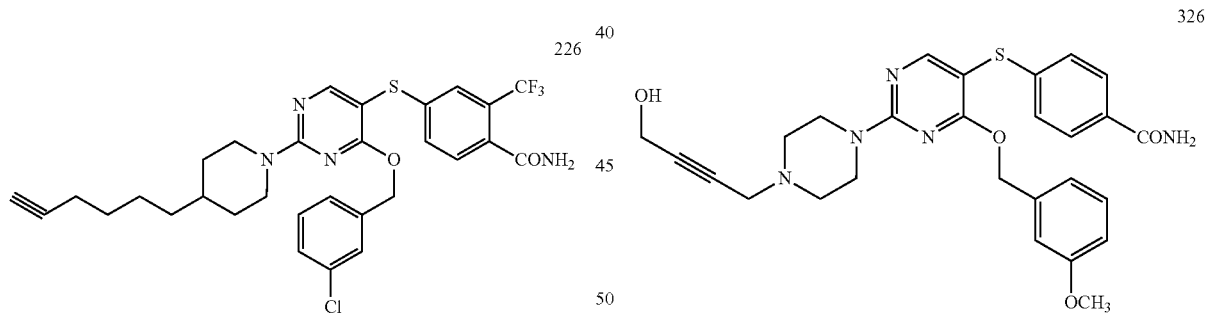

355
-continued
336
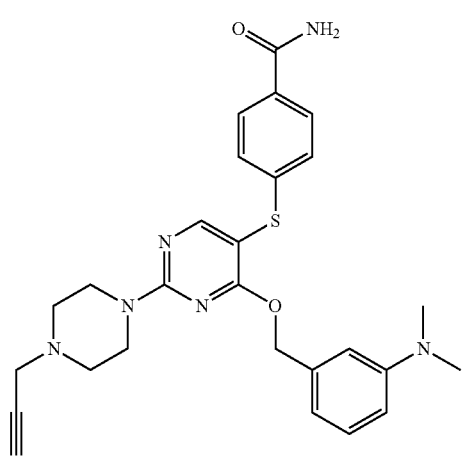
339
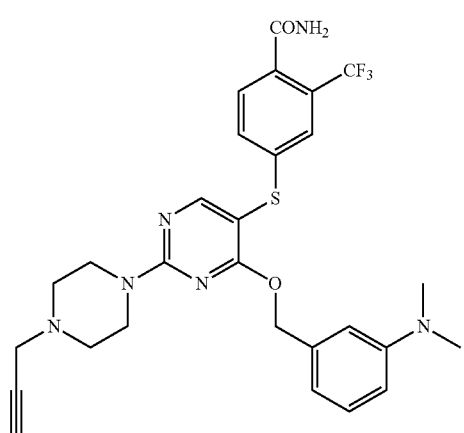
348
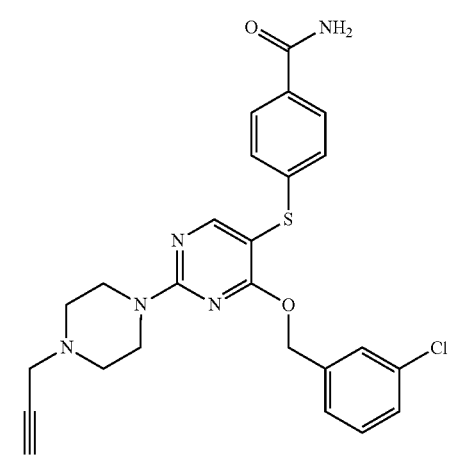
356
-continued
354
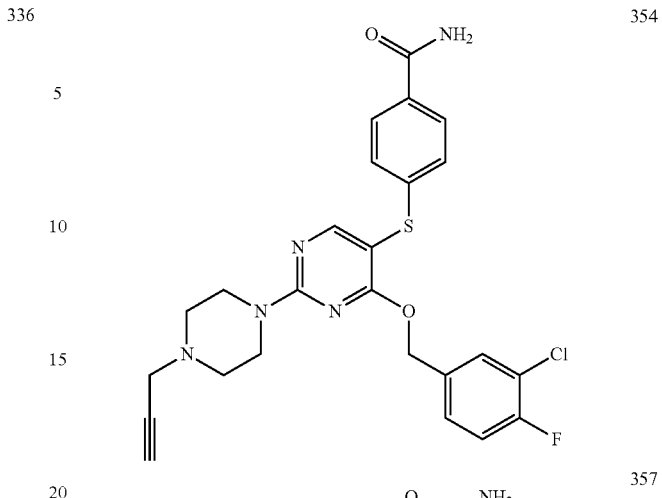
357
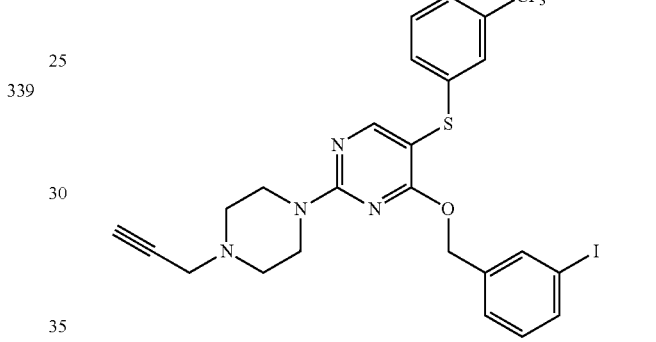
360
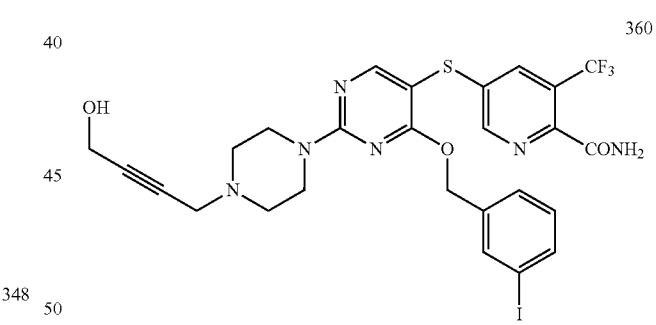
363
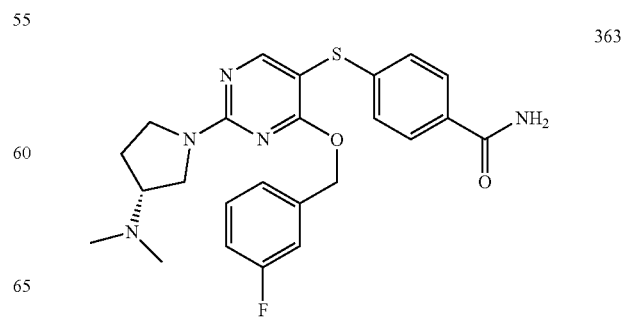

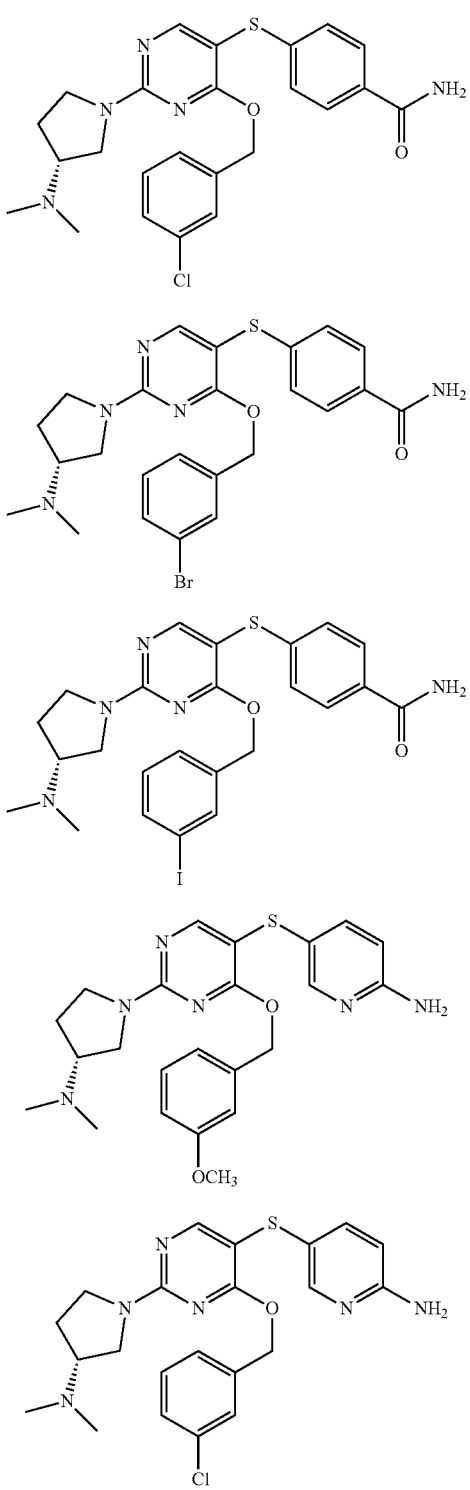

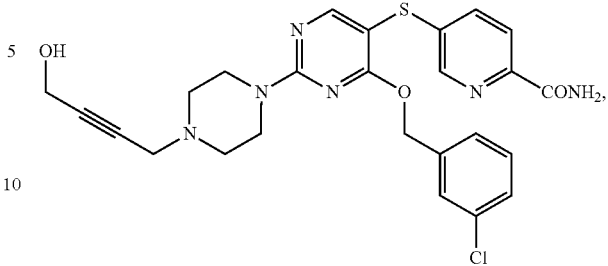

or a pharmaceutically acceptable salt thereof.

14. The method of claim 1, wherein hematological malignancy is selected from the group consisting of acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), Mantle cell lymphoma, B-cell lymphoma, acute lymphoblastic T cell leukemia (T-ALL), acute promyelocytic leukemia, and multiple myeloma.

15. The method of claim 14, wherein hematological malignancy is selected from the group consisting of acute lymphoblastic leukemia (ALL), acute myelogenous leukemia (AML), chronic myelogenous leukemia (CML), chronic lymphocytic leukemia (CLL), cutaneous T-cell lymphoma (CTCL), and peripheral T-cell lymphoma (PTCL).

16. The method of claim 1, wherein solid tumor is selected from the group consisting of colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, gallbladder cancer, laryngeal cancer, oral cancer, penile cancer, glandular tumors, rectal cancer, small intestine cancer, sarcoma, carcinoma, melanoma, urethral cancer, and vaginal cancer.

17. The method of claim 16, wherein solid tumor is selected from the group consisting of pancreatic cancer and breast cancer.

18. The method of claim 1, wherein the cancer is refractory to treatment with Hsp90 inhibitors.

19. The method of claim 1, further comprising administering to the subject a therapeutically effective amount of a second chemotherapeutic agent.

\* \* \* \* \*

UNITED STATES PATENT AND TRADEMARK OFFICE
CERTIFICATE OF CORRECTION

PATENT NO. : 10,160,729 B2
APPLICATION NO. : 15/842755
DATED : December 25, 2018
INVENTOR(S) : Gabriela Chiosis et al.

Page 1 of 5

It is certified that error appears in the above-identified patent and that said Letters Patent is hereby corrected as shown below:

In the Claims

In Claim 11, Column 328, beginning at Line 21 and ending at Line 22, please delete:
"wherein $R^2$ –O-CH$_2$-Ring A."
And insert:
-- wherein $R^2$ is –O-CH$_2$-Ring A. --

In Claim 13, Column 328, beginning at Line 60 and ending at Line 66, please delete the structure:

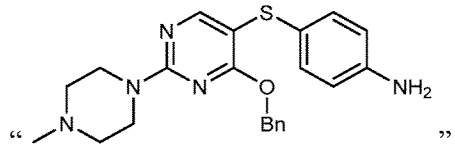

And insert the structure:

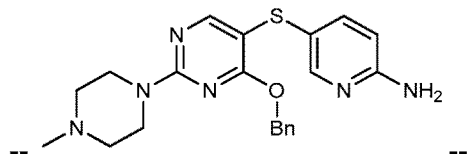

In Claim 13, Column 329, beginning at Line 49 and ending at Line 56, please delete the structure:

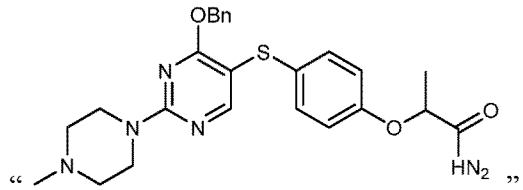

Signed and Sealed this
Ninth Day of April, 2019

Andrei Iancu
*Director of the United States Patent and Trademark Office*

CERTIFICATE OF CORRECTION (continued)
U.S. Pat. No. 10,160,729 B2

And insert the structure:

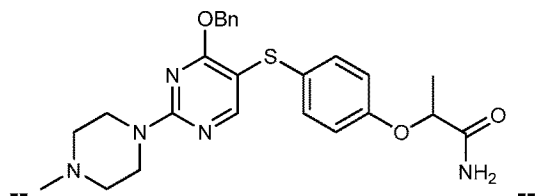

In Claim 13, Column 346, beginning at Line 20 and ending at Line 37, please delete the structure:

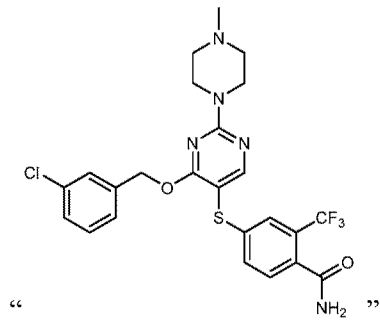

And insert the structure:

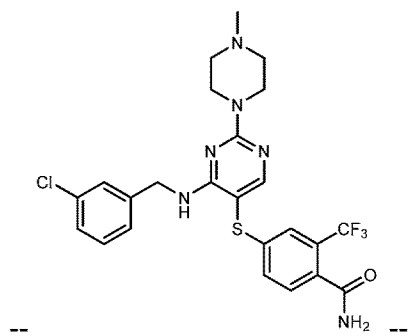

In Claim 13, Column 347, beginning at Line 1 and ending at Line 13, please delete the structure:

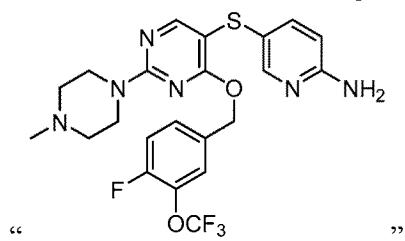

And insert the structure:

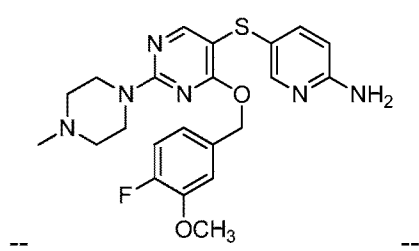

CERTIFICATE OF CORRECTION (continued)
U.S. Pat. No. 10,160,729 B2

In Claim 13, Column 349, beginning at Line 27 and ending at Line 37, please delete the structure:

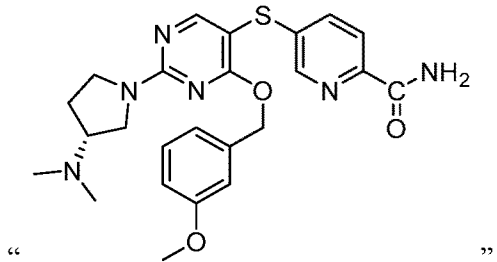

"                                                    "

And insert the structure:

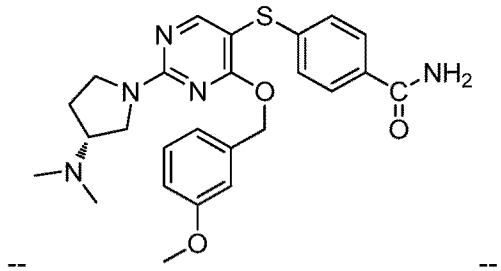

--                                                    --

In Claim 13, Column 352, beginning at Line 1 and ending at Line 13, please delete the structure:

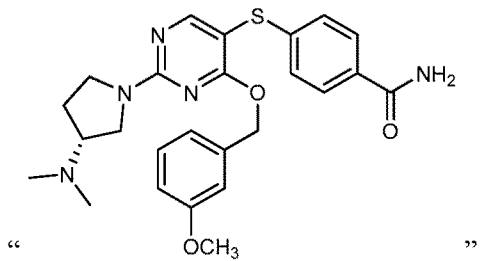

"                                                    "

And insert the structure:

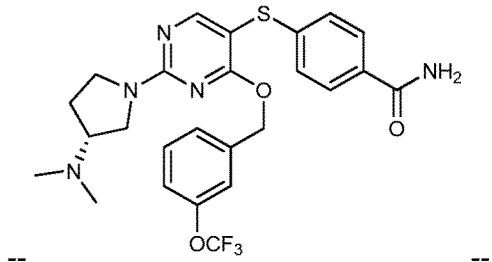

--                                                    --

In Claim 13, Column 353, beginning at Line 41 and ending at Line 50, please delete the structure:

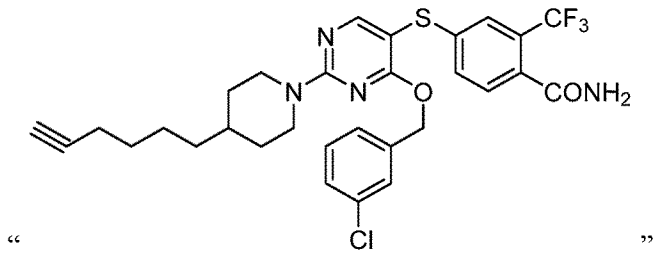

"                                                    "

And insert the structure:

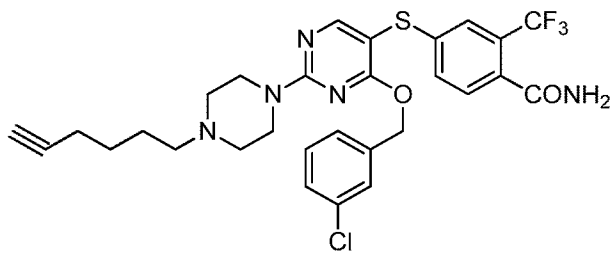
--                                                              --
In Claim 13, Column 354, beginning at Line 1 and ending at Line 13, please delete the structure:
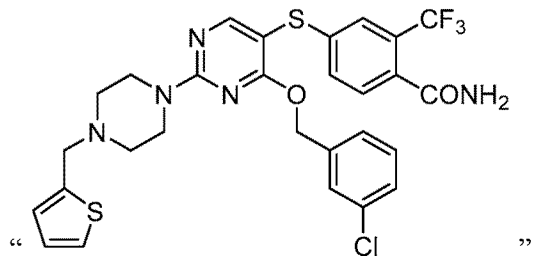
"                                          "
And insert the structure:
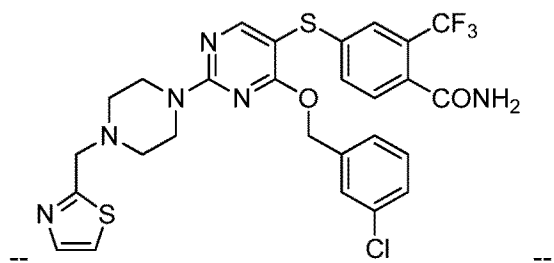
--                                                              --
In Claim 13, Column 354, beginning at Line 14 and ending at Line 24, please delete the structure:
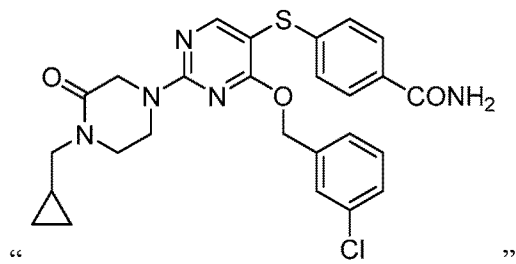
"                                          "
And insert the structure:
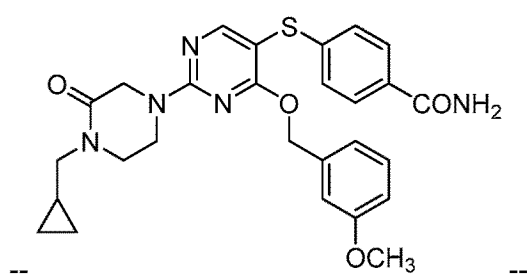
--                                                              --
In Claim 13, Column 356, beginning at Line 40 and ending at Line 52, please delete the structure:

CERTIFICATE OF CORRECTION (continued)
U.S. Pat. No. 10,160,729 B2

Page 5 of 5

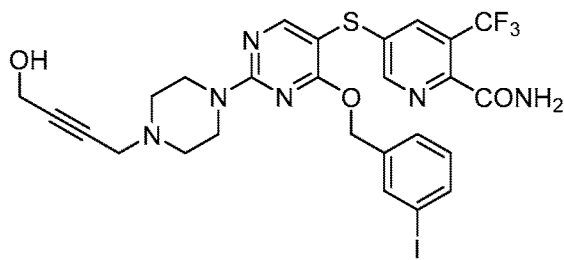

"

"

And insert the structure:

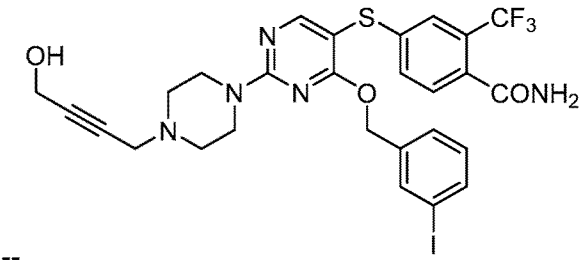

-- --

In Claim 13, Column 358, beginning at Line 1 and ending at Line 13, please delete the structure:

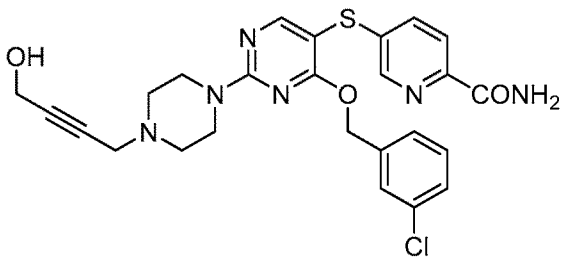

"

"

And insert the structure:

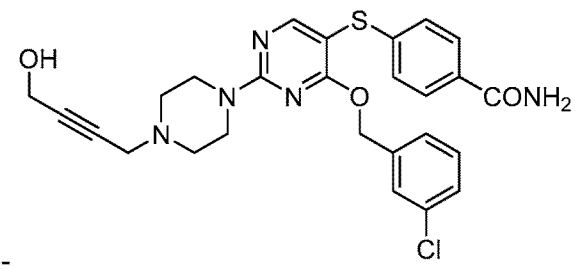

-- --